US010519110B2

(12) United States Patent
Asano et al.

(10) Patent No.: US 10,519,110 B2
(45) Date of Patent: Dec. 31, 2019

(54) HETEROCYCLIC COMPOUND

(71) Applicant: TAKEDA PHARMACEUTICAL COMPANY LIMITED, Osaka (JP)

(72) Inventors: Yasutomi Asano, Fujisawa (JP); Takuto Kojima, Fujisawa (JP); Osamu Kurasawa, Fujisawa (JP); Tzu-Tshin Wong, Acton, MA (US); Yasuhiro Hirata, Fujisawa (JP); Naoki Iwamura, Fujisawa (JP); Bunnai Saito, Fujisawa (JP); Yuta Tanaka, Fujisawa (JP); Ryosuke Arai, Fujisawa (JP); Shinichi Imamura, Fujisawa (JP); Kazuko Yonemori, Fujisawa (JP); Yasufumi Miyamoto, Fujisawa (JP); Shuji Kitamura, Fujisawa (JP); Osamu Sano, Fujisawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/175,144

(22) Filed: Oct. 30, 2018

(65) Prior Publication Data
US 2019/0062274 A1 Feb. 28, 2019

Related U.S. Application Data

(62) Division of application No. 15/565,891, filed as application No. PCT/JP2016/062418 on Apr. 19, 2016, now Pat. No. 10,189,785.

(30) Foreign Application Priority Data

Apr. 20, 2015 (JP) .................. 2015-086195

(51) Int. Cl.
| | | |
|---|---|---|
| *C07D 211/58* | (2006.01) |
| *C07F 9/6509* | (2006.01) |
| *C07D 401/14* | (2006.01) |
| *A61K 31/437* | (2006.01) |
| *A61K 31/443* | (2006.01) |
| *A61K 31/4433* | (2006.01) |
| *A61K 31/4436* | (2006.01) |
| *A61K 31/4439* | (2006.01) |
| *A61K 31/444* | (2006.01) |
| *A61K 31/4468* | (2006.01) |
| *A61K 31/451* | (2006.01) |
| *A61K 31/452* | (2006.01) |
| *A61K 31/4709* | (2006.01) |
| *A61K 31/498* | (2006.01) |
| *A61K 31/506* | (2006.01) |
| *A61K 31/517* | (2006.01) |
| *A61K 31/5355* | (2006.01) |
| *A61K 31/661* | (2006.01) |
| *A61K 33/22* | (2006.01) |
| *C07D 215/42* | (2006.01) |

(Continued)

(52) U.S. Cl.
CPC .......... *C07D 211/58* (2013.01); *A61K 31/437* (2013.01); *A61K 31/443* (2013.01); *A61K 31/444* (2013.01); *A61K 31/4433* (2013.01); *A61K 31/4436* (2013.01); *A61K 31/4439* (2013.01); *A61K 31/4468* (2013.01); *A61K 31/451* (2013.01); *A61K 31/452* (2013.01); *A61K 31/4709* (2013.01); *A61K 31/498* (2013.01); *A61K 31/506* (2013.01); *A61K 31/517* (2013.01); *A61K 31/5355* (2013.01); *A61K 31/661* (2013.01); *A61K 33/22* (2013.01); *A61P 3/00* (2018.01); *A61P 35/00* (2018.01); *C07B 59/002* (2013.01); *C07D 215/42* (2013.01); *C07D 401/06* (2013.01); *C07D 401/12* (2013.01); *C07D 401/14* (2013.01); *C07D 405/06* (2013.01); *C07D 409/12* (2013.01); *C07D 413/06* (2013.01); *C07D 413/14* (2013.01); *C07D 417/06* (2013.01); *C07D 417/12* (2013.01); *C07D 417/14* (2013.01); *C07D 471/04* (2013.01); *C07D 487/04* (2013.01); *C07D 498/04* (2013.01); *C07D 513/04* (2013.01); *C07D 519/00* (2013.01); *C07F 5/02* (2013.01); *C07F 9/6509* (2013.01); *C07B 2200/05* (2013.01); *Y02P 20/55* (2015.11)

(58) Field of Classification Search
None
See application file for complete search history.

(56) References Cited

U.S. PATENT DOCUMENTS

| 6,492,393 B1 | 12/2002 | Breitfelder et al. |
| 7,241,758 B2 | 7/2007 | Hao et al. |

(Continued)

FOREIGN PATENT DOCUMENTS

| WO | 1997/045119 A1 | 5/1997 |
| WO | 2008/038841 A1 | 4/2008 |
| WO | 2008/084300 A1 | 7/2008 |

OTHER PUBLICATIONS

Lee et al., "Myriocin, a serine palmitoyltransferase inhibitor, suppresses tumor growth in a murine melanoma model by inhibiting de novo sphingolipid synthesis," Cancer Biol. Ther., 13(2): 92-100 (2012).

(Continued)

*Primary Examiner* — Zinna Northington Davis
(74) *Attorney, Agent, or Firm* — Casimir Jones, S.C.; Anne M. Reynolds

(57) ABSTRACT

The present invention relates to a compound which can be useful for the treatment or prevention of SPT-related diseases including cancer and congenital diseases associated with sphingolipid accumulation (including Niemann-Pick disease).

5 Claims, No Drawings

(51) Int. Cl.

| | | |
|---|---|---|
| C07D 401/06 | (2006.01) | |
| C07D 401/12 | (2006.01) | |
| C07D 409/12 | (2006.01) | |
| C07D 413/06 | (2006.01) | |
| C07D 417/06 | (2006.01) | |
| C07D 417/12 | (2006.01) | |
| C07D 417/14 | (2006.01) | |
| C07D 471/04 | (2006.01) | |
| C07D 487/04 | (2006.01) | |
| C07D 498/04 | (2006.01) | |
| C07D 513/04 | (2006.01) | |
| C07D 519/00 | (2006.01) | |
| C07F 5/02 | (2006.01) | |
| A61P 3/00 | (2006.01) | |
| A61P 35/00 | (2006.01) | |
| C07B 59/00 | (2006.01) | |
| C07D 405/06 | (2006.01) | |
| C07D 413/14 | (2006.01) | |

(56) References Cited

U.S. PATENT DOCUMENTS

| | | | |
|---|---|---|---|
| 8,470,816 | B2 | 6/2013 | Ikeura et al. |
| 8,592,454 | B2 | 11/2013 | Shirai et al. |
| 8,697,739 | B2 | 4/2014 | Barnes et al. |
| 2006/0079542 | A1 | 4/2006 | Nestor |
| 2007/0135450 | A1 | 6/2007 | Nestor |
| 2008/0287479 | A1 | 11/2008 | Hutchings et al. |
| 2009/0042772 | A1 | 2/2009 | Nestor |
| 2009/0156572 | A1 | 6/2009 | Ikeura et al. |
| 2014/0171363 | A1 | 6/2014 | Barnes et al. |
| 2014/0243286 | A1 | 8/2014 | Arnold et al. |

OTHER PUBLICATIONS

International Search Report mailed in International Patent Application No. PCT/JP2016/062418 (dated Jul. 19, 2016).

Barelier et al., "Fragment-based deconstruction of Bcl-xL inhibitors." J Med Chem. Mar. 25, 2010;53(6):2577-88.

Database Caplus [Online], Chemical Abstracts Service, Columbus, Ohio, US; Apr. 3, 2008, Japan Tobacco Inc., Japan: "Preparation of thiadiazolone derivatives as TNF-.alpha. converting enzyme", Database accession No. 2008: 410465, 13 pages.

Extended European Search Report dated Sep. 11, 2018, European Application No. 16783163.5, 7 pages.

International Preliminary Report on Patentability, English Translation, PCT/JP2017/037503, dated May 2, 2019, 7 pages.

Yaguchi, et al. "Antitumor activity of a novel and orally available inhibitor of serine palmitoyltransferase." Biochemical and Biophysical Research Communications, 2017, 484(3):493-500.

HETEROCYCLIC COMPOUND

CROSS-REFERENCE TO RELATED APPLICATIONS

This application is a divisional of U.S. patent application Ser. No. 15/565,891, filed Oct. 11, 2017, which is a national phase application under 35 U.S.C. § 371 of PCT International Application No. PCT/JP2016/062418, filed Apr. 19, 2016, which claims priority to Japanese Application No. 2015-086195, filed Apr. 20, 2015, each of which is hereby incorporated by reference in its entirety.

TECHNICAL FIELD

The present invention relates to a novel compound or a salt thereof which can have an inhibitory effect on serine palmitoyltransferase (hereinafter, also referred to as "SPT"). The present invention further relates to a medicament which can be useful for the prevention or treatment of SPT-related diseases including cancer and congenital diseases associated with sphingolipid accumulation including Niemann-Pick disease, etc., comprising the compound or a salt thereof.

BACKGROUND OF THE INVENTION

SPT is an enzyme that catalyzes the reaction through which L-serine and palmitoyl coenzyme A are condensed to synthesize 3-ketodihydrosphingosine, and is involved in the biosynthesis of sphingolipids. SPT is constituted by a plurality of subunits. 3 types of SPT subunits are known: SPT1 (also called SPTLC1), SPT2 (also called SPTLC2) and SPT3 (also called SPTLC3). A complex consisting of subunits SPT1 and SPT2 and a complex consisting of subunits SPT1 and SPT3 are known as SPT as a subunit complex.

The sphingolipids include ceramide, sphingomyelin, ganglioside and the like. The sphingolipids are constituents of cell membranes and are known to play an important role in maintenance of homeostasis of the membranes and signal transduction while having various physiological activities. Myriocin, which has an inhibitory effect on SPT, is known to inhibit the growth of activated lymphocytes, to inhibit the growth of mouse melanoma cell lines, and to exhibit an antitumor effect on mouse melanoma tumor models (Non Patent Literature 1).

Compounds described in Patent Literatures 1 to 6, etc., have been known so far as compounds having an antitumor effect.

CITATION LIST

Patent Literature

Patent Literature 1: International Publication No. WO2010/032856
Patent Literature 2: International Publication No. WO2009/072643
Patent Literature 3: International Publication No. WO2008/038841
Patent Literature 4: International Publication No. WO2013/033270
Patent Literature 5: International Publication No. WO2012/013716
Patent Literature 6: International Publication No. WO2001/036403

Non Patent Literature

Non Patent Literature 1: Cancer Biology & Therapy 2012, 13: 92-100

SUMMARY OF INVENTION

Technical Problem

An object of the present invention is to provide a compound that has an excellent SPT inhibitory effect and is sufficiently satisfactory as a medicament.

Solution to Problem

The present inventors have conducted diligent studies in light of the object described above and consequently completed the present invention by finding that a compound represented by the formula given below can have the activity of inhibiting SPT. Specifically, the present invention relates to at least the following aspects:

[1] A compound represented by a formula:

(I)

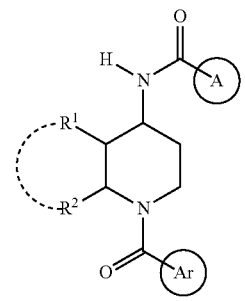

[Formula 1]

wherein ring Ar represents an optionally further substituted aromatic heterocycle or an optionally further substituted $C_{6-14}$ aromatic hydrocarbon ring;

ring A represents an optionally further substituted $C_{6-14}$ aromatic hydrocarbon ring or an optionally further substituted heterocycle;

$R^1$ represents an optionally substituted $C_{6-14}$ aryl group, an optionally substituted $C_{3-10}$ cycloalkyl group or an optionally substituted heterocyclic group except that when $R^1$ is an optionally substituted heterocyclic group, $R^1$ is represented by a formula:

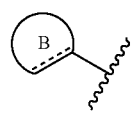

[Formula 2]

wherein ring B represents an optionally further substituted heterocycle, and

[Formula 3]
represents a single bond or a double bond, or a formula:

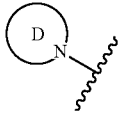
[Formula 4]

wherein ring D represents an optionally further substituted nitrogen-containing heterocycle,
$R^2$ represents a hydrogen atom, or
$R^1$ and $R^2$ are bonded to each other to form an optionally substituted 5- or 6-membered aromatic heterocycle or an optionally substituted benzene ring
or a salt thereof (in the present specification, the compound or a salt thereof is also referred to as "compound (I)").

[2] The compound or a salt thereof according to [1], wherein
ring Ar is
(I) an aromatic heterocycle optionally substituted by 1 to 3 substituents selected from
(1) a halogen atom,
(2) a cyano group,
(3) a hydroxy group,
(4) an optionally halogenated $C_{1-6}$ alkyl group,
(5) a $C_{3-10}$ cycloalkyl group,
(6) an optionally halogenated $C_{1-6}$ alkoxy group,
(7) a hydroxy-$C_{1-6}$ alkoxy group,
(8) a $C_{3-10}$ cycloalkyloxy group,
(9) a $C_{1-6}$ alkyl-carbonyl group,
(10) a $C_{1-6}$ alkoxy-carbonyl group,
(11) an amino group,
(12) a mono- or di-$C_{1-6}$ alkylamino group,
(13) a mono- or di-$C_{1-6}$ alkyl-carbonylamino group,
(14) a mono- or di-$C_{3-10}$ cycloalkyl-carbonylamino group,
(15) a 5- to 14-membered aromatic heterocyclic group, and
(16) a $C_{1-6}$ alkylsulfonyl group,
or
(II) a $C_{6-14}$ aromatic hydrocarbon ring optionally substituted by 1 to 3 substituents selected from
(1) a halogen atom,
(2) a cyano group,
(3) an optionally halogenated $C_{1-6}$ alkyl group,
(4) a $C_{3-10}$ cycloalkyl group,
(5) an optionally halogenated $C_{1-6}$ alkoxy group,
(6) a mono- or di-$C_{1-6}$ alkylamino group,
(7) a $C_{1-6}$ alkyl-5- to 14-membered aromatic heterocyclic group, and
(8) a $C_{1-6}$ alkylsulfonyl group;
ring A is
(I) a $C_{6-14}$ aromatic hydrocarbon ring optionally substituted by 1 to 3 substituents selected from
(1) a halogen atom,
(2) a cyano group,
(3) an optionally halogenated $C_{1-6}$ alkyl group,
(4) an optionally halogenated $C_{1-6}$ alkoxy group, and
(5) a $C_{1-6}$ alkylsulfonyl group,
or
(II) a heterocycle optionally substituted by 1 to 3 substituents selected from
(1) a halogen atom,
(2) an optionally halogenated $C_{1-6}$ alkyl group,
(3) a $C_{3-10}$ cycloalkyl group,
(4) an optionally halogenated $C_{1-6}$ alkoxy group,
(5) a hydroxy-$C_{1-6}$ alkoxy group,
(6) a $C_{1-6}$ alkoxy-$C_{1-6}$ alkoxy group,
(7) a 3- to 14-membered non-aromatic heterocycle-$C_{1-6}$ alkoxy group,
(8) a 3- to 14-membered non-aromatic heterocyclyloxy-$C_{1-6}$ alkoxy group,
(9) a mono- or di-$C_{1-6}$ alkylamino-$C_{1-6}$ alkoxy group,
(10) a mono- or di-$C_{7-16}$ aralkyl phosphate-$C_{1-6}$ alkoxy group,
(11) a 5- to 14-membered aromatic heterocyclic group,
(12) a 5- to 14-membered aromatic heterocyclyloxy group,
(13) a $C_{1-6}$ alkylsulfonyl group, and
(14) a $C_{1-6}$ alkylsulfanyl group;
$R^1$ is
(I) a $C_{6-14}$ aryl group optionally substituted by 1 to 3 substituents selected from
(1) a halogen atom,
(2) an optionally halogenated $C_{1-6}$ alkyl group, and
(3) a $C_{1-6}$ alkoxy group,
(II) a $C_{3-10}$ cycloalkyl group, or
(III) an optionally substituted heterocyclic group represented by any of
(1) a heterocyclic group represented by a formula:

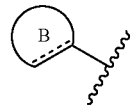
[Formula 5]

which is selected from pyrazolyl, thienyl and pyridyl and optionally substituted by 1 to 3 $C_{1-6}$ alkyl groups, and
(2) a nitrogen-containing heterocyclic group represented by a formula:

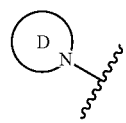
[Formula 6]

which is selected from pyrazol-1-yl, 1,2,3-triazol-1-yl and piperidinyl;
$R^2$ is a hydrogen atom; or
$R^1$ and $R^2$ are bonded to each other to form
(I) a 5- or 6-membered aromatic heterocycle optionally substituted by 1 to 3 substituents selected from
(1) a halogen atom,
(2) an optionally halogenated $C_{1-6}$ alkyl group,
(3) a $C_{7-20}$ alkyl group,
(4) a hydroxy-$C_{1-6}$ alkyl group,
(5) a $C_{1-6}$ alkoxy-$C_{1-6}$ alkyl group,
(6) an optionally halogenated $C_{3-10}$ cycloalkyl-$C_{1-6}$ alkyl group,
(7) a $C_{3-10}$ cycloalkyl group,
(8) a $C_{1-6}$ alkoxy-$C_{7-16}$ aralkyl group,
(9) a 3- to 14-membered non-aromatic heterocyclic group,
(10) an optionally halogenated $C_{1-6}$ alkyl-3- to 14-membered non-aromatic heterocyclic group,
(11) a $C_{1-6}$ alkyl-3- to 14-membered non-aromatic heterocycle-$C_{1-6}$ alkyl group,
(12) a carbamoyl-$C_{1-6}$ alkyl group,
(13) an amino-$C_{1-6}$ alkyl group,

(14) a $C_{1-6}$ alkoxy-carbonylamino-$C_{1-6}$ alkyl group,

(15) a fluorenyl-$C_{1-6}$ alkoxy-carbonylamino-$C_{1-6}$ alkyl group, and

(16) a mono- or di-$C_{1-6}$ alkyl nitrogen-containing heterocycle-$C_{1-6}$ alkyl-nitrogen-containing heterocycle-κ²N (boron halide)-$C_{1-6}$ alkyl-carbonylamino-$C_{1-6}$ alkyl group, or (II) a benzene ring optionally substituted by one halogen atom.

[3] The compound or a salt thereof according to [1] or [2], wherein $R^1$ represents a $C_{6-14}$ aryl group optionally substituted by 1 to 3 substituents selected from (1) a halogen atom, (2) an optionally halogenated $C_{1-6}$ alkyl group and (3) a $C_{1-6}$ alkoxy group, $R^2$ is a hydrogen atom, or $R^1$ and $R^2$ are bonded to each other to form a 5- or 6-membered aromatic heterocycle optionally substituted by 1 to 3 substituents selected from (1) a halogen atom, (2) an optionally halogenated $C_{1-6}$ alkyl group, (3) a $C_{7-20}$ alkyl group, (4) a hydroxy-$C_{1-6}$ alkyl group, (5) a $C_{1-6}$ alkoxy-$C_{1-6}$ alkyl group, (6) an optionally halogenated $C_{3-10}$ cycloalkyl-$C_{1-6}$ alkyl group, (7) a $C_{3-10}$ cycloalkyl group, (8) a $C_{1-6}$ alkoxy-$C_{7-16}$ aralkyl group, (9) a 3- to 14-membered non-aromatic heterocyclic group, (10) an optionally halogenated $C_{1-6}$ alkyl-3- to 14-membered non-aromatic heterocyclic group, (11) a $C_{1-6}$ alkyl-3- to 14-membered non-aromatic heterocycle-$C_{1-6}$ alkyl group, (12) a carbamoyl-$C_{1-6}$ alkyl group, (13) an amino-$C_{1-6}$ alkyl group, (14) a $C_{1-6}$ alkoxy-carbonylamino-$C_{1-6}$ alkyl group, (15) a fluorenyl-$C_{1-6}$ alkoxy-carbonylamino-$C_{1-6}$ alkyl group, and (16) a mono- or di-$C_{1-6}$ alkyl nitrogen-containing heterocycle-$C_{1-6}$ alkyl-nitrogen-containing heterocycle-κ²N (boron halide)-$C_{1-6}$ alkyl-carbonylamino-$C_{1-6}$ alkyl group.

[4] The compound or a salt thereof according to [1] or [3], wherein ring Ar represents an aromatic heterocycle optionally substituted by 1 to 3 substituents selected from (1) a halogen atom, (2) a cyano group, (3) a hydroxy group, (4) an optionally halogenated $C_{1-6}$ alkyl group, (5) a $C_{3-10}$ cycloalkyl group, (6) an optionally halogenated $C_{1-6}$ alkoxy group, (7) a hydroxy-$C_{1-6}$ alkoxy group, (8) a $C_{3-10}$ cycloalkyloxy group, (9) a $C_{1-6}$ alkyl-carbonyl group, (10) a $C_{1-6}$ alkoxy-carbonyl group, (11) an amino group, (12) a mono- or di-$C_{1-6}$ alkylamino group, (13) a mono- or di-$C_{1-6}$ alkyl-carbonylamino group, (14) a mono- or di-$C_{3-10}$ cycloalkyl-carbonylamino group, (15) a 5- to 14-membered aromatic heterocyclic group, and (16) a $C_{1-6}$ alkylsulfonyl group.

[5] The compound or a salt thereof according to any of [1] to [4], wherein (I) ring A represents a heterocycle optionally substituted by 1 to 3 substituents selected from (1) a halogen atom, (2) an optionally halogenated $C_{1-6}$ alkyl group, (3) a $C_{3-10}$ cycloalkyl group, (4) an optionally halogenated $C_{1-6}$ alkoxy group, (5) a hydroxy-$C_{1-6}$ alkoxy group, (6) a $C_{1-6}$ alkoxy-$C_{1-6}$ alkoxy group, (7) a 3- to 14-membered non-aromatic heterocycle-$C_{1-6}$ alkoxy group, (8) a 3- to 14-membered non-aromatic heterocyclyloxy-$C_{1-6}$ alkoxy group, (9) a mono- or di-$C_{1-6}$ alkylamino-$C_{1-6}$ alkoxy group, (10) a mono- or di-$C_{7-16}$ aralkyl phosphate-$C_{1-6}$ alkoxy group, (11) a 5- to 14-membered aromatic heterocyclic group, (12) a 5- to 14-membered aromatic heterocyclyloxy group, (13) a $C_{1-6}$ alkylsulfonyl group, and (14) a $C_{1-6}$ alkylsulfanyl group, $R^1$ represents a $C_{6-14}$ aryl group optionally substituted by 1 to 3 substituents selected from (1) a halogen atom, (2) an optionally halogenated $C_{1-6}$ alkyl group and (3) a $C_{1-6}$ alkoxy group, and $R^2$ represents a hydrogen atom, or (II) ring A represents a $C_{6-14}$ aromatic hydrocarbon ring optionally substituted by 1 to 3 substituents selected from (1) a halogen atom, (2) a cyano group, (3) an optionally halogenated $C_{1-6}$ alkyl group, (4) an optionally halogenated $C_{1-6}$ alkoxy group, and (5) a $C_{1-6}$ alkylsulfonyl group, and $R^1$ and $R^2$ are bonded to each other to form a 5- or 6-membered aromatic heterocycle optionally substituted by 1 to 3 substituents selected from (1) a halogen atom, (2) an optionally halogenated $C_{1-6}$ alkyl group, (3) a $C_{7-20}$ alkyl group, (4) a hydroxy-$C_{1-6}$ alkyl group, (5) a $C_{1-6}$ alkoxy-$C_{1-6}$ alkyl group, (6) an optionally halogenated $C_{3-10}$ cycloalkyl-$C_{1-6}$ alkyl group, (7) a $C_{3-10}$ cycloalkyl group, (8) a $C_{1-6}$ alkoxy-$C_{7-16}$ aralkyl group, (9) a 3- to 14-membered non-aromatic heterocyclic group, (10) an optionally halogenated $C_{1-6}$ alkyl-3- to 14-membered non-aromatic heterocyclic group, (11) a $C_{1-6}$ alkyl-3- to 14-membered non-aromatic heterocycle-$C_{1-6}$ alkyl group, (12) a carbamoyl-$C_{1-6}$ alkyl group, (13) an amino-$C_{1-6}$ alkyl group, (14) a $C_{1-6}$ alkoxy-carbonylamino-$C_{1-6}$ alkyl group, (15) a fluorenyl-$C_{1-6}$ alkoxy-carbonylamino-$C_{1-6}$ alkyl group, and (16) a mono- or di-$C_{1-6}$ alkyl nitrogen-containing heterocycle-$C_{1-6}$ alkyl-nitrogen-containing heterocycle-κ2N (boron halide)-$C_{1-6}$ alkyl-carbonylamino-$C_{1-6}$ alkyl group.

[6] N-((3S,4R)-1-((8-Chloroquinoxalin-6-yl)carbonyl)-3-phenylpiperidin-4-yl)-1-methyl-3-(trifluoromethyl)-1H-pyrazole-5-carboxamide or a salt thereof.

[7] N-((7S)-4-((5,6-Dimethoxypyridin-3-yl)carbonyl)-1-isopropyl-4,5,6,7-tetrahydro-1H-pyrazolo[4,3-b]pyridin-7-yl)-2-(trifluoromethoxy)benzamide or a salt thereof.

[8] A medicament comprising a compound or a salt thereof according to any of [1] to [7].

[9] The medicament according to [8], wherein the medicament is a SPT inhibitor.

[10] The medicament according to [8] or [9], wherein the medicament is a prophylactic or therapeutic agent for cancer.

[11] The medicament according to [8] or [9], wherein the medicament is a prophylactic or therapeutic agent for Niemann-Pick disease.

[12] A method for inhibiting SPT in a mammal, comprising administering an effective amount of a compound or a salt thereof according to any of [1] to [7] to the mammal.

[13] A method for preventing or treating cancer in a mammal, comprising administering an effective amount of a compound or a salt thereof according to any of [1] to [7] to the mammal.

[14] A method for preventing or treating Niemann-Pick disease in a mammal, comprising administering an effective amount of a compound or a salt thereof according to any of [1] to [7] to the mammal.

[15] The compound or a salt thereof according to any of [1] to [7] for use in the prevention or treatment of cancer.

[16] The compound or a salt thereof according to any of [1] to [7] for use in the prevention or treatment of Niemann-Pick disease.

[17] Use of a compound or a salt thereof according to any of [1] to [7] for the production of a prophylactic or therapeutic agent for cancer.

[18] Use of a compound or a salt thereof according to any of [1] to [7] for the production of a prophylactic or therapeutic agent for Niemann-Pick disease.

Advantageous Effects of Invention

The compound or the medicament of the present invention can have an excellent inhibitory effect on SPT. Thus, the compound or the medicament of the present invention can be used as a SPT inhibitor and can be useful as a prophylactic or therapeutic agent for diseases that are probably influenced by SPT, for example, cancer.

DETAILED DESCRIPTION OF THE INVENTION

Hereinafter, the compound of the present invention, a method for producing the same and use of the same will be described in detail.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxycarbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH(C$_3$H$_7$)—, —CH(CH(CH$_3$)$_2$)—, —(CH(CH$_3$))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, —CH$_2$—CH$_2$—CH$_2$—C(CH$_3$)$_2$— and —C(CH$_3$)$_2$—CH$_2$—CH$_2$—CH$_2$—.

In the present specification, examples of the "$C_{2-6}$ alkenylene group" include —CH=CH—, —CH$_2$—CH=CH—, —CH=CH—CH$_2$—, —C(CH$_3$)$_2$—CH=CH—, —CH=CH—C(CH$_3$)$_2$—, —CH$_2$—CH=CH—CH$_2$—, —CH$_2$—CH$_2$—CH=CH—, —CH=CH—CH$_2$—CH$_2$—, —CH=CH—CH=CH—, —CH=CH—CH$_2$—CH$_2$—CH$_2$— and —CH$_2$—CH$_2$—CH$_2$—CH=CH—.

In the present specification, examples of the "$C_{2-6}$ alkynylene group" include —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—, —C≡C—CH$_2$—CH$_2$—, —C≡C—C≡C—, —C≡C—CH$_2$—CH$_2$—CH$_2$— and —CH$_2$—CH$_2$—CH$_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "$C_{7-20}$ alkyl group" include heptyl, octyl, decyl, octadecyl, nonadecyl and icosyl.

Hereinafter, the definition of each symbol in the formula (I) will be described in detail.

The "aromatic heterocycle" in the "optionally further substituted aromatic heterocycle" represented by ring Ar is preferably quinoxaline, pyridine, thiophene, furan, pyrrole, pyrazole, thiazole, isoxazole, pyridine, pyrimidine, pyridazine, benzothiophene, benzofuran, benzimidazole, benzoxazole, benzothiazole, benzotriazole, pyrrolopyridine, pyrazolopyridine, imidazopyrimidine, imidazopyridine, imidazopyridazine, thienopyridine, 1H-indazole, 2H-indazole, quinoline, quinazoline or triazolopyridine.

The "aromatic heterocycle" in the "optionally further substituted aromatic heterocycle" represented by ring Ar is more preferably quinoxaline, thiophene, pyrrole, pyrazole, thiazole, isoxazole, pyridine, pyridazine, benzothiophene, benzofuran, benzimidazole, benzoxazole, benzothiazole, benzotriazole, pyrrolopyridine, pyrazolopyridine, imidazopyrimidine, imidazopyridine, imidazopyridazine, thienopyridine, 1H-indazole, 2H-indazole, quinoline, quinazoline or triazolopyridine.

The "aromatic heterocycle" in the "optionally further substituted aromatic heterocycle" represented by ring Ar is further preferably quinoxaline or imidazopyridine.

In an alternative embodiment, the "aromatic heterocycle" in the "optionally further substituted aromatic heterocycle" represented by ring Ar is preferably pyridine, furan, pyrazole, thiazole, isoxazole, pyrimidine, pyridazine, benzothiophene, benzimidazole, benzothiazole, imidazopyridine or quinoxaline, more preferably pyridine.

The "$C_{6-14}$ aromatic hydrocarbon ring" in the "optionally further substituted $C_{6-14}$ aromatic hydrocarbon ring" represented by ring Ar is preferably benzene or naphthalene, more preferably benzene.

Ring Ar is preferably (I) an aromatic heterocycle (particularly, quinoxaline, pyridine, thiophene, furan, pyrrole, pyrazole, thiazole, isoxazole, pyridine, pyrimidine, pyridazine, benzothiophene, benzofuran, benzimidazole, benzoxazole, benzothiazole, benzotriazole, pyrrolopyridine, pyrazolopyridine, imidazopyrimidine, imidazopyridine, imidazopyridazine, thienopyridine, 1H-indazole, 2H-indazole, quinoline, quinazoline, triazolopyridine) optionally substituted by 1 to 3 substituents selected from (1) a halogen atom (particularly, a chlorine atom, a fluorine atom, a bromine atom), (2) a cyano group, (3) a hydroxy group, (4) an optionally halogenated $C_{1-6}$ alkyl group (particularly, methyl, difluoromethyl, trifluoromethyl), (5) a $C_{3-10}$ cycloalkyl group (particularly, cyclopropyl), (6) an optionally halogenated $C_{1-6}$ alkoxy group (particularly, methoxy, ($^{2}H_3$) methoxy, difluoromethoxy, trifluoromethoxy, ethoxy, 2,2-difluoroethoxy, 2,2,2-trifluoroethoxy, isopropoxy), (7) a hydroxy-$C_{1-6}$ alkoxy group (particularly, 2-hydroxyethoxy), (8) a $C_{3-10}$ cycloalkyloxy group (particularly, cyclohexyloxy), (9) a $C_{1-6}$ alkyl-carbonyl group (particularly, acetyl),

(10) a $C_{1-6}$ alkoxy-carbonyl group (particularly, methoxycarbonyl, ethoxycarbonyl),

(11) an amino group,

(12) a mono- or di-$C_{1-6}$ alkylamino group (particularly, methylamino, dimethylamino),

(13) a mono- or di-$C_{1-6}$ alkyl-carbonylamino group (particularly, acetylamino),

(14) a mono- or di-$C_{3-10}$ cycloalkyl-carbonylamino group (particularly, cyclopropylcarbonylamino, di(cyclopropylcarbonyl)amino),

(15) a 5- to 14-membered aromatic heterocyclic group (particularly, pyrazolyl), and

(16) a $C_{1-6}$ alkylsulfonyl group (particularly, isopropylsulfonyl), or (II) a $C_{6-14}$ aromatic hydrocarbon ring (particularly, benzene, naphthalene) optionally substituted by 1 to 3 (particularly, 1) substituents selected from (1) a halogen atom (particularly, a chlorine atom, a fluorine atom, a bromine atom), (2) a cyano group, (3) an optionally halogenated $C_{1-6}$ alkyl group (particularly, methyl, difluoromethyl, trifluoromethyl), (4) a $C_{3-10}$ cycloalkyl group (particularly, cyclopropyl), (5) an optionally halogenated $C_{1-6}$ alkoxy group (particularly, methoxy, trifluoromethoxy, ethoxy, isopropoxy), (6) a mono- or di-$C_{1-6}$ alkylamino group (particularly, dimethylamino), (7) a $C_{1-6}$ alkyl-5- to 14-membered aromatic heterocyclic group (particularly, methyl-1,2,4-oxadiazolyl), and (8) a $C_{1-6}$ alkylsulfonyl group (particularly, methylsulfonyl).

Ring Ar is more preferably
(I) an aromatic heterocycle (particularly, quinoxaline, thiophene, pyrrole, pyrazole, thiazole, isoxazole, pyridine, pyridazine, benzothiophene, benzofuran, benzimidazole, benzoxazole, benzothiazole, benzotriazole, pyrrolopyridine, pyrazolopyridine, imidazopyrimidine, imidazopyridine, imidazopyridazine, thienopyridine, 1H-indazole, 2H-indazole, quinoline, quinazoline, triazolopyridine) optionally substituted by 1 to 3 substituents selected from
  (1) a halogen atom (particularly, a chlorine atom, a fluorine atom, a bromine atom),
  (2) a cyano group,
  (3) a hydroxy group,
  (4) a $C_{1-6}$ alkyl group (particularly, methyl),
  (5) a $C_{3-10}$ cycloalkyl group (particularly, cyclopropyl),
  (6) an optionally halogenated $C_{1-6}$ alkoxy group (particularly, methoxy, ($^2H_3$) methoxy, 2,2-difluoroethoxy, 2,2,2-trifluoroethoxy),
  (7) a $C_{1-6}$ alkyl-carbonyl group (particularly, acetyl),
  (8) a $C_{1-6}$ alkoxy-carbonyl group (particularly, methoxycarbonyl, ethoxycarbonyl),
  (9) an amino group,
  (10) a mono- or di-$C_{1-6}$ alkylamino group (particularly, dimethylamino),
  (11) a mono- or di-$C_{1-6}$ alkyl-carbonylamino group (particularly, acetylamino),
  (12) a mono- or di-$C_{3-10}$ cycloalkyl-carbonylamino group (particularly, cyclopropylcarbonylamino, di(cyclopropylcarbonyl)amino),
  (13) a 5- to 14-membered aromatic heterocyclic group (particularly, pyrazolyl), and
  (14) a $C_{1-6}$ alkylsulfonyl group (particularly, isopropylsulfonyl),
or
(II) a $C_{6-14}$ aromatic hydrocarbon ring (particularly, benzene, naphthalene) optionally substituted by 1 to 3 (particularly, 1) substituents selected from
  (1) a halogen atom (particularly, a chlorine atom, a fluorine atom, a bromine atom),
  (2) a cyano group,
  (3) an optionally halogenated $C_{1-6}$ alkyl group (particularly, methyl, difluoromethyl),
  (4) a $C_{3-10}$ cycloalkyl group (particularly, cyclopropyl),
  (5) an optionally halogenated $C_{1-6}$ alkoxy group (particularly, methoxy, trifluoromethoxy, ethoxy), and
  (6) a $C_{1-6}$ alkylsulfonyl group (particularly, methylsulfonyl).

Ring Ar is further preferably an 8- to 14-membered fused bicyclic aromatic heterocycle (particularly, quinoxaline, imidazopyridine) optionally substituted by 1 to 3 substituents selected from
(1) a halogen atom (particularly, a chlorine atom),
(2) a $C_{1-6}$ alkyl group (particularly, methyl), and
(3) a $C_{1-6}$ alkoxy group (particularly, methoxy).

The "$C_{6-14}$ aromatic hydrocarbon ring" in the "optionally further substituted $C_{6-14}$ aromatic hydrocarbon ring" represented by ring A is preferably benzene or naphthalene, particularly preferably benzene.

The "heterocycle" in the "optionally further substituted heterocycle" represented by ring A is preferably thiophene, furan, pyrazole, thiazole, pyridine, oxazole, isoxazole, imidazole, pyrazine, benzofuran, 1,3-benzodioxole, 2,3-dihydrobenzofuran, dihydrooxazole or dihydropyridine.

The "heterocycle" in the "optionally further substituted heterocycle" represented by ring A is more preferably pyrazole, pyridine, oxazole, isoxazole, thiazole, imidazole or pyrazine, further preferably pyridine or pyrazole.

In an alternative embodiment, the "heterocycle" in the "optionally further substituted heterocycle" represented by ring A is more preferably thiophene, furan, pyrazole, thiazole, pyridine, benzofuran, 1,3-benzodioxole or 2,3-dihydrobenzofuran.

Ring A is preferably
(I) a $C_{6-14}$ aromatic hydrocarbon ring (particularly, benzene, naphthalene) optionally substituted by 1 to 3 (particularly, 1 or 2) substituents selected from
  (1) a halogen atom (particularly, a fluorine atom, a chlorine atom),
  (2) a cyano group,
  (3) an optionally halogenated $C_{1-6}$ alkyl group (particularly, methyl, trifluoromethyl),
  (4) an optionally halogenated $C_{1-6}$ alkoxy group (particularly, methoxy, difluoromethoxy, trifluoromethoxy), and
  (5) a $C_{1-6}$ alkylsulfonyl group (particularly, methylsulfonyl),
or
(II) a heterocycle (particularly, thiophene, furan, pyrazole, thiazole, pyridine, oxazole, isoxazole, imidazole, pyrazine, benzofuran, 1,3-benzodioxole, 2,3-dihydrobenzofuran, dihydrooxazole, dihydropyridine) optionally substituted by 1 to 3 substituents selected from
  (1) a halogen atom (particularly, a chlorine atom, a bromine atom),
  (2) an oxo group,
  (3) an optionally halogenated $C_{1-6}$ alkyl group (particularly, methyl, difluoromethyl, 2,2-difluoroethyl, trifluoromethyl, isopropyl, tert-butyl),
  (4) a $C_{3-10}$ cycloalkyl group (particularly, cyclopropyl),
  (5) an optionally halogenated $C_{1-6}$ alkoxy group (particularly, methoxy, difluoromethoxy, ethoxy, 2,2-difluoroethoxy, 2,2,2-trifluoroethoxy),
  (6) a hydroxy-$C_{1-6}$ alkoxy group (particularly, 2-hydroxyethoxy),
  (7) a $C_{1-6}$ alkoxy-$C_{1-6}$ alkoxy group (particularly, 2-methoxyethoxy),
  (8) a 3- to 14-membered non-aromatic heterocycle-$C_{1-6}$ alkoxy group (particularly, morpholinylethoxy, morpholinylpropoxy),
  (9) a 3- to 14-membered non-aromatic heterocyclyloxy-$C_{1-6}$ alkoxy group (e.g., tetrahydropyranyloxyethoxy),
  (10) a mono- or di-$C_{1-6}$ alkylamino-$C_{1-6}$ alkoxy group (particularly, dimethylamino-ethoxy, dimethylaminopropoxy),
  (11) a mono- or di-$C_{7-16}$ aralkylphosphate-$C_{1-6}$ alkoxy group (particularly, dibenzylphosphateethoxy),
  (12) a 5- to 14-membered aromatic heterocyclic group (particularly, pyrazolyl),
  (13) a 5- to 14-membered aromatic heterocyclyloxy group (particularly, triazolopyridinyloxy),
  (14) a $C_{1-6}$ alkylsulfonyl group (particularly, methylsulfonyl), and
  (15) a $C_{1-6}$ alkylsulfanyl group (particularly, methylsulfanyl).

Ring A is more preferably
(I) a $C_{6-14}$ aromatic hydrocarbon ring (particularly, benzene) optionally substituted by 1 to 3 (particularly, 1) substituents selected from
  (1) a halogen atom (particularly, a chlorine atom),
  (2) a cyano group,
  (3) an optionally halogenated $C_{1-6}$ alkyl group (particularly, trifluoromethyl),
  (4) an optionally halogenated $C_{1-6}$ alkoxy group (particularly, difluoromethoxy, trifluoromethoxy), and (5) a $C_{1-6}$ alkylsulfonyl group (particularly, methylsulfonyl), (II) a 5- or 6-membered monocyclic aromatic heterocycle (particularly, pyrazole, pyridine, oxazole, isoxazole, thiazole, imidazole, pyrazine) optionally substituted by 1 to 3 substituents selected from (1) a halogen atom (particularly, a chlorine atom, a bromine atom), (2) an optionally halogenated $C_{1-6}$ alkyl group (particularly, methyl, difluoromethyl, 2,2-difluoroethyl, trifluoromethyl, isopropyl, tert-butyl), (3) a $C_{3-10}$ cycloalkyl group (particularly, cyclopropyl), (4) an optionally halogenated $C_{1-6}$ alkoxy group (particularly, methoxy, difluoromethoxy, ethoxy, 2,2-difluoroethoxy, 2,2,2-trifluoroethoxy), (5) a hydroxy-$C_{1-6}$ alkoxy group (particularly, 2-hydroxyethoxy), (6) a $C_{1-6}$ alkoxy-$C_{1-6}$ alkoxy group (particularly, 2-methoxyethoxy), (7) a 3- to 14-membered non-aromatic heterocycle-$C_{1-6}$ alkoxy group (particularly, morpholinylethoxy, morpholinylpropoxy), (8) a 3- to 14-membered non-aromatic heterocyclyloxy-$C_{1-6}$ alkoxy group (e.g., tetrahydropyranyloxyethoxy), (9) a mono- or di-$C_{1-6}$ alkylamino-$C_{1-6}$ alkoxy group (particularly, dimethylamino-ethoxy, dimethylaminopropoxy),

(10) a mono- or di-$C_{7-16}$ aralkylphosphate-$C_{1-6}$ alkoxy group (particularly, dibenzylphosphateethoxy),

(11) a 5- to 14-membered aromatic heterocyclic group (particularly, pyrazolyl),

(12) a 5- to 14-membered aromatic heterocyclyloxy group (particularly, triazolopyridinyloxy),

(13) a $C_{1-6}$ alkylsulfonyl group (particularly, methylsulfonyl), and

(14) a $C_{1-6}$ alkylsulfanyl group (particularly, methylsulfanyl), or (III) a 3- to 8-membered monocyclic non-aromatic heterocycle (particularly, dihydrooxazole, dihydropyridine) optionally substituted by 1 to 3 (particularly, 1 or 2) substituents selected from (1) a $C_{1-6}$ alkyl group (particularly, methyl), and (2) an oxo group.

Ring A is further preferably a 5- or 6-membered monocyclic aromatic heterocycle (particularly, pyridine or pyrazole) optionally substituted by 1 to 3 substituents selected from a halogen atom (particularly, a chlorine atom), an optionally halogenated $C_{1-6}$ alkyl group (particularly, methyl, trifluoromethyl), and an optionally halogenated $C_{1-6}$ alkoxy group (particularly, difluoromethoxy, ethoxy).

$R^1$ is preferably (I) a $C_{6-14}$ aryl group (particularly, phenyl) optionally substituted by 1 to 3 (particularly, 1 or 2) substituents selected from (1) a halogen atom (particularly, a fluorine atom, a chlorine atom), (2) an optionally halogenated $C_{1-6}$ alkyl group (particularly, methyl, trifluoromethyl), and (3) a $C_{1-6}$ alkoxy group (particularly, methoxy), (II) a $C_{3-10}$ cycloalkyl group (particularly, cyclopropyl, cyclopentyl, cyclohexyl), or (III) an optionally substituted heterocyclic group represented by any of (1) a heterocyclic group represented by a formula:

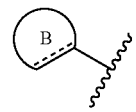

[Formula 5]

which is selected from pyrazolyl (particularly, pyrazol-3-yl, pyrazol-4-yl), thienyl (particularly, thiophen-2-yl) and pyridyl (particularly, pyridin-3-yl, pyridin-4-yl) and optionally substituted by 1 to 3 $C_{1-6}$ alkyl groups (particularly, methyl), and (2) a nitrogen-containing heterocyclic group represented by a formula:

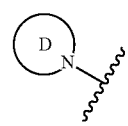

[Formula 6]

which is selected from pyrazol-1-yl, 1,2,3-triazol-1-yl and piperidinyl.

$R^1$ is more preferably phenyl optionally substituted by 1 to 3 (particularly, 1) halogen atoms (particularly, a fluorine atom).

$R^2$ is preferably a hydrogen atom.

In an alternative embodiment, ring Ar is more preferably (I) an aromatic heterocycle (particularly, pyridine, furan, pyrazole, thiazole, isoxazole, pyrimidine, pyridazine, benzothiophene, benzimidazole, benzothiazole, imidazopyridine, quinoxaline) optionally substituted by 1 to 3 (particularly, 1 or 2) substituents selected from (1) a halogen atom (particularly, a chlorine atom), (2) an optionally halogenated $C_{1-6}$ alkoxy group (particularly, methoxy, difluoromethoxy, ethoxy, isopropoxy), (3) a hydroxy-$C_{1-6}$ alkoxy group (particularly, 2-hydroxyethoxy), (4) a $C_{3-10}$ cycloalkyloxy group (particularly, cyclohexyloxy), (5) an optionally halogenated $C_{1-6}$ alkyl group (particularly, methyl, trifluoromethyl), and (6) a mono- or di-$C_{1-6}$ alkylamino group (particularly, methylamino, dimethylamino), or (II) a $C_{6-14}$ aromatic hydrocarbon ring (particularly, benzene) optionally substituted by 1 to 3 substituents selected from (1) a halogen atom (particularly, a fluorine atom, a chlorine atom), (2) a cyano group, (3) an optionally halogenated $C_{1-6}$ alkyl group (particularly, trifluoromethyl), (4) an optionally halogenated $C_{1-6}$ alkoxy group (particularly, methoxy, trifluoromethoxy, ethoxy, isopropoxy), (5) a mono- or di-$C_{1-6}$ alkylamino group (particularly, dimethylamino), (6) a $C_{1-6}$ alkyl-5- to 14-membered aromatic heterocyclic group (particularly, methyl-1,2,4-oxadiazolyl), and (7) a $C_{1-6}$ alkylsulfonyl group (particularly, methylsulfonyl).

In an alternative embodiment, ring Ar is further preferably
(I) a 5- or 6-membered monocyclic aromatic heterocycle (particularly, pyridine) optionally substituted by 1 to 3 (particularly, 2) substituents selected from
  (1) a halogen atom (particularly, a chlorine atom), and
  (2) a $C_{1-6}$ alkoxy group (particularly, methoxy),
or
(II) a $C_{6-14}$ aromatic hydrocarbon ring (particularly, benzene) optionally substituted by 1 to 3 (particularly, 2) substituents selected from a $C_{1-6}$ alkoxy group (particularly, methoxy).

In an alternative embodiment, ring A is more preferably
(I) a $C_{6-14}$ aromatic hydrocarbon ring (preferably benzene, naphthalene) optionally substituted by 1 to 3 (particularly, 1 or 2) substituents selected from
  (1) a halogen atom (particularly, a fluorine atom, a chlorine atom),
  (2) a cyano group,
  (3) an optionally halogenated $C_{1-6}$ alkyl group (particularly, methyl, trifluoromethyl),
  (4) an optionally halogenated $C_{1-6}$ alkoxy group (particularly, methoxy, difluoromethoxy, trifluoromethoxy), and
  (5) a $C_{1-6}$ alkylsulfonyl group (particularly, methylsulfonyl),
or
(II) a heterocycle (particularly, thiophene, furan, pyrazole, thiazole, pyridine, benzofuran, 1,3-benzodioxole, 2,3-dihydrobenzofuran) optionally substituted by 1 to 3 (particularly, 1 or 2) substituents selected from
  (1) a halogen atom (particularly, a chlorine atom), and
  (2) an optionally halogenated $C_{1-6}$ alkyl group (particularly, methyl, trifluoromethyl).

In an alternative embodiment, ring A is further preferably a $C_{6-14}$ aromatic hydrocarbon ring (particularly, benzene) optionally substituted by 1 to 3 (particularly, 1 or 2) substituents selected from
(1) a halogen atom (particularly, a chlorine atom),
(2) an optionally halogenated $C_{1-6}$ alkyl group (particularly, trifluoromethyl), and
(3) an optionally halogenated $C_{1-6}$ alkoxy group (particularly, trifluoromethoxy).

In an alternative embodiment, $R^1$ and $R^2$ are more preferably bonded to each other to form
(I) a 5- or 6-membered aromatic heterocycle (particularly, pyrazole, imidazole, isothiazole, isoxazole, pyridine) optionally substituted by 1 to 3 (particularly, 1 or 2) substituents selected from
  (1) a halogen atom (particularly, a chlorine atom, a bromine atom),
  (2) an optionally halogenated $C_{1-6}$ alkyl group (particularly, methyl, ethyl, 2,2-difluoroethyl, 2,2,2-trifluoroethyl, propyl, isopropyl, butyl, isobutyl, 2,2-dimethylpropyl),
  (3) a $C_{7-20}$ alkyl group (particularly, octadecyl),
  (4) a hydroxy-$C_{1-6}$ alkyl group (particularly, 3-hydroxy-3-methylbutyl),
  (5) a $C_{1-6}$ alkoxy-$C_{1-6}$ alkyl group (particularly, 2-methoxyethyl),
  (6) an optionally halogenated $C_{3-10}$ cycloalkyl-$C_{1-6}$ alkyl group (particularly, cyclopropylmethyl, 1-fluorocyclopropylmethyl),
  (7) a $C_{3-10}$ cycloalkyl group (particularly, cyclobutyl, cyclopentyl),
  (8) a $C_{1-6}$ alkoxy-$C_{7-16}$ aralkyl group (particularly, methoxybenzyl),
  (9) a 3- to 14-membered non-aromatic heterocyclic group (particularly, tetrahydropyranyl),
  (10) an optionally halogenated $C_{1-6}$ alkyl-3- to 14-membered non-aromatic heterocyclic group (particularly, 2,2,2-trifluoroethylazetidinyl),
  (11) a $C_{1-6}$ alkyl-3- to 14-membered non-aromatic heterocycle-$C_{1-6}$ alkyl group (particularly, methyloxetanylmethyl),
  (12) a carbamoyl-$C_{1-6}$ alkyl group (particularly, carbamoylmethyl),
  (13) an amino-$C_{1-6}$ alkyl group (particularly, aminopentyl),
  (14) a $C_{1-6}$ alkoxy-carbonylamino-$C_{1-6}$ alkyl group (particularly, tert-butoxycarbonylaminopentyl),
  (15) a fluorenyl-$C_{1-6}$ alkoxy-carbonylamino-$C_{1-6}$ alkyl group (particularly, fluorenylmethoxycarbonylaminopentyl), and
  (16) a mono- or di-$C_{1-6}$ alkyl nitrogen-containing heterocycle-$C_{1-6}$ alkyl-nitrogen-containing heterocycle-$\kappa^2$N (boron halide)-$C_{1-6}$ alkyl-carbonylamino-$C_{1-6}$ alkyl group (particularly, dimethylpyrrolyl-$\kappa$N-methylene-pyrrolyl-$\kappa$N (difluoroboron)-propanoylaminopentyl),
or
(II) a benzene ring optionally substituted by one halogen atom (particularly, a chlorine atom).

In an alternative embodiment, $R^1$ and $R^2$ are further preferably bonded to each other to form a 5- or 6-membered monocyclic aromatic heterocycle (particularly, pyrazole) optionally substituted by 1 to 3 (particularly, 1) substituents selected from
(1) an optionally halogenated $C_{1-6}$ alkyl group (particularly, methyl, ethyl, 2,2-difluoroethyl, isopropyl).

Preferable specific examples of the compound (I) include the following: Compound (AB):
Compound (I) wherein
ring Ar is
(I) an aromatic heterocycle (particularly, quinoxaline, pyridine, thiophene, furan, pyrrole, pyrazole, thiazole, isoxazole, pyridine, pyrimidine, pyridazine, benzothiophene, benzofuran, benzimidazole, benzoxazole, benzothiazole, benzotriazole, pyrrolopyridine, pyrazolopyridine, imidazopyrimidine, imidazopyridine, imidazopyridazine, thienopyridine, 1H-indazole, 2H-indazole, quinoline, quinazoline, triazolopyridine) optionally substituted by 1 to 3 substituents selected from
  (1) a halogen atom (particularly, a chlorine atom, a fluorine atom, a bromine atom),
  (2) a cyano group,
  (3) a hydroxy group,
  (4) an optionally halogenated $C_{1-6}$ alkyl group (particularly, methyl, trifluoromethyl),
  (5) a $C_{3-10}$ cycloalkyl group (particularly, cyclopropyl),
  (6) an optionally halogenated $C_{1-6}$ alkoxy group (particularly, methoxy, ($^2H_3$) methoxy, difluoromethoxy, ethoxy, 2,2-difluoroethoxy, 2,2,2-trifluoroethoxy, isopropoxy),
  (7) a hydroxy-$C_{1-6}$ alkoxy group (particularly, 2-hydroxyethoxy),
  (8) a $C_{3-10}$ cycloalkyloxy group (particularly, cyclohexyloxy),
  (9) a $C_{1-6}$ alkyl-carbonyl group (particularly, acetyl),
  (10) a $C_{1-6}$ alkoxy-carbonyl group (particularly, methoxycarbonyl, ethoxycarbonyl),
  (11) an amino group,
  (12) a mono- or di-$C_{1-6}$ alkylamino group (particularly, methylamino, dimethylamino),
  (13) a mono- or di-$C_{1-6}$ alkyl-carbonylamino group (particularly, acetylamino),

(14) a mono- or di-$C_{3-10}$ cycloalkyl-carbonylamino group (particularly, cyclopropylcarbonylamino, di(cyclopropylcarbonyl)amino),

(15) a 5- to 14-membered aromatic heterocyclic group (particularly, pyrazolyl), and

(16) a $C_{1-6}$ alkylsulfonyl group (particularly, isopropylsulfonyl), or (II) a $C_{6-14}$ aromatic hydrocarbon ring (particularly, benzene, naphthalene) optionally substituted by 1 to 3 (particularly, 1) substituents selected from (1) a halogen atom (particularly, a chlorine atom, a fluorine atom, a bromine atom), (2) a cyano group, (3) an optionally halogenated $C_{1-6}$ alkyl group (particularly, methyl, difluoromethyl, trifluoromethyl), (4) a $C_{3-10}$ cycloalkyl group (particularly, cyclopropyl), (5) an optionally halogenated $C_{1-6}$ alkoxy group (particularly, methoxy, trifluoromethoxy, ethoxy, isopropoxy), (6) a mono- or di-$C_{1-6}$ alkylamino group (particularly, dimethylamino), (7) a $C_{1-6}$ alkyl-5- to 14-membered aromatic heterocyclic group (particularly, methyl-1,2,4-oxadiazolyl), and (8) a $C_{1-6}$ alkylsulfonyl group (particularly, methylsulfonyl);

ring A is (I) a $C_{6-14}$ aromatic hydrocarbon ring (particularly, benzene, naphthalene) optionally substituted by 1 to 3 (particularly, 1 or 2) substituents selected from (1) a halogen atom (particularly, a fluorine atom, a chlorine atom), (2) a cyano group, (3) an optionally halogenated $C_{1-6}$ alkyl group (particularly, methyl, trifluoromethyl), (4) an optionally halogenated $C_{1-6}$ alkoxy group (particularly, methoxy, difluoromethoxy, trifluoromethoxy), and (5) a $C_{1-6}$ alkylsulfonyl group (particularly, methylsulfonyl), or (II) a heterocycle (particularly, thiophene, furan, pyrazole, thiazole, pyridine, oxazole, isoxazole, imidazole, pyrazine, benzofuran, 1,3-benzodioxole, 2,3-dihydrobenzofuran, dihydrooxazole, dihydropyridine) optionally substituted by 1 to 3 substituents selected from (1) a halogen atom (particularly, a chlorine atom, a bromine atom), (2) an optionally halogenated $C_{1-6}$ alkyl group (particularly, methyl, difluoromethyl, 2,2-difluoroethyl, trifluoromethyl, isopropyl, tert-butyl), (3) a $C_{3-10}$ cycloalkyl group (particularly, cyclopropyl), (4) an optionally halogenated $C_{1-6}$ alkoxy group (particularly, methoxy, difluoromethoxy, ethoxy, 2,2-difluoroethoxy, 2,2,2-trifluoroethoxy), (5) a hydroxy-$C_{1-6}$ alkoxy group (particularly, 2-hydroxyethoxy), (6) a $C_{1-6}$ alkoxy-$C_{1-6}$ alkoxy group (particularly, 2-methoxyethoxy), (7) a 3- to 14-membered non-aromatic heterocycle-$C_{1-6}$ alkoxy group (particularly, morpholinylethoxy, morpholinylpropoxy), (8) a 3- to 14-membered non-aromatic heterocyclyloxy-$C_{1-6}$ alkoxy group (e.g., tetrahydropyranyloxyethoxy), (9) a mono- or di-$C_{1-6}$ alkylamino-$C_{1-6}$ alkoxy group (particularly, dimethylamino-ethoxy, dimethylaminopropoxy),

(10) a mono- or di-$C_{7-16}$ aralkylphosphate-$C_{1-6}$ alkoxy group (particularly, dibenzylphospateethoxy),

(11) a 5- to 14-membered aromatic heterocyclic group (particularly, pyrazolyl),

(12) a 5- to 14-membered aromatic heterocyclyloxy group (particularly, triazolopyridinyloxy),

(13) a $C_{1-6}$ alkylsulfonyl group (particularly, methylsulfonyl), and

(14) a $C_{1-6}$ alkylsulfanyl group (particularly, methylsulfanyl);

$R^1$ is (I) a $C_{6-14}$ aryl group (particularly, phenyl) optionally substituted by 1 to 3 (particularly, 1 or 2) substituents selected from (1) a halogen atom (particularly, a fluorine atom, a chlorine atom), (2) an optionally halogenated $C_{1-6}$ alkyl group (particularly, methyl, trifluoromethyl), and (3) a $C_{1-6}$ alkoxy group (particularly, methoxy), (II) a $C_{3-10}$ cycloalkyl group (particularly, cyclopropyl, cyclopentyl, cyclohexyl), or (III) an optionally substituted heterocyclic group represented by any of (1) a heterocyclic group represented by a formula:

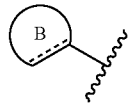

[Formula 7]

which is selected from pyrazolyl (particularly, pyrazol-3-yl, pyrazol-4-yl), thienyl (particularly, thiophen-2-yl) and pyridyl (particularly, pyridin-3-yl, pyridin-4-yl) and optionally substituted by 1 to 3 $C_{1-6}$ alkyl groups (particularly, methyl), and (2) a nitrogen-containing heterocyclic group represented by a formula:

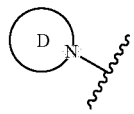

[Formula 8]

which is selected from pyrazol-1-yl, 1,2,3-triazol-1-yl and piperidinyl;

$R^2$ is a hydrogen atom; or $R^1$ and $R^2$ are bonded to each other to form (I) a 5- or 6-membered aromatic heterocycle (particularly, pyrazole, imidazole, isothiazole, isoxazole, pyridine) optionally substituted by 1 to 3 (particularly, 1 or 2) substituents selected from (1) a halogen atom (particularly, a chlorine atom, a bromine atom), (2) an optionally halogenated $C_{1-6}$ alkyl group (particularly, methyl, ethyl, 2,2-difluoroethyl, 2,2,2-trifluoroethyl, propyl, isopropyl, butyl, isobutyl, 2,2-dimethylpropyl), (3) a $C_{7-20}$ alkyl group (particularly, octadecyl), (4) a hydroxy-$C_{1-6}$ alkyl group (particularly, 3-hydroxy-3-methylbutyl), (5) a $C_{1-6}$ alkoxy-$C_{1-6}$ alkyl group (particularly, 2-methoxyethyl), (6) an optionally halogenated $C_{3-10}$ cycloalkyl-$C_{1-6}$ alkyl group (particularly, cyclopropylmethyl, 1-fluorocyclopropylmethyl), (7) a $C_{3-10}$ cycloalkyl group (particularly, cyclobutyl, cyclopentyl), (8) a $C_{1-6}$ alkoxy-$C_{7-16}$ aralkyl group (particularly, methoxybenzyl), (9) a 3- to 14-membered non-aromatic heterocyclic group (particularly, tetrahydropyranyl),

(10) an optionally halogenated $C_{1-6}$ alkyl-3- to 14-membered non-aromatic heterocyclic group (particularly, 2,2,2-trifluoroethylazetidinyl),

(11) a $C_{1-6}$ alkyl-3- to 14-membered non-aromatic heterocycle-$C_{1-6}$ alkyl group (particularly, methyloxetanylmethyl),

(12) a carbamoyl-$C_{1-6}$ alkyl group (particularly, carbamoylmethyl),

(13) an amino-$C_{1-6}$ alkyl group (particularly, aminopentyl),

(14) a $C_{1-6}$ alkoxy-carbonylamino-$C_{1-6}$ alkyl group (particularly, tert-butoxycarbonylaminopentyl),

(15) a fluorenyl-$C_{1-6}$ alkoxy-carbonylamino-$C_{1-6}$ alkyl group (particularly, fluorenylmethoxycarbonylaminopentyl), and

(16) a mono- or di-$C_{1-6}$ alkyl nitrogen-containing heterocycle-$C_{1-6}$ alkyl-nitrogen-containing heterocycle-$\kappa^2 N$ (boron halide)-$C_{1-6}$ alkyl-carbonylamino-$C_{1-6}$ alkyl group (particularly, dimethylpyrrolyl-$\kappa N$-methylene-pyrrolyl-$\kappa N$ (difluoroboron)-propanoylaminopentyl), or (II) a benzene ring optionally substituted by one halogen atom (particularly, a chlorine atom).

Compound (B-1):

Compound (AB) wherein ring Ar is (I) an aromatic heterocycle (particularly, quinoxaline, thiophene, pyrrole, pyrazole, thiazole, isoxazole, pyridine, pyridazine, benzothiophene, benzofuran, benzimidazole, benzoxazole, benzothiazole, benzotriazole, pyrrolopyridine, pyrazolopyridine, imidazopyrimidine, imidazopyridine, imidazopyridazine, thienopyridine, 1H-indazole, 2H-indazole, quinoline, quinazoline, triazolopyridine) optionally substituted by 1 to 3 substituents selected from (1) a halogen atom (particularly, a chlorine atom, a fluorine atom, a bromine atom), (2) a cyano group, (3) a hydroxy group, (4) a $C_{1-6}$ alkyl group (particularly, methyl), (5) a $C_{3-10}$ cycloalkyl group (particularly, cyclopropyl), (6) an optionally halogenated $C_{1-6}$ alkoxy group (particularly, methoxy, ($^2H_3$) methoxy, 2,2-difluoroethoxy, 2,2,2-trifluoroethoxy), (7) a $C_{1-6}$ alkyl-carbonyl group (particularly, acetyl), (8) a $C_{1-6}$ alkoxy-carbonyl group (particularly, methoxycarbonyl, ethoxycarbonyl), (9) an amino group,

(10) a mono- or di-$C_{1-6}$ alkylamino group (particularly, dimethylamino),

(11) a mono- or di-$C_{1-6}$ alkyl-carbonylamino group (particularly, acetylamino),

(12) a mono- or di-$C_{3-10}$ cycloalkyl-carbonylamino group (particularly, cyclopropylcarbonylamino, di(cyclopropylcarbonyl)amino),

(13) a 5- to 14-membered aromatic heterocyclic group (particularly, pyrazolyl), and

(14) a $C_{1-6}$ alkylsulfonyl group (particularly, isopropylsulfonyl), or (II) a $C_{6-14}$ aromatic hydrocarbon ring (particularly, benzene, naphthalene) optionally substituted by 1 to 3 (particularly, 1) substituents selected from (1) a halogen atom (particularly, a chlorine atom, a fluorine atom, a bromine atom), (2) a cyano group, (3) an optionally halogenated $C_{1-6}$ alkyl group (particularly, methyl, difluoromethyl), (4) a $C_{3-10}$ cycloalkyl group (particularly, cyclopropyl), (5) an optionally halogenated $C_{1-6}$ alkoxy group (particularly, methoxy, trifluoromethoxy, ethoxy), and (6) a $C_{1-6}$ alkylsulfonyl group (particularly, methylsulfonyl); ring A is (I) a $C_{6-14}$ aromatic hydrocarbon ring (particularly, benzene) optionally substituted by 1 to 3 (particularly, 1) substituents selected from (1) a halogen atom (particularly, a chlorine atom), (2) a cyano group, (3) an optionally halogenated $C_{1-6}$ alkyl group (particularly, trifluoromethyl), (4) an optionally halogenated $C_{1-6}$ alkoxy group (particularly, difluoromethoxy, trifluoromethoxy), and (5) a $C_{1-6}$ alkylsulfonyl group (particularly, methylsulfonyl), (II) a 5- or 6-membered monocyclic aromatic heterocycle (particularly, pyrazole, pyridine, oxazole, isoxazole, thiazole, imidazole, pyrazine) optionally substituted by 1 to 3 substituents selected from (1) a halogen atom (particularly, a chlorine atom, a bromine atom), (2) an optionally halogenated $C_{1-6}$ alkyl group (particularly, methyl, difluoromethyl, 2,2-difluoroethyl, trifluoromethyl, isopropyl, tert-butyl), (3) a $C_{3-10}$ cycloalkyl group (particularly, cyclopropyl), (4) an optionally halogenated $C_{1-6}$ alkoxy group (particularly, methoxy, difluoromethoxy, ethoxy, 2,2-difluoroethoxy, 2,2,2-trifluoroethoxy), (5) a hydroxy-$C_{1-6}$ alkoxy group (particularly, 2-hydroxyethoxy), (6) a $C_{1-6}$ alkoxy-$C_{1-6}$ alkoxy group (particularly, 2-methoxyethoxy), (7) a 3- to 14-membered non-aromatic heterocycle-$C_{1-6}$ alkoxy group (particularly, morpholinylethoxy, morpholinylpropoxy), (8) a 3- to 14-membered non-aromatic heterocyclyloxy-$C_{1-6}$ alkoxy group (e.g., tetrahydropyranyloxyethoxy), (9) a mono- or di-$C_{1-6}$ alkylamino-$C_{1-6}$ alkoxy group (particularly, dimethylamino-ethoxy, dimethylaminopropoxy),

(10) a mono- or di-$C_{7-16}$ aralkylphosphate-$C_{1-6}$ alkoxy group (particularly, dibenzylphosphateethoxy),

(11) a 5- to 14-membered aromatic heterocyclic group (particularly, pyrazolyl),

(12) a 5- to 14-membered aromatic heterocyclyloxy group (particularly, triazolopyridinyloxy),

(13) a $C_{1-6}$ alkylsulfonyl group (particularly, methylsulfonyl), and

(14) a $C_{1-6}$ alkylsulfanyl group (particularly, methylsulfanyl), or (III) a 3- to 8-membered monocyclic non-aromatic heterocycle (particularly, dihydrooxazole, dihydropyridine) optionally substituted by 1 to 3 (particularly, 1 or 2) substituents selected from (1) a $C_{1-6}$ alkyl group (particularly, methyl), and (2) an oxo group;

$R^1$ is (I) a $C_{6-14}$ aryl group (particularly, phenyl) optionally substituted by 1 to 3 (particularly, 1 or 2) substituents selected from
  (1) a halogen atom (particularly, a fluorine atom, a chlorine atom),
  (2) an optionally halogenated $C_{1-6}$ alkyl group (particularly, methyl, trifluoromethyl), and
  (3) a $C_{1-6}$ alkoxy group (particularly, methoxy), (II) $C_{3-10}$ cycloalkyl (particularly, cyclopropyl, cyclopentyl, cyclohexyl), or (III) an optionally substituted heterocyclic group represented by any of
  (1) a heterocyclic group represented by a formula:

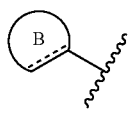

[Formula 9]

which is selected from pyrazolyl (particularly, pyrazol-3-yl, pyrazol-4-yl), thienyl (particularly, thiophen-2-yl) and pyridyl (particularly, pyridin-3-yl, pyridin-4-yl) and optionally substituted by 1 to 3 $C_{1-6}$ alkyl groups (particularly, methyl), and
  (2) a nitrogen-containing heterocyclic group represented by a formula:

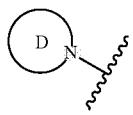

[Formula 10]

which is selected from pyrazol-1-yl, 1,2,3-triazol-1-yl and piperidinyl; and $R^2$ is a hydrogen atom.

Compound (B-2):
  Compound (B-1) wherein
    ring Ar is an 8- to 14-membered fused bicyclic aromatic heterocycle (particularly, quinoxaline, imidazopyridine) optionally substituted by 1 to 3 substituents selected from
    (1) a halogen atom (particularly, a chlorine atom),
    (2) a $C_{1-6}$ alkyl group (particularly, methyl), and
    (3) a $C_{1-6}$ alkoxy group (particularly, methoxy);
    ring A is a 5- or 6-membered monocyclic aromatic heterocycle (particularly, pyridine or pyrazole) optionally substituted by 1 to 3 substituents selected from a halogen atom (particularly, a chlorine atom), an optionally halogenated $C_{1-6}$ alkyl group (particularly, methyl, trifluoromethyl), and an optionally halogenated $C_{1-6}$ alkoxy group (particularly, difluoromethoxy, ethoxy); and
    $R^1$ is phenyl optionally substituted by 1 to 3 (particularly, 1) halogen atoms (particularly, a fluorine atom).

Compound (A-1):
  Compound (AB) wherein
    ring Ar is
(I) an aromatic heterocycle (particularly, pyridine, furan, pyrazole, thiazole, isoxazole, pyrimidine, pyridazine, benzothiophene, benzimidazole, benzothiazole, imidazopyridine, quinoxaline) optionally substituted by 1 to 3 (particularly, 1 or 2) substituents selected from
  (1) a halogen atom (particularly, a chlorine atom),
  (2) an optionally halogenated $C_{1-6}$ alkoxy group (particularly, methoxy, difluoromethoxy, ethoxy, isopropoxy),
  (3) a hydroxy-$C_{1-6}$ alkoxy group (particularly, 2-hydroxyethoxy),
  (4) a $C_{3-10}$ cycloalkyloxy group (particularly, cyclohexyloxy),
  (5) an optionally halogenated $C_{1-6}$ alkyl group (particularly, methyl, trifluoromethyl), and
  (6) a mono- or di-$C_{1-6}$ alkylamino group (particularly, methylamino, dimethylamino),
or (II) a $C_{6-14}$ aromatic hydrocarbon ring (particularly, benzene) optionally substituted by 1 to 3 substituents selected from
  (1) a halogen atom (particularly, a fluorine atom, a chlorine atom),
  (2) a cyano group,
  (3) an optionally halogenated $C_{1-6}$ alkyl group (particularly, trifluoromethyl),
  (4) an optionally halogenated $C_{1-6}$ alkoxy group (particularly, methoxy, trifluoromethoxy, ethoxy, isopropoxy),
  (5) a mono- or di-$C_{1-6}$ alkylamino group (particularly, dimethylamino),
  (6) a $C_{1-6}$ alkyl-5- to 14-membered aromatic heterocyclic group (particularly, methyl-1,2,4-oxadiazolyl), and
  (7) a $C_{1-6}$ alkylsulfonyl group (particularly, methylsulfonyl); ring A is (I) a $C_{6-14}$ aromatic hydrocarbon ring (preferably benzene, naphthalene) optionally substituted by 1 to 3 (particularly, 1 or 2) substituents selected from
  (1) a halogen atom (particularly, a fluorine atom, a chlorine atom),
  (2) a cyano group,
  (3) an optionally halogenated $C_{1-6}$ alkyl group (particularly, methyl, trifluoromethyl),
  (4) an optionally halogenated $C_{1-6}$ alkoxy group (particularly, methoxy, difluoromethoxy, trifluoromethoxy), and
  (5) a $C_{1-6}$ alkylsulfonyl group (particularly, methylsulfonyl),
or (II) a heterocycle (particularly, thiophene, furan, pyrazole, thiazole, pyridine, benzofuran, 1,3-benzodioxole, 2,3-dihydrobenzofuran) optionally substituted by 1 to 3 (particularly, 1 or 2) substituents selected from
  (1) a halogen atom (particularly, a chlorine atom), and
  (2) an optionally halogenated $C_{1-6}$ alkyl group (particularly, methyl, trifluoromethyl); and $R^1$ and $R^2$ are bonded to each other to form
(I) a 5- or 6-membered aromatic heterocycle (particularly, pyrazole, imidazole, isothiazole, isoxazole, pyridine) optionally substituted by 1 to 3 (particularly, 1 or 2) substituents selected from
  (1) a halogen atom (particularly, a chlorine atom, a bromine atom),
  (2) an optionally halogenated $C_{1-6}$ alkyl group (particularly, methyl, ethyl, 2,2-difluoroethyl, 2,2,2-trifluoroethyl, propyl, isopropyl, butyl, isobutyl, 2,2-dimethylpropyl),
  (3) a $C_{7-20}$ alkyl group (particularly, octadecyl),
  (4) a hydroxy-$C_{1-6}$ alkyl group (particularly, 3-hydroxy-3-methylbutyl),
  (5) a $C_{1-6}$ alkoxy-$C_{1-6}$ alkyl group (particularly, 2-methoxyethyl),
  (6) an optionally halogenated $C_{3-10}$ cycloalkyl-$C_{1-6}$ alkyl group (particularly, cyclopropylmethyl, 1-fluorocyclopropylmethyl),
  (7) a $C_{3-10}$ cycloalkyl group (particularly, cyclobutyl, cyclopentyl), (8) a $C_{1-6}$ alkoxy-$C_{7-16}$ aralkyl group (particularly, methoxybenzyl), (9) a 3- to 14-membered non-aromatic heterocyclic group (particularly, tetrahydropyranyl),

(10) an optionally halogenated $C_{1-6}$ alkyl-3- to 14-membered non-aromatic heterocyclic group (particularly, 2,2,2-trifluoroethylazetidinyl),

(11) a $C_{1-6}$ alkyl-3- to 14-membered non-aromatic heterocycle-$C_{1-6}$ alkyl group (particularly, methyloxetanylmethyl),

(12) a carbamoyl-$C_{1-6}$ alkyl group (particularly, carbamoylmethyl),

(13) an amino-$C_{1-6}$ alkyl group (particularly, aminopentyl),

(14) a $C_{1-6}$ alkoxy-carbonylamino-$C_{1-6}$ alkyl group (particularly, tert-butoxycarbonylaminopentyl),

(15) a fluorenyl-$C_{1-6}$ alkoxy-carbonylamino-$C_{1-6}$ alkyl group (particularly, fluorenylmethoxycarbonylaminopentyl), and

(16) a mono- or di-$C_{1-6}$ alkyl nitrogen-containing heterocycle-$C_{1-6}$ alkyl-nitrogen-containing heterocycle-$\kappa^2 N$ (boron halide)-$C_{1-6}$ alkyl-carbonylamino-$C_{1-6}$ alkyl group (particularly, dimethylpyrrolyl-$\kappa N$-methylene-pyrrolyl-$\kappa N$ (difluoroboron)-propanoylaminopentyl), or (II) a benzene ring optionally substituted by one halogen atom (particularly, a chlorine atom).

Compound (A-2):
  Compound (A-1) wherein
  ring Ar is
(I) a 5- or 6-membered monocyclic aromatic heterocycle (particularly, pyridine) optionally substituted by 1 to 3 (particularly, 2) substituents selected from
  (1) a halogen atom (particularly, a chlorine atom), and
  (2) a $C_{1-6}$ alkoxy group (particularly, methoxy),
or
(II) a $C_{6-14}$ aromatic hydrocarbon ring (particularly, benzene) optionally substituted by 1 to 3 (particularly, 2) substituents selected from a $C_{1-6}$ alkoxy group (particularly, methoxy);
  ring A is a $C_{6-14}$ aromatic hydrocarbon ring (particularly, benzene) optionally substituted by 1 to 3 (particularly, 1 or 2) substituents selected from
(1) a halogen atom (particularly, a chlorine atom),
(2) an optionally halogenated $C_{1-6}$ alkyl group (particularly, trifluoromethyl), and
(3) an optionally halogenated $C_{1-6}$ alkoxy group (particularly, trifluoromethoxy); and
  $R^1$ and $R^2$ are bonded to each other to form a 5- or 6-membered monocyclic aromatic heterocycle (particularly, pyrazole) optionally substituted by 1 to 3 (particularly, 1) substituents selected from an optionally halogenated $C_{1-6}$ alkyl group (particularly, methyl, ethyl, 2,2-difluoroethyl, isopropyl).

Compound (AB-1):
  Compound (AB) wherein
  ring Ar is an aromatic heterocycle (particularly, quinoxaline, pyridine, thiophene, furan, pyrrole, pyrazole, thiazole, isoxazole, pyridine, pyrimidine, pyridazine, benzothiophene, benzofuran, benzimidazole, benzoxazole, benzothiazole, benzotriazole, pyrrolopyridine, pyrazolopyridine, imidazopyrimidine, imidazopyridine, imidazopyridazine, thienopyridine, 1H-indazole, 2H-indazole, quinoline, quinazoline, triazolopyridine) optionally substituted by 1 to 3 substituents selected from
  (1) a halogen atom (particularly, a chlorine atom, a fluorine atom, a bromine atom),
  (2) a cyano group,
  (3) a hydroxy group,
  (4) an optionally halogenated $C_{1-6}$ alkyl group (particularly, methyl, trifluoromethyl),
  (5) a $C_{3-10}$ cycloalkyl group (particularly, cyclopropyl),
  (6) an optionally halogenated $C_{1-6}$ alkoxy group (particularly, methoxy, $(^2H_3)$ methoxy, difluoromethoxy, ethoxy, 2,2-difluoroethoxy, 2,2,2-trifluoroethoxy, isopropoxy),
  (7) a hydroxy-$C_{1-6}$ alkoxy group (particularly, 2-hydroxyethoxy),
  (8) a $C_{3-10}$ cycloalkyloxy group (particularly, cyclohexyloxy),
  (9) a $C_{1-6}$ alkyl-carbonyl group (particularly, acetyl),
  (10) a $C_{1-6}$ alkoxy-carbonyl group (particularly, methoxycarbonyl, ethoxycarbonyl),
  (11) an amino group,
  (12) a mono- or di-$C_{1-6}$ alkylamino group (particularly, methylamino, dimethylamino),
  (13) a mono- or di-$C_{1-6}$ alkyl-carbonylamino group (particularly, acetylamino),
  (14) a mono- or di-$C_{3-10}$ cycloalkyl-carbonylamino group (particularly, cyclopropylcarbonylamino, di(cyclopropylcarbonyl)amino),
  (15) a 5- to 14-membered aromatic heterocyclic group (particularly, pyrazolyl), and
  (16) a $C_{1-6}$ alkylsulfonyl group (particularly, isopropylsulfonyl),
  (I) ring A is a heterocycle (particularly, thiophene, furan, pyrazole, thiazole, pyridine, oxazole, isoxazole, imidazole, pyrazine, benzofuran, 1,3-benzodioxole, 2,3-dihydrobenzofuran, dihydrooxazole, dihydropyridine) optionally substituted by 1 to 3 substituents selected from
  (1) a halogen atom (particularly, a chlorine atom, a bromine atom),
  (2) an optionally halogenated $C_{1-6}$ alkyl group (particularly, methyl, difluoromethyl, 2,2-difluoroethyl, trifluoromethyl, isopropyl, tert-butyl),
  (3) a $C_{3-10}$ cycloalkyl group (particularly, cyclopropyl),
  (4) an optionally halogenated $C_{1-6}$ alkoxy group (particularly, methoxy, difluoromethoxy, ethoxy, 2,2-difluoroethoxy, 2,2,2-trifluoroethoxy),
  (5) a hydroxy-$C_{1-6}$ alkoxy group (particularly, 2-hydroxyethoxy),
  (6) a $C_{1-6}$ alkoxy-$C_{1-6}$ alkoxy group (particularly, 2-methoxyethoxy),
  (7) a 3- to 14-membered non-aromatic heterocycle-$C_{1-6}$ alkoxy group (particularly, morpholinylethoxy, morpholinylpropoxy),
  (8) a 3- to 14-membered non-aromatic heterocyclyloxy-$C_{1-6}$ alkoxy group (e.g., tetrahydropyranyloxyethoxy),
  (9) a mono- or di-$C_{1-6}$ alkylamino-$C_{1-6}$ alkoxy group (particularly, dimethylamino-ethoxy, dimethylaminopropoxy),
  (10) a mono- or di-$C_{7-16}$ aralkylphosphate-$C_{1-6}$ alkoxy group (particularly, dibenzylphosphateethoxy),
  (11) a 5- to 14-membered aromatic heterocyclic group (particularly, pyrazolyl),
  (12) a 5- to 14-membered aromatic heterocyclyloxy group (particularly, triazolopyridinyloxy),
  (13) a $C_{1-6}$ alkylsulfonyl group (particularly, methylsulfonyl), and
  (14) a $C_{1-6}$ alkylsulfanyl group (particularly, methylsulfanyl),
  $R^1$ is a $C_{6-14}$ aryl group (particularly, phenyl) optionally substituted by 1 to 3 (particularly, 1 or 2) substituents selected from (1) a halogen atom (particularly, a fluorine atom, a chlorine atom), (2) an optionally halogenated $C_{1-6}$ alkyl group (particularly, methyl, trifluoromethyl) and (3) a $C_{1-6}$ alkoxy group (particularly, methoxy), and $R^2$ is a hydrogen atom, or (II) ring A is a $C_{6-14}$ aromatic hydrocarbon ring (particularly, benzene, naphthalene) optionally substituted by 1 to 3 (particularly, 1 or 2) substituents selected from (1) a halogen atom (particularly, a fluorine atom, a chlorine atom), (2) a cyano group, (3) an optionally halogenated $C_{1-6}$ alkyl group (particularly, methyl, trifluoromethyl), (4) an optionally halogenated $C_{1-6}$ alkoxy group (particularly, methoxy, difluoromethoxy, trifluoromethoxy), and (5) a $C_{1-6}$ alkylsulfonyl group (particularly, methylsulfonyl), and $R^1$ and $R^2$ are bonded to each other to form a 5- or 6-membered aromatic heterocycle (particularly, pyrazole, imidazole, isothiazole, isoxazole, pyridine) optionally substituted by 1 to 3 (particularly, 1 or 2) substituents selected from (1) a halogen atom (particularly, a chlorine atom, a bromine atom), (2) an optionally halogenated $C_{1-6}$ alkyl group (particularly, methyl, ethyl, 2,2-difluoroethyl, 2,2,2-trifluoroethyl, propyl, isopropyl, butyl, isobutyl, 2,2-dimethylpropyl), (3) a $C_{7-20}$ alkyl group (particularly, octadecyl), (4) a hydroxy-$C_{1-6}$ alkyl group (particularly, 3-hydroxy-3-methylbutyl), (5) a $C_{1-6}$ alkoxy-$C_{1-6}$ alkyl group (particularly, 2-methoxyethyl), (6) an optionally halogenated $C_{3-10}$ cycloalkyl-$C_{1-6}$ alkyl group (particularly, cyclopropylmethyl, 1-fluorocyclopropylmethyl), (7) a $C_{3-10}$ cycloalkyl group (particularly, cyclobutyl, cyclopentyl), (8) a $C_{1-6}$ alkoxy-$C_{7-16}$ aralkyl group (particularly, methoxybenzyl), (9) a 3- to 14-membered non-aromatic heterocyclic group (particularly, tetrahydropyranyl),

(10) an optionally halogenated $C_{1-6}$ alkyl-3- to 14-membered non-aromatic heterocyclic group (particularly, 2,2,2-trifluoroethylazetidinyl),

(11) a $C_{1-6}$ alkyl-3- to 14-membered non-aromatic heterocycle-$C_{1-6}$ alkyl group (particularly, methyloxetanylmethyl),

(12) a carbamoyl-$C_{1-6}$ alkyl group (particularly, carbamoylmethyl),

(13) an amino-$C_{1-6}$ alkyl group (particularly, aminopentyl),

(14) a $C_{1-6}$ alkoxy-carbonylamino-$C_{1-6}$ alkyl group (particularly, tert-butoxycarbonylaminopentyl),

(15) a fluorenyl-$C_{1-6}$ alkoxy-carbonylamino-$C_{1-6}$ alkyl group (particularly, fluorenylmethoxycarbonylaminopentyl), and

(16) a mono- or di-$C_{1-6}$ alkyl nitrogen-containing heterocycle-$C_{1-6}$ alkyl-nitrogen-containing heterocycle-κ2N (boron halide)-$C_{1-6}$ alkyl-carbonylamino-$C_{1-6}$ alkyl group (particularly, dimethylpyrrolyl-κN-methylene-pyrrolyl-κN (difluoroboron)-propanoylaminopentyl).

Compound (AB-2):

Compound (AB-1) wherein (I) ring A is a 5- or 6-membered monocyclic aromatic heterocycle (particularly, pyrazole, pyridine, oxazole, isoxazole, thiazole, imidazole, pyrazine) optionally substituted by 1 to 3 substituents selected from (1) a halogen atom (particularly, a chlorine atom, a bromine atom), (2) an optionally halogenated $C_{1-6}$ alkyl group (particularly, methyl, difluoromethyl, 2,2-difluoroethyl, trifluoromethyl, isopropyl, tert-butyl), (3) a $C_{3-10}$ cycloalkyl group (particularly, cyclopropyl), (4) an optionally halogenated $C_{1-6}$ alkoxy group (particularly, methoxy, difluoromethoxy, ethoxy, 2,2-difluoroethoxy, 2,2,2-trifluoroethoxy), (5) a hydroxy-$C_{1-6}$ alkoxy group (particularly, 2-hydroxyethoxy), (6) a $C_{1-6}$ alkoxy-$C_{1-6}$ alkoxy group (particularly, 2-methoxyethoxy), (7) a 3- to 14-membered non-aromatic heterocycle-$C_{1-6}$ alkoxy group (particularly, morpholinylethoxy, morpholinylpropoxy), (8) a 3- to 14-membered non-aromatic heterocyclyloxy-$C_{1-6}$ alkoxy group (e.g., tetrahydropyranyloxyethoxy), (9) a mono- or di-$C_{1-6}$ alkylamino-$C_{1-6}$ alkoxy group (particularly, dimethylamino-ethoxy, dimethylaminopropoxy),

(10) a mono- or di-$C_{7-16}$ aralkyl phosphate-$C_{1-6}$ alkoxy group (particularly, dibenzylphosphateethoxy),

(11) a 5- to 14-membered aromatic heterocyclic group (particularly, pyrazolyl),

(12) a 5- to 14-membered aromatic heterocyclyloxy group (particularly, triazolopyridinyloxy),

(13) a $C_{1-6}$ alkylsulfonyl group (particularly, methylsulfonyl), and

(14) a $C_{1-6}$ alkylsulfanyl group (particularly, methylsulfanyl); and $R^1$ is a $C_{6-14}$ aryl group (particularly, phenyl) optionally substituted by 1 to 3 (particularly, 1 or 2) substituents selected from (1) a halogen atom (particularly, a fluorine atom, a chlorine atom), (2) an optionally halogenated $C_{1-6}$ alkyl group (particularly, methyl, trifluoromethyl), and (3) a $C_{1-6}$ alkoxy group (particularly, methoxy), or (II) ring A is a $C_{6-14}$ aromatic hydrocarbon ring (preferably benzene, naphthalene) optionally substituted by 1 to 3 (particularly, 1 or 2) substituents selected from (1) a halogen atom (particularly, a fluorine atom, a chlorine atom), (2) a cyano group, (3) an optionally halogenated $C_{1-6}$ alkyl group (particularly, methyl, trifluoromethyl), (4) an optionally halogenated $C_{1-6}$ alkoxy group (particularly, methoxy, difluoromethoxy, trifluoromethoxy), and (5) a $C_{1-6}$ alkylsulfonyl group (particularly, methylsulfonyl); and $R^1$ and $R^2$ are bonded to each other to form a 5- or 6-membered aromatic heterocycle (particularly, pyrazole, imidazole, isothiazole, isoxazole, pyridine) optionally substituted by 1 to 3 (particularly, 1 or 2) substituents selected from (1) a halogen atom (particularly, a chlorine atom, a bromine atom), (2) an optionally halogenated $C_{1-6}$ alkyl group (particularly, methyl, ethyl, 2,2-difluoroethyl, 2,2,2-trifluoroethyl, propyl, isopropyl, butyl, isobutyl, 2,2-dimethylpropyl), (3) a $C_{7-20}$ alkyl group (particularly, octadecyl), (4) a hydroxy-$C_{1-6}$ alkyl group (particularly, 3-hydroxy-3-methylbutyl), (5) a $C_{1-6}$ alkoxy-$C_{1-6}$ alkyl group (particularly, 2-methoxyethyl), (6) an optionally halogenated $C_{3-10}$ cycloalkyl-$C_{1-6}$ alkyl group (particularly, cyclopropylmethyl, 1-fluorocyclopropylmethyl), (7) a $C_{3-10}$ cycloalkyl group (particularly, cyclobutyl, cyclopentyl), (8) a $C_{1-6}$ alkoxy-$C_{7-16}$ aralkyl group (particularly, methoxybenzyl), (9) a 3- to 14-membered non-aromatic heterocyclic group (particularly, tetrahydropyranyl),

(10) an optionally halogenated $C_{1-6}$ alkyl-3- to 14-membered non-aromatic heterocyclic group (particularly, 2,2,2-trifluoroethylazetidinyl),

(11) a $C_{1-6}$ alkyl-3- to 14-membered non-aromatic heterocycle-$C_{1-6}$ alkyl group (particularly, methyloxetanylmethyl),

(12) a carbamoyl-$C_{1-6}$ alkyl group (particularly, carbamoylmethyl),

(13) an amino-$C_{1-6}$ alkyl group (particularly, aminopentyl),

(14) a $C_{1-6}$ alkoxy-carbonylamino-$C_{1-6}$ alkyl group (particularly, tert-butoxycarbonylaminopentyl),

(15) a fluorenyl-$C_{1-6}$ alkoxy-carbonylamino-$C_{1-6}$ alkyl group (particularly, fluorenylmethoxycarbonylaminopentyl), and

(16) a mono- or di-$C_{1-6}$ alkyl nitrogen-containing heterocycle-$C_{1-6}$ alkyl-nitrogen-containing heterocycle-$\kappa^2 N$ (boron halide)-$C_{1-6}$ alkyl-carbonylamino-$C_{1-6}$ alkyl group (particularly, dimethylpyrrolyl-$\kappa N$-methylene-pyrrolyl-$\kappa N$ (difluoroboron)-propanoylaminopentyl).

Compound (AB-3):
Compound (AB-2) wherein
(I) ring A is a 5- or 6-membered monocyclic aromatic heterocycle (particularly, pyridine, pyrazole) optionally substituted by 1 to 3 substituents selected from a halogen atom (particularly, a chlorine atom), an optionally halogenated $C_{1-6}$ alkyl group (particularly, methyl, trifluoromethyl), and an optionally halogenated $C_{1-6}$ alkoxy group (particularly, difluoromethoxy, ethoxy); and
$R^1$ is phenyl optionally substituted by 1 to 3 (particularly, 1) halogen atoms (particularly, a fluorine atom), or
(II) ring A is a $C_{6-14}$ aromatic hydrocarbon ring (particularly, benzene) optionally substituted by 1 to 3 (particularly, 1 or 2) substituents selected from
(1) a halogen atom (particularly, a chlorine atom),
(2) an optionally halogenated $C_{1-6}$ alkyl group (particularly, trifluoromethyl), and
(3) an optionally halogenated $C_{1-6}$ alkoxy group (particularly, trifluoromethoxy); and
$R^1$ and $R^2$ are bonded to each other to form a 5- or 6-membered monocyclic aromatic heterocycle (particularly, pyrazole) optionally substituted by 1 to 3 (particularly, 1) substituents selected from
(1) an optionally halogenated $C_{1-6}$ alkyl group (particularly, methyl, ethyl, 2,2-difluoroethyl, isopropyl).

Compound (B-3):
Compound (I) wherein
ring Ar is an 8- to 14-membered fused bicyclic aromatic heterocycle (particularly, quinoxaline) optionally substituted by 1 to 3 substituents selected from a halogen atom (particularly, a chlorine atom) and a $C_{1-6}$ alkyl group (particularly, methyl);
ring A is a 5- or 6-membered monocyclic aromatic heterocycle (particularly, pyridine or pyrazole) optionally substituted by 1 to 3 substituents selected from a halogen atom (particularly, a chlorine atom), an optionally halogenated $C_{1-6}$ alkyl group (particularly, methyl, trifluoromethyl), and an optionally halogenated $C_{1-6}$ alkoxy group (particularly, difluoromethoxy, ethoxy);
$R^1$ is a $C_{6-14}$ aryl group (particularly, phenyl) optionally substituted by 1 to 3 (particularly, 1) halogen atom (particularly, a fluorine atom); and
$R^2$ is a hydrogen atom.

Compound (A-3):
Compound (I) wherein
ring Ar is a 5- or 6-membered monocyclic aromatic heterocycle (particularly, pyridine) optionally substituted by 1 to 3 (particularly, 2) substituents selected from (1) a halogen atom (particularly, a chlorine atom), and (2) a $C_{1-6}$ alkoxy group (particularly, methoxy);
ring A is a $C_{6-14}$ aromatic hydrocarbon ring (particularly, benzene) optionally substituted by 1 to 3 (particularly, 1 or 2) substituents selected from
(1) a halogen atom (particularly, a chlorine atom),
(2) an optionally halogenated $C_{1-6}$ alkyl group (particularly, trifluoromethyl), and
(3) an optionally halogenated $C_{1-6}$ alkoxy group (particularly, trifluoromethoxy); and
$R^1$ and $R^2$ are bonded to each other to form a 5- or 6-membered monocyclic aromatic heterocycle (particularly, pyrazole) optionally substituted by 1 to 3 (particularly, 1) substituents selected from an optionally halogenated $C_{1-6}$ alkyl group (particularly, methyl, ethyl, 2,2-difluoroethyl, isopropyl).

Compound (AB-4):
Compound (I) wherein
ring Ar is
(I) an 8- to 14-membered fused bicyclic aromatic heterocycle (particularly, quinoxaline) optionally substituted by 1 to 3 substituents selected from a halogen atom (particularly, a chlorine atom) and a $C_{1-6}$ alkyl group (particularly, methyl), or
(II) a 5- or 6-membered monocyclic aromatic heterocycle (particularly, pyridine) optionally substituted by 1 to 3 (particularly, 2) substituents selected from (1) a halogen atom (particularly, a chlorine atom), and (2) a $C_{1-6}$ alkoxy group (particularly, methoxy);
ring A is
(I) a 5- or 6-membered monocyclic aromatic heterocycle (particularly, pyridine or pyrazole) optionally substituted by 1 to 3 substituents selected from (1) a halogen atom (particularly, a chlorine atom), (2) an optionally halogenated $C_{1-6}$ alkyl group (particularly, methyl, trifluoromethyl), and (3) an optionally halogenated $C_{1-6}$ alkoxy group (particularly, difluoromethoxy, ethoxy), or
(II) a $C_{6-14}$ aromatic hydrocarbon ring (particularly, benzene) optionally substituted by 1 to 3 (particularly, 1 or 2) substituents selected from (1) a halogen atom (particularly, a chlorine atom), (2) an optionally halogenated $C_{1-6}$ alkyl group (particularly, trifluoromethyl), and (3) an optionally halogenated $C_{1-6}$ alkoxy group (particularly, trifluoromethoxy);
$R^1$ is a $C_{6-14}$ aryl group (particularly, phenyl) optionally substituted by 1 to 3 (particularly, 1) halogen atom (particularly, a fluorine atom);
$R^2$ is a hydrogen atom; or
$R^1$ and $R^2$ are bonded to each other to form a 5- or 6-membered monocyclic aromatic heterocycle (particularly, pyrazole) optionally substituted by 1 to 3 (particularly, 1) substituents selected from an optionally halogenated $C_{1-6}$ alkyl group (particularly, methyl, ethyl, 2,2-difluoroethyl, isopropyl).

The salt of the compound (I) is preferably a pharmacologically acceptable salt. Examples thereof include a salt with an inorganic base, a salt with an organic base, a salt with an inorganic acid, a salt with an organic acid and a salt with a basic or acidic amino acid.

Preferable examples of the salt with an inorganic base include: an alkali metal salt such as sodium salt, potassium salt and the like; an alkaline earth metal salt such as calcium salt, magnesium salt and the like; and an aluminum salt and an ammonium salt.

Preferable examples of the salt with an organic base include a salt with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine or N,N-dibenzylethylenediamine.

Preferable examples of the salt with an inorganic acid include a salt with hydrochloric acid, hydrobromic acid, nitric acid, sulfuric acid or phosphoric acid.

Preferable examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferable examples of the salt with a basic amino acid include a salt with arginine, lysine or ornithine.

Preferable examples of the salt with an acidic amino acid include a salt with aspartic acid or glutamic acid.

The method for producing the compound of the present invention will be described below.

A starting material or a reagent used in each step in the production method given below and the obtained compound may each form a salt. Examples of such a salt include the same as the aforementioned salt of the compound of the present invention, and the like.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, chromatography or the like according to a routine method.

If a starting material or a reagent compound for each step is commercially available, the commercially available product can be used directly.

In the reaction of each step, the reaction time may differ depending on the reagent or the solvent used and is usually 1 minute to 48 hours, preferably 10 minutes to 8 hours, unless otherwise specified.

In the reaction of each step, the reaction temperature may differ depending on the reagent or the solvent used and is usually −78° C. to 300° C., preferably −78° C. to 150° C., unless otherwise specified.

In the reaction of each step, the pressure may differ depending on the reagent or the solvent used and is usually 1 atm to 20 atm, preferably 1 atm to 3 atm, unless otherwise specified.

In the reaction of each step, a microwave synthesis apparatus, for example, Initiator manufactured by Biotage Japan Ltd., may be used. The reaction temperature may differ depending on the reagent or the solvent used and is usually room temperature to 300° C., preferably 50° C. to 250° C., unless otherwise specified. The reaction time may differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In the reaction of each step, this reaction is carried out without a solvent or by dissolution or suspension in an appropriate solvent, unless otherwise specified. Specific examples of the solvent include a solvent described in Examples and the following:

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

Two or more of these solvents may be used as a mixture at an appropriate ratio.

In the case of using a base in the reaction of each step, for example, the following base or a base described in Examples is used:

inorganic bases: sodium hydroxide, magnesium hydroxide and the like;
basic salts: sodium carbonate, calcium carbonate, sodium bicarbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like; and
organic lithiums: n-butyllithium and the like.

In the case of using an acid or an acidic catalyst in the reaction of each step, for example, the following acid or acidic catalyst or an acid or an acidic catalyst described in Examples is used:

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like; and Lewis acids: boron trifluoride-diethyl ether complex, zinc iodide, anhydrous aluminum chloride, anhydrous zinc chloride, anhydrous iron chloride and the like.

The reaction of each step is carried out according to a method known per se in the art, for example, a method described in The Fifth Series of Experimental Chemistry, Vol. 13 to Vol. 19 (edited by The Chemical Society of Japan); Shin Jikken Kagaku Koza (New Experimental Chemistry in English), Vol. 14 to Vol. 15 (edited by The Chemical Society of Japan); Syntheses in the Organic Chemistry Laboratory, Revised, 2nd Ed. (L. F. Tietze, Th. Eicher, Nankodo Co., Ltd.); Organic Name Reactions; The Reaction Mechanism and Essence, Revised (Hideo Tougo, Kodansha Ltd.); Organic Syntheses Collective Volume I to VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, published by Kagaku-Dojin Publishing Company, Inc.); Comprehensive Organic Transformations (VCH Publishers, Inc.) (1989), etc., or a method described in Examples, unless otherwise specified.

In each step, the protection or deprotection reaction of a functional group is carried out according to a method known per se in the art, for example, a method described in "Protective Groups in Organic Synthesis, 4th Ed." (Theodora W. Greene, Peter G. M. Wuts), Wiley-Interscience (2007); "Protecting Groups, 3rd Ed." (P. J. Kocienski) Thieme Medical Publishers (2004), etc., or a method described in Examples.

Examples of a protective group for a hydroxy group in an alcohol or a phenolic hydroxy group or the like include: an ether-type protective group such as methoxymethyl ether, benzyl ether, tert-butyldimethylsilyl ether, tetrahydropyranyl ether and the like; a carboxylic acid ester-type protective group such as acetic acid ester and the like; a sulfonic acid ester-type protective group such as methanesulfonic acid ester and the like; a carbonic acid ester-type protective group such as tert-butyl carbonate and the like; and the like.

Examples of a protective group for a carbonyl group in an aldehyde include: an acetal-type protective group such as dimethylacetal and the like; a cyclic acetal-type protective group such as 1,3-dioxane and the like; and the like.

Examples of a protective group for a carbonyl group in a ketone include: a ketal-type protective group such as dimethylketal and the like; a cyclic ketal-type protective group such as 1,3-dioxane and the like; an oxime-type protective group such as O-methyloxime and the like; a hydrazone-type protective group such as N,N-dimethylhydrazone and the like; and the like.

Examples of a protective group for a carboxyl group include: an ester-type protective group such as methyl ester and the like; an amide-type protective group such as N,N-dimethylamide and the like; and the like Examples of a protective group for a thiol include: an ether-type protective group such as benzyl thioether and the like; an ester-type protective group such as thioacetic acid ester, thiocarbonate, thiocarbamate and the like; and the like.

Examples of a protective group for an amino group or an aromatic heterocycle such as imidazole, pyrrole, indole or the like include: a carbamate-type protective group such as benzyl carbamate and the like; an amide-type protective group such as acetamide and the like; an alkylamine-type protective group such as N-triphenylmethylamine and the like; a sulfonamide-type protective group such as methanesulfonamide and the like; and the like.

These protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate or trialkylsilyl halide (e.g., trimethylsilyl iodide, trimethylsilyl bromide) or a reduction method.

In the case of carrying out reduction reaction in each step, examples of the reducing agent used include: metal hydrides such as lithium aluminum hydride, sodium triacetoxyborohydride, sodium cyanoborohydride, diisobutyl aluminum hydride (DIBAL-H), sodium borohydride, tetramethylammonium triacetoxyborohydride and the like; boranes such as a borane-tetrahydrofuran complex and the like; Raney nickel; Raney cobalt; hydrogen; formic acid; triethylsilane and the like. In the case of reducing a carbon-carbon double bond or triple bond, a method using a catalyst such as palladium-carbon, a Lindlar's catalyst or the like can be used.

In the case of carrying out oxidation reaction in each step, examples of the oxidizing agent used include: peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodates such as sodium periodate and the like; a high-valent iodine reagent such as iodosylbenzene and the like; a reagent having manganese, such as manganese dioxide, potassium permanganate and the like; leads such as lead tetraacetate and the like; a reagent having chromium, such as pyridinium chlorochromate (PCC), pyridinium dichromate (PDC), Jones reagents and the like; halogen compounds such as N-bromosuccinimide (NBS) and the like; oxygen; ozone; a sulfur trioxide-pyridine complex; osmium tetroxide; selenium dioxide; 2,3-dichloro-5,6-dicyano-1,4-benzoquinone (DDQ); and the like.

In the case of carrying out radical cyclization reaction in each step, examples of the radical initiator used include: an azo compound such as azobisisobutyronitrile (AIBN) and the like; a water-soluble radical initiator such as 4-4'-azobis-4-cyanopentanoic acid (ACPA) and the like; triethylboron in the presence of air or oxygen; benzoyl peroxide; and the like. Examples of the radical reaction agent used include tributylstannane, tris(trimethylsilyl)silane, 1,1,2,2-tetraphenyldisilane, diphenylsilane, samarium iodide and the like.

In the case of carrying out Wittig reaction in each step, examples of the Wittig reagent used include alkylidenephosphoranes and the like. The alkylidenephosphoranes can be prepared by a method known per se in the art, for example, the reaction between a phosphonium salt and a strong base.

In the case of carrying out Horner-Emmons reaction in each step, examples of the reagent used include: phosphonoacetic acid esters such as methyl dimethylphosphonoacetate, ethyl diethylphosphonoacetate and the like; and a base such as alkali metal hydrides, organic lithiums and the like.

In the case of carrying out Friedel-Crafts reaction in each step, examples of the reagent used include a combination of a Lewis acid and an acid chloride and a combination of a Lewis acid and an alkylating agent (e.g., alkyl halides, alcohols, olefins, etc.). Alternatively, an organic acid or an inorganic acid may be used instead of the Lewis acid, and an acid anhydride such as acetic anhydride or the like may be used instead of the acid chloride.

In the case of carrying out aromatic nucleophilic substitution reaction in each step, a nucleophile (e.g., amines, imidazole, etc.) and a base (e.g., basic salts, organic bases, etc.) are used as reagents.

In the case of carrying out nucleophilic addition reaction using a carbanion, nucleophilic 1,4-addition reaction (Michael addition reaction) using a carbanion or nucleophilic substitution reaction using a carbanion in each step, examples of the base used for generating the carbanion include organic lithiums, metal alkoxides, inorganic bases, organic bases and the like.

In the case of carrying out Grignard reaction in each step, examples of the Grignard reagent include: aryl magnesium halides such as phenyl magnesium bromide and the like; and alkyl magnesium halides such as methyl magnesium bromide and the like. The Grignard reagent can be prepared by a method known per se in the art, for example, the reaction between alkyl halide or aryl halide and metal magnesium with ether or tetrahydrofuran as a solvent.

In the case of carrying out Knoevenagel condensation reaction in each step, an active methylene compound flanked by two electron-attracting groups (e.g., malonic acid, diethyl malonate, malononitrile, etc.) and a base (e.g., organic bases, metal alkoxides, inorganic bases) are used as reagents.

In the case of carrying out Vilsmeier-Haack reaction in each step, phosphoryl chloride and an amide derivative (e.g., N,N-dimethylformamide, etc.) are used as reagents.

In the case of carrying out azidation reaction of alcohols, alkyl halides or sulfonic acid esters in each step, examples of the azidating agent used include diphenylphosphorylazide (DPPA), trimethylsilylazide, sodium azide and the like. In the case of azidating, for example, alcohols, a method using diphenylphosphorylazide and 1,8-diazabicyclo[5.4.0]undec-7-ene (DBU), a method using trimethylsilylazide and a Lewis acid, or the like can be used.

In the case of carrying out reductive amination reaction in each step, examples of the reducing agent used include sodium triacetoxyborohydride, sodium cyanoborohydride, hydrogen, formic acid and the like. When the substrate is an amine compound, examples of the carbonyl compound used include p-formaldehyde as well as aldehydes such as acetaldehyde and the like, and ketones such as cyclohexanone and the like. When the substrate is a carbonyl compound, examples of the amines used include: ammonia; primary amine such as methylamine and the like; secondary amine such as dimethylamine and the like; and the like.

In the case of carrying out Mitsunobu reaction in each step, azodicarboxylic acid esters (e.g., diethyl azodicarboxylate (DEAD), diisopropyl azodicarboxylate (DIAD), etc.) and triphenylphosphine are used as reagents.

In the case of carrying out esterification reaction, amidation reaction or ureation reaction in each step, examples of the reagent used include: an acyl halide form of acid chloride, acid bromide and the like; and activated carboxylic acids such as an acid anhydride, an active ester form, a sulfuric acid ester form and the like. Examples of the activator for carboxylic acid include: a carbodiimide condensing agent such as 1-ethyl-3-(3-dimethylaminopropyl) carbodiimide hydrochloride (WSCD) and the like; a triazine condensing agent such as 4-(4,6-dimethoxy-1,3,5-triazin-2-yl)-4-methylmorpholinium chloride-n-hydrate (DMT-MM) and the like; a carbonic acid ester condensing agent such as 1,1-carbonyldiimidazole (CDI) and the like; diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformate such as ethyl chloroformate and the like; O-(7-azabenzotriazol-1-yl)-N,N,N',N'-tetramethyluronium hexafluorophosphate (HATU); sulfuric acid; and combinations thereof; and the like. In the case of using a carbodiimide condensing agent, an additive such as 1-hydroxybenzotriazole (HOBt), N-hydroxysuccinimide (HOSu), dimethylaminopyridine (DMAP) or the like may be further added for the reaction.

In the case of carrying out coupling reaction in each step, examples of the metal catalyst used include: a palladium compound such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; a nickel compound such as tetrakis(triphenylphosphine)nickel(0) and the like; a rhodium compound such as tris(triphenylphosphine)rhodium(III) chloride and the like; a cobalt compound; a copper compound such as copper oxide, copper(I) iodide and the like; a platinum compound; and the like. A base may be further added for the reaction. Examples of such a base include inorganic bases, basic salts and the like.

In the case of carrying out thiocarbonylation reaction in each step, diphosphorus pentasulfide is typically used as a thiocarbonylating agent. A reagent having a 1,3,2,4-dithiadiphosphetane-2,4-disulfide structure such as 2,4-bis(4-methoxyphenyl-1,3,2,4-dithiadiphosphetane-2,4-disulfide (Lawesson's reagent) or the like may be used instead of diphosphorus pentasulfide.

In the case of carrying out Wohl-Ziegler reaction in each step, examples of the halogenating agent used include N-iodosuccinimide, N-bromosuccinimide (NBS), N-chlorosuccinimide (NCS), bromine, sulfuryl chloride and the like. The reaction can be accelerated by the further addition of a radical initiator such as heat, light, benzoyl peroxide, azobisisobutyronitrile or the like for the reaction.

In the case of carrying out halogenation reaction of a hydroxy group in each step, examples of the halogenating agent used include a hydrohalic acid and an acid halide of an inorganic acid, specifically, hydrochloric acid, thionyl chloride, phosphorus oxychloride and the like for chlorination, and 48% hydrobromic acid and the like for bromination. Also, a method for obtaining an alkyl halide form from an alcohol by the action of triphenylphosphine and carbon tetrachloride or carbon tetrabromide or the like may be used. Alternatively, a method for synthesizing an alkyl halide form through 2-stage reactions involving the conversion of an alcohol to sulfonic acid ester and the subsequent reaction with lithium bromide, lithium chloride or sodium iodide may be used.

In the case of carrying out Arbuzov reaction in each step, examples of the reagent used include: alkyl halides such as ethyl bromoacetate and the like; and phosphites such as triethyl phosphite, tri(isopropyl) phosphite and the like.

In the case of carrying out sulfonic acid esterification reaction in each step, examples of the sulfonylating agent used include methanesulfonyl chloride, p-toluenesulfonyl chloride, methanesulfonic anhydride, p-toluenesulfonic anhydride and the like.

In the case of carrying out hydrolysis reaction in each step, an acid or a base is used as a reagent. In the case of carrying out acid hydrolysis reaction of tert-butyl ester, formic acid, triethylsilane or the like may be added for reductively trapping a by-product tert-butyl cation.

In the case of carrying out dehydration reaction in each step, examples of the dehydrating agent used include sulfuric acid, diphosphorus pentoxide, phosphorus oxychloride, N,N'-dicyclohexylcarbodiimide, alumina, polyphosphoric acid and the like.

In the case of carrying out alkylation reaction of alcohols, amines or an aromatic heterocycle having a NH group in the ring (e.g., imidazole, pyrazole) or the like in each step, examples of the alkylating agent include optionally substituted alkyl halide (e.g., iodomethane), optionally substituted alkyl having an optionally substituted $C_{1-6}$ alkylsulfonyloxy group as a leaving group, optionally substituted alkyl having a $C_{6-14}$ arylsulfonyloxy group optionally substituted by a $C_{1-6}$ alkyl group, sodium 2-chloro-2,2-difluoroacetate, 2,2-difluoro-2-(fluorosulfonyl)acetic acid and the like. Examples of the base used include organic lithiums, metal alkoxides, inorganic bases, organic bases and the like.

In the case of carrying out coupling reaction in each step, examples of the coupling reaction include Suzuki coupling, Stille coupling, Buchwald coupling, Negishi coupling, Heck coupling, cyanation reaction using copper cyanide or zinc cyanide, and the like. The reagent, such as a metal catalyst, a phosphine ligand, and a base, used in the coupling reaction can be used according to a method known per se in the art [e.g., a method described in J. F. Hartwig, S. Shekhar, Q. Shen, F. Barrios-Landeros, in The Chemistry of Anilines, Z. Rappoport, Ed., Wiley-Interscience, New York (2007); L. Jiang, S. L. Buchwald, in Metal-Catalyzed Cross-Coupling Reactions, 2nd Ed., A. de Meijere, F. Diederich, Eds., Wiley-VCH, Weinheim, Germany (2004); J. F. Hartwig, in Handbook of Organopalladium Chemistry for Organic Synthesis, A. de Meijere, F. Diederich, Eds., Wiley, New York (2002); J. F. Hartwig, in Modern Amination Methods, A. Ricci, Ed., Wiley-VCH, Weinheim, (2000)] or a method equivalent thereto, in addition to the reagent mentioned above.

In the case of carrying out Michael reaction in each step, examples of the reagent used include acrylic acid esters.

Examples of the reaction conditions include conditions under which the reaction is carried out in an acid solvent such as acetic acid, and base (e.g., organic bases, metal alkoxides, inorganic bases) addition conditions.

In the case of carrying out decarboxylation reaction of a carboxylic acid in each step, an acid or a base is used. Hydrolysis of an ester and decarboxylation of a carboxylic acid may be performed in one step.

In the case of carrying out oximation reaction and imination reaction of a ketone in each step, hydroxylamine or amine is used as a reagent. The reaction can be accelerated by the addition of an acid or a base (e.g., organic bases, inorganic bases) or by the removal of water from the reaction system using a Dean-Stark apparatus.

In the case of carrying out halogenation reaction of an aromatic ring in each step, examples of the reagent used include N-iodosuccinimide, N-bromosuccinimide (NBS), N-chlorosuccinimide (NCS), bromine, sulfuryl chloride and the like.

In the case of carrying out Curtius reaction in each step, examples of the reagent used include diphenylphosphorylazide (DPPA), trimethylsilylazide, sodium azide and the like.

Hereinafter, the method for producing the compound (I) will be described.

Each symbol in the reaction schemes given below represents the same meaning as above, unless otherwise specified. Each starting compound can be readily obtained as a commercially available product or can be produced by a method known per se in the art or a method equivalent thereto, unless a specific method for producing the starting compound is mentioned.

Compound (Ia) included in the compound (I) can be produced by a method shown in the following reaction scheme 1 or a method equivalent thereto:

Reaction scheme 1

[Formula 11]

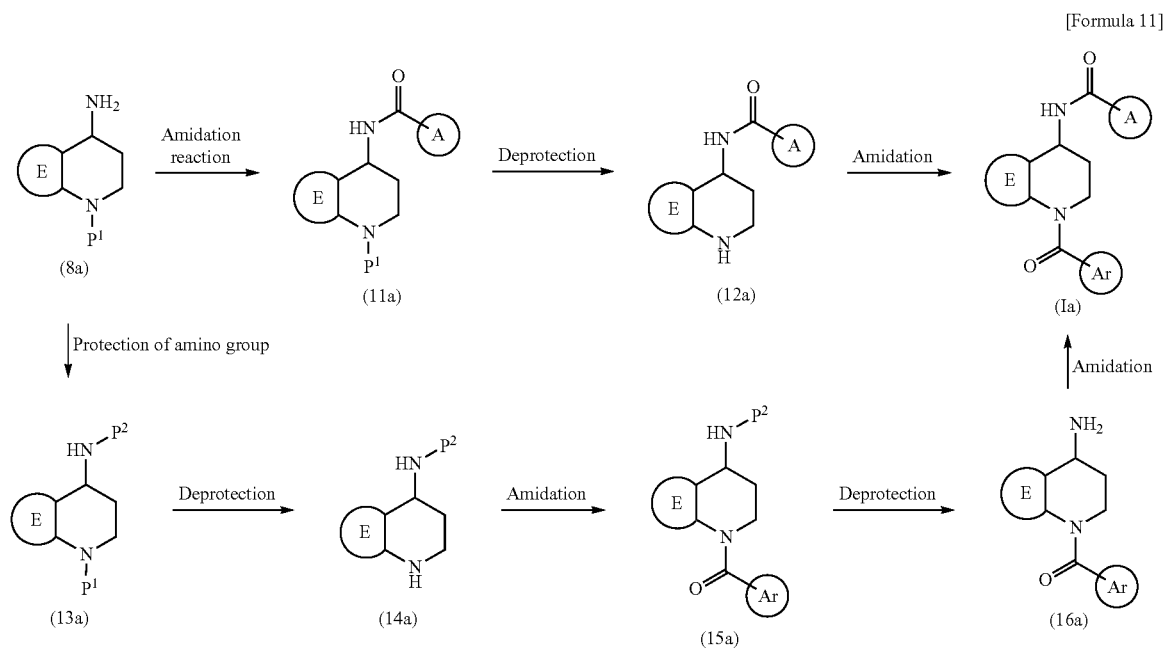

In the reaction scheme, ring represents an optionally substituted 5- or 6-membered aromatic heterocycle or benzene ring,
$P^1$ and $P^2$ represent different protective groups for an amino group (e.g., a benzyl group and a tert-butoxycarbonyl group) which can be deprotected under different reaction conditions, and the other symbols represent the same meaning as above.

Examples of the "optionally substituted 5- or 6-membered aromatic heterocycle" represented by ring F include the "optionally substituted 5- or 6-membered aromatic heterocycle" formed by $R^1$ and $R^2$ bonded to each other.

Compound (8a) can be produced by a method shown in the following reaction scheme 2 or a method equivalent thereto:

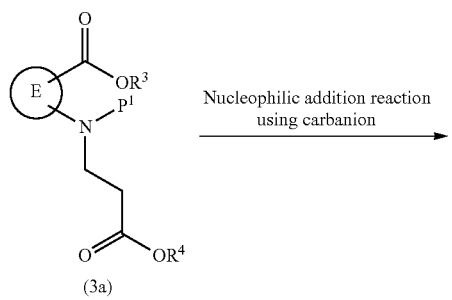

(3a)

Nucleophilic addition reaction using carbanion

Reaction scheme 2

[Formula 12]

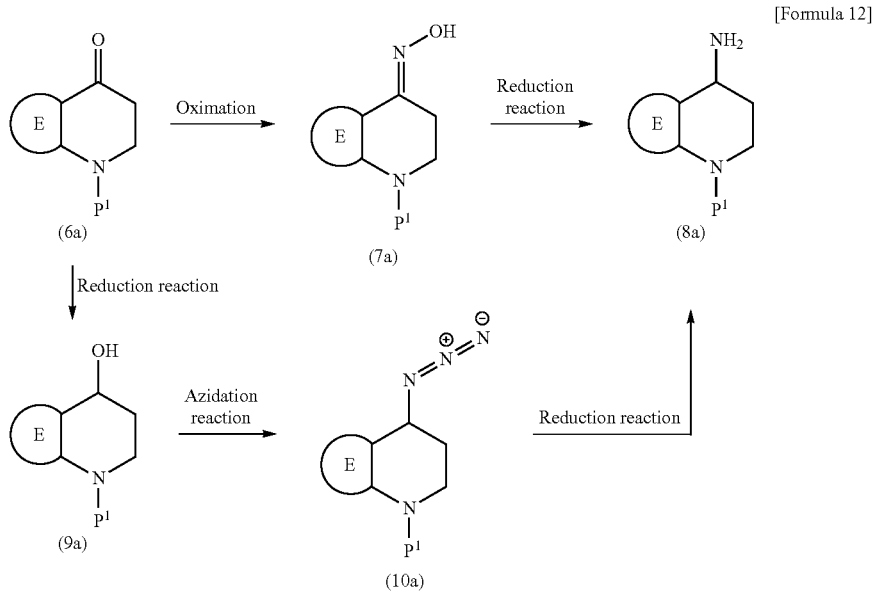

In the reaction scheme, each symbol represents the same meaning as above.

Compound (6a) can be produced from compound (1a) by a method shown in the following reaction scheme 3 or a method equivalent thereto:

Reaction scheme 3

[Formula 13]

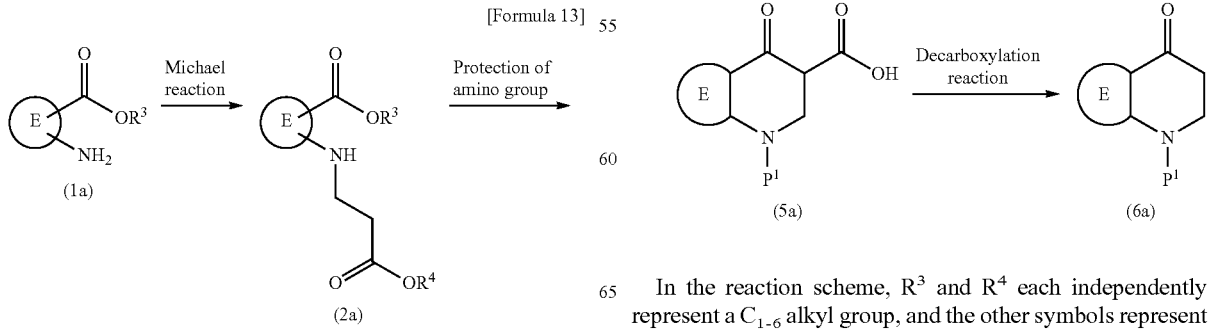

In the reaction scheme, $R^3$ and $R^4$ each independently represent a $C_{1-6}$ alkyl group, and the other symbols represent the same meaning as above.

Compound (1a) is commercially available or can be produced by a method known per se in the art or a method equivalent thereto.

Compound (16a) for use in reaction scheme 1 can also be produced by a method shown in the following reaction scheme 4 or a method equivalent thereto:

Reaction scheme 4

[Formula 14]

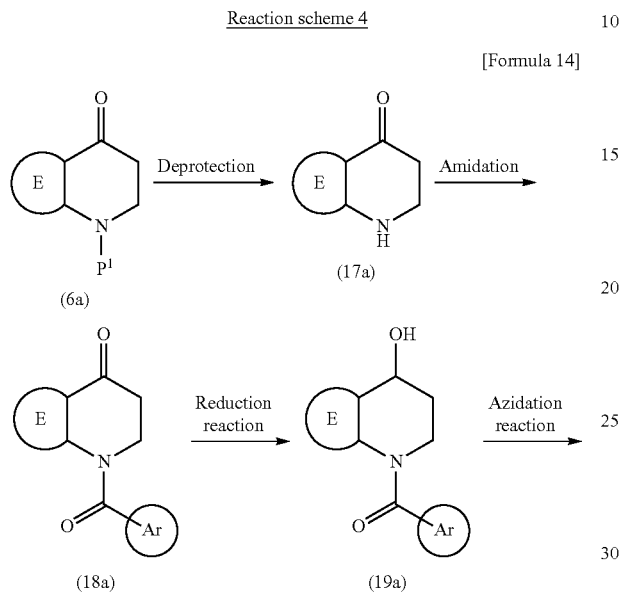

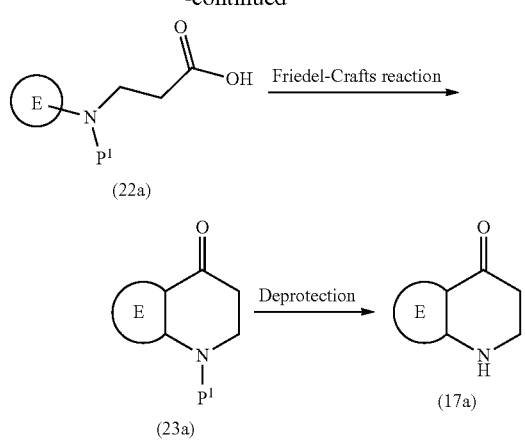

In the reaction scheme, each symbol represents the same meaning as above.

Compound (21a) is commercially available or can be produced by a method known per se in the art or a method equivalent thereto.

Compound (18a) for use in reaction scheme 4 can also be produced by a method shown in the following reaction scheme 6 or a method equivalent thereto:

Reaction scheme 6

[Formula 16]

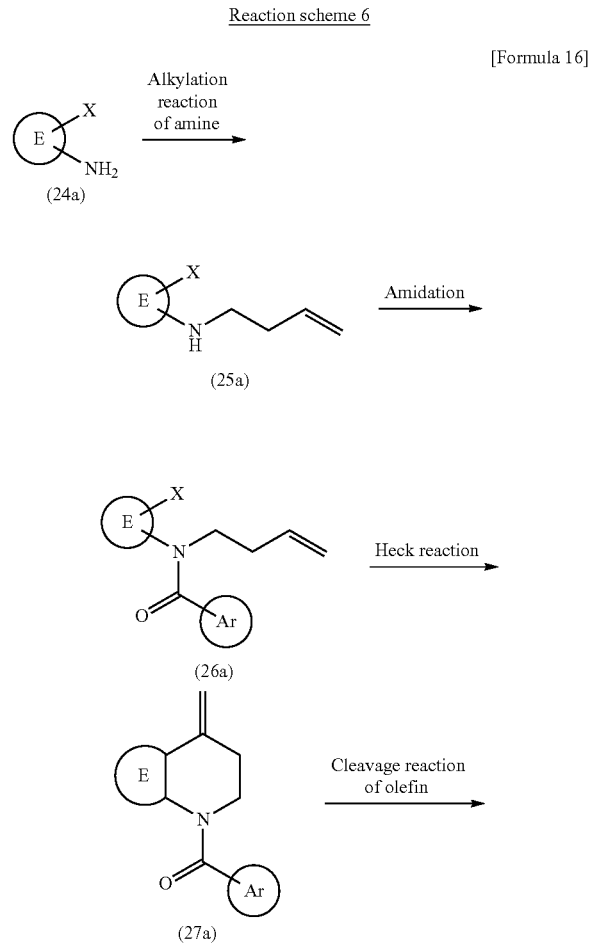

In the reaction scheme, each symbol represents the same meaning as above.

Compound (17a) can also be produced by a method shown in the following reaction scheme 5 or a method equivalent thereto:

Reaction scheme 5

[Formula 15]

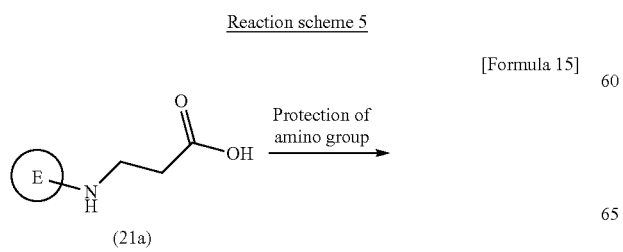

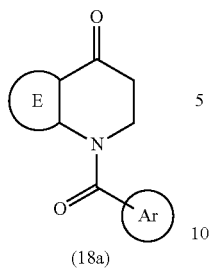

(18a)

In the reaction scheme, X represents a halogen atom (e.g., a bromine atom, an iodine atom), an optionally halogenated $C_{1-6}$ alkylsulfonyloxy group (e.g., methanesulfonyloxy, ethanesulfonyloxy, trichloromethanesulfonyloxy, trifluoromethanesulfonyloxy (triflate)), or an optionally substituted $C_{6-14}$ arylsulfonyloxy group (e.g., a p-toluenesulfonyl group), and the other symbols represent the same meaning as above.

Compound (24a) is commercially available or can be produced by a method known per se in the art or a method equivalent thereto.

Compound (25a) can be produced from compound (24a) through reaction with 4-bromo-1-butene in the presence of a base (e.g., organic bases, metal alkoxides, inorganic bases).

Compound (27a) can be produced by subjecting compound (26a) to intramolecular Heck reaction. The reagents and the reaction conditions mentioned above can be used as a metal catalyst, a phosphine ligand, and a base.

Compound (18a') included in the compound (18a) can be produced by a method shown in the following reaction scheme 7 or a method equivalent thereto:

Reaction scheme 7

[Formula 17]

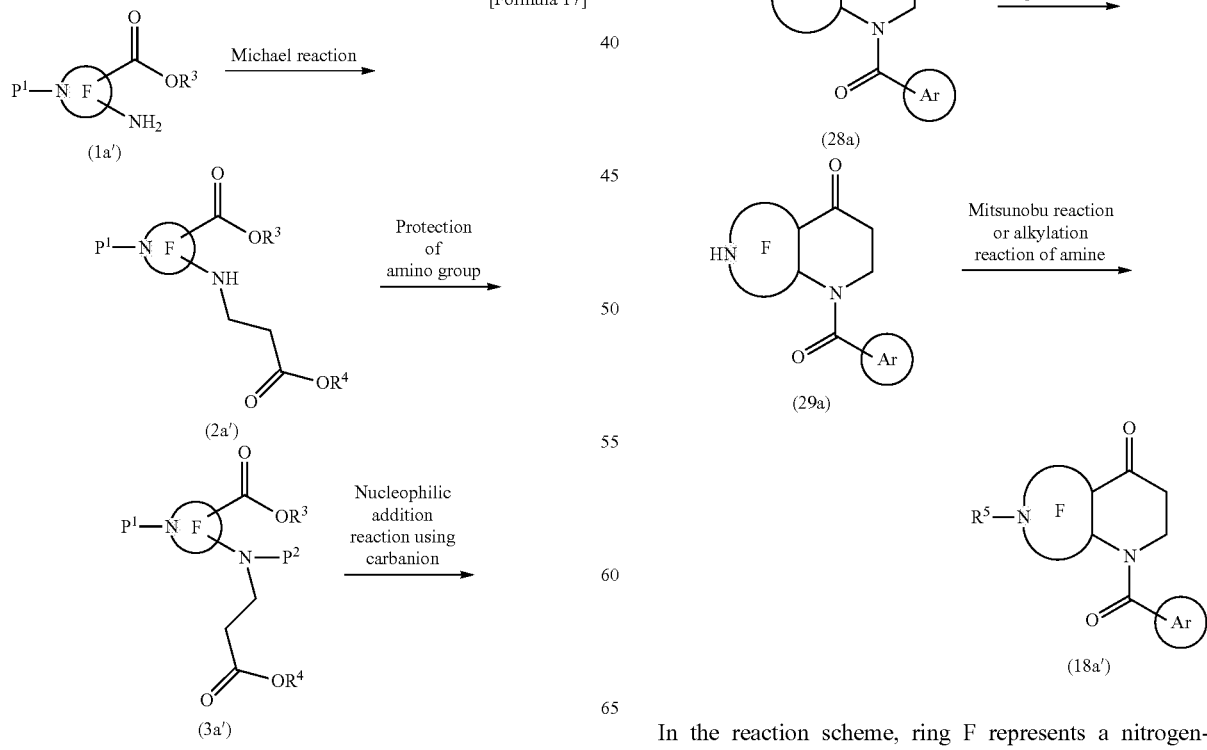

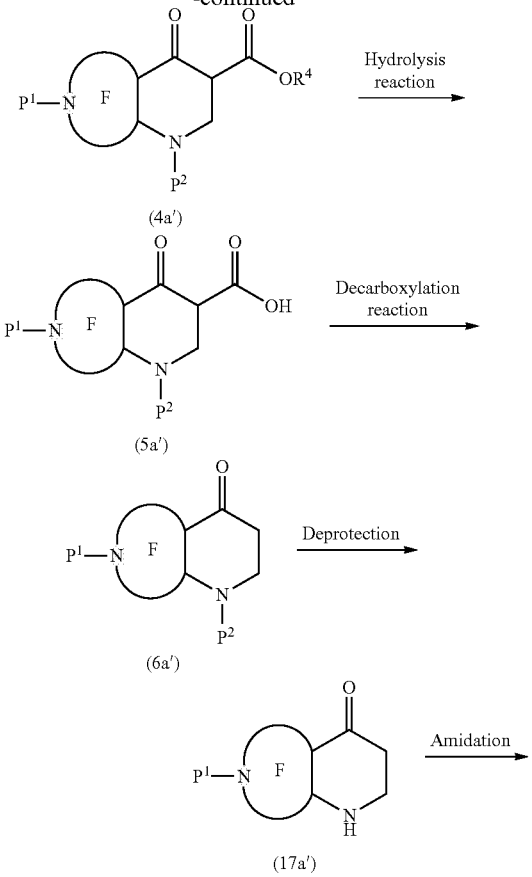

In the reaction scheme, ring F represents a nitrogen-containing 5-membered aromatic heterocycle, $R^5$ represents an optionally substituted $C_{1-20}$ alkyl group, and the other symbols represent the same meaning as above.

Examples of the nitrogen-containing 5-membered aromatic heterocycle represented by ring F include a 5-membered ring containing one or more nitrogen atoms as a ring-constituting atom, among the 5- or 6-membered aromatic heterocycles in the "optionally substituted 5- or 6-membered aromatic heterocycle" formed by $R^1$ and $R^2$ bonded thereto.

Compound (1a') is commercially available or can be produced by a method known per se in the art or a method equivalent thereto.

As mentioned later, other compounds included in the compound (I) or salts thereof can also be produced by the conversion of a substituent (i.e., the introduction of a substituent or functional group conversion) in the compound (I) by the application of an approach known per se in the art.

For example, as shown in the following reaction scheme 8, compound (Ia-1) or compound (Ia-2) can be produced by introducing a substituent to compound (Ia).

Reaction scheme 8

[Formula 18]

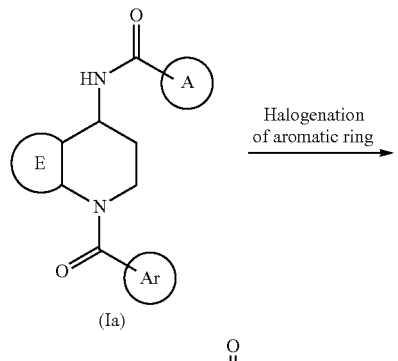

(Ia)

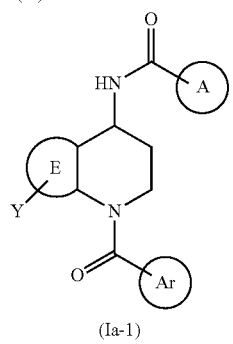

(Ia-1)

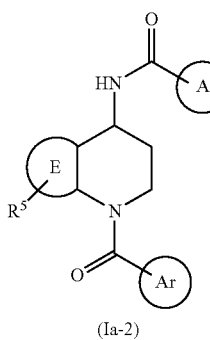

(Ia-2)

In the reaction scheme, Y represents a halogen atom (e.g., a bromine atom, an iodine atom), $R^5$ represents a substituent, and the other symbols represent the same meaning as above.

Compound (Ib) included in the compound (I) can be produced by a method shown in the following reaction scheme 9 or a method equivalent thereto:

Reaction scheme 9

[Formula 19]

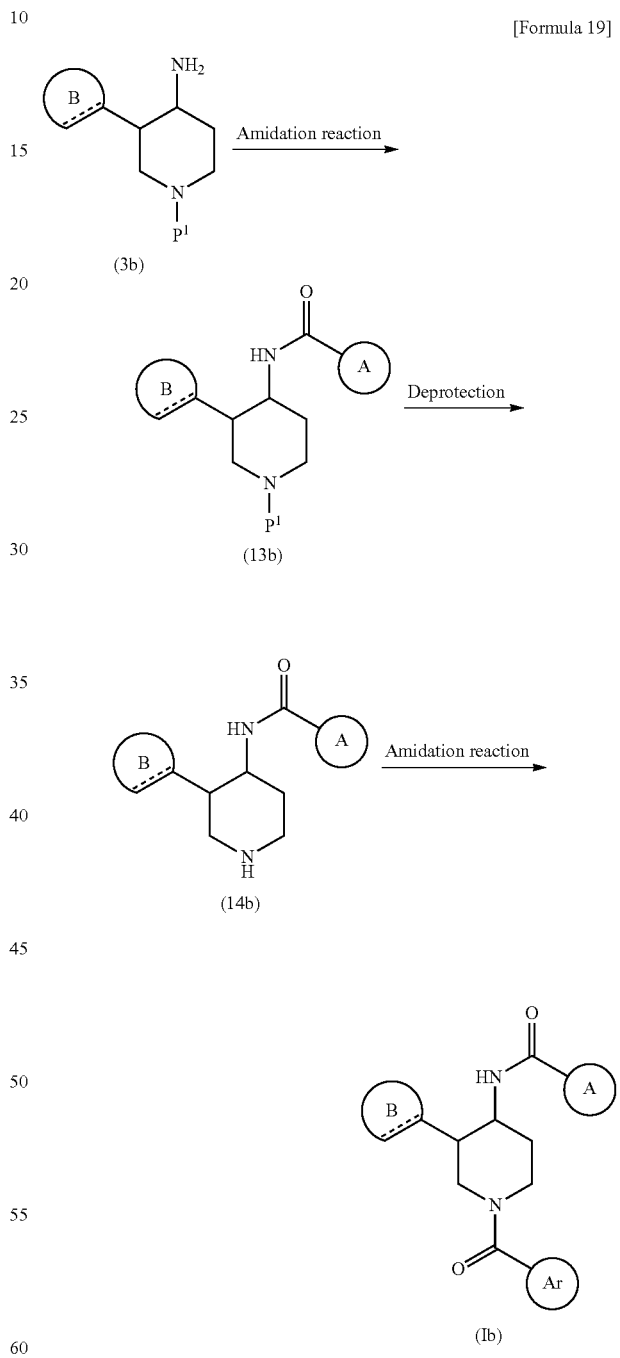

In the reaction scheme, each symbol represents the same meaning as above.

Compound (3b) can be produced by a method shown in the following reaction scheme 10 or a method equivalent thereto:

Reaction scheme 10

[Formula 20]

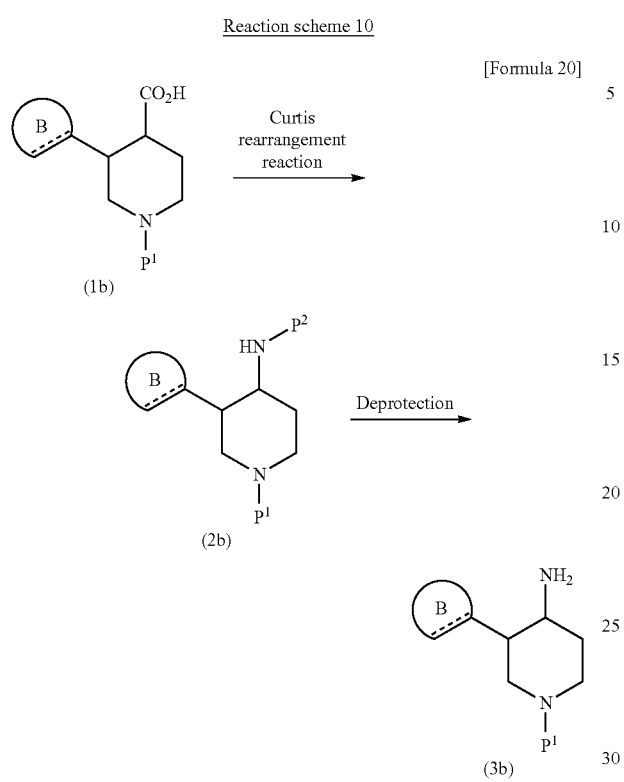

In the reaction scheme, each symbol represents the same meaning as above.

Compound (1b) is commercially available or can be produced by a method known per se in the art or a method equivalent thereto.

Compound (3b) can be produced by a method shown in the following reaction scheme 11 or a method equivalent thereto:

Reaction scheme 11

[Formula 21]

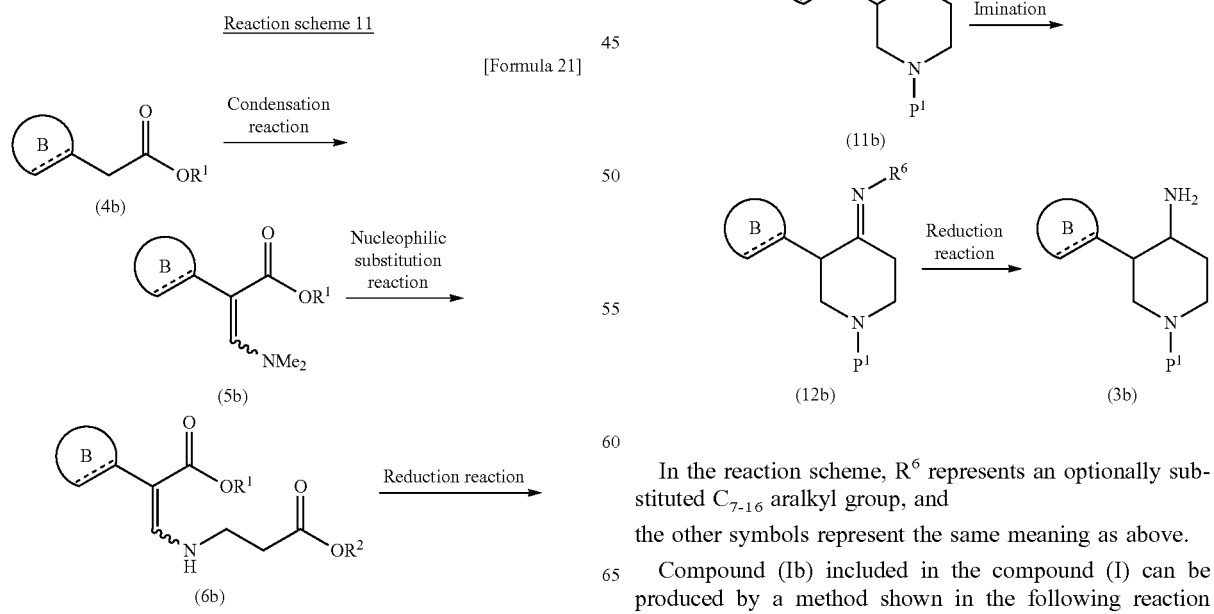

In the reaction scheme, $R^6$ represents an optionally substituted $C_{7-16}$ aralkyl group, and
the other symbols represent the same meaning as above.

Compound (Ib) included in the compound (I) can be produced by a method shown in the following reaction scheme 12 or a method equivalent thereto:

Reaction scheme 12

[Formula 22]

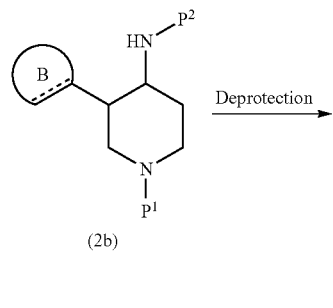

(2b)

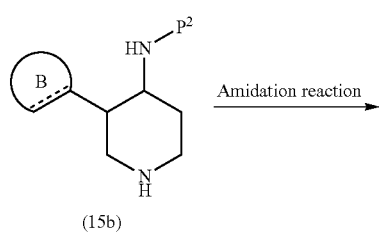

(15b)

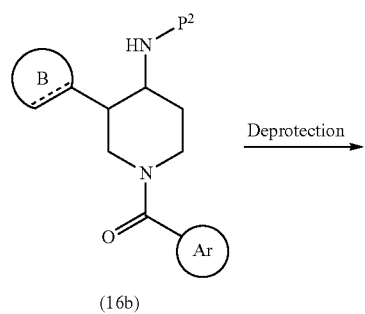

(16b)

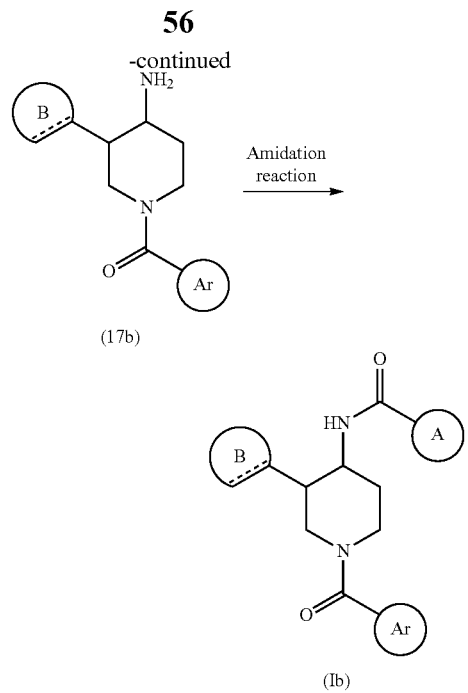

In the reaction scheme, each symbol represents the same meaning as above.

As mentioned later, other compounds included in the compound (I) or salts thereof can also be produced by the conversion of a substituent (i.e., the introduction of a substituent or functional group conversion) in the compound (I) by the application of an approach known per se in the art.

For example, when compound (Ib) has a leaving group (e.g., a halogen atom, a sulfonyl ester group) in ring A, compound (Ib-1) can be produced by a method shown in the reaction scheme 13 given below or a method equivalent thereto.

When compound (Ib) has a protected hydroxy group (e.g., a methoxy group, a benzyloxy group) in ring A, compound (Ib-2) can be produced by a method shown in the following reaction scheme 13 or a method equivalent thereto:

Reaction scheme 13

[Formula 23]

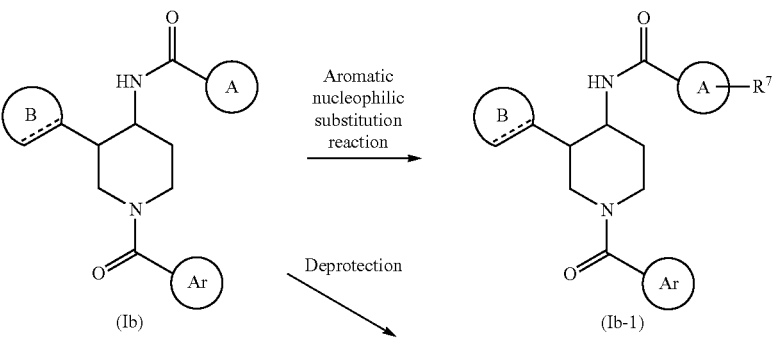

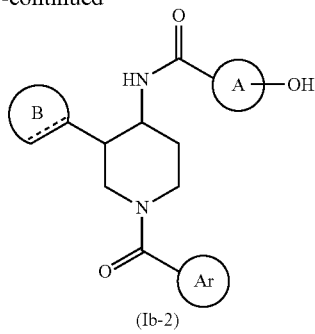
(Ib-2)
In the reaction scheme, $R^7$ represents an optionally substituted $C_{1-6}$ alkoxy group or an optionally substituted $C_{1-6}$ alkylamino group, and
the other symbols represent the same meaning as above.
Compound (Ib-3) included in the compound (I) can be produced by a method shown in the following reaction scheme 14 or a method equivalent thereto:
Reaction scheme 14
[Formula 24]
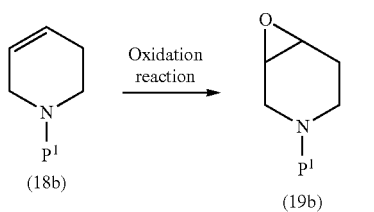
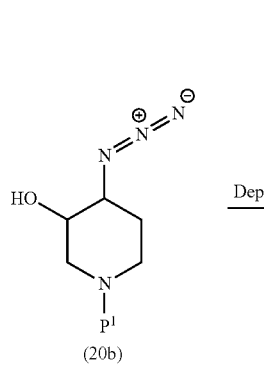
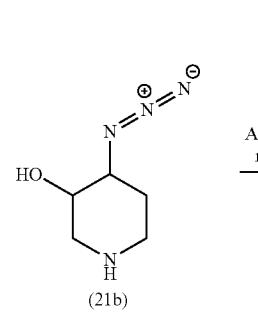
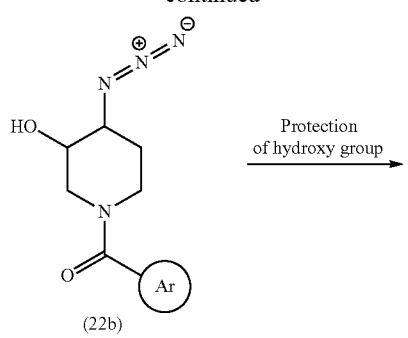
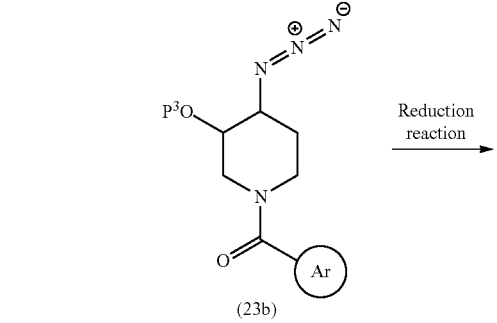
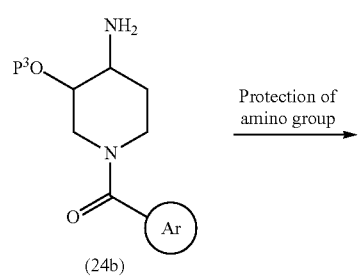
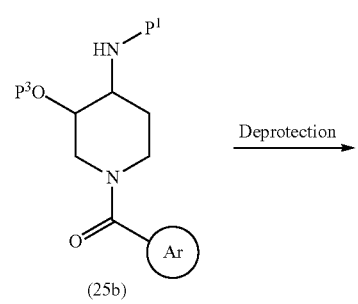

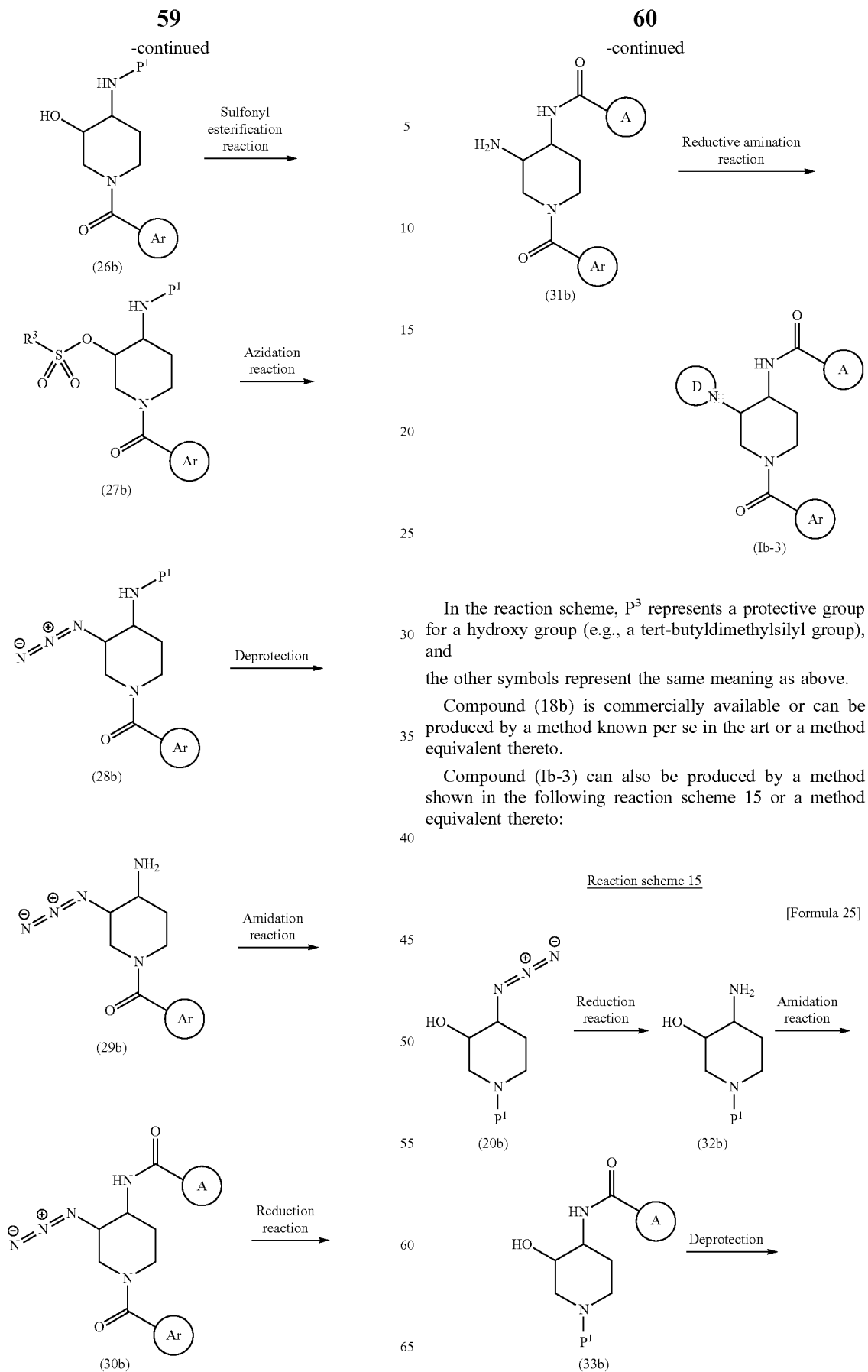

In the reaction scheme, $P^3$ represents a protective group for a hydroxy group (e.g., a tert-butyldimethylsilyl group), and the other symbols represent the same meaning as above.

Compound (18b) is commercially available or can be produced by a method known per se in the art or a method equivalent thereto.

Compound (Ib-3) can also be produced by a method shown in the following reaction scheme 15 or a method equivalent thereto:

Reaction scheme 15

[Formula 25]

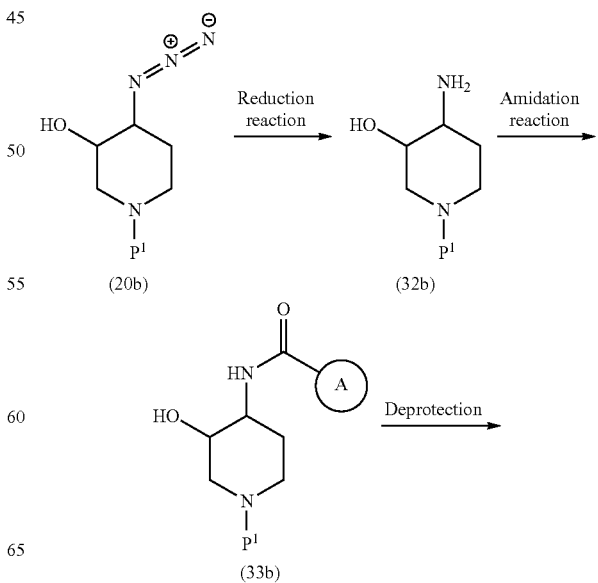

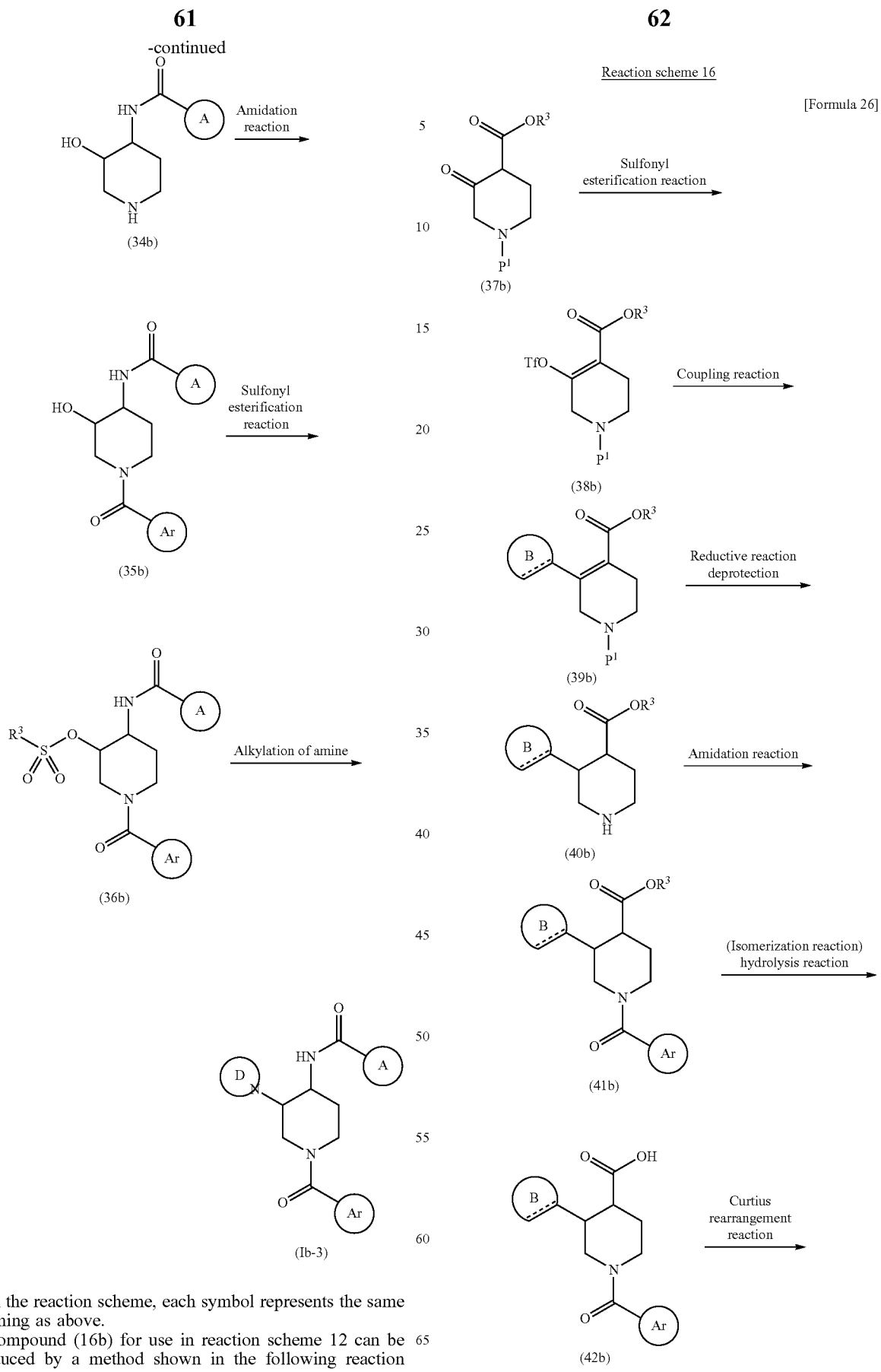
In the reaction scheme, each symbol represents the same meaning as above.
Compound (16b) for use in reaction scheme 12 can be produced by a method shown in the following reaction scheme 16 or a method equivalent thereto:

-continued

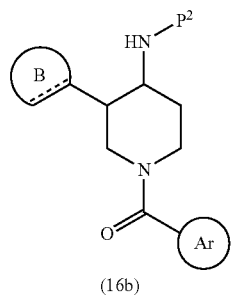

(16b)

In the reaction scheme, each symbol represents the same meaning as above.

Compound (37b) is commercially available or can be produced by a method known per se in the art or a method equivalent thereto.

Compound (38b) can be produced through the reaction of compound (37b) with trifluoromethanesulfonic anhydride in the presence of a base (e.g., organic bases, metal alkoxides, inorganic bases).

In the conversion of compound (41b) to compound (42b), a base (e.g., organic bases, metal alkoxides, inorganic bases) can be used for isomerization, if necessary.

Depending on the type of a substituent in a starting compound, the starting compound differing in substituent therefrom can be produced by the application of an approach known per se in the art using a compound produced by any of the production methods described above as a starting material.

The compound (I), which is a product of these reactions, or a salt thereof may be produced as a single compound or as a mixture.

The compound (I) thus obtained or a salt thereof can be isolated and/or purified by a separation approach known per se in the art, for example, concentration, concentration under reduced pressure, solvent extraction, crystallization, recrystallization, dissolution, chromatography or the like.

The compound (I) obtained in a free form can be converted to a salt of interest by a method known per se in the art or a method equivalent thereto. On the other hand, the compound (I) obtained in a salt form can be converted to a free form or a different salt of interest by a method known per se in the art or a method equivalent thereto.

Other compounds included in the compound (I) or salts thereof can also be produced by the conversion of a substituent (i.e., the introduction of a substituent or functional group conversion) in the compound (I) thus obtained by the application of an approach known per se in the art.

A general method known in the art is used as a method for the introduction of a substituent or the functional group conversion. Examples thereof include conversion of a halogen atom (e.g., fluorine, chlorine, bromine, iodine) or an optionally halogenated $C_{1-6}$ alkylsulfonyl-oxy group [e.g., methanesulfonyloxy, ethanesulfonyloxy, trichloromethanesulfonyloxy, trifluoromethanesulfonyloxy (triflate)] to a methyl group, a cyclopropyl group, a vinyl group, a cyano group, a formyl group, a carbonyl group, a carboxyl group, a hydroxy group, an amino group, a boryl group or the like, conversion of a formyl group to an ethynyl group through Seyferth-Gilbert homologation reaction, conversion to a carboxy group by hydrolysis of an ester, conversion of a carboxy group to a carbamoyl group by amidation, conversion of a carboxy group to a hydroxymethyl group by reduction, conversion of a carbonyl group to an alcohol form by reduction or alkylation, reductive amination of a carbonyl group, oximation of a carbonyl group, acylation of an amino group, ureation of an amino group, sulfonylation of an amino group, alkylation of an amino group, substitution or amination of active halogen using amine, alkylation of a hydroxy group and substitution or amination of a hydroxy group.

For this introduction of a substituent or functional group conversion, a protective group is introduced beforehand to a reactive site, if present, at which unintended reaction occurs, by an approach known per se in the art according to the need, and after the reaction of interest, the protective group can be removed again by an approach known per se in the art to produce a compound included in the scope of the present invention.

When a starting compound or an intermediate has, for example, an amino group, a carboxyl group or a hydroxy group as a substituent, the group may be protected with a protective group as generally used in peptide chemistry or the like. In this case, after the reaction, the protective group can be removed according to the need to obtain the compound of interest.

When the compound (I) has isomers such as optical isomers, stereoisomers, positional isomers, rotational isomers or the like, either of the isomers and a mixture thereof are both included in the compound (I). When the compound (I) has, for example, optical isomers, the optical isomers resolved from a racemate are also included in the compound (I). These isomers can each be obtained as a single product by a synthesis approach and a separation approach known per se in the art (e.g., concentration, solvent extraction, column chromatography, recrystallization).

The compound (I) may be crystalline. A single crystal form and a mixture of crystal forms are both included in the compound (I). The crystals can be produced by crystallization by the application of a crystallization method known per se in the art.

Also, the compound (I) may be a pharmaceutically acceptable cocrystal or cocrystal salt. In this context, the cocrystal or the cocrystal salt means a crystalline substance constituted by two or more unique solids at room temperature, each having distinctive physical properties (e.g., structure, melting point, heat of melting, hygroscopicity, stability). The cocrystal and the cocrystal salt can be produced according to a cocrystallization method known per se in the art.

The compound (I) may be a hydrate, a non-hydrate, a solvate or a non-solvate. All of them are included in the compound (I).

A compound labeled or substituted with an isotope (e.g., $^2$H, $^3$H, $^{11}$C, $^{14}$C, $^{18}$F, $^{35}$S, $^{125}$I) or the like is also included in the compound (I). The compound (I) labeled or substituted with an isotope can be used as, for example, a tracer (PET tracer), in positron emission tomography (PET) and can be useful in fields of medical diagnosis and the like.

The compound (I) may be a prodrug.

The prodrug of the compound (I) refers to a compound that is converted to the compound (I) through a reaction caused by an enzyme, gastric acid or the like under physiological conditions in vivo, i.e., a compound that is converted to the compound (I) by enzymatic oxidation, reduction, hydrolysis, etc., or a compound that is converted to the compound (I) by hydrolysis, etc., caused by gastric acid or the like.

Examples of the prodrug of the compound (I) include:
(1) a compound in which amino of the compound (I) is acylated, alkylated or phosphorylated (e.g., a compound in which amino of the compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, ethoxycarbonylated, tert-butoxycarbonylated, acetylated, cyclopropylcarbonylated, etc.);

(2) a compound in which hydroxy of the compound (I) is acylated, alkylated, phosphorylated or borated (e.g., a compound in which hydroxy of the compound (I) is acetylated, palmitoylated, propanoylated, pivaloylated, succinylated, fumarylated, alanylated, dimethylaminomethylcarbonylated, etc.); and (3) a compound in which carboxy of the compound (I) is esterified or amidated (e.g., a compound in which carboxy of the compound (I) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, methylamidated, etc.). These compounds can be produced from the compound (I) by a method known per se in the art.

The prodrug of the compound (I) may be converted to the compound (I) under physiological conditions as described in Iyakuhin No Kaihatsu (Development of Pharmaceuticals in English), Vol. 7, Molecular Design, p. 163-198, Hirokawa Shoten Ltd. (1990).

The compound (I) or the prodrug thereof (in the present specification, these are also collectively referred to as the "compound of the present invention") can have SPT inhibitory activity and can be useful as a prophylactic or therapeutic agent for cancer, a cancer growth inhibitor, a cancer metastasis inhibitor, a prophylactic or therapeutic agent for Niemann-Pick disease, an anti-inflammatory agent, an immunomodulatory agent, an antianxiety agent and an anticonvulsant agent.

The compound of the present invention can have selective inhibitory activity against SPT. In addition, the compound of the present invention can be expected to be also excellent in efficacy development, pharmacokinetics (e.g., absorbability, distribution, metabolism, excretion), solubility (e.g., water solubility), interaction with other medicaments (e.g., drug-metabolizing enzyme inhibitory effect), safety (e.g., acute toxicity, chronic toxicity, genotoxicity, reproductive toxicity, cardiotoxicity, carcinogenicity, central toxicity) and stability (e.g., chemical stability, stability against enzymes) and can therefore be useful as a medicament.

The compound of the present invention can have selective inhibitory activity against SPT and can therefore be useful as a prophylactic or therapeutic agent for cancer with reduced toxicity to normal cells.

Thus, the compound of the present invention is capable of inhibiting excessive (abnormal) SPT effects in a mammal (e.g., a mouse, a rat, a hamster, a rabbit, a cat, a dog, cattle, sheep, a monkey, a human).

The compound of the present invention can be used as a medicament such as a prophylactic or therapeutic agent for diseases that are probably influenced by SPT (in the present specification, also referred to as "SPT-related diseases"), for example, cancer [e.g., large intestine cancer (e.g., colon cancer, rectal cancer, anus cancer, familial colorectal cancer, hereditary non-polyposis colorectal cancer, gastrointestinal stromal tumor), lung cancer (e.g., non-small cell lung cancer (lung adenocarcinoma, etc.), small-cell lung cancer, malignant mesothelioma), mesothelioma, pancreatic cancer (e.g., ductal pancreatic cancer, pancreatic endocrine tumor), throat cancer, voice box cancer, head and neck cancer, esophageal cancer, stomach cancer (e.g., papillary adenocarcinoma, mucous adenocarcinoma, adenosquamous carcinoma), duodenal cancer, small intestine cancer, breast cancer (e.g., invasive ductal breast cancer, noninvasive ductal breast cancer, inflammatory breast cancer), ovarian cancer (e.g., epithelial ovarian cancer, extragonadal germ cell tumor, ovarian germ cell tumor, ovarian tumor of low malignant potential), testicular tumor, prostate cancer (e.g., hormone-dependent prostate cancer, hormone-independent prostate cancer, castration-resistant prostate cancer), liver cancer (e.g., hepatocellular cancer, primary liver cancer, extrahepatic bile duct cancer), thyroid cancer (e.g., medullary thyroid cancer), kidney cancer (e.g., renal cell cancer (e.g., clear cell renal cell carcinoma), transitional cell cancer of the renal pelvis and ureter), uterine cancer (e.g., uterine cervical cancer, uterine body cancer, uterine sarcoma), gestational choriocarcinoma, brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basalioma, malignant melanoma), sarcoma (e.g., rhabdomyosarcoma, leiomyosarcoma, soft tissue sarcoma, spindle cell sarcoma), malignant bone tumor, bladder cancer, blood cancer (e.g., multiple myeloma, leukemia, malignant lymphoma, Hodgkin disease, chronic myeloproliferative disease), primary unknown cancer], a cancer growth inhibitor, a cancer metastasis inhibitor, an apoptosis promoter, a therapeutic agent for premalignant lesions (e.g., myelodysplastic syndrome) or the like.

The compound of the present invention can also be useful as a prophylactic agent or a therapeutic agent for other SPT-related diseases (e.g., heart diseases (cardiomegaly, acute heart failure and chronic heart failure including congestive heart failure, cardiomyopathy, angina pectoris, myocarditis, arrhythmia, tachycardia, myocardial infarction, etc.), myocardial ischemia, venous insufficiency, post-myocardial infarction heart failure, hypertension, cor pulmonale, arteriosclerosis including atherosclerosis (aneurysm, coronary arteriosclerosis, cerebral arteriosclerosis, peripheral arteriosclerosis, etc.), vascular hypertrophy, vascular hypertrophy or occlusion and organ disorder after intervention (percutaneous transluminal coronary angioplasty, stent placement, coronary angioscopy, intravascular ultrasonography, intracoronary thrombolytic therapy, etc.), vascular reocclusion or restenosis after bypass surgery, respiratory diseases (acute pulmonary disorder), bone diseases (non-metabolic bone diseases such as fracture, refracture, bone deformity or osteoarthritis, osteosarcoma, myeloma, dysostosis, scoliosis and the like; bone defect, osteoporosis, osteomalacia, rachitis, osteitis fibrosa, renal osteodystrophy, Behcet's disease in bone, ankylosing spondylitis, chronic rheumatoid arthritis, osteoarthritis knees and destruction of joint tissues in similar diseases thereto, etc.), diabetic complications (retinopathy, nephropathy, neuropathy, macroangiopathy, etc.), chronic rheumatoid arthritis, osteoarthritis, rheumatoid myelitis, neurodegenerative diseases (Alzheimer's disease, Parkinson's disease, amyotrophic lateral sclerosis, AIDS encephalopathy, etc.), central nervous system disorders (disorders such as cerebral hemorrhage and cerebral infarction and the like, and sequelae or complications thereof, spinal cord injury, cerebral edema, encephalomyelitis, etc.), dementia, dysmnesia, impaired consciousness, amnesia, anxiety symptoms, myotonia symptoms, ischemic peripheral circulatory disturbance, deep vein thrombosis, obstructive peripheral circulatory disturbance, arteriosclerosis obliterans, thromboangiitis obliterans, diabetic complications (neuropathy, nephropathy, retinopathy, cataract, macroangiopathy, osteopenia, diabetic hyperosmolar coma, infection, diabetic gangrene, oral dryness, decline in hearing, cerebrovascular accident, peripheral arterial disease, etc.), disturbance of metabolism or malnutrition (hyperlipidemia, hypercholesterolemia, low-HDL cholesterol, impaired glucose tolerance, etc.), insulin resistance syndrome, syndrome X, metabolic syndrome, cerebrovascular accident (asymptomatic cerebrovascular accident, transient ischemic attack, cerebral apoplexy, vascular dementia, hypertensive encephalopathy, cerebral infarction, etc.), cerebral edema, cerebral circulatory disturbance, recurrence and sequelae of cerebrovascular accident (neurological signs, mental signs, subjective symptoms, disturbance in activities of daily living, etc.), renal diseases (nephritis, glomerulonephritis, glomerulosclerosis, renal failure, thrombotic microangiopathy, diabetic nephropathy, nephrotic syndrome, hypertensive nephrosclerosis, complications of dialysis, organopathy including nephritis caused by radiation, etc.), eye diseases (glaucoma, ocular hypertension, etc.), thrombosis, multiple organ failure, endothelial dysfunction, hepatic diseases (hepatitis including hepatitis C, liver cirrhosis, etc.), gastrointestinal diseases (gastritis, gastric ulcer, stomach cancer, disorders after gastric surgery, esophageal ulcer, pancreatitis, colorectal polyp, cholelithiasis, inflammatory bowel disease (IBD), etc.), blood or hematopoietic diseases (polycythemia, vascular purpura, disseminated intravascular coagulation, multiple myeloma, etc.), urological or male genital diseases (cystitis, benign prostatic hyperplasia, sexually transmitted disease, etc.), gynecological diseases (climacteric disorder, gestosis, endometriosis, ovarian disease, mammary gland disease, sexually transmitted disease, etc.), infectious diseases (viral infection caused by cytomegalovirus, influenza virus, herpes virus or the like, rickettsial infection, bacterial infection, etc.), toxemia (sepsis, septic shock, endotoxin shock, gram negative sepsis, toxin shock syndrome, etc.), congenital diseases associated with sphingolipid accumulation (Fabry disease, Niemann-Pick disease (e.g., types A, B, C, D), Gaucher disease, Tay-Sachs disease)), skin diseases (contact dermatitis, etc.), painful affection (acute and chronic pain, persistent pain (alganesthesia, analgesia, etc.), etc.), inflammation-related diseases and immune-related diseases.

Particularly, the compound of the present invention can be useful as a prophylactic or therapeutic agent for cancer or a prophylactic or therapeutic agent for Niemann-Pick disease.

The compound of the present invention can be orally or parenterally administered as a medicament containing the compound of the present invention alone or as a mixture with a pharmacologically acceptable carrier to a mammal (preferably a human).

Hereinafter, the medicament comprising the compound of the present invention (also referred to as the "medicament of the present invention") will be described in detail. Examples of the dosage form of the medicament of the present invention include an oral preparation such as tablets (e.g., sugar-coated tablets, film-coated tablets, sublingual tablets, buccal tablets and rapidly orally disintegrating tablets), pills, granules, powders, capsules (e.g., soft capsules and microcapsules), syrups, emulsions, suspensions, films (e.g., orally disintegrating films and patch films for application to the oral mucosa) and the like. Other examples of the dosage form of the medicament of the present invention include a parenteral preparation such as injections, transfusions, transdermal preparations (e.g., iontophoresis dermal preparations), suppositories, ointments, transnasal preparations, transpulmonary preparations, eye drops and the like. Alternatively, the medicament of the present invention may be a controlled-release preparation such as a rapid-release preparation, a sustained-release preparation (e.g., a sustained-release microcapsule) or the like.

The medicament of the present invention can be produced by a production method known in the art (e.g., a method described in Japanese Pharmacopoeia) generally used in the field of pharmaceutical technology. If necessary, the medicament of the present invention can appropriately contain an appropriate amount of an additive usually used in the pharmaceutical field, such as an excipient, a binder, a disintegrant, a lubricant, a sweetener, a surfactant, a suspending agent, an emulsifier, a colorant, a preservative, a fragrance, a corrigent, a stabilizer, a viscosity modifier and the like.

Examples of the pharmacologically acceptable carrier described above include these additives.

For example, the tablets can be produced using an excipient, a binder, a disintegrant, a lubricant and the like. The pills and the granules can be produced using an excipient, a binder and a disintegrant. The powders and the capsules can be produced using an excipient and the like. The syrups can be produced using a sweetener and the like. The emulsions or the suspensions can be produced using a suspending agent, a surfactant, an emulsifier and the like.

Examples of the excipient include lactose, saccharose, glucose, starch, sucrose, microcrystalline cellulose, licorice powder, mannitol, sodium bicarbonate, calcium phosphate and calcium sulfate.

Examples of the binder include a solution containing 5 to 10% by weight of starch paste, a solution containing 10 to 20% by weight of gum arabic or gelatin, a solution containing 1 to 5% by weight of tragacanth, a carboxymethylcellulose solution, a sodium alginate solution and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, carboxymethylcellulose sodium, methylcellulose and bentonite.

Examples of the emulsifier include gum arabic, tragacanth, gelatin and polysorbate 80.

When the medicament of the present invention is, for example, tablets, the tablets can be produced according to a method known per se in the art by adding, for example, an excipient (e.g., lactose, saccharose, starch), a disintegrant (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethylene glycol 6000) to the compound of the present invention and molding the mixture by compression, followed by coating, if necessary, by a method known per se in the art for the purpose of taste masking, enteric properties or durability. For example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm GmbH, Germany, methacrylic acid-acrylic acid copolymer) and a dye (e.g., iron red, titanium dioxide) are used as coating agents for the coating.

The injections include intravenous injections as well as subcutaneous injections, intracutaneous injections, intramuscular injections, intraperitoneal injections, drip injections and the like.

Such injections are prepared by a method known per se in the art, i.e., by dissolving, suspending or emulsifying the compound of the present invention in a sterile aqueous solution or oily solution. Examples of the aqueous solution include saline, an isotonic solution containing glucose or an additional adjuvant (e.g., D-sorbitol, D-mannitol, sodium chloride) and the like. The aqueous solution may contain an appropriate solubilizing agent, for example, an alcohol (e.g., ethanol), a polyalcohol (e.g., propylene glycol, polyethylene glycol) or a nonionic surfactant (e.g., polysorbate 80, HCO-50). Examples of the oily solution include sesame oil, soybean oil and the like. The oily solution may contain an appropriate solubilizing agent. Examples of the solubilizing agent include benzyl benzoate, benzyl alcohol and the like. The injections may be further supplemented with a buffer (e.g., a phosphate buffer solution, a sodium acetate buffer solution), a soothing agent (e.g., benzalkonium chloride, procaine hydrochloride), a stabilizer (e.g., human serum albumin, polyethylene glycol), a preservative (e.g., benzyl alcohol, phenol) or the like. Ampules are usually filled with the prepared injection solutions.

The content of the compound of the present invention in the medicament of the present invention differs depending on the form of the preparation and is usually approximately 0.01 to approximately 100% by weight, preferably approximately 2 to approximately 85% by weight, more preferably approximately 5 to approximately 70% by weight, with respect to the whole preparation.

The content of the additive in the medicament of the present invention differs depending on the form of the preparation and is usually approximately 1 to approximately 99.9% by weight, preferably approximately 10 to approximately 90% by weight, with respect to the whole preparation.

The compound of the present invention can be used stably, low toxically and safely. The daily dose of the compound of the present invention can differ depending on the status and body weight of a patient, the type of the compound, an administration route, etc. In the case of, for example, oral administration to a patient for the purpose of treating cancer, the daily dose in adult (body weight: approximately 60 kg) can be approximately 1 to approximately 1000 mg, preferably approximately 3 to approximately 300 mg, more preferably approximately to approximately 200 mg, of the compound of the present invention, which can be administered in one portion or in two or three portions.

In the case of parenterally administering the compound of the present invention, the compound of the present invention is usually administered in the form of a solution (e.g., an injection). The single dose of the compound of the present invention also can differ depending on a recipient, a target organ, symptoms, an administration method, etc. For example, usually approximately 0.01 to approximately 100 mg, preferably approximately 0.01 to approximately 50 mg, more preferably approximately 0.01 to approximately 20 mg, of the compound of the present invention per kg of body weight can be administered by intravenous injection.

The compound of the present invention can be used in combination with an additional drug. Specifically, the compound of the present invention can be used in combination with a drug such as a hormone therapeutic, a chemotherapeutic, an immunotherapeutic, an agent inhibiting the effects of a cell growth factor and its receptor, or the like. The compound of the present invention can be further used in combination with an enzyme replacement therapeutic, a Chaperone therapeutic, a substrate reduction therapeutic, a cyclodextrin preparation, gene therapy to express a therapeutic enzyme protein, or cell therapy such as bone marrow transplantation and the like, for congenital diseases associated with sphingolipid accumulation (including Niemann-Pick disease) or the like. Hereinafter, the drug that may be used in combination with the compound of the present invention is referred to as a concomitant drug.

Examples of the "hormone therapeutic" that may be used include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), contraceptive pills, mepitiostane, testololactone, aminoglutethimide, LH-RH agonists (e.g., goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgen (e.g., flutamide, bicalutamide, nilutamide, enzalutamide), 5α-reductase inhibitors (e.g., finasteride, epristeride, dutasteride), adrenal corticosteroid agents (e.g., dexamethasone, prednisolone, betamethasone, triamcinolone), androgen synthesis inhibitors (e.g., abiraterone), retinoid and agents delaying retinoid metabolism (e.g., liarozole), thyroid hormones and DDS (drug delivery system) preparations thereof.

Examples of the "chemotherapeutic" that may be used include an alkylating agent, an antimetabolite, an anticancer antibiotic and a plant-derived anticancer agent.

Examples of the "alkylating agent" that may be used include nitrogen mustard, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, Ribomustin, temozolomide, treosulfan, trofosfamide, zinostatin stimalamer, adozelesin, cystemustine, bizelesin and DDS preparations thereof.

Examples of the "antimetabolite" that may be used include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, galocitabine, emitefur, capecitabine), aminopterin, nelarabine, leucovorin calcium, Tabloid, butocine, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine and DDS preparations thereof.

Examples of the "anticancer antibiotic" that may be used include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride and DDS preparations (e.g., PEG liposomal doxorubicin) thereof.

Examples of the "plant-derived anticancer agent" that may be used include etoposide, etoposide phosphate, vinblastine sulfate, vincristine sulfate, vindesine sulfate, teniposide, paclitaxel, docetaxel, cabazitaxel, vinorelbine and DDS preparations thereof.

Examples of the "immunotherapeutic" that may be used include picibanil, Krestin, schizophyllan, lentinan, ubenimex, interferon, interleukin, macrophage colony-stimulating factor, granulocyte colony-stimulating factor, erythropoietin, lymphotoxin, BCG vaccines, *Corynebacterium parvum*, levamisole, polysaccharide K, procodazol, anti-CTLA4 antibodies (e.g., ipilimumab, tremelimumab), anti-PD-1 antibodies (e.g., nivolumab, pembrolizumab) and anti-PD-L1 antibodies.

The "cell growth factor" in the "agent inhibiting the effects of a cell growth factor and its receptor" can be any substance that promotes the growth of cells. Typical examples thereof include a factor that is a peptide having a molecular weight of 20,000 or smaller and exerts its effects at a low concentration through binding to its receptor. Specific examples of the cell growth factor that may be used include (1) EGF (epidermal growth factor) or a substance having activity substantially identical thereto [e.g., TGFα], (2) insulin or a substance having activity substantially identical thereto [e.g., insulin, IGF (insulin-like growth factor)-1, IGF-2], (3) FGF (fibroblast growth factor) or a substance having activity substantially identical thereto [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin].

The "receptor of the cell growth factor" can be any receptor having the ability to bind to any of the cell growth factor described above. Specific examples of the receptor that may be used include EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor and the like.

Examples of the "agent inhibiting the effects of a cell growth factor and its receptor" that may be used include EGF inhibitors, TGFα inhibitors, heregulin inhibitors, insulin inhibitors, IGF inhibitors, FGF inhibitors, KGF inhibitors, CSF inhibitors, EPO inhibitors, IL-2 inhibitors, NGF inhibitors, PDGF inhibitors, TGFβ inhibitors, HGF inhibitors, VEGF inhibitors, angiopoietin inhibitors, EGF receptor inhibitors, HER2 inhibitors, HER4 inhibitors, insulin receptor inhibitors, IGF-1 receptor inhibitors, IGF-2 receptor inhibitors, FGF receptor-1 inhibitors, FGF receptor-2 inhibitors, FGF receptor-3 inhibitors, FGF receptor-4 inhibitors, VEGF receptor inhibitors, Tie-2 inhibitors, PDGF receptor inhibitors, Abl inhibitors, Raf inhibitors, FLT3 inhibitors, c-Kit inhibitors, Src inhibitors, PKC inhibitors, Smo inhibitors, ALK inhibitors, ROR1 inhibitors, Trk inhibitors, Ret inhibitors, mTOR inhibitors, Aurora inhibitors, PLK inhibitors, MEK (MEK1/2) inhibitors, MET inhibitors, CDK inhibitors, Akt inhibitors, ERK inhibitors, PI3K inhibitors and the like. More specific examples of the agent that may be used include anti-VEGF antibodies (e.g., bevacizumab, ramucirumab), anti-HER2 antibodies (e.g., trastuzumab, pertuzumab), anti-EGFR antibodies (e.g., cetuximab, panitumumab, matuzumab, nimotuzumab), anti-HGF antibodies, imatinib, erlotinib, gefitinib, sorafenib, sunitinib, dasatinib, lapatinib, vatalanib, ibrutinib, bosutinib, cabozantinib, crizotinib, alectinib, vismodegib, axitinib, motesanib, nilotinib, 6-[4-(4-ethylpiperazin-1-ylmethyl)phenyl]-N-[1(R)-phenylethyl]-7H-pyrrolo[2,3-d]pyrimidin-4-amine (AEE-788), vandetanib, temsirolimus, everolimus, enzastaurin, tozasertib, phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazapin-2-ylamino]benzoic acid, N-[2-methoxy-5-[(E)-2-(2,4,6-trimethoxyphenyl)vinylsulfonylmethyl]phenyl] glycine sodium salt (ON-1910Na), volasertib, selumetinib, trametinib, N-[2(R),3-dihydroxypropoxy]-3,4-difluoro-2-(2-fluoro-4-iodophenylamino)benzamide (PD-0325901), bosutinib, regorafenib, afatinib, idelalisib, ceritinib, dabrafenib and the like.

In addition to the drugs described above, examples also include L-asparaginase, L-arginase, arginine deiminase, aceglatone, procarbazine hydrochloride, protoporphyrin-cobalt complex salt, mercury hematoporphyrin-sodium, topoisomerase I inhibitors (e.g., irinotecan, topotecan, indotecan, indimitecan), topoisomerase II inhibitors (e.g., sobuzoxane), differentiation inducers (e.g., retinoid, vitamins D), other angiogenesis inhibitors (e.g., fumagillin, shark extracts, COX-2 inhibitors), α-blockers (e.g., tamsulosin hydrochloride), bisphosphonic acids (e.g., pamidronate, zoledronate), thalidomide, lenalidomide, pomalidomide, 5-azacytidine, decitabine, proteasome inhibitors (e.g., bortezomib, carfilzomib, ixazomib), NEDD8 inhibitors (e.g., pevonedistat), UAE inhibitors, PARP inhibitors (e.g., olaparib, niraparib, veliparib), antitumor antibodies such as anti-CD20 antibodies (e.g., rituximab, obinutuzumab), anti-CCR4 antibodies (e.g., mogamulizumab) and the like, antibody-drug conjugates (e.g., trastuzumab emtansine, brentuximab vedotin) or the like.

Examples of the "enzyme replacement therapeutic" include agalsidase α, agalsidase β, olipudase alfa, alglucerase and the like.

Examples of the "Chaperone therapeutic" include migalastat and the like.

Examples of the "substrate reduction therapeutic" include miglustat and the like.

Examples of the "cyclodextrin preparation" include hydroxyprolyl-β, γ-cyclodextrin and the like.

Examples of the "gene therapy" include a treatment method which involves transferring a vector of adeno-associated virus (AAV) or the like to a normal gene, and the like.

Examples of the "cell therapy" include a treatment method which involves transplanting hematopoietic stem cell source such as a bone marrow stem cell, a peripheral blood stem cell or the like.

The combination of the compound of the present invention and the concomitant drug can produce excellent effects such as: (1) the dose of the compound of the present invention or the concomitant drug can be reduced as compared with the administration of the compound of the present invention or the concomitant drug alone; (2) the concomitant drug can be selected for combined use with the compound of the present invention according to the symptoms (mild, serious, etc.) of a patient; (3) the period of treatment can be set longer; (4) a sustained therapeutic effect can be achieved; (5) a synergistic effect can be obtained by the combined use of the compound of the present invention and the concomitant drug; and the like.

Hereinafter, the combined use of the compound of the present invention and the concomitant drug is referred to as the "combination drug of the present invention".

For use of the combination drug of the present invention, the time of administration of the compound of the present invention and the time of administration of the concomitant drug are not limited, and the compound of the present invention and the concomitant drug may be administered simultaneously or in a staggered manner to a recipient. In the case of administration in a staggered manner, the staggered manner differs depending on active ingredients to be administered, a dosage form and an administration method. In the case of first administering, for example, the concomitant drug, the compound of the present invention can be administered within 1 minute to 3 days, preferably within 10 minutes to 1 day, more preferably within 15 minutes to 1 hour, after the administration of the concomitant drug. In the case of first administering the compound of the present invention, the concomitant drug can be administered within 1 minute to 1 day, preferably within 10 minutes to 6 hours, more preferably within 15 minutes to 1 hour, after the administration of the compound of the present invention. The dose of the concomitant drug can abide by a dose clinically used and can be appropriately selected according to a recipient, an administration route, a disease, a combination, etc.

Examples of the administration mode of the compound of the present invention and the concomitant drug used in combination include (1) the administration of a single preparation obtained by simultaneously formulating the compound of the present invention and the concomitant drug, (2) the simultaneous administration through the same administration route of two preparations obtained by separately formulating the compound of the present invention and the concomitant drug, (3) the administration through the same administration route in a staggered manner of two preparations obtained by separately formulating the compound of the present invention and the concomitant drug, (4) the simultaneous administration through different administration routes of two preparations obtained by separately formulating the compound of the present invention and the concomitant drug, and (5) the administration through different administration routes in a staggered manner of two preparations obtained by separately formulating the compound of the present invention and the concomitant drug (e.g., administration in the order of the compound of the present invention and then the concomitant drug, or in the reverse order).

The dose of the concomitant drug can be appropriately selected on the basis of a dose clinically used. The mixing ratio between the compound of the present invention and the concomitant drug can be appropriately selected according to a recipient, an administration route, a target disease, symptoms, a combination, etc. When the recipient is, for example, a human, 0.01 to 100 parts by weight of the concomitant drug can be used with respect to 1 part by weight of the compound of the present invention.

The compound of the present invention or the combination drug of the present invention can be further used in combination with a non-drug therapy. Specifically, the compound of the present invention or the combination drug of the present invention may be combined with a non-drug therapy, for example, (1) surgery, (2) induced hypertension chemotherapy using angiotensin II or the like, (3) gene therapy, (4) thermotherapy, (5) cryotherapy, (6) laser cauterization or (7) radiotherapy.

The compound of the present invention or the combination drug of the present invention is used, for example, before or after the surgery or the like or before or after treatment involving two or three of these therapies in combination to produce effects such as prevention of development of resistance, prolonged disease-free survival, inhibition of cancer metastasis or recurrence, life prolongation and the like.

Also, the treatment with the compound of the present invention or the combination drug of the present invention may be combined with supportive care [(i) the administration of an antibiotic (e.g., a β-lactam antibiotic such as Panasporin and the like, a macrolide antibiotic such as clarithromycin and the like) against various intercurrent infections, (ii) the administration of a high-calorie infusion, an amino acid preparation or multivitamin for the improvement of malnutrition, (iii) the administration of morphine for pain relief, (iv) the administration of a drug improving adverse reactions such as nausea, vomiting, anorexia, diarrhea, leukopenia, thrombocytopenia, decreased hemoglobin concentration, alopecia, liver damage, kidney damage, DIC, fever and the like and (v) the administration of a drug for inhibiting multidrug resistance of cancer, etc.].

The present invention will be described further specifically with reference to Examples, Test Examples and Formulation Examples given below. However, the present invention is not intended to be limited by them, and various changes or modifications may be made therein without departing from the scope of the present invention.

Examples

In Examples below, the term "room temperature" usually means approximately 10° C. to approximately 35° C. A ratio used for a mixed solvent represents a volume ratio unless otherwise specified. % represents % by weight unless otherwise specified.

The term "NH" in silica gel column chromatography represents that an aminopropylsilane-bound silica gel was used. A ratio used for elution solvents represents a volume ratio unless otherwise specified.

In Examples below, the following abbreviations are used:
mp: melting point
MS: mass spectrum
M: molar concentration
$CDCl_3$: deuterated chloroform
$DMSO$-$d_6$: deuterated dimethyl sulfoxide
$^1H$ NMR: proton nuclear magnetic resonance
LC/MS: liquid chromatograph-mass spectrometer
ESI: electrospray ionization
APCI: atmospheric pressure chemical ionization
DME: 1,2-dimethoxyethane
DMA: N,N-dimethylacetamide
DMF: N,N-dimethylformamide
HATU: 2-(7-azabenzotriazol-1-yl)-1,1,3,3-tetramethyluronium hexafluorophosphate
HOBt: 1-hydroxybenzotriazole
DPPA: diphenylphosphorylazide
mCPBA: m-chloroperbenzoic acid
TBAF: tetra-n-butylammonium fluoride
DBU: 1,8-diazabicyclo[5.4.0]undec-7-ene
THF: tetrahydrofuran $^1H$ NMR was measured by Fourier transform NMR. ACD/SpecManager (trade name) or the like was used in analysis. No mention was made about the very broad peaks of protons of a hydroxy group, an amino group and the like.

MS was measured by LC/MS. ESI or APCI was used as an ionization method. Data was indicated by actually measured values (found). In general, molecular ion peaks ([M+H]$^+$, [M−H]$^−$ and the like) are observed. For example, in the case of a compound having a tert-butoxycarbonyl group, a fragment ion peak derived from the elimination of the tert-butoxycarbonyl group or the tert-butyl group is observed. In the case of a compound having a hydroxy group, a fragment ion peak derived from the elimination of $H_2O$ may be observed. In the case of a salt, a molecular ion peak or fragment ion peak of a free form is usually observed.

Example 1A

2-Chloro-N-(4-(3,4-dimethoxybenzoyl)-2-methyl-4,5,6,7-tetrahydro-2H-pyrazolo[4,3-b]pyridin-7-yl)benzamide A) Methyl 1-methyl-4-nitro-1H-pyrazole-3-carboxylate To a suspension of 4-nitro-1H-pyrazole-3-carboxylic acid (62 g) and potassium carbonate (221 g) in DMF (700 mL), dimethyl sulfate (121 g) was added dropwise under ice cooling, and the mixture was stirred at room temperature for 14 hours. The reaction mixture was poured to water, followed by extraction with ethyl acetate. The extract was dried over anhydrous sodium sulfate, and the solvent was distilled off under reduced pressure. The residue was purified by silica gel column chromatography (ethyl acetate/petroleum ether) to obtain the title compound (30 g).

$^1$H NMR (400 MHz, CDCl$_3$) δ 4.01 (3H, s), 4.03 (3H, s), 8.18 (1H, s).

B) Methyl 4-amino-1-methyl-1H-pyrazole-3-carboxylate

To a solution of methyl 1-methyl-4-nitro-1H-pyrazole-3-carboxylate (10 g) in methanol (200 mL), palladium-carbon (10%) (2 g) was added, and the mixture was stirred at room temperature for 6 hours in a hydrogen atmosphere (45 psi). Palladium-carbon was filtered off, and then, the filtrate was concentrated to obtain the title compound (8.57 g).

$^1$H NMR (400 MHz, CDCl$_3$) δ 3.86 (3H, s), 3.92 (3H, s), 4.08 (2H, brs), 6.96 (1H, s).

C) Methyl 4-[(3-methoxy-3-oxopropyl)amino]-1-methyl-1H-pyrazole-3-carboxylate

To a mixture of methyl 4-amino-1-methyl-1H-pyrazole-3-carboxylate (7.67 g) and methyl acrylate (5.45 g), acetic acid (0.77 g) was added, and the resulting mixture was stirred at 135° C. for 1 hour under irradiation with microwave. The reaction mixture was cooled to room temperature and then diluted with ethyl acetate. The reaction mixture was washed with a saturated aqueous solution of sodium bicarbonate and saturated brine and then dried over anhydrous sodium sulfate, and the solvent was distilled off under reduced pressure. The residue was purified by silica gel column chromatography (ethyl acetate/petroleum ether) to obtain the title compound (6.76 g).

$^1$H NMR (400 MHz, CDCl$_3$) δ 2.61 (2H, t, J=6.8 Hz), 3.28-3.35 (2H, m), 3.70 (3H, s), 3.87 (3H, s), 3.89 (3H, s), 5.03 (1H, t, J=6.4 Hz), 6.88 (1H, s).

D) Methyl 4-[benzyl(3-methoxy-3-oxopropyl)amino]-1-methyl-1H-pyrazole-3-carboxylate A mixture of methyl 4-[(3-methoxy-3-oxopropyl)amino]-1-methyl-1H-pyrazole-3-carboxylate (1.2 g), benzyl bromide (1.0 g) and potassium carbonate (1.4 g) in 2-butanone (20 mL) was stirred for 12 hours under reflux. The reaction mixture was cooled to room temperature, and then, the insoluble matter was filtered off. The solvent in the filtrate was distilled off under reduced pressure, and the residue was purified by silica gel column chromatography (ethyl acetate/petroleum ether) to obtain the title compound (1.22 g).

$^1$H NMR (400 MHz, CDCl$_3$) δ 2.44 (2H, t, J=7.2 Hz), 3.31 (2H, t, J=7.2 Hz), 3.55 (3H, s), 3.80 (3H, s), 3.87 (3H, s), 4.16 (2H, s), 6.97 (1H, s), 7.14-7.28 (5H, m).

E) Methyl 4-benzyl-2-methyl-7-oxo-4,5,6,7-tetrahydro-2H-pyrazolo[4,3-b]pyridine-6-carboxylate To a solution of methyl 4-[benzyl(3-methoxy-3-oxopropyl)amino]-1-methyl-1H-pyrazole-3-carboxylate (1.22 g) in THF (20 mL), lithium bis(trimethylsilyl)amide (1 M solution in THF) (6.3 mL) was added dropwise at −20° C., and the mixture was stirred for 2 hours. A saturated aqueous solution of ammonium chloride was poured to the reaction mixture, followed by extraction with ethyl acetate. The extract was dried over anhydrous sodium sulfate, and the solvent was distilled off under reduced pressure to obtain the title compound (0.93 g).

$^1$H NMR (400 MHz, CDCl$_3$) δ 3.34 (1H, dd, J$_1$=4.2 Hz, J$_2$=11.4 Hz), 3.50-3.62 (2H, m), 3.68 (3H, s), 3.80 (3H, s), 4.08 (2H, d, J=2.4 Hz), 6.62 (1H, s), 7.21-7.34 (5H, m).

F) 4-Benzyl-2-methyl-2,4,5,6-tetrahydro-7H-pyrazolo[4,3-b]pyridin-7-one

A solution of methyl 4-benzyl-2-methyl-7-oxo-4,5,6,7-tetrahydro-2H-pyrazolo[4,3-b]pyridine-6-carboxylate (3.2 g) in 6 N hydrochloric acid (40 mL) was stirred for 2 hours under reflux. The reaction mixture was neutralized with a 2 N aqueous sodium hydroxide solution, followed by extraction with ethyl acetate. The extract was dried over anhydrous sodium sulfate, and the solvent was distilled off under reduced pressure to obtain the title compound (1.83 g).

$^1$H NMR (400 MHz, CDCl$_3$) δ 2.69 (2H, t, J=6.8 Hz), 3.25 (2H, t, J=6.8 Hz), 3.85 (3H, s), 4.12 (2H, s), 6.67 (1H, s), 7.28-7.41 (5H, m).

G) 2-Methyl-2,4,5,6-tetrahydro-7H-pyrazolo[4,3-b]pyridin-7-one

To a solution of 4-benzyl-2-methyl-2,4,5,6-tetrahydro-7H-pyrazolo[4,3-b]pyridin-7-one (1.83 g) in methanol (50 mL), palladium-carbon (10%) (0.3 g) and acetic acid (50 mg) were added, and the mixture was stirred at room temperature for 12 hours in a hydrogen atmosphere. Palladium-carbon was filtered off, and then, the filtrate was concentrated to obtain the title compound (0.73 g).

$^1$H NMR (400 MHz, CDCl$_3$) δ 2.64 (2H, t, J=6.8 Hz), 3.46-3.51 (2H, m), 3.89 (3H, s), 6.93 (1H, s).

H) 4-(3,4-Dimethoxybenzoyl)-2-methyl-2,4,5,6-tetrahydro-7H-pyrazolo[4,3-b]pyridin-7-one To a solution of 2-methyl-2,4,5,6-tetrahydro-7H-pyrazolo[4,3-b]pyridin-7-one (0.73 g) and triethylamine (1.47 g) in THF (20 mL), 3,4-dimethoxybenzoyl chloride (1.16 g) was gradually added, and the mixture was stirred at room temperature for 18 hours. Ethyl acetate was added to the reaction mixture. The reaction mixture was washed with a saturated aqueous solution of sodium carbonate and saturated brine and then dried over anhydrous sodium sulfate, and the solvent was distilled off under reduced pressure. The residue was purified by silica gel column chromatography (ethyl acetate/petroleum ether) to obtain the title compound (382 mg).

$^1$H NMR (400 MHz, CDCl$_3$) δ 2.81 (2H, t, J=6.4 Hz), 3.95 (3H, s), 3.98 (3H, s), 4.03 (3H, s), 4.19 (2H, t, J=6.4 Hz), 6.95 (1H, d, J=8.8 Hz), 7.10-7.17 (2H, m).

I) (3,4-Dimethoxyphenyl)(7-hydroxy-2-methyl-2,5,6,7-tetrahydro-4H-pyrazolo[4,3-b]pyridin-4-yl)methanone To a solution of 4-(3,4-dimethoxybenzoyl)-2-methyl-2,4,5,6-tetrahydro-7H-pyrazolo[4,3-b]pyridin-7-one (380 mg) in methanol (20 mL), sodium tetrahydroborate (137 mg) was gradually added, and the mixture was stirred at room temperature for 1 hour. Water was added to the reaction mixture, and the mixture was further stirred for 30 minutes. After extraction with dichloromethane, the extract was washed with saturated brine and then dried over anhydrous sodium sulfate, and the solvent was distilled off under reduced pressure to obtain the title compound (384 mg).

$^1$H NMR (400 MHz, CDCl$_3$) δ 1.85-2.00 (2H, m), 3.70-3.80 (2H, m), 3.78 (3H, s), 3.86 (3H, s), 3.88 (3H, s), 4.68-4.74 (1H, m), 5.32 (1H, d, J=4.8 Hz), 7.05-7.14 (3H, m), 8.17 (1H, brs).

J) (7-Azido-2-methyl-2,5,6,7-tetrahydro-4H-pyrazolo[4,3-b]pyridin-4-yl)(3,4-dimethoxyphenyl)methanone To a solution of (3,4-dimethoxyphenyl)(7-hydroxy-2-methyl-2,5,6,7-tetrahydro-4H-pyrazolo[4,3-b]pyridin-4-yl)methanone (384 mg) in toluene (10 mL) and dichloromethane (10 mL), DPPA (0.84 g) was added dropwise at 0° C. in a nitrogen atmosphere. After stirring for 10 minutes, DBU (0.5 g) was added thereto, and the mixture was stirred at room temperature for 3 hours. The solvent was distilled off under reduced pressure, and the residue was purified by silica gel column chromatography (ethyl acetate/petroleum ether) to obtain the title compound (330 mg).

$^1$H NMR (400 MHz, DMSO-d$_6$) δ 1.91-2.02 (1H, m), 2.03-2.17 (1H, m), 3.63-3.72 (1H, m), 3.85 (3H, s), 3.87 (3H, s), 3.87-3.91 (1H, m), 3.93 (3H, s), 4.97 (1H, t, J=4.0 Hz), 7.05-7.23 (3H, m), 8.26 (1H, brs).

K) (7-Amino-2-methyl-2,5,6,7-tetrahydro-4H-pyrazolo[4,3-b]pyridin-4-yl)(3,4-dimethoxyphenyl)methanone To a solution of (7-azido-2-methyl-2,5,6,7-tetrahydro-4H-pyrazolo[4,3-b]pyridin-4-yl)(3,4-dimethoxyphenyl)methanone (330 mg) in methanol (10 mL) and dichloromethane (3 mL), palladium-carbon (10%) (30 mg) was added, and the mixture was stirred at room temperature for 5 hours in a hydrogen atmosphere. Palladium-carbon was filtered off, and then, the filtrate was concentrated to obtain the title compound (295 mg).

$^1$H NMR (400 MHz, DMSO-d$_6$) δ 1.76-1.90 (1H, m), 2.01-2.12 (1H, m), 2.48 (2H, brs), 3.58-3.72 (2H, m), 3.77 (3H, s), 3.79 (3H, s), 3.82 (3H, s), 4.15-4.21 (1H, m), 6.98-7.07 (3H, m), 8.14 (1H, brs).

L) 2-Chloro-N-(4-(3,4-dimethoxybenzoyl)-2-methyl-4,5,6,7-tetrahydro-2H-pyrazolo[4,3-b]pyridin-7-yl)benzamide To a solution of (7-amino-2-methyl-2,5,6,7-tetrahydro-4H-pyrazolo[4,3-b]pyridin-4-yl)(3,4-dimethoxyphenyl)methanone (283 mg) and triethylamine (270 mg) in THF (15 mL) and dichloromethane (5 mL), 2-chlorobenzoyl chloride (188 mg) was gradually added under ice cooling, and the mixture was stirred at room temperature for 1 hour. Dichloromethane was added to the reaction mixture. The reaction mixture was washed with a saturated aqueous solution of sodium carbonate and saturated brine and then dried over anhydrous sodium sulfate, and the solvent was distilled off under reduced pressure. The residue was purified by silica gel column chromatography (ethyl acetate/petroleum ether) to obtain the title compound (200 mg).

$^1$H NMR (400 MHz, DMSO-d$_6$) δ 1.91-2.02 (1H, m), 2.05-2.16 (1H, m), 3.70-3.90 (11H, m), 5.17-5.24 (1H, m), 7.00-7.10 (3H, m), 7.35-7.51 (4H, m), 8.17 (1H, brs), 8.84 (1H, d, J=8.0 Hz).

Example 2A

2-Chloro-N-(4-(3,4-dimethoxybenzoyl)-1-methyl-4,5,6,7-tetrahydro-1H-pyrazolo[4,3-b]pyridin-7-yl)benzamide

A) Methyl 1-methyl-4-nitro-1H-pyrazole-5-carboxylate

To a suspension of 4-nitro-1H-pyrazole-3-carboxylic acid (37 g) and potassium carbonate (97.6 g) in DMF (600 mL), dimethyl sulfate (71.2 g) was added dropwise under ice cooling, and the mixture was stirred at room temperature for 16 hours. The reaction mixture was poured to water, followed by extraction with ethyl acetate. The extract was dried over anhydrous sodium sulfate, and the solvent was distilled off under reduced pressure. The residue was purified by silica gel column chromatography (ethyl acetate/petroleum ether) to obtain the title compound (8.62 g).

$^1$H NMR (400 MHz, CDCl$_3$) δ 4.02 (3H, s), 4.03 (3H, s), 8.01 (1H, s).

B) Methyl 4-amino-1-methyl-1H-pyrazole-5-carboxylate

To a solution of methyl 1-methyl-4-nitro-1H-pyrazole-5-carboxylate (8.62 g) in methanol (100 mL), palladium-carbon (10%) (0.86 g) was added, and the mixture was stirred at room temperature for 4 hours in a hydrogen atmosphere (40 psi). Palladium-carbon was filtered off, and then, the filtrate was concentrated to obtain the title compound (4.71 g).

$^1$H NMR (400 MHz, CDCl$_3$) δ 3.91 (3H, s), 4.03 (3H, s), 4.15 (2H, brs), 7.07 (1H, s).

C) Methyl 4-[(3-methoxy-3-oxopropyl)amino]-1-methyl-1H-pyrazole-5-carboxylate To a mixture of methyl 4-amino-1-methyl-1H-pyrazole-5-carboxylate (4.71 g) and methyl acrylate (3.14 g), acetic acid (0.4 g) was added, and the resulting mixture was stirred at 165° C. for 1 hour under irradiation with microwave. The reaction mixture was cooled to room temperature and then diluted with ethyl acetate. The reaction mixture was washed with a saturated aqueous solution of sodium bicarbonate and saturated brine and then dried over anhydrous sodium sulfate, and the solvent was distilled off under reduced pressure. The residue was purified by silica gel column chromatography (ethyl acetate/petroleum ether) to obtain the title compound (2.25 g).

¹H NMR (400 MHz, CDCl₃) δ 2.61 (2H, t, J=6.4 Hz), 3.38-3.46 (2H, m), 3.70 (3H, s), 3.89 (3H, s), 4.03 (3H, s), 5.04 (1H, brs), 7.06 (1H, s).

D) Methyl 4-[benzyl(3-methoxy-3-oxopropyl)amino]-1-methyl-1H-pyrazole-5-carboxylate A mixture of methyl 4-[(3-methoxy-3-oxopropyl)amino]-1-methyl-1H-pyrazole-5-carboxylate (2.25 g), benzyl bromide (1.91 g) and potassium carbonate (2.58 g) in 2-butanone (50 mL) was stirred for 16 hours under reflux. The reaction mixture was cooled to room temperature, and then, the insoluble matter was filtered off. The solvent in the filtrate was distilled off under reduced pressure, and the residue was purified by silica gel column chromatography (ethyl acetate/petroleum ether) to obtain the title compound (2.38 g).

¹H NMR (400 MHz, CDCl₃) δ 2.51 (2H, t, J=7.5 Hz), 3.34 (2H, t, J=7.5 Hz), 3.62 (3H, s), 3.89 (3H, s), 4.10 (3H, s), 4.21 (2H, s), 7.28-7.41 (6H, m).

E) Methyl 4-benzyl-1-methyl-7-oxo-4,5,6,7-tetrahydro-2H-pyrazolo[4,3-b]pyridine-6-carboxylate To a solution of methyl 4-[benzyl(3-methoxy-3-oxopropyl)amino]-1-methyl-1H-pyrazole-5-carboxylate (2.38 g) in THF (50 mL), lithium bis(trimethylsilyl)amide (1 M solution in THF) (18 mL) was added dropwise at −20° C., and the mixture was stirred for 2 hours. A saturated aqueous solution of ammonium chloride was poured to the reaction mixture, followed by extraction with ethyl acetate. The extract was dried over anhydrous sodium sulfate, and the solvent was distilled off under reduced pressure to obtain the title compound (2.13 g).

¹H NMR (400 MHz, CDCl₃) δ 3.37 (1H, dd, J₁=4.2 Hz, J₂=11.4 Hz), 3.51 (1H, dd, J₁=4.2 Hz, J₂=8.4 Hz), 3.55-3.65 (1H, m), 3.74 (3H, s), 4.08 (3H, s), 4.27 (2H, d, J=4.2 Hz), 7.01 (1H, s), 7.24-7.41 (5H, m).

F) 4-Benzyl-1-methyl-2,4,5,6-tetrahydro-7H-pyrazolo[4,3-b]pyridin-7-one

A solution of methyl 4-benzyl-1-methyl-7-oxo-4,5,6,7-tetrahydro-2H-pyrazolo[4,3-b]pyridine-6-carboxylate (2.13 g) in 6 N hydrochloric acid (20 mL) was stirred for hours under reflux. The reaction mixture was concentrated, and then, a saturated aqueous solution of sodium carbonate was added to the residue, followed by extraction with ethyl acetate. The extract was dried over anhydrous sodium sulfate. The solvent was distilled off under reduced pressure, and the residue was purified by silica gel column chromatography (ethyl acetate/petroleum ether) to obtain the title compound (290 mg).

¹H NMR (400 MHz, CDCl₃) δ 2.57 (2H, t, J=7.2 Hz), 3.21 (2H, t, J=7.2 Hz), 4.07 (3H, s), 4.24 (2H, s), 7.00 (1H, s), 7.24-7.41 (5H, m).

G) 1-Methyl-2,4,5,6-tetrahydro-7H-pyrazolo[4,3-b]pyridin-7-one

To a solution of 4-benzyl-1-methyl-2,4,5,6-tetrahydro-7H-pyrazolo[4,3-b]pyridin-7-one (280 mg) in methanol (20 mL), palladium-carbon (10%) (30 mg) and acetic acid (50 mg) were added, and the mixture was stirred at room temperature for 16 hours in a hydrogen atmosphere. Palladium-carbon was filtered off, and then, the filtrate was concentrated to obtain the title compound (140 mg).

¹H NMR (400 MHz, CDCl₃) δ 2.57 (2H, t, J=6.8 Hz), 3.50 (2H, t, J=6.8 Hz), 3.85 (1H, brs), 4.06 (3H, s), 7.05 (1H, s).

H) 4-(3,4-Dimethoxybenzoyl)-1-methyl-2,4,5,6-tetrahydro-7H-pyrazolo[4,3-b]pyridin-7-one To a solution of 1-methyl-2,4,5,6-tetrahydro-7H-pyrazolo[4,3-b]pyridin-7-one (570 mg) and triethylamine (763 mg) in THF (20 mL), 3,4-dimethoxybenzoyl chloride (908 mg) was gradually added, and the mixture was stirred at room temperature for 2 hours. Ethyl acetate was added to the reaction mixture. The reaction mixture was washed with a saturated aqueous solution of sodium carbonate and saturated brine and then dried over anhydrous sodium sulfate, and the solvent was distilled off under reduced pressure. The residue was purified by silica gel column chromatography (ethyl acetate/petroleum ether) to obtain the title compound (950 mg).

¹H NMR (400 MHz, DMSO-d₆) δ 2.75 (2H, t, J=6.3 Hz), 3.78 (3H, s), 3.82 (3H, s), 3.98-4.15 (5H, m), 7.00-7.10 (1H, m), 7.12-7.23 (2H, m), 7.30-7.70 (1H, brs).

I) (3,4-Dimethoxyphenyl)(7-hydroxy-1-methyl-2,5,6,7-tetrahydro-4H-pyrazolo[4,3-b]pyridin-4-yl)methanone To a solution of 4-(3,4-dimethoxybenzoyl)-1-methyl-2,4,5,6-tetrahydro-7H-pyrazolo[4,3-b]pyridin-7-one (400 mg) in methanol (20 mL), sodium tetrahydroborate (144 mg) was gradually added, and the mixture was stirred at room temperature for 1 hour. Water was added to the reaction mixture, and the mixture was further stirred for 30 minutes. After extraction with dichloromethane, the extract was washed with saturated brine and then dried over anhydrous sodium sulfate, and the solvent was distilled off under reduced pressure to obtain the title compound (418 mg).

¹H NMR (400 MHz, CDCl₃) δ 2.02-2.12 (2H, m), 2.28-2.36 (1H, m), 3.50-3.65 (1H, m), 3.89 (6H, s), 3.92 (3H, s), 4.00-4.20 (1H, m), 4.88-4.94 (1H, m), 6.87 (1H, d, J=8.0 Hz), 7.02-7.10 (2H, m).

J) (7-Azido-1-methyl-2,5,6,7-tetrahydro-4H-pyrazolo[4,3-b]pyridin-4-yl)(3,4-dimethoxyphenyl)methanone To a solution of (3,4-dimethoxyphenyl)(7-hydroxy-1-methyl-2,5,6,7-tetrahydro-4H-pyrazolo[4,3-b]pyridin-4-yl)methanone (412 mg) in toluene (10 mL) and dichloromethane (10 mL), DPPA (1.07 g) was added dropwise at 0° C. in a nitrogen atmosphere. After stirring for 10 minutes, DBU (589 mg) was added thereto, and the mixture was stirred at room temperature for 3 hours. The solvent was distilled off under reduced pressure, and the residue was purified by silica gel column chromatography (dichloromethane/methanol) to obtain the title compound (415 mg).

¹H NMR (400 MHz, DMSO-d₆) δ 2.03-2.20 (2H, m), 3.18-3.30 (1H, m), 3.40-3.60 (1H, m), 3.79 (3H, s), 3.82 (3H, s), 3.86 (3H, s), 5.19 (1H, t, J=4.0 Hz), 7.31 (1H, d, J=8.0 Hz), 7.05-7.14 (2H, m).

K) (7-Amino-1-methyl-2,5,6,7-tetrahydro-4H-pyrazolo[4,3-b]pyridin-4-yl)(3,4-dimethoxyphenyl)methanone To a solution of (7-azido-1-methyl-2,5,6,7-tetrahydro-4H-pyrazolo[4,3-b]pyridin-4-yl)(3,4-dimethoxyphenyl)

methanone (415 mg) in methanol (20 mL), palladium-carbon (10%) (40 mg) was added, and the mixture was stirred at room temperature for 3 hours in a hydrogen atmosphere. Palladium-carbon was filtered off, and then, the filtrate was concentrated to obtain the title compound (350 mg).

$^1$H NMR (400 MHz, DMSO-$d_6$) δ 1.86-2.05 (2H, m), 3.15-3.30 (1H, m), 3.60-3.75 (1H, m), 3.78 (3H, s), 3.81 (3H, s), 3.83 (3H, s), 4.00-4.04 (1H, m), 7.00-7.08 (3H, m), 7.70-8.10 (1H, brs).

L) 2-Chloro-N-(4-(3,4-dimethoxybenzoyl)-1-methyl-4,5,6,7-tetrahydro-1H-pyrazolo[4,3-b]pyridin-7-yl)benzamide To a solution of (7-amino-1-methyl-2,5,6,7-tetrahydro-4H-pyrazolo[4,3-b]pyridin-4-yl)(3,4-dimethoxyphenyl)methanone (340 mg) and triethylamine (325 mg) in THF (20 mL), 2-chlorobenzoyl chloride (226 mg) was gradually added under ice cooling, and the mixture was stirred at room temperature for 2 hours. Dichloromethane was added to the reaction mixture. The reaction mixture was washed with a saturated aqueous solution of sodium carbonate and saturated brine and then dried over anhydrous sodium sulfate, and the solvent was distilled off under reduced pressure. The residue was purified by silica gel column chromatography (ethyl acetate/petroleum ether and dichloromethane/methanol) and recrystallized from ethyl acetate/petroleum ether to obtain the title compound (250 mg).

$^1$H NMR (400 MHz, DMSO-$d_6$) δ 1.98-2.20 (2H, m), 3.57-3.72 (1H, m), 3.74-3.83 (9H, m), 3.84-4.00 (1H, m), 5.38-5.45 (1H, m), 6.98-7.10 (3H, m), 7.35-7.52 (4H, m), 7.70-8.30 (1H, brs), 9.07 (1H, d, J=8.4 Hz).

Example 3A

2-Chloro-N-(7-(3,4-dimethoxybenzoyl)-2-methyl-4,5,6,7-tetrahydro-2H-pyrazolo[3,4-b]pyridin-4-yl)benzamide A) Methyl 3-(4-bromo-1-methyl-1H-pyrazol-3-ylamino)propanoate A mixture of 4-bromo-1-methyl-1H-pyrazol-3-amine (3.50 g), methyl acrylate (8 mL), 4-(dimethylamino)pyridine (0.49 g) and DMF (3 mL) was stirred at 135° C. for 3 hours and 30 minutes under irradiation with microwave. Water and ethyl acetate were added to the reaction mixture to separate an organic layer. The aqueous layer was subjected to extraction with ethyl acetate. The combined extract was washed with saturated brine and dried over anhydrous sodium sulfate, and the solvent was distilled off under reduced pressure. The residue was purified by silica gel column chromatography (ethyl acetate/petroleum ether) to obtain the title compound (3.20 g).

MS: [M+H]$^+$ 261.8.

B) Methyl 3-(benzyl(4-bromo-1-methyl-1H-pyrazol-3-yl)amino)propanoate

To a mixture of methyl 3-(4-bromo-1-methyl-1H-pyrazol-3-ylamino)propanoate (6.0 g), potassium carbonate (4.7 g) and acetonitrile (50 mL), benzyl bromide (4.3 g) was added at room temperature, and the resulting mixture was stirred overnight at 70° C. The insoluble matter was filtered off, and the filtrate was concentrated under reduced pressure. The residue was purified by silica gel column chromatography (ethyl acetate/petroleum ether) to obtain the title compound (7.3 g).

MS: [M+H]$^+$ 351.8.

C) Methyl 3-(benzyl(4-cyano-1-methyl-1H-pyrazol-3-yl)amino)propanoate

A mixture of methyl 3-(benzyl(4-bromo-1-methyl-1H-pyrazol-3-yl)amino)propanoate (6.0 g), copper(I) cyanide (12.2 g) and DMF (50 mL) was stirred overnight at 150° C. The insoluble matter was filtered off, and the filtrate was subjected to extraction with ethyl acetate. The extract was washed with saturated brine and dried over anhydrous sodium sulfate, and the solvent was distilled off under reduced pressure. The residue was purified by silica gel column chromatography (ethyl acetate/petroleum ether) to obtain the title compound (4.0 g).

MS: [M+H]$^+$ 299.0.

D) Methyl 3-(benzyl(3-methoxy-3-oxopropyl)amino)-1-methyl-1H-pyrazole-4-carboxylate A mixture of methyl 3-(benzyl(4-cyano-1-methyl-1H-pyrazol-3-yl)amino)propanoate (4.0 g), potassium hydroxide (9.8 g), ethanol (4 mL) and water (40 mL) was stirred at 100° C. for 48 hours. The reaction mixture was diluted to pH 8 with 2 N hydrochloric acid and concentrated under reduced pressure. To a mixture of the residue, potassium carbonate (7.4 g) and DMF (50 mL), iodomethane (9.5 g) was added, and the resulting mixture was stirred overnight at 50° C. The insoluble matter was filtered off, and the filtrate was diluted with water, followed by extraction with ethyl acetate. The extract was washed with saturated brine and dried over anhydrous sodium sulfate, and the solvent was distilled off under reduced pressure to obtain the title compound (3.3 g).

MS: [M+H]$^+$ 331.9.

E) 7-Benzyl-2-methyl-6,7-dihydro-2H-pyrazolo[3,4-b]pyridin-4(5H)-one

To a solution of methyl 3-(benzyl(3-methoxy-3-oxopropyl)amino)-1-methyl-1H-pyrazole-4-carboxylate (2.8 g) in THF (20 mL), a 1 M solution of sodium bis(trimethylsilyl)amide in THF (15.1 mL) was added at −5° C., and the mixture was stirred at the same temperature as above for 40 minutes. The reaction mixture was diluted with a saturated aqueous solution of ammonium chloride, followed by extraction with ethyl acetate. The extract was washed with saturated brine and dried over anhydrous sodium sulfate, and the solvent was distilled off under reduced pressure. A mixture of the residue, sodium hydroxide (1.5 g), THF (20 mL) and water (20 mL) was stirred at 70° C. for 6 hours. The reaction mixture was diluted to pH 9 with 1 N hydrochloric acid, followed by extraction with ethyl acetate. The extract was washed with saturated brine and dried over anhydrous sodium sulfate, and the solvent was distilled off under reduced pressure. The residue was purified by silica gel column chromatography (ethyl acetate/petroleum ether) to obtain the title compound (1.2 g).

MS: [M+H]$^+$ 242.0.

F) 7-Benzyl-2-methyl-6,7-dihydro-2H-pyrazolo[3,4-b]pyridin-4(5H)-one oxime

A mixture of 7-benzyl-2-methyl-6,7-dihydro-2H-pyrazolo[3,4-b]pyridin-4(5H)-one (1.2 g), sodium acetate (1.7 g), hydroxylamine hydrochloride (1.4 g) and ethanol (15 mL) was stirred overnight under conditions of heating to reflux. The reaction mixture was concentrated under reduced pressure, and the residue was diluted to pH 9 with a saturated aqueous solution of sodium carbonate. The resulting precipitate was collected by filtration to obtain the title compound (1.0 g).

MS: [M+H]$^+$ 257.0.

G) 7-Benzyl-2-methyl-4,5,6,7-tetrahydro-2H-pyrazolo[3,4-b]pyridin-4-amine

A mixture of 7-benzyl-2-methyl-6,7-dihydro-2H-pyrazolo[3,4-b]pyridin-4(5H)-one oxime (872 mg), Raney nickel (1.6 g) and methanol (15 mL) was stirred overnight at 40° C. in a hydrogen atmosphere. The insoluble matter was filtered off, and the filtrate was concentrated under reduced pressure to obtain the title compound (800 mg).

MS: [M+H]$^+$ 243.0.

H) tert-Butyl 7-benzyl-2-methyl-4,5,6,7-tetrahydro-2H-pyrazolo[3,4-b]pyridin-4-ylcarbamate To a solution of 7-benzyl-2-methyl-4,5,6,7-tetrahydro-2H-pyrazolo[3,4-b]pyridin-4-amine (800 mg) in dichloromethane (12 mL), triethylamine (668 mg) and di-tert-butyl dicarbonate (864 mg) were added at room temperature. After stirring at the same temperature as above for 2 hours, the reaction mixture was diluted with water, followed by extraction with dichloromethane. The extract was washed with saturated brine and dried over anhydrous sodium sulfate, and the solvent was distilled off under reduced pressure. The residue was purified by silica gel column chromatography (ethyl acetate/petroleum ether) to obtain the title compound (715 mg).

MS: [M+H]$^+$ 343.0.

I) tert-Butyl 2-methyl-4,5,6,7-tetrahydro-2H-pyrazolo[3,4-b]pyridin-4-ylcarbamate A mixture of tert-butyl 7-benzyl-2-methyl-4,5,6,7-tetrahydro-2H-pyrazolo[3,4-b]pyridin-4-yl carbamate (698 mg), 10% palladium-carbon (containing 50% water, 200 mg), acetic acid (0.5 mL) and THF (5 mL) was stirred at room temperature for 3 days in a hydrogen atmosphere. The insoluble matter was filtered off, and the filtrate was diluted to pH 9 with a saturated aqueous solution of sodium carbonate, followed by extraction with ethyl acetate. The extract was washed with saturated brine and dried over anhydrous sodium sulfate, and the solvent was distilled off under reduced pressure to obtain the title compound (480 mg).

MS: [M+H]$^+$ 253.1.

J) tert-Butyl 7-(3,4-dimethoxybenzoyl)-2-methyl-4,5,6,7-tetrahydro-2H-pyrazolo[3,4-b]pyridin-4-ylcarbamate To a mixture of tert-butyl 2-methyl-4,5,6,7-tetrahydro-2H-pyrazolo[3,4-b]pyridin-4-ylcarbamate (139 mg), triethylamine (89 mg) and dichloromethane (3 mL), 3,4-dimethoxybenzoyl chloride (133 mg) was added under ice cooling, and the resulting mixture was stirred overnight at room temperature. The reaction mixture was diluted with ice-cold water, followed by extraction with dichloromethane. The extract was washed with saturated brine and dried over anhydrous sodium sulfate, and the solvent was distilled off under reduced pressure. The residue was purified by thin-layer silica gel column chromatography (ethyl acetate) to obtain the title compound (150 mg).

MS: [M+H]$^+$ 416.9.

K) (4-Amino-2-methyl-5,6-dihydro-2H-pyrazolo[3,4-b]pyridin-7(4H)-yl)(3,4-dimethoxy phenyl)methanone tert-Butyl 7-(3,4-dimethoxybenzoyl)-2-methyl-4,5,6,7-tetrahydro-2H-pyrazolo[3,4-b]pyridin-4-ylcarbamate (150 mg) was dissolved in dichloromethane (2 mL). To the solution, TFA (2 mL) was added, and the mixture was stirred at room temperature for 4 hours. The reaction mixture was diluted with water and then diluted to pH 9 with a saturated aqueous solution of sodium carbonate, followed by extraction with dichloromethane. The extract was washed with saturated brine and dried over anhydrous sodium sulfate, and the solvent was distilled off under reduced pressure to obtain the title compound (106 mg).

MS: [M+H]$^+$ 317.0.

L) 2-Chloro-N-(7-(3,4-dimethoxybenzoyl)-2-methyl-4,5,6,7-tetrahydro-2H-pyrazolo[3,4-b]pyridin-4-yl)benzamide To a mixture of (4-amino-2-methyl-5,6-dihydro-2H-pyrazolo[3,4-b]pyridin-7(4H)-yl)(3,4-dimethoxy phenyl)methanone (108 mg), pyridine (54 mg) and dichloromethane (1.5 mL), 2-chlorobenzoyl chloride (77 mg) was added under ice cooling, and the resulting mixture was stirred at room temperature for 2 hours. The reaction mixture was diluted with ice-cold water, followed by extraction with dichloromethane. The extract was washed with saturated brine and dried over anhydrous sodium sulfate, and the solvent was distilled off under reduced pressure. The residue was purified by reverse-phase HPLC to obtain the title compound (89 mg).

$^1$H NMR (400 MHz, CDCl$_3$) δ 2.11-2.17 (1H, m), 2.30-2.37 (1H, m), 3.72 (3H, s), 3.79-3.85 (1H, m), 3.87 (3H, s), 3.92 (3H, s), 4.05-4.11 (1H, m), 5.33-5.37 (1H, m), 6.42 (1H, d, J=7.2 Hz), 6.82-6.84 (1H, m), 7.13-7.15 (2H, m), 7.33-7.42 (4H, m), 7.69-7.71 (1H, m).

Example 17A

2-Chloro-N-[4-(3,4-dimethoxybenzoyl)-3-methyl-4,5,6,7-tetrahydro[1,2]oxazolo[4,3-b]pyridin-7-yl]benzamide A) 5-Methyl-4-nitro-1,2-oxazole-3-carboxylic acid To a solution of 5-methyl-1,2-oxazole-3-carboxylic acid (50.84 g) in concentrated sulfuric acid (500 mL), sodium nitrate (50.99 g) was gradually added at room temperature. The reaction mixture was stirred at 50° C. for 16 hours. After cooling to room temperature, the reaction solution was gradually added to ice, followed by extraction with ethyl acetate. The extract was washed with water and saturated brine and then dried over anhydrous sodium sulfate to obtain the title compound (51.6 g).

$^1$H NMR (400 MHz, DMSO-d$_6$) δ 2.28 (3H, s), 10.66 (1H, brs).

B) Methyl 5-methyl-4-nitro-1,2-oxazole-3-carboxylate

To a solution of 5-methyl-4-nitro-1,2-oxazole-3-carboxylic acid (40 g) in methanol (900 mL), thionyl chloride (80 mL) was added dropwise under ice cooling. The reaction solution was stirred at room temperature for 3 days, and then, methanol was distilled off under reduced pressure. Ethyl acetate was added to the residue, and the mixture was washed with saturated brine. The reaction mixture was dried over anhydrous magnesium sulfate, and the solvent was distilled off under reduced pressure to obtain the title compound (44.22 g).

$^1$H NMR (300 MHz, CDCl$_3$) δ2.86 (3H, s), 4.04 (3H, s).

C) Methyl 4-amino-5-methyl-1,2-oxazole-3-carboxylate

To a solution of ammonium chloride (55.7 g) in water (400 mL), a solution of methyl 5-methyl-4-nitro-1,2-oxazole-3-carboxylate (13 g) in methanol (100 mL) was added. A zinc powder (54.5 g) was gradually added to the reaction mixture under ice cooling, and the mixture was then stirred at 5° C. for 1.5 hours. The insoluble matter was filtered off, and the filtrate was subjected to extraction with ethyl acetate. The extract was washed with saturated brine and dried over anhydrous magnesium sulfate, and the solvent was distilled off under reduced pressure to obtain the title compound (9.47 g).

$^1$H NMR (300 MHz, CDCl$_3$) δ 1.55 (2H, brs), 2.85 (3H, s), 4.03 (3H, s).

D) Methyl 4-[(3-methoxy-3-oxopropyl)amino]-5-methyl-1,2-oxazole-3-carboxylate To a mixture of methyl 4-amino-5-methyl-1,2-oxazole-3-carboxylate (27.8 g) and methyl acrylate (55 mL), BF$_3$.Et$_2$O (12.64 g) was added dropwise at room temperature, and the resulting mixture was then stirred at 80° C. for 9 hours. The reaction mixture was cooled to room temperature and then diluted with ethyl acetate. The reaction mixture was washed with a saturated aqueous solution of sodium bicarbonate and saturated brine and then dried over anhydrous sodium sulfate, and the solvent was distilled off under reduced pressure. The residue was purified by silica gel column chromatography (ethyl acetate/petroleum ether) to obtain the title compound (35.7 g).

$^1$H NMR (400 MHz, CDCl$_3$) δ 2.48 (3H, s), 2.54 (2H, d, J=6.4 Hz), 3.29 (2H, d, J=6.8 Hz), 3.62 (3H, s), 3.69 (3H, s), 4.40 (1H, brs).

E) Methyl 4-[(4-methoxybenzyl)(3-methoxy-3-oxopropyl)amino]-5-methyl-1,2-oxazole-3-carboxylate A mixture of methyl 4-[(3-methoxy-3-oxopropyl)amino]-5-methyl-1,2-oxazole-3-carboxylate (15.7 g), 4-methoxybenzyl bromide (19.5 g) and potassium carbonate (17.97 g) in 2-butanone (200 mL) was stirred for 6 hours under reflux. The reaction mixture was cooled to room temperature, and then, the insoluble matter was filtered off. The solvent in the filtrate was distilled off under reduced pressure, and the residue was purified by silica gel column chromatography (ethyl acetate/petroleum ether) to obtain the title compound (12.02 g).

$^1$H NMR (400 MHz, CDCl$_3$) δ 2.05 (3H, s), 2.36 (2H, d, J=6.8 Hz), 3.36 (2H, d, J=6.8 Hz), 3.62 (3H, s), 3.77 (3H, s), 4.00 (3H, s), 4.04 (2H, s), 6.77 (2H, d, J=8.8 Hz), 7.07 (2H, d, J=8.8 Hz).

F) Methyl 4-(4-methoxybenzyl)-3-methyl-7-oxo-4,5,6,7-tetrahydro[1,2]oxazolo[4,3-b]pyridine-6-carboxylate A solution of methyl 4-[(4-methoxybenzyl)(3-methoxy-3-oxopropyl)amino]-5-methyl-1,2-oxazole-3-carboxylate (12.02 g) in THF (50 mL) was added dropwise to a mixture of t-BuOK (9.31 g) and THF (200 mL) at −20° C. The reaction mixture was stirred for 30 minutes, and then, a saturated aqueous solution of ammonium chloride was poured thereto, followed by extraction with ethyl acetate. The extract was dried over anhydrous sodium sulfate, and the solvent was distilled off under reduced pressure to obtain the title compound (9.02 g).

$^1$H NMR (400 MHz, CDCl$_3$) δ 2.20 (3H, s), 3.79 (3H, s), 3.81 (3H, s), 3.90 (2H, s), 4.09 (2H, s), 6.88 (2H, d, J=8.4 Hz), 7.18 (2H, d, J=8.4 Hz).

G) 4-(4-Methoxybenzyl)-3-methyl-5,6-dihydro[1,2]oxazolo[4,3-b]pyridin-7(4H)-one A mixture of methyl 4-(4-methoxybenzyl)-3-methyl-7-oxo-4,5,6,7-tetrahydro[1,2]oxazolo[4,3-b]pyridine-6-carboxylate (9.02 g), aluminum oxide (100 g) and 1,4-dioxane (700 mL) was stirred for 30 minutes under reflux. The reaction mixture was cooled to room temperature, and then, the insoluble matter was filtered off. The solvent in the filtrate was distilled off under reduced pressure to obtain the title compound (3.46 g).

MS: [M+H]$^+$ 272.9.

H) 4-(4-Methoxybenzyl)-3-methyl-4,5,6,7-tetrahydro[1,2]oxazolo[4,3-b]pyridin-7-ol To a solution of 4-(4-methoxybenzyl)-3-methyl-5,-dihydro[1,2]oxazolo[4,3-b]pyridin-7(4H)-one (3.46 g) in methanol (100 mL), sodium tetrahydroborate (960 mg) was gradually added, and the mixture was stirred at 15° C. for 1 hour. Water was added to the reaction mixture, and the mixture was further stirred for 30 minutes. After extraction with ethyl acetate, the extract was washed with saturated brine and then dried over anhydrous sodium sulfate, and the solvent was distilled off under reduced pressure. The residue was purified by silica gel column chromatography (ethyl acetate/petroleum ether) to obtain the title compound (1.2 g).

$^1$H NMR (400 MHz, CDCl$_3$) δ 1.94-2.05 (2H, m), 2.38 (3H, s), 2.56 (1H, s), 2.82-2.91 (1H, m), 3.03-3.11 (1H, m), 3.81 (3H, s), 4.11 (1H, d, J=14.8 Hz), 4.24 (1H, d, J=14.8 Hz), 4.94-5.01 (1H, m), 6.88 (2H, d, J=8.0 Hz), 7.22 (2H, d, J=8.0 Hz).

I) 2-Chlorobenzamide

To a 4 M solution of ammonia in THF (40 mL), a solution of 2-chlorobenzoyl chloride (5 g) in THF (20 mL) was added dropwise under ice cooling, and the mixture was stirred at room temperature for 2 hours. Ethyl acetate was added to the reaction mixture. The reaction mixture was washed with water and then dried over anhydrous magnesium sulfate, and the solvent was distilled off under reduced pressure to obtain the title compound (4.6 g).

MS: [M+H]$^+$ 155.7.

J) tert-Butyl (2-chlorobenzoyl)carbamate

To a suspension of 60% sodium hydride (in oil) (0.32 g) in THF (15 mL), a solution of 2-chlorobenzamide (0.62 g) in THF was added dropwise under ice cooling, and the mixture was stirred at 15° C. for 20 minutes. A solution of Boc$_2$O (0.87 g) in THF (15 mL) was slowly added to the reaction mixture, and the mixture was stirred at 15° C. for 30 minutes. A saturated aqueous solution of ammonium chloride was added to the reaction mixture, followed by extraction with ethyl acetate. The extract was washed with saturated brine and then dried over anhydrous magnesium sulfate, and the solvent was distilled off under reduced pressure. The residue was purified by silica gel column chromatography (ethyl acetate/petroleum ether) to obtain the title compound (0.88 g).

$^1$H NMR (400 MHz, CDCl$_3$) δ 1.29 (9H, s), 7.14-7.31 (3H, m), 7.37 (1H, d, J=7.6 Hz), 7.64 (1H, brs).

K) tert-Butyl (2-chlorobenzoyl)[4-(4-methoxybenzyl)-3-methyl-4,5,6,7-tetrahydro[1,2]oxazolo[4,3-b]pyridin-7-yl]carbamate In a nitrogen atmosphere, to a solution of tert-butyl (2-chlorobenzoyl)carbamate (366 mg), 4-(4-methoxybenzyl)-3-methyl-4,5,6,7-tetrahydro[1,2]oxazolo[4,3-b]pyridin-7-ol (356 mg) and triphenylphosphine (3.75 g) in THF (20 mL), DEAD (2.26 g) was added dropwise at 0° C., and then, the mixture was stirred for 30 minutes. The mixture was further stirred at room temperature for 16 hours. The solvent was distilled off under reduced pressure, and the residue was purified by silica gel column chromatography (ethyl acetate/petroleum ether). The obtained residue was purified by HPLC to obtain the title compound (270 mg).

$^1$H NMR (400 MHz, CDCl$_3$) δ 1.13 (9H, s), 2.06-2.15 (1H, m), 2.33 (3H, s), 2.60-2.73 (1H, m), 2.88-2.98 (1H, m), 3.08-3.14 (1H, m), 3.82 (3H, s), 4.03 (1H, d, J=14.4 Hz), 4.30 (1H, d, J=14.4 Hz), 5.84-5.94 (1H, m), 6.89 (2H, d, J=8.8 Hz), 7.26-7.38 (5H, m), 7.51 (1H, d, J=6.0 Hz).

L) tert-Butyl (2-chlorobenzoyl)(3-methyl-4,5,6,7-tetrahydro[1,2]oxazolo[4,3-b]pyridin-7-yl)carbamate A solution of tert-butyl (2-chlorobenzoyl)[4-(4-methoxybenzyl)-3-methyl-4,5,6,7-tetrahydro[1,2]oxazolo[4,3-b]pyridin-7-yl]carbamate (270 mg) and 1-chloroethyl chloroformate (2.27 g) in 1,2-dichloroethane (20 mL) was stirred for 2 hours under reflux. The reaction mixture was concentrated under reduced pressure, and the residue was dissolved in methanol (20 mL). The solution was stirred for 2 hours under reflux. The reaction mixture was concentrated under reduced pressure to obtain the title compound (260 mg).

MS: [M+H]$^+$ 392.0.

M) 2-Chloro-N-(3-methyl-4,5,6,7-tetrahydro[1,2]oxazolo[4,3-b]pyridin-7-yl)benzamide A mixture of tert-butyl (2-chlorobenzoyl)(3-methyl-4,5,6,7-tetrahydro[1,2]oxazolo[4,3-b]pyridin-7-yl)carbamate (260 mg), trifluoroacetic acid (3 mL) and dichloromethane (12 mL) was stirred at 15° C. for 3 hours. The solvent in the reaction mixture was distilled off under reduced pressure to obtain the title compound (240 mg).

$^1$H NMR (400 MHz, CDCl$_3$) δ 1.90-2.03 (1H, m), 2.30 (3H, s), 2.52-2.61 (1H, m), 2.93 (1H, brs), 3.25-3.40 (2H, m), 5.33-5.42 (1H, m), 6.68 (1H, brs), 7.30-7.44 (3H, m), 7.69-7.74 (1H, m).

N) 2-Chloro-N-[4-(3,4-dimethoxybenzoyl)-3-methyl-4,5,6,7-tetrahydro[1,2]oxazolo[4,3-b]pyridin-7-yl]benzamide To a solution of 2-chloro-N-(3-methyl-4,5,6,7-tetrahydro[1,2]oxazolo[4,3-b]pyridin-7-yl)benzamide (240 mg) and triethylamine (250 mg) in THF (15 mL), 3,4-dimethoxybenzoyl chloride (198 mg) was gradually added under ice cooling, and the mixture was stirred for 30 minutes. The solvent in the reaction mixture was distilled off under reduced pressure. The residue was purified by HPLC to obtain the title compound (75 mg).

$^1$H NMR (400 MHz, CDCl$_3$) δ 1.96-2.10 (1H, m), 2.39 (3H, s), 2.50-2.60 (1H, m), 3.78-3.88 (1H, m), 3.92 (3H, s), 3.94 (3H, s), 4.05-4.15 (1H, m), 5.35-5.44 (1H, m), 6.78 (1H, d, J=6.0 Hz), 6.91 (1H, d, J=8.4 Hz), 7.12-7.21 (2H, m), 7.30-7.42 (3H, m), 7.71 (1H, d, J=7.6 Hz).

Example 18A

2-Chloro-N-{4-(3,4-dimethoxybenzoyl)-1-[(3-methyloxetan-3-yl)methyl]-4,5,6,7-tetrahydro-1H-pyrazolo[4,3-b]pyridin-7-yl}benzamide A mixture of an isomer mixture of 2-chloro-N-[4-(3,4-dimethoxybenzoyl)-4,5,6,7-tetrahydro-2H-pyrazolo[4,3-b]pyridin-7-yl]benzamide and 2-chloro-N-[4-(3,4-dimethoxybenzoyl)-4,5,6,7-tetrahydro-1H-pyrazolo[4,3-b]pyridin-7-yl]benzamide (150 mg), 3-(chloromethyl)-3-methyloxetane (45.1 mg), potassium carbonate (94 mg) and DMF (10 mL) was stirred at 50° C. for 15 hours. Water was added to the reaction mixture, followed by extraction with ethyl acetate. The extract was washed with saturated brine and then dried over anhydrous magnesium sulfate, and the solvent was distilled off under reduced pressure. The residue was purified by silica gel column chromatography (ethyl acetate) to obtain the title compound (37 mg).

$^1$H NMR (300 MHz, DMSO-d$_6$) δ 1.19 (3H, s), 1.90-2.21 (2H, m), 3.54-3.75 (1H, m), 3.77 (3H, s), 3.81 (3H, s), 3.83-3.98 (1H, m), 4.17-4.36 (4H, m), 4.62 (1H, d, J=5.7 Hz), 4.71 (1H, d, J=5.7 Hz), 5.26-5.42 (1H, m), 6.98-7.11 (3H, m), 7.34-7.54 (4H, m), 8.03 (1H, brs), 9.10 (1H, d, J=8.7 Hz).

Example 30A

2-Chloro-N-[4-(3,4-dimethoxybenzoyl)-4,5,6,7-tetrahydro[1,2]thiazolo[4,3-b]pyridin-7-yl]benzamide A) Ethyl (2E)-cyano({[(4-methylphenyl)sulfonyl]oxy}imino)acetate To a solution of ethyl (2E)-cyano(hydroxyimino)acetate (41.63 g) and triethylamine (45.53 g) in ethyl acetate (300 mL), p-toluenesulfonyl chloride (57.2 g) was gradually added under ice cooling. The reaction mixture was stirred at room temperature for 2 hours. The insoluble matter was filtered off, and the filtrate was concentrated under reduced pressure. Water (300 mL) was added to the residue, and the mixture was stirred for 15 minutes. The deposited precipitate was filtered and dried under reduced pressure to obtain the title compound (49.18 g).

$^1$H NMR (400 MHz, CDCl$_3$) δ 1.38 (3H, t, J=7.2 Hz), 2.48 (3H, s), 4.41 (2H, q, J=7.2 Hz), 7.41 (2H, d, J=8.0 Hz), 7.92 (2H, d, J=8.4 Hz).

B) Diethyl 4-amino-1,2-thiazole-3,5-dicarboxylate

A mixture of ethyl (2E)-cyano({[(4-methylphenyl)sulfonyl]oxy}imino)acetate (37.1 g) and ethyl 2-mercaptoacetate (22.53 g) in ethanol, pyridine (12.36 g) was added dropwise such that the temperature of the solution was 35 to 40° C. The reaction solution was stirred at room temperature for 3 hours, then triethylamine (20 mL) was added thereto, and the mixture was further stirred for 30 minutes. The reaction mixture was added to ice water, followed by extraction with ethyl acetate. The extract was washed with saturated brine and dried over anhydrous magnesium sulfate, and the solvent was distilled off under reduced pressure to obtain the title compound (28.45 g).

$^1$H NMR (400 MHz, CDCl$_3$) δ 1.38 (3H, t, J=7.2 Hz), 1.45 (3H, t, J=7.2 Hz), 4.36 (2H, q, J=7.2 Hz), 4.45 (2H, q, J=7.2 Hz), 6.49 (2H, brs).

C) 4-Amino-1,2-thiazole-3-carboxylic acid hydrochloride

A solution of diethyl 4-amino-1,2-thiazole-3,5-dicarboxylate (28.45 g) in concentrated hydrochloric acid (110 mL) was stirred for 4 hours under reflux. The reaction solution was cooled to room temperature and then left standing overnight. The deposited crystals were collected by filtration, washed with acetone and then dried to obtain the title compound (11.79 g).

$^1$H NMR (400 MHz, D$_2$O) δ 8.89 (1H, s).

D) Methyl 4-amino-1,2-thiazole-3-carboxylate

To a solution of 4-amino-1,2-thiazole-3-carboxylic acid hydrochloride (23.4 g) in methanol (800 mL), thionyl chloride (30 mL) was added dropwise under ice cooling. The reaction solution was stirred at room temperature for 2 days, and then, methanol was distilled off under reduced pressure. Ethyl acetate was added to the residue, and the mixture was washed with saturated brine. The reaction mixture was dried over anhydrous magnesium sulfate, and the solvent was distilled off under reduced pressure to obtain the title compound (17.1 g).

$^1$H NMR (400 MHz, CDCl$_3$) δ 3.97 (3H, s), 4.93 (2H, brs), 7.56 (1H, s).

E) Methyl 4-[(3-methoxy-3-oxopropyl)amino]-1,2-thiazole-3-carboxylate

To a mixture of methyl 4-amino-1,2-thiazole-3-carboxylate (18.2 g) and methyl acrylate (18 mL), acetic acid (0.69 g) was added, and the mixture was stirred at 190° C. for 1.5 hours under irradiation with microwave. The reaction mixture was cooled to room temperature and then diluted with ethyl acetate. The reaction mixture was washed with a saturated aqueous solution of sodium carbonate and saturated brine and then dried over anhydrous sodium sulfate, and the solvent was distilled off under reduced pressure. The residue was purified by silica gel column chromatography (ethyl acetate/petroleum ether) to obtain the title compound (5.6 g).

$^1$H NMR (400 MHz, CDCl$_3$) δ 2.68 (2H, t, J=6.8 Hz), 3.48 (2H, t, J=5.6 Hz), 3.73 (3H, s), 3.98 (3H, s), 6.31 (1H, brs), 7.40 (1H, s).

F) Methyl 4-[benzyl(3-methoxy-3-oxopropyl)amino]-1,2-thiazole-3-carboxylate

A mixture of methyl 4-[(3-methoxy-3-oxopropyl)amino]-1,2-thiazole-3-carboxylate (5.63 g), benzyl bromide (5.93 g) and potassium carbonate (6.36 g) in 2-butanone (100 mL) was stirred for 8 hours under reflux. The reaction mixture was cooled to room temperature, and then, the insoluble matter was filtered off. The solvent in the filtrate was distilled off under reduced pressure, and the residue was purified by silica gel column chromatography (ethyl acetate/petroleum ether) to obtain the title compound (6.43 g).

$^1$H NMR (300 MHz, CDCl$_3$) δ 2.55 (2H, t, J=7.5 Hz), 3.43 (2H, t, J=7.5 Hz), 3.61 (3H, s), 3.99 (3H, s), 4.29 (2H, s), 7.24-7.38 (5H, m), 7.95 (1H, s).

G) Methyl 4-benzyl-7-oxo-4,5,6,7-tetrahydro[1,2]thiazolo[4,3-b]pyridine-6-carboxylate A solution of methyl 4-[benzyl(3-methoxy-3-oxopropyl)amino]-1,2-thiazole-3-carboxylate (6.45 g) in THF (20 mL) was added dropwise to a mixture of t-BuOK (4.33 g) and THF (80 mL) at −20° C. The reaction mixture was stirred for 50 minutes, and then, a saturated aqueous solution of ammonium chloride was poured thereto, followed by extraction with ethyl acetate. The extract was dried over anhydrous sodium sulfate, and the solvent was distilled off under reduced pressure to obtain the title compound (6.12 g).

$^1$H NMR (400 MHz, CDCl$_3$) δ 3.73 (3H, s), 4.09 (2H, s), 4.21 (2H, s), 6.92 (1H, s), 7.20-7.38 (5H, m), 11.76 (1H, s).

H) 4-Benzyl-5,6-dihydro[1,2]thiazolo[4,3-b]pyridin-7(4H)-one

A mixture of methyl 4-benzyl-7-oxo-4,5,6,7-tetrahydro[1,2]thiazolo[4,3-b]pyridine-6-carboxylate (6.12 g), aluminum oxide (90 g) and 1,4-dioxane (600 mL) was stirred for 2 hours under reflux. The reaction mixture was cooled to room temperature, and then, the insoluble matter was filtered off. The solvent in the filtrate was distilled off under reduced pressure to obtain the title compound (3.66 g).

MS: [M+H]$^+$ 244.9.

I) 4-Benzyl-4,5,6,7-tetrahydro[1,2]thiazolo[4,3-b]pyridin-7-ol

To a solution of 4-benzyl-5,6-dihydro[1,2]thiazolo[4,3-b]pyridin-7(4H)-one (3.66 g) in methanol (80 mL), sodium tetrahydroborate (1.14 g) was gradually added, and the mixture was stirred at 15° C. for 1 hour. Water was added to the reaction mixture, followed by extraction with ethyl acetate. The extract was washed with saturated brine and then dried over anhydrous sodium sulfate, and the solvent was distilled off under reduced pressure to obtain the title compound (2.87 g).

$^1$H NMR (300 MHz, CDCl$_3$) δ 2.02-2.28 (2H, m), 2.88 (1H, brs), 3.10-3.22 (1H, m), 3.25-3.39 (1H, m), 4.33 (2H, s), 4.92 (1H, t, J=5.1 Hz), 7.05 (1H, s), 7.25-7.46 (5H, m).

J) 7-Azido-4-benzyl-4,5,6,7-tetrahydro[1,2]thiazolo[4,3-b]pyridine

To a solution of 4-benzyl-4,5,6,7-tetrahydro[1,2]thiazolo[4,3-b]pyridin-7-ol (370 mg) in toluene (15 mL) and dichloromethane (15 mL), DPPA (1.24 g) was added dropwise at 0° C. in a nitrogen atmosphere. After stirring for 30 minutes, DBU (680 mg) was added thereto, and the mixture was stirred at room temperature for 16 hours. The solvent was distilled off under reduced pressure, and the residue was purified by silica gel column chromatography (ethyl acetate/petroleum ether) to obtain the title compound (390 mg).

$^1$H NMR (400 MHz, CDCl$_3$) δ 1.94-2.02 (1H, m), 2.02-2.14 (1H, m), 3.02-3.10 (1H, m), 3.17-3.25 (1H, m), 4.24 (1H, d, J=15.6 Hz), 4.30 (1H, d, J=15.2 Hz), 4.75 (1H, t, J=4.4 Hz), 7.06 (1H, s), 7.11-7.38 (5H, m).

K) 4-Benzyl-4,5,6,7-tetrahydro[1,2]thiazolo[4,3-b]pyridin-7-amine

To a solution of 7-azido-4-benzyl-4,5,6,7-tetrahydro[1,2]thiazolo[4,3-b]pyridine (380 mg) in methanol (20 mL), palladium-carbon (10%) (40 mg) was added, and the mixture was stirred at room temperature for 3 hours in a hydrogen atmosphere. Palladium-carbon was filtered off, and then, the filtrate was concentrated to obtain the title compound (280 mg).

$^1$H NMR (300 MHz, CDCl$_3$) δ 1.65 (2H, brs), 1.76-1.90 (1H, m), 2.12-2.24 (1H, m), 3.05-3.36 (2H, m), 4.00-4.06 (1H, m), 4.25 (2H, s), 6.95 (1H, s), 7.20-7.38 (5H, m).

L) N-(4-Benzyl-4,5,6,7-tetrahydro[1,2]thiazolo[4,3-b]pyridin-7-yl)-2-chlorobenzamide To a solution of 4-benzyl-4,5,6,7-tetrahydro[1,2]thiazolo[4,3-b]pyridin-7-amine (210 mg) and triethylamine (261 mg) in THF (10 mL), 2-chlorobenzoyl chloride (226 mg) was gradually added under ice cooling, and the mixture was stirred at 15° C. for 1 hour. Dichloromethane was added to the reaction mixture. The reaction mixture was washed with a saturated aqueous solution of sodium carbonate and saturated brine and then dried over anhydrous sodium sulfate, and the solvent was distilled off under reduced pressure. The residue was purified by silica gel column chromatography (ethyl acetate/petroleum ether) to obtain the title compound (210 mg).

$^1$H NMR (300 MHz, CDCl$_3$) δ 2.00-2.15 (1H, m), 2.68-2.70 (1H, m), 3.21-3.42 (2H, m), 4.34 (2H, s), 5.16-5.30 (1H, m), 6.89 (1H, d, J=5.7 Hz), 7.05 (1H, s), 7.20-7.42 (8H, m), 7.72 (1H, d, J=2.1 Hz).

M) 2-Chloro-N-(4,5,6,7-tetrahydro[1,2]thiazolo[4,3-b]pyridin-7-yl)benzamide

A mixture of N-(4-benzyl-4,5,6,7-tetrahydro[1,2]thiazolo[4,3-b]pyridin-7-yl)-2-chlorobenzamide (180 mg), aluminum chloride (313 mg) and toluene (10 mL) was stirred at 50° C. for 4 hours. The reaction mixture was cooled to room temperature, and then, a saturated aqueous solution of sodium bicarbonate was added to the reaction mixture, followed by extraction with ethyl acetate. The extract was washed with saturated brine and then dried over anhydrous sodium sulfate, and the solvent was distilled off under reduced pressure to obtain the title compound (120 mg).

MS: [M+H]$^+$ 293.8.

N) 2-Chloro-N-[4-(3,4-dimethoxybenzoyl)-4,5,6,7-tetrahydro[1,2]thiazolo[4,3-b]pyridin-7-yl]benzamide To a solution of 2-chloro-N-(4,5,6,7-tetrahydro[1,2]thiazolo[4,3-b]pyridin-7-yl)benzamide (120 mg) and triethylamine (124 mg) in THF (10 mL), 3,4-dimethoxybenzoyl chloride (98 mg) was gradually added at 15° C., and the mixture was stirred for 30 minutes. The solvent in the reaction mixture was distilled off under reduced pressure, and the residue was purified by HPLC to obtain the title compound (30 mg).

$^1$H NMR (400 MHz, CDCl$_3$) δ 1.92-2.09 (1H, m), 2.74-2.84 (1H, m), 3.84-3.90 (1H, m), 3.92 (3H, s), 3.95 (3H, s), 4.09-4.20 (1H, m), 5.22-5.37 (1H, m), 6.93 (1H, d, J=8.4 Hz), 7.03 (1H, d, J=5.6 Hz), 7.05-7.13 (2H, m), 7.30-7.44 (3H, m), 7.72-7.80 (1H, m), 9.21 (1H, brs).

Example 36A

2-Chloro-N-(4-(3,4-dimethoxybenzoyl)-1-isopropyl-4,5,6,7-tetrahydro-1H-pyrazolo[4,3-b]pyridin-7-yl)benzamide A) Methyl 1-isopropyl-4-nitro-1H-pyrazole-5-carboxylate A mixture of 4-nitro-1H-pyrazole-5-carboxylic acid (10 g), tosylic acid monohydrate (0.605 g) and methanol (120 mL) was stirred overnight at 65° C. The solvent was distilled off under reduced pressure, and the residue was diluted with an excessive amount of an aqueous potassium carbonate solution, followed by extraction with ethyl acetate (200 mL). The aqueous layer was adjusted to pH 7 to 8 using 6 N hydrochloric acid, followed by extraction with an ethyl acetate-tetrahydrofuran mixed solution (3/1, v/v, 200 mL). The organic layers were combined, washed with saturated brine and dried over anhydrous magnesium sulfate, and the solvent was distilled off under reduced pressure. The residue was dissolved in N,N'-dimethylformamide (200 mL). To the solution, sodium hydride (60%, 3.06 g) was added in small portions under ice cooling. After stirring at the same temperature as above for 20 minutes, propyl 2-iodide (19.1 mL) was added dropwise thereto over 20 minutes. The mixture was stirred at the same temperature as above for 1 hour and at room temperature for 5 hours. The reaction mixture was cooled to 10° C. and diluted with water (500 mL), followed by extraction with ethyl acetate (300 mL) twice. The extract was washed with a saturated aqueous solution of sodium bicarbonate and saturated brine and dried over anhydrous magnesium sulfate, and the solvent was distilled off under reduced pressure. The residue was purified by silica gel column chromatography (ethyl acetate/hexane) to obtain the title compound (3.59 g).

$^1$H NMR (300 MHz, DMSO-d$_6$) δ 1.43 (6H, d, J=6.6 Hz), 3.99 (3H, s), 4.64-4.79 (1H, m), 8.41 (1H, s).

B) Methyl 4-amino-1-isopropyl-1H-pyrazole-5-carboxylate

A mixture of methyl 1-isopropyl-4-nitro-1H-pyrazole-5-carboxylate (3.57 g), 10% palladium-carbon (containing 50% water, 0.18 g) and methanol (60 mL) was stirred at room temperature for 2 hours in a hydrogen atmosphere. The insoluble matter was filtered off through celite, and the filtrate was concentrated under reduced pressure. The residue was diluted with ethyl acetate, washed with saturated brine and dried over anhydrous magnesium sulfate, and the solvent was distilled off under reduced pressure to obtain the title compound (3.02 g).

$^1$H NMR (300 MHz, DMSO-d$_6$) δ 1.30 (6H, d, J=6.6 Hz), 3.79 (3H, s), 5.00 (2H, s), 5.21 (1H, dt, J=13.1, 6.5 Hz), 7.05 (1H, s).

C) Methyl 4-(benzyl(3-methoxy-3-oxopropyl)amino)-1-isopropyl-1H-pyrazole-5-carboxylate A mixture of methyl 4-amino-1-isopropyl-1H-pyrazole-5-carboxylate (2.92 g), methyl acrylate (13.7 g), 4-(dimethylamino)pyridine (0.389 g) and N,N'-dimethylformamide (20 mL) was stirred at 100° C. for 3 days. The reaction mixture was cooled to room temperature, and redundant methyl acrylate was distilled off under reduced pressure. Benzyl bromide (2.84 mL) and potassium carbonate (3.30 g) were added to the residue, and the mixture was stirred at room temperature for 8 hours. The reaction mixture was diluted with water (200 mL), followed by extraction with ethyl acetate (200 mL). The extract was washed with saturated brine and dried over anhydrous magnesium sulfate, and the solvent was distilled off under reduced pressure. The residue was purified by silica gel column chromatography (ethyl acetate/hexane) to obtain the title compound (4.34 g).

$^1$H NMR (300 MHz, DMSO-$d_6$) δ 1.34 (6H, d, J=6.6 Hz), 2.40-2.47 (2H, m), 3.22 (2H, t, J=7.3 Hz), 3.50 (3H, s), 3.80 (3H, s), 4.14 (2H, s), 5.12-5.25 (1H, m), 7.17-7.26 (1H, m), 7.27-7.31 (4H, m), 7.41 (1H, s).

D) 4-Benzyl-1-isopropyl-5,6-dihydro-1H-pyrazolo[4,3-b]pyridin-7(4H)-one

To a solution of methyl 4-(benzyl(3-methoxy-3-oxopropyl)amino)-1-isopropyl-1H-pyrazole-5-carboxylate (4.24 g) in tetrahydrofuran (80 mL), a 1.9 M solution of sodium bis(trimethylsilyl)amide in tetrahydrofuran (6.83 mL) was added dropwise at room temperature. After stirring at the same temperature as above for 1 hour, a 1.9 M solution of sodium bis(trimethylsilyl)amide in tetrahydrofuran (3.10 mL) was added thereto, and the mixture was further stirred for 30 minutes, followed by the addition of a 1.9 M solution of sodium bis(trimethylsilyl)amide in tetrahydrofuran (1.86 mL). After stirring at the same temperature as above for 1 hour, a 2 M aqueous sodium hydroxide solution (59 mL) was added thereto, and the reaction mixture was stirred at 70° C. for 3 hours. The reaction mixture was diluted with water (150 mL), followed by extraction with ethyl acetate (150 mL+50 mL). The extract was washed with saturated brine and dried over anhydrous magnesium sulfate, and the solvent was distilled off under reduced pressure to obtain the title compound (2.89 g).

$^1$H NMR (300 MHz, DMSO-$d_6$) δ 1.33 (6H, d, J=6.6 Hz), 2.45-2.53 (2H, m), 3.12-3.19 (2H, m), 4.30 (2H, s), 5.16 (1H, quin, J=6.6 Hz), 7.25-7.42 (6H, m).

E) 4-Benzyl-1-isopropyl-4,5,6,7-tetrahydro-1H-pyrazolo[4,3-b]pyridin-7-amine A mixture of 4-benzyl-1-isopropyl-5,6-dihydro-1H-pyrazolo[4,3-b]pyridin-7(4H)-one (900 mg), pyridine (1.32 g), hydroxylamine hydrochloride (1.16 g) and ethanol (20 mL) was stirred at 80 to 90° C. for 6 hours. The solvent was distilled off under reduced pressure. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. A mixture of the residue, Raney nickel (8 g) and methanol (20 mL) was stirred at room temperature for 2 hours in a hydrogen atmosphere. The insoluble matter was filtered off through celite, and the celite was washed with methanol-water (3/1). The filtrate was concentrated under reduced pressure. The residue was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (643 mg).

MS: [M+H]$^+$ 271.0.

F) N-(4-Benzyl-1-isopropyl-4,5,6,7-tetrahydro-1H-pyrazolo[4,3-b]pyridin-7-yl)-2-chlorobenzamide To a solution of 4-benzyl-1-isopropyl-4,5,6,7-tetrahydro-1H-pyrazolo[4,3-b]pyridin-7-amine (640 mg) in tetrahydrofuran (12 mL), triethylamine (0.66 mL) and 2-chlorobenzoyl chloride (0.36 mL) were added at room temperature. After stirring at the same temperature as above for 1 hour, the reaction mixture was diluted with ethyl acetate and washed with a saturated aqueous solution of sodium bicarbonate. The extract was washed with saturated brine and dried over anhydrous magnesium sulfate, and the solvent was distilled off under reduced pressure. The residue was purified by silica gel column chromatography (ethyl acetate/hexane) to obtain the title compound (927 mg).

$^1$H NMR (300 MHz, DMSO-$d_6$) δ 1.31-1.41 (6H, m), 1.87-2.07 (2H, m), 2.74-2.97 (2H, m), 3.92 (1H, d, J=14.3 Hz), 4.23 (1H, d, J=14.3 Hz), 4.36-4.46 (1H, m), 5.25-5.32 (1H, m), 7.00 (1H, s), 7.23-7.50 (9H, m), 9.03 (1H, d, J=8.5 Hz).

G) 2-Chloro-N-(1-isopropyl-4,5,6,7-tetrahydro-1H-pyrazolo[4,3-b]pyridin-7-yl)benzamide To a solution of N-(4-benzyl-1-isopropyl-4,5,6,7-tetrahydro-1H-pyrazolo[4,3-b]pyridin-7-yl)-2-chlorobenzamide (900 mg) in acetonitrile (12 mL), 1-chloroethyl chloroformate (472 mg) was added at room temperature. The mixture was stirred at 80° C. for 1 hour. The solvent was distilled off under reduced pressure, and methanol (5 mL) was added to the residue. The mixture was stirred at 70° C. for 1 hour. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (416 mg).

$^1$H NMR (300 MHz, DMSO-$d_6$) δ 1.35 (6H, dd, J=6.5, 1.0 Hz), 1.78-1.92 (2H, m), 2.98-3.07 (2H, m), 4.39 (1H, dt, J=13.0, 6.6 Hz), 4.47-4.51 (1H, m), 5.23-5.31 (1H, m), 6.91 (1H, s), 7.32-7.51 (4H, m), 9.01 (1H, d, J=8.7 Hz).

H) 2-Chloro-N-(4-(3,4-dimethoxybenzoyl)-1-isopropyl-4,5,6,7-tetrahydro-1H-pyrazolo[4,3-b]pyridin-7-yl)benzamide To a solution of 2-chloro-N-(1-isopropyl-4,5,6,7-tetrahydro-1H-pyrazolo[4,3-b]pyridin-7-yl)benzamide (300 mg) in pyridine (5 mL), 3,4-dimethoxybenzoyl chloride (283 mg) was added at room temperature. After stirring at the same temperature as above for 1 hour, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) and added to ethyl acetate-hexane. The deposit was collected by filtration to obtain the title compound (387 mg).

$^1$H NMR (300 MHz, DMSO-$d_6$) δ 1.41 (6H, d, J=6.4 Hz), 1.94-2.20 (2H, m), 3.57-3.98 (8H, m), 4.45-4.58 (1H, m), 5.38-5.49 (1H, m), 6.97-7.08 (3H, m), 7.34-7.53 (4H, m), 7.99 (1H, brs), 9.12 (1H, d, J=8.7 Hz).

Example 54A

N-(3-Bromo-4-(3-chloro-4-methoxybenzoyl)-1-methyl-4,5,6,7-tetrahydro-1H-pyrazol[4,3-b]pyridin-7-yl)-2-chlorobenzamide To a solution of 2-chloro-N-(4-(3-chloro-4-methoxybenzoyl)-1-methyl-4,5,6,7-tetrahydro-1H-pyrazolo[4,3-b]pyridin-7-yl)benzamide (95 mg) in ethyl acetate (2.0 mL), N-bromosuccinimide (38.7 mg) was added under ice cooling, and the mixture was stirred overnight at room temperature. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then crystallized from ethyl acetate/diisopropyl ether to obtain the title compound (37.5 mg).
$^1$H NMR (300 MHz, CDCl$_3$) δ 2.04-2.20 (1H, m), 2.21-2.39 (1H, m), 3.70 (1H, t, J=11.0 Hz), 3.85 (3H, s), 3.96 (3H, s), 4.08 (1H, d, J=16.0 Hz), 5.51-5.66 (1H, m), 6.64 (1H, m), 6.95 (1H, d, J=8.5 Hz), 7.31-7.45 (3H, m), 7.53 (1H, d, J=8.3 Hz), 7.63-7.73 (2H, m).

Example 74A

2-Chloro-N-((7S)-4-(3,4-dimethoxybenzoyl)-1-isopropyl-4,5,6,7-tetrahydro-1H-pyrazolo[4,3-b]pyridin-7-yl)benzamide 2-Chloro-N-(4-(3,4-dimethoxybenzoyl)-1-isopropyl-4,5,6,7-tetrahydro-1H-pyrazolo[4,3-b]pyridin-7-yl)benzamide (400 mg) was fractionated by SFC (column: CHIRALCEL ODH, 20 mm ID×250 mm L, mobile phase: carbon dioxide/methanol=770/230), and a fraction having a smaller retention time was concentrated under reduced pressure. The residue was added to ethyl acetate-hexane. The deposit was collected by filtration to obtain the title compound (158 mg). Since the title compound of Example 75A was determined to be an R form, this compound was determined to be an S form.
$^1$H NMR (300 MHz, DMSO-d$_6$) δ 1.41 (6H, d, J=6.4 Hz), 1.95-2.19 (2H, m), 3.56-3.95 (8H, m), 4.45-4.59 (1H, m), 5.39-5.47 (1H, m), 6.94-7.08 (3H, m), 7.34-7.54 (4H, m), 8.03 (1H, brs), 9.12 (1H, d, J=8.7 Hz).
>99.9% ee Example 75A 2-Chloro-N-((7R)-4-(3,4-dimethoxybenzoyl)-1-isopropyl-4,5,6,7-tetrahydro-1H-pyrazolo[4,3-b]pyridin-7-yl)benzamide A fraction having a larger retention time in the optical resolution operation of Example 74A was concentrated under reduced pressure. The residue was added to ethyl acetate-hexane. The deposit was collected by filtration to obtain the title compound (169 mg). The absolute structure was determined to be an R form by single-crystal X-ray analysis.
$^1$H NMR (300 MHz, DMSO-d$_6$) δ 1.41 (6H, d, J=6.4 Hz), 1.95-2.20 (2H, m), 3.54-3.94 (8H, m), 4.44-4.59 (1H, m), 5.37-5.49 (1H, m), 6.98-7.07 (3H, m), 7.35-7.53 (4H, m), 8.00 (1H, brs), 9.12 (1H, d, J=8.5 Hz).
>99.9% ee Example 113A 2-Chloro-N-(3-chloro-4-(3,4-dimethoxybenzoyl)-1-methyl-4,5,6,7-tetrahydro-1H-pyrazolo[4,3-b]pyridin-7-yl)benzamide To a solution of 2-chloro-N-(4-(3,4-dimethoxybenzoyl)-1-methyl-4,5,6,7-tetrahydro-1H-pyrazolo[4,3-b]pyridin-7-yl)benzamide (200 mg) in DMF (2.0 mL), N-chlorosuccinimide (70.4 mg) was added at room temperature, and the mixture was stirred overnight at the same temperature as above. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and reverse-phase HPLC and then crystallized from THF/ethyl acetate/diisopropyl ether to obtain the title compound (16.5 mg).
$^1$H NMR (300 MHz, DMSO-d$_6$) δ 1.90-2.04 (1H, m), 2.05-2.18 (1H, m), 3.76 (6H, s), 3.81 (3H, s), 3.88-4.00 (2H, m), 5.29-5.50 (1H, m), 7.01 (1H, d, J=8.3 Hz), 7.07-7.24 (2H, m), 7.34-7.59 (4H, m), 9.13 (1H, d, J=8.5 Hz).

Example 117A

2-Chloro-N-(7-(3,4-dimethoxybenzoyl)-3-methyl-4,5,6,7-tetrahydro[1,2]thiazolo[5,4-b]pyridin-4-yl)benzamide A) Methyl 3-methyl-5-((phenoxycarbonyl)amino)isothiazole-4-carboxylate To a solution of phenyl chloroformate (24.7 mL) in acetonitrile (300 mL), potassium thiocyanate (19.1 g) was added at 0° C., and the mixture was stirred at room temperature for 1 hour in a nitrogen atmosphere. Methyl 3-aminobut-2-enoate (22.6 g) was added thereto, and the mixture was stirred at room temperature for 30 minutes. The reaction mixture was cooled to 0° C., then bromine (10.1 mL) was added thereto, and the mixture was stirred at room temperature for 30 minutes. The reaction mixture was added to water/ethyl acetate. The insoluble matter was filtered off, and the filtrate was subjected to extraction with ethyl acetate. The solvent was concentrated under reduced pressure. The residue was washed with ethyl acetate/diisopropyl ether to obtain the title compound (18.6 g).
MS: [M+H]$^+$ 293.2.

B) Methyl 5-amino-3-methylisothiazole-4-carboxylate

To a mixture of methyl 3-methyl-5-((phenoxycarbonyl)amino)isothiazole-4-carboxylate (36.3 g), water (25 mL) and N,N-dimethylformamide (250 mL), sodium carbonate (26.3 g) was added, and the resulting mixture was stirred at 90° C. for 1 hour. The reaction mixture was added to water, and the mixture was filtered through celite. The filtrate was subjected to extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (12.3 g).
MS: [M+H]$^+$ 173.2.

C) Methyl 5-((3-methoxy-3-oxopropyl)amino)-3-methylisothiazole-4-carboxylate

To a mixed solution of methyl 5-amino-3-methylisothiazole-4-carboxylate (12.0 g), methyl acrylate (62.8 mL) and N,N-dimethylformamide (25 mL), N,N-dimethyl-4-aminopyridine (0.85 g) was added, and the mixture was stirred at 100° C. for 15 hours in a nitrogen atmosphere. The reaction mixture was added to water, followed by extraction with ethyl acetate. The extract was washed with water and saturated brine and dried over anhydrous magnesium sulfate, and the solvent was distilled off under reduced pressure. The residue was purified by silica gel column chromatography (ethyl acetate/hexane) and silica gel column chromatography (NH, ethyl acetate/hexane) to obtain the title compound (7.4 g). methyl acrylate

MS: [M+H]$^+$ 259.1.

D) Methyl 5-(benzyl(3-methoxy-3-oxopropyl) amino)-3-methylisothiazole-4-carboxylate To a mixture of methyl 5-((3-methoxy-3-oxopropyl) amino)-3-methylisothiazole-4-carboxylate (6.10 g), sodium iodide (0.35 g), cesium carbonate (23.1 g) and 2-butanone (47 mL), (bromomethyl)benzene (8.4 mL) was added, and the resulting mixture was refluxed for 5 hours and then cooled to room temperature. N,N-Dimethylacetamide (47 mL) and (bromomethyl)benzene (5.5 mL) were added to the reaction mixture, and the mixture was stirred at room temperature for 15 hours in a nitrogen atmosphere. The reaction mixture was added to water, followed by extraction with ethyl acetate. The extract was washed with water and saturated brine and dried over anhydrous magnesium sulfate, and the solvent was distilled off under reduced pressure. The residue was purified by silica gel column chromatography (ethyl acetate/hexane) to obtain the title compound (5.1 g).

MS: [M+H]$^+$ 349.3.

E) Methyl 7-benzyl-3-methyl-4-oxo-4,5,6,7-tetrahydroisothiazolo[5,4-b]pyridine-5-carboxylate To a solution of methyl 5-(benzyl(3-methoxy-3-oxopropyl)amino)-3-methylisothiazole-4-carboxylate (4.40 g) in tetrahydrofuran (63 mL), a 1.9 M solution of sodium bis(trimethylsilyl)amide in tetrahydrofuran (13.3 mL) was added at 0° C. After stirring at the same temperature as above for 5 minutes, a saturated ammonium chloride solution was added thereto, followed by extraction with ethyl acetate. The extract was washed with water and saturated brine and dried over anhydrous magnesium sulfate, and the solvent was distilled off under reduced pressure. The residue was purified by silica gel column chromatography (ethyl acetate/hexane) to obtain the title compound (1.76 g).

MS: [M+H]$^+$ 317.2.

F) 7-Benzyl-3-methyl-6,7-dihydroisothiazolo[5,4-b]pyridin-4(5H)-one

To a solution of methyl 7-benzyl-3-methyl-4-oxo-4,5,6,7-tetrahydroisothiazolo[5,4-b]pyridine-5-carboxylate (1.73 g) in tetrahydrofuran (27 mL), a 2.0 M aqueous sodium hydroxide solution (27 mL) was added at room temperature. The mixture was stirred at 60° C. for 3 d hours and cooled to room temperature, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (983 mg).

MS: [M+H]$^+$ 259.1.

G) 7-Benzyl-3-methyl-4,5,6,7-tetrahydroisothiazolo[5,4-b]pyridin-4-ol

To a solution of 7-benzyl-3-methyl-6,7-dihydroisothiazolo[5,4-b]pyridin-4(5H)-one (970 mg) in methanol (15 mL), sodium borohydride (142 mg) was added at 0° C., and the mixture was stirred at room temperature for 30 minutes in a nitrogen atmosphere. The reaction mixture was poured to water, followed by extraction with ethyl acetate. The extract was washed with water and saturated brine and dried over anhydrous magnesium sulfate, and the solvent was distilled off under reduced pressure. The residue was purified by silica gel column chromatography (ethyl acetate) to obtain the title compound (972 mg).

MS: [M+H]$^+$ 261.2.

H) 4-Azido-7-benzyl-3-methyl-4,5,6,7-tetrahydroisothiazolo[5,4-b]pyridine

To a solution of 7-benzyl-3-methyl-4,5,6,7-tetrahydroisothiazolo[5,4-b]pyridin-4-ol (950 mg) and DBU (1.64 mL) in toluene (15 mL), DPPA (2.35 mL) was added dropwise at 0° C., and the mixture was stirred at room temperature for 15 hours in a nitrogen atmosphere. The reaction mixture was purified by silica gel column chromatography (ethyl acetate), and the solvent was distilled off under reduced pressure. The residue was purified again by silica gel column chromatography (ethyl acetate/hexane) to obtain the title compound (833 mg).

$^1$H NMR (300 MHz, CDCl$_3$) δ 1.76-2.02 (1H, m), 2.03-2.16 (1H, m), 2.38 (3H, s), 3.02-3.39 (2H, m), 4.38 (2H, s), 4.50-4.66 (1H, m), 7.19-7.48 (5H, m).

I) 7-Benzyl-3-methyl-4,5,6,7-tetrahydroisothiazolo[5,4-b]pyridin-4-amine

A mixture of 4-azido-7-benzyl-3-methyl-4,5,6,7-tetrahydroisothiazolo[5,4-b]pyridine (820 mg), 10% palladium-carbon (containing 50% water, 82 mg) and methanol (15 mL) was stirred at room temperature for 3 hours in a hydrogen atmosphere. The insoluble matter was filtered off, and the solvent in the filtrate was distilled off under reduced pressure to obtain the title compound (742 mg).

MS: [M+H]$^+$ 260.2.

J) N-(7-Benzyl-3-methyl-4,5,6,7-tetrahydroisothazolo[5,4-b]pyridin-4-yl)-2-chlorobenzamide To a solution of 7-benzyl-3-methyl-4,5,6,7-tetrahydroisothiazolo[5,4-b]pyridin-4-amine (730 mg) and triethylamine (0.79 mL) in tetrahydrofuran (10 mL), 2-chlorobenzoyl chloride (0.38 mL) was added dropwise, and the mixture was stirred at room temperature for 15 hours. The solvent in the reaction mixture was distilled off under reduced pressure. The residue was purified by silica gel column chromatography (NH, ethyl acetate), and ethyl acetate was distilled off under reduced pressure. The residue was purified again by silica gel column chromatography (ethyl acetate/hexane) to obtain the title compound (459 mg).

MS: [M+H]$^+$ 398.2.

K) 2-Chloro-N-(3-methyl-4,5,6,7-tetrahydroisothiazolo[5,4-b]pyridin-4-yl)benzamide To a solution of N-(7-benzyl-3-methyl-4,5,6,7-tetrahydroisothiazolo[5,4-b]pyridin-4-yl)-2-chlorobenzamide (410 mg) in toluene (10 mL), aluminum chloride (687 mg) was added, and the mixture was stirred at 60° C. for 2 hours. The reaction mixture was purified by silica gel column chromatography (NH, ethyl acetate/methanol), and the solvent was distilled off under reduced pressure. The residue was washed with ethyl acetate to obtain the title compound (251 mg).

MS: [M+H]$^+$ 308.2.

L) 2-Chloro-N-(7-(3,4-dimethoxybenzoyl)-3-methyl-4,5,6,7-tetrahydro[1,2]thiazolo[5,4-b]pyridin-4-yl)benzamide To a solution of 2-chloro-N-(3-methyl-4,5,6,7-tetrahydroisothiazolo[5,4-b]pyridin-4-yl)benzamide (145 mg) in pyridine (2.0 mL), 3,4-dimethoxybenzoyl chloride (113 mg) was added dropwise, and the mixture was stirred at room temperature for 30 minutes. The solvent in the reaction mixture was distilled off under reduced pressure. Then, the residue was purified by silica gel column chromatography (NH, ethyl acetate), and the solvent was distilled off under reduced pressure. The residue was purified again by silica gel column chromatography (ethyl acetate/hexane), and the solvent was distilled off under reduced pressure. The obtained residue was washed with ethyl acetate/hexane to obtain the title compound (23.6 mg).

$^1$H NMR (300 MHz, DMSO-d$_6$) δ 1.94-2.22 (2H, m), 2.38 (3H, s), 3.69-3.97 (7H, m), 4.02-4.17 (1H, m), 5.24-5.38 (1H, m), 6.94-7.24 (3H, m), 7.28-7.59 (4H, m), 8.80 (1H, d, J=8.3 Hz).

Example 118A

2-Chloro-N-(7-(3-chloro-4-methoxybenzoyl)-3-methyl-4,5,6,7-tetrahydro[1,2]thiazolo[5,4-b]pyridin-4-yl)benzamide To a mixture of 2-chloro-N-(3-methyl-4,5,6,7-tetrahydroisothiazolo[5,4-b]pyridin-4-yl)benzamide (102 mg), 3-chloro-4-methoxybenzoic acid (186 mg), triethylamine (0.231 mL) and N,N-dimethylformamide (2.0 mL), HATU (504 mg) was added, and the resulting mixture was stirred at room temperature for 18 hours. The solvent in the reaction mixture was distilled off under reduced pressure. Then, the residue was purified by silica gel column chromatography (NH, ethyl acetate), and the solvent was distilled off under reduced pressure. The residue was purified again by silica gel column chromatography (ethyl acetate/hexane). The residue was added to ethyl acetate/diisopropyl ether. The obtained deposit was collected by filtration to obtain the title compound (49.5 mg).

$^1$H NMR (300 MHz, DMSO-d$_6$) δ 2.01-2.22 (2H, m), 2.38 (3H, s), 3.69-4.18 (5H, m), 5.09-5.51 (1H, m), 7.18-7.63 (6H, m), 7.68 (1H, d, J=2.1 Hz), 8.77 (1H, d, J=8.3 Hz).

Example 126A

4-Chloro-N-(4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethyl)benzamide

A) Methyl 1-(2,2-difluoroethyl)-4-nitro-1H-pyrazole-5-carboxylate

To a mixture of methyl 4-nitro-1H-pyrazole-5-carboxylate (7.00 g), 2,2-difluoroethanol (3.69 g), triphenylphosphine (14.0 g) and THF (120 mL), a 1.9 M solution of diisopropyl azodicarboxylate in toluene (28.0 mL) was added dropwise under ice cooling, and the reaction mixture was stirred at room temperature for 3 hours in a nitrogen atmosphere. The reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) and then washed with ethyl acetate/diisopropyl ether to obtain the title compound (7.11 g).

$^1$H NMR (300 MHz, CDCl$_3$) δ 4.03 (3H, s), 4.75 (2H, td, J=13.2, 4.1 Hz), 5.80-6.41 (1H, m), 8.10 (1H, s).

B) Methyl 4-amino-1-(2,2-difluoroethyl)-1H-pyrazole-5-carboxylate

A mixture of methyl 1-(2,2-difluoroethyl)-4-nitro-1H-pyrazole-5-carboxylate (7.10 g), 10% palladium-carbon (0.964 g) and methanol (200 mL) was stirred overnight at room temperature in a hydrogen atmosphere. The insoluble matter was filtered off, and the filtrate was concentrated under reduced pressure. The residue was washed with diisopropyl ether to obtain the title compound (4.62 g).

MS: [M+H]$^+$ 205.9.

C) Methyl 1-(2,2-difluoroethyl)-4-((3-methoxy-3-oxopropyl)amino)-1H-pyrazole-5-carboxylate A mixture of methyl 4-amino-1-(2,2-difluoroethyl)-1H-pyrazole-5-carboxylate (4.60 g), methyl acrylate (20.2 mL), 4-(dimethylamino)pyridine (548 mg) and DMF (25 mL) was stirred at 100° C. for 2 days in a nitrogen atmosphere. The reaction mixture was concentrated under reduced pressure. The residue was purified by silica gel column chromatography (ethyl acetate/hexane) to obtain the title compound (2.46 g).

MS: [M+H]$^+$ 291.9.

D) Methyl 4-(benzyl(3-methoxy-3-oxopropyl)amino)-1-(2,2-difluoroethyl)-1H-pyrazole-5-carboxylate To a mixture of methyl 1-(2,2-difluoroethyl)-4-((3-methoxy-3-oxopropyl)amino)-1H-pyrazole-5-carboxylate (2.45 g), potassium carbonate (2.33 g) and DMF (30 mL), benzyl bromide (1.31 mL) was added, and the resulting mixture was stirred at room temperature for 3 hours. The reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (2.88 g).

MS: [M+H]$^+$ 382.0.

E) 4-Benzyl-1-(2,2-difluoroethyl)-5,6-dihydro-1H-pyrazolo[4,3-b]pyridin-7(4H)-one To a solution of methyl 4-(benzyl(3-methoxy-3-oxopropyl)amino)-1-(2,2-difluoroethyl)-1H-pyrazole-5-carboxylate (2.10 g) in THF (30 mL), a 1 M solution of sodium bis(trimethylsilyl)amide in THF (8.26 mL) was added at room temperature, and the mixture was stirred at the same temperature as above for 2 hours. A 2 M aqueous sodium hydroxide solution (27.5 mL) was added thereto, and the reaction mixture was stirred at 70° C. for 3 hours. The reaction mixture was neutralized with 2 M hydrochloric acid, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (910 mg).
MS: [M+H]$^+$ 291.9.

F) 4-Benzyl-1-(2,2-difluoroethyl)-5,6-dihydro-1H-pyrazolo[4,3-b]pyridin-7(4H)-one oxime A mixture of 4-benzyl-1-(2,2-difluoroethyl)-5,6-dihydro-1H-pyrazolo[4,3-b]pyridin-7(4H)-one (910 mg), pyridine (1.24 g), hydroxylamine hydrochloride (1.09 g) and ethanol (10 mL) was stirred overnight at 90° C. The solvent in the reaction mixture was distilled off under reduced pressure, and the residue was diluted with a saturated aqueous solution of sodium bicarbonate, followed by extraction with ethyl acetate. The extract was washed with saturated brine and dried over anhydrous magnesium sulfate, and the solvent was distilled off under reduced pressure to obtain the title compound (933 mg).
MS: [M+H]$^+$ 306.9.

G) 4-Benzyl-1-(2,2-difluoroethyl)-4,5,6,7-tetrahydro-1H-pyrazolo[4,3-b]pyridin-7-amine A mixture of 4-benzyl-1-(2,2-difluoroethyl)-5,6-dihydro-1H-pyrazolo[4,3-b]pyridin-7(4H)-one oxime (930 mg), Raney nickel (10 g) and methanol (40 mL) was stirred overnight at room temperature in a hydrogen atmosphere. The insoluble matter was filtered off, and the filtrate was concentrated under reduced pressure. The residue was purified by silica gel column chromatography (NH, ethyl acetate/hexane) to obtain the title compound (702 mg).
MS: [M+H]$^+$ 292.9.

H) tert-Butyl (4-benzyl-1-(2,2-difluoroethyl)-4,5,6,7-tetrahydro-1H-pyrazolo[4,3-b]pyridin-7-yl)carbamate To a solution of 4-benzyl-1-(2,2-difluoroethyl)-4,5,6,7-tetrahydro-1H-pyrazolo[4,3-b]pyridin-7-amine (700 mg) and triethylamine (0.668 mL) in THF (7 mL), di-tert-butyl dicarbonate (0.612 mL) was added dropwise at room temperature. After stirring at the same temperature as above for 2 hours, the reaction mixture was concentrated under reduced pressure. The residue was purified by silica gel column chromatography (ethyl acetate/hexane) to obtain the title compound (826 mg).
MS: [M+H]$^+$ 393.0.

I) tert-Butyl (1-(2,2-difluoroethyl)-4,5,6,7-tetrahydro-1H-pyrazolo[4,3-b]pyridin-7-yl)carbamate A mixture of tert-butyl (4-benzyl-1-(2,2-difluoroethyl)-4,5,6,7-tetrahydro-1H-pyrazolo[4,3-b]pyridin-7-yl)carbamate (825 mg), 10% palladium-carbon (containing 50% water, 112 mg), acetic acid (2.0 mL) and methanol (20 mL) was stirred at room temperature for 4 hours in a hydrogen atmosphere. The insoluble matter was filtered off, and the filtrate was concentrated under reduced pressure. The residue was washed with diisopropyl ether to obtain the title compound (625 mg).
MS: [M+H]$^+$ 302.9.

J) tert-Butyl (4-(5-chloro-6-methoxynicotinoyl)-1-(2,2-difluoroethyl)-4,5,6,7-tetrahydro-1H-pyrazolo[4,3-b]pyridin-7-yl)carbamate A mixture of tert-butyl (1-(2,2-difluoroethyl)-4,5,6,7-tetrahydro-1H-pyrazolo[4,3-b]pyridin-7-yl)carbamate (310 mg), 5-chloro-6-methoxynicotinic acid (250 mg), HATU (585 mg), triethylamine (0.429 mL) and DMF (4.0 mL) was stirred at room temperature for 3 hours, and then, the reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (466 mg).
MS: [M+H]$^+$ 472.0.

K) (7-Amino-1-(2,2-difluoroethyl)-6,7-dihydro-1H-pyrazolo[4,3-b]pyridin-4(5H)-yl)(5-chloro-6-methoxypyridin-3-yl)methanone dihydrochloride tert-Butyl (4-(5-chloro-6-methoxynicotinoyl)-1-(2,2-difluoroethyl)-4,5,6,7-tetrahydro-1H-pyrazolo[4,3-b]pyridin-7-yl)carbamate (466 mg) was dissolved in methanol (5 mL). To the solution, a 4 M solution of hydrogen chloride in ethyl acetate (2.47 mL) was added, and the mixture was stirred overnight at room temperature. The reaction mixture was concentrated under reduced pressure, and the residue was washed with ethyl acetate to obtain the title compound (422 mg).
MS: [M+H]$^+$ 371.9.

L) 4-Chloro-N-(4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethyl)benzamide A mixture of (7-amino-1-(2,2-difluoroethyl)-6,7-dihydro-1H-pyrazolo[4,3-b]pyridin-4(5H)-yl)(5-chloro-6-methoxypyridin-3-yl)methanone dihydrochloride (210 mg), 4-chloro-2-(trifluoromethyl)benzoic acid (138 mg), HATU (269 mg), triethylamine (0.197 mL) and DMF (3.0 mL) was stirred at room temperature for 4 hours, and then, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then crystallized from ethyl acetate/diisopropyl ether to obtain the title compound (101 mg).
$^1$H NMR (300 MHz, DMSO-d$_6$) δ 1.91-2.24 (2H, m), 3.70 (1H, d, J=10.4 Hz), 3.77-3.96 (1H, m), 4.01 (3H, s), 4.38-4.70 (2H, m), 5.41 (1H, d, J=4.1 Hz), 6.14-6.68 (1H, m), 7.62 (1H, d, J=8.3 Hz), 7.86 (1H, d, J=8.7 Hz), 7.91 (1H, s), 8.04 (1H, s), 8.12 (1H, brs), 8.29 (1H, s), 9.22 (1H, d, J=7.9 Hz).

Example 132A

N-(4-((5,6-Dimethoxypyridin-3-yl)carbonyl)-1-isopropyl-4,5,6,7-tetrahydro-1H-pyrazolo[4,3-b]pyridin-7-yl)-2-(trifluoromethoxy)benzamide

A) tert-Butyl (4-benzyl-1-isopropyl-4,5,6,7-tetrahydro-1H-pyrazolo[4,3-b]pyridin-7-yl)carbamate To a solution of 4-benzyl-1-isopropyl-4,5,6,7-tetrahydro-1H-pyrazolo[4,3-b]pyridin-7-amine (811 mg) and triethylamine (0.836 mL) in tetrahydrofuran (10 mL), di-tert-butyl dicarbonate (0.766 mL) was added at room temperature.

After stirring at the same temperature as above for 1 hour, the reaction mixture was diluted with ethyl acetate and washed with water. The extract was washed with saturated brine and dried over anhydrous magnesium sulfate, and the solvent was distilled off under reduced pressure. The residue was purified by silica gel column chromatography (ethyl acetate/hexane) to obtain the title compound (1.06 g).
MS: [M+H]$^+$ 371.0.

B) tert-Butyl (1-isopropyl-4,5,6,7-tetrahydro-1H-pyrazolo[4,3-b]pyridin-7-yl)carbamate A mixture of tert-butyl (4-benzyl-1-isopropyl-4,5,6,7-tetrahydro-1H-pyrazolo[4,3-b]pyridin-7-yl)carbamate (1.06 g), 10% palladium-carbon (containing 50% water, 319 mg), methanol (20 mL) and acetic acid (2 mL) was stirred overnight at room temperature in a hydrogen atmosphere. The insoluble matter was filtered off, and the filtrate was concentrated under reduced pressure. The residue was diluted with ethyl acetate/THF and washed with a saturated aqueous solution of sodium bicarbonate. The extract was washed with saturated brine and dried over anhydrous magnesium sulfate, and the solvent was distilled off under reduced pressure to obtain the title compound (780 mg).
MS: [M+H]$^+$ 281.0.

C) tert-Butyl (4-(5,6-dimethoxynicotinoyl)-1-isopropyl-4,5,6,7-tetrahydro-1H-pyrazolo[4,3-b]pyridin-7-yl)carbamate A mixture of tert-butyl (1-isopropyl-4,5,6,7-tetrahydro-1H-pyrazolo[4,3-b]pyridin-7-yl)carbamate (260 mg), 5,6-dimethoxynicotinic acid (221 mg), HATU (529 mg), triethylamine (0.388 mL) and DMF (4 mL) was stirred at room temperature for 4 hours, and then, the reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (359 mg).
MS: [M+H]$^+$ 446.1.

D) (7-Amino-1-isopropyl-6,7-dihydro-1H-pyrazolo[4,3-b]pyridin-4(5H)-yl)(5,6-dimethoxypyridin-3-yl)methanone dihydrochloride tert-Butyl (4-(5,6-dimethoxynicotinoyl)-1-isopropyl-4,5,6,7-tetrahydro-1H-pyrazolo[4,3-b]pyridin-7-yl)carbamate (359 mg) was dissolved in methanol (3 mL). To the solution, a 4 M solution of hydrogen chloride in ethyl acetate (2.02 mL) was added, and the mixture was stirred overnight at room temperature. The reaction mixture was concentrated under reduced pressure, and the residue was washed with ethyl acetate to obtain the title compound (303 mg).
MS: [M+H]$^+$ 346.0.

E) N-(4-((5,6-Dimethoxypyridin-3-yl)carbonyl)-1-isopropyl-4,5,6,7-tetrahydro-1H-pyrazolo[4,3-b]pyridin-7-yl)-2-(trifluoromethoxy)benzamide A mixture of (7-amino-1-isopropyl-6,7-dihydro-1H-pyrazolo[4,3-b]pyridin-4(5H)-yl)(5,6-dimethoxypyridin-3-yl)methanone dihydrochloride (300 mg), 2-(trifluoromethoxy)benzoic acid (192 mg), HATU (409 mg), triethylamine (0.300 mL) and DMF (3.0 mL) was stirred at room temperature for 4 hours, and then, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then crystallized from THF/ethyl acetate/diisopropyl ether to obtain the title compound (203 mg).
$^1$H NMR (300 MHz, CDCl$_3$) δ 1.42 (3H, d, J=6.4 Hz), 1.48 (3H, d, J=6.4 Hz), 2.25 (2H, d, J=3.8 Hz), 3.43-3.68 (1H, m), 3.91 (3H, s), 4.07 (3H, s), 4.14-4.33 (1H, m), 4.37-4.55 (1H, m), 5.48-5.70 (1H, m), 6.78 (1H, d, J=8.5 Hz), 7.23-7.27 (1H, m), 7.32 (1H, d, J=8.1 Hz), 7.41-7.49 (1H, m), 7.52-7.62 (1H, m), 7.89 (1H, d, J=1.9 Hz), 7.99 (1H, dd, J=7.7, 1.9 Hz), 8.20 (1H, brs).

Example 133A

N-(4-((5,6-Dimethoxypyridin-3-yl)carbonyl)-1-methyl-4,5,6,7-tetrahydro-H-pyrazolo[4,3-b]pyridin-7-yl)-2-(trifluoromethoxy)benzamide A) 4-Benzyl-1-methyl-5,6-dihydro-1H-pyrazolo[4,3-b]pyridin-7(4H)-one oxime A mixture of 4-benzyl-1-methyl-5,6-dihydro-1H-pyrazolo[4,3-b]pyridin-7(4H)-one (26 g), pyridine (25.8 mL), hydroxylamine hydrochloride (11.0 g) and ethanol (150 mL) was stirred overnight in a nitrogen atmosphere under conditions of heating to reflux. The solvent was distilled off under reduced pressure, and the residue was purified by silica gel column chromatography (ethyl acetate/petroleum ether) to obtain the title compound (22 g).
MS: [M+H]$^+$ 257.2.

B) 4-Benzyl-1-methyl-4,5,6,7-tetrahydro-1H-pyrazolo[4,3-b]pyridin-7-amine

A mixture of 4-benzyl-1-methyl-5,6-dihydro-1H-pyrazolo[4,3-b]pyridin-7(4H)-one oxime (16 g), Raney nickel (10 g) and methanol (600 mL) was stirred overnight at room temperature in a hydrogen atmosphere. The insoluble matter was filtered off, and the filtrate was concentrated under reduced pressure to obtain the title compound (11 g).
MS: [M+H]$^+$ 243.0.

C) tert-Butyl (4-benzyl-1-methyl-4,5,6,7-tetrahydro-1H-pyrazolo[4,3-b]pyridin-7-yl)carbamate To a solution of 4-benzyl-1-methyl-4,5,6,7-tetrahydro-1H-pyrazolo[4,3-b]pyridin-7-amine (3.40 g) and triethylamine (3.91 mL) in THF (50 mL), di-tert-butyl dicarbonate (3.37 g) was added dropwise at room temperature. After stirring at the same temperature as above for 1 hour, the reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (4.70 g).
MS: [M+H]$^+$ 343.0.

D) tert-Butyl (1-methyl-4,5,6,7-tetrahydro-1H-pyrazolo[4,3-b]pyridin-7-yl)carbamate A mixture of tert-butyl (4-benzyl-1-methyl-4,5,6,7-tetrahydro-1H-pyrazolo[4,3-b]pyridin-7-yl)carbamate (4.70 g), 10% palladium-carbon (containing 50% water, 1.46 g), acetic acid (5.0 mL) and methanol (100 mL) was stirred at room temperature for 10 hours in a hydrogen atmosphere. The insoluble matter was filtered off, and the filtrate was concentrated under reduced pressure. The residue was purified by silica gel column chromatography (NH, ethyl acetate/hexane) and then washed with diisopropyl ether to obtain the title compound (2.06 g).

MS: [M+H]$^+$ 253.0.

E) tert-Butyl (4-(5,6-dimethoxynicotinoyl)-1-methyl-4,5,6,7-tetrahydro-1H-pyrazolo[4,3-b]pyridin-7-yl)carbamate A mixture of tert-butyl (1-methyl-4,5,6,7-tetrahydro-1H-pyrazolo[4,3-b]pyridin-7-yl)carbamate (260 mg), 5,6-dimethoxynicotinic acid (245 mg), HATU (588 mg), triethylamine (0.431 mL) and DMF (4 mL) was stirred at room temperature for 4 hours, and then, the reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (411 mg).

MS: [M+H]$^+$ 418.0.

F) (7-Amino-1-methyl-6,7-dihydro-1H-pyrazolo[4,3-b]pyridin-4(5H)-yl)(5,6-dimethoxypyridin-3-yl)methanone dihydrochloride tert-Butyl (4-(5,6-dimethoxynicotinoyl)-1-methyl-4,5,6,7-tetrahydro-1H-pyrazolo[4,3-b]pyridin-7-yl)carbamate (411 mg) was dissolved in methanol (4 mL). To the solution, a 4 M solution of hydrogen chloride in ethyl acetate (2.46 mL) was added, and the mixture was stirred overnight at room temperature. The reaction mixture was concentrated under reduced pressure, and the residue was washed with ethyl acetate to obtain the title compound (340 mg).

MS: [M+H]$^+$ 318.0.

G) N-(4-((5,6-Dimethoxypyridin-3-yl)carbonyl)-1-methyl-4,5,6,7-tetrahydro-1H-pyrazolo[4,3-b]pyridin-7-yl)-2-(trifluoromethoxy)benzamide A mixture of (7-amino-1-methyl-6,7-dihydro-1H-pyrazolo[4,3-b]pyridin-4(5H)-yl)(5,6-dimethoxypyridin-3-yl)methanone dihydrochloride (340 mg), 2-(trifluoromethoxy)benzoic acid (233 mg), HATU (497 mg), triethylamine (0.364 mL) and DMF (4.0 mL) was stirred at room temperature for 4 hours, and then, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then crystallized from THF/ethyl acetate/diisopropyl ether to obtain the title compound (184 mg).

$^1$H NMR (300 MHz, DMSO-d$_6$CDCl$_3$) δ 2.15-2.37 (2H, m), 3.43-3.65 (1H, m), 3.82 (3H, s), 3.91 (3H, s), 4.07 (3H, s), 4.12-4.32 (1H, m), 5.49-5.68 (1H, m), 6.75 (1H, d, J=8.1 Hz), 7.21-7.28 (1H, m), 7.31 (1H, s), 7.40-7.50 (1H, m), 7.51-7.62 (1H, m), 7.88 (1H, d, J=1.9 Hz), 7.95-8.04 (1H, m), 8.06-8.42 (1H, m).

Example 153A

4-Chloro-N-(4-((5,6-dimethoxypyridin-3-yl)carbonyl)-1-ethyl-4,5,6,7-tetrahydro-1H-pyrazolo[4,3-b]pyridin-7-yl)-2-(trifluoromethyl)benzamide A) Methyl 1-ethyl-4-nitro-1H-pyrazole-5-carboxylate Methyl 4-nitro-1H-pyrazole-5-carboxylate (15 g) was dissolved in DMF (250 mL). To the solution, sodium hydride (60%, 5.3 g) was added in small portions under ice cooling. Ethyl iodide (20.5 g) was added thereto, and the mixture was stirred at room temperature for 4 hours. The reaction mixture was added to water, followed by extraction with ethyl acetate. The extract was washed with saturated brine and dried over anhydrous sodium sulfate, and the solvent was distilled off under reduced pressure. The residue was purified by silica gel column chromatography (ethyl acetate/petroleum ether) to obtain the title compound (3.7 g).

MS: [M+H]$^+$ 200.1.

B) Methyl 4-amino-1-ethyl-1H-pyrazole-5-carboxylate

A mixture of methyl 1-ethyl-4-nitro-1H-pyrazole-5-carboxylate (1.6 g), 10% palladium-carbon (0.16 g) and methanol (50 mL) was stirred overnight at room temperature in a hydrogen atmosphere. The insoluble matter was filtered off, and the filtrate was concentrated under reduced pressure to obtain the title compound (1.2 g).

$^1$H NMR (500 MHz, CDCl$_3$) δ 1.36 (3H, t, J=7.0 Hz), 3.91 (3H, s), 4.44 (2H, q, J=7.0 Hz), 7.09 (1H, s).

C) Methyl 4-(benzyl(3-methoxy-3-oxopropyl)amino)-1-ethyl-1H-pyrazole-5-carboxylate A mixture of methyl 4-amino-1-ethyl-1H-pyrazole-5-carboxylate (1.2 g), methyl acrylate (6.11 g), 4-(dimethylamino)pyridine (0.17 g) and DMF (60 mL) was stirred at 120° C. for 3 days. The reaction mixture was cooled to room temperature, and redundant methyl acrylate was distilled off under reduced pressure. Benzyl bromide (1.42 g) and potassium carbonate (2.28 g) were added to the residue, and the mixture was stirred at 80° C. for 1.5 hours. The reaction mixture was diluted with water, followed by extraction with ethyl acetate. The extract was washed with saturated brine and dried over anhydrous sodium sulfate, and the solvent was distilled off under reduced pressure. The residue was purified by silica gel column chromatography (ethyl acetate/petroleum ether) to obtain the title compound (2.0 g).

MS: [M+H]$^+$ 346.0.

D) 4-Benzyl-1-ethyl-5,6-dihydro-1H-pyrazolo[4,3-b]pyridin-7(4H)-one

To a solution of methyl 4-(benzyl(3-methoxy-3-oxopropyl)amino)-1-ethyl-1H-pyrazole-5-carboxylate (2.0 g) in THF (20 mL), a 2 M solution of sodium bis(trimethylsilyl)amide in THF (4.4 mL) was added under ice cooling, and the mixture was stirred at the same temperature as above for 30 minutes. A 6 M aqueous sodium hydroxide solution (16.9 mL) was added thereto, and the reaction mixture was stirred overnight under reflux conditions. The reaction mixture was diluted with water, followed by extraction with ethyl acetate. The extract was washed with saturated brine and dried over anhydrous sodium sulfate, and the solvent was distilled off under reduced pressure to obtain the title compound (2.2 g).

MS: [M+H]$^+$ 256.2.

E) 4-Benzyl-1-ethyl-5,6-dihydro-1H-pyrazolo[4,3-b]pyridin-7(4H)-one oxime

A mixture of 4-benzyl-1-ethyl-5,6-dihydro-1H-pyrazolo[4,3-b]pyridin-7(4H)-one (3.5 g), pyridine (3.25 g), hydroxylamine hydrochloride (1.42 g) and ethanol (60 mL) was stirred overnight at 90° C. The solvent was distilled off under reduced pressure. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/petroleum ether) to obtain the title compound (3.2 g).
MS: [M+H]$^+$ 271.3

F) 4-Benzyl-1-ethyl-4,5,6,7-tetrahydro-1H-pyrazolo[4,3-b]pyridin-7-amine

A mixture of 4-benzyl-1-ethyl-5,6-dihydro-1H-pyrazolo[4,3-b]pyridin-7(4H)-one oxime (2.8 g), Raney nickel (2.8 g) and methanol (100 mL) was stirred overnight at room temperature in a hydrogen atmosphere. The insoluble matter was filtered off, and the filtrate was concentrated under reduced pressure to obtain the title compound (2.0 g).
$^1$H NMR (500 MHz, DMSO-d$_6$) δ 1.30 (3H, t, J=7.0 Hz), 1.65-1.69 (1H, m), 1.74 (2H, brs), 1.84-1.92 (1H, m), 2.70-2.79 (2H, m), 3.91-3.95 (2H, m), 4.00-4.13 (2H, m), 4.14 (1H, d, J=7.5 Hz), 6.89 (1H, s), 7.24-7.27 (1H, m), 7.31-7.36 (4H, m).

G) tert-Butyl (4-benzyl-1-ethyl-4,5,6,7-tetrahydro-1H-pyrazolo[4,3-b]pyridin-7-yl)carbamate To a solution of 4-benzyl-1-ethyl-4,5,6,7-tetrahydro-1H-pyrazolo[4,3-b]pyridin-7-amine (1.66 g) in THF (32.4 mL), triethylamine (1.81 mL) and di-tert-butyl dicarbonate (1.58 mL) were added at room temperature. After stirring at the same temperature as above for 1 hour, the reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (1.89 g).
$^1$H NMR (300 MHz, CDCl$_3$) δ 1.37-1.57 (12H, m), 1.93-2.13 (2H, m), 2.53-2.63 (1H, m), 2.98 (1H, d, J=11.5 Hz), 3.93-4.13 (3H, m), 4.22 (1H, d, J=14.3 Hz), 4.83 (1H, s), 4.93 (1H, d, J=2.8 Hz), 7.25-7.38 (6H, m).

H) tert-Butyl (1-ethyl-4,5,6,7-tetrahydro-1H-pyrazolo[4,3-b]pyridin-7-yl)carbamate A mixture of tert-butyl (4-benzyl-1-ethyl-4,5,6,7-tetrahydro-1H-pyrazolo[4,3-b]pyridin-7-yl)carbamate (1.89 g), 10% palladium-carbon (containing 50% water, 282 mg), acetic acid (4.82 mL) and methanol (48.2 mL) was stirred at room temperature for 4 hours in a hydrogen atmosphere. The insoluble matter was filtered off, and the filtrate was concentrated under reduced pressure. The residue was purified by silica gel column chromatography (NH, ethyl acetate/hexane) to obtain the title compound (1.22 g).
$^1$H NMR (300 MHz, CDCl$_3$) δ 1.40 (3H, t, J=7.3 Hz), 1.47 (9H, s), 1.93-2.01 (2H, m), 3.00 (1H, d, J=5.7 Hz), 3.12 (1H, brs), 3.17-3.28 (1H, m), 4.04 (2H, q, J=7.2 Hz), 4.88-4.99 (2H, m), 7.06 (1H, s).

I) tert-Butyl (4-(5,6-dimethoxynicotinoyl)-1-ethyl-4,5,6,7-tetrahydro-1H-pyrazolo[4,3-b]pyridin-7-yl)carbamate A mixture of tert-butyl (1-ethyl-4,5,6,7-tetrahydro-1H-pyrazolo[4,3-b]pyridin-7-yl)carbamate (500 mg), 5,6-dimethoxynicotinic acid (447 mg), HATU (1.07 g), triethylamine (0.785 mL) and DMF (9.39 mL) was stirred at room temperature for 3 hours, and then, the reaction mixture was diluted with water, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (601 mg).
MS: [M+H]$^+$ 432.1.

J) (7-Amino-1-ethyl-6,7-dihydro-1H-pyrazolo[4,3-b]pyridin-4(5H)-yl)(5,6-dimethoxypyridin-3-yl)methanone dihydrochloride tert-Butyl (4-(5,6-dimethoxynicotinoyl)-1-ethyl-4,5,6,7-tetrahydro-1H-pyrazolo[4,3-b]pyridin-7-yl)carbamate (601 mg) was dissolved in methanol (6.96 mL). To the solution, a 4 M solution of hydrogen chloride in ethyl acetate (3.48 mL) was added, and the mixture was stirred overnight at room temperature. The reaction mixture was concentrated under reduced pressure to obtain the title compound (596 mg).
$^1$H NMR (300 MHz, DMSO-d$_6$) δ 1.37 (3H, t, J=7.2 Hz), 1.99-2.34 (2H, m), 3.72-3.78 (1H, m), 3.83 (3H, s), 3.93 (3H, s), 4.23 (1H, brs), 4.72-4.87 (1H, m), 7.39 (1H, d, J=1.7 Hz), 7.85 (1H, d, J=1.9 Hz), 8.57-8.83 (3H, m).

K) 4-Chloro-N-(4-((5,6-dimethoxypyridin-3-yl)carbonyl)-1-ethyl-4,5,6,7-tetrahydro-1H-pyrazolo[4,3-b]pyridin-7-yl)-2-(trifluoromethyl)benzamide A mixture of (7-amino-1-ethyl-6,7-dihydro-1H-pyrazolo[4,3-b]pyridin-4(5H)-yl)(5,6-dimethoxypyridin-3-yl)methanone dihydrochloride (180 mg), 4-chloro-2-(trifluoromethyl)benzoic acid (130 mg), HATU (254 mg), triethylamine (0.248 mL) and DMF (2.23 mL) was stirred overnight at room temperature, and then, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then washed with ethyl acetate/diisopropyl ether to obtain the title compound (110 mg).
$^1$H NMR (300 MHz, DMSO-d$_6$) δ 1.37 (3H, t, J=7.2 Hz), 2.01 (2H, d, J=10.7 Hz), 3.56-3.73 (1H, m), 3.83 (3H, s), 3.93 (4H, s), 4.06 (2H, q, J=7.1 Hz), 5.35-5.42 (1H, m), 7.36 (1H, d, J=1.9 Hz), 7.60 (1H, d, J=8.3 Hz), 7.81-7.86 (2H, m), 7.90 (1H, d, J=1.9 Hz), 9.25 (1H, d, J=8.1 Hz).

Example 155A

N-(4-((5,6-Dimethoxypyridin-3-yl)carbonyl)-1-ethyl-4,5,6,7-tetrahydro-1H-pyrazolo[4,3-b]pyridin-7-yl)-2-(trifluoromethoxy)benzamide A mixture of (7-amino-1-ethyl-6,7-dihydro-1H-pyrazolo[4,3-b]pyridin-4(5H)-yl)(5,6-dimethoxypyridin-3-yl)methanone dihydrochloride (180 mg), 2-(trifluoromethoxy)benzoic acid (119 mg), HATU (254 mg), triethylamine (0.248 mL) and DMF (2.23 mL) was stirred overnight at room temperature, and then, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then washed with ethyl acetate/diisopropyl ether to obtain the title compound (139 mg).

$^1$H NMR (300 MHz, DMSO-d$_6$) δ 1.35 (3H, t, J=7.2 Hz), 3.61-3.76 (1H, m), 3.82 (3H, s), 3.92 (3H, s), 4.05 (2H, s), 5.37-5.48 (1H, m), 7.36 (1H, d, J=1.9 Hz), 7.46 (2H, d, J=1.4 Hz), 7.56-7.62 (2H, m), 7.82 (1H, d, J=1.9 Hz), 9.08-9.19 (1H, m).

Example 160A (N-((7S)-4-(3,4-Dimethoxybenzoyl)-1-(5-((3-(4,4-difluoro-5,7-dimethyl-3a-azonia-4-bora(IV)-4H-4a-aza-s-indacen-3-yl)propanoyl)amino)pentyl)-4,5,6,7-tetrahydro-1H-pyrazolo[4,3-b]pyridin-7-yl)-2-(trifluoromethoxy)benzamide A) Methyl 4-((3-methoxy-3-oxopropyl)amino)-1-(tetrahydro-2H-pyran-2-yl)-1H-pyrazole-3-carboxylate To a solution of methyl 4-amino-1-(tetrahydro-2H-pyran-2-yl)-1H-pyrazole-3-carboxylate (6.2 g) and N,N-dimethyl-4-aminopyridine (300 mg) in DMF (50 mL), methyl acrylate (24.79 mL) was added at room temperature, and the mixture was stirred at 100° C. for 6 days. The solvent was distilled off under reduced pressure, and the residue was purified by silica gel column chromatography (ethyl acetate/hexane) to obtain the title compound (8.08 g).

$^1$H NMR (300 MHz, CDCl$_3$) δ 1.53-1.74 (3H, m), 1.93-2.12 (3H, m), 2.63 (2H, t, J=6.7 Hz), 3.34 (2H, q, J=6.6 Hz), 3.62-3.69 (1H, m), 3.70 (3H, s), 3.90 (3H, s), 4.07 (1H, dd, J=11.0, 2.3 Hz), 5.05 (1H, t, J=6.3 Hz), 5.35 (1H, dd, J=8.7, 3.3 Hz), 7.13 (1H, s).

B) Methyl 4-(benzyl(3-methoxy-3-oxopropyl) amino)-1-(tetrahydro-2H-pyran-2-yl)-1H-pyrazole-3-carboxylate To a solution of methyl 4-((3-methoxy-3-oxopropyl) amino)-1-(tetrahydro-2H-pyran-2-yl)-1H-pyrazole-3-carboxylate (8.05 g) and potassium carbonate (7.15 g) in DMF (100 mL), benzyl bromide (4.00 mL) was added at room temperature, and the reaction mixture was stirred overnight at room temperature. The solvent was distilled off under reduced pressure, and the residue was partitioned into water and ethyl acetate. The organic layer was washed with saturated brine and dried over anhydrous sodium sulfate, and the solvent was distilled off under reduced pressure. The residue was purified by silica gel column chromatography (ethyl acetate/hexane) to obtain the title compound (10.18 g).

$^1$H NMR (300 MHz, CDCl$_3$) δ 1.56-1.74 (3H, m), 1.79-2.10 (3H, m), 2.48 (2H, t, J=7.3 Hz), 3.34 (2H, t, J=7.3 Hz), 3.58 (3H, s), 3.60-3.72 (1H, m), 3.92 (3H, s), 4.03 (1H, d, J=11.1 Hz), 4.21 (2H, s), 5.34 (1H, d, J=9.0 Hz), 7.07-7.40 (6H, m).

C) 4-Benzyl-2-(tetrahydro-2H-pyran-2-yl)-2,4,5,6-tetrahydro-7H-pyrazolo[4,3-b]pyridin-7-one To a solution of methyl 4-(benzyl(3-methoxy-3-oxopropyl)amino)-1-(tetrahydro-2H-pyran-2-yl)-1H-pyrazole-3-carboxylate (10.1 g) in THF (150 mL), a 1.9 M solution of sodium bis(trimethylsilyl)amide in THF (19.86 mL) was added at room temperature, and the reaction mixture was stirred at room temperature for 2 hours. A 2 M aqueous sodium hydroxide solution (126 mL) was added to the reaction mixture at room temperature, and the mixture was stirred overnight at 70° C. The reaction solution was neutralized by the addition of 2 M hydrochloric acid at room temperature, followed by extraction with ethyl acetate. The organic layer was washed with saturated brine and dried over anhydrous magnesium sulfate, and the solvent was distilled off under reduced pressure. The residue was washed with diisopropyl ether to obtain the title compound (4.26 g).

$^1$H NMR (300 MHz, CDCl$_3$) δ 1.48-1.72 (3H, m), 1.90-2.16 (3H, m), 2.64-2.74 (2H, m), 3.13-3.25 (2H, m), 3.59-3.72 (1H, m), 3.90-4.05 (1H, m), 4.14 (2H, s), 5.30-5.44 (1H, m), 7.03 (1H, s), 7.21-7.49 (5H, m).

D) 2-(Tetrahydro-2H-pyran-2-yl)-2,4,5,6-tetrahydro-7H-pyrazolo[4,3-b]pyridin-7-one A mixture of 4-benzyl-2-(tetrahydro-2H-pyran-2-yl)-2,4,5,6-tetrahydro-7H-pyrazolo[4,3-b]pyridin-7-one (4 g), 10% palladium-carbon (200 mg), acetic acid (10 mL) and methanol (100 mL) was stirred overnight at room temperature in a hydrogen atmosphere. The insoluble matter was filtered off, and the filtrate was concentrated under reduced pressure to obtain the title compound (4.06 g).

$^1$H NMR (300 MHz, CDCl$_3$) δ 1.55-1.73 (3H, m), 1.90-2.15 (3H, m), 2.62-2.72 (2H, m), 3.45-3.56 (2H, m), 3.61-3.76 (1H, m), 3.94-4.07 (1H, m), 5.33-5.43 (1H, m), 6.98 (1H, s), 7.19 (1H, s).

E) 4-(3,4-Dimethoxybenzoyl)-2-(tetrahydro-2H-pyran-2-yl)-2,4,5,6-tetrahydro-7H-pyrazolo[4,3-b] pyridin-7-one To a solution of 2-(tetrahydro-2H-pyran-2-yl)-2,4,5,6-tetrahydro-7H-pyrazolo[4,3-b]pyridin-7-one (2.8 g) in pyridine (80 mL), 3,4-dimethoxybenzoyl chloride (3.81 g) was added at 0° C., and the mixture was stirred overnight at room temperature. The solvent was distilled off under reduced pressure, and the residue was partitioned into 1 N hydrochloric acid and ethyl acetate. The organic layer was washed with a saturated aqueous solution of sodium carbonate and saturated brine and then dried over anhydrous sodium sulfate, and the solvent was distilled off under reduced pressure. The residue was purified by silica gel column chromatography (ethyl acetate/hexane) to obtain the title compound (1.51 g).

$^1$H NMR (300 MHz, CDCl$_3$) δ 1.60-1.76 (3H, m), 1.94-2.03 (1H, m), 2.06-2.20 (2H, m), 2.71-2.84 (2H, m), 3.62-3.76 (1H, m), 3.92 (3H, s), 3.94 (3H, s), 3.99-4.07 (1H, m), 4.12-4.20 (2H, m), 5.47 (1H, dd, J=8.1, 3.8 Hz), 6.88-6.96 (1H, m), 7.05-7.15 (2H, m), 8.13 (1H, brs).

F) 4-(3,4-Dimethoxybenzoyl)-1,4,5,6-tetrahydro-7H-pyrazolo[4,3-b]pyridin-7-one

To 4-(3,4-dimethoxybenzoyl)-2-(tetrahydro-2H-pyran-2-yl)-2,4,5,6-tetrahydro-7H-pyrazolo[4,3-b]pyridin-7-one (1.5 g), a 2 M solution of hydrogen chloride in methanol (20 mL) was added at 0° C., and the mixture was stirred at room temperature for 2 hours. The solvent was distilled off under reduced pressure, and the residue was partitioned into ethyl acetate and a saturated aqueous solution of sodium carbonate. The organic layer was washed with saturated brine and then dried over anhydrous sodium sulfate, and the solvent was distilled off under reduced pressure. Diisopropyl ether was added to the residue, and the deposited solid was collected by filtration to obtain the title compound (617.2 mg).

$^1$H NMR (300 MHz, DMSO-$d_6$) δ 2.74 (2H, t, J=6.4 Hz), 3.78 (3H, s), 3.82 (3H, s), 4.06 (2H, t, J=6.2 Hz), 7.01-7.10 (1H, m), 7.12-7.23 (2H, m), 7.68 (1H, brs), 13.85 (1H, brs).

G) tert-Butyl (5-(4-(3,4-dimethoxybenzoyl)-7-oxo-4,5,6,7-tetrahydro-1H-pyrazolo[4,3-b]pyridin-1-yl)pentyl)carbamate To a mixture of 4-(3,4-dimethoxybenzoyl)-1,4,5,6-tetrahydro-7H-pyrazolo[4,3-b]pyridin-7-one (300 mg), tert-butyl (5-hydroxypentyl)carbamate (0.30 mL), tributylphosphine (0.50 mL) and toluene (20 mL), (E)-diazene-1,2-diylbis(piperidin-1-ylmethanone) (502 mg) was added at room temperature, and the reaction mixture was stirred overnight at room temperature. The insoluble matter was filtered off, and then, the reaction mixture was diluted with water, followed by extraction with ethyl acetate. The extract was washed with 1 M hydrochloric acid, a saturated aqueous solution of sodium carbonate and saturated brine and dried over anhydrous sodium sulfate, and the solvent was distilled off under reduced pressure. The residue was purified by silica gel column chromatography (ethyl acetate/hexane) to obtain the title compound (497 mg).

$^1$H NMR (300 MHz, CDCl$_3$) δ 1.15-1.66 (15H, m), 2.74 (2H, t, J=6.5 Hz), 3.65 (2H, q, J=6.0 Hz), 3.91 (3H, s), 3.94 (3H, s), 4.17 (2H, t, J=6.3 Hz), 4.33-4.65 (3H, m), 6.90 (1H, d, J=8.7 Hz), 7.03-7.17 (2H, m), 7.43 (1H, brs).

H) tert-Butyl (5-(4-(3,4-dimethoxybenzoyl)-7-hydroxy-4,5,6,7-tetrahydro-1H-pyrazolo[4,3-b]pyridin-1-yl)pentyl)carbamate To a solution of tert-butyl (5-(4-(3,4-dimethoxybenzoyl)-7-oxo-4,5,6,7-tetrahydro-1H-pyrazolo[4,3-b]pyridin-1-yl)pentyl)carbamate (484 mg) in methanol (10 mL), sodium borohydride (38 mg) was added at 0° C., and the mixture was stirred at room temperature for 3 hours. An excessive amount of 1 N hydrochloric acid was added thereto at 0° C. The solvent was distilled off under reduced pressure, and the residue was partitioned into ethyl acetate and water. The organic layer was washed with saturated brine and then dried over anhydrous sodium sulfate, and the solvent was distilled off under reduced pressure to obtain the title compound (423.9 mg).

$^1$H NMR (300 MHz, CDCl$_3$) δ 1.31-1.66 (14H, m), 1.83-2.01 (1H, m), 2.01-2.15 (1H, m), 2.98-3.20 (3H, m), 3.64 (1H, brs), 3.77 (1H, brs), 3.89 (3H, s), 3.92 (3H, s), 4.04-4.23 (2H, m), 4.57 (1H, brs), 4.68 (1H, brs), 4.76-5.04 (1H, m), 6.88 (1H, d, J=8.3 Hz), 7.00-7.12 (2H, m), 7.75-8.56 (1H, m).

I) tert-Butyl (5-(7-azido-4-(3,4-dimethoxybenzoyl)-4,5,6,7-tetrahydro-1H-pyrazolo[4,3-b]pyridin-1-yl)pentyl)carbamate To a mixed solution of tert-butyl (5-(4-(3,4-dimethoxybenzoyl)-7-hydroxy-4,5,6,7-tetrahydro-1H-pyrazolo[4,3-b]pyridin-1-yl)pentyl)carbamate (410 mg) in toluene (10 mL) and DMF (1 mL), DPPA (0.36 mL) and DBU (0.25 mL) were added at room temperature, and the mixture was stirred overnight at 50° C. in an argon atmosphere. Water was added to the reaction solution, followed by extraction with ethyl acetate. The extract was washed with a 10% aqueous citric acid solution, a saturated aqueous solution of sodium carbonate and saturated brine and then dried over anhydrous sodium sulfate, and the solvent was distilled off under reduced pressure. The residue was purified by silica gel column chromatography (ethyl acetate/hexane) to obtain the title compound (368.2 mg).

$^1$H NMR (300 MHz, CDCl$_3$) δ 1.30-1.57 (15H, m), 1.78-2.00 (2H, m), 2.09-2.35 (1H, m), 3.12 (2H, q, J=6.5 Hz), 3.55-3.71 (1H, m), 3.90 (3H, s), 3.93 (3H, s), 4.12 (2H, q, J=7.1 Hz), 4.57 (1H, brs), 4.67 (1H, t, J=3.6 Hz), 6.89 (1H, d, J=8.8 Hz), 6.96-7.16 (2H, m), 8.19 (1H, brs).

J) tert-Butyl (5-(7-amino-4-(3,4-dimethoxybenzoyl)-4,5,6,7-tetrahydro-1H-pyrazolo[4,3-b]pyridin-1-yl)pentyl)carbamate A mixture of tert-butyl (5-(7-azido-4-(3,4-dimethoxybenzoyl)-4,5,6,7-tetrahydro-1H-pyrazolo[4,3-b]pyridin-1-yl)pentyl)carbamate (360 mg), 10% palladium-carbon (40 mg) and methanol (10 mL) was stirred overnight at room temperature in a hydrogen atmosphere. The insoluble matter was filtered off, and the filtrate was concentrated under reduced pressure to obtain the title compound (313.6 mg).

$^1$H NMR (300 MHz, CDCl$_3$) δ 1.27-2.00 (19H, m), 2.02-2.24 (1H, m), 3.11 (2H, q, J=6.5 Hz), 3.51-3.72 (1H, m), 3.90 (3H, s), 3.92 (3H, s), 4.03-4.31 (3H, m), 4.63 (1H, brs), 6.88 (1H, d, J=8.7 Hz), 7.02-7.15 (2H, m), 8.19 (1H, brs).

K) tert-Butyl (5-(4-(3,4-dimethoxybenzoyl)-7-((2-(trifluoromethoxy)benzoyl)amino)-4,5,6,7-tetrahydro-1H-pyrazolo[4,3-b]pyridin-1-yl)pentyl)carbamate To a mixture of tert-butyl (5-(7-amino-4-(3,4-dimethoxybenzoyl)-4,5,6,7-tetrahydro-1H-pyrazolo[4,3-b]pyridin-1-yl)pentyl)carbamate (300 mg), 2-(trifluoromethoxy)benzoic acid (152 mg), WSC (143 mg), HOBt (125 mg) and DMF (10 mL), WSC (143 mg) was added at 0° C., and the resulting mixture was stirred at room temperature for 3 hours. Then, the solvent was distilled off under reduced pressure. Ethyl acetate and a saturated aqueous solution of sodium carbonate were added to the residue. The separated organic layer was washed with saturated brine and then dried over anhydrous sodium sulfate, and the solvent was distilled off under reduced pressure. The residue was purified by silica gel column chromatography (ethyl acetate/hexane) to obtain the title compound (410 mg).

$^1$H NMR (300 MHz, CDCl$_3$) δ 1.25-1.51 (13H, m), 1.61-1.94 (3H, m), 2.22 (2H, brs), 2.89 (2H, d, J=6.2 Hz), 3.55 (1H, brs), 3.90 (3H, s), 3.93 (3H, s), 3.98-4.09 (2H, m), 4.53 (1H, brs), 5.48-5.66 (1H, m), 6.90 (1H, d, J=8.4 Hz), 7.02-7.11 (2H, m), 7.22 (1H, d, J=7.2 Hz), 7.30 (1H, d, J=8.2 Hz), 7.37-7.47 (1H, m), 7.49-7.60 (1H, m), 7.64-8.50 (2H, m).

L) (N-((7S)-4-(3,4-Dimethoxybenzoyl)-1-(5-((3-(4,4-difluoro-5,7-dimethyl-3a-azonia-4-bora(IV)-4H-4a-aza-s-indacen-3-yl)propanoyl)amino)pentyl)-4,5,6,7-tetrahydro-1H-pyrazolo[4,3-b]pyridin-7-yl)-2-(trifluoromethoxy)benzamide tert-Butyl (5-(4-(3,4-dimethoxybenzoyl)-7-((2-(trifluoromethoxy)benzoyl)amino)-4,5,6,7-tetrahydro-1H-pyrazolo

[4,3-b]pyridin-1-yl)pentyl)carbamate (161 mg) was fractionated by SFC (column: CHIRALPAK IB, 20 mm ID×250 mm L, mobile phase: carbon dioxide/methanol=860/140), and a fraction having a smaller retention time was concentrated under reduced pressure. A 4 M solution of hydrogen chloride in ethyl acetate (5 mL) was added to the residue, and the mixture was stirred at room temperature for 3 hours. The reaction mixture was concentrated under reduced pressure, and the obtained residue was dissolved in DMF (3 mL). 3-(4,4-Difluoro-5,7-dimethyl-3a-azonia-4-bora(IV)-4H-4a-aza-s-indacen-3-yl)propionic acid (29.3 mg), HOBt (20 mg) and triethylamine (0.042 mL) were dissolved in DMF (3 mL). To the solution, WSC (23 mg) was added at 0° C. The reaction mixture was stirred overnight at room temperature, and then, the solvent was distilled off under reduced pressure. The residue was partitioned into ethyl acetate and water. The organic layer was washed with saturated brine and then dried over anhydrous sodium sulfate, and the solvent was distilled off under reduced pressure. The residue was purified by reverse-phase HPLC to obtain the title compound (21.2 mg).

$^1$H NMR (300 MHz, METHANOL-$d_4$) δ 1.26-1.37 (3H, m), 1.41-1.56 (2H, m), 1.76-1.98 (2H, m), 2.27 (4H, s), 2.49 (3H, s), 2.56 (2H, t, J=7.6 Hz), 3.04-3.25 (5H, m), 3.55-3.77 (1H, m), 3.82 (3H, s), 3.87 (3H, s), 4.02-4.17 (3H, m), 5.54 (1H, t, J=3.9 Hz), 6.20 (1H, s), 6.29 (1H, d, J=4.1 Hz), 6.97-7.01 (1H, m), 7.03 (1H, s), 7.08 (2H, dt, J=4.3, 2.2 Hz), 7.36-7.43 (2H, m), 7.46 (1H, dd, J=7.5, 1.1 Hz), 7.52-7.63 (2H, m), 7.78-7.96 (1H, m), 8.11 (1H, brs).

Example 162A

N-((7S)-4-((5,6-Dimethoxypyridin-3-yl)carbonyl)-1-isopropyl-4,5,6,7-tetrahydro-1H-pyrazolo[4,3-b]pyridin-7-yl)-2-(trifluoromethoxy)benzamide N-(4-((5,6-Dimethoxypyridin-3-yl)carbonyl)-1-isopropyl-4,5,6,7-tetrahydro-1H-pyrazolo[4,3-b]pyridin-7-yl)-2-(trifluoromethoxy)benzamide (300 mg) was fractionated by SFC (column: CHIRALPAK AD, 50 mm ID×500 mm L, mobile phase: carbon dioxide/methanol=700/300), and a fraction having a larger retention time was concentrated under reduced pressure. The residue was crystallized from ethyl acetate/diisopropyl ether to obtain the title compound (123 mg).

$^1$H NMR (300 MHz, DMSO-$d_6$CDCl$_3$) δ 1.42 (3H, d, J=6.4 Hz), 1.48 (3H, d, J=6.6 Hz), 2.16-2.30 (2H, m), 3.45-3.66 (1H, m), 3.91 (3H, s), 4.07 (3H, s), 4.12-4.35 (1H, m), 4.47 (1H, quin, J=6.6 Hz), 5.56-5.67 (1H, m), 6.78 (1H, d, J=8.5 Hz), 7.24-7.28 (1H, m), 7.32 (1H, d, J=8.3 Hz), 7.41-7.50 (1H, m), 7.52-7.61 (1H, m), 7.89 (1H, d, J=1.7 Hz), 8.00 (1H, dd, J=7.7, 1.9 Hz), 8.23 (1H, brs).

Example 165A

4-Chloro-N-((7S)-4-((5,6-dimethoxypyridin-3-yl)carbonyl)-1-ethyl-4,5,6,7-tetrahydro-1H-pyrazolo[4,3-b]pyridin-7-yl)-2-(trifluoromethyl)benzamide 4-Chloro-N-(4-((5,6-dimethoxypyridin-3-yl)carbonyl)-1-ethyl-4,5,6,7-tetrahydro-1H-pyrazolo[4,3-b]pyridin-7-yl)-2-(trifluoromethyl)benzamide (90.0 mg) was fractionated by SFC (column: CHIRALCEL OJ-H, 20 mm ID×250 mm L, mobile phase: carbon dioxide/methanol=840/160), and a fraction having a larger retention time was concentrated under reduced pressure. The residue was crystallized from ethyl acetate/diisopropyl ether to obtain the title compound (31.2 mg).

$^1$H NMR (300 MHz, CDCl$_3$) δ 1.44 (3H, t, J=7.3 Hz), 2.13-2.35 (2H, m), 3.44-3.61 (1H, m), 3.90 (3H, s), 4.04-4.27 (6H, m), 5.42-5.57 (1H, m), 6.27-6.45 (1H, m), 7.21-7.76 (1H, m), 7.48 (1H, d, J=8.1 Hz), 7.57-7.64 (1H, m), 7.70-7.74 (1H, m), 7.83-7.86 (1H, m), 7.90-8.36 (1H, m).

Example 170A

4-Chloro-N-((7S)-4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethyl)benzamide 4-Chloro-N-(4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethyl)benzamide (1.08 g) was fractionated by SFC (column: CHIRALPAK AS-H, 20 mm ID×250 mm L, mobile phase: carbon dioxide/methanol=840/160), and a fraction having a smaller retention time was concentrated under reduced pressure. The residue was crystallized from ethyl acetate/diisopropyl ether to obtain the title compound (457 mg).

$^1$H NMR (300 MHz, CDCl$_3$) δ 2.09-2.37 (2H, m), 3.36-3.72 (1H, m), 3.95-4.26 (4H, m), 4.35-4.61 (2H, m), 5.42-5.65 (1H, m), 5.90-6.45 (2H, m), 7.45-7.54 (1H, m), 7.56-7.65 (1H, m), 7.68-7.74 (1H, m), 7.78-7.85 (1H, m), 7.86-8.55 (2H, m).

Example 171A

N-((7S)-4-((5,6-Dimethoxypyridin-3-yl)carbonyl)-1-methyl-4,5,6,7-tetrahydro-1H-pyrazolo[4,3-b]pyridin-7-yl)-2-(trifluoromethoxy)benzamide N-(4-((5,6-Dimethoxypyridin-3-yl)carbonyl)-1-methyl-4,5,6,7-tetrahydro-1H-pyrazolo[4,3-b]pyridin-7-yl)-2-(trifluoromethoxy)benzamide (976 mg) was fractionated by SFC (column: CHIRALPAK AS-H, 20 mm ID×250 mm L, mobile phase: carbon dioxide/methanol=880/120), and a fraction having a smaller retention time was concentrated under reduced pressure. The residue was crystallized from ethyl acetate/diisopropyl ether to obtain the title compound (380 mg).

$^1$H NMR (300 MHz, CDCl$_3$) δ 2.12-2.35 (2H, m), 3.44-3.65 (1H, m), 3.82 (3H, s), 3.91 (3H, s), 4.07 (3H, s), 4.12-4.36 (1H, m), 5.51-5.66 (1H, m), 6.77 (1H, d, J=8.3 Hz), 7.22-7.35 (2H, m), 7.40-7.49 (1H, m), 7.51-7.60 (1H, m), 7.88 (1H, s), 7.93-8.45 (2H, m).

Example 172A

2-Chloro-N-(7-(3,4-dimethoxybenzoyl)-1,3-dimethyl-4,5,6,7-tetrahydro-1H-pyrazolo[3,4-b]pyridin-4-yl)benzamide A) 4-Bromo-1,3-dimethyl-1H-pyrazol-5-amine To a solution of 1,3-dimethyl-1H-pyrazol-5-amine (8.77 g) in ethyl acetate (180 mL), N-bromosuccinimide (14.75 g) was added under ice cooling, and the mixture was stirred at room temperature for 2 hours in a nitrogen atmosphere. The reaction mixture was diluted with a saturated aqueous solution of sodium bicarbonate, followed by extraction with ethyl acetate. The extract was washed with a saturated aqueous solution of sodium bicarbonate and saturated brine and dried over anhydrous magnesium sulfate, and the solvent was distilled off under reduced pressure. The residue was purified by silica gel column chromatography (NH, ethyl acetate/hexane) to obtain the title compound (12.6 g).
MS: [M+H]$^+$ 189.9

B) 4-Bromo-N-(but-3-en-1-yl)-1,3-dimethyl-1H-pyrazol-5-amine

4-Bromo-1,3-dimethyl-1H-pyrazol-5-amine (12.3 g) was dissolved in DMF (120 mL). To the solution, sodium hydride (60%, 5.18 g) was added in small portions at room temperature. After stirring at the same temperature as above for 20 minutes, 4-bromobut-1-ene (16.4 mL) was added dropwise thereto, and the mixture was stirred overnight at the same temperature as above in a nitrogen atmosphere. Water was added to the reaction mixture, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (4.75 g).
MS: [M+H]$^+$ 243.9

C) N-(4-Bromo-1,3-dimethyl-1H-pyrazol-5-yl)-N-(but-3-en-1-yl)-3,4-dimethoxybenzamide 4-Bromo-N-(but-3-en-1-yl)-1,3-dimethyl-1H-pyrazol-5-amine (4.73 g) was dissolved in pyridine (40 mL). To the solution, 3,4-dimethoxybenzoyl chloride (5.83 g) was added. The mixture was stirred at 90° C. for 5 hours in a nitrogen atmosphere. Water was added to the reaction mixture, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (6.52 g).
MS: [M+H]$^+$ 408.0

D) (3,4-Dimethoxyphenyl)(1,3-dimethyl-4-methylene-5,6-dihydro-1H-pyrazolo[3,4-b]pyridin-7(4H)-yl)methanone A mixture of N-(4-bromo-1,3-dimethyl-1H-pyrazol-5-yl)-N-(but-3-en-1-yl)-3,4-dimethoxybenzamide (6.51 g), tri-ortho-tolylphosphine (728 mg), palladium(II) acetate (358 mg), triethylamine (4.84 g) and acetonitrile (150 mL) was stirred overnight at 80° C. in a nitrogen atmosphere. The reaction mixture was concentrated under reduced pressure, and the residue was purified by silica gel column chromatography (ethyl acetate/hexane) to obtain the title compound (1.75 g).
MS: [M+H]$^+$ 328.0

E) 7-(3,4-Dimethoxybenzoyl)-1,3-dimethyl-6,7-dihydro-1H-pyrazolo[3,4-b]pyridin-4(5H)-one A mixed solution of (3,4-dimethoxyphenyl)(1,3-dimethyl-4-methylene-5,6-dihydro-1H-pyrazolo[3,4-b]pyridin-7(4H)-yl)methanone (1.73 g), sodium periodate (4.52 g) and osmium oxide (fixation catalyst I) (403 mg) in acetonitrile (15 mL)-acetone (15 mL)-water (15 mL) was stirred overnight at room temperature. The insoluble matter was filtered off, and the filtrate was diluted with a saturated aqueous solution of sodium thiosulfate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (600 mg).
MS: [M+H]$^+$ 330.0

F) (3,4-Dimethoxyphenyl)(4-(hydroxyimino)-1,3-dimethyl-5,6-dihydro-1H-pyrazolo[3,4-b]pyridin-7(4H)-yl)methanone A mixture of 7-(3,4-dimethoxybenzoyl)-1,3-dimethyl-6,7-dihydro-1H-pyrazolo[3,4-b]pyridin-4(5H)-one (593 mg), pyridine (712 mg), hydroxylamine hydrochloride (626 mg) and ethanol (10 mL) was stirred at 90° C. for 3 hours in a nitrogen atmosphere. The solvent was distilled off under reduced pressure, and the residue was diluted with a saturated aqueous solution of sodium bicarbonate, followed by extraction with THF/ethyl acetate. The extract was washed with saturated brine and dried over anhydrous magnesium sulfate, and the solvent was distilled off under reduced pressure to obtain the title compound (577 mg).
MS: [M+H]$^+$ 345.0

G) (4-Amino-1,3-dimethyl-5,6-dihydro-1H-pyrazolo[3,4-b]pyridin-7(4H)-yl)(3,4-dimethoxyphenyl)methanone A mixture of (3,4-dimethoxyphenyl)(4-(hydroxyimino)-1,3-dimethyl-5,6-dihydro-1H-pyrazolo[3,4-b]pyridin-7(4H)-yl)methanone (563 mg), a 2 M solution of ammonia in methanol (8.17 mL), Raney nickel (1 g) and methanol (30 mL) was stirred overnight at room temperature in a hydrogen atmosphere. The insoluble matter was filtered off, and the filtrate was concentrated under reduced pressure. The residue was purified by silica gel column chromatography (NH, ethyl acetate/hexane) to obtain the title compound (445 mg).
MS: [M+H]$^+$ 331.0

H) 2-Chloro-N-(7-(3,4-dimethoxybenzoyl)-1,3-dimethyl-4,5,6,7-tetrahydro-1H-pyrazolo[3,4-b]pyridin-4-yl)benzamide To a solution of (4-amino-1,3-dimethyl-5,6-dihydro-1H-pyrazolo[3,4-b]pyridin-7(4H)-yl)(3,4-dimethoxyphenyl)methanone (441 mg) in pyridine (4 mL), 2-chlorobenzoyl chloride (280 mg) was added at room temperature. After stirring at the same temperature as above for 3 hours, the reaction mixture was concentrated under reduced pressure. The residue was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) and then crystallized from methanol/ethyl acetate to obtain the title compound (255 mg).
$^1$H NMR (300 MHz, CDCl$_3$) δ 2.07-2.21 (2H, m), 2.27 (3H, s), 3.50 (3H, s), 3.64-3.80 (1H, m), 3.93 (3H, s), 3.95 (3H, s), 4.06-4.20 (1H, m), 5.24-5.39 (1H, m), 6.24-6.40 (1H, m), 6.85-6.99 (1H, m), 7.23-7.28 (2H, m), 7.30-7.43 (3H, m), 7.62-7.75 (1H, m).

Example 178A

N-((7S)-4-((5,6-Dimethoxypyridin-3-yl)carbonyl)-1-ethyl-4,5,6,7-tetrahydro-1H-pyrazolo[4,3-b]pyridin-7-yl)-2-(trifluoromethoxy)benzamide N-(4-((5,6-Dimethoxypyridin-3-yl)carbonyl)-1-ethyl-4,5,6,7-tetrahydro-1H-pyrazolo[4,3-b]pyridin-7-yl)-2-(trifluoromethoxy)benzamide (90.0 mg) was fractionated by SFC (column: CHIRALPAK AS-H, 20 mm ID×250 mm L, mobile phase: carbon dioxide/methanol=860/140), and a fraction having a smaller retention time was concentrated under reduced pressure. The residue was crystallized from ethyl acetate/hexane to obtain the title compound (31.1 mg).

$^1$H NMR (300 MHz, CDCl$_3$) δ 1.42 (3H, t, J=7.3 Hz), 2.16-2.32 (2H, m), 3.47-3.68 (1H, m), 3.91 (3H, s), 4.05-4.55 (6H, m), 5.52-5.65 (1H, m), 6.78 (1H, d, J=8.3 Hz), 7.24-7.28 (1H, m), 7.29-7.35 (1H, m), 7.40-7.50 (1H, m), 7.52-7.64 (1H, m), 7.89 (1H, d, J=1.9 Hz), 8.00 (1H, dd, J=7.7, 1.9 Hz), 8.05-8.45 (1H, m).

Example 192A

N-(4-((5,6-Dimethoxypyridin-3-yl)carbonyl)-1,3-dimethyl-4,5,6,7-tetrahydro-1H-pyrazolo[4,3-b]pyridin-7-yl)-2-(trifluoromethoxy)benzamide

A) tert-Butyl (4-(5,6-dimethoxynicotinoyl)-1,3-dimethyl-4,5,6,7-tetrahydro-1H-pyrazolo[4,3-b]pyridin-7-yl)carbamate To a solution of tert-butyl (4-(5,6-dimethoxynicotinoyl)-1-methyl-4,5,6,7-tetrahydro-1H-pyrazolo[4,3-b]pyridin-7-yl)carbamate (400 mg) in acetonitrile (2.40 mL), a solution of N-bromosuccinimide (171 mg) in acetonitrile (2.40 mL) was added under ice cooling, and the mixture was stirred at the same temperature as above for 1 hour and at room temperature for 2 hours. The reaction mixture was concentrated under reduced pressure and diluted with ethyl acetate. The reaction mixture was washed with water, a saturated aqueous solution of ammonium chloride and saturated brine in this order and dried over anhydrous magnesium sulfate. The solvent was distilled off under reduced pressure. A mixture of the obtained residue (334 mg), dichloro[1,1'-bis(diphenylphosphino)ferrocene]palladium(II) (24.6 mg), potassium carbonate (186 mg), 2,4,6-trimethyl-1,3,5,2,4,6-trioxatriborinane (169 mg) and DME (3.37 mL) was stirred at 110° C. for 1 hour under irradiation with microwave. 2,4,6-Trimethyl-1,3,5,2,4,6-trioxatriborinane (101.4 mg) was added to the reaction mixture, and the mixture was stirred at 110° C. for 1 hour under irradiation with microwave. The reaction mixture was purified by silica gel column chromatography (NH, ethyl acetate/hexane) to obtain the title compound (124 mg).

MS: [M+H]$^+$ 432.1

B) N-(4-((5,6-Dimethoxypyridin-3-yl)carbonyl)-1,3-dimethyl-4,5,6,7-tetrahydro-1H-pyrazolo[4,3-b]pyridin-7-yl)-2-(trifluoromethoxy)benzamide tert-Butyl (4-(5,6-dimethoxynicotinoyl)-1,3-dimethyl-4,5,6,7-tetrahydro-1H-pyrazolo[4,3-b]pyridin-7-yl)carbamate (124 mg) was dissolved in THF (1.44 mL). To the solution, TFA (1.07 mL) was added, and the mixture was stirred at room temperature for 4 days. The reaction mixture was concentrated under reduced pressure. A mixture of the residue, 2-(trifluoromethoxy)benzoic acid (177 mg), HATU (163 mg), triethylamine (0.239 mL) and DMF (2.0 mL) was stirred overnight at room temperature in a nitrogen atmosphere. Then, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then crystallized from THF/ethyl acetate/diisopropyl ether to obtain the title compound (85.6 mg).

$^1$H NMR (300 MHz, CDCl$_3$) δ 1.64-2.20 (4H, m), 2.21-2.36 (1H, m), 3.59-3.79 (4H, m), 3.92 (3H, s), 4.07 (3H, s), 4.11-4.25 (1H, m), 5.49-5.66 (1H, m), 6.71 (1H, d, J=8.5 Hz), 7.29-7.39 (2H, m), 7.46 (1H, dd, J=7.5, 1.1 Hz), 7.51-7.61 (1H, m), 7.93-8.01 (2H, m).

Example 193A

2-Chloro-N-(7-(3,4-dimethoxybenzoyl)-1-methyl-4,5,6,7-tetrahydro-1H-pyrrazolo[3,4-b]pyridin-4-yl)benzamide

A) 4-Bromo-N-(but-3-en-1-yl)-1-methyl-1H-pyrazol-5-amine

4-Bromo-1-methyl-1H-pyrazol-5-amine (5.00 g) was dissolved in DMF (80 mL). To the solution, sodium hydride (60%, 1.70 g) was added in small portions at room temperature. After stirring at the same temperature as above for 20 minutes, 4-bromobut-1-ene (5.77 mL) was added dropwise thereto, and the mixture was stirred overnight at 50° C. in a nitrogen atmosphere. Water was added to the reaction mixture, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (1.27 g).

MS: [M+H]$^+$ 229.8

B) N-(4-Bromo-1-methyl-1H-pyrazol-5-yl)-N-(but-3-en-1-yl)-3,4-dimethoxybenzamide 4-Bromo-N-(but-3-en-1-yl)-1-methyl-1H-pyrazol-5-amine (1.25 g) was dissolved in pyridine (15 mL). To the solution, 3,4-dimethoxybenzoyl chloride (1.64 g) was added, and the mixture was stirred overnight at 90° C. in a nitrogen atmosphere. The reaction mixture was concentrated under reduced pressure, and the residue was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (2.01 g).

MS: [M+H]$^+$ 393.9

C) (3,4-Dimethoxyphenyl)(1-methyl-4-methylene-5,6-dihydro-1H-pyrazolo[3,4-b]pyridin-7(4H)-yl)methanone A mixture of N-(4-bromo-1-methyl-1H-pyrazol-5-yl)-N-(but-3-en-1-yl)-3,4-dimethoxybenzamide (2.00 g), tri-ortho-tolylphosphine (232 mg), palladium(II) acetate (114 mg), triethylamine (1.54 g) and acetonitrile (50 mL) was stirred overnight at 80° C. in a nitrogen atmosphere. The reaction mixture was concentrated under reduced pressure, and the residue was purified by silica gel column chromatography (ethyl acetate/hexane). The residue was washed with diisopropyl ether to obtain the title compound (733 mg).

MS: [M+H]$^+$ 314.0

D) 7-(3,4-Dimethoxybenzoyl)-1-methyl-6,7-dihydro-1H-pyrazolo[3,4-b]pyridin-4(5H)-one A mixed solution of (3,4-dimethoxyphenyl)(1-methyl-4-methylene-5,6-dihydro-1H-pyrazolo[3,4-b]pyridin-7(4H)-yl)methanone (730 mg), sodium periodate (1.99 g) and osmium oxide (fixation catalyst I) (178 mg) in acetonitrile (5 mL)-acetone (5 mL)-water (5 mL) was stirred at room temperature for 5 hours. The insoluble matter was filtered off, and the filtrate was diluted with a saturated aqueous solution of sodium thiosulfate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (195 mg).

MS: [M+H]$^+$ 316.0

E) (3,4-Dimethoxyphenyl)(4-(hydroxyimino)-1-methyl-5,6-dihydro-1H-pyrazolo[3,4-b]pyridin-7(4H)-yl)methanone A mixture of 7-(3,4-dimethoxybenzoyl)-1-methyl-6,7-dihydro-1H-pyrazolo[3,4-b]pyridin-4(5H)-one (193 mg), pyridine (242 mg), hydroxylamine hydrochloride (213 mg) and ethanol (3 mL) was stirred overnight at 90° C. in a nitrogen atmosphere. The solvent was distilled off under reduced pressure, and the residue was diluted with a saturated aqueous solution of sodium bicarbonate, followed by extraction with ethyl acetate. The extract was washed with saturated brine and dried over anhydrous magnesium sulfate, and the solvent was distilled off under reduced pressure to obtain the title compound (171 mg).

MS: [M+H]$^+$ 331.0

F) (4-Amino-1-methyl-5,6-dihydro-1H-pyrazolo[3,4-b]pyridin-7(4H)-yl)(3,4-dimethoxyphenyl)methanone A mixture of (3,4-dimethoxyphenyl)(4-(hydroxyimino)-1-methyl-5,6-dihydro-1H-pyrazolo[3,4-b]pyridin-7(4H)-yl)methanone (170 mg), a 2 M solution of ammonia in methanol (2.57 mL), Raney nickel (1 g) and methanol (10 mL) was stirred at room temperature for 3 hours in a hydrogen atmosphere. The insoluble matter was filtered off, the filtrate was concentrated under reduced pressure to obtain the title compound (153 mg).

MS: [M+H]$^+$ 317.0

G) 2-Chloro-N-(7-(3,4-dimethoxybenzoyl)-1-methyl-4,5,6,7-tetrahydro-1H-pyrazolo[3,4-b]pyridin-4-yl)benzamide To a solution of (4-amino-1-methyl-5,6-dihydro-1H-pyrazolo[3,4-b]pyridin-7(4H)-yl)(3,4-dimethoxyphenyl)methanone (153 mg) in pyridine (3.0 mL), 2-chlorobenzoyl chloride (93 mg) was added at room temperature. After stirring at the same temperature as above for 2 hours in a nitrogen atmosphere, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then crystallized from ethyl acetate/diisopropyl ether to obtain the title compound (71.9 mg).

$^1$H NMR (300 MHz, CDCl$_3$) δ 1.99-2.15 (1H, m), 2.17-2.33 (1H, m), 3.59 (3H, s), 3.77-3.90 (1H, m), 3.92 (3H, s), 3.95 (3H, s), 4.03-4.16 (1H, m), 5.26-5.41 (1H, m), 6.38 (1H, d, J=7.2 Hz), 6.92 (1H, d, J=8.3 Hz), 7.20-7.30 (2H, m), 7.30-7.43 (3H, m), 7.52 (1H, s), 7.64-7.72 (1H, m).

Example 201A

2-Chloro-N-(7-chloro-1-(3,4-dimethoxybenzoyl)-1,2,3,4-tetrahydroquinolin-4-yl)benzamide

A) N-(3-Chlorophenyl)-N-((4-methylphenyl)sulfonyl)-beta-alanine

A mixture of 3-chloroaniline (25.50 g), acrylic acid (13.7 mL) and toluene (100 mL) was stirred at 110° C. for 16 hours. The reaction mixture was acidified with 1 N hydrochloric acid, and then, water and ethyl acetate were added thereto to separate an organic layer. The aqueous layer was subjected to extraction with ethyl acetate. The combined extracts were washed with water and saturated brine and dried over anhydrous magnesium sulfate, and then, the solvent was distilled off under reduced pressure. A mixture of the residue, p-toluenesulfonyl chloride (41.00 g), pyridine (35 mL) and toluene (200 mL) was stirred at room temperature for 100 hours. The solvent was distilled off under reduced pressure, and then, the mixture was diluted with 1 N hydrochloric acid. Ethyl acetate was added thereto to separate an organic layer. The aqueous layer was subjected to extraction with ethyl acetate. The combined extracts were washed with water and saturated brine and dried over anhydrous magnesium sulfate, and then, the solvent was distilled off under reduced pressure to obtain the title compound (59.80 g).

MS: [M+H]$^+$ 353.9.

B) 7-Chloro-2,3-dihydroquinolin-4(1H)-one

To a solution of N-(3-chlorophenyl)-N-((4-methylphenyl)sulfonyl)-beta-alanine (30.00 g) in THF (500 mL), a catalytic amount of DMF and oxalyl chloride (17.5 mL) were added at 0° C. After stirring at room temperature for 1 hour, the solvent was distilled off under reduced pressure. The obtained solid was dissolved in nitroethane (400 mL). To the solution, aluminum chloride (47.60 g) was added at 0° C., and then, the mixture was stirred at room temperature for 1 hour. The reaction mixture was poured to ice, followed by extraction with ethyl acetate. The extract was washed with water and saturated brine and dried over anhydrous magnesium sulfate, and then, the solvent was distilled off under reduced pressure. The residue was purified by silica gel column chromatography (ethyl acetate/hexane) to obtain the title compound (7.60 g).

MS: [M+H]$^+$ 182.0.

C) tert-Butyl 7-chloro-4-hydroxy-3,4-dihydroquinoline-1(2H)-carboxylate

To a solution of 7-chloro-2,3-dihydroquinolin-4(1H)-one (7.60 g) in THF (100 mL), di-tert-butyl dicarbonate (10.1 mL) and N,N-dimethyl-4-aminopyridine (2.10 g) were added at room temperature. After stirring at the same temperature as above for 14 hours, the reaction mixture was concentrated under reduced pressure, and water was added thereto, followed by extraction with ethyl acetate. The extract was washed with water and saturated brine and dried over anhydrous magnesium sulfate. Then, the solvent was distilled off under reduced pressure, and the residue was purified by silica gel column chromatography (ethyl acetate/hexane). To a solution of the obtained oil in THF (150 mL) and methanol (75 mL), sodium borohydride (1.60 g) was added at 0° C. After stirring at the same temperature as above for 1 hour, the mixture was further stirred at room temperature for 1 hour. Water was added to the reaction mixture, and then, the reaction mixture was concentrated under reduced pressure, followed by extraction with ethyl acetate. The extract was washed with water and saturated brine and dried over anhydrous magnesium sulfate, and then, the solvent was distilled off under reduced pressure to obtain the title compound (10.30 g).

$^1$H NMR (300 MHz, CDCl$_3$) δ 1.54 (9H, s), 1.71-1.85 (1H, m), 1.86-2.12 (1H, m), 3.47-3.75 (1H, m), 3.89-4.08 (1H, m), 4.65-4.78 (1H, m), 7.04 (1H, dd, J=8.3, 2.1 Hz), 7.30 (1H, d, J=8.3 Hz), 7.91 (1H, d, J=1.9 Hz).

D) tert-Butyl 4-amino-7-chloro-3,4-dihydroquinoline-1(2H)-carboxylate hydrochloride To a solution of tert-butyl 7-chloro-4-hydroxy-3,4-dihydroquinoline-1(2H)-carboxylate (5.00 g) in toluene (100 mL), diphenylphosphorylazide (4.5 mL) and diazabicycloundecene (3.1 mL) were added at room temperature. After stirring at the same temperature as above for 18 hours, the reaction mixture was diluted with water, followed by extraction with ethyl acetate. The solvent was distilled off under reduced pressure, and then, the residue was purified by silica gel column chromatography (ethyl acetate/hexane). A mixture of the obtained oil, triphenylphosphine (8.30 g), THF (400 mL) and water (40 mL) was stirred at 100° C. for 2 hours. The reaction mixture was concentrated under reduced pressure, and water was added thereto, followed by extraction with ethyl acetate. The extract was washed with water and saturated brine and dried over anhydrous magnesium sulfate, and then, the solvent was distilled off under reduced pressure. The residue was diluted with diethyl ether, and a 4 M solution of hydrogen chloride in ethyl acetate was added thereto, and the obtained precipitate was collected by filtration to obtain the title compound (2.50 g).

$^1$H NMR (300 MHz, CDCl$_3$) δ 1.49 (9H, s), 1.94-2.10 (1H, m), 2.10-2.24 (1H, m), 3.59-3.77 (1H, m), 3.79-3.92 (1H, m), 4.49 (1H, brs), 7.22 (1H, dd, J=8.3, 2.3 Hz), 7.55 (1H, d, J=8.3 Hz), 7.88 (1H, d, J=2.3 Hz), 8.60 (3H, brs).

E) tert-Butyl 7-chloro-4-((2-chlorobenzoyl)amino)-3,4-dihydroquinoline-1(2H)-carboxylate A mixture of tert-butyl 4-amino-7-chloro-3,4-dihydroquinoline-1(2H)-carboxylate hydrochloride (2.50 g), 2-chlorobenzoyl chloride (1.1 mL), triethylamine (2.5 mL) and THF (50 mL) was stirred at room temperature for 2 hours. Then, the reaction mixture was concentrated under reduced pressure, and water was added thereto, followed by extraction with ethyl acetate. The extract was washed with 1 N hydrochloric acid, a saturated aqueous solution of sodium bicarbonate and saturated brine and dried over anhydrous magnesiumسulfate, and then, the solvent was distilled off under reduced pressure. The residue was purified by silica gel column chromatography (ethyl acetate/hexane) to obtain the title compound (3.10 g).

$^1$H NMR (300 MHz, CDCl$_3$) δ 1.55 (9H, s), 2.09-2.32 (2H, m), 3.65-3.81 (1H, m), 3.87-4.03 (1H, m), 5.29-5.39 (1H, m), 6.39 (1H, d, J=7.5 Hz), 7.04 (1H, dd, J=8.3, 2.3 Hz), 7.27-7.43 (4H, m), 7.67-7.75 (1H, m), 7.88 (1H, d, J=2.1 Hz).

F) 2-Chloro-N-(7-chloro-1,2,3,4-tetrahydroquinolin-4-yl)benzamide hydrochloride A mixture of tert-butyl 7-chloro-4-((2-chlorobenzoyl)amino)-3,4-dihydroquinoline-1(2H)-carboxylate (3.10 g) and a 4 M solution of hydrogen chloride in ethyl acetate (20 mL) was stirred at room temperature for 1 hour. Diethyl ether was added to the reaction, and the mixture was stirred for 30 minutes. The obtained precipitate was collected by filtration to obtain the title compound (2.40 g).

$^1$H NMR (300 MHz, DMSO-d$_6$) δ 1.87-1.98 (2H, m), 3.27 (2H, t, J=5.7 Hz), 4.98-5.18 (1H, m), 6.46 (2H, brs), 6.54-6.66 (2H, m), 7.13 (1H, d, J=7.9 Hz), 7.32-7.53 (4H, m), 8.82 (1H, d, J=8.3 Hz).

G) 2-Chloro-N-(7-chloro-1-(3,4-dimethoxybenzoyl)-1,2,3,4-tetrahydroquinolin-4-yl)benzamide To a solution of 3,4-dimethoxybenzoic acid (0.48 g) in THF (15 mL), a catalytic amount of DMF and oxalyl chloride (0.28 mL) were added. The mixture was stirred at room temperature for 1 hour, and then, the solvent was distilled off under reduced pressure. To a suspension of the obtained solid in THF (15 mL), 2-chloro-N-(7-chloro-1,2,3,4-tetrahydroquinolin-4-yl)benzamide hydrochloride (0.79 g) and triethylamine (0.69 mL) were added, and the mixture was stirred at 50° C. for 3 hours. The reaction mixture was concentrated under reduced pressure, and water was added thereto, followed by extraction with ethyl acetate. The extract was washed with 1 N hydrochloric acid, a saturated aqueous solution of sodium bicarbonate and saturated brine and dried over anhydrous magnesium sulfate, and then, the solvent was distilled off under reduced pressure. The residue was purified by silica gel column chromatography (ethyl acetate/hexane) to obtain the title compound (0.89 g).

$^1$H NMR (300 MHz, CDCl$_3$) δ 2.08-2.25 (1H, m), 2.28-2.49 (1H, m), 3.76-3.89 (1H, m), 3.84 (3H, s), 3.91 (3H, s), 4.00-4.17 (1H, m), 5.33-5.49 (1H, m), 6.56 (1H, d, J=8.0 Hz), 6.80 (1H, d, J=8.3 Hz), 6.98-7.15 (4H, m), 7.29-7.44 (4H, m), 7.68-7.78 (1H, m).

Example 204A

2-Chloro-N-(1-(3,4-dimethoxybenzoyl)-1,2,3,4-tetrahydroquinolin-4-yl)benzamide

A) N-((4-Methylphenyl)sulfonyl)-N-phenyl-beta-alanine

A mixture of N-phenyl-beta-alanine (18.90 g), p-toluenesulfonyl chloride (21.80 g), pyridine (18.5 mL) and toluene (100 mL) was stirred at 100° C. for 15 hours. The reaction mixture was concentrated under reduced pressure, and water was added thereto, followed by extraction with ethyl acetate. The extract was washed with water and saturated brine and dried over anhydrous magnesium sulfate, and then, the solvent was distilled off under reduced pressure to obtain the title compound (30.80 g).

MS: [M+H]$^+$ 319.9.

B) 2,3-Dihydroquinolin-4(1H)-one

To a solution of N-((4-methylphenyl)sulfonyl)-N-phenyl-beta-alanine (30.80 g) and DMF (0.5 mL) in THF (500 mL), oxalyl chloride (9.9 mL) was added at 0° C. The mixture was stirred at 0° C. for 1 hour. Then, the solvent was distilled off under reduced pressure, and the mixture was dried in a nitrogen atmosphere. The obtained solid was dissolved in nitroethane (500 mL). To the solution, aluminum chloride (27.00 g) was added at 0° C. The reaction mixture was stirred at room temperature for 2 hours, then poured to ice and basified with an aqueous sodium hydroxide solution. Then, the insoluble matter was filtered off through Celite. The obtained solution was subjected to extraction with ethyl acetate. The extract was washed with water and saturated brine and then dried over anhydrous magnesium sulfate, and the solvent was distilled off under reduced pressure. Acetic acid (30 mL) and concentrated hydrochloric acid (30 mL) were added to the obtained oil, and the mixture was stirred under conditions of heating to reflux for 4 hours. The reaction was cooled to room temperature, then poured to ice and basified with an aqueous sodium hydroxide solution. After extraction with ethyl acetate, the extract was washed with water and saturated brine and then dried over anhydrous magnesium sulfate, and the solvent was distilled off under reduced pressure to obtain the title compound (9.80 g).

MS: $[M+H]^+$ 148.0.

C) 1-(3,4-Dimethoxybenzoyl)-2,3-dihydroquinolin-4(1H)-one

A mixture of 2,3-dihydroquinolin-4(1H)-one (2.70 g), ethylene glycol (2.1 mL), p-toluenesulfonic acid monohydrate (1.80 g), molecular sieves (4 Å, 3.00 g) and toluene (100 mL) was stirred under the conditions for 3 hours. The reaction mixture was cooled to room temperature. Then, sodium bicarbonate was added thereto, and the mixture was diluted with water, followed by extraction with ethyl acetate. The extract was washed with water and saturated brine and then dried over anhydrous magnesium sulfate, and the solvent was distilled off under reduced pressure.

To a solution of 3,4-dimethoxybenzoic acid (3.40 g) in THF (50 mL), a catalytic amount of DMF and oxalyl chloride (1.9 mL) were added at 0° C., and the mixture was stirred at room temperature for 30 minutes. The solvent was distilled off under reduced pressure, and then, the mixture was dried in a nitrogen atmosphere. The obtained solid was dissolved in THF (100 mL). To the solution, the oil obtained above and triethylamine (3.9 mL) were added, and the mixture was stirred at room temperature for 2 hours. The reaction mixture was concentrated under reduced pressure, and water was added thereto, followed by extraction with ethyl acetate. The extract was washed with 6 N hydrochloric acid, and then, the solvent was distilled off under reduced pressure. THF and 6 N hydrochloric acid were added to the residue, and the mixture was stirred at room temperature for 1 hour. The mixture was concentrated under reduced pressure again, and water was added thereto, followed by extraction with ethyl acetate. The extract was washed with a saturated aqueous solution of sodium bicarbonate and saturated brine and dried over anhydrous magnesium sulfate, and then, the solvent was distilled off under reduced pressure. Toluene was added thereto, and the insoluble matter was filtered off. Then, the residue was purified by silica gel column chromatography (ethyl acetate/hexane) to obtain the title compound (0.90 g).

MS: $[M+H]^+$ 311.9.

D) (3,4-Dimethoxyphenyl)(4-hydroxy-3,4-dihydroquinolin-1(2H)-yl)methanone

To a solution of 1-(3,4-dimethoxybenzoyl)-2,3-dihydroquinolin-4(1H)-one (0.90 g) in THF (15 mL) and methanol (7 mL), sodium borohydride (0.11 g) was added at 0° C. After stirring at room temperature for 2 hours, water was added to the reaction mixture. The reaction mixture was concentrated under reduced pressure, and water was added thereto, followed by extraction with ethyl acetate. The extract was washed with water and saturated brine and dried over anhydrous magnesium sulfate, and then, the solvent was distilled off under reduced pressure. The residue was purified by silica gel column chromatography (ethyl acetate/hexane) to obtain the title compound (0.62 g).

MS: $[M+H]^+$ 314.0.

E) (4-Amino-3,4-dihydroquinolin-1(2H)-yl)(3,4-dimethoxyphenyl)methanone hydrochloride To a solution of (3,4-dimethoxyphenyl)(4-hydroxy-3,4-dihydroquinolin-1(2H)-yl)methanone (0.62 g) in toluene (10 mL), trifluoroborane diethyl ether complex (0.25 mL) was added at 0° C., and then, trimethylsilylazide (0.29 mL) was added at the same temperature as above. The reaction mixture was stirred at room temperature for 1 hour and then stirred at 50° C. for 1 hour. The reaction was cooled to room temperature, and then, water was added thereto, followed by extraction with ethyl acetate. The extract was washed with water and saturated brine and dried over anhydrous magnesium sulfate, and then, the solvent was distilled off under reduced pressure. A mixture of the residue, 10% palladium-carbon (containing 50% water, 200 mg) and ethyl acetate (10 mL) was stirred at room temperature for 2 hours in a hydrogen atmosphere. The insoluble matter was filtered off, and the solvent was distilled off under reduced pressure. Ethyl acetate was added to the obtained residue, and then, a 4 M solution of hydrogen chloride in ethyl acetate (1 mL), then diethyl ether were added. The obtained precipitate was collected by filtration to obtain the title compound (0.42 g).

MS: $[M+H]^+$ 335.0 ($M^+$+Na).

F) 2-Chloro-N-(1-(3,4-dimethoxybenzoyl)-1,2,3,4-tetrahydroquinolin-4-yl)benzamide A mixture of (4-amino-3,4-dihydroquinolin-1(2H)-yl)(3,4-dimethoxyphenyl)methanone hydrochloride (0.20 g), 2-chlorobenzoyl chloride (0.075 mL), triethylamine (0.12 mL) and THF (15 mL) was stirred at 50° C. for 4 hours and then diluted with water, followed by extraction with ethyl acetate. The extract was washed with 1 N hydrochloric acid, a saturated aqueous solution of sodium bicarbonate and saturated brine and dried over anhydrous magnesium sulfate. Then, the solvent was distilled off under reduced pressure, and the residue was crystallized from ethyl acetate/hexane to obtain the title compound (169 mg).

$^1$H NMR (300 MHz, CDCl$_3$) δ 2.09-2.28 (1H, m), 2.33-2.53 (1H, m), 3.77 (3H, s), 3.79-3.96 (1H, m), 3.88 (3H, s), 4.06-4.23 (1H, m), 5.38-5.54 (1H, m), 6.59 (1H, d, J=8.1 Hz), 6.75 (1H, d, J=8.1 Hz), 6.89 (1H, dd, J=8.0, 1.2 Hz), 6.96-7.06 (3H, m), 7.06-7.12 (1H, m), 7.30-7.49 (4H, m), 7.69-7.80 (1H, m).

Example 217A

2-Chloro-N-(7-chloro-1-(3,4-dimethoxybenzoyl)-1,2,3,4-tetrahydro-1,8-naphthyridin-4-yl)benzamide

A) N-(6-Chloropyridin-2-yl)-beta-alanine

A mixture of 2-amino-6-chloropyridine (100 g), methyl acrylate methyl acrylate (117 g) and acetic acid (34 mL) was stirred at 120° C. for 72 hours. The reaction was cooled to room temperature. Then, a 6 N aqueous sodium hydroxide solution (375 mL) was added thereto, and the mixture was stirred under conditions of heating to reflux for 5 hours. The reaction mixture was cooled to room temperature, and then, unreacted 2-amino-6-chloropyridine starting material was extracted with diethyl ether. The remaining aqueous layer was adjusted to pH=4 to 5 with 3 N hydrochloric acid, and the precipitate was collected by filtration. The solid collected by filtration was dissolved in ethyl acetate, washed with saturated brine and dried over anhydrous sodium sulfate. Then, the solvent was distilled off under reduced pressure to obtain the title compound (60 g).

$^1$HNMR (300 MHz, MeOD) δ 2.58 (2H, t, J=6.8 Hz), 3.54 (2H, t, J=6.8 Hz), 6.38 (1H, dd, J=8.4, 0.6 Hz), 6.49 (1H, dd, J=7.2, 0.6 Hz), 7.33 (1H, dd, J=8.4, 7.4 Hz).

B) 7-Chloro-2,3-dihydro-1,8-naphthyridin-4(1H)-one

A mixture of N-(6-chloropyridin-2-yl)-beta-alanine (40 g) and Eaton's Reagent (600 mL) was stirred at 75° C. for 3 hours. The reaction mixture was poured to ice water and basified to pH=10 with sodium hydroxide, followed by extraction with ethyl acetate. The extract was washed with saturated brine and dried over anhydrous sodium sulfate. The solvent was distilled off under reduced pressure, and the residue was purified by silica gel column chromatography (ethyl acetate) to obtain the title compound.

MS: [M+H]$^+$ 182.8.

C) 7-Chloro-1-(3,4-dimethoxybenzoyl)-2,3-dihydro-1,8-naphthyridin-4(1H)-one trifluoroacetic Acid Salt To a solution of 7-chloro-2,3-dihydro-1,8-naphthyridin-4(1H)-one (0.6 g) in THF (30 mL), a 1 M solution of lithium bis(trimethylsilyl)amide in hexane (3.3 mL) was added at −75° C. to −70° C. The reaction mixture was stirred at the same temperature as above for 30 minutes, and then, a solution of 3,4-dimethoxybenzoyl chloride (0.8 g) in THF (5 mL) was added thereto over 30 minutes. The temperature of the reaction mixture was raised to room temperature, and the reaction mixture was poured to water, followed by extraction with ethyl acetate. The extract was washed with saturated brine and dried over anhydrous sodium sulfate, and then, the solvent was distilled off under reduced pressure. The residue was purified by reverse-phase HPLC to obtain the title compound (28 mg).

MS: [M+H]$^+$ 346.9.

D) (4-Amino-7-chloro-3,4-dihydro-1,8-naphthyridin-1(2H)-yl)(3,4-dimethoxyphenyl)methanone A mixture of 7-chloro-1-(3,4-dimethoxybenzoyl)-2,3-dihydro-1,8-naphthyridin-4(1H)-one trifluoroacetic acid salt (28 mg), hydroxylamine hydrochloride (15 mg) and pyridine (5 mL) was stirred under conditions of heating to reflux for 4 hours. The reaction mixture was concentrated under reduced pressure, and water was added thereto, followed by extraction with ethyl acetate. The extract was washed with saturated brine and dried over anhydrous magnesium sulfate, and then, the solvent was distilled off under reduced pressure. The residue was purified by silica gel column chromatography (ethyl acetate). To a solution of the obtained residue and molybdenum trioxide (14 mg) in THF (2 mL) and methanol (2 mL), sodium borohydride (12 mg) was added, and the mixture was stirred at room temperature for 14 hours. Water was added to the reaction, and the mixture was concentrated under reduced pressure. Water was added thereto, followed by extraction with ethyl acetate. The extract was washed with saturated brine and dried over anhydrous magnesium sulfate, and then, the solvent was distilled off under reduced pressure to obtain the title compound (24 mg).

MS: [M+H]$^+$ 348.0.

E) 2-Chloro-N-(7-chloro-1-(3,4-dimethoxybenzoyl)-1,2,3,4-tetrahydro-1,8-naphthyridin-4-yl)benzamide A mixture of (4-amino-7-chloro-3,4-dihydro-1,8-naphthyridin-1(2H)-yl)(3,4-dimethoxyphenyl)methanone (24 mg), 2-chlorobenzoyl chloride (0.012 mL), triethylamine (0.020 mL) and THF (5 mL) was stirred at room temperature for 64 hours. The reaction mixture was concentrated under reduced pressure, and water was added thereto, followed by extraction with ethyl acetate. The extract was washed with a saturated aqueous solution of sodium bicarbonate and saturated brine and dried over anhydrous magnesium sulfate, and then, the solvent was distilled off under reduced pressure to obtain the title compound (12 mg).

$^1$H NMR (300 MHz, CDCl$_3$) δ 2.19-2.33 (1H, m), 2.39-2.51 (1H, m), 3.84 (3H, s), 3.89 (3H, s), 3.91-4.03 (1H, m), 4.06-4.25 (1H, m), 5.38-5.59 (1H, m), 6.46-6.62 (1H, m), 6.73 (1H, d, J=8.3 Hz), 6.85-6.93 (1H, m), 6.93-7.00 (1H, m), 7.12 (1H, d, J=1.9 Hz), 7.31-7.46 (3H, m), 7.66-7.82 (2H, m).

Example 4B

2-Chloro-N-(trans-1-(3,4-dimethoxybenzoyl)-3-phenylpiperidin-4-yl)benzamide

A) tert-Butyl trans-4-(((benzyloxy)carbonyl)amino)-3-phenylpiperidine-1-carboxylate To a solution of trans-1-(tert-butoxycarbonyl)-3-phenylpiperidine-4-carboxylic acid (1.0 g) in toluene (25 mL), diphenyl phosphorazidate (0.77 mL) and triethylamine (0.50 mL) were added at room temperature, and the mixture was heated to reflux for 1 hour. Benzyl alcohol (0.41 mL) was added to the reaction mixture at room temperature, and the mixture was heated to reflux for 5 hours. Water was added to the reaction mixture, followed by extraction with ethyl acetate. The organic layer was washed with water and saturated brine and then dried over anhydrous sodium sulfate, and the solvent was distilled off under reduced pressure. The residue was purified by silica gel column chromatography (ethyl acetate/hexane) to obtain the title compound (1.35 g).

$^1$H NMR (300 MHz, CDCl$_3$) δ 1.46 (9H, s), 2.10-2.27 (1H, m), 2.46-2.64 (1H, m), 2.67-2.98 (2H, m), 3.83-4.03 (1H, m), 4.11-4.30 (2H, m), 4.47 (1H, brs), 4.70 (1H, d, J=5.8 Hz), 4.95 (2H, s), 7.09-7.49 (10H, m).

B) tert-Butyl trans-4-amino-3-phenylpiperidine-1-carboxylate

A mixture of tert-butyl trans-4-(((benzyloxy)carbonyl)amino)-3-phenylpiperidine-1-carboxylate (1.3 g), 10% palladium-carbon (200 mg) and methanol (30 mL) was stirred overnight at room temperature in a hydrogen atmosphere. The insoluble matter was filtered off, and the filtrate was concentrated under reduced pressure to obtain the title compound (863.5 mg).
$^1$H NMR (300 MHz, CDCl$_3$) δ 1.46 (9H, s), 1.74 (3H, brs), 1.83-2.04 (1H, m), 2.39 (1H, td, J=11.0, 4.1 Hz), 2.66-2.93 (2H, m), 3.01 (1H, td, J=10.7, 3.9 Hz), 3.99-4.35 (2H, m), 7.03-7.42 (5H, m).

C) tert-Butyl trans-4-((2-chlorobenzoyl)amino)-3-phenylpiperidine-1-carboxylate To a mixture of tert-butyl trans-4-amino-3-phenylpiperidine-1-carboxylate (484 mg), triethylamine (0.15 mL) and THF (10 mL), 2-chlorobenzoyl chloride (0.11 mL) was added at 0° C. After stirring overnight at room temperature, water was added to the reaction mixture, followed by extraction with ethyl acetate. The organic layer was washed with 1 N hydrochloric acid, a saturated aqueous solution of sodium carbonate and saturated brine and then dried over anhydrous sodium sulfate, and the solvent was distilled off under reduced pressure. The residue was purified by silica gel column chromatography (ethyl acetate/hexane) to obtain the title compound (247.6 mg).
$^1$H NMR (300 MHz, CDCl$_3$) δ 1.47 (9H, s), 2.26-2.45 (1H, m), 2.61-2.76 (1H, m), 2.76-2.90 (1H, m), 2.90-3.06 (1H, m), 4.17-4.38 (2H, m), 4.38-4.59 (1H, m), 5.84 (1H, d, J=8.3 Hz), 7.11-7.40 (10H, m).

D) 2-Chloro-N-(trans-1-(3,4-dimethoxybenzoyl)-3-phenylpiperidin-4-yl)benzamide To tert-butyl trans-4-((2-chlorobenzoyl)amino)-3-phenylpiperidine-1-carboxylate (240 mg), a 4 M solution of hydrogen chloride in ethyl acetate (10 mL) was added under ice cooling, and the mixture was stirred at room temperature for 2 hours. The reaction mixture was concentrated under reduced pressure, and the obtained residue was dissolved in pyridine (5 mL). To the solution, 3,4-dimethoxybenzoyl chloride (117 mg) was added at 0° C. The reaction mixture was stirred overnight at room temperature, and then, the solvent was distilled off under reduced pressure. The residue was partitioned into 1 N hydrochloric acid and ethyl acetate. The organic layer was washed with a saturated aqueous solution of sodium carbonate and saturated brine and then dried over anhydrous sodium sulfate, and the solvent was distilled off under reduced pressure. The residue was purified by silica gel column chromatography (ethyl acetate/hexane) to obtain the title compound (217.3 mg).
$^1$H NMR (300 MHz, DMSO-d$_6$) δ 1.37-1.68 (1H, m), 1.82-2.17 (1H, m), 2.70-2.90 (1H, m), 2.90-3.30 (2H, m), 3.78 (6H, s), 3.61-4.06 (1H, m), 4.42 (2H, d, J=10.9 Hz), 6.88 (1H, d, J=6.8 Hz), 6.92-7.05 (3H, m), 7.10-7.49 (8H, m), 8.27 (1H, d, J=8.9 Hz).

Example 23B

N-((3S,4R)-1-((8-Chloroquinoxalin-6-yl)carbonyl)-3-phenylpiperidin-4-yl)-1,3-dimethyl-1H-pyrazole-5-carboxamide

A) Methyl 8-chloroquinoxaline-6-carboxylate

A mixture of methyl 3,4-diamino-5-chlorobenzoate (2.80 g), a 40% aqueous oxalaldehyde solution (2.43 g), methanol (20 mL) and THF (10 mL) was stirred overnight at room temperature. The reaction mixture was diluted with a saturated aqueous solution of sodium bicarbonate, followed by extraction with THF/ethyl acetate. The extract was washed with saturated brine and dried over anhydrous magnesium sulfate, and the solvent was distilled off under reduced pressure. The residue was washed with ethyl acetate to obtain the title compound (1.28 g).
MS: [M+H]$^+$ 222.8.

B) 8-Chloroquinoxaline-6-carboxylic acid

A mixture of methyl 8-chloroquinoxaline-6-carboxylate (1.27 g), a 8 M aqueous sodium hydroxide solution (7.13 mL), methanol (2 mL) and THF (10 mL) was stirred at 50° C. for 10 hours. The reaction mixture was concentrated under reduced pressure, and the residue was washed with water and diisopropyl ether to obtain the title compound (1.11 g).
MS: [M+H]$^+$ 209.0.

C) (3S,4R)-tert-Butyl 3-phenyl-4-(2,2,2-trifluoroacetamido)piperidine-1-carboxylate To a solution of (3S,4R)-tert-butyl 4-amino-3-phenylpiperidine-1-carboxylate (2.50 g) and triethylamine (2.5 mL) in THF (50 mL), trifluoroacetic anhydride (1.4 mL) was added under ice cooling, and the mixture was stirred at room temperature for 2 hours. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (2.80 g).
$^1$H NMR (300 MHz, CDCl$_3$) δ 1.46 (9H, s), 1.81 (2H, d, J=4.9 Hz), 3.09-3.19 (1H, m), 3.19-3.69 (2H, m), 3.56-4.14 (2H, m), 4.31-4.45 (1H, m), 5.91 (1H, brs), 7.18-7.25 (2H, m), 7.29-7.38 (3H, m).

D) 2,2,2-Trifluoro-N-((3S,4R)-3-phenylpiperidin-4-yl)acetamide hydrochloride To a solution of (3S,4R)-tert-butyl 3-phenyl-4-(2,2,2-trifluoroacetamido)piperidine-1-carboxylate (2.77 g) in methanol (5 mL), a 4 M solution of hydrochloric acid in cyclopentyl methyl ether (9.5 mL) was added, and the mixture was stirred at room temperature for 2 hours. The reaction mixture was concentrated under reduced pressure, and the residue was washed with diisopropyl ether to obtain the title compound (2.01 g).
MS: [M+H]$^+$ 273.0.

E) N-((3S,4R)-1-(8-Chloroquinoxaline-6-carbonyl)-3-phenylpiperidin-4-yl)-2,2,2-trifluoroacetamide A mixture of 2,2,2-trifluoro-N-((3S,4R)-3-phenylpiperidin-4-yl)acetamide hydrochloride (1.40 g), 8-chloroquinoxaline-6-carboxylic acid (1.23 g), HATU (2.24 g), triethylamine (2.0 mL) and DMF (10 mL) was stirred at room temperature for 3 hours. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under F) ((3S,4R)-4-Amino-3-phenylpiperidin-1-yl)(8-chloroquinoxalin-6-yl)methanone To a solution of N-((3S,4R)-1-(8-chloroquinoxaline-6-carbonyl)-3-phenylpiperidin-4-yl)-2,2,2-trifluoroacetamide (1.98 g) in methanol (10 mL), a 2 M aqueous sodium hydroxide solution (9.5 mL) was added at room temperature, and the mixture was stirred at the same temperature as above for 2 hours. The reaction mixture was neutralized with 1 M hydrochloric acid, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) to obtain the title compound (1.32 g).
MS: [M+H]+ 367.0.

G) N-((3S,4R)-1-((8-Chloroquinoxalin-6-yl)carbonyl)-3-phenylpiperidin-4-yl)-1,3-dimethyl-1H-pyrazole-5-carboxamide A mixture of ((3S,4R)-4-amino-3-phenylpiperidin-1-yl)(8-chloroquinoxalin-6-yl)methanone (200 mg), 1,3-dimethyl-1H-pyrazole-5-carboxylic acid (92 mg), HATU (249 mg), triethylamine (0.228 mL) and DMF (2 mL) was stirred at room temperature for 2 hours. Then, the reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (NH, ethyl acetate/hexane) and then crystallized from ethyl acetate/diisopropyl ether to obtain the title compound (209 mg).
$^1$H NMR (300 MHz, CDCl$_3$) δ 1.74-2.15 (2H, m), 2.20 (3H, s), 3.11-3.48 (1H, m), 3.51-3.97 (2H, m), 4.02 (3H, s), 4.20-4.69 (2H, m), 5.48-5.79 (1H, m), 5.89 (1H, brs), 7.06-7.52 (6H, m), 7.63-8.25 (2H, m), 8.98 (2H, brs).

Example 24B

N-((3S,4R)-1-(8-Chloroquinoxaline-6-carbonyl)-3-phenylpiperidin-4-yl)-6-(2-morpholinoethoxy)nicotinamide A) 6-Chloro-N-((3S,4R)-1-(8-chloroquinoxaline-6-carbonyl)-3-phenylpiperidin-4-yl)nicotinamide To a solution of ((3S,4R)-4-amino-3-phenylpiperidin-1-yl)(8-chloroquinoxalin-6-yl)methanone (200 mg), 6-chloronicotinic acid (103 mg) and triethylamine (0.227 ml) in DMF (2 ml), HATU (249 mg) was added at room temperature. After stirring at room temperature for 1 hour in a dry atmosphere, a saturated aqueous solution of sodium bicarbonate was added thereto, followed by extraction with ethyl acetate. The extract was washed with water and saturated brine and then dried over sodium sulfate, and the solvent was distilled off under reduced pressure. The residue was purified by silica gel column chromatography (ethyl acetate/hexane). The obtained solid was washed with diisopropyl ether to obtain the title compound (273 mg).
MS: [M+H]+ 506.1

B) N-((3S,4R)-1-(8-Chloroquinoxaline-6-carbonyl)-3-phenylpiperidin-4-yl)-6-(2-morpholinoethoxy)nicotinamide To a solution of N-(2-hydroxyethyl)morpholine (0.072 ml) in THF (1.3 ml), sodium hydride (60%, 24.17 mg) was added at 0° C. After stirring at 0° C. for 20 minutes, 6-chloro-N-((3S,4R)-1-(8-chloroquinoxaline-6-carbonyl)-3-phenylpiperidin-4-yl)nicotinamide (60 mg) was added thereto, and the mixture was stirred at 70° C. for 1.5 hours. A saturated aqueous solution of ammonium chloride was added to the reaction mixture at room temperature, followed by extraction with ethyl acetate. The extract was washed with water and saturated brine and then dried over anhydrous sodium sulfate, and the solvent was distilled off. The residue was purified by silica gel column chromatography (ethyl acetate/hexane) to obtain the title compound (18.40 mg).
$^1$H NMR (300 MHz, DMSO) δ 1.65-2.09 (2H, m), 2.34-2.47 (5H, m), 2.62-2.72 (2H, m), 3.50-3.68 (6H, m), 3.99-4.50 (4H, m, J=5.5, 5.5 Hz), 4.52-4.76 (1H, m), 6.84 (1H, d, J=8.7 Hz), 7.07-7.41 (5H, m), 7.87-8.29 (4H, m), 8.36-8.50 (1H, m), 9.01-9.20 (2H, m, J=19.6 Hz).

Example 31B

N-((3S,4R)-1-((8-Chloroquinoxalin-6-yl)carbonyl)-3-phenylpiperidin-4-yl)-3-(difluoromethoxy)pyridine-2-carboxamide To a solution of 3-(difluoromethoxy)picolinic acid (70.5 mg), ((3S,4R)-4-amino-3-phenylpiperidin-1-yl)(8-chloroquinoxalin-6-yl)methanone (97.2 mg) and N-ethyldiisopropylamine (0.139 mL) in DMF (2.0 mL), HATU (161 mg) was added at room temperature, and the mixture was stirred for 3 hours. Water was added to the reaction mixture, followed by extraction with ethyl acetate/THF. The extract was washed with a saturated aqueous solution of potassium carbonate, water and saturated brine and then dried over anhydrous magnesium sulfate, and the solvent was distilled off under reduced pressure. The residue was purified by silica gel column chromatography (NH, ethyl acetate/hexane) to obtain the title compound (121 mg).
$^1$H NMR (300 MHz, DMSO-d$_6$) δ 1.61-2.15 (2H, m), 3.34-3.47 (1H, m), 3.48-3.74 (2H, m), 3.78-3.99 (1H, m), 4.09-4.49 (1H, m), 4.52-4.69 (1H, m), 6.72-7.45 (6H, m), 7.57 (1H, dd, J=8.4, 4.6 Hz), 7.72 (1H, d, J=7.7 Hz), 8.02 (1H, d, J=11.1 Hz), 8.13 (1H, brs), 8.45 (1H, d, J=3.8 Hz), 8.55-8.74 (1H, m), 8.97-9.20 (2H, m).

Example 42B

N-((3S,4R)-1-((8-Chloroquinoxalin-6-yl)carbonyl)-3-phenylpiperidin-4-yl)-6-oxo-1,6-dihydropyridine-2-carboxamide A) N-((3S,4R)-1-(8-Chloroquinoxaline-6-carbonyl)-3-phenylpiperidin-4-yl)-6-methoxypicolinamide To a solution of 6-methoxypicolinic acid (0.052 g), ((3S,4R)-4-amino-3-phenylpiperidin-1-yl)(8-chloroquinoxalin-6-yl)methanone (0.083 g) and N-ethyldiisopropylamine (0.12 mL) in DMF (2.0 mL), HATU (0.13 g) was added at room temperature, and the mixture was stirred for 16 hours. Water was added to the reaction mixture, followed by extraction with ethyl acetate/THF. The extract was washed with a saturated aqueous solution of potassium carbonate, water and saturated brine and then dried over anhydrous magnesium sulfate, and the solvent was distilled off under reduced pressure. The residue was purified by silica gel column chromatography (ethyl acetate/hexane) to obtain the title compound (0.11 g).
MS: [M+H]$^+$ 502.1.

B) N-((3S,4R)-1-((8-Chloroquinoxalin-6-yl)carbonyl)-3-phenylpiperidin-4-yl)-6-oxo-1,6-dihydropyridine-2-carboxamide In a nitrogen atmosphere, pyridinium chloride (0.18 g) was added to a mixture of N-((3S,4R)-1-(8-chloroquinoxaline-6-carbonyl)-3-phenylpiperidin-4-yl)-6-methoxypicolinamide (0.077 g) and DMF (0.2 mL) at room temperature, and the resulting mixture was stirred at 130° C. for 16 hours. To the reaction mixture, 1 M hydrochloric acid was added at room temperature, and the deposit was collected by filtration and washed with water. The obtained solid was dissolved in THF, and the solvent was distilled off under reduced pressure. The residue was purified by silica gel column chromatography (methanol/ethyl acetate) to obtain the title compound (0.019 g).
$^1$H NMR (300 MHz, DMSO-d$_6$) δ 1.57-2.14 (2H, m), 3.35-4.45 (6H, m), 4.47-4.61 (1H, m), 6.60-6.79 (1H, m), 6.94-7.43 (6H, m), 7.58-7.73 (1H, m), 7.94-8.49 (3H, m), 9.01-9.25 (2H, m).

Example 45B

N-((3S,4R)-1-((8-Methoxyquinoxalin-6-yl)carbonyl)-3-phenylpiperidin-4-yl)-3-(trifluoromethyl)pyridine-2-carboxamide A) tert-Butyl (3S,4R)-3-phenyl-4-(((3-(trifluoromethyl)pyridin-2-yl)carbonyl)amino)piperidine-1-carboxylate To a solution of 3-(trifluoromethyl)picolinic acid (2.57 g), tert-butyl (3S,4R)-4-amino-3-phenylpiperidine-1-carboxylate (3.1 g) and HOBt (2.27 g) in DMF (40 mL), WSC (2.95 mL) was added under ice cooling, and the mixture was stirred overnight at room temperature. The solvent was distilled off under reduced pressure, and water was added to the residue, followed by extraction with ethyl acetate. The extract was washed with saturated brine and then dried over anhydrous sodium sulfate, and the solvent was distilled off under reduced pressure. The residue was purified by silica gel column chromatography (ethyl acetate/hexane) to obtain the title compound (5.02 g).
MS: [M+H–Boc]$^+$350.2.

B) N-((3S,4R)-3-Phenylpiperidin-4-yl)-3-(trifluoromethyl)pyridine-2-carboxamide hydrochloride To tert-butyl (3S,4R)-3-phenyl-4-(((3-(trifluoromethyl)pyridin-2-yl)carbonyl)amino)piperidine-1-carboxylate (4.29 g), a 4 M solution of hydrogen chloride in ethyl acetate (50 mL) was added under ice cooling, and the mixture was stirred at room temperature for 3 hours. The solvent was distilled off under reduced pressure to obtain the title compound (4.29 g).
$^1$H NMR (300 MHz, DMSO-d$_6$) δ 1.89 (1H, d, J=13.4 Hz), 2.10-2.32 (1H, m), 2.92-3.15 (1H, m), 3.19-3.36 (2H, m), 3.39-3.55 (1H, m), 3.74 (1H, q, J=11.4 Hz), 4.62 (1H, d, J=6.2 Hz), 7.16-7.38 (5H, m), 7.69 (1H, dd, J=7.8, 4.8 Hz), 8.24 (1H, d, J=7.5 Hz), 8.83 (1H, d, J=4.3 Hz), 8.94 (1H, d, J=9.2 Hz), 9.27 (1H, d, J=9.2 Hz), 9.77 (1H, d, J=9.0 Hz).

C) 2-Methoxy-6-nitroaniline

To a solution of 2-amino-3-nitrophenol (9.12 g) and potassium carbonate (13.6 g) in DMF (100 mL), iodomethane (4.44 mL) was added at room temperature, and the mixture was stirred at room temperature for 2 hours. Water was added to the reaction mixture at room temperature. The deposited solid was collected by filtration and washed with water and hexane to obtain the title compound (9.85 g).
$^1$H NMR (300 MHz, DMSO-d$_6$) δ 3.88 (3H, s), 6.61 (1H, dd, J=8.9, 7.7 Hz), 6.95-7.17 (3H, m), 7.59 (1H, dd, J=8.9, 1.3 Hz).

D) 4-Bromo-2-methoxy-6-nitroaniline

To a solution of 2-methoxy-6-nitroaniline (9.12 g) in acetonitrile (100 mL), N-bromosuccinimide (10.8 g) was added at room temperature, and the mixture was stirred at 70° C. for 4 hours. An aqueous sodium thiosulfate solution was added to the reaction mixture at room temperature. The deposited solid was collected by filtration and washed with water and hexane to obtain the title compound (11.77 g).
$^1$H NMR (300 MHz, DMSO-d$_6$) δ 3.91 (3H, s), 7.20 (1H, d, J=2.1 Hz), 7.25 (2H, brs), 7.72 (1H, d, J=2.1 Hz).

E) N-(4-Bromo-2-methoxy-6-nitrophenyl)acetamide

To a solution of 4-bromo-2-methoxy-6-nitroaniline (11.8 g) and acetic anhydride (6.74 mL) in acetic acid (40 mL), concentrated sulfuric acid (2.54 mL) was added at room temperature, and the mixture was stirred at 70° C. for 2 hours. Water was added to the reaction mixture at room temperature, and the deposited solid was collected by filtration and washed with water. The solid was dried by azeotroping with toluene, and suspended in ethyl acetate. The solid was collected by filtration and washed with ethyl acetate and diisopropyl ether to obtain the title compound (9.55 g).
$^1$H NMR (300 MHz, DMSO-d$_6$) δ 2.01 (3H, s), 3.93 (3H, s), 7.62 (1H, d, J=2.1 Hz), 7.66 (1H, d, J=2.1 Hz), 9.91 (1H, s).

F) N-(4-Cyano-2-methoxy-6-nitrophenyl)acetamide

A solution of N-(4-bromo-2-methoxy-6-nitrophenyl)acetamide (2.04 g), zinc dicyanide (1.76 g) and tetrakis(triphenylphosphine)palladium (857 mg) in DMF (20 mL) was stirred at 170° C. for 1 hour under irradiation with microwave. The reaction mixture was neutralized by the addition of an aqueous potassium carbonate solution, followed by extraction with ethyl acetate and THF. The extract was washed with water and saturated brine and then dried over anhydrous magnesium sulfate, and the solvent was distilled off under reduced pressure. The residue was washed with ethyl acetate and diisopropyl ether to obtain the title compound (967 mg).
$^1$H NMR (300 MHz, DMSO-d$_6$) δ 2.07 (3H, s), 3.97 (3H, s), 7.90 (1H, d, J=1.7 Hz), 8.02 (1H, d, J=1.7 Hz), 10.29 (1H, s).

G) Methyl 4-amino-3-methoxy-5-nitrobenzoate

To a solution of N-(4-cyano-2-methoxy-6-nitrophenyl)acetamide (967 mg) in ethanol (10 mL), a 8 M aqueous sodium hydroxide solution (5.14 mL) was added at room temperature, and the mixture was heated to reflux for 3 hours. To the reaction mixture, 2 M hydrochloric acid (20.6 mL) was added at 0° C., and the deposited solid was collected by filtration. To a solution of the obtained solid and potassium carbonate (1.11 g) in DMF (15 mL), iodomethane (0.39 mL) was added at room temperature, and the mixture was stirred at room temperature for 2 hours. Water was added to the reaction mixture, and the deposited solid was collected by filtration and washed with water and hexane to obtain the title compound (579 mg).

$^1$H NMR (300 MHz, DMSO-$d_6$) δ 3.84 (3H, s), 3.94 (3H, s), 7.41 (1H, d, J=1.7 Hz), 7.67 (2H, brs), 8.27 (1H, d, J=1.7 Hz).

H) Methyl 3,4-diamino-5-methoxybenzoate

A mixture of methyl 4-amino-3-methoxy-5-nitrobenzoate (579 mg), 10% palladium-carbon (347 mg), methanol (20 mL) and THF (10 mL) was stirred overnight at room temperature in a hydrogen atmosphere. The insoluble matter was filtered off, and the filtrate was concentrated under reduced pressure to obtain the title compound (522.8 mg).

$^1$H NMR (300 MHz, DMSO-$d_6$) δ 3.73 (3H, s), 3.76 (3H, s), 4.74 (2H, s), 4.81 (2H, s), 6.83 (1H, d, J=1.7 Hz), 6.97 (1H, d, J=1.7 Hz).

I) Methyl 8-methoxyquinoxaline-6-carboxylate

To a solution of methyl 3,4-diamino-5-methoxybenzoate (528 mg) in methanol (5 mL) and THF (10 mL), a 40% aqueous oxalaldehyde solution (0.46 mL) was added at room temperature, and the mixture was stirred at room temperature for 2 hours. Water was added to the reaction mixture, followed by extraction with ethyl acetate. The extract was washed with water and saturated brine and then dried over anhydrous magnesium sulfate, and the solvent was distilled off under reduced pressure. The residue was purified by silica gel column chromatography (ethyl acetate/hexane) to obtain the title compound (249 mg).

$^1$H NMR (300 MHz, DMSO-$d_6$) δ 3.96 (3H, s), 4.08 (3H, s), 7.66 (1H, d, J=1.5 Hz), 8.22 (1H, d, J=1.5 Hz), 9.01 (1H, d, J=1.7 Hz), 9.06 (1H, d, J=1.7 Hz).

J) 8-Methoxyquinoxaline-6-carboxylic acid

To a solution of methyl 8-methoxyquinoxaline-6-carboxylate (249 mg) in methanol (2 mL) and THF (4 mL), a 1 M aqueous sodium hydroxide solution (5.14 mL) was added at room temperature, and the mixture was stirred at room temperature for 2 hours. To the reaction mixture, 1 M hydrochloric acid was added at room temperature, and the deposited solid was collected by filtration and washed with water and diisopropyl ether to obtain the title compound (160.4 mg).

$^1$H NMR (300 MHz, DMSO-$d_6$) δ 4.07 (3H, s), 7.67 (1H, d, J=1.5 Hz), 8.20 (1H, d, J=1.7 Hz), 8.99 (1H, d, J=1.7 Hz), 9.04 (1H, d, J=1.7 Hz), 13.53 (1H, brs).

K) N-((3S,4R)-1-((8-Methoxyquinoxalin-6-yl)carbonyl)-3-phenylpiperidin-4-yl)-3-(trifluoromethyl)pyridine-2-carboxamide To a solution of N-((3S,4R)-3-phenylpiperidin-4-yl)-3-(trifluoromethyl)pyridine-2-carboxamide hydrochloride (100 mg), 8-methoxyquinoxaline-6-carboxylic acid (62 mg), HOBt (61 mg) and triethylamine (0.11 mL) in DMF (1 mL), WSC (0.07 mL) was added at room temperature, and the mixture was stirred at room temperature for 16 hours. An aqueous potassium carbonate solution was added to the reaction mixture at room temperature, followed by extraction with ethyl acetate. The extract was washed with water and saturated brine and then dried over anhydrous magnesium sulfate, and the solvent was distilled off under reduced pressure. The residue was purified by silica gel column chromatography (NH, methanol/ethyl acetate) to obtain the title compound (79.6 mg).

$^1$H NMR (300 MHz, DMSO-$d_6$) δ 1.62-2.12 (2H, m), 3.28-3.90 (4H, m), 3.91-4.11 (3H, m), 4.17-4.54 (1H, m), 4.55-4.71 (1H, m), 7.09-7.47 (6H, m), 7.50-7.77 (2H, m), 8.24 (1H, d, J=8.1 Hz), 8.69-9.11 (4H, m).

Example 47B

N-((3S,4R)-1-((8-Chloroquinoxalin-6-yl)carbonyl)-3-phenylpiperidin-4-yl)-6-(2-hydroxyethoxy)-4-(trifluoromethyl)nicotinamide

A) N-((3S,4R)-1-((8-Chloroquinoxalin-6-yl)carbonyl)-3-phenylpiperidin-4-yl)-6-(2-(tetrahydro-2H-pyran-2-yloxy)ethoxy)-4-(trifluoromethyl)nicotinamide To a solution of 2-(tetrahydro-2H-pyran-2-yloxy)ethanol (0.59 mL) in THF (10 mL), sodium hydride (60%, 178 mg) was added at 0° C., and the mixture was stirred at 0° C. for 3 hours. 6-Chloro-N-((3S,4R)-1-((8-chloroquinoxalin-6-yl)carbonyl)-3-phenylpiperidin-4-yl)-4-(trifluoromethyl)nicotinamide (500 mg) was added to the reaction mixture, and the mixture was stirred overnight at room temperature. A saturated aqueous solution of ammonium chloride was added to the reaction mixture at room temperature, followed by extraction with ethyl acetate. The extract was washed with water and saturated brine and then dried over anhydrous sodium sulfate, and the solvent was distilled off under reduced pressure. The residue was purified by silica gel column chromatography (NH, methanol/ethyl acetate) to obtain the title compound (313 mg).

$^1$H NMR (300 MHz, CDCl$_3$) δ 1.43-1.59 (3H, m), 1.66-1.91 (2H, m), 2.05-2.29 (2H, m), 3.24-3.57 (2H, m), 3.57-4.08 (6H, m), 4.30-4.81 (5H, m), 5.66 (1H, brs), 7.02 (1H, s), 7.14-7.49 (6H, m), 7.60-8.23 (3H, m), 8.97 (2H, brs).

B) N-((3S,4R)-1-((8-Methoxyquinoxalin-6-yl)carbonyl)-3-phenylpiperidin-4-yl)-3-(trifluoromethyl)pyridine-2-carboxamide To N-((3S,4R)-1-((8-chloroquinoxalin-6-yl)carbonyl)-3-phenylpiperidin-4-yl)-6-(2-(tetrahydro-2H-pyran-2-yloxy)ethoxy)-4-(trifluoromethyl)nicotinamide (300 mg), a 4 M solution of hydrogen chloride in ethyl acetate (20 mL) was added, and the mixture was stirred at room temperature for 3 hours. The reaction mixture was concentrated under reduced pressure, and the obtained residue was purified by silica gel column chromatography (ethyl acetate/hexane) to obtain the title compound (161.3 mg).

$^1$H NMR (300 MHz, DMSO-$d_6$) δ 1.51-1.96 (1H, m), 1.98-2.15 (1H, m), 3.35-4.02 (6H, m), 4.21-4.53 (3H, m), 4.59 (1H, brs), 4.86 (1H, t, J=5.5 Hz), 6.90-7.48 (6H, m), 7.86 (1H, d, J=10.5 Hz), 7.96-8.21 (2H, m), 8.72 (1H, d, J=8.3 Hz), 9.10 (2H, d, J=19.4 Hz).

Example 48B

Dibenzyl 2-((5-(((3S,4R)-1-((8-chloroquinoxalin-6-yl)carbonyl)-3-phenylpiperidin-4-yl)carbamoyl)-4-(trifluoromethyl)pyridin-2-yl)oxy)ethyl phosphate To a mixture of N-((3S,4R)-1-((8-chloroquinoxalin-6-yl)carbonyl)-3-phenylpiperidin-4-yl)-6-(2-hydroxyethoxy)-4-(trifluoromethyl)nicotinamide (120 mg), tetrabenzyl diphosphate (151 mg) and THF (5 mL), a 1.9 M solution of sodium bis(trimethylsilyl)amide in THF (0.26 mL) was added at 0° C. After stirring at 0° C. for 2 hours, a saturated aqueous solution of sodium carbonate was added to the reaction mixture at 0° C., followed by extraction with ethyl acetate. The organic layer was washed with saturated brine and then dried over anhydrous sodium sulfate, and the solvent was distilled off under reduced pressure. The residue was purified by silica gel column chromatography (ethyl acetate/hexane) to obtain the title compound (47.9 mg).

$^1$H NMR (300 MHz, CDCl$_3$) δ 1.79 (2H, brs), 2.13 (2H, brs), 3.31 (1H, brs), 3.67 (2H, brs), 3.84-4.01 (1H, m), 4.20-4.32 (2H, m), 4.37-4.57 (3H, m), 4.73 (1H, brs), 4.83-5.12 (4H, m), 6.15 (1H, brs), 6.86 (1H, s), 7.05-7.42 (13H, m), 7.51-8.22 (3H, m), 8.96 (2H, brs).

Example 55B

N-(cis-1'-(3,4-Dimethoxybenzoyl)-1,3'-bipiperidin-4'-yl)-2-(trifluoromethoxy)benzamide A) (cis-4-Azido-3-hydroxypiperidin-1-yl)(3,4-dimethoxyphenyl)methanone To a solution of tert-butyl 5,6-dihydropyridine-1(2H)-carboxylate (5.1 g) in toluene (50 mL), 70% m-CPBA (7.4 g) was added at room temperature, and the mixture was stirred at room temperature for 16 hours. The deposit was filtered off, and the solvent in the filtrate was distilled off under reduced pressure. An aqueous sodium thiosulfate solution was added to the residue, followed by extraction with ethyl acetate. The extract was washed with a saturated aqueous solution of sodium bicarbonate and saturated brine and then dried over anhydrous magnesium sulfate, and the solvent was distilled off under reduced pressure to obtain tert-butyl 7-oxa-3-azabicyclo[4.1.0]heptane-3-carboxylate (6.8 g).

To a solution of tert-butyl 7-oxa-3-azabicyclo[4.1.0]heptane-3-carboxylate (8.1 g) in DMF (80 mL), THF (60 mL) and water (20 mL), sodium azide (8.0 g) was added at room temperature, and the mixture was stirred at 90° C. for 3 hours in a nitrogen atmosphere. Water was added to the reaction mixture at room temperature, followed by extraction with ethyl acetate. The extract was washed with water and saturated brine and then dried over anhydrous magnesium sulfate, and the solvent was distilled off under reduced pressure. A 4 M solution of hydrogen chloride in ethyl acetate (50 mL) was added to the obtained residue at room temperature, and the mixture was stirred at room temperature for 20 minutes. The solvent was distilled off under reduced pressure. To a solution of the obtained residue, 3,4-dimethoxybenzoic acid (7.5 g), HOBt (8.1 g) and triethylamine (28 mL) in DMF (80 mL), WSC (7.1 mL) was added at room temperature, and the mixture was stirred for 16 hours. Water was added to the reaction mixture, followed by extraction with ethyl acetate/THF. The extract was washed with a saturated aqueous solution of potassium carbonate, water and saturated brine and then dried over anhydrous magnesium sulfate, and the solvent was distilled off under reduced pressure. The residue was purified by silica gel column chromatography (NH, ethyl acetate/hexane) to obtain the title compound (3.6 g).

MS: [M+H]$^+$ 307.0.

B) (cis-4-Azido-3-((tert-butyldimethylsilyl)oxy)piperidin-1-yl)(3,4-dimethoxyphenyl)methanone To a solution of (cis-4-azido-3-hydroxypiperidin-1l-yl)(3,4-dimethoxyphenyl)methanone (1.0 g) and imidazole (1.24 g) in DMF (10 mL), TBSCl (1.6 g) was added at room temperature, and the mixture was stirred for 2 hours. Water was added to the reaction mixture, followed by extraction with ethyl acetate. The extract was washed with water and saturated brine and then dried over anhydrous magnesium sulfate, and the solvent was distilled off under reduced pressure. The residue was purified by silica gel column chromatography (ethyl acetate/hexane) to obtain the title compound (1.3 g).

MS: [M+H]$^+$ 421.2.

C) tert-Butyl (cis-3-((tert-butyldimethylsilyl)oxy)-1-(3,4-dimethoxybenzoyl)piperidin-4-yl)carbamate A mixture of (cis-4-azido-3-((tert-butyldimethylsilyl)oxy)piperidin-1-yl)(3,4-dimethoxyphenyl)methanone (1.3 g), 10% palladium-carbon (0.76 g) and THF (20 mL) was stirred at room temperature for 16 hours in a hydrogen atmosphere (1 atm). The reaction mixture was filtered, and the solvent in the filtrate was distilled off under reduced pressure.

To a solution of the obtained residue and triethylamine (1.3 mL) in THF (20 mL), di-tert-butyl dicarbonate (0.84 mL) was added at room temperature, and the mixture was stirred for 10 minutes. Water was added to the reaction mixture, followed by extraction with ethyl acetate. The extract was washed with water and saturated brine and then dried over anhydrous magnesium sulfate, and the solvent was distilled off under reduced pressure. The residue was purified by silica gel column chromatography (NH, ethyl acetate/hexane) to obtain the title compound (1.3 g).

MS: [M+H]$^+$ 495.3.

D) tert-Butyl (cis-1-(3,4-dimethoxybenzoyl)-3-hydroxypiperidin-4-yl)carbamate

To a solution of tert-butyl (cis-3-((tert-butyldimethylsilyl)oxy)-1-(3,4-dimethoxybenzoyl)piperidin-4-yl)carbamate (1.3 g) in THF (20 mL), a 1.0 M solution of TBAF in THF (7.5 mL) was added at room temperature, and the mixture was stirred for 10 minutes. Water was added to the reaction mixture, followed by extraction with ethyl acetate. The extract was washed with water and saturated brine and then dried over anhydrous magnesium sulfate, and the solvent was distilled off under reduced pressure. The residue was purified by silica gel column chromatography (NH, methanol/ethyl acetate) to obtain the title compound (0.83 g).

MS: [M+H]$^+$ 381.2.

E) N-(cis-3-Azido-1-(3,4-dimethoxybenzoyl)piperidin-4-yl)-2-(trifluoromethoxy)benzamide To a solution of tert-butyl (cis-1-(3,4-dimethoxybenzoyl)-3-hydroxypiperidin-4-yl)carbamate (0.40 g) and triethylamine (0.44 mL) in THF (5 mL), methanesulfonyl chloride (0.12 mL) was added under ice cooling, and the mixture was stirred for 10 minutes. Water was added to the reaction mixture, followed by extraction with ethyl acetate. The extract was washed with water and saturated brine and then dried over anhydrous magnesium sulfate, and the solvent was distilled off under reduced pressure. To a solution of the residue in DMF (5 mL), sodium azide (0.16 g) and sodium acetate (0.18 g) were added at room temperature, and the mixture was stirred at 80° C. for 30 minutes, at 100° C. for 30 minutes and at 120° C. for 1 hour in a nitrogen atmosphere. Water was added to the reaction mixture at room temperature, followed by extraction with ethyl acetate. The extract was washed with water and saturated brine and then dried over anhydrous magnesium sulfate, and the solvent was distilled off under reduced pressure. A 4 M solution of hydrogen chloride in ethyl acetate (5.0 mL) was added to the obtained residue at room temperature, and the mixture was stirred at room temperature for 10 minutes. The solvent was distilled off under reduced pressure. To a solution of the residue in DMF (5.0 mL), 2-(trifluoromethoxy)benzoic acid (0.32 g), HOBt monohydrate (0.25 g), triethylamine (0.74 mL) and WSC (0.37 mL) were added at room temperature, and the mixture was stirred at room temperature for 16 hours. Water was added to the reaction mixture, followed by extraction with ethyl acetate. The extract was washed with water and saturated brine and then dried over anhydrous magnesium sulfate, and the solvent was distilled off under reduced pressure. The residue was purified by silica gel column chromatography (NH, ethyl acetate/hexane) to obtain the title compound (0.092 g).

MS: [M+H]$^+$ 494.1.

F) N-(cis-1'-(3,4-Dimethoxybenzoyl)-1,3'-bipiperidin-4'-yl)-2-(trifluoromethoxy)benzamide A mixture of N-(cis-3-azido-1-(3,4-dimethoxybenzoyl) piperidin-4-yl)-2-(trifluoromethoxy)benzamide (0.092 g), 10% palladium-carbon (0.092 g) and methanol (5.0 mL) was stirred at room temperature for 1 hour in a hydrogen atmosphere (1 atm). The reaction mixture was filtered, and the solvent in the filtrate was distilled off under reduced pressure. To a mixture of the obtained residue, glutaraldehyde (0.20 mL), DMF (3.0 mL) and acetic acid (1.0 mL), sodium triacetoxyborohydride (0.25 g) was added at room temperature, and the resulting mixture was stirred at room temperature for 30 minutes. An aqueous potassium carbonate solution was added to the reaction mixture, followed by extraction with ethyl acetate. The extract was back-extracted with 2 N hydrochloric acid and basified with an aqueous potassium carbonate solution, followed by extraction with ethyl acetate. The extract was washed with water and saturated brine and then dried over anhydrous magnesium sulfate, and the solvent was distilled off under reduced pressure. The residue was purified by silica gel column chromatography (NH, ethyl acetate/hexane) to obtain the title compound (0.020 g).

$^1$H NMR (300 MHz, DMSO-d$_6$) δ 1.22-1.59 (7H, m), 1.60-1.87 (2H, m), 2.28-2.50 (6H, m), 3.08-3.28 (1H, m), 3.35-3.70 (1H, m), 3.78 (3H, s), 3.79 (3H, s), 4.45-4.66 (1H, m), 6.89-7.04 (3H, m), 7.40-7.64 (4H, m), 8.46 (1H, d, J=8.1 Hz).

Example 59B

5-Chloro-N-((3S,4R)-1-((8-chloroquinoxalin-6-yl) carbonyl)-3-(4-fluorophenyl)piperidin-4-yl)-1,3-dimethyl-1H-pyrazole-4-carboxamide A) (3S,4R)-tert-Butyl 4-(5-chloro-1,3-dimethyl-1H-pyrazole-4-carboxamide)-3-(4-fluorophenyl)piperidine-1-carboxylate A solution of 5-chloro-1,3-dimethyl-1H-pyrazole-4-carboxylic acid (148 mg), HATU (420 mg) and N-ethyldiisopropylamine (0.3 mL) in DMF (3 mL) was stirred at room temperature for 15 minutes. 5-Chloro-N-((3S,4R)-3-(4-fluorophenyl)piperidin-4-yl)-1,3-dimethyl-1H-pyrazole-4-carboxamide (250 mg) was added to the reaction mixture at room temperature, and the mixture was stirred at room temperature for 16 hours. Water was added to the reaction mixture, followed by extraction with ethyl acetate. The extract was washed with water and saturated brine and then dried over anhydrous sodium sulfate, and the solvent was distilled off under reduced pressure. The residue was purified by silica gel column chromatography (ethyl acetate/hexane) to obtain the title compound (210 mg).

MS: [M+H–100]$^+$ 450.9.

B) 5-Chloro-N-((3S,4R)-3-(4-fluorophenyl)piperidin-4-yl)-1,3-dimethyl-1H-pyrazole-4-carboxamide To a solution of (3S,4R)-tert-butyl 4-(5-chloro-1,3-dimethyl-1H-pyrazole-4-carboxamide)-3-(4-fluorophenyl)piperidine-1-carboxylate (0.73 g) in dichloromethane (4 mL), TFA (1 mL) was added at room temperature, and the mixture was stirred at room temperature for 2 hours. The solvent was distilled off under reduced pressure. A saturated aqueous solution of sodium bicarbonate was added to the residue, followed by extraction with ethyl acetate. The extract was washed with water and saturated brine and then dried over anhydrous sodium sulfate, and the solvent was distilled off under reduced pressure to obtain a crude product of the title compound. This compound was used in the next step without purification.

MS: [M+H]$^+$ 350.9.

C) 5-Chloro-N-((3S,4R)-1-((8-chloroquinoxalin-6-yl)carbonyl)-3-(4-fluorophenyl)piperidin-4-yl)-1,3-dimethyl-1H-pyrazole-4-carboxamide A solution of 8-chloroquinoxaline-6-carboxylic acid (65.4 mg), HATU (163 mg) and N-ethyldiisopropylamine (0.13 mL) in DMF (2 mL) was stirred at room temperature for 15 minutes. 5-Chloro-N-((3S,4R)-3-(4-fluorophenyl)piperidin-4-yl)-1,3-dimethyl-1H-pyrazole-4-carboxamide (100 mg) was added to the reaction mixture at room temperature, and the mixture was stirred at room temperature for 16 hours. Water was added to the reaction mixture, followed by extraction with ethyl acetate. The extract was washed with water and saturated brine and then dried over anhydrous sodium sulfate, and the solvent was distilled off under reduced pressure. The residue was purified by silica gel column chromatography (ethyl acetate/hexane) to obtain the title compound (110 mg).

$^1$H NMR (400 MHz, DMSO-d$_6$) δ 1.70-2.21 (5H, m), 3.39-3.41 (1H, m), 3.50-3.68 (5H, m), 3.79-3.88 (1H, m), 4.15-4.40 (1H, m), 4.55 (1H, brs), 7.03-7.05 (1H, m), 7.11-7.22 (2H, m), 7.34 (1H, brs), 7.78-7.85 (1H, m), 7.98-8.02 (1H, m), 8.12 (1H, brs), 9.07-9.13 (2H, m).

Example 74B

N-((3S,4R)-1-((8-Methylquinoxalin-6-yl)carbonyl)-3-phenylpiperidin-4-yl)-3-(trifluoromethyl)pyridine-2-carboxamide A) Methyl 8-methylquinoxaline-6-carboxylate A mixture of methyl 8-chloroquinoxaline-6-carboxylate (199 mg), 2,4,6-trimethylboroxine (449 mg), a 2 M aqueous potassium carbonate solution (0.67 mL), 1,1'-bis(diphenylphosphino)ferrocene-palladium(II) dichloride-dichloromethane complex (62 mg) and DMF (20 mL) was stirred at 140° C. for 30 minutes under irradiation with microwave. Water was added to the reaction mixture, and the mixture was filtered through Celite. The filtrate was subjected to extraction with ethyl acetate. The extract was washed with water and saturated brine and then dried over anhydrous magnesium sulfate, and the solvent was distilled off under reduced pressure. The residue was purified by silica gel column chromatography (ethyl acetate/hexane) to obtain the title compound (89.3 mg).
$^1$H NMR (300 MHz, DMSO-d$_6$) δ 2.79 (3H, s), 3.96 (3H, s), 8.20 (1H, dd, J=1.7, 0.9 Hz), 8.49 (1H, d, J=1.5 Hz), 9.08 (1H, d, J=1.7 Hz), 9.09 (1H, d, J=1.9 Hz).

B) 8-Methylquinoxaline-6-carboxylic acid

To a solution of methyl 8-methylquinoxaline-6-carboxylate (89.3 mg) in methanol (1 mL) and THF (2 mL), a 1 M aqueous sodium hydroxide solution (2 mL) was added at room temperature, and the mixture was stirred at room temperature for 2 hours. To the reaction mixture, 1 M hydrochloric acid was added at room temperature, and the solvent was distilled off under reduced pressure. The residue was washed with water and dissolved in ethyl acetate and toluene. The solvent was distilled off under reduced pressure to obtain the title compound (46 mg).
$^1$H NMR (300 MHz, DMSO-d$_6$) δ 2.78 (3H, s), 8.18 (1H, d, J=0.8 Hz), 8.46 (1H, d, J=1.5 Hz), 9.05 (1H, d, J=1.8 Hz), 9.06 (1H, d, J=1.8 Hz), 13.43 (1H, brs).

C) N-((3S,4R)-1-((8-Methylquinoxalin-6-yl)carbonyl)-3-phenylpiperidin-4-yl)-3-(trifluoromethyl)pyridine-2-carboxamide To a solution of N-((3S,4R)-3-phenylpiperidin-4-yl)-3-(trifluoromethyl)pyridine-2-carboxamide hydrochloride (80 mg), 8-methylquinoxaline-6-carboxylic acid (39 mg), HOBt (42 mg) and triethylamine (0.04 mL) in DMF (5 mL), WSC (0.06 mL) was added at 0° C., and the mixture was stirred overnight at room temperature. The solvent was distilled off under reduced pressure, and the residue was diluted with water and ethyl acetate. The separated organic layer was washed with saturated brine and then dried over anhydrous sodium sulfate, and the solvent was distilled off under reduced pressure. The residue was purified by silica gel column chromatography (NH, ethyl acetate/hexane) to obtain the title compound (43.9 mg).
$^1$H NMR (300 MHz, DMSO-d$_6$) δ 1.64-2.12 (2H, m), 2.79 (1H, brs), 3.32 (3H, s), 3.36 (1H, brs), 3.42-3.67 (2H, m), 3.68-4.01 (1H, m), 4.20-4.52 (1H, m), 4.63 (1H, brs), 7.04-7.48 (5H, m), 7.60-7.80 (2H, m), 7.81-8.04 (1H, m), 8.24 (1H, d, J=7.5 Hz), 8.68-8.87 (1H, m), 9.00 (2H, d, J=18.8 Hz).

Example 81B

N-((3S,4R)-1-((8-Chloroquinoxalin-6-yl)carbonyl)-3-phenylpiperidin-4-yl)-1-methyl-3-(trifluoromethyl)-1H-pyrazole-5-carboxamide To a solution of 1-methyl-3-(trifluoromethyl)-1H-pyrazole-5-carboxylic acid (0.075 g), a 0.24 M solution of ((3S,4R)-4-amino-3-phenylpiperidin-1-yl)(8-chloroquinoxalin-6-yl)methanone in DMF (1.1 mL), HOBt (0.052 g) and triethylamine (0.11 mL) in DMF (1.0 mL), WSC (0.071 mL) was added at room temperature, and the mixture was stirred for 16 hours. Water was added to the reaction mixture, followed by extraction with ethyl acetate/THF. The extract was washed with a saturated aqueous solution of potassium carbonate, water and saturated brine and then dried over anhydrous magnesium sulfate, and the solvent was distilled off under reduced pressure. The residue was purified by silica gel column chromatography (NH, ethyl acetate/hexane) to obtain the title compound (0.10 g).
$^1$H NMR (300 MHz, DMSO-d$_6$) δ 1.57-2.12 (2H, m), 3.34-3.48 (1H, m), 3.51-3.83 (2H, m), 3.87 (3H, s), 3.91-4.10 (1H, m), 4.11-4.46 (1H, m), 4.48-4.76 (1H, m), 7.07-7.45 (6H, m), 8.03 (1H, d, J=9.6 Hz), 8.13 (1H, brs), 8.46 (1H, d, J=9.0 Hz), 8.99-9.19 (2H, m).

Example 97B

2-Chloro-N-(cis-1-(3,4-dimethoxybenzoyl)-3-(pyridin-3-yl)piperidin-4-yl)benzamide A) Ethyl 1-benzyl-5-[(trifluoromethane)sulfonyloxy]-1,2,3,6-tetrahydropyridine-4-carboxylate To a saturated aqueous solution of sodium bicarbonate (200 mL), ethyl 1-benzyl-3-oxopiperidine-4-carboxylate hydrochloride (25 g) was added, followed by extraction with ether (200 mL). This ether solution was added dropwise to a suspension solution of sodium hydride (60%, 6.68 g) in ether (100 mL) at 0° C., and the mixture was stirred at 0° C. for 30 minutes. Trifluoromethanesulfonic anhydride (17.7 mL) was added thereto at 0° C., and the mixture was stirred for 2 hours. A saturated aqueous solution of ammonium chloride was added to the reaction mixture at 0° C. The mixture was partitioned into the separated organic and aqueous layers. The organic layer was washed with saturated brine and then dried over anhydrous sodium sulfate, and the solvent was distilled off under reduced pressure to obtain the title compound (28 g).
$^1$H NMR (300 MHz, CDCl$_3$) δ 1.31 (3H, t, J=7.1 Hz), 2.57-2.59 (2H, m), 2.63-2.65 (2H, m), 3.18 (2H, s), 3.63 (2H, s), 4.24-2.43 (2H, m), 7.27-7.35 (5H, m).

B) Ethyl 1-benzyl-5-(pyridin-3-yl)-1,2,3,6-tetrahydropyridine-4-carboxylate

A solution of 1-benzyl-5-[(trifluoromethane)sulfonyloxy]-1,2,3,6-tetrahydropyridine-4-carboxylate (10 g), pyridine-3-boronic acid (3.2 g), potassium carbonate (7.02 g), tetrakis(triphenylphosphine)palladium (2.06 g) in DMF (20 mL) was stirred at 90° C. for 16 hours. The reaction mixture was filtered through Celite and washed with ethyl acetate. The solvent in the filtrate was distilled off under reduced pressure, and the residue was purified by silica gel column chromatography (ethyl acetate/hexane) to obtain the title compound (4.0 g).

$^1$H NMR (300 MHz, DMSO-$d_6$) δ 0.81 (3H, t, J=7.1 Hz), 2.45-2.50 (2H, m), 2.60-2.64 (2H, m), 3.22 (2H, m), 3.63 (2H, s), 3.85 (2H, q, J=7.0 Hz), 7.24-7.27 (2H, m), 7.31-7.40 (3H, m), 7.56-7.62 (4H, m).

C) cis-Ethyl 1-benzyl-5-(pyridin-3-yl)-1,2,3,6-tetrahydropyridine-4-carboxylate

A mixture of 1-benzyl-5-(pyridin-3-yl)-1,2,3,6-tetrahydropyridine-4-carboxylate (1.5 g), 10% palladium-carbon (200 mg), 10% palladium hydroxide-carbon (500 mg), acetic acid (0.5 mL) and ethanol (60 mL) was stirred at 65° C. for 48 hours in a 300 psi hydrogen atmosphere. The insoluble matter was filtered off, and the filtrate was concentrated under reduced pressure to obtain the title compound (800 mg).

MS: [M+H]$^+$ 235.2.

D) cis-Ethyl 1-[(3,4-dimethoxyphenyl)carbonyl]-3-(pyridin-3-yl)piperidine-4-carboxylate To a solution of (cis-1-benzyl-5-(pyridin-3-yl)-1,2,3,6-tetrahydropyridine-4-carboxylate (5.5 g) in dichloromethane (25 mL), N,N-diisopropylethylamine (12.83 mL) was added at 0° C., followed by the addition of a solution of 3,4-dimethoxybenzoyl chloride in dichloromethane (3 mL). After stirring at room temperature for 30 minutes, the mixture was diluted with dichloromethane, washed with a saturated aqueous solution of sodium bicarbonate and then dried over anhydrous sodium sulfate, and the solvent was distilled off under reduced pressure. The residue was purified by reverse-phase HPLC to obtain the title compound (1.6 g).

MS: [M+H]$^+$ 398.9.

E) 2-(Trimethylsilyl)ethyl N-[cis-1-[(3,4-dimethoxyphenyl)carbonyl]-3-(pyridin-3-yl)piperidin-4-yl]carbamate To a solution of cis-ethyl 1-[(3,4-dimethoxyphenyl)carbonyl]-3-(pyridin-3-yl)piperidine-4-carboxylate (200 mg) in methanol (5 mL) and THF (5 mL), a solution of lithium hydroxide (72 mg) in water (1 mL) was added at room temperature, and the mixture was stirred at room temperature for 16 hours. The solvent was distilled off under reduced pressure, and the residue was diluted with water. The liquid property of the solution was adjusted to near pH=4 by the addition of 4 M hydrochloric acid. After extraction with dichloromethane, the extract was washed with water and saturated brine and then dried over anhydrous sodium sulfate, and the solvent was distilled off under reduced pressure to obtain a solid. To a solution of the obtained solid (150 mg) in toluene (10 mL), DPPA (0.2 mL) and triethylamine (0.2 mL) were added at room temperature, and the mixture was stirred at 50° C. for 2 hours. Trimethylsilyl ethanol (0.75 mL) was added to the reaction mixture at room temperature, and the mixture was stirred at 100° C. for 6 hours. The solvent was distilled off under reduced pressure. The residue was purified by silica gel column chromatography (ethyl acetate/hexane) to obtain the title compound (100 mg).

MS: [M+H]$^+$ 486.4.

F) 2-Chloro-N-(cis-1-(3,4-dimethoxybenzoyl)-3-(pyridin-3-yl)piperidin-4-yl)benzamide To a solution of 2-(trimethylsilyl)ethyl N-[cis-1-[(3,4-dimethoxyphenyl)carbonyl]-3-(pyridin-3-yl)piperidin-4-yl] carbamate (130 mg) in THF (1 mL), a 1 M solution of TBAF in THF (2 mL) was added, and the mixture was heated to reflux for 2 hours. The reaction mixture was concentrated under reduced pressure, and the obtained residue was dissolved in dichloromethane (5 mL). To the solution, N,N-diisopropylethylamine (0.1 mL) was added at 0° C., followed by the addition of 2-chlorobenzoyl chloride (0.04 mL) at 0° C. After stirring at room temperature for 30 minutes, a saturated aqueous solution of sodium bicarbonate was added thereto, followed by extraction with dichloromethane. The extract was dried over anhydrous sodium sulfate, and the solvent was distilled off under reduced pressure. The residue was purified by silica gel column chromatography (ethyl acetate/hexane) to obtain the title compound (70 mg).

$^1$H NMR (400 MHz, DMSO-$d_6$) δ 1.66-1.68 (1H, m), 1.90-2.07 (2H, m), 3.18-3.37 (2H, m), 3.55-3.60 (1H, m), 3.78 (3H, s), 3.80 (3H, s), 3.81-4.64 (2H, m), 6.98-7.10 (3H, m), 7.26-7.49 (4H, m), 7.66-7.68 (2H, m), 7.73-8.50 (3H, m).

Example 117B

2-Chloro-N-(trans-1-(3,4-dimethoxybenzoyl)-3-(pyridin-3-yl)piperidin-4-yl)benzamide A) 2-(Trimethylsilyl)ethyl N-[trans-1-[(3,4-dimethoxyphenyl)carbonyl]-3-(pyridin-3-yl)piperidin-4-yl]carbamate To a solution of cis-ethyl 1-[(3,4-dimethoxyphenyl)carbonyl]-3-(pyridin-3-yl)piperidine-4-carboxylate (500 mg) in THF (10 mL), a 1 M solution of lithium diisopropylamide in THF (3.75 mL) was added dropwise at −78° C., and the mixture was stirred at −78° C. for 4 hours. Ethanol (10 mL) was added thereto at −78° C., and the mixture was stirred at room temperature for 10 minutes. The solvent was distilled off under reduced pressure to obtain a solid (420 mg), and 300 mg of the obtained solid was dissolved in ethanol (6 mL) and THF (6 mL). To the solution, a solution of lithium hydroxide (90 mg) in water (1 mL) was added at room temperature, and the mixture was stirred at room temperature for 6 hours. The solvent was distilled off under reduced pressure, and the residue was diluted with water. The liquid property of the solution was adjusted to near pH=5 by the addition of 4 M hydrochloric acid. After extraction with dichloromethane, the extract was washed with water and saturated brine and then dried over anhydrous sodium sulfate, and the solvent was distilled off under reduced pressure to obtain a solid. To a solution of the obtained solid (250 mg) in toluene (10 mL), DPPA (0.41 mL) and triethylamine (0.35 mL) were added at room temperature, and the mixture was stirred at 50° C. for 2 hours. Trimethylsilyl ethanol (0.75 mL) was added to the reaction mixture at room temperature, and the mixture was stirred at 100° C. for 6 hours. The solvent was distilled off under reduced pressure, and the residue was purified by silica gel column chromatography (ethyl acetate/hexane) to obtain the title compound (210 mg).

MS: [M+H]$^+$ 486.0.

B) 2-Chloro-N-(trans-1-(3,4-dimethoxybenzoyl)-3-(pyridin-3-yl)piperidin-4-yl)benzamide To a solution of 2-(trimethylsilyl)ethyl N-[trans-1-[(3,4-dimethoxyphenyl)carbonyl]-3-(pyridin-3-yl)piperidin-4-yl] carbamate (800 mg) in THF (1 mL), a 1 M solution of TBAF in THF (3 mL) was added, and the mixture was heated to reflux for 2 hours. The reaction mixture was concentrated under reduced pressure to obtain a residue (500 mg), and 70 mg of the obtained residue was dissolved in dichloromethane (5 mL). To the solution, N,N-diisopropylethylamine (0.11 mL) was added at 0° C., followed by the addition of 2-chlorobenzoyl chloride (40 mg) at 0° C. After stirring at room temperature for 30 minutes, a saturated aqueous solution of sodium bicarbonate was added thereto, followed by extraction with dichloromethane. The extract was dried over anhydrous sodium sulfate, and the solvent was distilled off under reduced pressure. The residue was purified by silica gel column chromatography (ethyl acetate/hexane) to obtain the title compound (22 mg).

$^1$H NMR (400 MHz, DMSO-d$_6$) δ 1.64-1.70 (1H, m), 1.79-1.84 (2H, m), 2.04-2.07 (1H, m), 3.18-3.24 (2H, m), 3.81 (6H, s), 4.41-4.43 (2H, m), 6.98-7.03 (4H, m), 7.27-7.35 (4H, m), 7.72-7.74 (1H, m), 7.99-8.01 (1H, m), 8.43-8.50 (2H, m).

Example 166B

5-Chloro-N-((3S,4R)-1-((8-chloroquinoxalin-6-yl)carbonyl)-3-phenylpiperidin-4-yl)-1,3-dimethyl-1H-pyrazole-4-carboxamide To a solution of 5-chloro-1,3-dimethyl-1H-pyrazole-4-carboxylic acid (0.012 g), ((3S,4R)-4-amino-3-phenylpiperidin-1-yl)(8-chloroquinoxalin-6-yl)methanone (0.022 g) and N-ethyldiisopropylamine (0.013 mL) in DMF (1.0 mL), HATU (0.027 g) was added at room temperature, and the mixture was stirred for 90 minutes. The reaction mixture was diluted with water (1 mL), followed by extraction with ethyl acetate (3 mL). Then, ethyl acetate (2 mL) was added to the aqueous layer, and the reaction mixture was subjected to extraction again. The extracts were combined and concentrated by blowing at 60° C. The residue was purified by preparative high-performance liquid chromatography (C18, mobile phase: acetonitrile/10 mM aqueous ammonium bicarbonate solution) to obtain the title compound (20.4 mg).

Example 170B

N-((3S,4R)-1-((8-Chloroquinoxalin-6-yl)carbonyl)-3-phenylpiperidin-4-yl)-3-ethoxy-1-methyl-1H-pyrazole-5-carboxamide To a solution of 3-ethoxy-1-methyl-1H-pyrazole-5-carboxylic acid (0.012 g), ((3S,4R)-4-amino-3-phenylpiperidin-1-yl) (8-chloroquinoxalin-6-yl)methanone (0.022 g) and N-ethyldiisopropylamine (0.013 mL) in DMF (1.0 mL), HATU (0.027 g) was added at room temperature, and the mixture was stirred for 90 minutes. The reaction mixture was diluted with water (1 mL), followed by extraction with ethyl acetate (3 mL). Then, ethyl acetate (2 mL) was added to the aqueous layer, and the reaction mixture was subjected to extraction again. The extracts were combined and concentrated by blowing at 60° C. The residue was purified by preparative high-performance liquid chromatography (C18, mobile phase: acetonitrile/10 mM aqueous ammonium bicarbonate solution) to obtain the title compound (23.1 mg).

Example 241B

N-((3S,4R)-1-((8-Chloroquinoxalin-6-yl)carbonyl)-3-phenylpiperidin-4-yl)-3-(trifluoromethyl)pyridine-2-carboxamide To a solution of 3-(trifluoromethoxy)picolinic acid (67.5 mg), ((3S,4R)-4-amino-3-phenylpiperidin-1-yl)(8-chloroquinoxalin-6-yl)methanone (99.0 mg), HOBt (51.8 mg) and triethylamine (0.113 mL) in DMF (1 mL), 1-[3-(dimethylamino)propyl]-3-ethylcarbodiimide (62.9 mg) was added at room temperature, and the mixture was stirred for 16 hours. Water was added to the reaction mixture, followed by extraction with ethyl acetate. The extract was washed with a saturated aqueous solution of potassium carbonate, water and saturated brine and then dried over anhydrous magnesium sulfate, and the solvent was distilled off under reduced pressure. The residue was purified by silica gel column chromatography (NH, ethyl acetate/hexane) to obtain the title compound (84 mg).

$^1$H NMR (300 MHz, DMSO-d$_6$) δ 1.60-2.12 (2H, m), 3.30-3.70 (3H, m), 3.71-4.12 (1H, m), 4.18-4.52 (1H, m), 4.53-4.72 (1H, m), 7.08-7.50 (5H, m), 7.61-7.77 (1H, m), 7.93-8.17 (2H, m), 8.24 (1H, d, J=8.9 Hz), 8.66-8.89 (2H, m), 9.00-9.21 (2H, m).

Example 242B

6-Chloro-N-((3S,4R)-1-((8-chloroquinoxalin-6-yl)carbonyl)-3-phenylpiperidin-4-yl)-4-(trifluoromethyl)nicotinamide To a solution of ((3S,4R)-4-amino-3-phenylpiperidin-1-yl)(8-chloroquinoxalin-6-yl)methanone (300 mg), 6-chloro-4-(trifluoromethyl)nicotinic acid (221 mg) and triethylamine (0.34 mL) in DMF (1.1 mL), HATU (373 mg) was added at room temperature, and the mixture was stirred at room temperature for 4 hours. A saturated aqueous solution of sodium bicarbonate was added to the reaction mixture, followed by extraction with ethyl acetate. The extract was washed with water and saturated brine and then dried over anhydrous sodium sulfate, and the solvent was distilled off under reduced pressure. The residue was purified by silica gel column chromatography (ethyl acetate/hexane) to obtain the title compound (284 mg).

$^1$H NMR (300 MHz, DMSO-d$_6$) δ 1.60-1.95 (1H, m), 2.01-2.13 (1H, m), 3.34-3.50 (2H, m), 3.53-3.98 (2H, m), 4.22-4.55 (1H, m), 4.56-4.67 (1H, m), 7.10-7.45 (5H, m), 7.98-8.17 (4H, m), 8.78-8.92 (1H, m), 9.02-9.19 (2H, m, J=18.8 Hz).

Example 245B

N-((3S,4R)-1-((8-Chloroquinoxalin-6-yl)carbonyl)-3-(4-fluorophenyl)piperidin-4-yl)-3-(trifluoromethyl)pyridine-2-carboxamide A) Ethyl 3-((3-ethoxy-3-oxopropyl)amino)-2-(4-fluorophenyl)propanoate To a solution of ethyl 2-(4-fluorophenyl)acetate (29 g) in DMF (120 mL), N,N-dimethylformamide dimethyl acetal (32 mL) was added at room temperature, and the mixture was stirred at 140° C. for 16 hours in a nitrogen atmosphere. β-Alanine ethyl ester hydrochloride (33 g) was added to the reaction mixture at room temperature, and the mixture was stirred at 80° C. for 2 hours. The solvent was distilled off under reduced pressure, and water was added thereto at room temperature, followed by extraction with ethyl acetate. The extract was washed with water and saturated brine and then dried over anhydrous magnesium sulfate, and the solvent was distilled off under reduced pressure. To a solution of the obtained residue in DMF (300 mL) and acetic acid (300 mL), sodium tetrahydroborate (36 g) was added gradually under ice cooling, and the mixture was stirred at room temperature for 1 hour. The reaction mixture was diluted with ethyl acetate (150 mL), and a 2 N aqueous sodium hydroxide solution (300 mL) was added slowly under ice cooling. Water (300 mL) was added to the reaction mixture, followed by extraction with ethyl acetate (100 mL, three times). The extract was washed with a saturated aqueous solution of potassium carbonate, water (100 mL, twice) and saturated brine (100 mL) and then dried over anhydrous magnesium sulfate, and the solvent was distilled off under reduced pressure. The residue was dissolved in ethyl acetate (500 mL), and oxalic acid (30 mL) was added thereto at room temperature, and the mixture was heated to reflux for 30 minutes. The deposit was collected by filtration and washed with ethyl acetate. The obtained solid was suspended in ethyl acetate and basified with an aqueous potassium carbonate solution, followed by extraction with ethyl acetate. The extract was washed with water and saturated brine and then dried over anhydrous magnesium sulfate, and the solvent was distilled off under reduced pressure to obtain the title compound (26 g).

MS: $[M+H]^+$ 312.1.

B) tert-Butyl 3-(4-fluorophenyl)-4-oxopiperidine-1-carboxylate

To a solution of ethyl 3-((3-ethoxy-3-oxopropyl)amino)-2-(4-fluorophenyl)propanoate (26 g) in THF (250 mL), 60% sodium hydride (60%, 11 g) was added under ice cooling, and the mixture was heated to reflux for 30 minutes in a nitrogen atmosphere. Water (250 mL) was added to the reaction mixture, followed by extraction with ethyl acetate (250 mL, 100 mL, three times). The extract was washed with saturated brine and then dried over anhydrous magnesium sulfate, and the solvent was distilled off under reduced pressure. A mixture of the obtained residue, concentrated hydrochloric acid (110 mL) and acetic acid (110 mL) was heated to reflux for 16 hours. The solvent was distilled off under reduced pressure.

To a solution of the obtained residue and triethylamine (35 mL) in THF (200 mL), di-tert-butyl dicarbonate (19 mL) was added at room temperature, and the mixture was stirred for 30 minutes. Water was added to the reaction mixture, followed by extraction with ethyl acetate. The extract was washed with water and saturated brine and then dried over anhydrous magnesium sulfate, and the solvent was distilled off under reduced pressure. The residue was purified by silica gel column chromatography (ethyl acetate/hexane) to obtain the title compound (15 g).

MS: $[M+H-Boc]^+$ 194.1.

C) (3S,4R)-tert-Butyl 3-(4-fluorophenyl)-4-(((R)-1-phenylethyl)amino)piperidine-1-carboxylate To a solution of tert-butyl 3-(4-fluorophenyl)-4-oxopiperidine-1-carboxylate (11 g) and (R)-1-phenylethanamine (6.1 mL) in toluene (120 mL), aluminum chloride (0.34 g) was added, and the mixture was heated to reflux for 16 hours in a nitrogen atmosphere. The solvent was distilled off under reduced pressure. A mixture of the obtained residue, a developed nickel catalyst (2.1 g) and ethanol (55 mL) was stirred at room temperature for 24 hours in a hydrogen atmosphere (0.5 MPa). The reaction mixture was filtered, and the solvent in the filtrate was distilled off under reduced pressure. The residue was suspended in toluene, and the solid was filtered off. The solvent in the filtrate was distilled off under reduced pressure, and the residue was purified by silica gel column chromatography (ethyl acetate/hexane) to obtain the title compound (2.4 g).

MS: $[M+H]^+$ 399.1.

D) (3S,4R)-tert-Butyl 4-amino-3-(4-fluorophenyl)piperidine-1-carboxylate

A mixture of (3S,4R)-tert-butyl 3-(4-fluorophenyl)-4-(((R)-1-phenylethyl)amino)piperidine-1-carboxylate (2.4 g), 10% palladium-carbon (1.1 g), methanol (30 mL) and acetic acid (3 mL) was stirred at room temperature for 6 hours in a hydrogen atmosphere (1 atm). The reaction mixture was filtered, and the solvent in the filtrate was distilled off under reduced pressure. The residue solid was collected by filtration and washed with hexane to obtain the title compound (0.95 g).

MS: $[M+H-100]^+$ 238.9.

E) (3S,4R)-tert-Butyl 3-(4-fluorophenyl)-4-(3-(trifluoromethyl)picolinamido)piperidine-1-carboxylate To a solution of 3-(trifluoromethyl)picolinic acid (0.41 g), (3S,4R)-tert-butyl 4-amino-3-(4-fluorophenyl)piperidine-1-carboxylate (0.53 g) and HOBt (0.37 g) in DMF (10 mL), WSC (0.47 mL) was added under ice cooling, and the mixture was stirred at room temperature for 3 hours. The solvent was distilled off under reduced pressure, and water was added to the reaction mixture, followed by extraction with ethyl acetate. The extract was washed with saturated brine and then dried over anhydrous sodium sulfate, and the solvent was distilled off under reduced pressure. The residue was purified by silica gel column chromatography (ethyl acetate/hexane) to obtain the title compound (0.74 g).

MS: $[M+H-100]^+$ 368.0.

F) N-((3S,4R)-1-((8-Chloroquinoxalin-6-yl)carbonyl)-3-(4-fluorophenyl)piperidin-4-yl)-3-(trifluoromethyl)pyridine-2-carboxamide To (3S,4R)-tert-butyl 3-(4-fluorophenyl)-4-(3-(trifluoromethyl)picolinamido)piperidine-1-carboxylate (0.73 g), a 4 M solution of hydrogen chloride in ethyl acetate (50 mL) was added under ice cooling, and the mixture was stirred at room temperature for 3 hours. The solvent was distilled off under reduced pressure to obtain N-((3S,4R)-3-(4-fluorophenyl)piperidin-4-yl)-3-(trifluoromethyl)picolinamide hydrochloride (0.64 g). To a solution of 8-chloroquinoxaline-6-carboxylic acid (0.063 g), N-((3S,4R)-3-(4-fluorophenyl)piperidin-4-yl)-3-(trifluoromethyl)picolinamide hydrochloride (0.10 g), HOBt (0.061 g) and triethylamine (0.17 mL) in DMF (1.0 mL), WSC (0.066 mL) was added at room temperature, and the mixture was stirred for 16 hours. Water was added to the reaction mixture, followed by extraction with ethyl acetate. The extract was washed with a saturated aqueous solution of potassium carbonate, water and saturated brine and then dried over anhydrous magnesium sulfate, and the solvent was distilled off under reduced pressure. The residue was purified by silica gel column chromatography (NH, ethyl acetate/hexane), and the obtained solid was washed with diisopropyl ether to obtain the title compound (0.079 g).

$^1$H NMR (300 MHz, DMSO-$d_6$) δ 1.58-2.16 (2H, m), 3.34-3.70 (3H, m), 3.72-4.00 (1H, m), 4.10-4.51 (1H, m), 4.54-4.66 (1H, m), 6.94-7.31 (3H, m), 7.32-7.51 (1H, m), 7.70 (1H, dd, J=7.3, 5.1 Hz), 8.01 (1H, d, J=11.5 Hz), 8.12 (1H, brs), 8.24 (1H, d, J=7.5 Hz), 8.74-8.89 (2H, m), 9.10 (2H, d, J=18.6 Hz).

Example 246B

3-Chloro-N-((3S,4R)-1-((8-chloroquinoxalin-6-yl)carbonyl)-3-phenylpiperidin-4-yl)pyridine-2-carboxamide To a solution of 3-chloropicolinic acid (62.4 mg), ((3S,4R)-4-amino-3-phenylpiperidin-1-yl)(8-chloroquinoxalin-6-yl)methanone (99.0 mg), HOBt (57 mg) and triethylamine (0.113 mL) in DMF (1 mL), 1-[3-(dimethylamino)propyl]-3-ethylcarbodiimide (62.9 mg) was added at room temperature, and the mixture was stirred for 16 hours. Water was added to the reaction mixture, followed by extraction with ethyl acetate. The extract was washed with a saturated aqueous solution of potassium carbonate, water and saturated brine and then dried over anhydrous magnesium sulfate, and the solvent was distilled off under reduced pressure. The residue was purified by silica gel column chromatography (NH, ethyl acetate/hexane) to obtain the title compound (82 mg).

$^1$H NMR (300 MHz, DMSO-d$_6$) δ 1.62-2.17 (2H, m), 3.33-3.69 (3H, m), 3.71-4.06 (1H, m), 4.14-4.54 (1H, m), 4.56-4.74 (1H, m), 7.07-7.42 (5H, m), 7.48 (1H, dd, J=8.2, 4.6 Hz), 7.95 (1H, dd, J=8.3, 1.3 Hz), 8.02 (1H, d, J=10.2 Hz), 8.13 (1H, brs), 8.46-8.54 (1H, m, J=4.6, 1.2 Hz), 8.65-8.83 (1H, m), 8.99-9.21 (2H, m).

Example 253B

N-(trans-1'-((5,6-Dimethoxypyridin-3-yl)carbonyl)-1,3'-bipiperidin-4'-yl)-2-(trifluoromethoxy)benzamide

A) trans-tert-Butyl 4-azido-3-hydroxypiperidine-1-carboxylate

A solution of a crude product of tert-butyl 7-oxa-3-azabicyclo[4.1.0]heptane-3-carboxylate (7.0 g), sodium azide (3.4 g) and ammonium chloride (2.8 g) in ethanol (80 mL) and water (80 mL) was stirred at 80° C. for 6 hours. Water was added to the reaction mixture at room temperature, followed by extraction with ethyl acetate. The extract was dried over anhydrous magnesium sulfate, and the solvent was distilled off under reduced pressure. The residue was purified by silica gel column chromatography (petroleum ether/ethyl acetate) to obtain the title compound (5.5 g).

MS: [M+H−100]$^+$143.1.

B) trans-tert-Butyl 3-hydroxy-4-(2-(trifluoromethoxy)benzamido)piperidine-1-carboxylate A mixture of trans-tert-butyl 4-azido-3-hydroxypiperidine-1-carboxylate (11 g), 10% palladium-carbon (1.1 g) and methanol (100 mL) was stirred at room temperature for 4 hours in a hydrogen atmosphere (1 atm). The reaction mixture was filtered, and the solvent in the filtrate was distilled off under reduced pressure. To a solution of the obtained residue, 2-(trifluoromethoxy)benzoic acid (9.0 g) and triethylamine (13 g) in DMF (50 mL), HATU (25 g) was added at room temperature, and the mixture was stirred for 12 hours. The solvent was distilled off under reduced pressure, and the residue was purified by silica gel column chromatography (petroleum ether/hexane) to obtain the title compound (14 g).

MS: [M+H−56]$^+$349.1.

C) N-(trans-1-(5,6-Dimethoxynicotinoyl)-3-hydroxypiperidin-4-yl)-2-(trifluoromethoxy)benzamide To trans-tert-butyl 3-hydroxy-4-(2-(trifluoromethoxy)benzamido)piperidine-1-carboxylate (14 g), a 4 M solution of hydrogen chloride in ethyl acetate (70 mL) was added at room temperature, and the mixture was stirred at room temperature for 6 hours. The solvent was distilled off under reduced pressure to obtain N-((3RS,4RS)-3-hydroxypiperidin-4-yl)-2-(trifluoromethoxy)benzamide hydrochloride. To a solution of the obtained N-(trans-3-hydroxypiperidin-4-yl)-2-(trifluoromethoxy)benzamide hydrochloride (6.0 g), 5,6-dimethoxynicotinic acid (3.3 g) and triethylamine (5.3 g) in DMF (30 mL), HATU (10 g) was added at room temperature, and the mixture was stirred for 12 hours. The solvent was distilled off under reduced pressure, and the residue was purified by reverse-phase HPLC to obtain the title compound (4.0 g).

MS: [M+H]$^+$ 470.2.

D) N-(trans-1'-((5,6-Dimethoxypyridin-3-yl)carbonyl)-1,3'-bipiperidin-4'-yl)-2-(trifluoromethoxy)benzamide A mixture of N-(trans-1-(5,6-dimethoxynicotinoyl)-3-hydroxypiperidin-4-yl)-2-(trifluoromethoxy)benzamide (0.94 g), methanesulfonyl chloride (0.69 g), triethylamine (0.61 g) and dichloromethane (10 mL) was stirred at room temperature for 1 hour. An aqueous sodium bicarbonate solution was added to the reaction mixture, followed by extraction with dichloromethane. The extract was dried over anhydrous sodium sulfate, and the solvent was distilled off under reduced pressure to obtain (3RS,4RS)-1-(5,6-dimethoxynicotinoyl)-4-(2-(trifluoromethoxy)benzamido)piperidin-3-yl methanesulfonate. To a solution of the obtained trans-1-(5,6-dimethoxynicotinoyl)-4-(2-(trifluoromethoxy)benzamido)piperidin-3-yl methanesulfonate (0.25 g) in acetonitrile (5.0 mL), piperidine (0.078 g) and cesium carbonate (0.30 g) were added at room temperature, and the mixture was stirred at room temperature for 14 hours. The solvent was distilled off under reduced pressure, and the residue was purified by preparative TLC to obtain the title compound (0.060 g).

$^1$H NMR (400 MHz, CDCl$_3$) δ 1.38-1.58 (7H, m), 2.43-2.55 (3H, m), 2.74-2.77 (5H, m), 3.91-4.90 (9H, m), 7.18 (2H, d, J=2.0 Hz), 7.32 (1H, d, J=8.4 Hz), 7.39-7.43 (1H, m), 7.50-7.54 (1H, m), 7.80 (1H, d, J=2.0 Hz), 7.98-8.00 (1H, m).

Example 255B

N-((3S,4R)-1-(5-Cyano-6-methoxynicotinoyl)-3-phenylpiperidin-4-yl)-2-(trifluoromethoxy)benzamide

A) (3S,4R)-tert-Butyl 3-phenyl-4-(2-(trifluoromethoxy)benzamido)piperidine-1-carboxylate To a solution of tert-butyl (3S,4R)-4-amino-3-phenylpiperidine-1-carboxylate (5.00 g) in pyridine (50 mL), 2-(trifluoromethoxy)benzoyl chloride (4.88 g) was added under ice cooling, and the mixture was stirred at room temperature for 2 hours. The solvent was distilled off under reduced pressure, and the residue was diluted with a saturated aqueous solution of sodium bicarbonate, followed by extraction with ethyl acetate. The extract was washed with saturated brine and then dried over anhydrous sodium sulfate, and the solvent was distilled off under reduced pressure. The residue was purified by silica gel column chromatography (NH, ethyl acetate/hexane) to obtain the title compound (1.80 g).

$^1$H NMR (300 MHz, CDCl$_3$) δ 1.45 (9H, brs), 1.85-2.03 (2H, m), 3.13-3.29 (1H, m), 3.30-3.69 (2H, m), 3.79-4.12 (2H, m), 4.52-4.72 (1H, m), 6.15-6.43 (1H, m), 7.26 (7H, s), 7.41-7.51 (1H, m), 7.79-7.87 (1H, m).

B) N-((3S,4R)-3-Phenylpiperidin-4-yl)-2-(trifluoromethoxy)benzamide hydrochloride To a solution of (3S,4R)-tert-butyl 3-phenyl-4-(2-(trifluoromethoxy)benzamido)piperidine-1-carboxylate (1.79 g) in methanol (3 mL), a 4 M solution of hydrogen chloride in cyclopentyl methyl ether (9.63 mL) was added at room temperature, and the mixture was stirred at room temperature for 2 hours. The solvent was distilled off under reduced pressure, and the residue was washed with diisopropyl ether to obtain the title compound (1.30 g).

MS: [M+H]$^+$ 365.0.

C) N-((3S,4R)-1-(5-Bromo-6-chloronicotinoyl)-3-phenylpiperidin-4-yl)-2-(trifluoromethoxy)benzamide To a solution of N-((3S,4R)-3-phenylpiperidin-4-yl)-2-(trifluoromethoxy)benzamide hydrochloride (267.2 mg), 5-bromo-6-chloronicotinic acid (173 mg) and triethylamine (0.278 ml) in dry DMF (3.0 ml), HATU (330 mg) was added at room temperature, and the mixture was stirred for 30 minutes. Water was added to the reaction mixture, and the resulting solid was collected by filtration and washed with water. The solid was further purified by silica gel column chromatography (ethyl acetate/hexane) and then crystallized from ethyl acetate/hexane to obtain the title compound (317 mg).

MS: [M+H]$^+$ 582.0

D) N-((3S,4R)-1-(5-Bromo-6-methoxynicotinoyl)-3-phenylpiperidin-4-yl)-2-(trifluoromethoxy)benzamide To a solution of methanol (0.017 ml) in dry THF (1.5 ml), sodium hydride (60%, 17.02 mg) was added at 0° C., and then, the mixture was stirred at 0° C. for 40 minutes. N-((3S,4R)-1-(5-Bromo-6-chloronicotinoyl)-3-phenylpiperidin-4-yl)-2-(trifluoromethoxy)benzamide (80 mg) was added to the reaction mixture, and then, the mixture was stirred at room temperature for 1 hour in a nitrogen atmosphere. A saturated aqueous solution of ammonium chloride was added to the reaction mixture at 0° C., followed by extraction with ethyl acetate. The extract was washed with saturated brine and then dried over anhydrous sodium sulfate, and the solvent was distilled off. The residue was crystallized from ethyl acetate/hexane to obtain the title compound (37.9 mg).

MS: [M+H]$^+$ 578.0

E) N-((3S,4R)-1-(5-Cyano-6-methoxynicotinoyl)-3-phenylpiperidin-4-yl)-2-(trifluoromethoxy)benzamide A mixture of N-((3S,4R)-1-(5-bromo-6-methoxynicotinoyl)-3-phenylpiperidin-4-yl)-2-(trifluoromethoxy)benzamide (69 mg), tris(dibenzylideneacetone)dipalladium), 2-dicyclohexylphosphino-2',6'-dimethoxy-1,1'-biphenyl (19.59 mg), zinc cyanide (28.0 mg), dry DMF (1.2 ml) and water (0.012 ml) was stirred at 120° C. for 20 minutes under irradiation with microwave. The reaction mixture was added to water at room temperature, followed by extraction with ethyl acetate. The extract was washed with saturated brine and then dried over anhydrous sodium sulfate, and the solvent was distilled off. The residue was purified by silica gel column chromatography (ethyl acetate/hexane) and then crystallized from ethyl acetate/diisopropyl ether to obtain the title compound (7.60 mg).

$^1$H NMR (300 MHz, DMSO) δ 1.54-1.89 (1H, m), 1.91-2.04 (1H, m), 3.17-3.39 (1H, m), 3.40-3.67 (2H, m), 3.69-3.93 (1H, m), 4.02 (3H, brs), 4.12-4.42 (1H, m), 4.53-4.63 (1H, m), 7.07-7.15 (1H, m), 7.17-7.44 (7H, m), 7.48-7.58 (1H, m), 8.22-8.66 (3H, m).

Example 412B

N-((3S,4R)-1-((8-Methoxyquinoxalin-6-yl)carbonyl)-3-phenylpiperidin-4-yl)-1-methyl-3-(trifluoromethyl)-1H-pyrazole-5-carboxamide A) tert-Butyl (3S,4R)-4-(((1-methyl-3-(trifluoromethyl)-1H-pyrazol-5-yl)carbonyl)amino)-3-phenylpiperidine-1-carboxylate To a solution of tert-butyl (3S,4R)-4-amino-3-phenylpiperidine-1-carboxylate (3.00 g), 1-methyl-3-(trifluoromethyl)-1H-pyrazole-5-carboxylic acid (2.53 g) and HOBt (2.20 g) in DMF (40 mL), WSC (2.86 mL) was added under ice cooling, and the mixture was stirred overnight at room temperature. The solvent was distilled off under reduced pressure, and water was added to the reaction mixture, followed by extraction with ethyl acetate. The extract was washed with saturated brine and then dried over anhydrous sodium sulfate, and the solvent was distilled off under reduced pressure. The residue was purified by silica gel column chromatography (ethyl acetate/hexane) to obtain the title compound (4.42 g).

$^1$H NMR (300 MHz, DMSO-d$_6$) δ 1.41 (9H, brs), 1.60-1.91 (2H, m), 3.14 (1H, d, J=3.6 Hz), 3.37-3.51 (1H, m), 3.58-3.87 (3H, m), 3.90 (3H, s), 4.49 (1H, brs), 6.80-7.47 (6H, m), 8.31 (1H, d, J=8.9 Hz).

B) N-((3S,4R)-3-Phenylpiperidin-4-yl)-1-methyl-3-(trifluoromethyl)-1H-pyrazole-5-carboxamide hydrochloride To tert-butyl (3S,4R)-4-(((1-methyl-3-(trifluoromethyl)-1H-pyrazol-5-yl)carbonyl)amino)-3-phenylpiperidine-1-carboxylate (4.42 g), a 4 M solution of hydrogen chloride in ethyl acetate (50 mL) was added under ice cooling, and the mixture was stirred at room temperature for 3 hours. The solvent was distilled off under reduced pressure to obtain the title compound (3.81 g).

$^1$H NMR (300 MHz, DMSO-d$_6$) δ 1.87 (1H, d, J=12.6 Hz), 2.23 (1H, ddd, J=14.1, 10.1, 4.1 Hz), 3.13-3.34 (3H, m), 3.45 (1H, dt, J=13.4, 3.9 Hz), 3.83 (3H, s), 4.05 (1H, t, J=13.0 Hz), 4.66 (1H, dd, J=9.7, 3.1 Hz), 7.08-7.34 (5H, m), 7.40 (1H, s), 8.75 (1H, d, J=9.8 Hz), 9.08 (1H, brs), 9.65 (1H, brs).

C) N-((3S,4R)-1-((8-Methoxyquinoxalin-6-yl)carbonyl)-3-phenylpiperidin-4-yl)-1-methyl-3-(trifluoromethyl)-1H-pyrazole-5-carboxamide To a solution of N-((3S,4R)-3-phenylpiperidin-4-yl)-1-methyl-3-(trifluoromethyl)-1H-pyrazole-5-carboxamide hydrochloride (200 mg), 8-methoxyquinoxaline-6-carboxylic acid (105 mg), HOBt (104 mg) and triethylamine (0.11 mL) in DMF (5 mL), WSC (0.14 mL) was added at room temperature, and the mixture was stirred overnight at room temperature. The reaction mixture was diluted with water and ethyl acetate. The separated organic layer was washed with saturated brine and then dried over anhydrous sodium sulfate, and the solvent was distilled off under reduced pressure. The residue was purified by silica gel column chromatography (methanol/ethyl acetate) to obtain the title compound (231.9 mg).

$^1$H NMR (300 MHz, DMSO-d$_6$) δ 1.63-2.11 (2H, m), 3.35-3.45 (1H, m), 3.49-3.78 (2H, m), 3.88 (3H, s), 3.92-4.12 (4H, m), 4.13-4.50 (1H, m), 4.62 (1H, brs), 7.02-7.43 (7H, m), 7.49-7.72 (1H, m), 8.45 (1H, d, J=8.7 Hz), 8.95 (2H, t, J=19.4 Hz).

Compounds of Examples 4A to 10A, 12A to 16A, 19A to 29A, 31A to 35A, 37A to 40A, 43A to 53A, 55A to 73A, 76A to 92A, 95A, 97A to 112A, 114A to 116A, 119A to 125A, 127A to 131A, 134A to 142A, 144A to 147A, 149A to 152A, 154A, 156A to 159A, 161A, 163A, 164A, 166A to 169A, 173A to 177A, 179A to 186A, 188A, 191A, 195A, 197A to 200A, 202A, 203A, 205A to 216A, 218A, 1B to 3B, 5B to 22B, 25B to 30B, 32B to 41B, 43B, 44B, 46B, 49B to 54B, 56B to 58B, 60B to 73B, 75B to 80B, 82B to 96B, 98B to 116B, 118B to 165B, 167B to 169B, 171B to 210B, 213B, 214B, 216B to 219B, 221B to 240B, 243B, 244B, 247B to 252B, 254B, 256B to 411B, and 413B to 462B in tables below were produced according to the methods described in the above Examples or methods equivalent thereto. The compounds of Examples are shown in tables below. In the tables, MS is indicated by actually measured values.

TABLE 1

| Ex. No. | IUPAC Name | Structure | Salt | MS |
| --- | --- | --- | --- | --- |
| 1A | 2-chloro-N-(4-(3,4-dimethoxybenzoyl)-2-methyl-4,5,6,7-tetrahydro-2H-pyrazolo[4,3-b]pyridin-7-yl)benzamide | 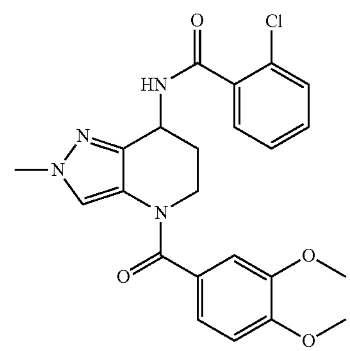 | | 455.1 |
| 2A | 2-chloro-N-(4-(3,4-dimethoxybenzoyl)-1-methyl-4,5,6,7-tetrahydro-1H-pyrazolo[4,3-b]pyridin-7-yl)benzamide | 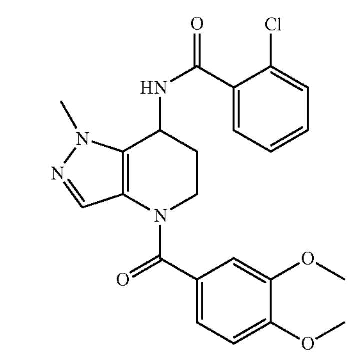 [SMILES: COc1ccc(C(=O)N2CCC(NC(=O)c3ccccc3Cl)c3c2cnn3C)cc1OC] | | 455.1 |
| 3A | 2-chloro-N-(7-(3,4-dimethoxybenzoyl)-2-methyl-4,5,6,7-tetrahydro-2H-pyrazolo[3,4-b]pyridin-4-yl)benzamide | 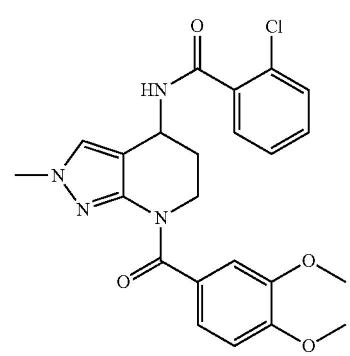 | | 455.0 |

TABLE 1-continued

| Ex. No. | IUPAC Name | Structure | Salt | MS |
|---|---|---|---|---|
| 4A | 2-chloro-N-(4-((1,3-dimethyl-1H-pyrazol-5-yl)carbonyl)-1-methyl-4,5,6,7-tetrahydro-1H-pyrazolo[4,3-b]pyridin-7-yl)benzamide | 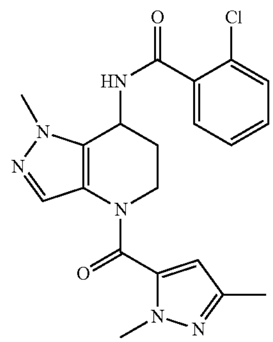 [SMILES: Cc1cc(C(=O)N2CCC(NC(=O)c3ccccc3Cl)c3c2cnn3C)n(C)n1] | | 413.1 |
| 5A | 2-chloro-N-(4-((6-chloropyridin-3-yl)carbonyl)-1-methyl-4,5,6,7-tetrahydro-1H-pyrazolo[4,3-b]pyridin-7-yl)benzamide | 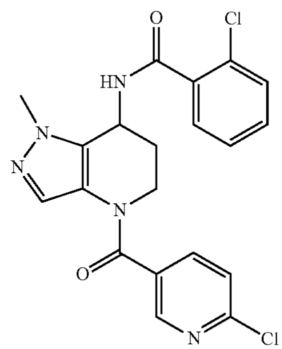 [SMILES: Cn1ncc2c1C(NC(=O)c1ccccc1Cl)CCN2C(=O)c1ccc(Cl)nc1] | | 430.0 |
| 6A | 2-chloro-N-(1-methyl-4-((6-(trifluoromethyl)pyridin-3-yl)carbonyl)-4,5,6,7-tetrahydro-1H-pyrazolo[4,3-b]pyridin-7-yl)benzamide | 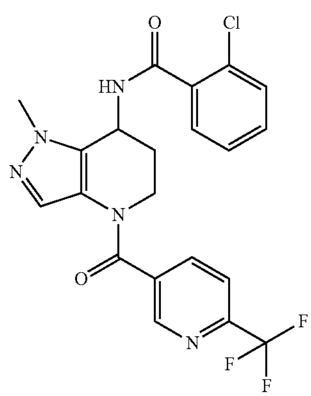 [SMILES: Cn1ncc2c1C(NC(=O)c1ccccc1Cl)CCN2C(=O)c1ccc(C(F)(F)F)nc1] | | 464.1 |
| 7A | N-(4-(1-benzothiophen-5-ylcarbonyl)-1-methyl-4,5,6,7-tetrahydro-1H-pyrazolo[4,3-b]pyridin-7-yl)-2-chlorobenzamide | 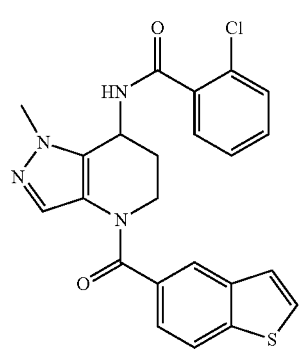 [SMILES: Cn1ncc2c1C(NC(=O)c1ccccc1Cl)CCN2C(=O)c1ccc2sccc2c1] | | 451.0 |

TABLE 1-continued

| Ex. No. | IUPAC Name | Structure | Salt | MS |
|---|---|---|---|---|
| 8A | 2-chloro-N-(4-(4-(dimethylamino)benzoyl)-1-methyl-4,5,6,7-tetrahydro-1H-pyrazolo[4,3-b]pyridin-7-yl)benzamide | 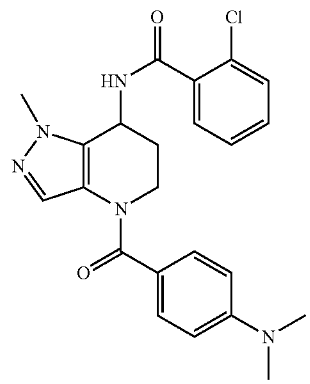 [SMILES: CN(C)c1ccc(C(=O)N2CCC(NC(=O)c3ccccc3Cl)c3c2cnn3C)cc1] | | 438.1 |
| 9A | 2-chloro-N-(1-methyl-4-(4-(5-methyl-1,2,4-oxadiazol-3-yl)benzoyl)-4,5,6,7-tetrahydro-1H-pyrazolo[4,3-b]pyridin-7-yl)benzamide | 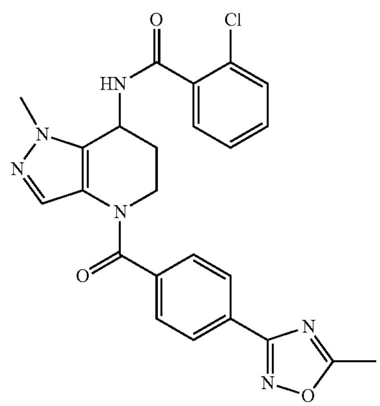 [SMILES: Cc1nc(-c2ccc(C(=O)N3CCC(NC(=O)c4ccccc4Cl)c4c3cnn4C)cc2)no1] | | 477.7 |
| 10A | 2-chloro-N-(4-((6-methoxypyridin-3-yl)carbonyl)-1-methyl-4,5,6,7-tetrahydro-1H-pyrazolo[4,3-b]pyridin-7-yl)benzamide | 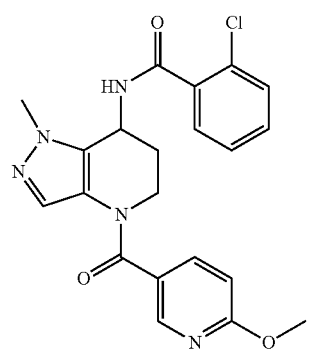 [SMILES: COc1ccc(C(=O)N2CCC(NC(=O)c3ccccc3Cl)c3c2cnn3C)cn1] | | 426.1 |
| 12A | 2-chloro-N-(4-(3,4-dimethoxybenzoyl)-2-(4-methoxybenzyl)-4,5,6,7-tetrahydro-2H-pyrazolo[4,3-b]pyridin-7-yl)benzamide | 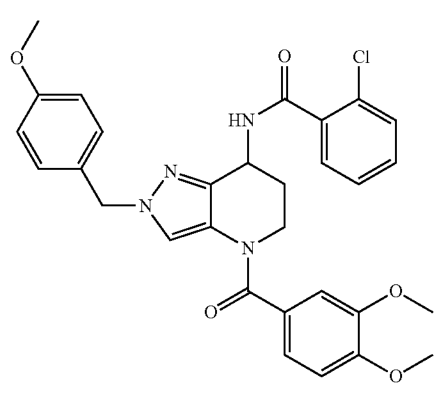 [SMILES: COc1ccc(Cn2cc3c(n2)C(NC(=O)c2ccccc2Cl)CCN3C(=O)c2ccc(OC)c(OC)c2)cc1] | | 561.2 |

TABLE 1-continued

| Ex. No. | IUPAC Name | Structure | Salt | MS |
|---|---|---|---|---|
| 13A | 2-chloro-N-(4-(3,4-dimethoxybenzoyl)-4,5,6,7-tetrahydro-2H-pyrazolo[4,3-b]pyridin-7-yl)benzamide | 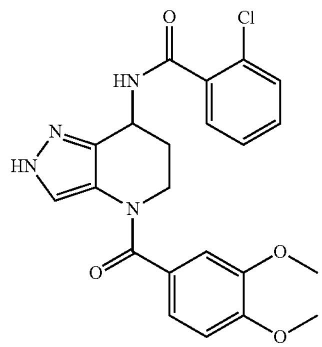 [SMILES: COc1ccc(C(=O)N2CCC(NC(=O)c3ccccc3Cl)c3n[nH]cc32)cc1OC] | | 441.1 |
| 14A | 2-chloro-N-(2-(cyclopropylmethyl)-4-(3,4-dimethoxybenzoyl)-4,5,6,7-tetrahydro-2H-pyrazolo[4,3-b]pyridin-7-yl)benzamide | 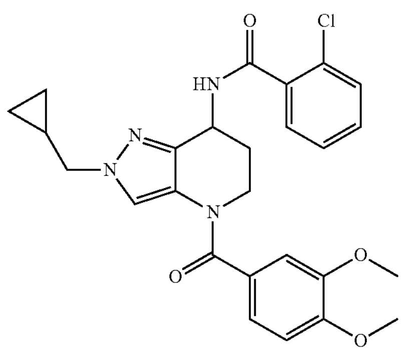 [SMILES: COc1ccc(C(=O)N2CCC(NC(=O)c3ccccc3Cl)c3nn(CC4CC4)cc32)cc1OC] | | 495.1 |
| 15A | 2-chloro-N-(2-methyl-4-(quinoxalin-6-ylcarbonyl)-4,5,6,7-tetrahydro-2H-pyrazolo[4,3-b]pyridin-7-yl)benzamide | 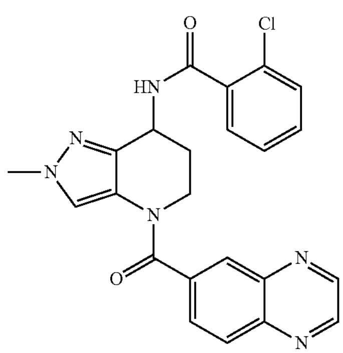 [SMILES: Cn1cc2c(n1)C(NC(=O)c1ccccc1Cl)CCN2C(=O)c1ccc2nccnc2c1] | | 447.1 |
| 16A | 2-chloro-N-(4-(3,5-diisopropoxybenzoyl)-2-methyl-4,5,6,7-tetrahydro-2H-pyrazolo[4,3-b]pyridin-7-yl)benzamide | 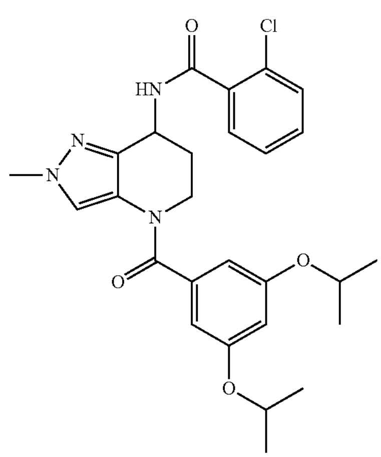 [SMILES: CC(C)Oc1cc(OC(C)C)cc(C(=O)N2CCC(NC(=O)c3ccccc3Cl)c3nn(C)cc32)c1] | | 511.2 |

TABLE 1-continued

| Ex. No. | IUPAC Name | Structure | Salt | MS |
|---|---|---|---|---|
| 17A | 2-chloro-N-(4-(3,4-dimethoxybenzoyl)-3-methyl-4,5,6,7-tetrahydro[1,2]oxazolo[4,3-b]pyridin-7-yl)benzamide | 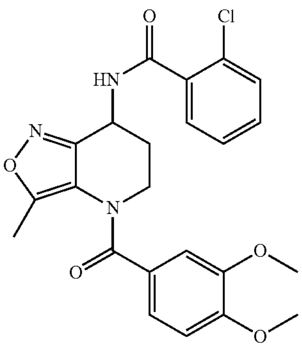 [SMILES: COc1ccc(C(=O)N2CCC(NC(=O)c3ccccc3Cl)c3noc(C)c32)cc1OC] | | 456.1 |
| 18A | 2-chloro-N-(4-(3,4-dimethoxybenzoyl)-1-((3-methyloxetan-3-yl)methyl)-4,5,6,7-tetrahydro-1H-pyrazolo[4,3-b]pyridin-7-yl)benzamide | 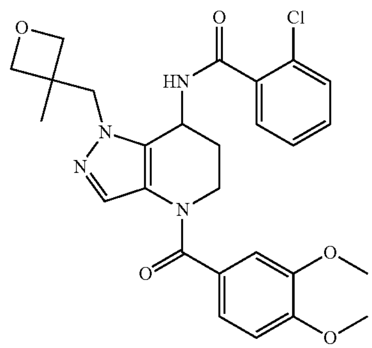 [SMILES: COc1ccc(C(=O)N2CCC(NC(=O)c3ccccc3Cl)c3c2cnn3CC2(C)COC2)cc1OC] | | 525.2 |
| 19A | 2-chloro-N-(4-(3,4-dimethoxybenzoyl)-2-((3-methyloxetan-3-yl)methyl)-4,5,6,7-tetrahydro-2H-pyrazolo[4,3-b]pyridin-7-yl)benzamide | 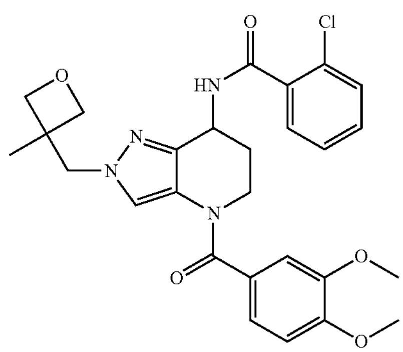 | | 525.2 |
| 20A | 2-chloro-N-(4-(3,4-dimethoxybenzoyl)-2-(2,2-dimethylpropyl)-4,5,6,7-tetrahydro-2H-pyrazolo[4,3-b]pyridin-7-yl)benzamide | 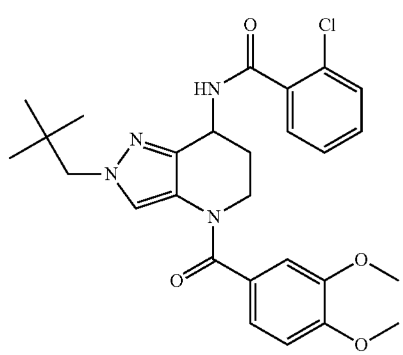 [SMILES: COc1ccc(C(=O)N2CCC(NC(=O)c3ccccc3Cl)c3nn(CC(C)(C)C)cc32)cc1OC] | | 511.2 |

TABLE 1-continued

| Ex. No. | IUPAC Name | Structure | Salt | MS |
|---|---|---|---|---|
| 21A | 2-chloro-N-(4-(3,4-dimethoxybenzoyl)-2-(tetrahydro-2H-pyran-4-yl)-4,5,6,7-tetrahydro-2H-pyrazolo[4,3-b]pyridin-7-yl)benzamide | 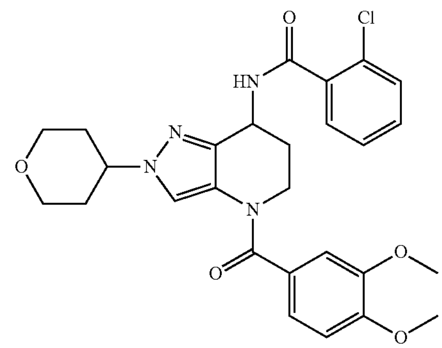 [SMILES: COc1ccc(C(=O)N2CCC(NC(=O)c3ccccc3Cl)c3nn(C4CCOCC4)cc32)cc1OC] | | 525.2 |
| 22A | 2-chloro-N-(4-(3,5-dimethoxybenzoyl)-2-methyl-4,5,6,7-tetrahydro-2H-pyrazolo[4,3-b]pyridin-7-yl)benzamide | 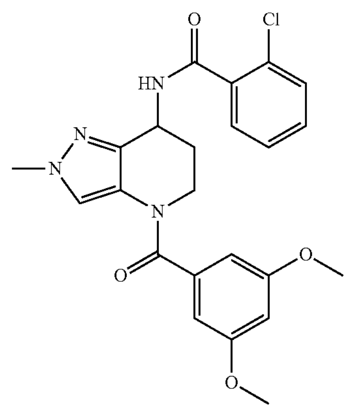 | | 455.1 |
| 23A | 2-chloro-N-(4-(3,4-diethoxybenzoyl)-2-methyl-4,5,6,7-tetrahydro-2H-pyrazolo[4,3-b]pyridin-7-yl)benzamide | 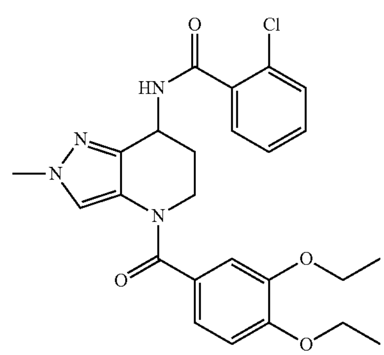 [SMILES: CCOc1ccc(C(=O)N2CCC(NC(=O)c3ccccc3Cl)c3nn(C)cc32)cc1OCC] | | 483.1 |
| 24A | N-(4-(3,4-dimethoxybenzoyl)-2-(4-methoxybenzyl)-4,5,6,7-tetrahydro-2H-pyrazolo[4,3-b]pyridin-7-yl)-2-methylbenzamide | 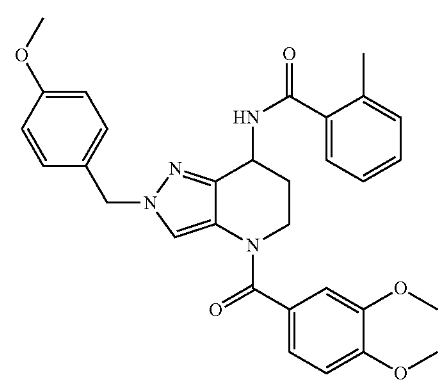 [SMILES: COc1ccc(Cn2cc3c(n2)C(NC(=O)c2ccccc2C)CCN3C(=O)c2ccc(OC)c(OC)c2)cc1] | | 541.3 |

TABLE 1-continued

| Ex. No. | IUPAC Name | Structure | Salt | MS |
|---|---|---|---|---|
| 25A | 2-chloro-N-(4-((2,6-dimethoxypyridin-3-yl)carbonyl)-2-methyl-4,5,6,7-tetrahydro-2H-pyrazolo[4,3-b]pyridin-7-yl)benzamide | 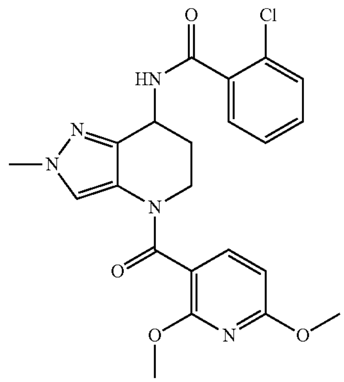 | | 456.1 |
| 26A | N-(4-(3,4-dimethoxybenzoyl)-4,5,6,7-tetrahydro-2H-pyrazolo[4,3-b]pyridin-7-yl)-2-methylbenzamide | 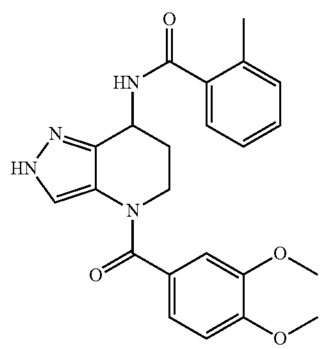 [SMILES: COc1ccc(C(=O)N2CCC(NC(=O)c3ccccc3C)c3n[nH]cc32)cc1OC] | | 421.2 |
| 27A | N-(4-(3,4-dimethoxybenzoyl)-2-ethyl-4,5,6,7-tetrahydro-2H-pyrazolo[4,3-b]pyridin-7-yl)-2-methylbenzamide | 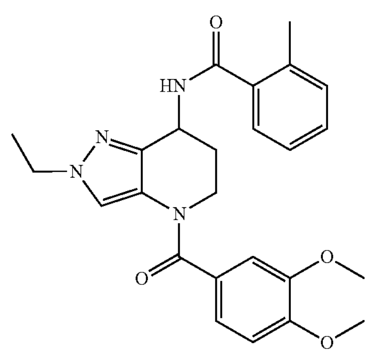 [SMILES: CCn1cc2c(n1)C(NC(=O)c1ccccc1C)CCN2C(=O)c1ccc(OC)c(OC)c1] | | 449.2 |
| 28A | N-(4-(3,4-dimethoxybenzoyl)-2-propyl-4,5,6,7-tetrahydro-2H-pyrazolo[4,3-b]pyridin-7-yl)-2-methylbenzamide | 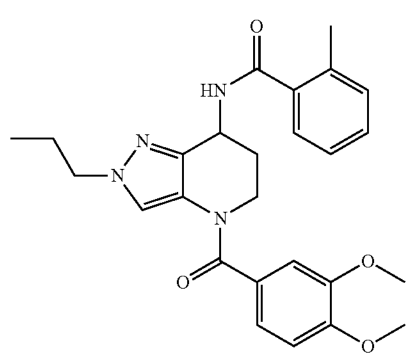 [SMILES: CCCn1cc2c(n1)C(NC(=O)c1ccccc1C)CCN2C(=O)c1ccc(OC)c(OC)c1] | | 463.2 |

TABLE 1-continued

| Ex. No. | IUPAC Name | Structure | Salt | MS |
|---|---|---|---|---|
| 29A | N-(4-(3,4-dimethoxybenzoyl)-2-isopropyl-4,5,6,7-tetrahydro-2H-pyrazolo[4,3-b]pyridin-7-yl)-2-methylbenzamide | 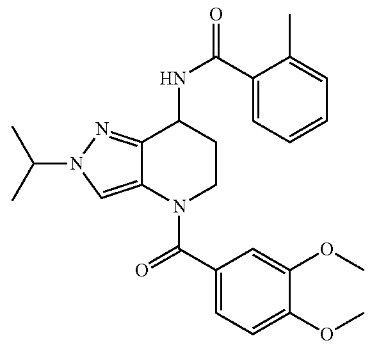 [SMILES: COc1ccc(C(=O)N2CCC(NC(=O)c3ccccc3C)c3nn(C(C)C)cc32)cc1OC] | | 463.2 |
| 30A | 2-chloro-N-(4-(3,4-dimethoxybenzoyl)-4,5,6,7-tetrahydro[1,2]thiazolo[4,3-b]pyridin-7-yl)benzamide | 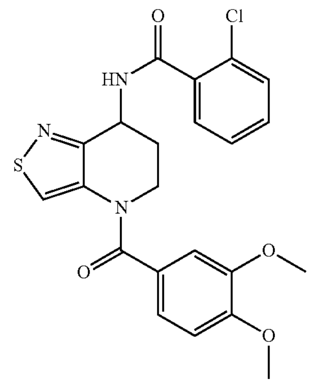 [SMILES: COc1ccc(C(=O)N2CCC(NC(=O)c3ccccc3Cl)c3nscc32)cc1OC] | | 458.1 |
| 31A | N-(4-(3,4-dimethoxybenzoyl)-2-(2-methoxyethyl)-4,5,6,7-tetrahydro-2H-pyrazolo[4,3-b]pyridin-7-yl)-2-methylbenzamide | 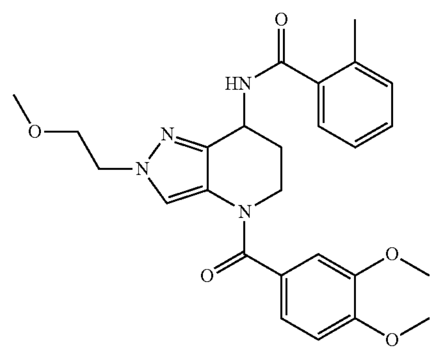 | | 479.2 |
| 32A | N-(2-(2-amino-2-oxoethyl)-4-(3,4-dimethoxybenzoyl)-4,5,6,7-tetrahydro-2H-pyrazolo[4,3-b]pyridin-7-yl)-2-methylbenzamide | 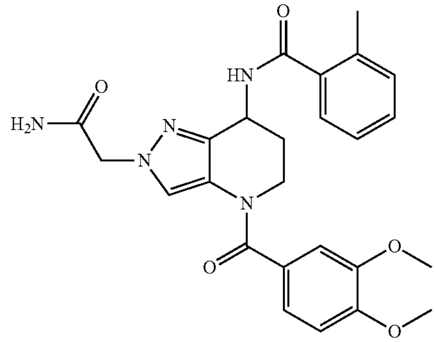 [SMILES: COc1ccc(C(=O)N2CCC(NC(=O)c3ccccc3C)c3nn(CC(N)=O)cc32)cc1OC] | | 478.2 |

TABLE 1-continued

| Ex. No. | IUPAC Name | Structure | Salt | MS |
|---|---|---|---|---|
| 33A | 2-chloro-N-(4-(3,4-dichlorobenzoyl)-1-methyl-4,5,6,7-tetrahydro-1H-pyrazolo[4,3-b]pyridin-7-yl)benzamide | 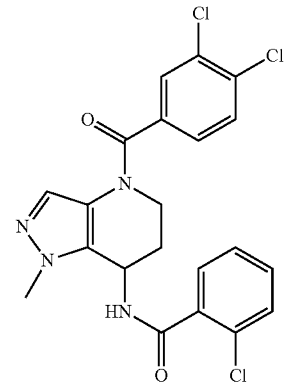 [SMILES: Cn1ncc2c1C(NC(=O)c1ccccc1Cl)CCN2C(=O)c1ccc(Cl)c(Cl)c1] | | 463.0 |
| 34A | 2-chloro-N-(4-(3-chloro-4-methoxybenzoyl)-1-methyl-4,5,6,7-tetrahydro-1H-pyrazolo[4,3-b]pyridin-7-yl)benzamide | 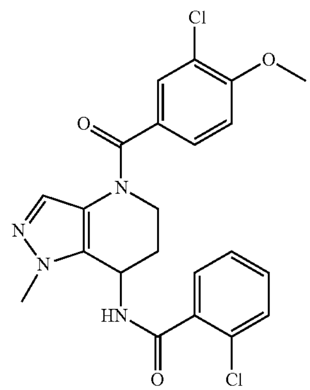 [SMILES: COc1ccc(C(=O)N2CCC(NC(=O)c3ccccc3Cl)c3c2cnn3C)cc1Cl] | | 459.1 |
| 35A | 2-chloro-N-(4-(4-chloro-3-methoxybenzoyl)-1-methyl-4,5,6,7-tetrahydro-1H-pyrazolo[4,3-b]pyridin-7-yl)benzamide | 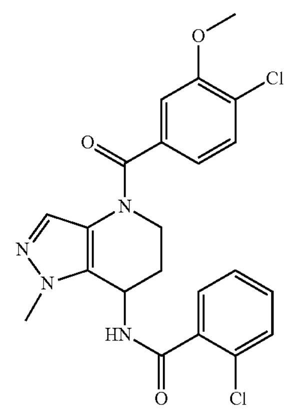 [SMILES: COc1cc(C(=O)N2CCC(NC(=O)c3ccccc3Cl)c3c2cnn3C)ccc1Cl] | | 459.1 |
| 36A | 2-chloro-N-(4-(3,4-dimethoxybenzoyl)-1-isopropyl-4,5,6,7-tetrahydro-1H-pyrazolo[4,3-b]pyridin-7-yl)benzamide | 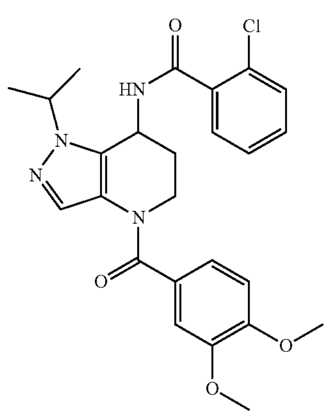 | | 483.1 |

TABLE 1-continued

| Ex. No. | IUPAC Name | Structure | Salt | MS |
|---------|-----------|-----------|------|-----|
| 37A | 2-chloro-N-(4-(3,5-dimethoxybenzoyl)-1-methyl-4,5,6,7-tetrahydro-1H-pyrazolo[4,3-b]pyridin-7-yl)benzamide | 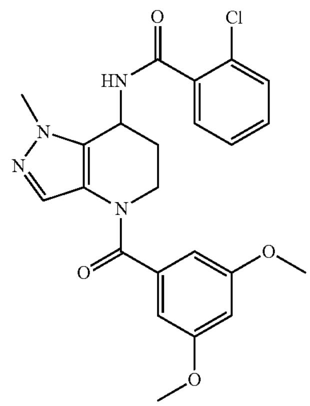 [SMILES: COc1cc(OC)cc(C(=O)N2CCC(NC(=O)c3ccccc3Cl)c3c2cnn3C)c1] | | 455.1 |
| 38A | 2-chloro-N-(4-(3,5-difluorobenzoyl)-1-methyl-4,5,6,7-tetrahydro-1H-pyrazolo[4,3-b]pyridin-7-yl)benzamide | 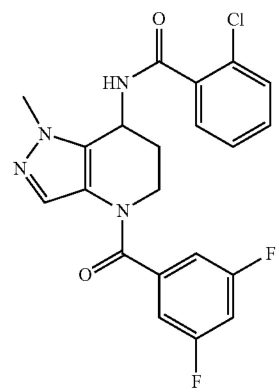 [SMILES: Cn1ncc2c1C(NC(=O)c1ccccc1Cl)CCN2C(=O)c1cc(F)cc(F)c1] | | 431.0 |
| 39A | 2-chloro-N-(4-(3,4-difluorobenzoyl)-1-methyl-4,5,6,7-tetrahydro-1H-pyrazolo[4,3-b]pyridin-7-yl)benzamide | 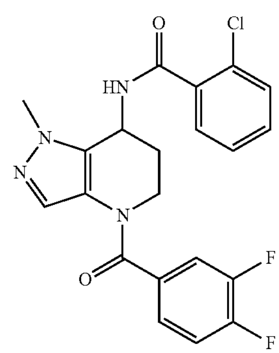 [SMILES: Cn1ncc2c1C(NC(=O)c1ccccc1Cl)CCN2C(=O)c1ccc(F)c(F)c1] | | 431.0 |
| 40A | 2-chloro-N-(1-methyl-4-(pyridazin-4-ylcarbonyl)-4,5,6,7-tetrahydro-1H-pyrazolo[4,3-b]pyridin-7-yl)benzamide | 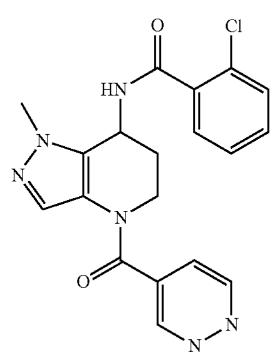 [SMILES: Cn1ncc2c1C(NC(=O)c1ccccc1Cl)CCN2C(=O)C1=CNNC=C1] | | 397.1 |

TABLE 1-continued

| Ex. No. | IUPAC Name | Structure | Salt | MS |
|---|---|---|---|---|
| 43A | N-(4-(1,3-benzothiazol-5-ylcarbonyl)-1-methyl-4,5,6,7-tetrahydro-1H-pyrazolo[4,3-b]pyridin-7-yl)-2-chlorobenzamide | 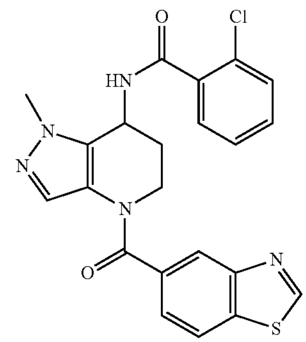 [SMILES: Cn1ncc2c1C(NC(=O)c1ccccc1Cl)CCN2C(=O)c1ccc2scnc2c1] | | 452.0 |
| 44A | 2-chloro-N-(4-(4-cyanobenzoyl)-1-methyl-4,5,6,7-tetrahydro-1H-pyrazolo[4,3-b]pyridin-7-yl)benzamide | 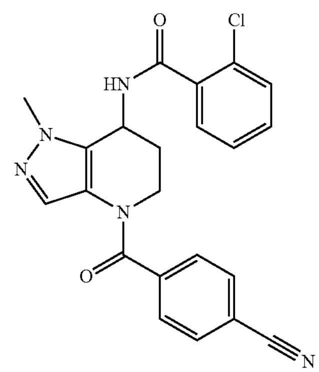 [SMILES: Cn1ncc2c1C(NC(=O)c1ccccc1Cl)CCN2C(=O)c1ccc(C#N)cc1] | | 420.1 |
| 45A | 2-chloro-N-(4-(3-cyanobenzoyl)-1-methyl-4,5,6,7-tetrahydro-1H-pyrazolo[4,3-b]pyridin-7-yl)benzamide | 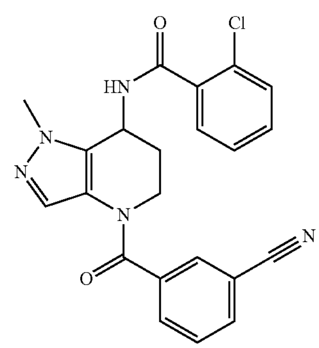 [SMILES: Cn1ncc2c1C(NC(=O)c1ccccc1Cl)CCN2C(=O)c1cccc(C#N)c1] | | 420.1 |
| 46A | 2-chloro-N-(1-methyl-4-(4-(methylsulfonyl)benzoyl)-4,5,6,7-tetrahydro-1H-pyrazolo[4,3-b]pyridin-7-yl)benzamide | 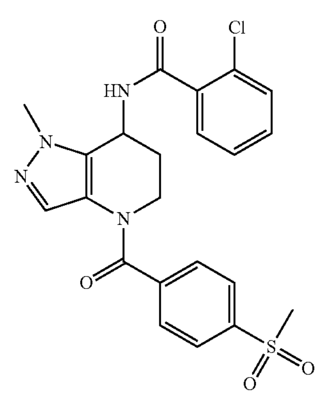 [SMILES: Cn1ncc2c1C(NC(=O)c1ccccc1Cl)CCN2C(=O)c1ccc(S(C)(=O)=O)cc1] | | 473.1 |

TABLE 1-continued

| Ex. No. | IUPAC Name | Structure | Salt | MS |
|---|---|---|---|---|
| 47A | 2-chloro-N-(4-(3-chloro-4-(methylsulfonyl)benzoyl)-1-methyl-4,5,6,7-tetrahydro-1H-pyrazolo[4,3-b]pyridin-7-yl)benzamide | 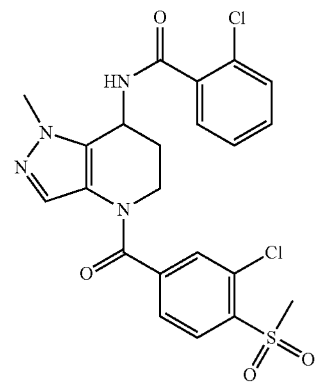 [SMILES: Cn1ncc2c1C(NC(=O)c1ccccc1Cl)CCN2C(=O)c1ccc(S(C)(=O)=O)c(Cl)c1] | | 507.0 |
| 48A | 2-chloro-N-(1-methyl-4-(3-(methylsulfonyl)benzoyl)-4,5,6,7-tetrahydro-1H-pyrazolo[4,3-b]pyridin-7-yl)benzamide | 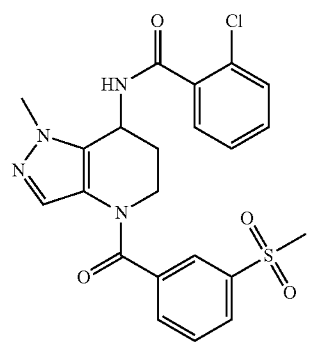 [SMILES: Cn1ncc2c1C(NC(=O)c1ccccc1Cl)CCN2C(=O)c1cccc(S(C)(=O)=O)c1] | | 473.1 |
| 49A | 2-chloro-N-(4-(4-chloro-3-(methylsulfonyl)benzoyl)-1-methyl-4,5,6,7-tetrahydro-1H-pyrazolo[4,3-b]pyridin-7-yl)benzamide | 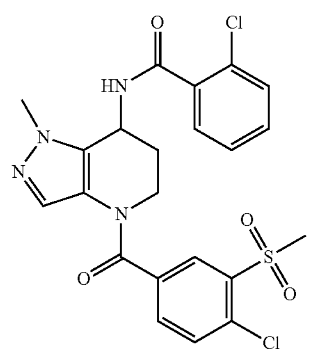 [SMILES: Cn1ncc2c1C(NC(=O)c1ccccc1Cl)CCN2C(=O)c1ccc(Cl)c(S(C)(=O)=O)c1] | | 507.0 |
| 50A | 2-chloro-N-(4-(3-chloro-4-(trifluoromethyl)benzoyl)-1-methyl-4,5,6,7-tetrahydro-1H-pyrazolo[4,3-b]pyridin-7-yl)benzamide | 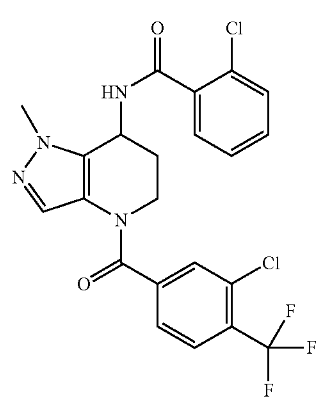 [SMILES: Cn1ncc2c1C(NC(=O)c1ccccc1Cl)CCN2C(=O)c1ccc(C(F)(F)F)c(Cl)c1] | | 497.0 |

TABLE 1-continued

| Ex. No. | IUPAC Name | Structure | Salt | MS |
|---|---|---|---|---|
| 51A | 2-chloro-N-(1-methyl-4-(pyrimidin-4-ylcarbonyl)-4,5,6,7-tetrahydro-1H-pyrazolo[4,3-b]pyridin-7-yl)benzamide | 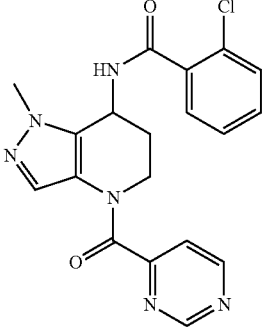 [SMILES: Cn1ncc2c1C(NC(=O)c1ccccc1Cl)CCN2C(=O)c1ccncn1] | | 397.1 |
| 52A | 2-chloro-N-(1-methyl-4-(3,4,5-trifluorobenzoyl)-4,5,6,7-tetrahydro-1H-pyrazolo[4,3-b]pyridin-7-yl)benzamide | 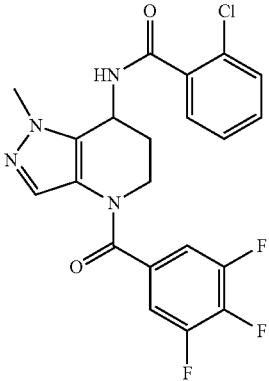 [SMILES: Cn1ncc2c1C(NC(=O)c1ccccc1Cl)CCN2C(=O)c1cc(F)c(F)c(F)c1] | | 446.9 |
| 53A | N-(4-(3,4-dimethoxybenzoyl)-1-methyl-4,5,6,7-tetrahydro-1H-pyrazolo[4,3-b]pyridin-7-yl)-2-fluorobenzamide | 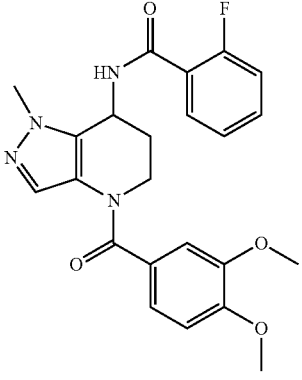 [SMILES: COc1ccc(C(=O)N2CCC(NC(=O)c3ccccc3F)c3c2cnn3C)cc1OC] | | 439.1 |
| 54A | N-(3-bromo-4-(3-chloro-4-methoxybenzoyl)-1-methyl-4,5,6,7-tetrahydro-1H-pyrazolo[4,3-b]pyridin-7-yl)-2-chlorobenzamide | 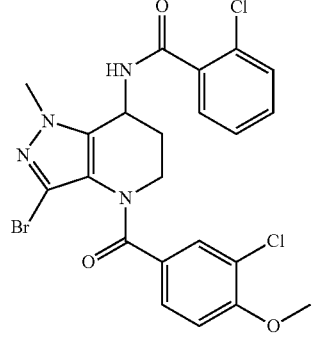 [SMILES: COc1ccc(C(=O)N2CCC(NC(=O)c3ccccc3Cl)c3c2c(Br)nn3C)cc1Cl] | | 536.9 |

TABLE 1-continued

| Ex. No. | IUPAC Name | Structure | Salt | MS |
|---|---|---|---|---|
| 55A | 3-chloro-N-(4-(3,4-dimethoxybenzoyl)-1-methyl-4,5,6,7-tetrahydro-1H-pyrazolo[4,3-b]pyridin-7-yl)benzamide | 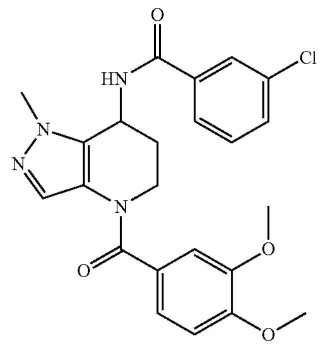 [SMILES: COc1ccc(C(=O)N2CCC(NC(=O)c3cccc(Cl)c3)c3c2cnn3C)cc1OC] | | 455.1 |
| 56A | 4-chloro-N-(4-(3,4-dimethoxybenzoyl)-1-methyl-4,5,6,7-tetrahydro-1H-pyrazolo[4,3-b]pyridin-7-yl)benzamide | 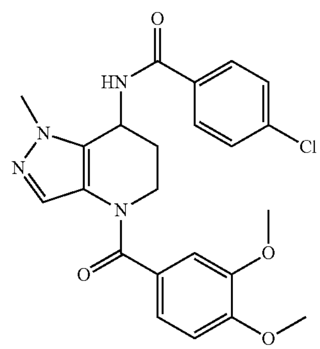 [SMILES: COc1ccc(C(=O)N2CCC(NC(=O)c3ccc(Cl)cc3)c3c2cnn3C)cc1OC] | | 455.1 |
| 57A | N-(4-(3,4-dimethoxybenzoyl)-1-methyl-4,5,6,7-tetrahydro-1H-pyrazolo[4,3-b]pyridin-7-yl)benzamide | 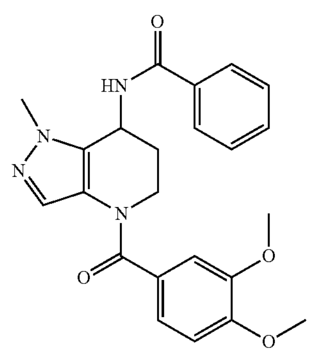 [SMILES: COc1ccc(C(=O)N2CCC(NC(=O)c3ccccc3)c3c2cnn3C)cc1OC] | | 421.1 |
| 58A | N-(4-(3,4-dimethoxybenzoyl)-1-methyl-4,5,6,7-tetrahydro-1H-pyrazolo[4,3-b]pyridin-7-yl)-3-fluorobenzamide | 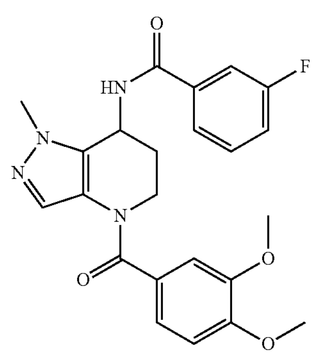 [SMILES: COc1ccc(C(=O)N2CCC(NC(=O)c3cccc(F)c3)c3c2cnn3C)cc1OC] | | 439.1 |

TABLE 1-continued

| Ex. No. | IUPAC Name | Structure | Salt | MS |
|---|---|---|---|---|
| 59A | N-(4-(3,4-dimethoxybenzoyl)-1-methyl-4,5,6,7-tetrahydro-1H-pyrazolo[4,3-b]pyridin-7-yl)-4-fluorobenzamide | 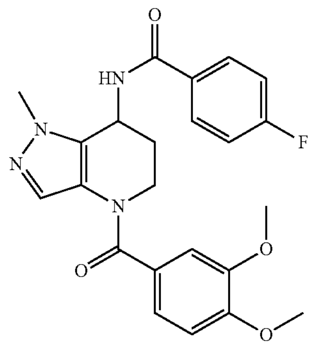 [SMILES: COc1ccc(C(=O)N2CCC(NC(=O)c3ccc(F)cc3)c3c2cnn3C)cc1OC] | | 439.1 |
| 60A | N-(4-(3,4-dimethoxybenzoyl)-1-methyl-4,5,6,7-tetrahydro-1H-pyrazolo[4,3-b]pyridin-7-yl)pyridine-2-carboxamide | 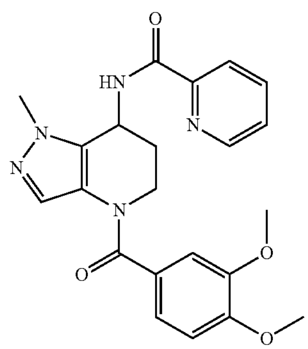 [SMILES: COc1ccc(C(=O)N2CCC(NC(=O)c3ccccn3)c3c2cnn3C)cc1OC] | | 422.1 |
| 61A | N-(4-(3,4-dimethoxybenzoyl)-1-methyl-4,5,6,7-tetrahydro-1H-pyrazolo[4,3-b]pyridin-7-yl)nicotinamide | 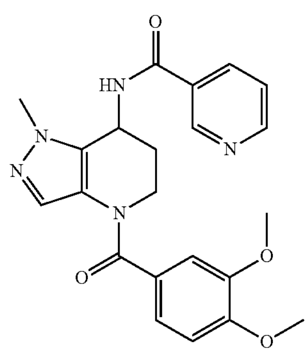 [SMILES: COc1ccc(C(=O)N2CCC(NC(=O)c3cccnc3)c3c2cnn3C)cc1OC] | | 422.1 |
| 62A | N-(4-(3,4-dimethoxybenzoyl)-1-methyl-4,5,6,7-tetrahydro-1H-pyrazolo[4,3-b]pyridin-7-yl)thiophene-2-carboxamide | 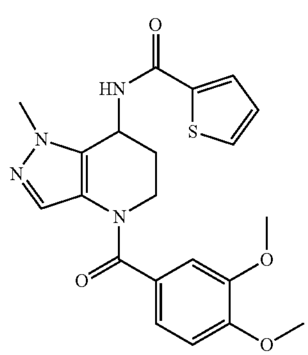 [SMILES: COc1ccc(C(=O)N2CCC(NC(=O)c3cccs3)c3c2cnn3C)cc1OC] | | 427.1 |

TABLE 1-continued

| Ex. No. | IUPAC Name | Structure | Salt | MS |
|---|---|---|---|---|
| 63A | N-(4-(3,4-dimethoxybenzoyl)-1-methyl-4,5,6,7-tetrahydro-1H-pyrazolo[4,3-b]pyridin-7-yl)-1,3-thiazole-2-carboxamide | 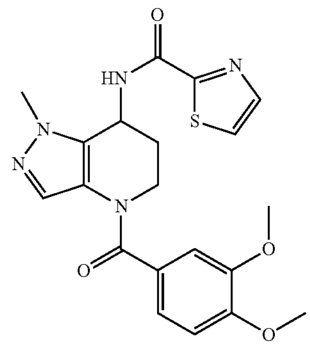 [SMILES: COc1ccc(C(=O)N2CCC(NC(=O)c3nccs3)c3c2cnn3C)cc1OC] | | 428.1 |
| 64A | 3-chloro-N-(4-(3,4-dimethoxybenzoyl)-1-methyl-4,5,6,7-tetrahydro-1H-pyrazolo[4,3-b]pyridin-7-yl)thiophene-2-carboxamide | 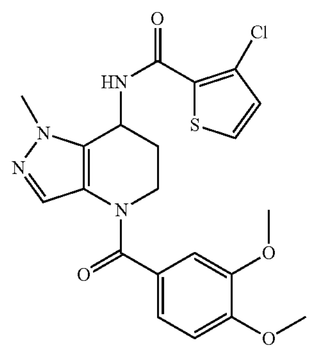 [SMILES: COc1ccc(C(=O)N2CCC(NC(=O)c3sccc3Cl)c3c2cnn3C)cc1OC] | | 461.1 |
| 65A | N-(4-(3,4-dimethoxybenzoyl)-1-methyl-4,5,6,7-tetrahydro-1H-pyrazolo[4,3-b]pyridin-7-yl)-2-furamide | 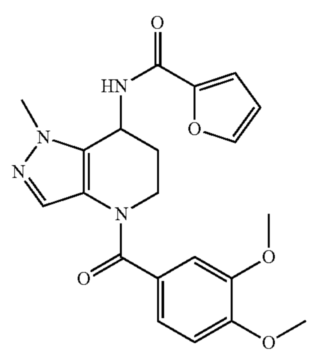 [SMILES: COc1ccc(C(=O)N2CCC(NC(=O)c3ccco3)c3c2cnn3C)cc1OC] | | 411.2 |
| 66A | N-(4-(3,4-dimethoxybenzoyl)-1-methyl-4,5,6,7-tetrahydro-1H-pyrazolo[4,3-b]pyridin-7-yl)isonicotinamide | 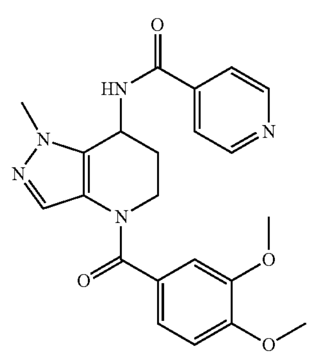 | | 422.1 |

TABLE 1-continued

| Ex. No. | IUPAC Name | Structure | Salt | MS |
|---|---|---|---|---|
| 67A | N-(4-(3,4-dimethoxybenzoyl)-1-methyl-4,5,6,7-tetrahydro-1H-pyrazolo[4,3-b]pyridin-7-yl)-3-(trifluoromethyl)benzamide | 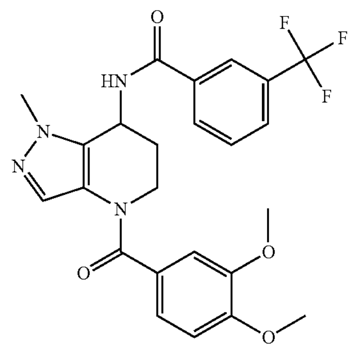 [SMILES: COc1ccc(C(=O)N2CCC(NC(=O)c3cccc(C(F)(F)F)c3)c3c2cnn3C)cc1OC] | | 489.1 |
| 68A | N-(4-(3,4-dimethoxybenzoyl)-1-methyl-4,5,6,7-tetrahydro-1H-pyrazolo[4,3-b]pyridin-7-yl)-4-(trifluoromethyl)benzamide | 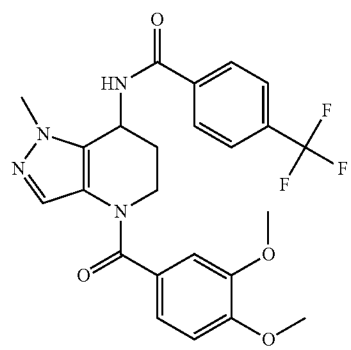 [SMILES: COc1ccc(C(=O)N2CCC(NC(=O)c3ccc(C(F)(F)F)cc3)c3c2cnn3C)cc1OC] | | 489.1 |
| 69A | N-(4-(3,4-dimethoxybenzoyl)-1-methyl-4,5,6,7-tetrahydro-1H-pyrazolo[4,3-b]pyridin-7-yl)-2-(trifluoromethyl)benzamide | 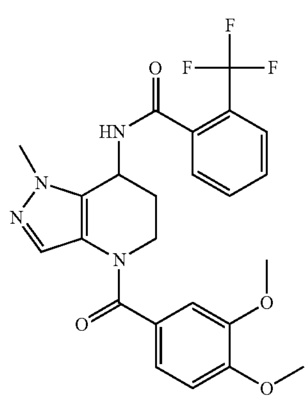 [SMILES: COc1ccc(C(=O)N2CCC(NC(=O)c3ccccc3C(F)(F)F)c3c2cnn3C)cc1OC] | | 489.1 |
| 70A | N-(4-(3,4-dimethoxybenzoyl)-1-methyl-4,5,6,7-tetrahydro-1H-pyrazolo[4,3-b]pyridin-7-yl)-3-methoxybenzamide | 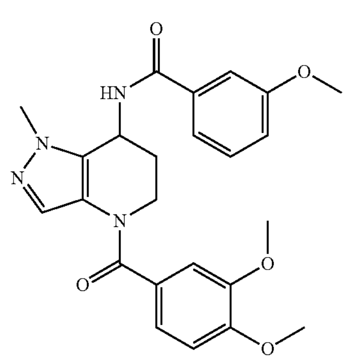 [SMILES: COc1cccc(C(=O)NC2CCN(C(=O)c3ccc(OC)c(OC)c3)c3cnn(C)c32)c1] | | 451.1 |

| Ex. No. | IUPAC Name | Structure | Salt | MS |
|---|---|---|---|---|
| 71A | N-(4-(3,4-dimethoxybenzoyl)-1-methyl-4,5,6,7-tetrahydro-1H-pyrazolo[4,3-b]pyridin-7-yl)-4-methoxybenzamide | 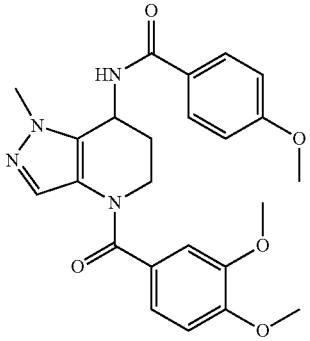 [SMILES: COc1ccc(C(=O)NC2CCN(C(=O)c3ccc(OC)c(OC)c3)c3cnn(C)c32)cc1] | | 451.1 |
| 72A | N-(4-(3,4-dimethoxybenzoyl)-1-methyl-4,5,6,7-tetrahydro-1H-pyrazolo[4,3-b]pyridin-7-yl)-2-methoxybenzamide | 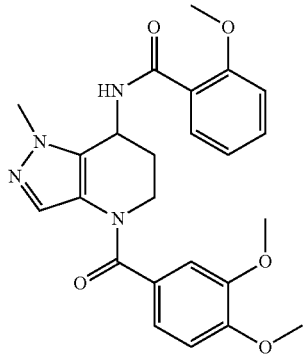 [SMILES: COc1ccc(C(=O)N2CCC(NC(=O)c3ccccc3OC)c3c2cnn3C)cc1OC] | | 451.1 |
| 73A | 2-chloro-N-(4-(3-methoxy-5-(trifluoromethoxy)benzoyl)-1-methyl-4,5,6,7-tetrahydro-1H-pyrazolo[4,3-b]pyridin-7-yl)benzamide | 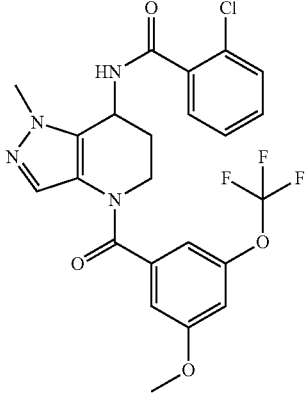 [SMILES: COc1cc(OC(F)(F)F)cc(C(=O)N2CCC(NC(=O)c3ccccc3Cl)c3c2cnn3C)c1] | | 509.1 |
| 74A | 2-chloro-N-((7S)-4-(3,4-dimethoxybenzoyl)-1-isopropyl-4,5,6,7-tetrahydro-1H-pyrazolo[4,3-b]pyridin-7-yl)benzamide | 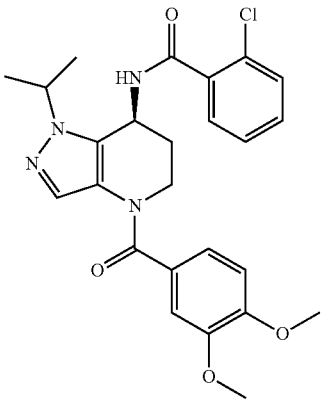 [SMILES: COc1ccc(C(=O)N2CC[C@H](NC(=O)c3ccccc3Cl)c3c2cnn3C(C)C)cc1OC] | | 483.1 |

TABLE 1-continued

| Ex. No. | IUPAC Name | Structure | Salt | MS |
|---|---|---|---|---|
| 75A | 2-chloro-N-((7R)-4-(3,4-dimethoxybenzoyl)-1-isopropyl-4,5,6,7-tetrahydro-1H-pyrazolo[4,3-b]pyridin-7-yl)benzamide | 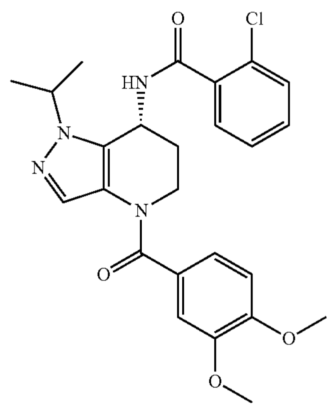 [SMILES: COc1ccc(C(=O)N2CC[C@@H](NC(=O)c3ccccc3Cl)c3c2cnn3C(C)C)cc1OC] | | 483.1 |
| 76A | N-(4-benzoyl-1-methyl-4,5,6,7-tetrahydro-1H-pyrazolo[4,3-b]pyridin-7-yl)-2-chlorobenzamide | 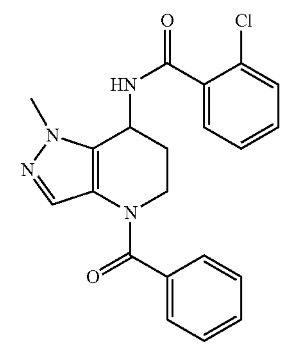 [SMILES: Cn1ncc2c1C(NC(=O)c1ccccc1Cl)CCN2C(=O)c1ccccc1] | | 395.1 |
| 77A | 2-chloro-N-(4-(4-methoxybenzoyl)-1-methyl-4,5,6,7-tetrahydro-1H-pyrazolo[4,3-b]pyridin-7-yl)benzamide | 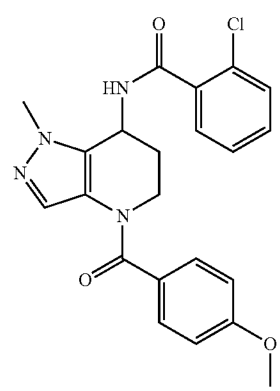 [SMILES: COc1ccc(C(=O)N2CCC(NC(=O)c3ccccc3Cl)c3c2cnn3C)cc1] | | 425.0 |
| 78A | N-(4-(3-chloro-4-methoxybenzoyl)-1-methyl-4,5,6,7-tetrahydro-1H-pyrazolo[4,3-b]pyridin-7-yl)-2-(trifluoromethyl)benzamide | 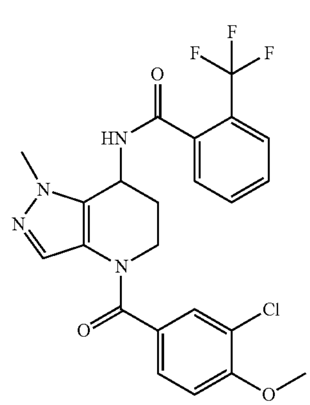 [SMILES: COc1ccc(C(=O)N2CCC(NC(=O)c3ccccc3C(F)(F)F)c3c2cnn3C)cc1Cl] | | 493.1 |

TABLE 1-continued

| Ex. No. | IUPAC Name | Structure | Salt | MS |
|---|---|---|---|---|
| 79A | 2-chloro-N-(4-((5,6-dimethoxypyridin-2-yl)carbonyl)-1-methyl-4,5,6,7-tetrahydro-1H-pyrazolo[4,3-b]pyridin-7-yl)benzamide | 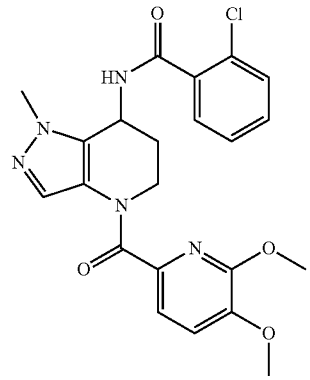 [SMILES: COc1ccc(C(=O)N2CCC(NC(=O)c3ccccc3Cl)c3c2cnn3C)nc1OC] | | 456.1 |
| 80A | 2-chloro-N-(4-((5,6-dimethoxypyridin-3-yl)carbonyl)-1-methyl-4,5,6,7-tetrahydro-1H-pyrazolo[4,3-b]pyridin-7-yl)benzamide | 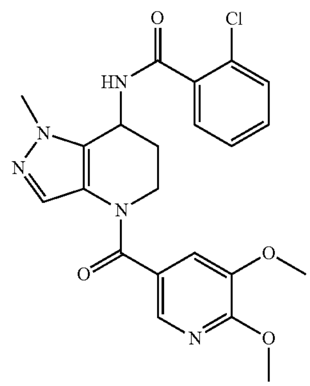 [SMILES: COc1cc(C(=O)N2CCC(NC(=O)c3ccccc3Cl)c3c2cnn3C)cnc1OC] | | 456.0 |
| 81A | 2-chloro-N-(4-(2-methoxyisonicotinoyl)-1-methyl-4,5,6,7-tetrahydro-1H-pyrazolo[4,3-b]pyridin-7-yl)benzamide | 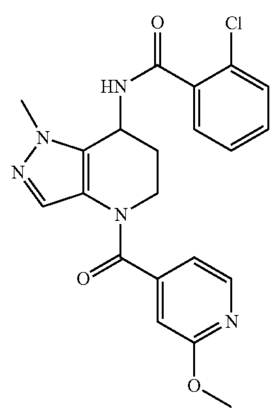 [SMILES: COc1cc(C(=O)N2CCC(NC(=O)c3ccccc3Cl)c3c2cnn3C)ccn1] | | 426.2 |
| 82A | 2-chloro-N-(4-(2-chloroisonicotinoyl)-1-methyl-4,5,6,7-tetrahydro-1H-pyrazolo[4,3-b]pyridin-7-yl)benzamide | 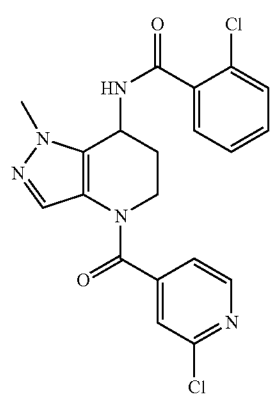 [SMILES: Cn1ncc2c1C(NC(=O)c1ccccc1Cl)CCN2C(=O)c1ccnc(Cl)c1] | | 430.0 |

TABLE 1-continued

| Ex. No. | IUPAC Name | Structure | Salt | MS |
|---|---|---|---|---|
| 83A | 2-chloro-N-(4-(3,4-dimethoxybenzoyl)-1-(2,2,2-trifluoroethyl)-4,5,6,7-tetrahydro-1H-pyrazolo[4,3-b]pyridin-7-yl)benzamide | 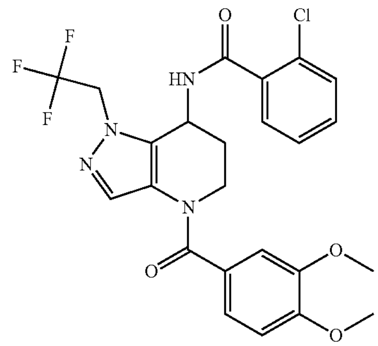 [SMILES: COc1ccc(C(=O)N2CCC(NC(=O)c3ccccc3Cl)c3c2cnn3CC(F)(F)F)cc1OC] | | 523.1 |
| 84A | 2-chloro-N-(4-((5-chloro-6-methoxypyridin-3-yl)carbonyl)-1-methyl-4,5,6,7-tetrahydro-1H-pyrazolo[4,3-b]pyridin-7-yl)benzamide | 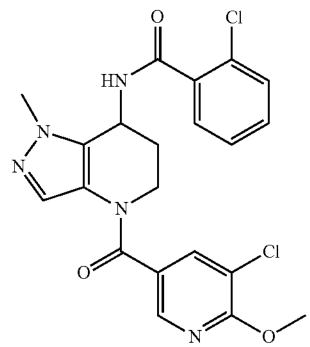 [SMILES: COc1ncc(C(=O)N2CCC(NC(=O)c3ccccc3Cl)c3c2cnn3C)cc1Cl] | | 460.1 |
| 85A | N-(4-((5-chloro-6-methoxypyridin-3-yl)carbonyl)-1-methyl-4,5,6,7-tetrahydro-1H-pyrazolo[4,3-b]pyridin-7-yl)-2-(trifluoromethyl)benzamide | 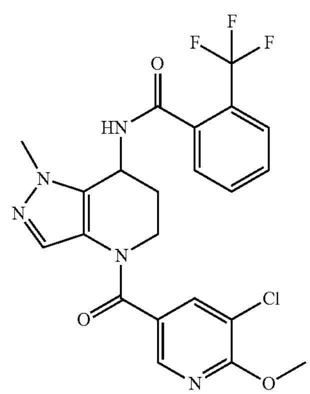 [SMILES: COc1ncc(C(=O)N2CCC(NC(=O)c3ccccc3C(F)(F)F)c3c2cnn3C)cc1Cl] | | 492.1 |
| 86A | 2,6-dichloro-N-(4-(3,4-dimethoxybenzoyl)-1-methyl-4,5,6,7-tetrahydro-1H-pyrazolo[4,3-b]pyridin-7-yl)benzamide | 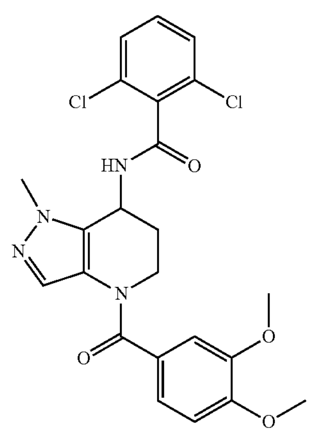 [SMILES: COc1ccc(C(=O)N2CCC(NC(=O)c3c(Cl)cccc3Cl)c3c2cnn3C)cc1OC] | | 489.1 |

TABLE 1-continued

| Ex. No. | IUPAC Name | Salt | MS |
|---|---|---|---|
| 87A | 2,3-dichloro-N-(4-(3,4-dimethoxybenzoyl)-1-methyl-4,5,6,7-tetrahydro-1H-pyrazolo[4,3-b]pyridin-7-yl)benzamide | | 489.0 |
| 88A | 2,4-dichloro-N-(4-(3,4-dimethoxybenzoyl)-1-methyl-4,5,6,7-tetrahydro-1H-pyrazolo[4,3-b]pyridin-7-yl)benzamide | | 489.1 |
| 89A | 2,5-dichloro-N-(4-(3,4-dimethoxybenzoyl)-1-methyl-4,5,6,7-tetrahydro-1H-pyrazolo[4,3-b]pyridin-7-yl)benzamide | | 489.1 |
| 90A | 4-chloro-N-(4-(3,4-dimethoxybenzoyl)-1-methyl-4,5,6,7-tetrahydro-1H-pyrazolo[4,3-b]pyridin-7-yl)-2-(trifluoromethyl)benzamide | | 521.0 |

TABLE 1-continued

| Ex. No. | IUPAC Name | Structure | Salt | MS |
|---|---|---|---|---|
| 91A | N-(4-(3,4-dimethoxybenzoyl)-1-methyl-4,5,6,7-tetrahydro-1H-pyrazolo[4,3-b]pyridin-7-yl)-4-(trifluoromethyl)nicotinamide | 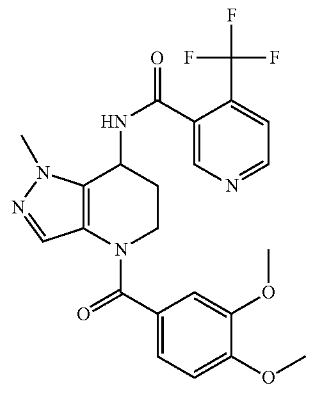 [SMILES: COc1ccc(C(=O)N2CCC(NC(=O)c3cnccc3C(F)(F)F)c3c2cnn3C)cc1OC] | | 490.1 |
| 92A | 2-chloro-N-(4-(3,4-dimethoxybenzoyl)-1-methyl-4,5,6,7-tetrahydro-1H-pyrazolo[4,3-b]pyridin-7-yl)nicotinamide | 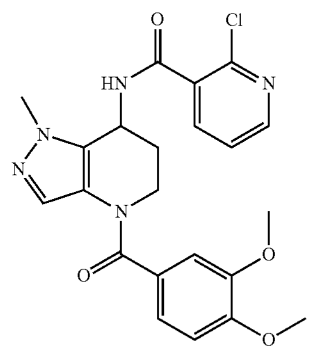 [SMILES: COc1ccc(C(=O)N2CCC(NC(=O)c3cccnc3Cl)c3c2cnn3C)cc1OC] | | 456.1 |
| 95A | N-(4-(3,4-dimethoxybenzoyl)-1-methyl-4,5,6,7-tetrahydro-1H-pyrazolo[4,3-b]pyridin-7-yl)-1-naphthamide | 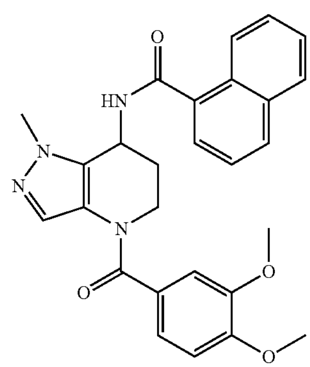 [SMILES: COc1ccc(C(=O)N2CCC(NC(=O)c3cccc4ccccc34)c3c2cnn3C)cc1OC] | | 471.2 |
| 97A | N-(4-(3,4-dimethoxybenzoyl)-1-methyl-4,5,6,7-tetrahydro-1H-pyrazolo[4,3-b]pyridin-7-yl)-2-naphthamide | 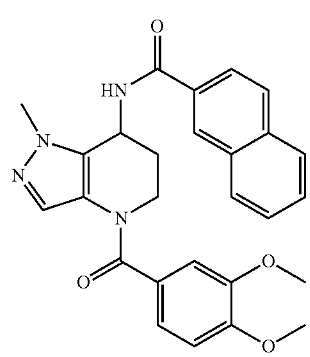 [SMILES: COc1ccc(C(=O)N2CCC(NC(=O)c3ccc4ccccc4c3)c3c2cnn3C)cc1OC] | | 471.2 |

TABLE 1-continued

| Ex. No. | IUPAC Name | Salt | MS |
|---|---|---|---|
| 98A | N-(4-(3,4-dimethoxybenzoyl)-1-methyl-4,5,6,7-tetrahydro-1H-pyrazolo[4,3-b]pyridin-7-yl)-2-(trifluoromethoxy)benzamide | | 505.1 |
| 99A | 2-cyano-N-(4-(3,4-dimethoxybenzoyl)-1-methyl-4,5,6,7-tetrahydro-1H-pyrazolo[4,3-b]pyridin-7-yl)benzamide | | 446.1 |
| 100A | N-(4-(3,4-dimethoxybenzoyl)-1-methyl-4,5,6,7-tetrahydro-1H-pyrazolo[4,3-b]pyridin-7-yl)-3-(trifluoromethyl)pyridine-2-carboxamide | | 487.9 |
| 101A | 3-chloro-N-(4-(3,4-dimethoxybenzoyl)-1-methyl-4,5,6,7-tetrahydro-1H-pyrazolo[4,3-b]pyridin-7-yl)pyridine-2-carboxamide | | 456.1 |

TABLE 1-continued

| Ex. No. | IUPAC Name | Structure | Salt | MS |
|---|---|---|---|---|
| 102A | 2-(difluoromethoxy)-N-(4-(3,4-dimethoxybenzoyl)-1-methyl-4,5,6,7-tetrahydro-1H-pyrazolo[4,3-b]pyridin-7-yl)benzamide | 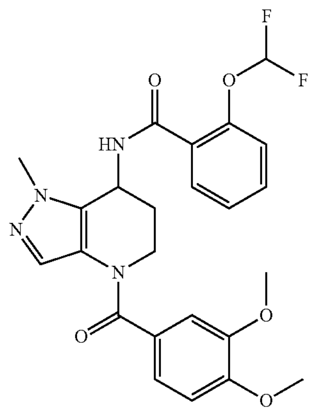 [SMILES: COc1ccc(C(=O)N2CCC(NC(=O)c3ccccc3OC(F)F)c3c2cnn3C)cc1OC] | | 487.1 |
| 103A | N-(4-(3,4-dimethoxybenzoyl)-1-methyl-4,5,6,7-tetrahydro-1H-pyrazolo[4,3-b]pyridin-7-yl)-2-(trifluoromethyl)nicotinamide | 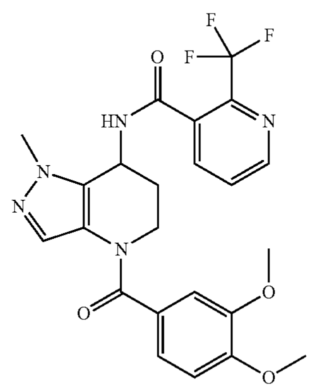 [SMILES: COc1ccc(C(=O)N2CCC(NC(=O)c3cccnc3C(F)(F)F)c3c2cnn3C)cc1OC] | | 490.1 |
| 104A | 3-chloro-N-(4-(3,4-dimethoxybenzoyl)-1-methyl-4,5,6,7-tetrahydro-1H-pyrazolo[4,3-b]pyridin-7-yl)isonicotinamide | 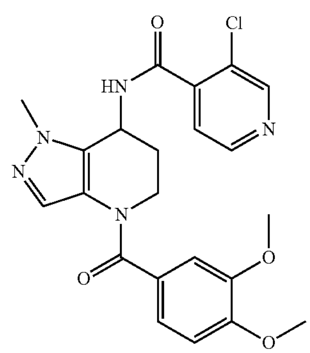 [SMILES: COc1ccc(C(=O)N2CCC(NC(=O)c3ccncc3Cl)c3c2cnn3C)cc1OC] | | 456.1 |
| 105A | N-(4-(3,4-dimethoxybenzoyl)-1-methyl-4,5,6,7-tetrahydro-1H-pyrazolo[4,3-b]pyridin-7-yl)-1-benzofuran-7-carboxamide | 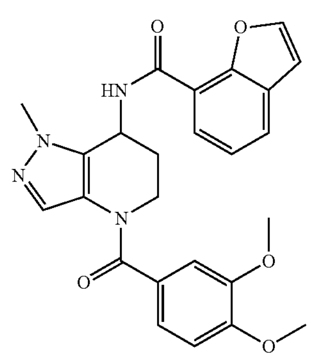 [SMILES: COc1ccc(C(=O)N2CCC(NC(=O)c3cccc4ccoc34)c3c2cnn3C)cc1OC] | | 461.1 |

TABLE 1-continued

| Ex. No. | IUPAC Name | Structure | Salt | MS |
|---|---|---|---|---|
| 106A | N-(4-(3,4-dimethoxybenzoyl)-1-methyl-4,5,6,7-tetrahydro-1H-pyrazolo[4,3-b]pyridin-7-yl)-2,3-dihydro-1-benozfuran-7-carboxamide | 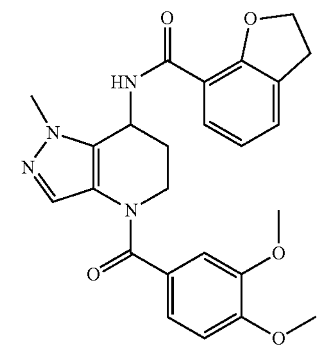 [SMILES: COc1ccc(C(=O)N2CCC(NC(=O)c3cccc4c3OCC4)c3c2cnn3C)cc1OC] | | 463.1 |
| 107A | 5-chloro-N-(4-(3,4-dimethoxybenzoyl)-1-methyl-4,5,6,7-tetrahydro-1H-pyrazolo[4,3-b]pyridin-7-yl)-1,3-benzodioxole-4-carboxamide | 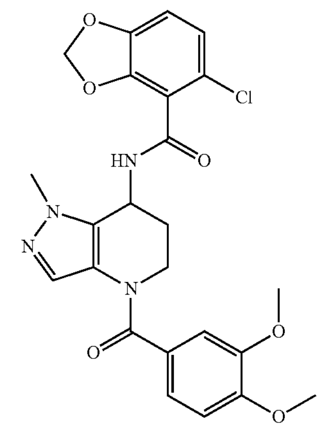 [SMILES: COc1ccc(C(=O)N2CCC(NC(=O)c3c(Cl)ccc4c3OCO4)c3c2cnn3C)cc1OC] | | 499.1 |
| 108A | N-(4-(3,4-dimethoxybenzoyl)-1-methyl-4,5,6,7-tetrahydro-1H-pyrazolo[4,3-b]pyridin-7-yl)-2-(methylsulfonyl)benzamide | 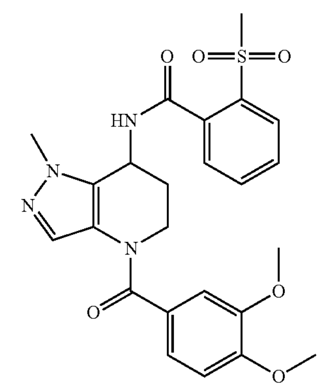 [SMILES: COc1ccc(C(=O)N2CCC(NC(=O)c3ccccc3S(C)(=O)=O)c3c2cnn3C)cc1OC] | | 499.1 |
| 109A | 2-chloro-N-(4-(3,4-dimethoxybenzoyl)-1-ethyl-4,5,6,7-tetrahydro-1H-pyrazolo[4,3-b]pyridin-7-yl)benzamide | 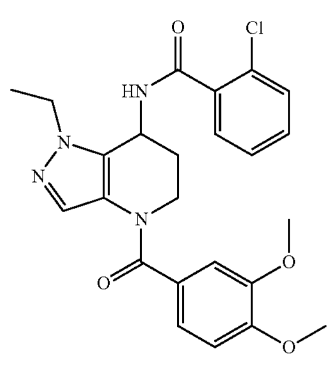 [SMILES: CCn1ncc2c1C(NC(=O)c1ccccc1Cl)CCN2C(=O)c1ccc(OC)c(OC)c1] | | 469.2 |

TABLE 1-continued

| Ex. No. | IUPAC Name | Structure | Salt | MS |
|---|---|---|---|---|
| 110A | N-(1-butyl-4-(3,4-dimethoxybenzoyl)-4,5,6,7-tetrahydro-1H-pyrazolo[4,3-b]pyridin-7-yl)-2-chlorobenzamide | 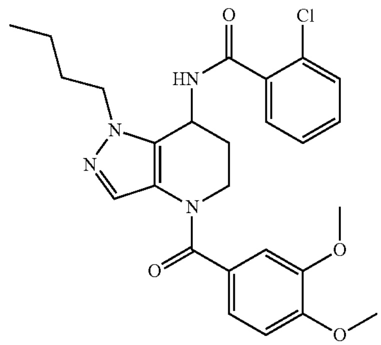 [SMILES: CCCCn1ncc2c1C(NC(=O)c1ccccc1Cl)CCN2C(=O)c1ccc(OC)c(OC)c1] | | 497.2 |
| 111A | 2-chloro-N-(1-cyclopentyl-4-(3,4-dimethoxybenzoyl)-4,5,6,7-tetrahydro-1H-pyrazolo[4,3-b]pyridin-7-yl)benzamide | 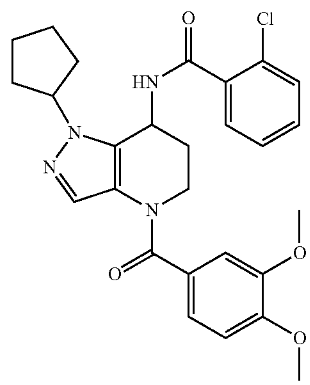 [SMILES: COc1ccc(C(=O)N2CCC(NC(=O)c3ccccc3Cl)c3c2cnn3C2CCCC2)cc1OC] | | 509.2 |
| 112A | 2-chloro-N-(4-(3,4-dimethoxybenzoyl)-1-propyl-4,5,6,7-tetrahydro-1H-pyrazolo[4,3-b]pyridin-7-yl)benzamide | 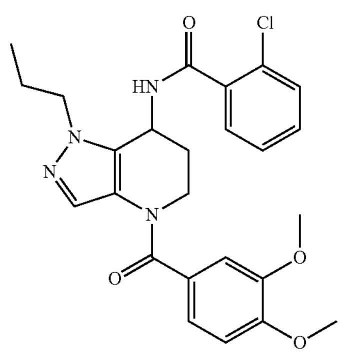 [SMILES: CCCn1ncc2c1C(NC(=O)c1ccccc1Cl)CCN2C(=O)c1ccc(OC)c(OC)c1] | | 483.0 |
| 113A | 2-chloro-N-(3-chloro-4-(3,4-dimethoxybenzoyl)-1-methyl-4,5,6,7-tetrahydro-1H-pyrazolo[4,3-b]pyridin-7-yl)benzamide | 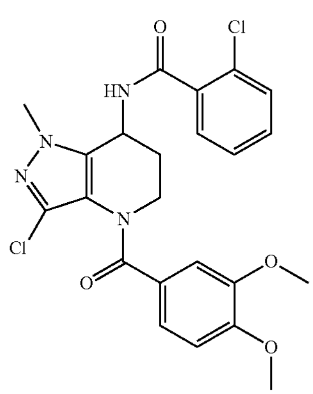 [SMILES: COc1ccc(C(=O)N2CCC(NC(=O)c3ccccc3Cl)c3c2c(Cl)nn3C)cc1OC] | | 488.9 |

TABLE 1-continued

| Ex. No. | IUPAC Name | Structure | Salt | MS |
|---|---|---|---|---|
| 114A | 4-chloro-N-(4-((5-chloro-6-methoxypyridin-3-yl)carbonyl)-1-methyl-4,5,6,7-tetrahydro-1H-pyrazolo[4,3-b]pyridin-7-yl)-2-(trifluoromethyl)benzamide | 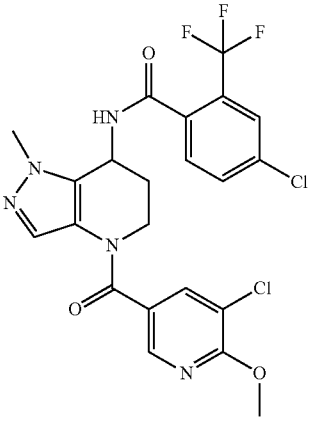 [SMILES: COc1ncc(C(=O)N2CCC(NC(=O)c3ccc(Cl)cc3C(F)(F)F)c3c2cnn3C)cc1Cl] | | 527.9 |
| 115A | 2-chloro-N-(4-(3-chloro-4-methoxybenzoyl)-1-cyclopentyl-4,5,6,7-tetrahydro-1H-pyrazolo[4,3-b]pyridin-7-yl)benzamide | 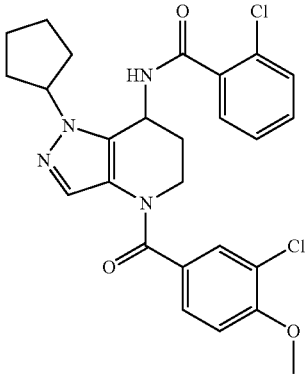 [SMILES: COc1ccc(C(=O)N2CCC(NC(=O)c3ccccc3Cl)c3c2cnn3C2CCCC2)cc1Cl] | | 513.0 |
| 116A | 2-chloro-N-(1-cyclopentyl-4-((5,6-dimethoxypyridin-3-yl)carbonyl)-4,5,6,7-tetrahydro-1H-pyrazolo[4,3-b]pyridin-7-yl)benzamide | 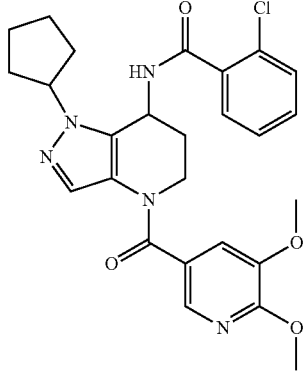 [SMILES: COc1cc(C(=O)N2CCC(NC(=O)c3ccccc3Cl)c3c2cnn3C2CCCC2)cnc1OC] | | 510.1 |
| 117A | 2-chloro-N-(7-(3,4-dimethoxybenzoyl)-3-methyl-4,5,6,7-tetrahydro[1,2]thiazolo[5,3-b]pyridin-4-yl)benzamide | 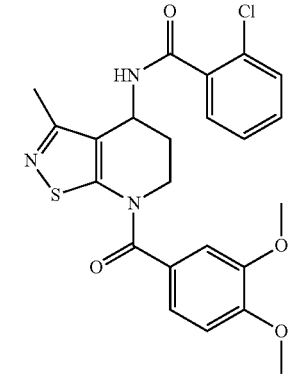 [SMILES: COc1ccc(C(=O)N2CCC(NC(=O)c3ccccc3Cl)c3c(C)nsc32)cc1OC] | | 472.0 |

TABLE 1-continued

| Ex. No. | IUPAC Name | Structure | Salt | MS |
|---|---|---|---|---|
| 118A | 2-chloro-N-(7-(3-chloro-4-methoxybenzoyl)-3-methyl-4,5,6,7-tetrahydro[1,2]thiazolo[5,4-b]pyridin-4-yl)benzamide | 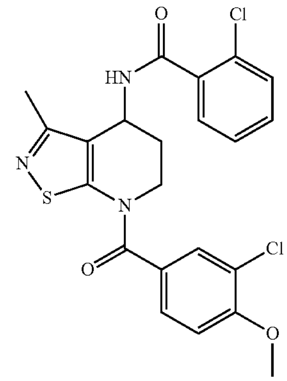 [SMILES: COc1ccc(C(=O)N2CCC(NC(=O)c3ccccc3Cl)c3c(C)nsc32)cc1Cl] | | 476.0 |
| 119A | 2-chloro-N-(4-(imidazo[1,2-a]pyridin-6-ylcarbonyl)-1-methyl-4,5,6,7-tetrahydro-1H-pyrazolo[4,3-b]pyridin-7-yl)benzamide | 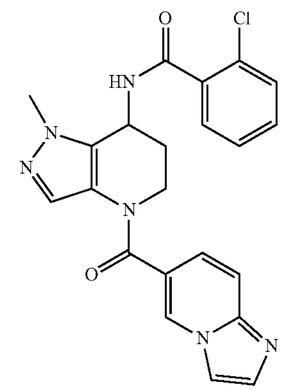 [SMILES: Cn1ncc2c1C(NC(=O)c1ccccc1Cl)CCN2C(=O)c1ccc2nccn2c1] | | 435.0 |
| 120A | 2-chloro-N-(4-(imidazo[1,2-a]pyridin-2-ylcarbonyl)-1-methyl-4,5,6,7-tetrahydro-1H-pyrazolo[4,3-b]pyridin-7-yl)benzamide | 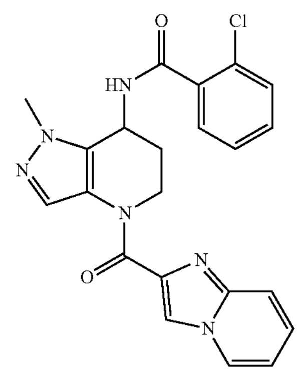 [SMILES: Cn1ncc2c1C(NC(=O)c1ccccc1Cl)CCN2C(=O)c1cn2ccccc2n1] | | 435.0 |
| 121A | 4-chloro-N-(4-(imidazo[1,2-a]pyridin-2-ylcarbonyl)-1-methyl-4,5,6,7-tetrahydro-1H-pyrazolo[4,3-b]pyridin-7-yl)-2-(trifluoromethyl)benzmaide | 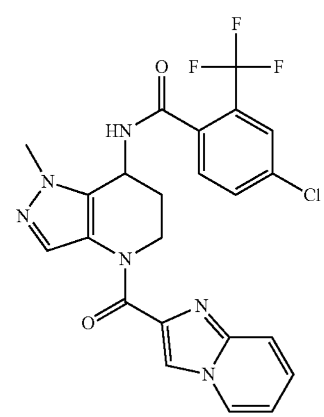 [SMILES: Cn1ncc2c1C(NC(=O)c1ccc(Cl)cc1C(F)(F)F)CCN2C(=O)c1cn2ccccc2n1] | | 503.0 |

TABLE 1-continued

| Ex. No. | IUPAC Name | Structure | Salt | MS |
|---|---|---|---|---|
| 122A | 2-chloro-N-(1-(2,2-difluoroethyl)-4-(3,4-dimethoxybenzoyl)-4,5,6,7-tetrahydro-1H-pyrazolo[4,3-b]pyridin-7-yl)benzamide | 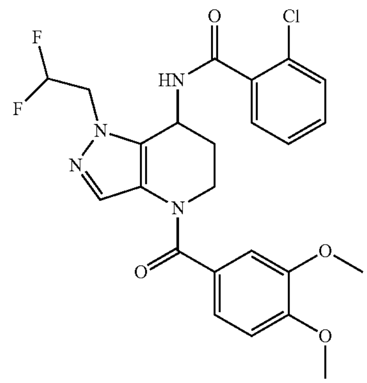 [SMILES: COc1ccc(C(=O)N2CCC(NC(=O)c3ccccc3Cl)c3c2cnn3CC(F)F)cc1OC] | | 505.0 |
| 123A | 4-chloro-N-(4-((5,6-dimethoxypyridin-3-yl)carbonyl)-1-isopropyl-4,5,6,7-tetrahydro-1H-pyrazolo[4,3-b]pyridin-7-yl)-2-(trifluoromethyl)benzamide | 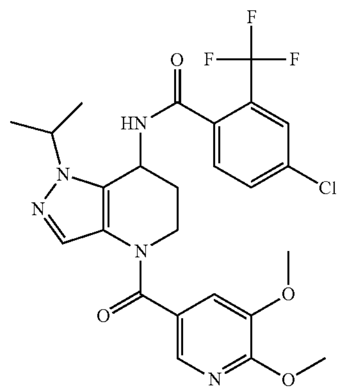 [SMILES: COc1cc(C(=O)N2CCC(NC(=O)c3ccc(Cl)cc3C(F)(F)F)c3c2cnn3C(C)C)cnc1OC] | | 552.0 |
| 124A | 2-chloro-N-(4-((5,6-dimethoxypyridin-3-yl)carbonyl)-1-isopropyl-4,5,6,7-tetrahydro-1H-pyrazolo[4,3-b]pyridin-7-yl)benzamide | 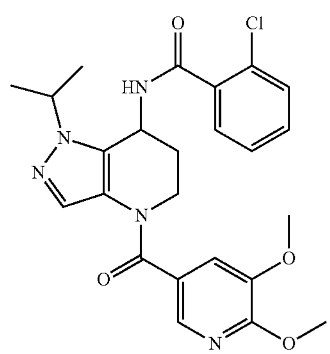 [SMILES: COc1cc(C(=O)N2CCC(NC(=O)c3ccccc3Cl)c3c2cnn3C(C)C)cnc1OC] | | 484.1 |
| 125A | 2-chloro-N-(4-((5-chloro-6-methoxypyridin-3-yl)carbonyl)-1-(2,2-difluoroethyl)-4,5,6,7-tetrahydro-1H-pyrazolo[4,3-b]pyridin-7-yl)benzamide | 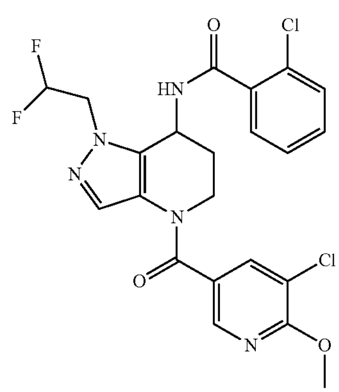 [SMILES: COc1ncc(C(=O)N2CCC(NC(=O)c3ccccc3Cl)c3c2cnn3CC(F)F)cc1Cl] | | 510.0 |

| Ex. No. | IUPAC Name | Structure | Salt | MS |
|---|---|---|---|---|
| 126A | 4-chloro-N-(4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethyl)benzamide | 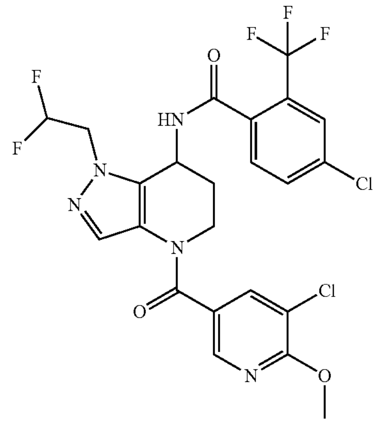 [SMILES: COc1ncc(C(=O)N2CCC(NC(=O)c3ccc(Cl)cc3C(F)(F)F)c3c2cnn3CC(F)F)cc1Cl] | | 577.9 |
| 127A | 4-chloro-N-(4-((5,6-dimethoxypyridin-3-yl)carbonyl)-1-methyl-4,5,6,7-tetrahydro-1H-pyrazolo[4,3-b]pyridin-7-yl)-2-(trifluoromethyl)benzamide | 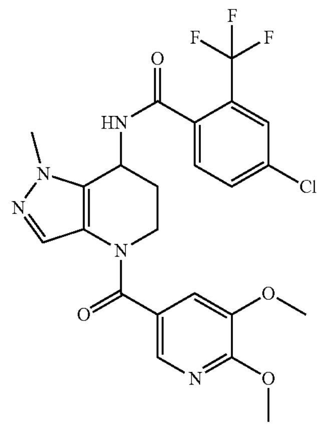 [SMILES: COc1cc(C(=O)N2CCC(NC(=O)c3ccc(Cl)cc3C(F)(F)F)c3c2cnn3C)cnc1OC] | | 524.0 |
| 128A | 2-chloro-N-(4-((5,6-dimethoxypyridin-3-yl)carbonyl)-1-propyl-4,5,6,7-tetrahydro-1H-pyrazolo[4,3-b]pyridin-7-yl)benzamide | 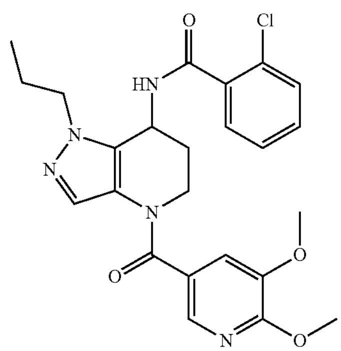 [SMILES: CCCn1ncc2c1C(NC(=O)c1ccccc1Cl)CCN2C(=O)c1cnc(OC)c(OC)c1] | | 484.1 |
| 129A | N-(4-((5,6-dimethoxypyridin-3-yl)carbonyl)-1-propyl-4,5,6,7-tetrahydro-1H-pyrazolo[4,3-b]pyridin-7-yl)-2-(trifluoromethoxy)benzamide | 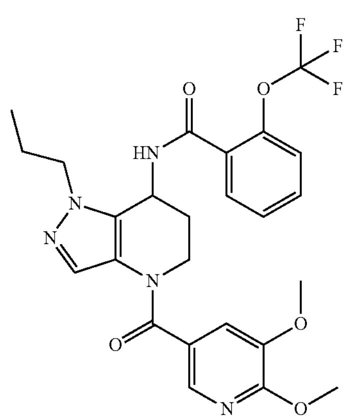 [SMILES: CCCn1ncc2c1C(NC(=O)c1ccccc1OC(F)(F)F)CCN2C(=O)c1cnc(OC)c(OC)c1] | | 534.1 |

TABLE 1-continued

| Ex. No. | IUPAC Name | Structure | Salt | MS |
| --- | --- | --- | --- | --- |
| 130A | 2-chloro-N-(4-((5-chloro-6-methoxypyridin-3-yl)carbonyl)-1-isopropyl-4,5,6,7-tetrahydro-1H-pyrazolo[4,3-b]pyridin-7-yl)benzamide | 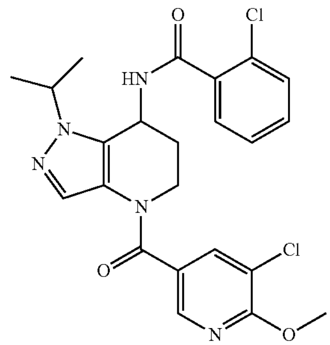 [SMILES: COc1ncc(C(=O)N2CCC(NC(=O)c3ccccc3Cl)c3c2cnn3C(C)C)cc1Cl] | | 488.0 |
| 131A | 4-chloro-N-(4-((5-chloro-6-methoxypyridin-3-yl)carbonyl)-1-isopropyl-4,5,6,7-tetrahydro-1H-pyrazolo[4,3-b]pyridin-7-yl)-2-(trifluoromethyl)benzamide | 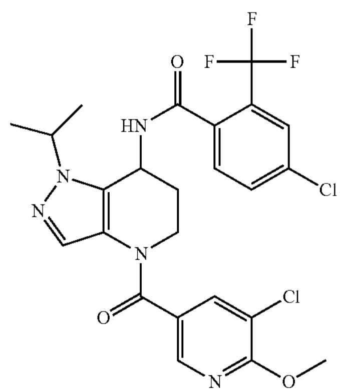 [SMILES: COc1ncc(C(=O)N2CCC(NC(=O)c3ccc(Cl)cc3C(F)(F)F)c3c2cnn3C(C)C)cc1Cl] | | 556.0 |
| 132A | N-(4-((5,6-dimethoxypyridin-3-yl)carbonyl)-1-isopropyl-4,5,6,7-tetrahydro-1H-pyrazolo[4,3-b]pyridin-7-yl)-2-(trifluoromethoxy)benzamide | 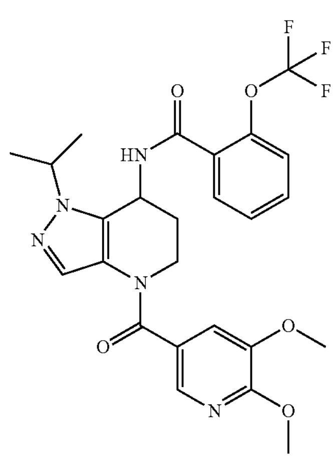 [SMILES: COc1cc(C(=O)N2CCC(NC(=O)c3ccccc3OC(F)(F)F)c3c2cnn3C(C)C)cnc1OC] | | 534.1 |

TABLE 1-continued

| Ex. No. | IUPAC Name | Structure | Salt | MS |
|---|---|---|---|---|
| 133A | N-(4-((5,6-dimethoxypyridin-3-yl)carbonyl)-1-methyl-4,5,6,7-tetrahydro-1H-pyrazolo[4,3-b]pyridin-7-yl)-2-(trifluoromethoxy)benzamide | 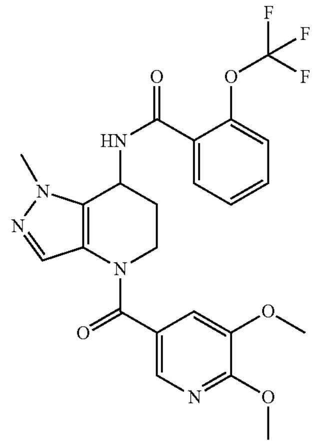 [SMILES: COc1cc(C(=O)N2CCC(NC(=O)c3ccccc3OC(F)(F)F)c3c2cnn3C)cnc1OC] | | 506.0 |
| 134A | 4-chloro-N-(4-((5-chloro-6-methoxypyridin-3-yl)carbonyl)-1-propyl-4,5,6,7-tetrahydro-1H-pyrazolo[4,3-b]pyridin-7-yl)-2-(trifluoromethyl)benzamide | 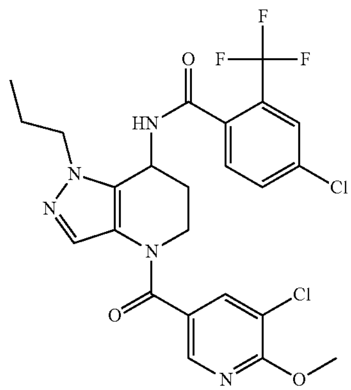 [SMILES: CCCn1ncc2c1C(NC(=O)c1ccc(Cl)cc1C(F)(F)F)CCN2C(=O)c1cnc(OC)c(Cl)c1] | | 556.0 |
| 135A | 2-chloro-N-(4-((5-chloro-6-methoxypyridin-3-yl)carbonyl)-1-propyl-4,5,6,7-tetrahydro-1H-pyrazolo[4,3-b]pyridin-7-yl)benzamide | 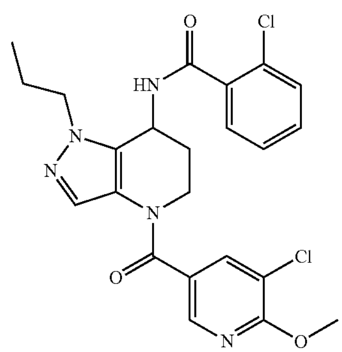 [SMILES: CCCn1ncc2c1C(NC(=O)c1ccccc1Cl)CCN2C(=O)c1cnc(OC)c(Cl)c1] | | 488.0 |
| 136A | N-(4-((5-chloro-6-methoxypyridin-3-yl)carbonyl)-1-propyl-4,5,6,7-tetrahydro-1H-pyrazolo[4,3-b]pyridin-7-yl)-2-(trifluoromethoxy)benzamide | 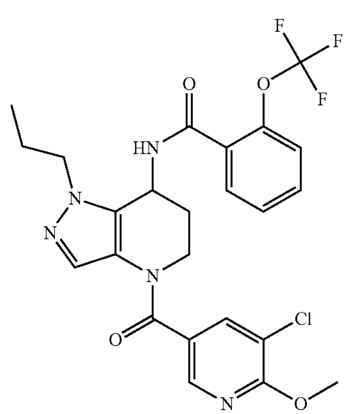 [SMILES: CCCn1ncc2c1C(NC(=O)c1ccccc1OC(F)(F)F)CCN2C(=O)c1cnc(OC)c(Cl)c1] | | 538.0 |

TABLE 1-continued

| Ex. No. | IUPAC Name | Structure | Salt | MS |
|---|---|---|---|---|
| 137A | 2-chloro-N-(1-methyl-4-((1-methyl-1H-benzimidazol-5-yl)carbonyl)-4,5,6,7-tetrahydro-1H-pyrazolo[4,3-b]pyridin-7-yl)benzamide | 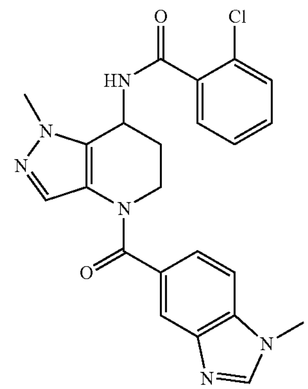 [SMILES: Cn1ncc2c1C(NC(=O)c1ccccc1Cl)CCN2C(=O)c1ccc2c(c1)ncn2C] | | 449.0 |
| 138A | N-(4-(1,3-benzothiazol-6-ylcarbonyl)-1-methyl-4,5,6,7-tetrahydro-1H-pyrazolo[4,3-b]pyridin-7-yl)-2-chlorobenzamide | 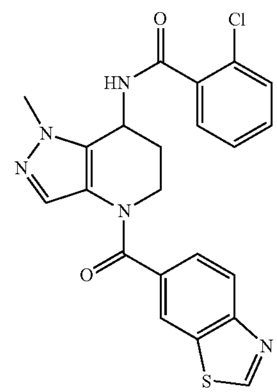 [SMILES: Cn1ncc2c1C(NC(=O)c1ccccc1Cl)CCN2C(=O)c1ccc2ncsc2c1] | | 451.9 |
| 139A | 2-chloro-N-(1-(2,2-difluoroethyl)-4-((5,6-dimethoxypyridin-3-yl)carbonyl)-4,5,6,7-tetrahydro-1H-pyrazolo[4,3-b]pyridin-7-yl)benzamide | 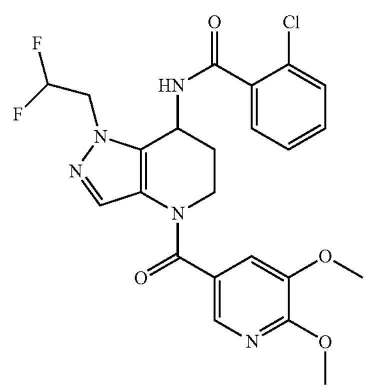 [SMILES: COc1cc(C(=O)N2CCC(NC(=O)c3ccccc3Cl)c3c2cnn3CC(F)F)cnc1OC] | | 506.0 |
| 140A | 2-chloro-N-(1-(2,2-difluoroethyl)-4-((5,6-dimethoxypryidin-3-yl)carbonyl)-4,5,6,7-tetrahydro-1H-pyrazolo[4,3-b]pyridin-7-yl)-4-fluorobenzamide | 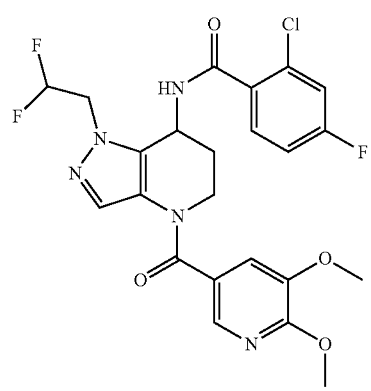 [SMILES: COc1cc(C(=O)N2CCC(NC(=O)c3ccc(F)cc3Cl)c3c2cnn3CC(F)F)cnc1OC] | | 524.0 |

TABLE 1-continued

| Ex. No. | IUPAC Name | Structure | Salt | MS |
|---|---|---|---|---|
| 141A | 4-chloro-N-(1-(2,2-difluoroethyl)-4-((5,6-dimethoxypyridin-3-yl)carbonyl)-4,5,6,7-tetrahydro-1H-pyrazolo[4,3-b]pyridin-7-yl)-2-(trifluoromethyl)benzamide | 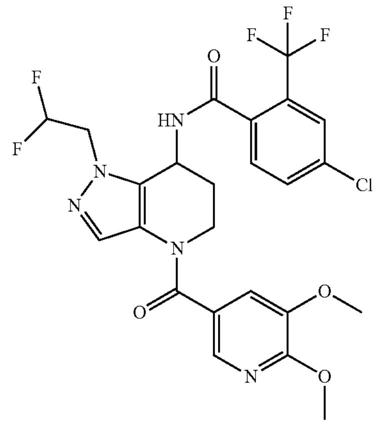 [SMILES: COc1cc(C(=O)N2CCC(NC(=O)c3ccc(Cl)cc3C(F)(F)F)c3c2cnn3CC(F)F)cnc1OC] | | 574.0 |
| 142A | N-(1-(2,2-difluoroethyl)-4-((5,6-dimethoxypyridin-3-yl)carbonyl)-4,5,6,7-tetrahydro-1H-pyrazolo[4,3-b]pyridin-7-yl)-2-(trifluoromethoxy)benzamide | 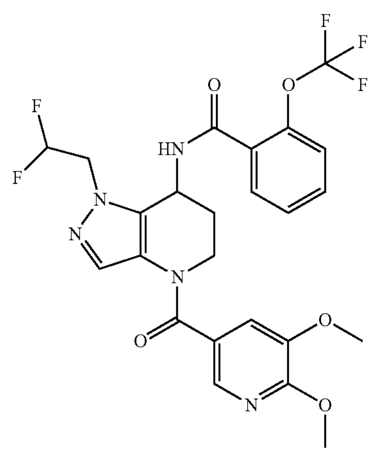 [SMILES: COc1cc(C(=O)N2CCC(NC(=O)c3ccccc3OC(F)(F)F)c3c2cnn3CC(F)F)cnc1OC] | | 556.0 |
| 144A | 2-chloro-N-(4-((5,6-dichloropyridin-3-yl)carbonyl)-1-methyl-4,5,6,7-tetrahydro-1H-pyrazolo[4,3-b]pyridin-7-yl)benzamide | 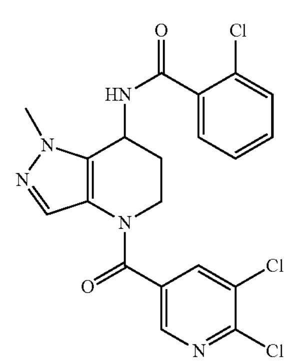 [SMILES: Cn1ncc2c1C(NC(=O)c1ccccc1Cl)CCN2C(=O)c1cnc(Cl)c(Cl)c1] | | 463.9 |

TABLE 1-continued

| Ex. No. | IUPAC Name | Structure | Salt | MS |
|---|---|---|---|---|
| 145A | N-(4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethoxy)benzamide | 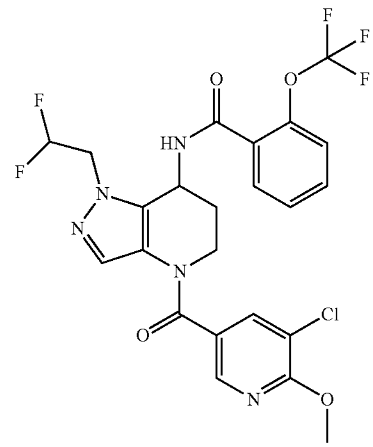 [SMILES: COc1ncc(C(=O)N2CCC(NC(=O)c3ccccc3OC(F)(F)F)c3c2cnn3CC(F)F)cc1Cl] | | 559.9 |
| 146A | 2-chloro-N-(4-((5-chloro-6-(cyclohexyloxy)pyridin-3-yl)carbonyl)-1-methyl-4,5,6,7-tetrahydro-1H-pyrazolo[4,3-b]pyridin-7-yl)benzamide | 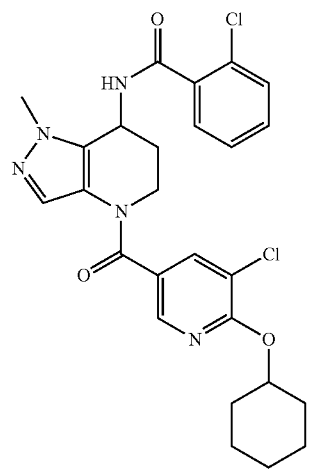 [SMILES: Cn1ncc2c1C(NC(=O)c1ccccc1Cl)CCN2C(=O)c1cnc(OC2CCCCC2)c(Cl)c1] | | 528.0 |
| 147A | 2-chloro-N-(4-((5-chloro-6-isopropoxypyridin-3-yl)carbonyl)-1-methyl-4,5,6,7-tetrahydro-1H-pyrazolo[4,3-b]pyridin-7-yl)benzamide | 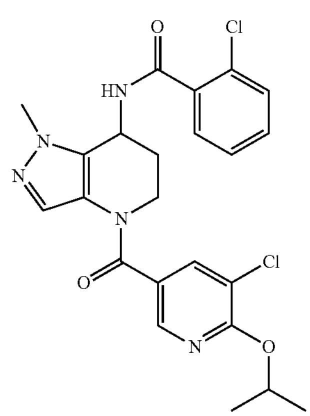 [SMILES: CC(C)Oc1ncc(C(=O)N2CCC(NC(=O)c3ccccc3Cl)c3c2cnn3C)cc1Cl] | | 486.0 |

TABLE 1-continued

| Ex. No. | IUPAC Name | Salt | MS |
|---|---|---|---|
| 149A | 2-chloro-N-(4-(3,4-dimethoxybenzoyl)-1-(2-methoxyethyl)-4,5,6,7-tetrahydro-1H-pyrazolo[4,3-b]pyridin-7-yl)benzamide | | 499.0 |
| 150A | 2-chloro-N-(4-((5-chloro-6-(2-hydroxyethoxy)pyridin-3-yl)carbonyl)-1-methyl-4,5,6,7-tetrahydro-1H-pyrazolo[4,3-b]pyridin-7-yl)benzamide | | 490.1 |
| 151A | 2-chloro-N-(4-((5-chloro-6-(methylamino)pyridin-3-yl)carbonyl)-1-methyl-4,5,6,7-tetrahydro-1H-pyrazolo[4,3-b]pyridin-7-yl)benzamide | | 459.2 |
| 152A | 2-chloro-N-(4-((5-chloro-6-(dimethylamino)pyridin-3-yl)carbonyl)-1-methyl-4,5,6,7-tetrahydro-1H-pyrazolo[4,3-b]pyridin-7-yl)benzamide | | 473.0 |

TABLE 1-continued

| Ex. No. | IUPAC Name | Structure | Salt | MS |
|---|---|---|---|---|
| 153A | 4-chloro-N-(4-((5,6-dimethoxypyridin-3-yl)carbonyl)-1-ethyl-4,5,6,7-tetrahydro-1H-pyrazolo[4,3-b]pyridin-7-yl)-2-(trifluoromethyl)benzamide | 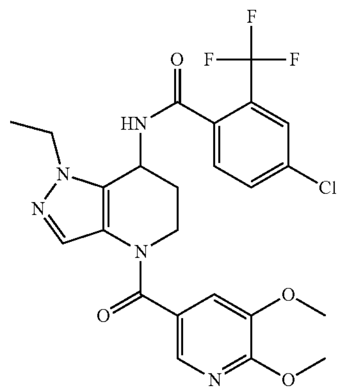 [SMILES: CCn1ncc2c1C(NC(=O)c1ccc(Cl)cc1C(F)(F)F)CCN2C(=O)c1cnc(OC)c(OC)c1] | | 538.1 |
| 154A | 2-chloro-N-(4-((5,6-dimethoxypyridin-3-yl)carbonyl)-1-ethyl-4,5,6,7-tetrrahydro-1H-pyrazolo[4,3-b]pyridin-7-yl)benzamide | 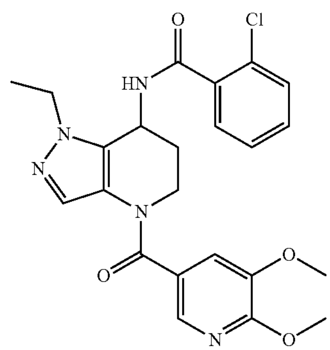 [SMILES: CCn1ncc2c1C(NC(=O)c1ccccc1Cl)CCN2C(=O)c1cnc(OC)c(OC)c1] | | 470.1 |
| 155A | N-(4-((5,6-dimethoxypyridin-3-yl)carbonyl)-1-ethyl-4,5,6,7-tetrahydro-1H-pyrazolo[4,3-b]pyridin-7-yl)-2-(trifluoromethoxy)benzamide | 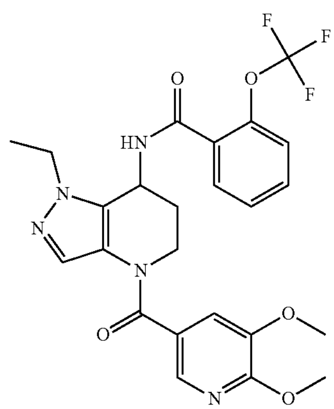 [SMILES: CCn1ncc2c1C(NC(=O)c1ccccc1OC(F)(F)F)CCN2C(=O)c1cnc(OC)c(OC)c1] | | 520.2 |
| 156A | N-(4-((5-chloro-6-methoxypyridin-3-yl)carbonyl)-1-isopropyl-4,5,6,7-tetrahydro-1H-pyrazolo[4,3-b]pyridin-7-yl)-2-(trifluoromethoxy)benzamide | 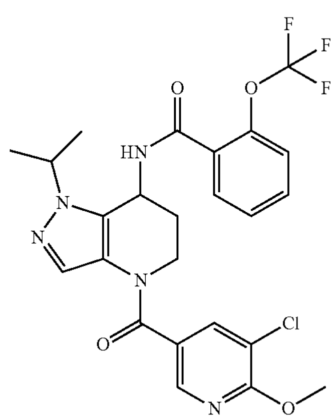 [SMILES: COc1ncc(C(=O)N2CCC(NC(=O)c3ccccc3OC(F)(F)F)c3c2cnn3C(C)C)cc1Cl] | | 538.1 |

TABLE 1-continued

| Ex. No. | IUPAC Name | Structure | Salt | MS |
|---|---|---|---|---|
| 157A | 4-chloro-N-(4-((5,6-dimethoxypyridin-3-yl)carbonyl)-1-isobutyl-4,5,6,7-tetrahydro-1H-pyrazolo[4,3-b]pyridin-7-yl)-2-(trifluoromethyl)benzamide | 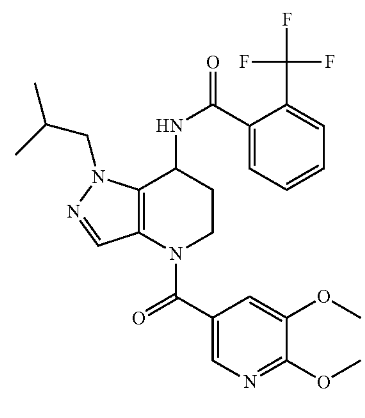 [SMILES: COc1cc(C(=O)N2CCC(NC(=O)c3ccccc3C(F)(F)F)c3c2cnn3CC(C)C)cnc1OC] | | 566.1 |
| 158A | N-(4-((5,6-dimethoxypyridin-3-yl)carbonyl)-1-isobutyl-4,5,6,7-tetrahydro-1H-pyrazolo[4,3-b]pyridin-7-yl)-2-(trifluoromethoxy)benzamide | 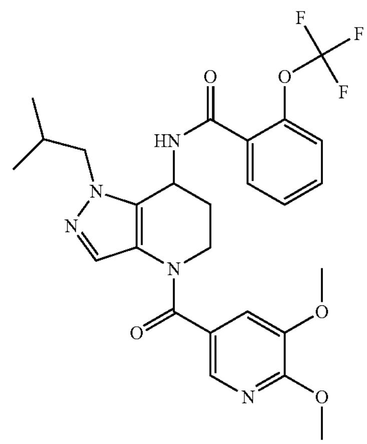 [SMILES: COc1cc(C(=O)N2CCC(NC(=O)c3ccccc3OC(F)(F)F)c3c2cnn3CC(C)C)cnc1OC] | | 548.2 |
| 159A | (N-((7R)-4-(3,4-dimethoxybenzoyl)-1-(5-((3-(4,4-difluoro-5,7-dimethyl-3a-azonia-4-bora(IV)-4H-4a-aza-s-indacene-3-yl)propanoyl)amino)pentyl)-4,5,6,7-tetrahydro-1H-pyrazolo[4,3-b]pyridin-7-yl)-2-(trifluoromethoxy)benzamide | 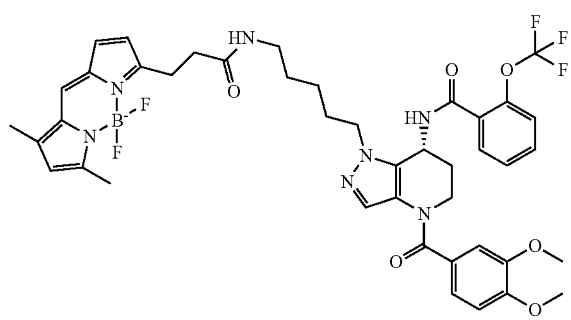 | | 850.2 |
| 160A | (N-((7S)-4-(3,4-dimethoxybenzoyl)-1-(5-((3-(4,4-difluoro-5,7-dimethyl-3a-azonia-4-bora(IV)-4H-4a-aza-s-indacene-3-yl)propanoyl)amino)pentyl)-4,5,6,7-tetrahydro-1H-pyrazolo[4,3-b]pyridin-7-yl)-2-(trifluoromethoxy)benzamide | 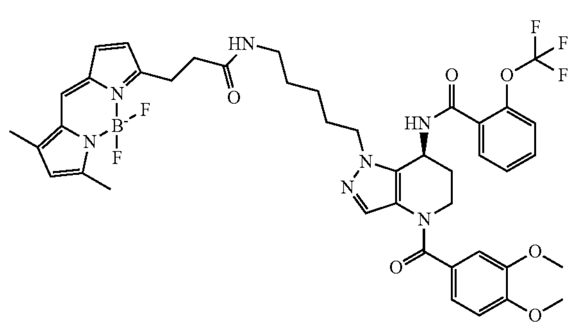 | | 850.3 |

TABLE 1-continued

| Ex. No. | IUPAC Name | Structure | Salt | MS |
|---|---|---|---|---|
| 161A | (N-(4-(3,4-dimethoxybenzoyl)-1-(5-((3-(4,4-difluoro-5,7-dimethyl-3a-azonia-4-bora(IV)-4H-4a-aza-s-indacene-3-yl)propanoyl)amino)pentyl)-4,5,6,7-tetrahydro-1H-pyrazolo[4,3-b]pyridin-7-yl)-2-(trifluoromethoxy)benzamide | 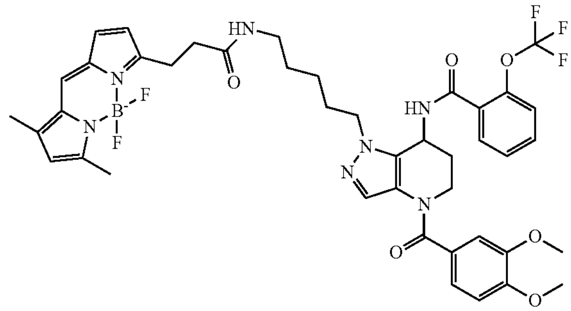 | | 850.3 |
| 162A | N-((7S)-4-((5,6-dimethoxypyridin-3-yl)carbonyl)-1-isopropyl-4,5,6,7-tetrahydro-1H-pyrazolo[4,3-b]pyridin-7-yl)-2-(trifluoromethoxy)benzamide | 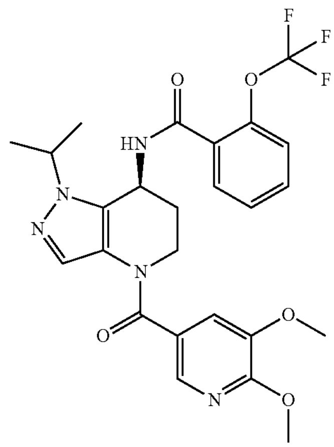 [SMILES: COc1cc(C(=O)N2CC[C@H](NC(=O)c3ccccc3OC(F)(F)F)c3c2cnn3C(C)C)cnc1OC] | | 534.2 |
| 163A | N-((7S)-1-isopropyl-4-((5-methoxy-6-oxo-1,6-dihydropyridin-3-yl)carbonyl)-4,5,6,7-tetrahydro-1H-pyrazolo[4,3-b]pyridin-7-yl)-2-(trifluoromethoxy)benzamide | 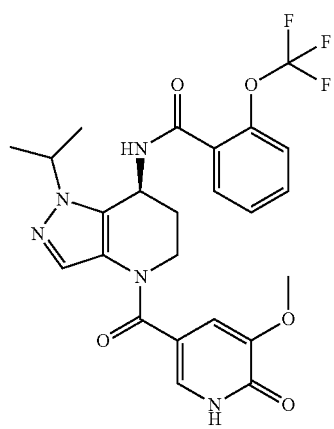 [SMILES: COc1cc(C(=O)N2CC[C@H](NC(=O)c3ccccc3OC(F)(F)F)c3c2cnn3C(C)C)c[nH]c1=O] | | 520.2 |
| 164A | 4-chloro-N-((7R)-4-((5,6-dimethoxypyridin-3-yl)carbonyl)-1-ethyl-4,5,6,7-tetrahydro-1H-pyrazolo[4,3-b]pyridin-7-yl)-2-(trifluoromethyl)benzamide | 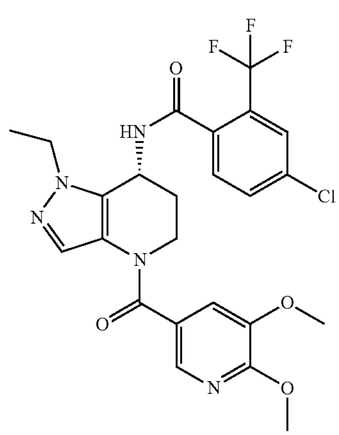 [SMILES: CCn1ncc2c1[C@H](NC(=O)c1ccc(Cl)cc1C(F)(F)F)CCN2C(=O)c1cnc(OC)c(OC)c1] | | 538.1 |

TABLE 1-continued

| Ex. No. | IUPAC Name | Structure | Salt | MS |
|---|---|---|---|---|
| 165A | 4-chloro-N-((7S)-4-((5,6-dimethoxypyridin-3-yl)carbonyl)-1-ethyl-4,5,6,7-tetrahydro-1H-pyrazolo[4,3-b]pyridin-7-yl)-2-(trifluoromethyl)benzamide | 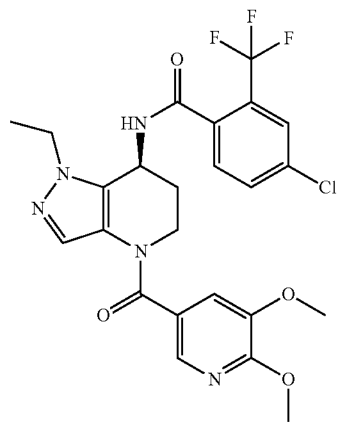 [SMILES: CCn1ncc2c1[C@@H](NC(=O)c1ccc(Cl)cc1C(F)(F)F)CCN2C(=O)c1cnc(OC)c(OC)c1] | | 538.1 |
| 166A | N-((7S)-4-((6-(difluoromethoxy)-5-methoxypyridin-3-yl)carbonyl)-1-isopropyl-4,5,6,7-tetrahydro-1H-pyrazolo[4,3-b]pyridin-7-yl)-2-(trifluoromethoxy)benzamide | 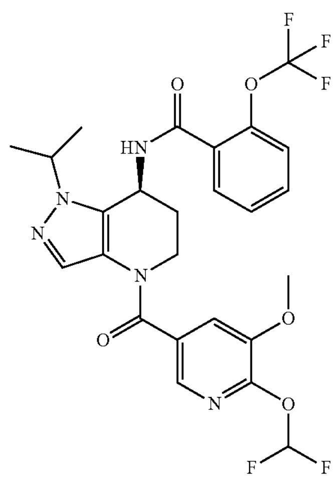 [SMILES: COc1cc(C(=O)N2CC[C@H](NC(=O)c3ccccc3OC(F)(F)F)c3c2cnn3C(C)C)cnc1OC(F)F] | | 570.2 |
| 167A | N-(1-cyclobutyl-4-(3,4-dimethoxybenzoyl)-4,5,6,7-tetrahydro-1H-pyrazolo[4,3-b]pyridin-7-yl)-2-(trifluoromethoxy)benzamide | 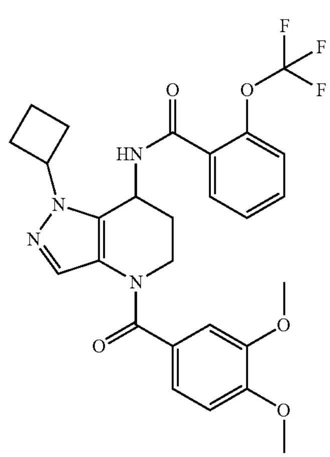 [SMILES: COc1ccc(C(=O)N2CCC(NC(=O)c3ccccc3OC(F)(F)F)c3c2cnn3C2CCC2)cc1OC] | | 545.2 |

TABLE 1-continued

| Ex. No. | IUPAC Name | Structure | Salt | MS |
|---|---|---|---|---|
| 168A | N-(4-(3,4-dimethoxybenzoyl)-1-(1-(2,2,2-trifluoroethyl)acetidin-3-yl)-4,5,6,7-tetrahydro-1H-pyrazolo[4,3-b]pyridin-7-yl)-2-(trifluoromethoxy)benzamide | 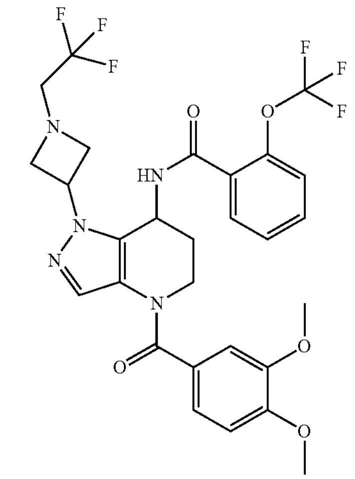 [SMILES: COc1ccc(C(=O)N2CCC(NC(=O)c3ccccc3OC(F)(F)F)c3c2cnn3C2CN(CC(F)(F)F)C2)cc1OC] | | 628.4 |
| 169A | N-(4-((5,6-dimethoxypyridin-3-yl)carbonyl)-1-methyl-4,5,6,7-tetrahydro-1H-pyrazolo[4,3-b]pyridin-7-yl)-1-methyl-3-(trifluoromethyl)-1H-pyrazole-5-carboxamide | 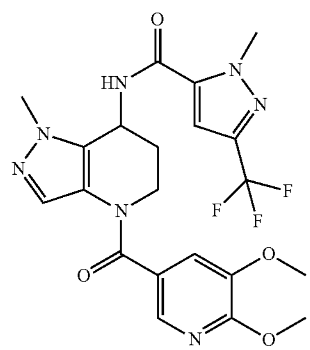 [SMILES: COc1cc(C(=O)N2CCC(NC(=O)c3cc(C(F)(F)F)nn3C)c3c2cnn3C)cnc1OC] | | 494.0 |
| 170A | 4-chloro-N-((7S)-4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethyl)benzamide | 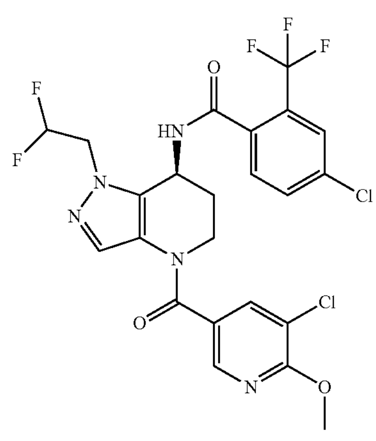 [SMILES: COc1ncc(C(=O)N2CC[C@H](NC(=O)c3ccc(Cl)cc3C(F)(F)F)c3c2cnn3CC(F)F)cc1Cl] | | 578.1 |

TABLE 1-continued

| Ex. No. | IUPAC Name | Structure | Salt | MS |
|---|---|---|---|---|
| 171A | N-((7S)-4-((5,6-dimethoxypyridin-3-yl)carbonyl)-1-methyl-4,5,6,7-tetrahydro-1H-pyrazolo[4,3-b]pyridin-7-yl)-2-(trifluoromethoxy)benzamide | 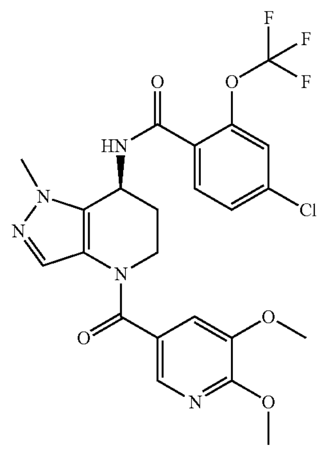 [SMILES: COc1cc(C(=O)N2CC[C@H](NC(=O)c3ccc(Cl)cc3OC(F)(F)F)c3c2cnn3C)cnc1OC] | | 506.2 |
| 172A | 2-chloro-N-(7-(3,4-dimethoxybenzoyl)-1,3-dimethyl-4,5,6,7-tetrahydro-1H-pyrazolo[3,4-b]pyridin-4-yl)benzamide | 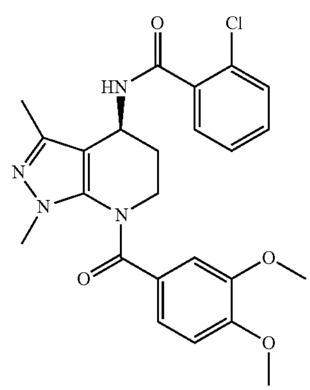 [SMILES: COc1ccc(C(=O)N2CC[C@H](NC(=O)c3ccccc3Cl)c3c(C)nn(C)c32)cc1OC] | | 469.2 |
| 173A | tert-butyl (5-(4-(3,4-dimethoxybenzoyl)-7-((2-(trifluoromethoxy)benzoyl)amino)-4,5,6,7-tetrahydro-1H-pyrazolo[4,3-b]pyridin-1-yl)pentyl)carbamate | 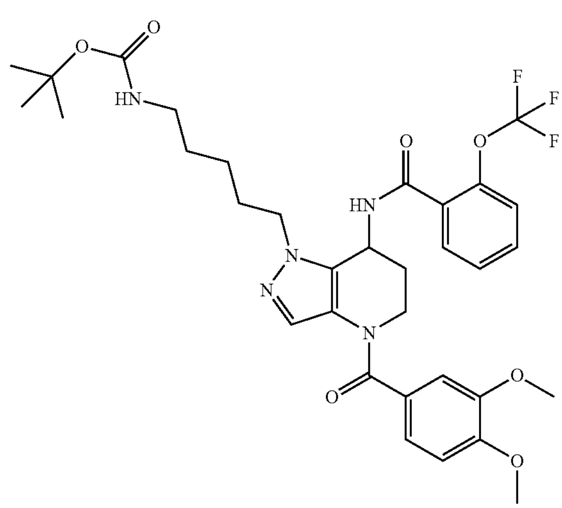 [SMILES: COc1ccc(C(=O)N2CCC(NC(=O)c3ccccc3OC(F)(F)F)c3c2cnn3CCCCCNC(=O)OC(C)(C)C)cc1OC] | | 676.4 |

TABLE 1-continued

| Ex. No. | IUPAC Name | Structure | Salt | MS |
|---|---|---|---|---|
| 174A | N-(1-(cyclopropylmethyl)-4-(3,4-dimethoxybenzoyl)-4,5,6,7-tetrahydro-1H-pyrazolo[4,3-b]pyridin-7-yl)-2-(trifluoromethoxy)benzamide | 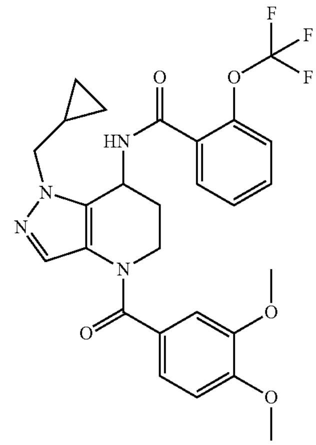 [SMILES: COc1ccc(C(=O)N2CCC(NC(=O)c3ccccc3OC(F)(F)F)c3c2cnn3CC2CC2)cc1OC] | | 545.2 |
| 175A | N-(4-(3,4-dimethoxybenzoyl)-1-((1-fluorocyclopropyl)methyl)-4,5,6,7-tetrahydro-1H-pyrazolo[4,3-b]pyridin-7-yl)-2-(trifluoromethoxy)benzamide | 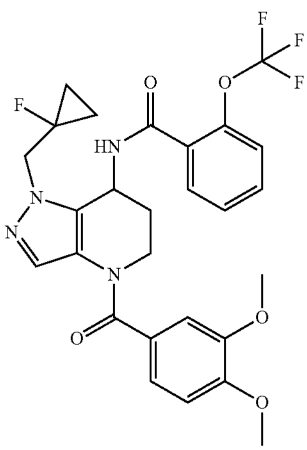 [SMILES: COc1ccc(C(=O)N2CCC(NC(=O)c3ccccc3OC(F)(F)F)c3c2cnn3CC2(F)CC2)cc1OC] | | 563.1 |
| 176A | N-(1-(5-aminopentyl)-4-(3,4-dimethoxybenzoyl)-4,5,6,7-tetrahydro-1H-pyrazolo[4,3-b]pyridin-7-yl)-2-(trifluoromethoxy)benzamide | 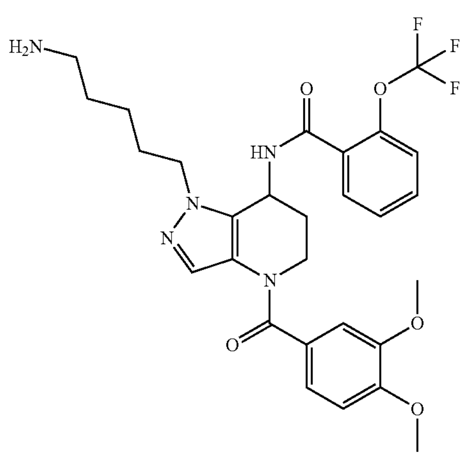 [SMILES: COc1ccc(C(=O)N2CCC(NC(=O)c3ccccc3OC(F)(F)F)c3c2cnn3CCCCCN)cc1OC] | 2HCl | 576.2 |

TABLE 1-continued

| Ex. No. | IUPAC Name | Structure | Salt | MS |
|---|---|---|---|---|
| 177A | N-((7R)-4-(5,6-dimethoxypyridin-3-yl)carbonyl)-1-methyl-4,5,6,7-tetrahydro-1H-pyrazolo[4,3-b]pyridin-7-yl)-2-(trifluoromethoxy)benzamide | 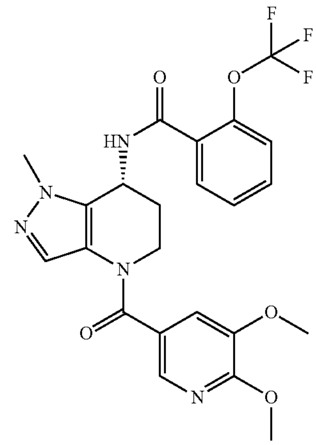 [SMILES: COc1cc(C(=O)N2CC[C@@H](NC(=O)c3ccccc3OC(F)(F)F)c3c2cnn3C)cnc1OC] | | 506.2 |
| 178A | N-((7S)-4-((5,6-dimethoxypyridin-3-yl)carbonyl)-1-ethyl-4,5,6,7-tetrahydro-1H-pyrazolo[4,3-b]pyridin-7-yl)-2-(trifluoromethoxy)benzamide | 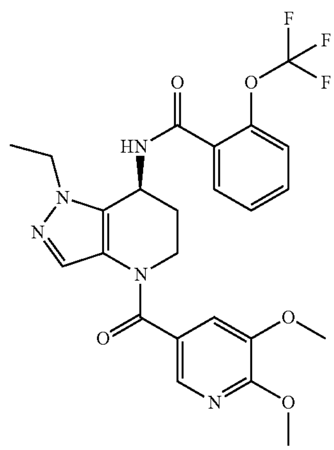 [SMILES: CCn1ncc2c1[C@@H](NC(=O)c1ccccc1OC(F)(F)F)CCN2C(=O)c1cnc(OC)c(OC)c1] | | 520.2 |
| 179A | N-((7R)-4-((5,6-dimethoxypyridin-3-yl)carbonyl)-1-ethyl-4,5,6,7-tetrahydro-1H-pyrazolo[4,3-b]pyridin-7-yl)-2-(trifluoromethoxy)benzamide | 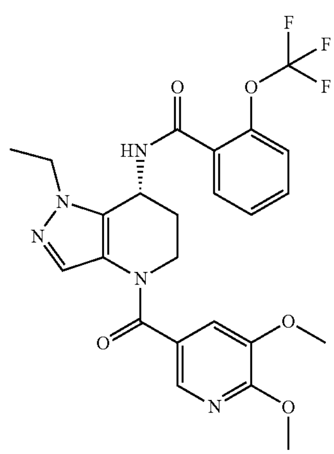 [SMILES: CCn1ncc2c1[C@H](NC(=O)c1ccccc1OC(F)(F)F)CCN2C(=O)c1cnc(OC)c(OC)c1] | | 520.2 |

TABLE 1-continued

| Ex. No. | IUPAC Name | Structure | Salt | MS |
|---|---|---|---|---|
| 180A | N-((7R)-4-((5,6-dimethoxypyridin-3-yl)carbonyl)-1-isopropyl-4,5,6,7-tetrahydro-1H-pyrazolo[4,3-b]pyridin-7-yl)-2-(trifluoromethoxy)benzamide | 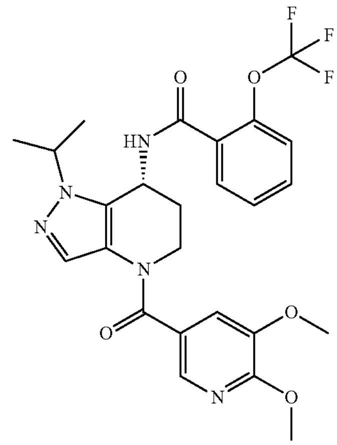 | | 534.1 |
| 181A | 9H-fluoren-9-ylmethyl (5-(4-(3,4-dimethoxybenzoyl)-7-((2-(trifluoromethoxy)benzoyl)amino)-4,5,6,7-tetrahydro-1H-pyrazolo[4,3-b]pyridin-1-yl)pentyl)carbamate | 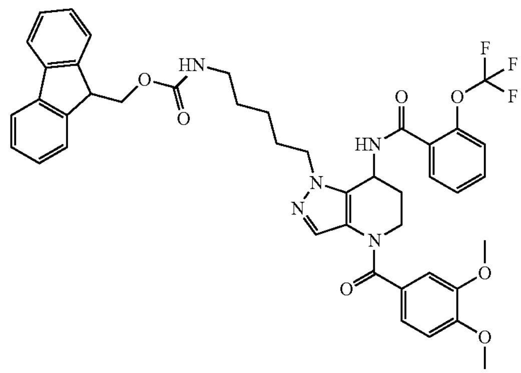 [SMILES: COc1ccc(C(=O)N2CCC(NC(=O)c3ccccc3OC(F)(F)F)c3c2cnn3CCCCCNC(=O)OCC2c3ccccc3-c3ccccc32)cc1OC] | | 798.4 |
| 182A | 2-chloro-N-(4-((5-chloro-6-ethoxypyridin-3-yl)carbonyl)-1-methyl-4,5,6,7-tetrahydro-1H-pyrazolo[4,3-b]pyridin-7-yl)benzamide | 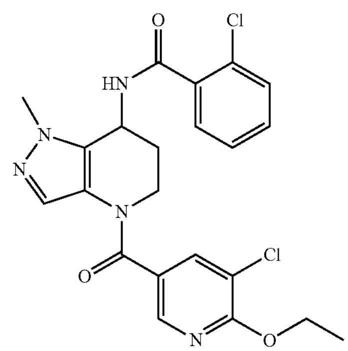 [SMILES: CCOc1ncc(C(=O)N2CCC(NC(=O)c3ccccc3Cl)c3c2cnn3C)cc1Cl] | | 473.9 |
| 183A | 4-chloro-N-(4-((5-chloro-6-oxo-1,6-dihydropyridin-3-yl)carbonyl)-1-isopropyl-4,5,6,7-tetrahydro-1H-pyrazolo[4,3-b]pyridin-7-yl)-2-(trifluoromethyl)benzamide | 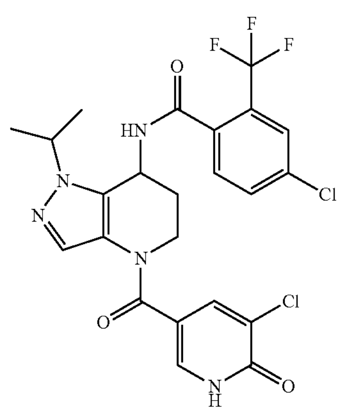 [SMILES: CC(C)n1ncc2c1C(NC(=O)c1ccc(Cl)cc1C(F)(F)F)CCN2C(=O)c1c[nH]c(=O)c(Cl)c1] | | 542.1 |

TABLE 1-continued

| Ex. No. | IUPAC Name | Structure | Salt | MS |
|---|---|---|---|---|
| 184A | 4-chloro-N-((7R)-4-((5-chloro-6-methoxypyridin-3-yl)carbonyl)-1-(2,2-difluoroethyl)-4,5,6,7-tetrahydro-1H-pyrazolo[4,3-b]pyridin-7-yl)-2-(trifluoromethyl)benzamide | 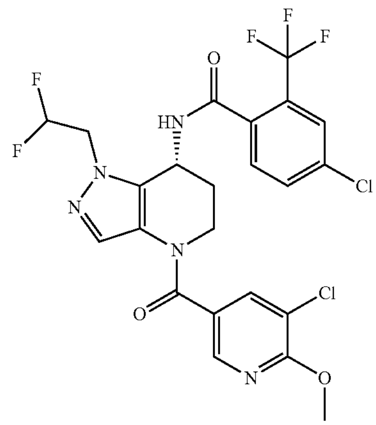 [SMILES: COc1ncc(C(=O)N2CC[C@@H](NC(=O)c3ccc(Cl)cc3C(F)(F)F)c3c2cnn3CC(F)F)cc1Cl] | | 578.1 |
| 185A | 4-chloro-N-(4-((5,6-dimethoxypyridin-3-yl)carbonyl)-1-propyl-4,5,6,7-tetrahydro-1H-pyrazolo[4,3-b]pyridin-7-yl)-2-(trifluoromethyl)benzamide | 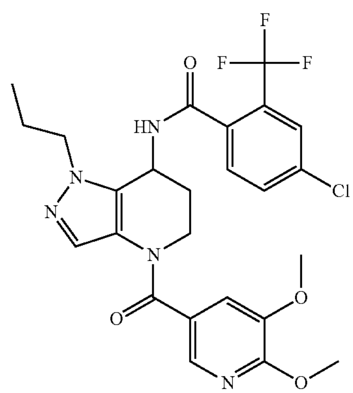 [SMILES: CCCn1ncc2c1C(NC(=O)c1ccc(Cl)cc1C(F)(F)F)CCN2C(=O)c1cnc(OC)c(OC)c1] | | 552.1 |
| 186A | 2-chloro-N-(4-(3,4-dimethoxybenzoyl)-1-(3-hydroxy-3-methylbutyl)-4,5,6,7-tetrahydro-1H-pyrazolo[4,3-b]pyridin-7-yl)benzamide | 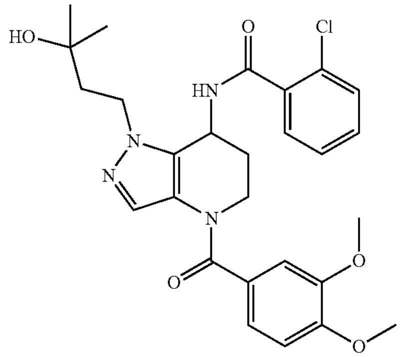 [SMILES: COc1ccc(C(=O)N2CCC(NC(=O)c3ccccc3Cl)c3c2cnn3CCC(C)(C)O)cc1OC] | | 527.2 |

TABLE 1-continued

| Ex. No. | IUPAC Name | Structure | Salt | MS |
|---|---|---|---|---|
| 188A | 2-chloro-N-(4-(3,4-dimethoxybenzoyl)-1-octadecyl-4,5,6,7-tetrahydro-1H-pyrazolo[4,3-b]pyridin-7-yl)benzamide | 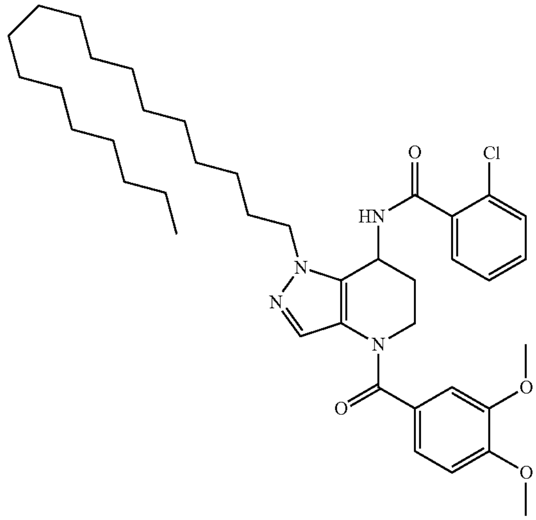 [SMILES: CCCCCCCCCCCCCCCCCCn1ncc2c1C(NC(=O)c1ccccc1Cl)CCN2C(=O)c1ccc(OC)c(OC)c1] | | 693.4 |
| 191A | 2-chloro-N-(4-(3,4-dimethoxybenzoyl)-1-isobutyl-4,5,6,7-tetrahydro-1H-pyrazolo[4,3-b]pyridin-7-yl)benzamide | 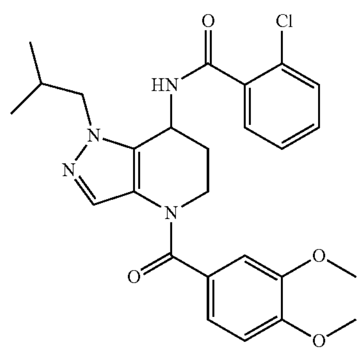 [SMILES: COc1ccc(C(=O)N2CCC(NC(=O)c3ccccc3Cl)c3c2cnn3CC(C)C)cc1OC] | | 497.2 |
| 192A | N-(4-((5,6-dimethoxypyridin-3-yl)carbonyl)-1,3-dimethyl-4,5,6,7-tetrahydro-1H-pyrazolo[4,3-b]pyridin-7-yl)-2-(trifluoromethoxy)benzamide | 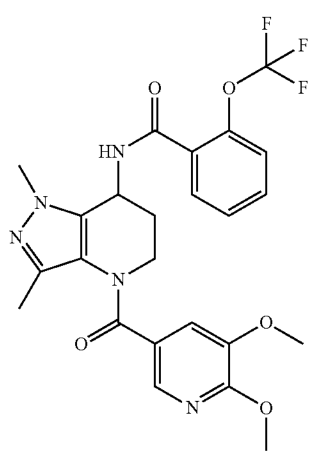 [SMILES: COc1cc(C(=O)N2CCC(NC(=O)c3ccccc3OC(F)(F)F)c3c2c(C)nn3C)cnc1OC] | | 520.2 |

TABLE 1-continued

| Ex. No. | IUPAC Name | Structure | Salt | MS |
|---|---|---|---|---|
| 193A | 2-chloro-N-(7-(3,4-dimethoxybenzoyl)-1-methyl-4,5,6,7-tetrahydro-1H-pyrazolo[3,4-b]pyridin-4-yl)benzamide | 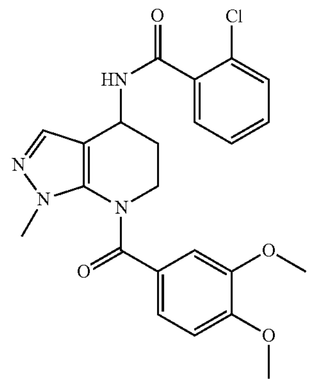 [SMILES: COc1ccc(C(=O)N2CCC(NC(=O)c3ccccc3Cl)c3cnn(C)c32)cc1OC] | | 455.1 |
| 195A | N-(7-chloro-1-(3,4-dimethoxybenzoyl)-1,2,3,4-tetrahydroquinolin-4-yl)benzamide | 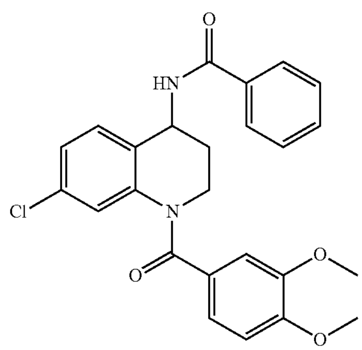 [SMILES: COc1ccc(C(=O)N2CCC(NC(=O)c3ccccc3)c3ccc(Cl)cc32)cc1OC] | | 451.1 |
| 197A | N-(7-chloro-1-(3,4-dimethoxybenzoyl)-1,2,3,4-tetrahydroquinolin-4-yl)pyridine-2-carboxamide | 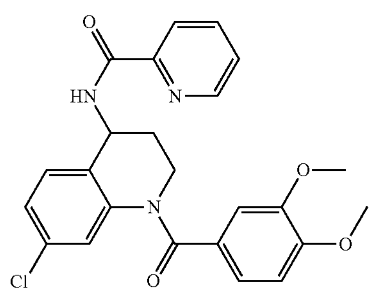 [SMILES: COc1ccc(C(=O)N2CCC(NC(=O)c3ccccn3)c3ccc(Cl)cc32)cc1OC] | CF3COOH | 452.0 |
| 198A | N-(7-chloro-1-(3,4-dimethoxybenzoyl)-1,2,3,4-tetrahydroquinolin-4-yl)thiophene-2-carboxamide | 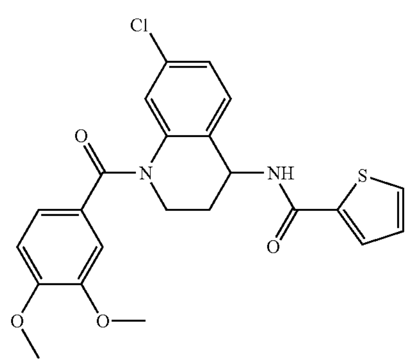 [SMILES: COc1ccc(C(=O)N2CCC(NC(=O)c3cccs3)c3ccc(Cl)cc32)cc1OC] | | 457.0 |

TABLE 1-continued

| Ex. No. | IUPAC Name | Structure | Salt | MS |
|---|---|---|---|---|
| 199A | N-(7-chloro-1-(3,4-dimethoxybenzoyl)-1,2,3,4-tetrahydroquinolin-4-yl)-1,3-thiazole-2-carboxamide | 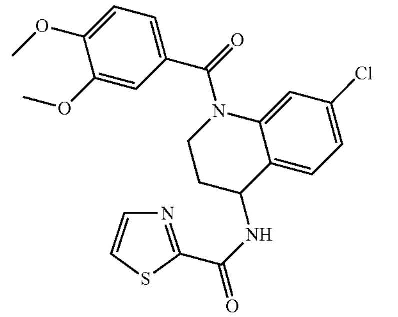 [SMILES: COc1ccc(C(=O)N2CCC(NC(=O)c3nccs3)c3ccc(Cl)cc32)cc1OC] | | 458.0 |
| 200A | N-(7-chloro-1-(3,4-dimethoxybenzoyl)-1,2,3,4-tetrahydroquinolin-4-yl)-4-methoxybenzamide | 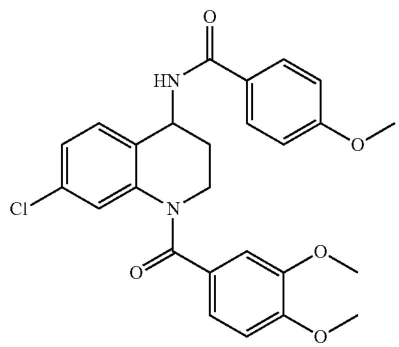 [SMILES: COc1ccc(C(=O)NC2CCN(C(=O)c3ccc(OC)c(OC)c3)c3cc(Cl)ccc32)cc1] | | 481.1 |
| 201A | 2-chloro-N-(7-chloro-1-(3,4-dimethoxybenzoyl)-1,2,3,4-tetrahydroquinolin-4-yl) benzamide | 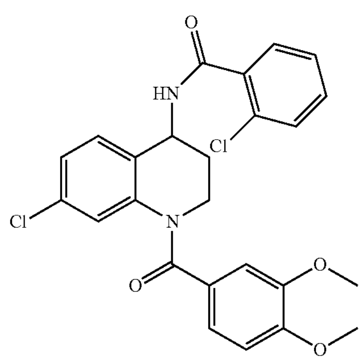 [SMILES: COc1ccc(C(=O)N2CCC(NC(=O)c3ccccc3Cl)c3ccc(Cl)cc32)cc1OC] | | 485.1 |
| 202A | N-(7-chloro-1-(3,4-dimethoxybenzoyl)-1,2,3,4-tetrahydroquinolin-4-yl)-4-(trifluoromethyl)benzamide | 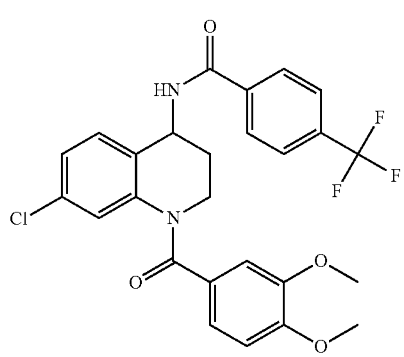 [SMILES: COc1ccc(C(=O)N2CCC(NC(=O)c3ccc(C(F)(F)F)cc3)c3ccc(Cl)cc32)cc1OC] | | 519.1 |

TABLE 1-continued

| Ex. No. | IUPAC Name | Salt | MS |
|---|---|---|---|
| 203A | N-(7-chloro-1-(3,4-dimethoxybenzoyl)-1,2,3,4-tetrahydroquinolin-4-yl)-6-(trifluoromethyl)nicotinamide | CF3COOH | 518.1 |
| 204A | 2-chloro-N-(1-(3,4-dimethoxybenzoyl)-1,2,3,4-tetrahydroquinolin-4-yl)benzamide | | 451.1 |
| 205A | N-(1-benzoyl-7-chloro-1,2,3,4-tetrahydroquinolin-4-yl)-2-chlorobenzamide | | 425.0 |
| 206A | 2-chloro-N-(7-chloro-1-(4-(trifluoromethoxy)benzoyl)-1,2,3,4-tetrahydroquinolin-4-yl)benzamide | | 509.1 |

TABLE 1-continued

| Ex. No. | IUPAC Name | Structure | Salt | MS |
|---|---|---|---|---|
| 207A | 2-chloro-N-(7-chloro-1-(2-furoyl)-1,2,3,4-tetrahydroquinolin-4-yl)benzamide | 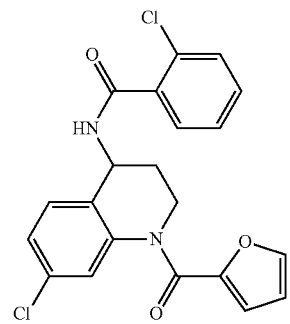 [SMILES: O=C(NC1CCN(C(=O)c2ccco2)c2cc(Cl)ccc21)c1ccccc1Cl] | | 414.9 |
| 208A | 2-chloro-N-(7-chloro-1-(1,2-oxazol-5-ylcarbonyl)-1,2,3,4-tetrahydroquinolin-4-yl)benzamide | 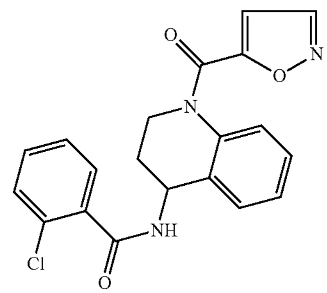 [SMILES: O=C(NC1CCN(C(=O)c2ccno2)c2ccccc21)c1ccccc1Cl] | | 416.0 |
| 209A | 2-chloro-N-(7-chloro-1-(pyridin-3-ylcarbonyl)-1,2,3,4-tetrahydroquinolin-4-yl)benzamide | 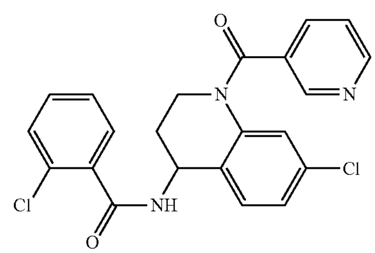 [SMILES: O=C(NC1CCN(C(=O)c2cccnc2)c2cc(Cl)ccc21)c1ccccc1Cl] | CF3COOH | 426.0 |
| 210A | 2-chloro-N-(7-chloro-1-(1,3-thiazol-2-ylcarbonyl)-1,2,3,4-tetrahydroquinolin-4-yl)benzamide | 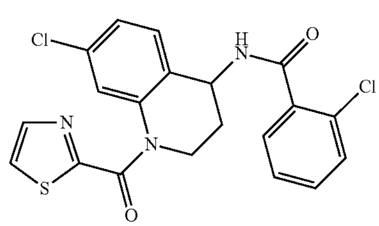 [SMILES: O=C(NC1CCN(C(=O)c2nccs2)c2cc(Cl)ccc21)c1ccccc1Cl] | | 432.0 |
| 211A | 2-chloro-N-(7-chloro-1-((1,3-dimethyl-1H-pyrazol-5-yl)carbonyl)-1,2,3,4-tetrahydroquinolin-4-yl)benzamide | 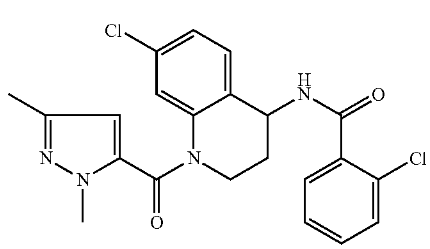 [SMILES: Cc1cc(C(=O)N2CCC(NC(=O)c3ccccc3Cl)c3ccc(Cl)cc32)n(C)n1] | | 443.1 |

TABLE 1-continued

| Ex. No. | IUPAC Name | Structure | Salt | MS |
|---|---|---|---|---|
| 212A | 2-chloro-N-(7-chloro-1-(4-fluorobenzoyl)-1,2,3,4-tetrahydroquinolin-4-yl)benzamide | 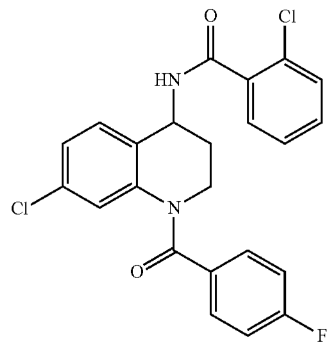 [SMILES: O=C(NC1CCN(C(=O)c2ccc(F)cc2)c2cc(Cl)ccc21)c1ccccc1Cl] | | 443.1 |
| 213A | 2-chloro-N-(7-chloro-1-(pyridin-3-ylcarbonyl)-1,2,3,4-tetrahydroquinolin-4-yl)benzamide | 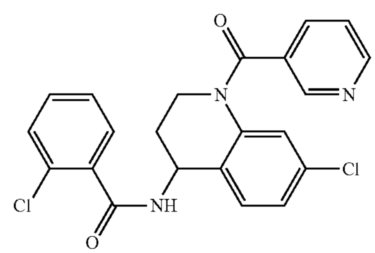 [SMILES: O=C(NC1CCN(C(=O)c2cccnc2)c2cc(Cl)ccc21)c1ccccc1Cl] | | 426.0 |
| 214A | 2-chloro-N-(7-chloro-1-(4-methoxybenzoyl)-1,2,3,4-tetrahydroquinolin-4-yl)benzamide | 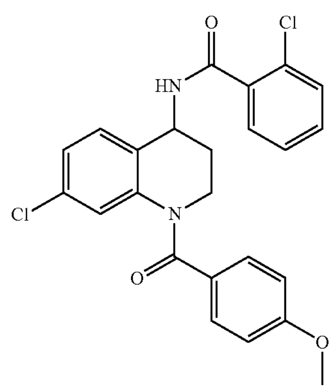 [SMILES: COc1ccc(C(=O)N2CCC(NC(=O)c3ccccc3Cl)c3ccc(Cl)cc32)cc1] | | 455.1 |
| 215A | 2-chloro-N-(7-chloro-1-(3-methoxybenzoyl)-1,2,3,4-tetrahydroquinolin-4-yl)benzamide | 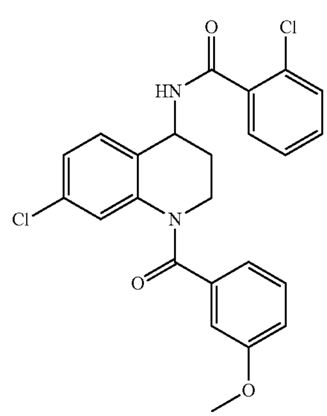 [SMILES: COc1cccc(C(=O)N2CCC(NC(=O)c3ccccc3Cl)c3ccc(Cl)cc32)c1] | | 455.1 |

TABLE 1-continued

| Ex. No. | IUPAC Name | Structure | Salt | MS |
|---|---|---|---|---|
| 216A | 2-chloro-N-(7-chloro-1-(2-methoxybenzoyl)-1,2,3,4-tetrahydroquinolin-4-yl)benzamide | 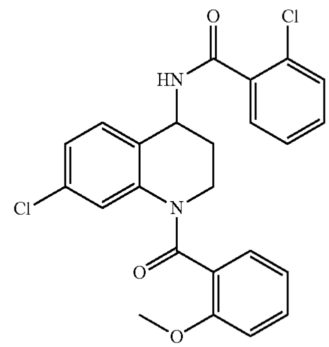 [SMILES: COc1ccccc1C(=O)N1CCC(NC(=O)c2ccccc2Cl)c2ccc(Cl)cc21] | | 455.1 |
| 217A | 2-chloro-N-(7-chloro-1-(3,4-dimethoxybenzoyl)-1,2,3,4-tetrahydro-1,8-naphthyridin-4-yl)benzamide | 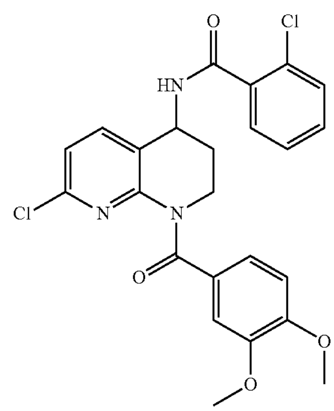 [SMILES: COc1ccc(C(=O)N2CCC(NC(=O)c3ccccc3Cl)c3ccc(Cl)nc32)cc1OC] | | 486.1 |
| 218A | 2-chloro-N-(7-chloro-1-((6-chloropyridin-3-yl)carbonyl)-1,2,3,4-tetrahydro-1,8-naphthyridin-4-yl)benzamide | 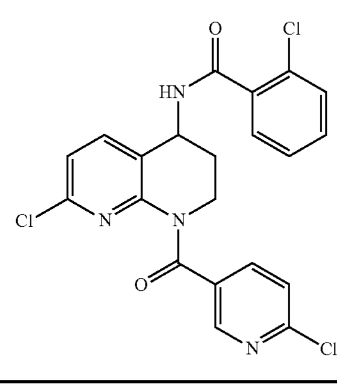 | | 461.1 |

TABLE 2-1

| Ex. No. | IUPAC Name | Structure | Salt | MS |
|---|---|---|---|---|
| 1B | 2-chloro-N-((3R,4S)-1-(3,4-dimethoxybenzoyl)-3-phenylpiperidin-4-yl)benzamide | 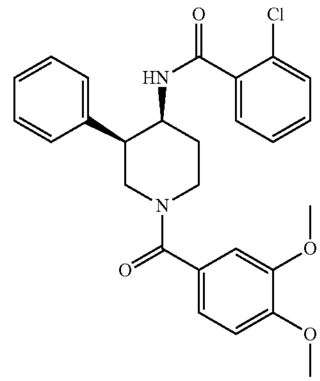 [SMILES: COc1ccc(C(=O)N2CC[C@H](NC(=O)c3ccccc3Cl)[C@H](c3ccccc3)C2)cc1OC] | | 479.0 |
| 2B | 2-chloro-N-((3S,4R)-1-(3,4-dimethoxybenzoyl)-3-phenylpiperidin-4-yl)benzamide | 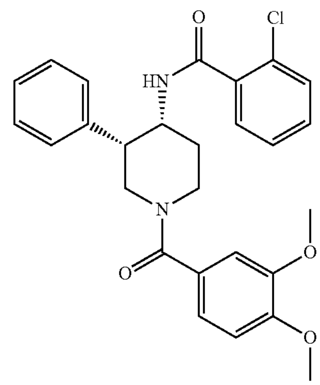 [SMILES: COc1ccc(C(=O)N2CC[C@@H](NC(=O)c3ccccc3Cl)[C@@H](c3ccccc3)C2)cc1OC] | | 479.0 |
| 3B | 2-chloro-N-((3R,4R)-1-(3,4-dimethoxybenzoyl)-3-phenylpiperidin-4-yl)benzamide | 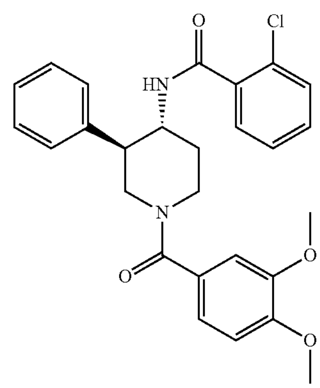 [SMILES: COc1ccc(C(=O)N2CC[C@@H](NC(=O)c3ccccc3Cl)[C@H](c3ccccc3)C2)cc1OC] | | 479.0 |
| 4B | 2-chloro-N-(trans-1-(3,4-dimethoxybenzoyl)-3-phenylpiperidin-4-yl)benzamide | 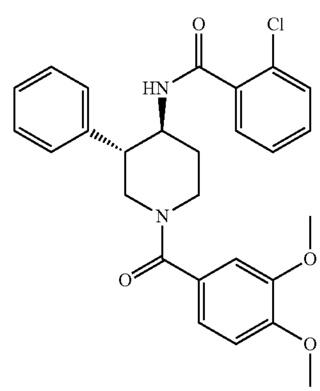 [SMILES: COc1ccc(C(=O)N2CC[C@H](NC(=O)c3ccccc3Cl)[C@@H](c3ccccc3)C2)cc1OC] | | 479.0 |

TABLE 2-1-continued

| Ex. No. | IUPAC Name | Structure | Salt | MS |
|---|---|---|---|---|
| 5B | 2-chloro-N-((3R,4R)-3-(3,4-dichlorophenyl)-1-(3,4-dimethoxybenzoyl)piperidin-4-yl)benzamide | 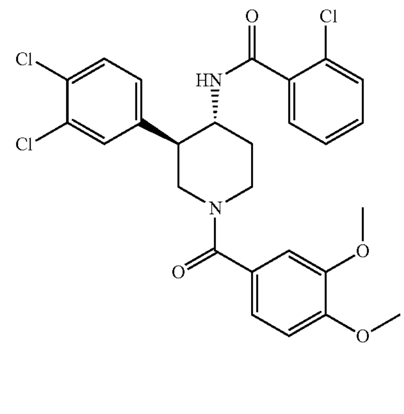 [SMILES: COc1ccc(C(=O)N2CC[C@@H](NC(=O)c3ccccc3Cl)[C@H](c3ccc(Cl)c(Cl)c3)C2)cc1OC] | | 546.8 |
| 6B | 2-chloro-N-(trans-1-(3,4-dimethoxybenzoyl)-3-(4-methylphenyl)piperidin-4-yl)benzamide | 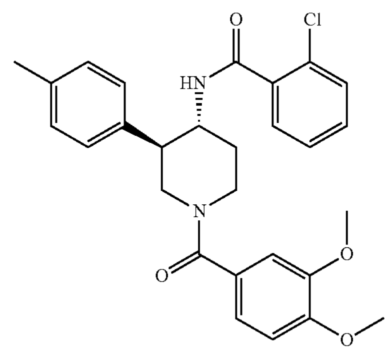 | | 493.1 |
| 7B | 2-chloro-N-(trans-3-(4-chlorophenyl)-1-(3,4-dimethoxybenzoyl)piperidin-4-yl)benzamide | 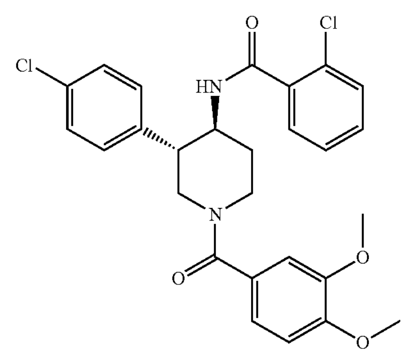 [SMILES: COc1ccc(C(=O)N2CC[C@H](NC(=O)c3ccccc3Cl)[C@@H](c3ccc(Cl)cc3)C2)cc1OC] | | 512.9 |
| 8B | 2-chloro-N-(trans-3-(3,5-dichlorophenyl)-1-(3,4-dimethoxybenzoyl)piperidin-4-yl)benzamide | 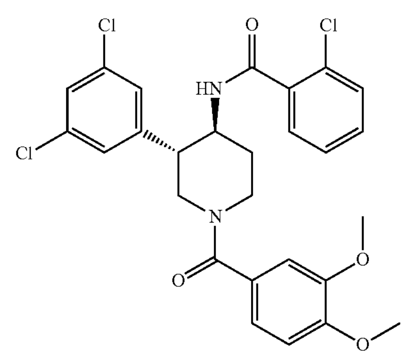 [SMILES: COc1ccc(C(=O)N2CC[C@H](NC(=O)c3ccccc3Cl)[C@@H](c3cc(Cl)cc(Cl)c3)C2)cc1OC] | | 546.9 |

TABLE 2-1-continued

| Ex. No. | IUPAC Name | Structure | Salt | MS |
|---|---|---|---|---|
| 9B | 2-chloro-N-(trans-3-(3-chloro-4-fluorophenyl)-1-(3,4-dimethoxybenzoyl)piperidin-4-yl)benzamide | 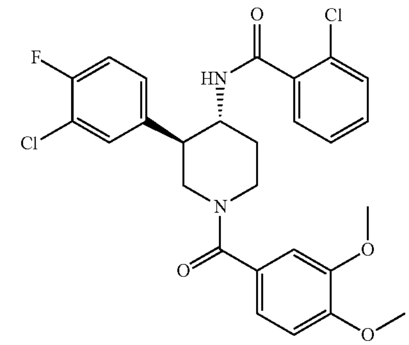 [SMILES: COc1ccc(C(=O)N2CC[C@@H](NC(=O)c3ccccc3Cl)[C@H](c3ccc(F)c(Cl)c3)C2)cc1OC] | | 531.0 |
| 10B | 2-chloro-N-(trans-1-(3,4-dimethoxybenzoyl)-3-(4-methoxyphenyl)piperidin-4-yl)benzamide | 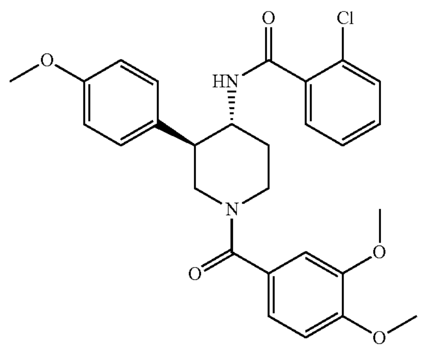 | | 509.1 |
| 11B | 2-chloro-N-(trans-1-(3,4-dimethoxybenzoyl)-3-(4-fluorophenyl)piperidin-4-yl)benzamide | 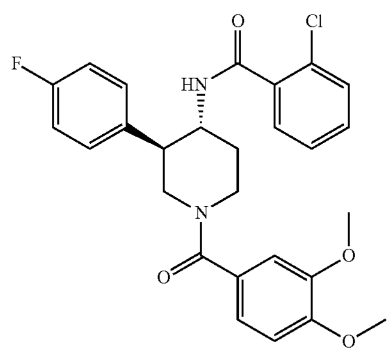 [SMILES: COc1ccc(C(=O)N2CC[C@@H](NC(=O)c3ccccc3Cl)[C@H](c3ccc(F)cc3)C2)cc1OC] | | 497.0 |
| 12B | 2-chloro-N-(trans-1-(3,4-dimethoxybenzoyl)-3-(4-fluoro-3-methylphenyl)piperidin-4-yl)benzamide | 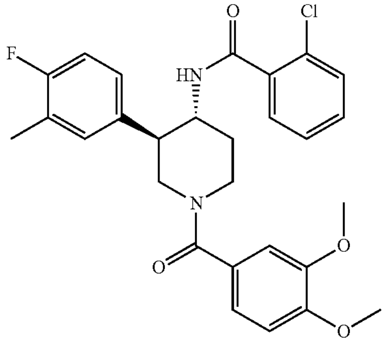 [SMILES: COc1ccc(C(=O)N2CC[C@@H](NC(=O)c3ccccc3Cl)[C@H](c3ccc(F)c(C)c3)C2)cc1OC] | | 511.0 |

TABLE 2-1-continued

| Ex. No. | IUPAC Name | Structure | Salt | MS |
|---|---|---|---|---|
| 13B | 2-chloro-N-(trans-1-(3,4-dimethoxybenzoyl)-3-(3-fluoro-4-methylphenyl)piperidin-4-yl)benzamide | 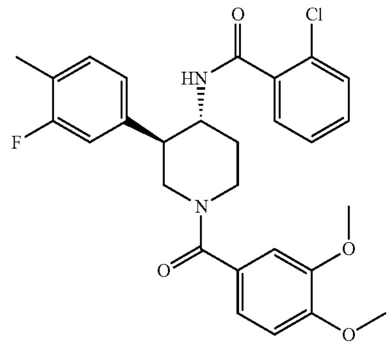 | | 511.0 |
| 14B | 2-chloro-N-(trans-3-(3-chlorophenyl)-1-(3,4-dimethoxybenzoyl)piperidin-4-yl)benzamide | 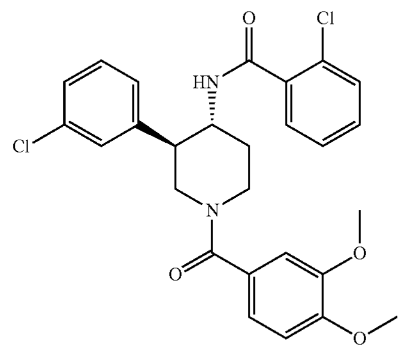 [SMILES: COc1ccc(C(=O)N2CC[C@@H](NC(=O)c3ccccc3Cl)[C@H](c3cccc(Cl)c3)C2)cc1OC] | | 513.0 |
| 15B | 2-chloro-N-(trans-3-(3-chloro-4-methylphenyl)-1-(3,4-dimethoxybenzoyl)piperidin-4-yl)benzamide | 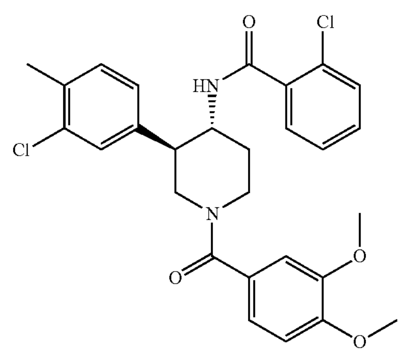 | | 527.0 |
| 16B | 2-chloro-N-(trans-3-(3,4-difluorophenyl)-1-(3,4-dimethoxybenzoyl)piperidin-4-yl)benzamide | 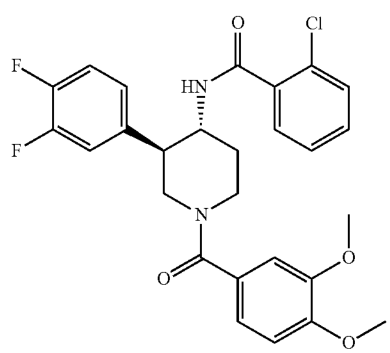 | | 515.0 |

TABLE 2-1-continued

| Ex. No. | IUPAC Name | Structure | Salt | MS |
|---|---|---|---|---|
| 17B | 2-chloro-N-(trans-3-(4-chloro-3-fluorophenyl)-1-(3,4-dimethoxybenzoyl)piperidin-4-yl)benzamide | 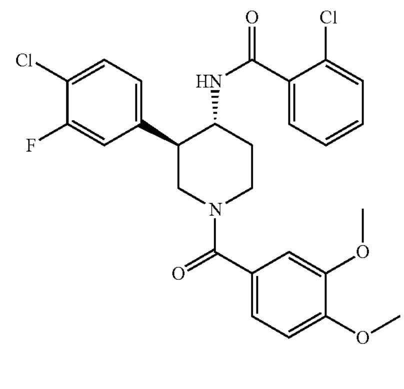 [SMILES: COc1ccc(C(=O)N2CC[C@@H](NC(=O)c3ccccc3Cl)[C@H](c3ccc(Cl)c(F)c3)C2)cc1OC] | | 530.9 |
| 18B | 2-chloro-N-(trans-1-(3,4-dimethoxybenzoyl)-3-(4-fluoro-2-methylphenyl)piperidin-4-yl)benzamide | 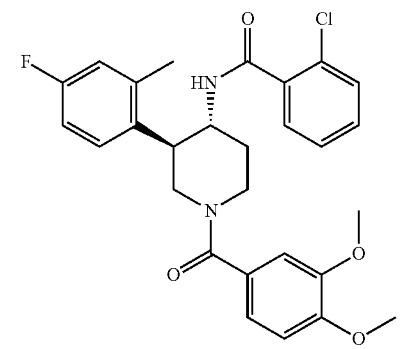 | | 511.0 |
| 19B | 2-chloro-N-(trans-3-(4-chloro-3-methylphenyl)-1-(3,4-dimethoxybenzoyl)piperidin-4-yl)benzamide | 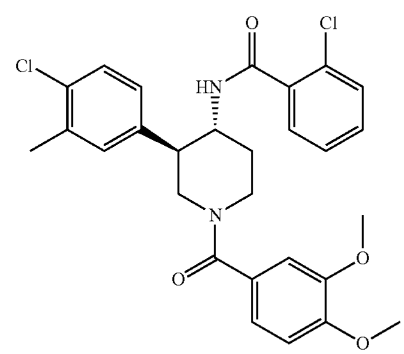 [SMILES: COc1ccc(C(=O)N2CC[C@@H](NC(=O)c3ccccc3Cl)[C@H](c3ccc(Cl)c(C)c3)C2)cc1OC] | | 527.0 |
| 20B | 2-chloro-N-((3S,4S)-3-(4-chloro-3-methylphenyl)-1-(3,4-dimethoxybenzoyl)piperidin-4-yl)benzamide | 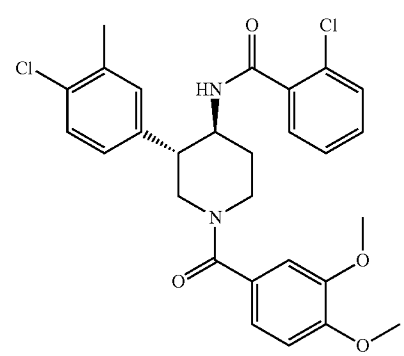 [SMILES: COc1ccc(C(=O)N2CC[C@H](NC(=O)c3ccccc3Cl)[C@@H](c3ccc(Cl)c(C)c3)C2)cc1OC] | | 527.0 |

TABLE 2-1-continued

| Ex. No. | IUPAC Name | Structure | Salt | MS |
|---|---|---|---|---|
| 21B | 2-chloro-N-(cis-3-(4-chlorophenyl)-1-(3,4-dimethoxybenzoyl)piperidin-4-yl)benzamide | 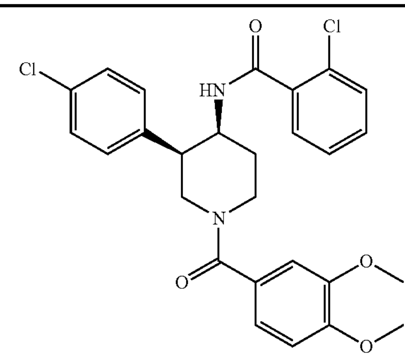 | | 513.0 |
| 22B | N-((3S,4R)-1-((8-chloroquinoxalin-6-yl)carbonyl)-3-phenylpiperidin-4-yl)-2-(difluoromethoxy)benzamide | 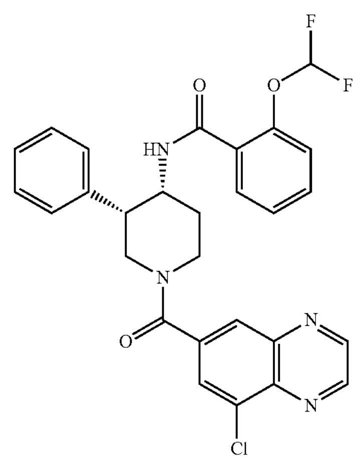 [SMILES: O=C(N[C@@H]1CCN(C(=O)c2cc(Cl)c3nccnc3c2)C[C@@H]1c1ccccc1)c1ccccc1OC(F)F] | | 537.1 |
| 23B | N-((3S,4R)-1-((8-chloroquinoxalin-6-yl)carbonyl)-3-phenylpiperidin-4-yl)-1,3-dimethyl-1H-pyrazole-5-carboxamide | 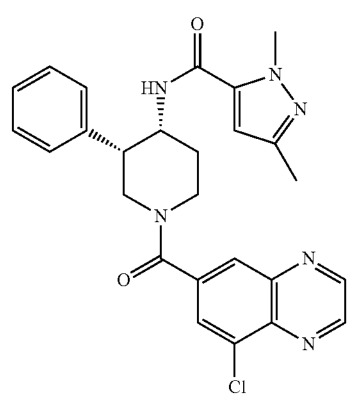 [SMILES: Cc1cc(C(=O)N[C@@H]2CCN(C(=O)c3cc(Cl)c4nccnc4c3)C[C@@H]2c2ccccc2)n(C)n1] | | 489.0 |
| 24B | N-((3S,4R)-1-((8-chloroquinoxalin-6-yl)carbonyl)-3-phenylpiperidin-4-yl)-6-(2-(morpholin-4-yl)ethoxy)nicotinamide | 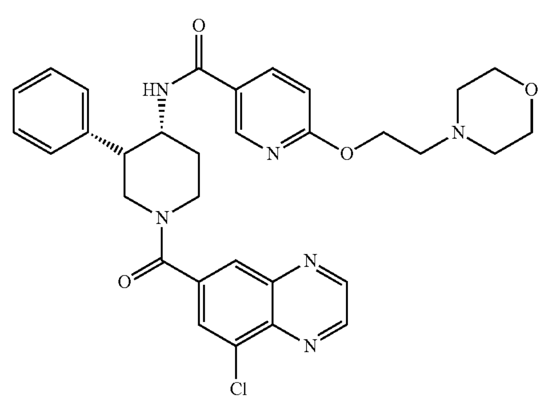 | | 601.1 |

TABLE 2-1-continued

| Ex. No. | IUPAC Name | Structure | Salt | MS |
|---|---|---|---|---|
| 25B | N-((3S,4R)-1-((8-chloroquinoxalin-6-yl)carbonyl)-3-phenylpiperidin-4-yl)-6-(2-(dimethylamino)ethoxy) nicotinamide | 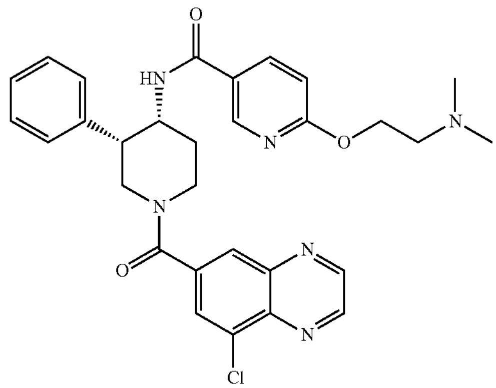 [SMILES: CN(C)CCOc1ccc(C(=O)N[C@@H]2CCN(C(=O)c3cc(Cl)c4nccnc4c3)C[C@@H]2c2ccccc2)cn1] | | 559.1 |
| 26B | N-((3S,4R)-3-phenyl-1-(quinazolin-6-ylcarbonyl) piperidin-4-yl)-3-(trifluoromethyl)pyridine-2-carboxamide | 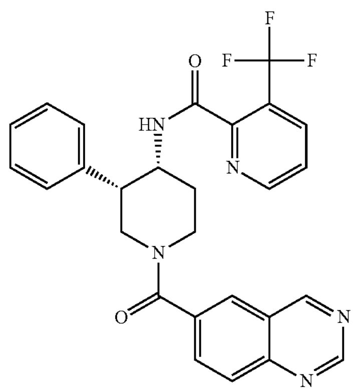 [SMILES: O=C(N[C@@H]1CCN(C(=O)c2ccc3ncncc3c2)C[C@@H]1c1ccccc1)c1ncccc1C(F)(F)F] | | 506.1 |
| 27B | N-((3S,4R)-1-((1-methyl-1H-imidazo[4,5-b]pyridin-6-yl) carbonyl)-3-phenylpiperidin-4-yl)-3-(trifluoromethyl)pyridine-2-carboxamide | 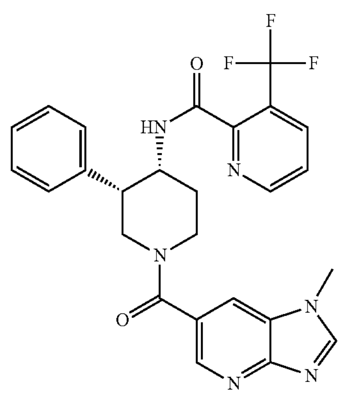 [SMILES: Cn1cnc2ncc(C(=O)N3CC[C@@H](NC(=O)c4ncccc4C(F)(F)F)[C@@H](c4ccccc4)C3)cc21] | | 509.2 |
| 28B | N-((3S,4R)-1-((8-chloroquinoxalin-6-yl)carbonyl)-3-phenylpiperidin-4-yl)-1,3-dimethyl-4-(trifluoromethyl)-1H-pyrazole-5-carboxamide | 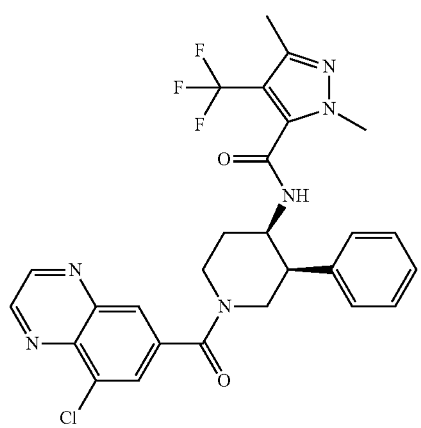 [SMILES: Cc1nn(C)c(C(=O)N[C@@H]2CCN(C(=O)c3cc(Cl)c4nccnc4c3)C[C@@H]2c2ccccc2)c1C(F)(F)F] | | 557.1 |

TABLE 2-1-continued

| Ex. No. | IUPAC Name | Structure | Salt | MS |
|---|---|---|---|---|
| 29B | N-((3S,4R)-1-((2-hydroxy-4-methyl-1,3-thiazol-5-yl)carbonyl)-3-phenylpiperidin-4-yl)-2-(trifluoromethoxy)benzamide | 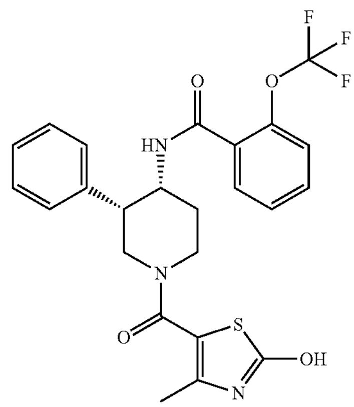 [SMILES: Cc1nc(O)sc1C(=O)N1CC[C@@H](NC(=O)c2ccccc2OC(F)(F)F)[C@@H](c2ccccc2)C1] | | 506.1 |
| 30B | ethyl 1-methyl-5-(((3S,4R)-3-phenyl-4-((2-(trifluoromethoxy)benzoyl)amino)piperidin-1-yl)carbonyl)-1H-pyrazole-3-carboxylate | 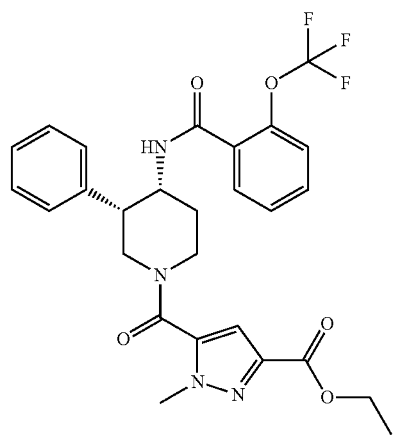 [SMILES: CCOC(=O)c1cc(C(=O)N2CC[C@@H](NC(=O)c3ccccc3OC(F)(F)F)[C@@H](c3ccccc3)C2)n(C)n1] | | 545.1 |
| 31B | N-((3S,4R)-1-((8-chloroquinoxalin-6-yl)carbonyl)-3-phenylpiperidin-4-yl)-3-(difluoromethoxy)pyridine-2-carboxamide | 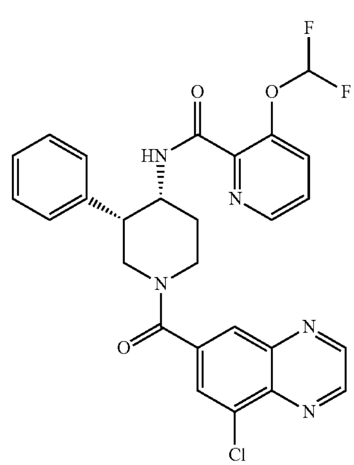 [SMILES: O=C(N[C@@H]1CCN(C(=O)c2cc(Cl)c3nccnc3c2)C[C@@H]1c1ccccc1)c1ncccc1OC(F)F] | | 538.1 |

TABLE 2-1-continued

| Ex. No. | IUPAC Name | Structure | Salt | MS |
|---|---|---|---|---|
| 32B | N-((3S,4R)-1-((8-chloroquinoxalin-6-yl)carbonyl)-3-phenylpiperidin-4-yl)-6-methoxypyridine-2-carboxamide | 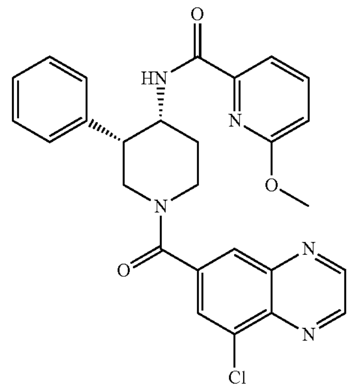 [SMILES: COc1cccc(C(=O)N[C@@H]2CCN(C(=O)c3cc(Cl)c4nccnc4c3)C[C@@H]2c2ccccc2)n1] | | 502.1 |
| 33B | N-((3S,4R)-1-((8-chloroquinoxalin-6-yl)carbonyl)-3-phenylpiperidin-4-yl)-3-methylpyridine-2-carboxamide | 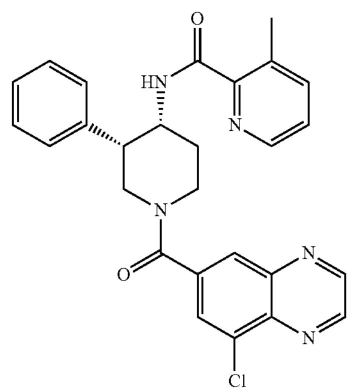 [SMILES: Cc1cccnc1C(=O)N[C@@H]1CCN(C(=O)c2cc(Cl)c3nccnc3c2)C[C@@H]1c1ccccc1] | | 486.1 |
| 34B | N-((3S,4R)-1-((1-(isopropylsulfonyl)-4-methyl-1H-pyrrol-3-yl)carbonyl)-3-phenylpiperidin-4-yl)-2-(trifluoromethoxy)benzamide | 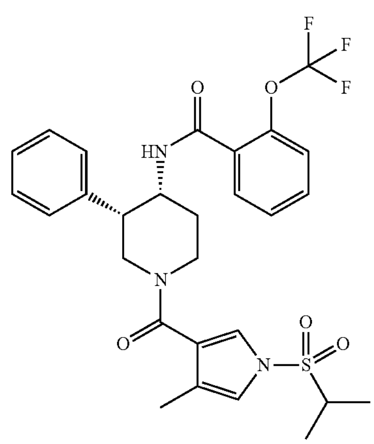 [SMILES: Cc1cn(S(=O)(=O)C(C)C)cc1C(=O)N1CC[C@@H](NC(=O)c2ccccc2OC(F)(F)F)[C@@H](c2ccccc2)C1] | | 578.1 |

TABLE 2-1-continued

| Ex. No. | IUPAC Name | Structure | Salt | MS |
|---|---|---|---|---|
| 35B | N-((3S,4R)-1-((5-((cyclopropylcarbonyl)amino)-3-methyl-2-thienyl)carbonyl)-3-phenylpiperidin-4-yl)-2-(trifluoromethoxy)benzamide | 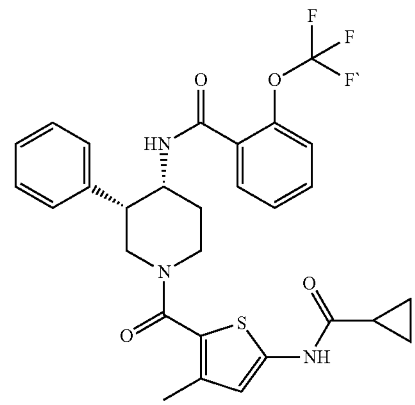 | | 572.1 |
| 36B | N-((3S,4R)-1-((2-acetamido-4-methyl-1,3-thiazol-5-yl)carbonyl)-3-phenylpiperidin-4-yl)-2-(trifluoromethoxy)benzamide | 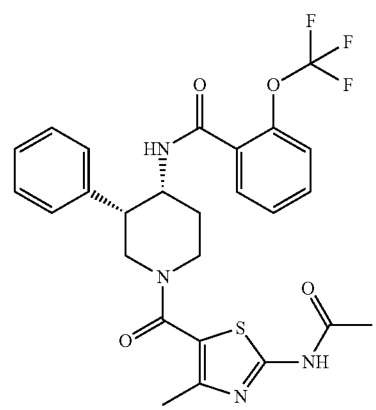 [SMILES: CC(=O)Nc1nc(C)c(C(=O)N2CC[C@@H](NC(=O)c3ccccc3OC(F)(F)F)[C@@H](c3ccccc3)C2)s1] | | 547.0 |
| 37B | N-((3S,4R)-1-((8-chloroquinoxalin-6-yl)carbonyl)-3-phenylpiperidin-4-yl)-6-(3-(morpholin-4-yl)propoxy)-4-(trifluoromethyl)nicotinamide | 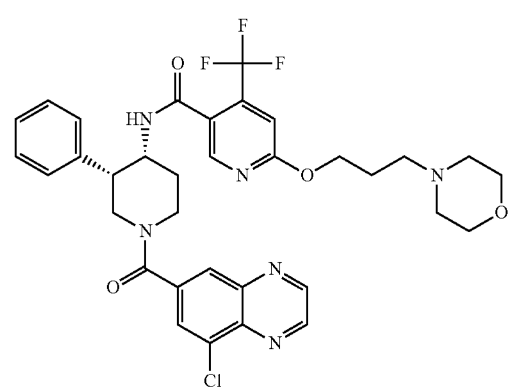 [SMILES: O=C(N[C@@H]1CCN(C(=O)c2cc(Cl)c3nccnc3c2)C[C@@H]1c1ccccc1)c1cnc(OCCCN2CCOCC2)cc1C(F)(F)F] | | 683.2 |

TABLE 2-1-continued

| Ex. No. | IUPAC Name | Structure | Salt | MS |
|---|---|---|---|---|
| 38B | N-((3S,4R)-1-((8-chloroquinoxalin-6-yl)carbonyl)-3-phenylpiperidin-4-yl)-6-(2-(dimethylamino)ethoxy)-4-(trifluoromethyl)nicotinamide | 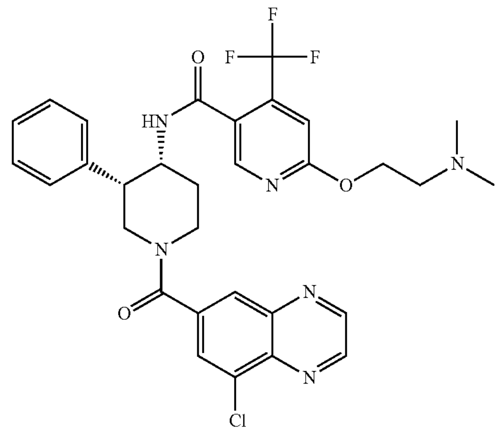 [SMILES: CN(C)CCOc1cc(C(F)(F)F)c(C(=O)N[C@@H]2CCN(C(=O)c3cc(Cl)c4nccnc4c3)C[C@@H]2c2ccccc2)cn1] | | 627.0 |
| 39B | N-((3S,4R)-1-((8-chloroquinoxalin-6-yl)carbonyl)-3-phenylpiperidin-4-yl)-6-(2-(morpholin-4-yl)ethoxy)-4-(trifluoromethyl)nicotinamide | 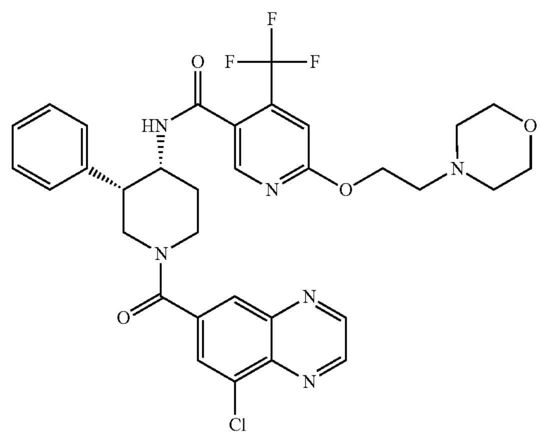 [SMILES: O=C(N[C@@H]1CCN(C(=O)c2cc(Cl)c3nccnc3c2)C[C@@H]1c1ccccc1)c1cnc(OCCN2CCOCC2)cc1C(F)(F)F] | | 669.2 |
| 40B | N-((3S,4R)-1-((8-chloroquinoxalin-6-yl)carbonyl)-3-phenylpiperidin-4-yl)-6-(3-(dimethylamino)propoxy)-4-(trifluoromethyl)nicotinamide | 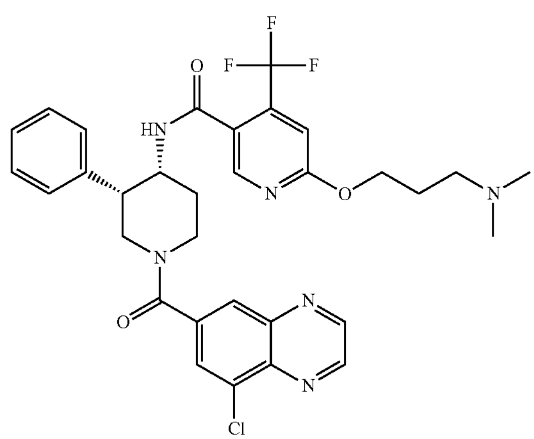 [SMILES: CN(C)CCCOc1cc(C(F)(F)F)c(C(=O)N[C@@H]2CCN(C(=O)c3cc(Cl)c4nccnc4c3)C[C@@H]2c2ccccc2)cn1] | | 641.1 |

TABLE 2-1-continued

| Ex. No. | IUPAC Name | Structure | Salt | MS |
|---|---|---|---|---|
| 41B | N-((3S,4R)-1-((8-chloroquinoxalin-6-yl)carbonyl)-3-phenylpiperidin-4-yl)-6-(3H-[1,2,3]triazolo(4,5-b]pyridin-3-yloxy)-4-(trifluoromethyl) nicotinamide | 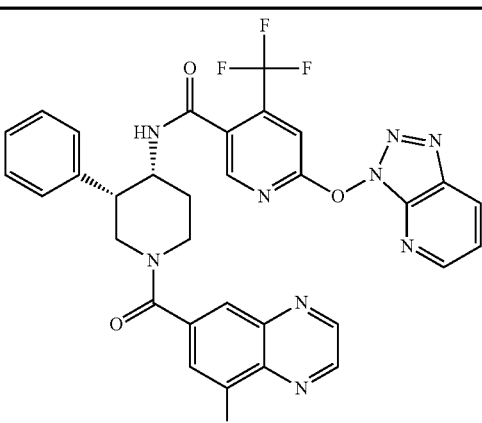 | | 672.3 |
| 42B | N-((3S,4R)-1-((8-chloroquinoxalin-6-yl)carbonyl)-3-phenylpiperidin-4-yl)-6-oxo-1,6-dihydropyridine-2-carboxamide | 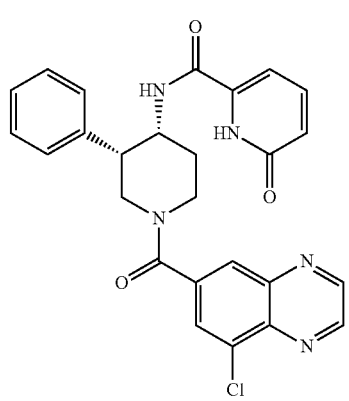 [SMILES: O=C(N[C@@H]1CCN(C(=O)c2cc(Cl)c3nccnc3c2)C[C@@H]1c1ccccc1)c1cccc(=O)[nH]1] | | 488.0 |
| 43B | N-((3S,4R)-1-((8-chloroquinoxalin-6-yl)carbonyl)-3-phenylpiperidin-4-yl)-3-methoxy-1-methyl-1H-pyrazole-5-carboxamide | 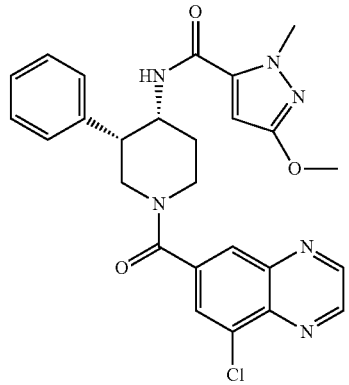 [SMILES: COc1cc(C(=O)N[C@@H]2CCN(C(=O)c3cc(Cl)c4nccnc4c3)C[C@@H]2c2ccccc2)n(C)n1] | | 505.1 |
| 44B | N-((3S,4R)-1-((5,6-dimethoxypyridin-2-yl)carbonyl)-3-phenylpiperidin-4-yl)-3-(trifluoromethyl)pyridine-2-carboxamide | 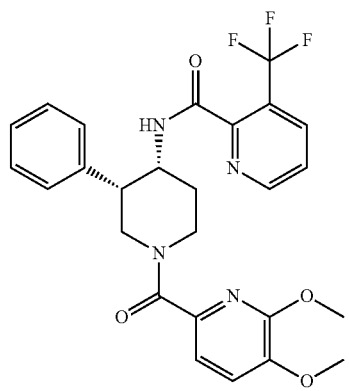 [SMILES: COc1ccc(C(=O)N2CC[C@@H](NC(=O)c3ncccc3C(F)(F)F)[C@@H](c3ccccc3)C2)nc1OC] | | 515.1 |

TABLE 2-1-continued

| Ex. No. | IUPAC Name | Structure | Salt | MS |
|---|---|---|---|---|
| 45B | N-((3S,4R)-1-((8-methoxyquinoxalin-6-yl)carbonyl)-3-phenylpiperidin-4-yl)-3-(trifluoromethyl)pyridine-2-carboxamide | 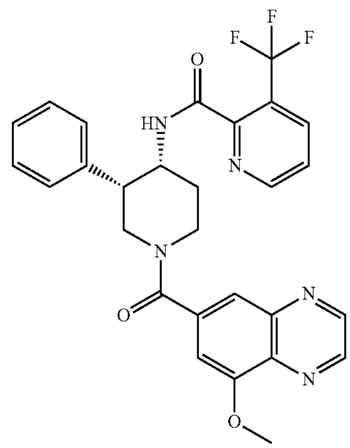 [SMILES: COc1cc(C(=O)N2CC[C@@H](NC(=O)c3ncccc3C(F)(F)F)[C@@H](c3ccccc3)C2)cc2nccnc12] | | 536.1 |
| 46B | N-((3S,4R)-1-((5-cyano-6-methoxy-2-methylpyridin-3-yl)carbonyl)-3-phenylpiperidin-4-yl)-3-(trifluoromethyl)pyridine-2-carboxamide | 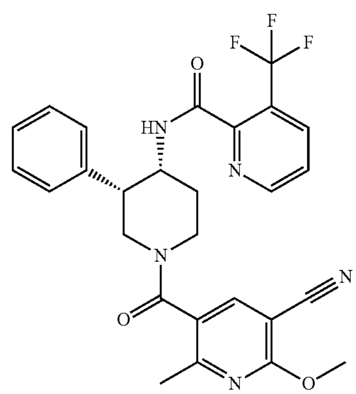 [SMILES: COc1nc(C)c(C(=O)N2CC[C@@H](NC(=O)c3ncccc3C(F)(F)F)[C@@H](c3ccccc3)C2)cc1C#N] | | 524.2 |
| 47B | N-((3S,4R)-1-((8-chloroquinoxalin-6-yl)carbonyl)-3-phenylpiperidin-4-yl)-6-(2-hydroxyethoxy)-4-(trifluoromethyl)nicotinamide | 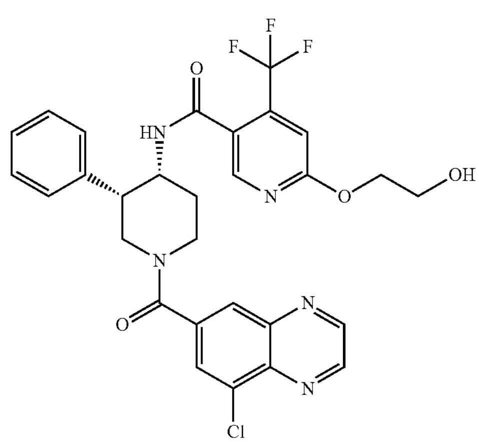 [SMILES: O=C(N[C@@H]1CCN(C(=O)c2cc(Cl)c3nccnc3c2)C[C@@H]1c1ccccc1)c1cnc(OCCO)cc1C(F)(F)F] | | 600.0 |

TABLE 2-1-continued

| Ex. No. | IUPAC Name | Structure | Salt | MS |
|---|---|---|---|---|
| 48B | dibenzyl 2-((5-(((3S,4R)-1-((8-chloroquinoxalin-6-yl)carbonyl)-3-phenylpiperidin-4-yl)carbamoyl)-4-(trifluoromethyl)pyridin-2-yl)oxy) ethyl phosphate | 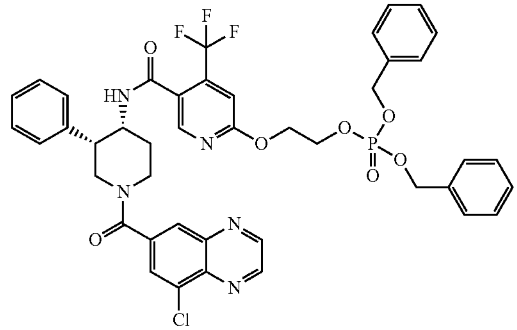 [SMILES: O=C(N[C@@H]1CCN(C(=O)c2cc(Cl)c3nccnc3c2)C[C@@H]1c1ccccc1)c1cnc(OCCOP(=O)(OCc2ccccc2)OCc2ccccc2)cc1C(F)(F)F] | | 860.1 |
| 49B | N-((3S,4R)-1-((1,4-dimethyl-1H-benzimidazol-6-yl)carbonyl)-3-phenylpiperidin-4-yl)-3-(trifluoromethyl)pyridine-2-carboxamide | 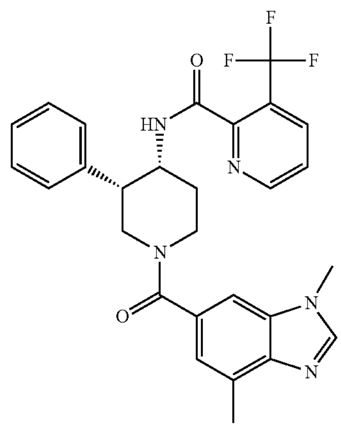 [SMILES: Cc1cc(C(=O)N2CC[C@@H](NC(=O)c3ncccc3C(F)(F)F)[C@@H](c3ccccc3)C2)cc2c1ncn2C] | | 522.1 |
| 50B | N-((3S,4R)-1-((4-chloro-1-methyl-1H-benzimidazol-6-yl)carbonyl)-3-phenylpiperidin-4-yl)-3-(trifluoromethyl)pyridine-2-carboxamide | 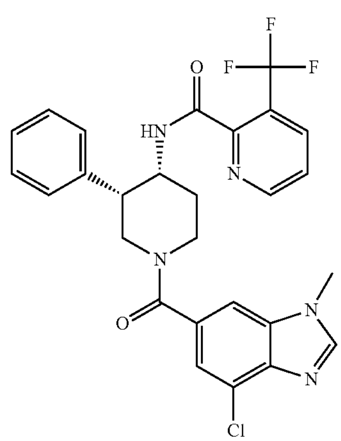 [SMILES: Cn1cnc2c(Cl)cc(C(=O)N3CC[C@@H](NC(=O)c4ncccc4C(F)(F)F)[C@@H](c4ccccc4)C3)cc21] | | 542.0 |

TABLE 2-1-continued

| Ex. No. | IUPAC Name | Structure | Salt | MS |
|---|---|---|---|---|
| 51B | N-((3S,4R)-1-((4-chloro-1-methyl-1H-benzimidazol-6-yl)carbonyl)-3-(4-fluorophenyl)piperidin-4-yl)-3-(trifluoromethyl)pyridine-2-carboxamide | 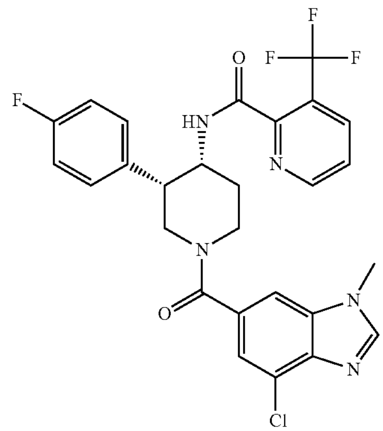 [SMILES: Cn1cnc2c(Cl)cc(C(=O)N3CC[C@@H](NC(=O)c4ncccc4C(F)(F)F)[C@@H](c4ccc(F)cc4)C3)cc21] | | 560.0 |
| 52B | N-((3S,4R)-1-((4-chloro-1-methyl-1H-benzimidazol-6-yl)carbonyl)-3-phenylpiperidin-4-yl)-1-methyl-3-(trifluoromethyl)-1H-pyrazole-5-carboxamide | 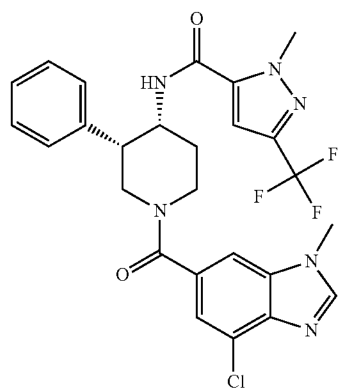 [SMILES: Cn1nc(C(F)(F)F)cc1C(=O)N[C@@H]1CCN(C(=O)c2cc(Cl)c3ncn(C)c3c2)C[C@@H]1c1ccccc1] | | 545.1 |
| 53B | N-((3S,4R)-1-((2-amino-4-methyl-1,3-thiazol-5-yl)carbonyl)-3-(4-fluorophenyl)piperidin-4-yl)-3-(trifluoromethyl)pyridine-2-carboxamide | 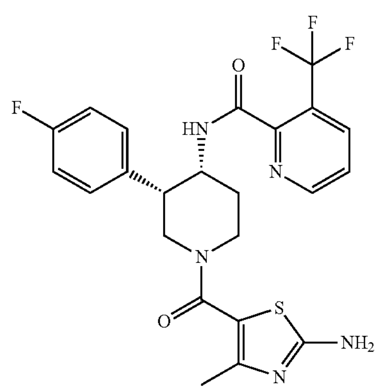 [SMILES: Cc1nc(N)sc1C(=O)N1CC[C@@H](NC(=O)c2ncccc2C(F)(F)F)[C@@H](c2ccc(F)cc2)C1] | | 508.1 |
| 54B | N-((3S,4R)-1-((2-acetamido-4-methyl-1,3-thiazol-5-yl)carbonyl)-3-(4-fluorophenyl)piperidin-4-yl)-3-(trifluoromethyl)pyridine-2-carboxamide | 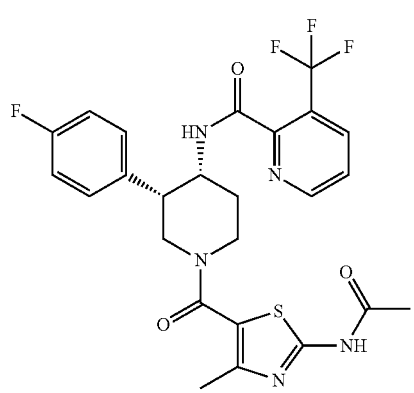 [SMILES: CC(=O)Nc1nc(C)c(C(=O)N2CC[C@@H](NC(=O)c3ncccc3C(F)(F)F)[C@@H](c3ccc(F)cc3)C2)s1] | | 550.1 |

TABLE 2-1-continued

| Ex. No. | IUPAC Name | Structure | Salt | MS |
|---|---|---|---|---|
| 55B | N-(cis-1'-(3,4-dimethoxybenzoyl)-1,3'-bipiperidin-4'-yl)-2-(trifluoromethoxy)benzamide | 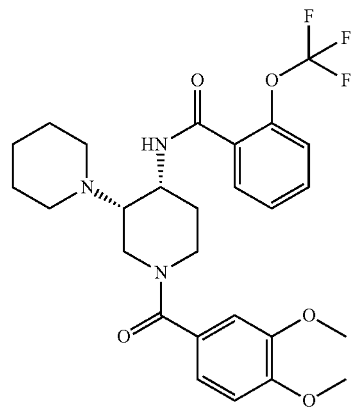 [SMILES: COc1ccc(C(=O)N2CC[C@@H](NC(=O)c3ccccc3OC(F)(F)F)[C@@H](N3CCCCC3)C2)cc1OC] | | 536.1 |
| 56B | N-((3S,4R)-1-((5,6-dimethoxy-1-oxidopyridin-3-yl)carbonyl)-3-phenylpiperidin-4-yl)-3-(trifluoromethyl)pyridine-2-carboxamide | 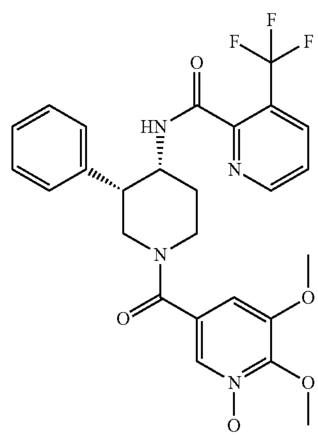 | | 531.1 |
| 57B | N-((3S,4R)-3-phenyl-1-(quinoxalin-6-ylcarbonyl)piperidin-4-yl)-2-(trifluoromethoxy)benzamide | 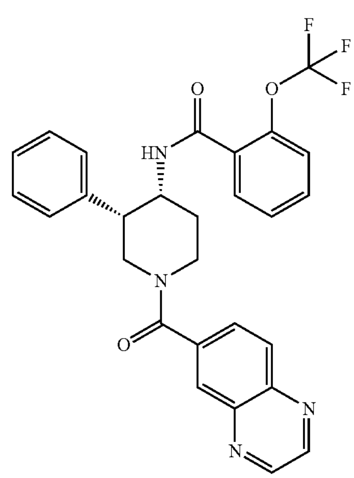 [SMILES: O=C(N[C@@H]1CCN(C(=O)c2ccc3nccnc3c2)C[C@@H]1c1ccccc1)c1ccccc1OC(F)(F)F] | | 521.0 |

TABLE 2-1-continued

| Ex. No. | IUPAC Name | Structure | Salt | MS |
|---|---|---|---|---|
| 58B | N-((3S,4R)-1-((8-chloroquinoxalin-6-yl)carbonyl)-3-(4-fluorophenyl)piperidin-4-yl)-1,3-dimethyl-1H-pyrazole-5-carboxamide | 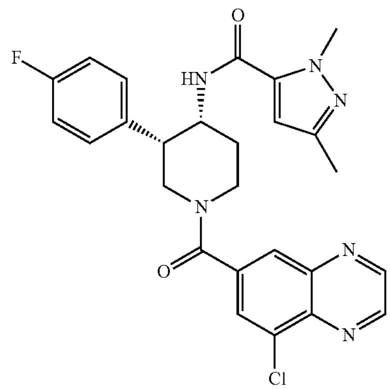 [SMILES: Cc1cc(C(=O)N[C@@H]2CCN(C(=O)c3cc(Cl)c4nccnc4c3)C[C@@H]2c2ccc(F)cc2)n(C)n1] | | 507.2 |
| 59B | 5-chloro-N-((3S,4R)-1-((8-chloroquinoxalin-6-yl)carbonyl)-3-(4-fluorophenyl)piperidin-4-yl)-1,3-dimethyl-1H-pyrazole-4-carboxamide | 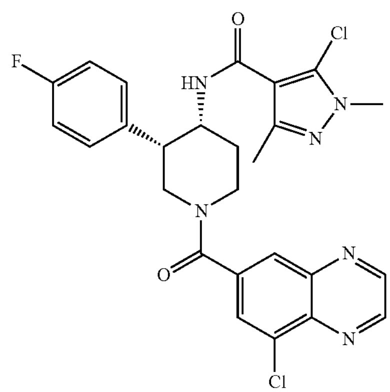 [SMILES: Cc1nn(C)c(Cl)c1C(=O)N[C@@H]1CCN(C(=O)c2cc(Cl)c3nccnc3c2)C[C@@H]1c1ccc(F)cc1] | | 541.2 |
| 60B | 5-chloro-N-((3S,4R)-1-((8-chloroquinoxalin-6-yl)carbonyl)-3-(4-fluorophenyl)piperidin-4-yl)-1-methyl-3-(trifluoromethyl)-1H-pyrazole-4-carboxamide | 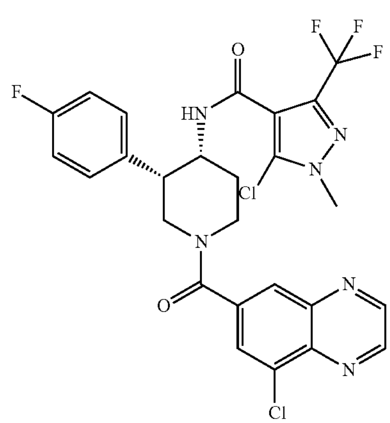 [SMILES: Cn1nc(C(F)(F)F)c(C(=O)N[C@@H]2CCN(C(=O)c3cc(Cl)c4nccnc4c3)C[C@@H]2c2ccc(F)cc2)c1Cl] | | 595.0 |

TABLE 2-1-continued

| Ex. No. | IUPAC Name | Structure | Salt | MS |
|---|---|---|---|---|
| 61B | N-((3S,4R)-1-((8-cyclopropylquinoxalin-6-yl)carbonyl)-3-(4-fluorophenyl)piperidin-4-yl)-3-(trifluoromethyl)pyridine-2-carboxamide | 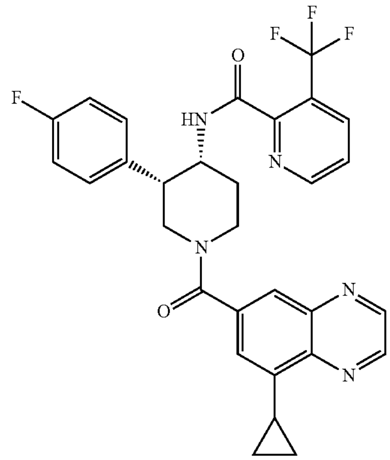 [SMILES: O=C(N[C@@H]1CCN(C(=O)c2cc(C3CC3)c3nccnc3c2)C[C@@H]1c1ccc(F)cc1)c1ncccc1C(F)(F)F] | | 564.1 |
| 62B | N-((3S,4R)-1-((8-chloroquinoxalin-6-yl)carbonyl)-3-phenylpiperidin-4-yl)-1-isopropyl-3-methyl-1H-pyrazole-5-carboxamide | 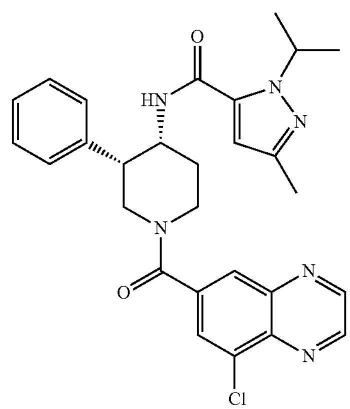 [SMILES: Cc1cc(C(=O)N[C@@H]2CCN(C(=O)c3cc(Cl)c4nccnc4c3)C[C@@H]2c2ccccc2)n(C(C)C)n1] | | 517.1 |
| 63B | N-((3S,4R)-3-phenyl-1-(quinoxalin-6-ylcarbonyl)piperidin-4-yl)-3-(trifluoromethyl)pyridine-2-carboxamide | 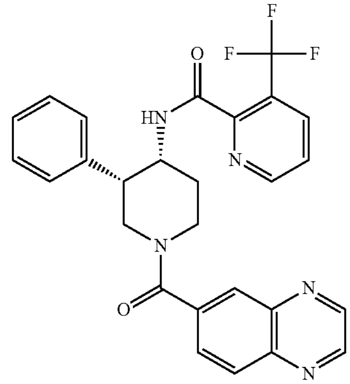 [SMILES: O=C(N[C@@H]1CCN(C(=O)c2ccc3nccnc3c2)C[C@@H]1c1ccccc1)c1ncccc1C(F)(F)F] | | 506.1 |

TABLE 2-1-continued

| Ex. No. | IUPAC Name | Structure | Salt | MS |
|---|---|---|---|---|
| 64B | N-((3S,4R)-1-((5,6-dimethoxypyridin-3-yl)carbonyl)-3-phenylpiperidin-4-yl)-3-(trifluoromethyl)pyridine-2-carboxamide | 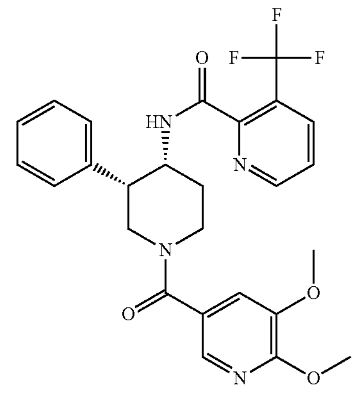 [SMILES: COc1cc(C(=O)N2CC[C@@H](NC(=O)c3ncccc3C(F)(F)F)[C@@H](c3ccccc3)C2)cnc1OC] | | 515.1 |
| 65B | N-((3S,4R)-1-((8-chloroimidazo[1,2-a]pyridin-6-yl)carbonyl)-3-phenylpiperidin-4-yl)-2-(trifluoromethoxy)benzamide | 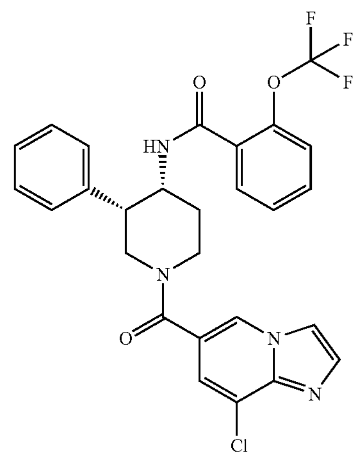 [SMILES: O=C(N[C@@H]1CCN(C(=O)c2cc(Cl)c3nccn3c2)C[C@@H]1c1ccccc1)c1ccccc1OC(F)(F)F] | | 543.0 |
| 66B | N-((3S,4R)-1-(3-(difluoromethyl)-4-methoxybenzoyl)-3-phenylpiperidin-4-yl)-2-(trifluoromethoxy)benzamide | 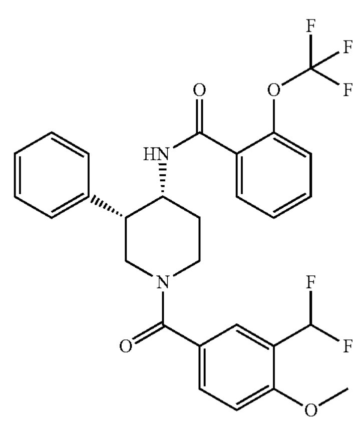 [SMILES: COc1ccc(C(=O)N2CC[C@@H](NC(=O)c3ccccc3OC(F)(F)F)[C@@H](c3ccccc3)C2)cc1C(F)F] | | 549.1 |

TABLE 2-1-continued

| Ex. No. | IUPAC Name | Structure | Salt | MS |
|---|---|---|---|---|
| 67B | N-((3S,4R)-1-(3-cyclopropyl-4-methoxybenzoyl)-3-phenylpiperidin-4-yl)-2-(trifluoromethoxy)benzamide | 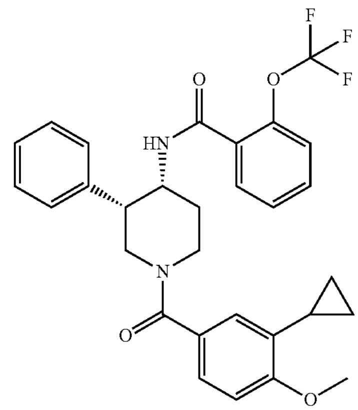 [SMILES: COc1ccc(C(=O)N2CC[C@@H](NC(=O)c3ccccc3OC(F)(F)F)[C@@H](c3ccccc3)C2)cc1C1CC1] | | 539.1 |
| 68B | N-((3S,4R)-1-((8-chloroquinoxalin-6-yl)carbonyl)-3-phenylpiperidin-4-yl)-3-cyclopropylpyridine-2-carboxamide | 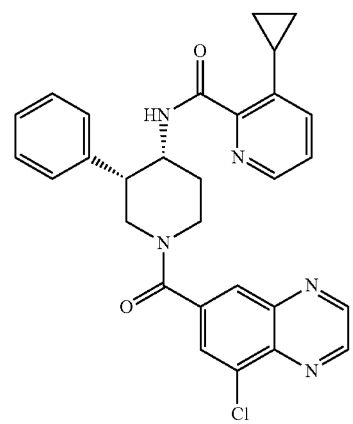 [SMILES: O=C(N[C@@H]1CCN(C(=O)c2cc(Cl)c3nccnc3c2)C[C@@H]1c1ccccc1)c1ncccc1C1CC1] | | 512.1 |
| 69B | N-((3S,4R)-1-((8-chloroquinoxalin-6-yl)carbonyl)-3-phenylpiperidin-4-yl)-5-methyl-2-oxo-2,3-dihydro-1,3-oxazole-4-carboxamide | 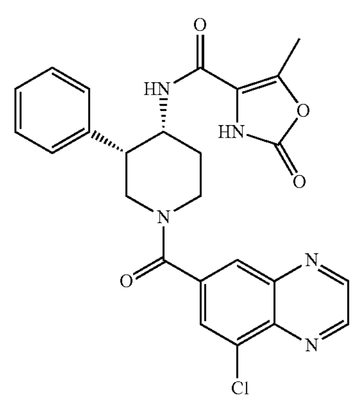 [SMILES: Cc1oc(=O)[nH]c1C(=O)N[C@@H]1CCN(C(=O)c2cc(Cl)c3nccnc3c2)C[C@@H]1c1ccccc1] | | 492.1 |

TABLE 2-1-continued

| Ex. No. | IUPAC Name | Structure | Salt | MS |
|---|---|---|---|---|
| 70B | N-((3S,4R)-1-((5,6-dimethoxypyridin-3-yl)carbonyl)-3-phenylpiperidin-4-yl)-2-(trifluoromethoxy)benzamide | 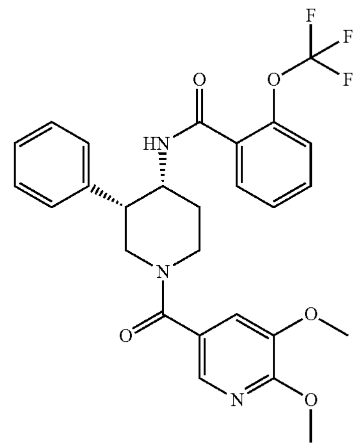 [SMILES: COc1cc(C(=O)N2CC[C@@H](NC(=O)c3ccccc3OC(F)(F)F)[C@@H](c3ccccc3)C2)cnc1OC] | | 530.2 |
| 71B | N-((3S,4R)-1-((8-chloroquinoxalin-6-yl)carbonyl)-3-phenylpiperidin-4-yl)-1,3,4-trimethyl-1H-pyrazole-5-carboxamide | 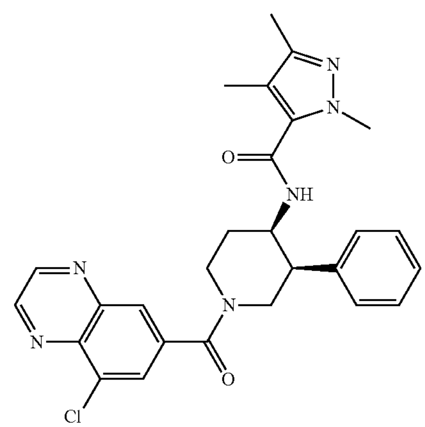 [SMILES: Cc1nn(C)c(C(=O)N[C@@H]2CCN(C(=O)c3cc(Cl)c4nccnc4c3)C[C@@H]2c2ccccc2)c1C] | | 503.1 |
| 72B | N-((3S,4R)-1-((3-methoxy-1-methyl-1H-pyrazol-5-yl)carbonyl)-3-phenylpiperidin-4-yl)-3-(trifluoromethyl)pyridine-2-carboxamide | 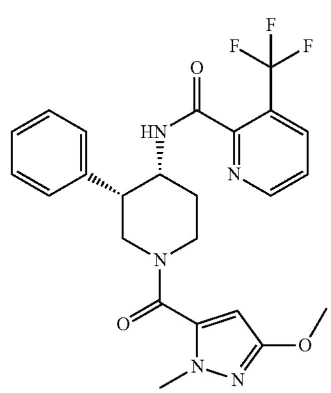 [SMILES: COc1cc(C(=O)N2CC[C@@H](NC(=O)c3ncccc3C(F)(F)F)[C@@H](c3ccccc3)C2)n(C)n1] | | 488.1 |

TABLE 2-1-continued

| Ex. No. | IUPAC Name | Structure | Salt | MS |
|---|---|---|---|---|
| 73B | N-((3S,4R)-1-((8-chloroquinoxalin-6-yl)carbonyl)-3-phenylpiperidin-4-yl)-3-(difluoromethoxy)-1-methyl-1H-pyrazole-5-carboxamide | 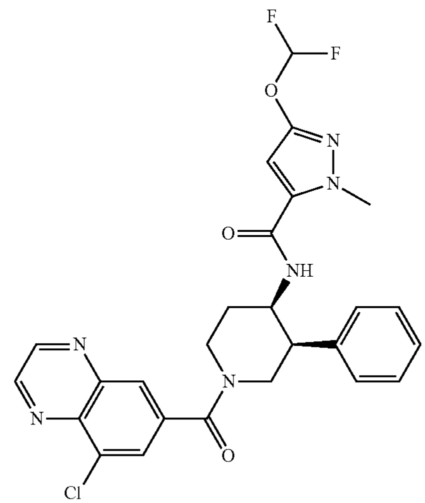 [SMILES: Cn1nc(OC(F)F)cc1C(=O)N[C@@H]1CCN(C(=O)c2cc(Cl)c3nccnc3c2)C[C@@H]1c1ccccc1] | | 541.1 |
| 74B | N-((3S,4R)-1-((8-methylquinoxalin-6-yl)carbonyl)-3-phenylpiperidin-4-yl)-3-(trifluoromethyl)pyridine-2-carboxamide | 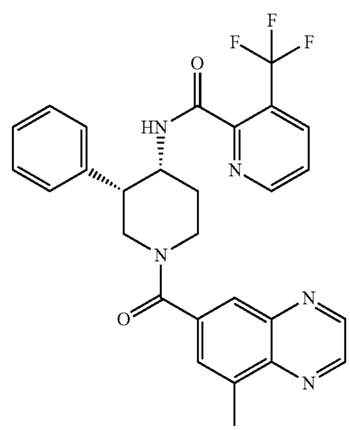 [SMILES: Cc1cc(C(=O)N2CC[C@@H](NC(=O)c3ncccc3C(F)(F)F)[C@@H](c3ccccc3)C2)cc2nccnc12] | | 520.2 |
| 75B | N-((3S,4R)-1-((3-methoxy-1-methyl-1H-pyrazol-5-yl)carbonyl)-3-phenylpiperidin-4-yl)-1-methyl-3-(trifluoromethyl)-1H-pyrazole-5-carboxamide | 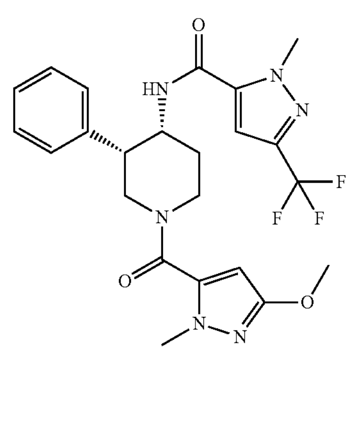 [SMILES: COc1cc(C(=O)N2CC[C@@H](NC(=O)c3cc(C(F)(F)F)nn3C)[C@@H](c3ccccc3)C2)n(C)n1] | | 491.1 |

TABLE 2-1-continued

| Ex. No. | IUPAC Name | Structure | Salt | MS |
|---|---|---|---|---|
| 76B | N-((3S,4R)-1-((4-acetyl-3,5-dimethyl-1H-pyrrol-2-yl)carbonyl)-3-phenylpiperidin-4-yl)-1-methyl-3-(trifluoromethyl)-1H-pyrazole-5-carboxamide | 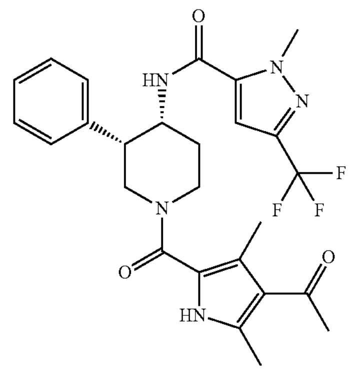 [SMILES: CC(=O)c1c(C)[nH]c(C(=O)N2CC[C@@H](NC(=O)c3cc(C(F)(F)F)nn3C)[C@@H](c3ccccc3)C2)c1C] | | 514.1 |
| 77B | N-((3S,4R)-1-((4-acetyl-3,5-dimethyl-1H-pyrrol-2-yl)carbonyl)-3-phenylpiperidin-4-yl)-3-(trifluoromethyl)pyridine-2-carboxamide | 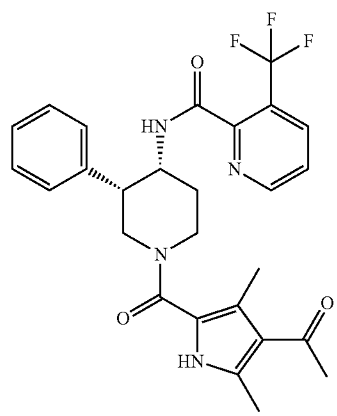 [SMILES: CC(=O)c1c(C)[nH]c(C(=O)N2CC[C@@H](NC(=O)c3ncccc3C(F)(F)F)[C@@H](c3ccccc3)C2)c1C] | | 513.0 |
| 78B | 4-chloro-N-((3S,4R)-1-((5-chloro-6-methoxypyridin-3-yl)carbonyl)-3-phenylpiperidin-4-yl)-2-(trifluoromethyl)benzamide | 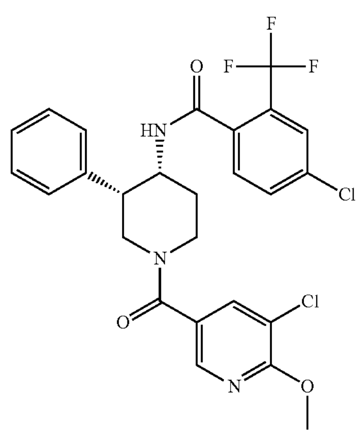 [SMILES: COc1ncc(C(=O)N2CC[C@@H](NC(=O)c3ccc(Cl)cc3C(F)(F)F)[C@@H](c3ccccc3)C2)cc1Cl] | | 552.1 |

TABLE 2-1-continued
| Ex. No. | IUPAC Name | Structure | Salt | MS |
|---|---|---|---|---|
| 79B | N-((3S,4R)-1-(imidazo[1,2-a]pyridin-6-ylcarbonyl)-3-phenylpiperidin-4-yl)-2-(trifluoromethoxy)benzamide | 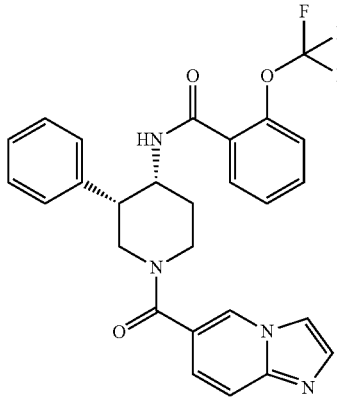 | | 509.2 |
| 80B | N-((3S,4R)-1-(imidazo[1,2-a]pyridin-2-ylcarbonyl)-3-phenylpiperidin-4-yl)-2-(trifluoromethoxy)benzamide | 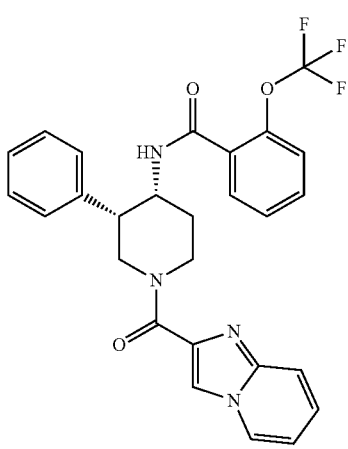 [SMILES: O=C(N[C@@H]1CCN(C(=O)c2cn3ccccc3n2)C[C@@H]1c1ccccc1)c1ccccc1OC(F)(F)F] | | 509.2 |
| 81B | N-((3S,4R)-1-((8-chloroquinoxalin-6-yl)carbonyl)-3-phenylpiperidin-4-yl)-1-methyl-3-(trifluoromethyl)-1H-pyrazole-5-carboxamide | 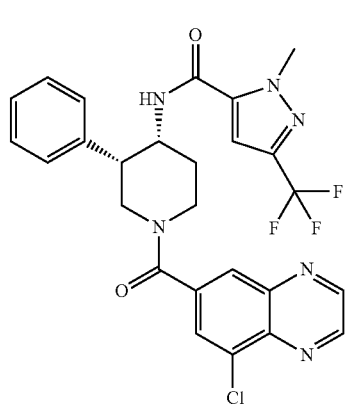 [SMILES: Cn1nc(C(F)(F)F)cc1C(=O)N[C@@H]1CCN(C(=O)c2cc(Cl)c3nccnc3c2)C[C@@H]1c1ccccc1] | | 543.3 |

TABLE 2-1-continued

| Ex. No. | IUPAC Name | Structure | Salt | MS |
|---|---|---|---|---|
| 82B | N-((3S,4R)-1-((5-methoxypyridin-2-yl)carbonyl)-3-phenylpiperidin-4-yl)-2-(trifluoromethoxy)benzamide | 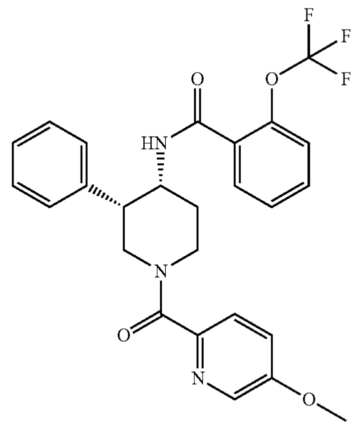 [SMILES: COc1ccc(C(=O)N2CC[C@@H](NC(=O)c3ccccc3OC(F)(F)F)[C@@H](c3ccccc3)C2)nc1] | | 500.1 |
| 83B | N-((3S,4R)-1-((5,6-dicyanopyridin-3-yl)carbonyl)-3-phenylpiperidin-4-yl)-2-(trifluoromethoxy)benzamide | 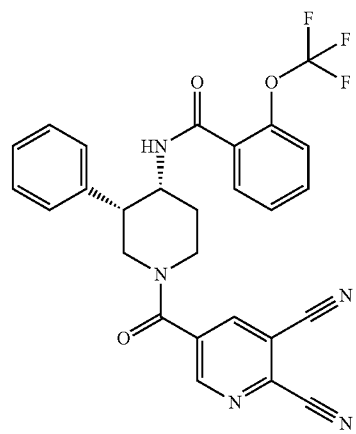 [SMILES: N#Cc1cc(C(=O)N2CC[C@@H](NC(=O)c3ccccc3OC(F)(F)F)[C@@H](c3ccccc3)C2)cnc1C#N] | | 520.1 |
| 84B | N-((3R,4R)-1-((8-chloroquinoxalin-6-yl)carbonyl)-3-phenylpiperidin-4-yl)-1-methyl-3-(trifluoromethyl)-1H-pyrazole-5-carboxamide | 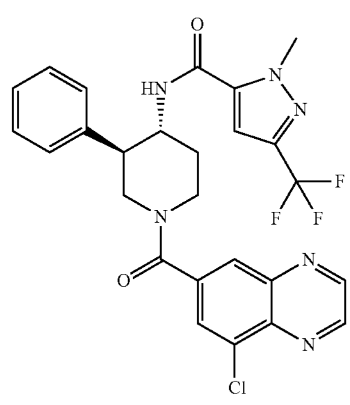 [SMILES: Cn1nc(C(F)(F)F)cc1C(=O)N[C@@H]1CCN(C(=O)c2cc(Cl)c3nccnc3c2)C[C@H]1c1ccccc1] | | 543.2 |

TABLE 2-1-continued

| Ex. No. | IUPAC Name | Structure | Salt | MS |
|---|---|---|---|---|
| 85B | N-((3S,4S)-1-((8-chloroquinoxalin-6-yl)carbonyl)-3-(4-fluorophenyl)piperdin-4-yl)-3-(trifluoromethyl)pyridine-2-carboxamide | 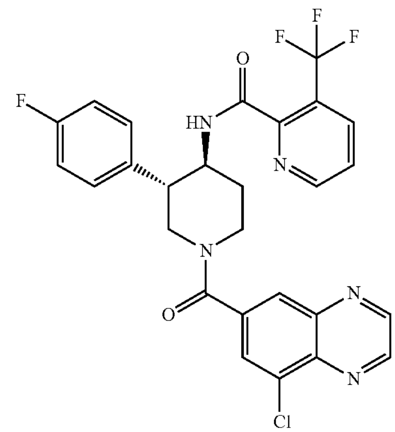 [SMILES: O=C(N[C@H]1CCN(C(=O)c2cc(Cl)c3nccnc3c2)C[C@@H]1c1ccc(F)cc1)c1ncccc1C(F)(F)F] | | 558.2 |
| 86B | N-((3S,4S)-1-((8-chloroquinoxalin-6-yl)carbonyl)-3-(4-fluorophenyl)piperidin-4-yl)-1-methyl-3-(trifluoromethyl)-1H-pyrazole-5-carboxamide | 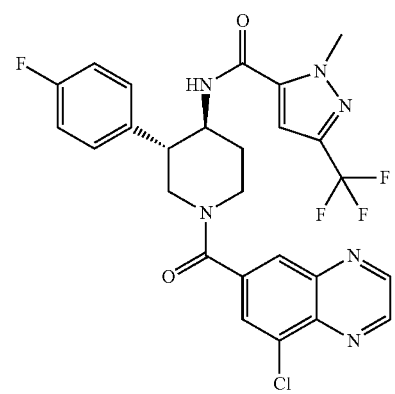 [SMILES: Cn1nc(C(F)(F)F)cc1C(=O)N[C@H]1CCN(C(=O)c2cc(Cl)c3nccnc3c2)C[C@@H]1c1ccc(F)cc1] | | 561.2 |
| 87B | N-((3S,4S)-1-((8-chloroquinoxalin-6-yl)carbonyl)-3-(4-(trifluoromethyl)phenyl)piperidin-4-yl)-3-(trifluoromethyl)pyridine-2-carboxamide | 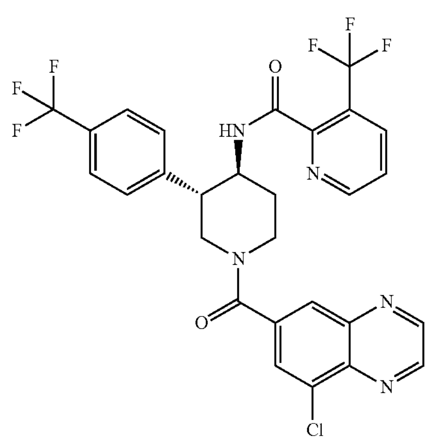 [SMILES: O=C(N[C@H]1CCN(C(=O)c2cc(Cl)c3nccnc3c2)C[C@@H]1c1ccc(C(F)(F)F)cc1)c1ncccc1C(F)(F)F] | | 608.2 |

TABLE 2-1-continued

| Ex. No. | IUPAC Name | Structure | Salt | MS |
|---|---|---|---|---|
| 88B | N-((3S,4S)-1-((8-chloroquinoxalin-6-yl)carbonyl)-3-(4-(trifluoromethyl)phenyl)piperidin-4-yl)-1-methyl-3-(trifluoromethyl)-1H-pyrazole-5-carboxamide | 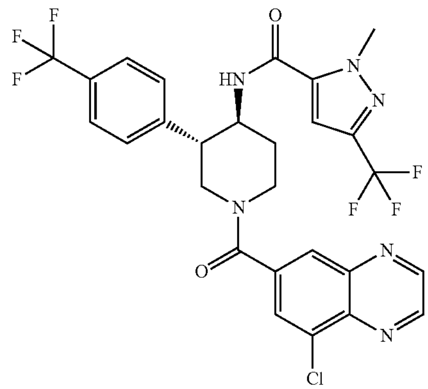 [SMILES: Cn1nc(C(F)(F)F)cc1C(=O)N[C@H]1CCN(C(=O)c2cc(Cl)c3nccnc3c2)C[C@@H]1c1ccc(C(F)(F)F)cc1] | | 611.1 |
| 89B | N-((3S,4S)-1-((8-chloroquinoxalin-6-yl)carbonyl)-3-phenylpiperidin-4-yl)-1-methyl-3-(trifluoromethyl)-1H-pyrazole-5-carboxamide | 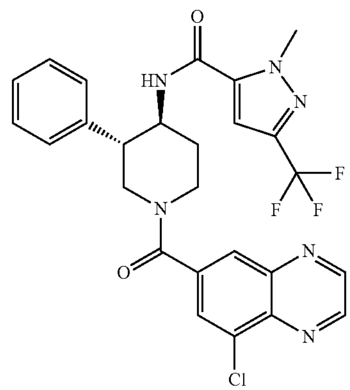 [SMILES: Cn1nc(C(F)(F)F)cc1C(=O)N[C@H]1CCN(C(=O)c2cc(Cl)c3nccnc3c2)C[C@@H]1c1ccccc1] | | 543.2 |
| 90B | N-((3R,4R)-1-((8-chloroquinoxalin-6-yl)carbonyl)-3-(4-fluorophenyl)piperidin-4-yl)-3-(trifluoromethyl)pyridine-2-carboxamide | 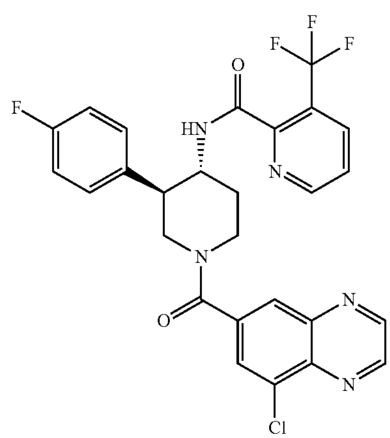 [SMILES: O=C(N[C@@H]1CCN(C(=O)c2cc(Cl)c3nccnc3c2)C[C@H]1c1ccc(F)cc1)c1ncccc1C(F)(F)F] | | 558.2 |
| 91B | N-((3R,4R)-1-((8-chloroquinoxalin-6-yl)carbonyl)-3-(4-fluorophenyl)piperidin-4-yl)-1-methyl-3-(trifluoromethyl)-1H-pyrazole-5-carboxamide | 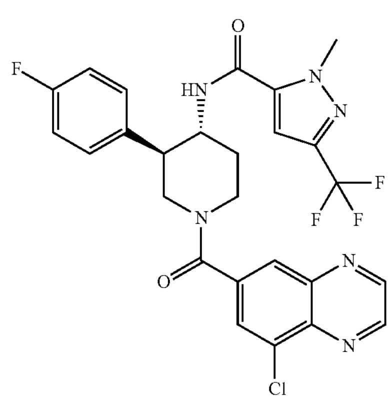 [SMILES: Cn1nc(C(F)(F)F)cc1C(=O)N[C@@H]1CCN(C(=O)c2cc(Cl)c3nccnc3c2)C[C@H]1c1ccc(F)cc1] | | 561.2 |

TABLE 2-1-continued

| Ex. No. | IUPAC Name | Structure | Salt | MS |
|---|---|---|---|---|
| 92B | N-((3R,4R)-1-((8-chloroquinoxalin-6-yl)carbonyl)-3-(4-(trifluoromethyl)phenyl)piperidin-4-yl)-3-(trifluoromethyl)pyridine-2-carboxamide | 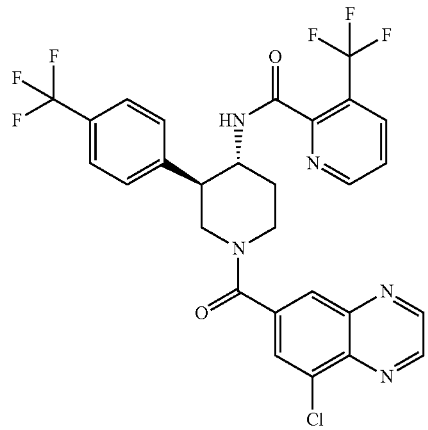 [SMILES: O=C(N[C@@H]1CCN(C(=O)c2cc(Cl)c3nccnc3c2)C[C@H]1c1ccc(C(F)(F)F)cc1)c1ncccc1C(F)(F)F] | | 608.2 |
| 93B | N-((3R,4R)-1-((8-chloroquinoxalin-6-yl)carbonyl)-3-(4-(trifluoromethyl)phenyl)piperidin-4-yl)-1-methyl-3-(trifluoromethyl)-1H-pyrazole-5-carboxamide | 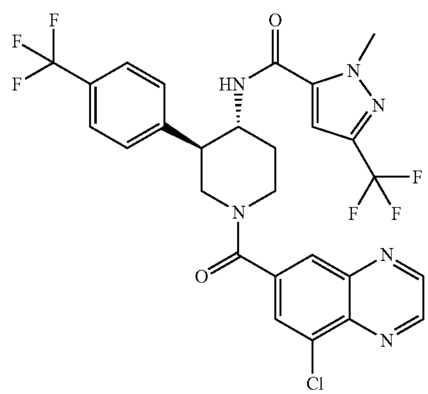 [SMILES: Cn1nc(C(F)(F)F)cc1C(=O)N[C@@H]1CCN(C(=O)c2cc(Cl)c3nccnc3c2)C[C@H]1c1ccc(C(F)(F)F)cc1] | | 611.1 |
| 94B | N-((3S,4R)-1-((8-chloroquinoxalin-6-yl)carbonyl)-3-phenylpiperidin-4-yl)-6-(2-(tetrahydro-2H-pyran-2-yloxy)ethoxy)-4-(trifluoromethyl)nicotinamide | 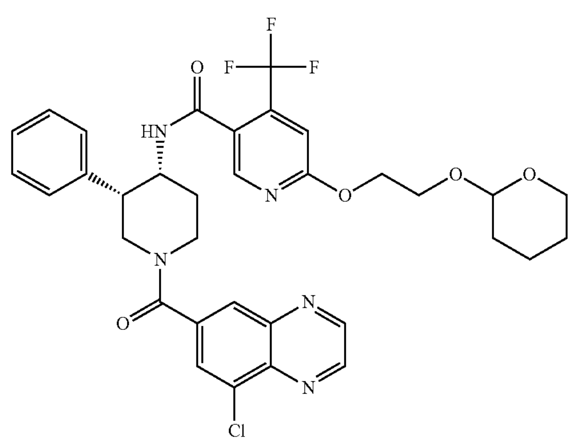 [SMILES: O=C(N[C@@H]1CCN(C(=O)c2cc(Cl)c3nccnc3c2)C[C@@H]1c1ccccc1)c1cnc(OCCOC2CCCCO2)cc1C(F)(F)F] | | 682.3 |

TABLE 2-1-continued

| Ex. No. | IUPAC Name | Structure | Salt | MS |
|---|---|---|---|---|
| 95B | N-((3S,4R)-1-((8-chloroquinoxalin-6-yl)carbonyl)-3-(4-fluorophenyl)piperidin-4-yl)-3-methoxy-1-methyl-1H-pyrazole-5-carboxamide | 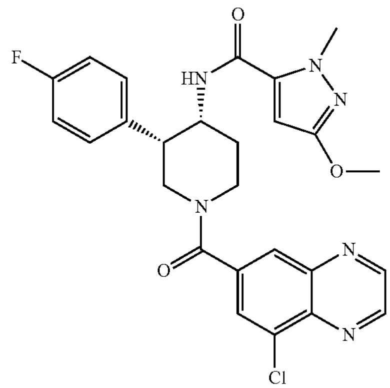 [SMILES: COc1cc(C(=O)N[C@@H]2CCN(C(=O)c3cc(Cl)c4nccnc4c3)C[C@@H]2c2ccc(F)cc2)n(C)n1] | | 523.2 |
| 96B | N-((3S,4R)-1-((8-chloroquinoxalin-6-yl)carbonyl)-3-(4-fluorophenyl)piperidin-4-yl)-1-methyl-3-(trifluoromethyl)-1H-pyrazole-5-carboxamide | 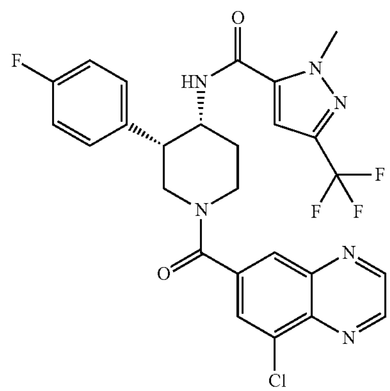 [SMILES: Cn1nc(C(F)(F)F)cc1C(=O)N[C@@H]1CCN(C(=O)c2cc(Cl)c3nccnc3c2)C[C@@H]1c1ccc(F)cc1] | | 561.1 |
| 97B | 2-chloro-N-(cis-1-(3,4-dimethoxybenzoyl)-3-(pyridin-3-yl)piperidin-4-yl)benzamide | 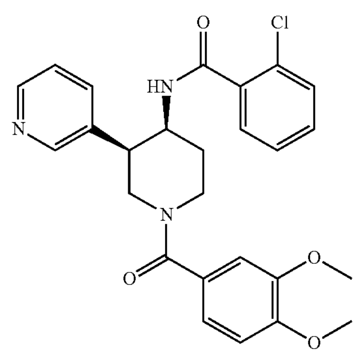 [SMILES: COc1ccc(C(=O)N2CC[C@H](NC(=O)c3ccccc3Cl)[C@H](c3cccnc3)C2)cc1OC] | | 480.2 |
| 98B | N-((3S,4R)-1-(3,4-dichlorobenzoyl)-3-phenylpiperidin-4-yl)-2-(trifluoromethoxy)benzamide | 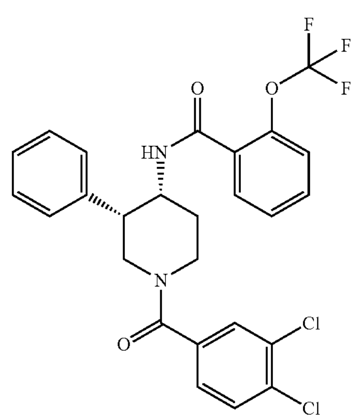 [SMILES: O=C(N[C@@H]1CCN(C(=O)c2ccc(Cl)c(Cl)c2)C[C@@H]1c1ccccc1)c1ccccc1OC(F)(F)F] | | 537.1 |

TABLE 2-1-continued

| Ex. No. | IUPAC Name | Structure | Salt | MS |
|---|---|---|---|---|
| 99B | N-((3S,4R)-1-(3-chloro-4-methoxybenzoyl)-3-phenylpiperidin-4-yl)-2-(trifluoromethoxy)benzamide | 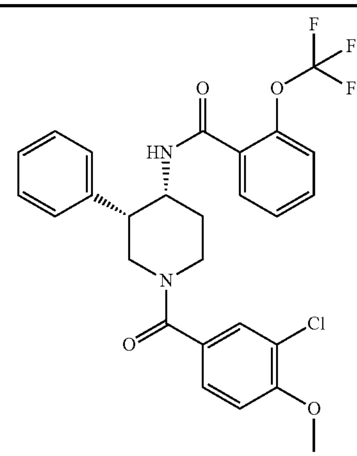 | | 533.1 |
| 100B | N-((3S,4R)-1-(4-methoxybenzoyl)-3-phenylpiperidin-4-yl)-2-(trifluoromethoxy)benzamide | 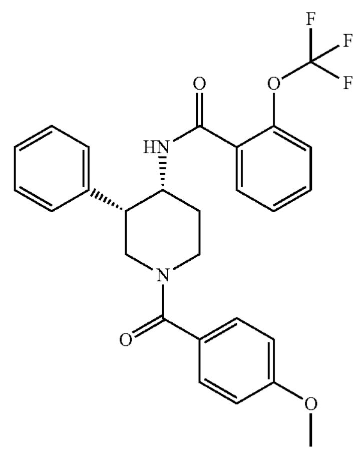 [SMILES: COc1ccc(C(=O)N2CC[C@@H](NC(=O)c3ccccc3OC(F)(F)F)[C@@H](c3ccccc3)C2)cc1] | | 499.1 |
| 101B | N-((3S,4R)-3-phenyl-1-(pyridazin-4-ylcarbonyl)piperidin-4-yl)-2-(trifluoromethoxy)benzamide | 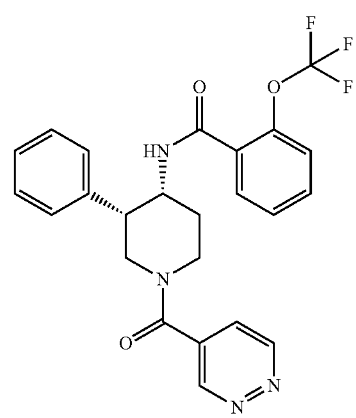 [SMILES: O=C(N[C@@H]1CCN(C(=O)c2ccnnc2)C[C@@H]1c1ccccc1)c1ccccc1OC(F)(F)F] | | 471.1 |

TABLE 2-1-continued

| Ex. No. | IUPAC Name | Structure | Salt | MS |
|---|---|---|---|---|
| 102B | N-((3S,4R)-1-(3-chloro-4-(methylsulfonyl)benzoyl)-3-phenylpiperidin-4-yl)-2-(trifluoromethoxy)benzamide | 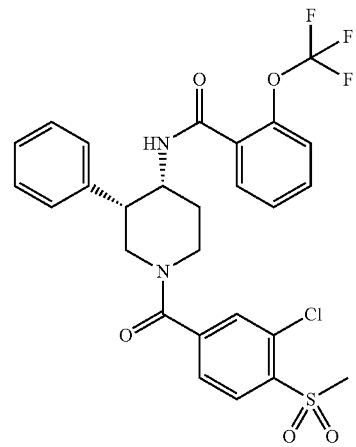 [SMILES: CS(=O)(=O)c1ccc(C(=O)N2CC[C@@H](NC(=O)c3ccccc3OC(F)(F)F)[C@@H](c3ccccc3)C2)cc1Cl] | | 581.1 |
| 103B | N-((3S,4R)-1-(1,3-benzothiazol-6-ylcarbonyl)-3-phenylpiperidin-4-yl)-2-(trifluoromethoxy)benzamide | 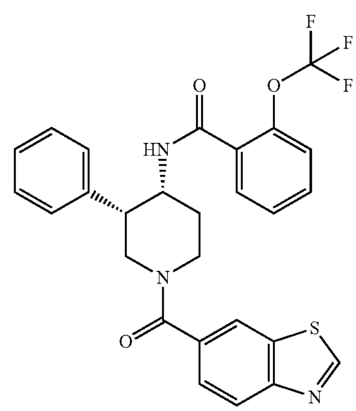 [SMILES: O=C(N[C@@H]1CCN(C(=O)c2ccc3ncsc3c2)C[C@@H]1c1ccccc1)c1ccccc1OC(F)(F)F] | | 526.2 |
| 104B | N-((3S,4R)-1-((1-methyl-1H-benzimidazol-6-yl)carbonyl)-3-phenylpiperidin-4-yl)-2-(trifluoromethoxy)benzamide | 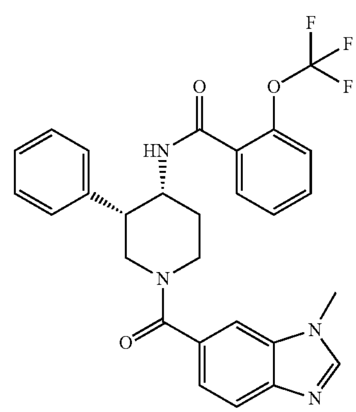 [SMILES: Cn1cnc2ccc(C(=O)N3CC[C@@H](NC(=O)c4ccccc4OC(F)(F)F)[C@@H](c4ccccc4)C3)cc21] | | 523.2 |

TABLE 2-1-continued

| Ex. No. | IUPAC Name | Structure | Salt | MS |
|---|---|---|---|---|
| 105B | N-((3S,4R)-1-(3,4-diethoxybenzoyl)-3-phenylpiperidin-4-yl)-2-(trifluoromethoxy)benzamide | 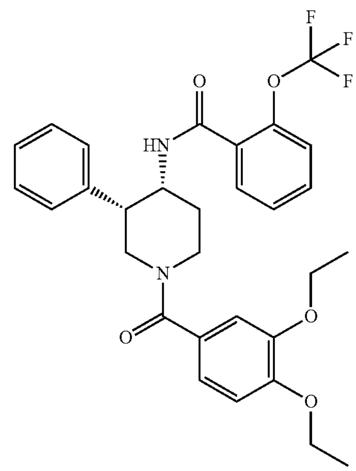 [SMILES: CCOc1ccc(C(=O)N2CC[C@@H](NC(=O)c3ccccc3OC(F)(F)F)[C@@H](c3ccccc3)C2)cc1OCC] | | 557.3 |
| 106B | N-((3S,4R)-1-(2-naphthoyl)-3-phenylpiperidin-4-yl)-2-(trifluoromethoxy)benzamide | 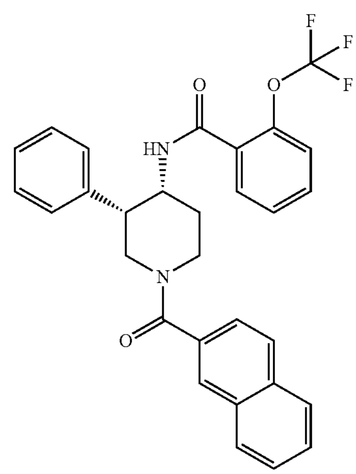 [SMILES: O=C(N[C@@H]1CCN(C(=O)c2ccc3ccccc3c2)C[C@@H]1c1ccccc1)c1ccccc1OC(F)(F)F] | | 519.2 |
| 107B | N-((3S,4R)-3-phenyl-1-(quinolin-6-ylcarbonyl)piperidin-4-yl)-2-(trifluoromethoxy)benzamide | 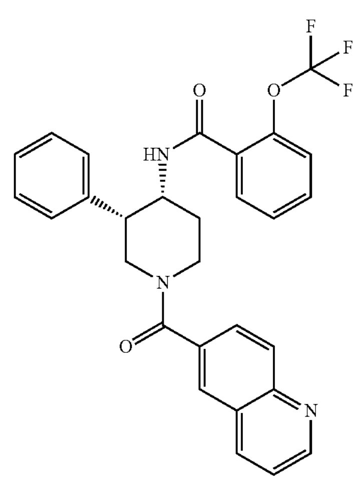 [SMILES: O=C(N[C@@H]1CCN(C(=O)c2ccc3ncccc3c2)C[C@@H]1c1ccccc1)c1ccccc1OC(F)(F)F] | | 520.2 |

TABLE 2-1-continued

| Ex. No. | IUPAC Name | Structure | Salt | MS |
|---|---|---|---|---|
| 108B | N-((3S,4R)-1-(2-chloro-4-methoxybenzoyl)-3-phenylpiperidin-4-yl)-2-(trifluoromethoxy)benzamide | 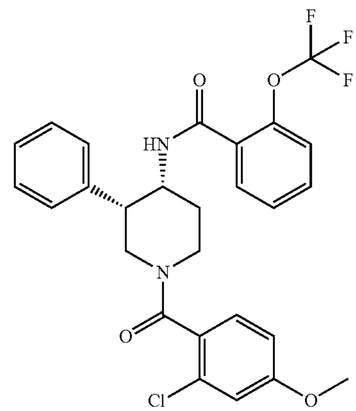 [SMILES: COc1ccc(C(=O)N2CC[C@@H](NC(=O)c3ccccc3OC(F)(F)F)[C@@H](c3ccccc3)C2)c(Cl)c1] | | 533.1 |
| 109B | N-((3S,4R)-1-(2-fluoro-4-methoxybenzoyl)-3-phenylpiperidin-4-yl)-2-(trifluoromethoxy)benzamide | 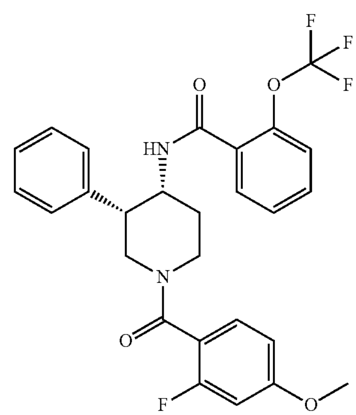 [SMILES: COc1ccc(C(=O)N2CC[C@@H](NC(=O)c3ccccc3OC(F)(F)F)[C@@H](c3ccccc3)C2)c(F)c1] | | 517.2 |
| 110B | N-((3S,4R)-3-phenyl-1-(4-(trifluoromethoxy)benzoyl)piperidin-4-yl)-2-(trifluoromethoxy)benzamide | 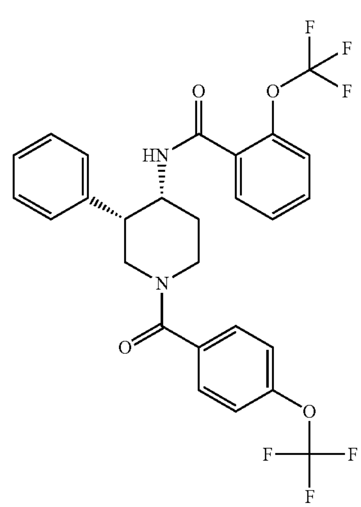 [SMILES: O=C(N[C@@H]1CCN(C(=O)c2ccc(OC(F)(F)F)cc2)C[C@@H]1c1ccccc1)c1ccccc1OC(F)(F)F] | | 553.1 |

TABLE 2-1-continued

| Ex. No. | IUPAC Name | Structure | Salt | MS |
|---|---|---|---|---|
| 111B | N-((3S,4R)-1-(4-methoxy-3,5-dimethylbenzoyl)-3-phenylpiperidin-4-yl)-2-(trifluoromethoxy)benzamide | 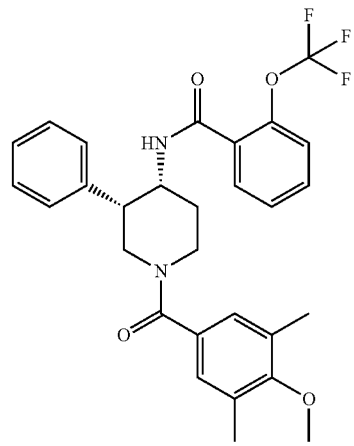 [SMILES: COc1c(C)cc(C(=O)N2CC[C@@H](NC(=O)c3ccccc3OC(F)(F)F)[C@@H](c3ccccc3)C2)cc1C] | | 527.2 |
| 112B | N-((3S,4R)-1-((5-chloro-6-methoxypyridin-3-yl)carbonyl)-3-phenylpiperidin-4-yl)-2-(trifluoromethoxy)benzamide | 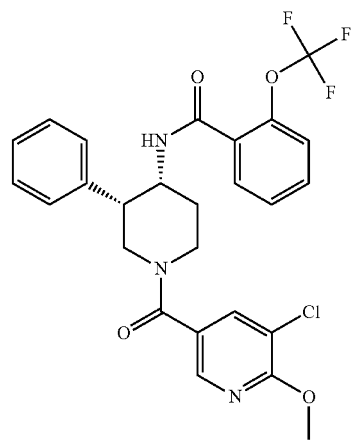 [SMILES: COc1ncc(C(=O)N2CC[C@@H](NC(=O)c3ccccc3OC(F)(F)F)[C@@H](c3ccccc3)C2)cc1Cl] | | 534.2 |
| 113B | 2-chloro-N-(cis-1-(3,4-dimethoxybenzoyl)-3-(4-methoxyphenyl)piperidin-4-yl)benzamide | 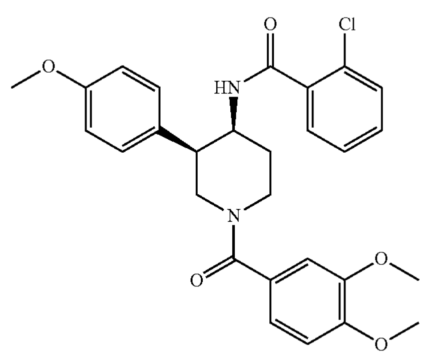 | | 509.2 |
| 114B | 2-chloro-N-(cis-1-(3,4-dimethoxybenzoyl)-3-(4-fluorophenyl)piperidin-4-yl)benzamide | 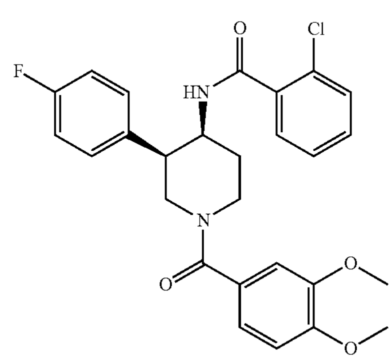 | | 497.1 |

TABLE 2-1-continued

| Ex. No. | IUPAC Name | Structure | Salt | MS |
|---|---|---|---|---|
| 115B | 2-chloro-N-(cis-1-(3,4-dimethoxybenzoyl)-3-(4-fluoro-3-methylphenyl)piperidin-4-yl)benzamide | 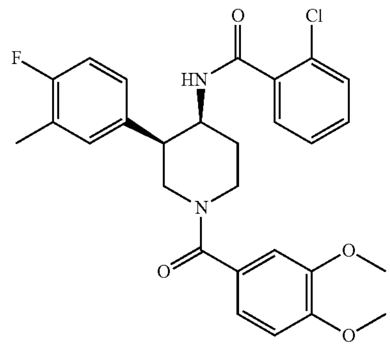 | | 511.1 |
| 116B | 2-chloro-N-(cis-1-(3,4-dimethoxybenzoyl)-3-(4-fluoro-2-methylphenyl)piperidin-4-yl)benzamide | 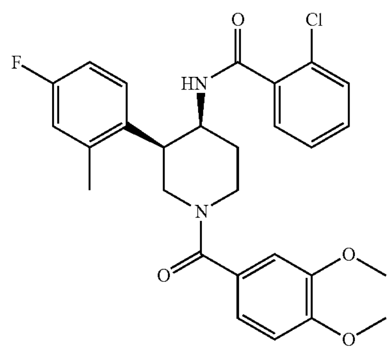 [SMILES: COc1ccc(C(=O)N2CC[C@H](NC(=O)c3ccccc3Cl)[C@H](c3ccc(F)cc3C)C2)cc1OC] | | 511.1 |
| 117B | 2-chloro-N-(trans-1-(3,4-dimethoxybenzoyl)-3-(pyridin-3-yl)piperidin-4-yl)benzamide | 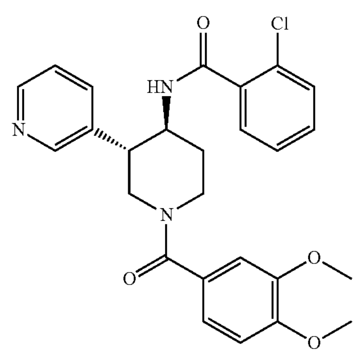 [SMILES: COc1ccc(C(=O)N2CC[C@H](NC(=O)c3ccccc3Cl)[C@@H](c3cccnc3)C2)cc1OC] | | 480.2 |
| 118B | 3-chloro-N-((3S,4R)-3-phenyl-1-(quinoxalin-6-ylcarbonyl)piperidin-4-yl)pyridine-2-carboxamide | 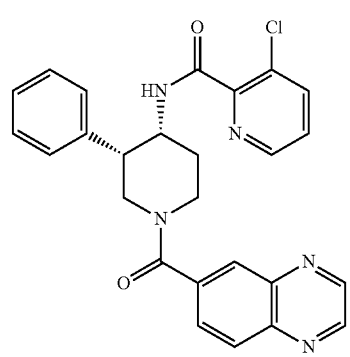 [SMILES: O=C(N[C@@H]1CCN(C(=O)c2ccc3nccnc3c2)C[C@@H]1c1ccccc1)c1ncccc1Cl] | | 472.1 |

TABLE 2-1-continued

| Ex. No. | IUPAC Name | Structure | Salt | MS |
|---|---|---|---|---|
| 119B | 2-chloro-N-((3S,4R)-3-phenyl-1-(quinoxalin-6-ylcarbonyl)piperidin-4-yl)nicotinamide | 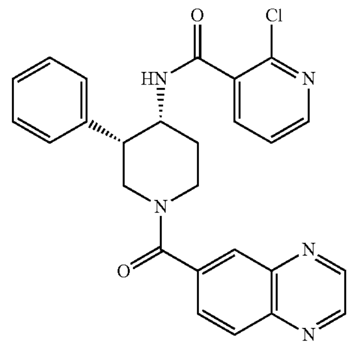 [SMILES: O=C(N[C@@H]1CCN(C(=O)c2ccc3nccnc3c2)C[C@@H]1c1ccccc1)c1cccnc1Cl] | | 472.1 |
| 120B | 3-chloro-N-((3S,4R)-3-phenyl-1-(quinoxalin-6-ylcarbonyl)piperidin-4-yl)pyrazine-2-carboxamide | 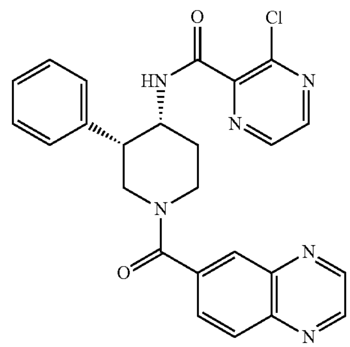 [SMILES: O=C(N[C@@H]1CCN(C(=O)c2ccc3nccnc3c2)C[C@@H]1c1ccccc1)c1nccnc1Cl] | | 473.0 |
| 121B | N-((3S,4R)-3-phenyl-1-(quinoxalin-6-ylcarbonyl)piperidin-4-yl)-4-(trifluoromethyl)nicotinamide | 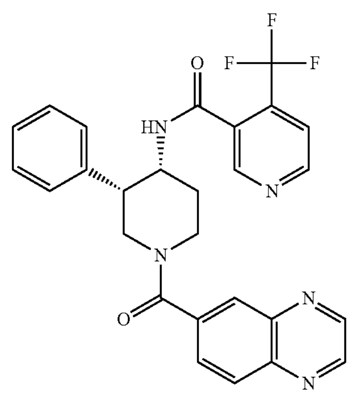 [SMILES: O=C(N[C@@H]1CCN(C(=O)c2ccc3nccnc3c2)C[C@@H]1c1ccccc1)c1cnccc1C(F)(F)F] | | 506.1 |
| 122B | N-((3S,4R)-3-phenyl-1-(quinoxalin-6-ylcarbonyl)piperidin-4-yl)-2-(trifluoromethyl)nicotinamide | 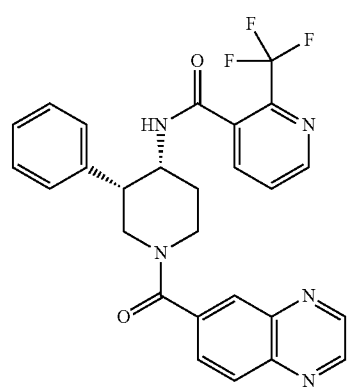 [SMILES: O=C(N[C@@H]1CCN(C(=O)c2ccc3nccnc3c2)C[C@@H]1c1ccccc1)c1cccnc1C(F)(F)F] | | 506.1 |

TABLE 2-1-continued

| Ex. No. | IUPAC Name | Structure | Salt | MS |
|---|---|---|---|---|
| 123B | 2-(methylsulfonyl)-N-((3S,4R)-3-phenyl-1-(quinoxalin-6-ylcarbonyl)piperidin-4-yl)benzamide | 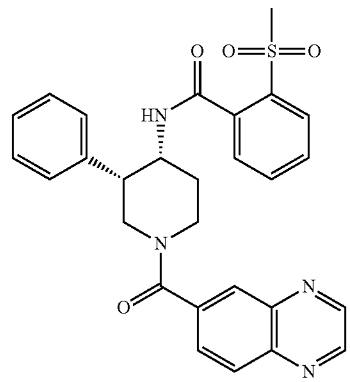 [SMILES: CS(=O)(=O)c1ccccc1C(=O)N[C@@H]1CCN(C(=O)c2ccc3nccnc3c2)C[C@@H]1c1ccccc1] | | 515.0 |
| 124B | 2-cyano-N-((3S,4R)-3-phenyl-1-(quinoxalin-6-ylcarbonyl)piperidin-4-yl)benzamide | 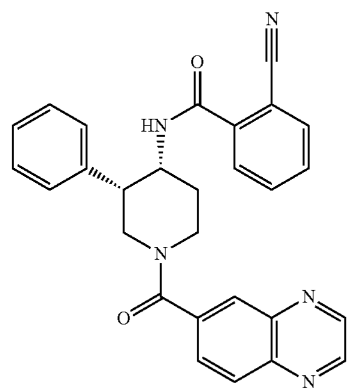 [SMILES: N#Cc1ccccc1C(=O)N[C@@H]1CCN(C(=O)c2ccc3nccnc3c2)C[C@@H]1c1ccccc1] | | 462.0 |
| 125B | 1-isopropyl-N-((3S,4R)-3-phenyl-1-(quinoxalin-6-ylcarbonyl)piperidin-4-yl)-1H-pyrazole-5-carboxamide | 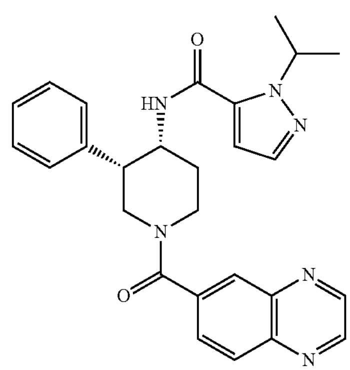 [SMILES: CC(C)n1nccc1C(=O)N[C@@H]1CCN(C(=O)c2ccc3nccnc3c2)C[C@@H]1c1ccccc1] | | 469.1 |
| 126B | 1-methyl-N-((3S,4R)-3-phenyl-1-(quinoxalin-6-ylcarbonyl)piperidin-4-yl)-1H-pyrazole-5-carboxamide | 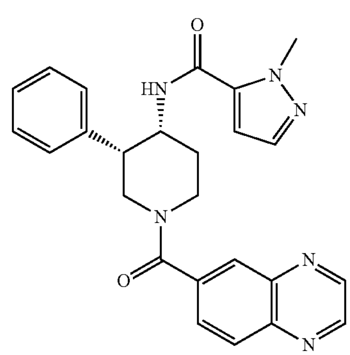 [SMILES: Cn1nccc1C(=O)N[C@@H]1CCN(C(=O)c2ccc3nccnc3c2)C[C@@H]1c1ccccc1] | | 441.1 |

TABLE 2-1-continued

| Ex. No. | IUPAC Name | Structure | Salt | MS |
|---|---|---|---|---|
| 127B | 1-methyl-N-((3S,4R)-3-phenyl-1-(quinoxalin-6-ylcarbonyl)piperidin-4-yl)-1H-imidazole-5-carboxamide | 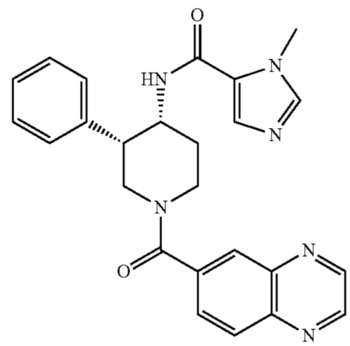 [SMILES: Cn1cncc1C(=O)N[C@@H]1CCN(C(=O)c2ccc3nccnc3c2)C[C@@H]1c1ccccc1] | | 441.0 |
| 128B | 1-methyl-N-((3S,4R)-3-phenyl-1-(quinoxalin-6-ylcarbonyl)piperidin-4-yl)-1H-imidazole-2-carboxamide | 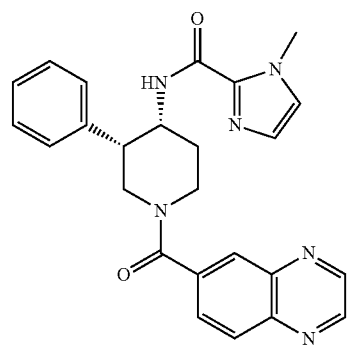 [SMILES: Cn1ccnc1C(=O)N[C@@H]1CCN(C(=O)c2ccc3nccnc3c2)C[C@@H]1c1ccccc1] | | 441.0 |
| 129B | 5-methyl-N-((3S,4R)-3-phenyl-1-(quinoxalin-6-ylcarbonyl)piperidin-4-yl)-1,3-thiazole-4-carboxamide | 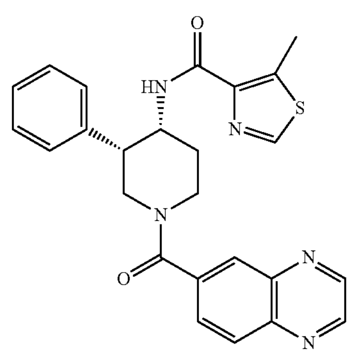 [SMILES: Cc1ocnc1C(=O)N[C@@H]1CCN(C(=O)c2ccc3nccnc3c2)C[C@@H]1c1ccccc1] | | 458.0 |
| 130B | 5-methyl-N-((3S,4R)-3-phenyl-1-(quinoxalin-6-ylcarbonyl)piperidin-4-yl)-1,3-oxazole-4-carboxamide | 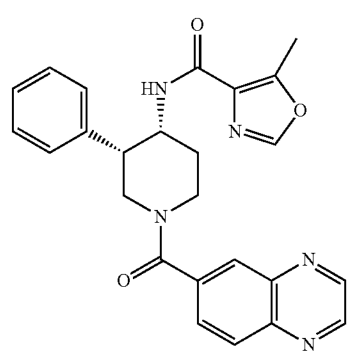 | | 442.1 |

TABLE 2-1-continued

| Ex. No. | IUPAC Name | Structure | Salt | MS |
|---|---|---|---|---|
| 131B | 5-methyl-2-oxo-N-((3S,4R)-3-phenyl-1-(quinoxalin-6-ylcarbonyl)piperidin-4-yl)-2,3-dihydro-1,3-oxazole-4-carboxamide | 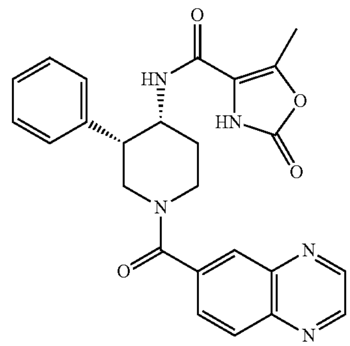 [SMILES: Cc1oc(=O)[nH]c1C(=O)N[C@@H]1CCN(C(=O)c2ccc3nccnc3c2)C[C@@H]1c1ccccc1] | | 458.0 |
| 132B | 5-chloro-1-methyl-N-((3S,4R)-3-phenyl-1-(quinoxalin-6-ylcarbonyl)piperidin-4-yl)-1H-pyrazole-4-carboxamide | 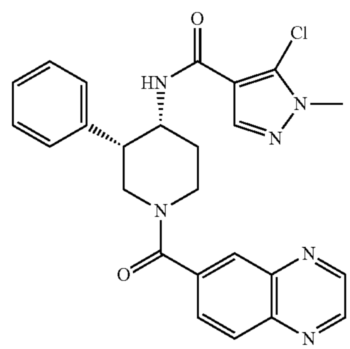 [SMILES: Cn1ncc(C(=O)N[C@@H]2CCN(C(=O)c3ccc4nccnc4c3)C[C@@H]2c2ccccc2)c1Cl] | | 475.1 |
| 133B | 1,3-dimethyl-N-((3S,4R)-3-phenyl-1-(quinoxalin-6-ylcarbonyl)piperidin-4-yl)-1H-pyrazole-5-carboxamide | 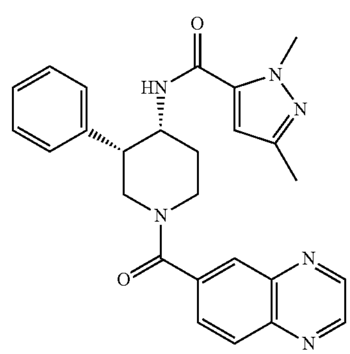 [SMILES: Cc1cc(C(=O)N[C@@H]2CCN(C(=O)c3ccc4nccnc4c3)C[C@@H]2c2ccccc2)n(C)n1] | | 455.1 |
| 134B | 1,3-dimethyl-N-((3S,4R)-3-phenyl-1-(quinoxalin-6-ylcarbonyl)piperidin-4-yl)-1H-pyrazole-4-carboxamide | 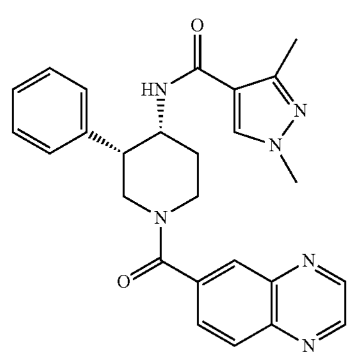 [SMILES: Cc1nn(C)cc1C(=O)N[C@@H]1CCN(C(=O)c2ccc3nccnc3c2)C[C@@H]1c1ccccc1] | | 455.1 |

TABLE 2-1-continued

| Ex. No. | IUPAC Name | Structure | Salt | MS |
|---|---|---|---|---|
| 135B | 5-methyl-N-((3S,4R)-3-phenyl-1-(quinoxalin-6-ylcarbonyl)piperidin-4-yl)-1,2-oxazole-4-carboxamide | 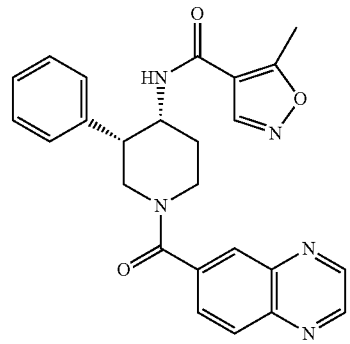 [SMILES: Cc1oncc1C(=O)N[C@@H]1CCN(C(=O)c2ccc3nccnc3c2)C[C@@H]1c1ccccc1] | | 442.1 |
| 136B | 3-chloro-N-((3S,4R)-1-((5,6-dimethoxypyridin-3-yl)carbonyl)-3-phenylpiperidin-4-yl)pyridine-2-carboxamide | 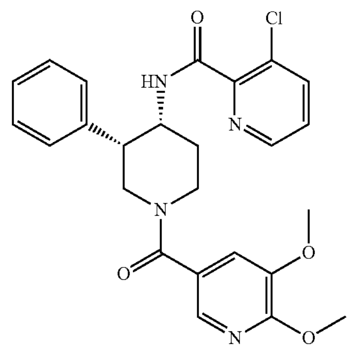 [SMILES: COc1cc(C(=O)N2CC[C@@H](NC(=O)c3ncccc3Cl)[C@@H](c3ccccc3)C2)cnc1OC] | | 481.0 |
| 137B | 2-chloro-N-((3S,4R)-1-((5,6-dimethoxypyridin-3-yl)carbonyl)-3-phenylpiperidin-4-yl)nicotinamide | 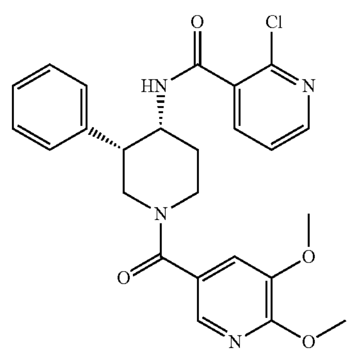 [SMILES: COc1cc(C(=O)N2CC[C@@H](NC(=O)c3cccnc3Cl)[C@@H](c3ccccc3)C2)cnc1OC] | | 481.1 |
| 138B | 3-chloro-N-((3S,4R)-1-((5,6-dimethoxypyridin-3-yl)carbonyl)-3-phenylpiperidin-4-yl)pyrazine-2-carboxamide | 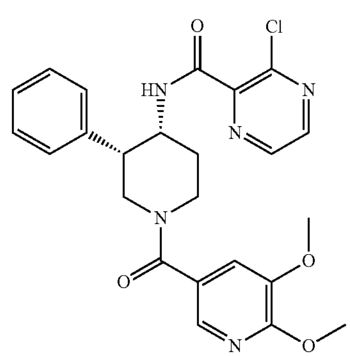 [SMILES: COc1cc(C(=O)N2CC[C@@H](NC(=O)c3nccnc3Cl)[C@@H](c3ccccc3)C2)cnc1OC] | | 481.9 |

TABLE 2-1-continued

| Ex. No. | IUPAC Name | Structure | Salt | MS |
|---|---|---|---|---|
| 139B | N-((3S,4R)-1-((5,6-dimethoxypyridin-3-yl)carbonyl)-3-phenylpiperidin-4-yl)-4-(trifluoromethyl)nicotinamide | 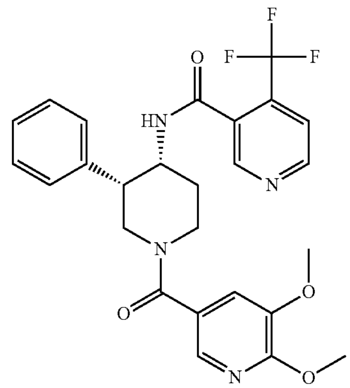 [SMILES: COc1cc(C(=O)N2CC[C@@H](NC(=O)c3cnccc3C(F)(F)F)[C@@H](c3ccccc3)C2)cnc1OC] | | 515.1 |
| 140B | N-((3S,4R)-1-((5,6-dimethoxypyridin-3-yl)carbonyl)-3-phenylpiperidin-4-yl)-2-(trifluoromethyl)nicotinamide | 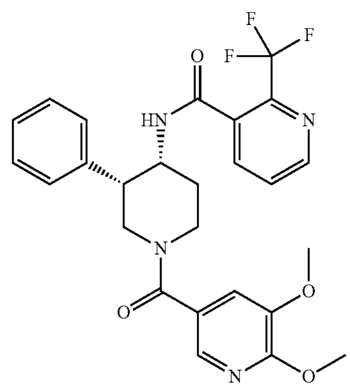 [SMILES: COc1cc(C(=O)N2CC[C@@H](NC(=O)c3cccnc3C(F)(F)F)[C@@H](c3ccccc3)C2)cnc1OC] | | 515.1 |
| 141B | N-((3S,4R)-1-((5,6-dimethoxypyridin-3-yl)carbonyl)-3-phenylpiperidin-4-yl)-2-(methylsulfonyl)benzamide | 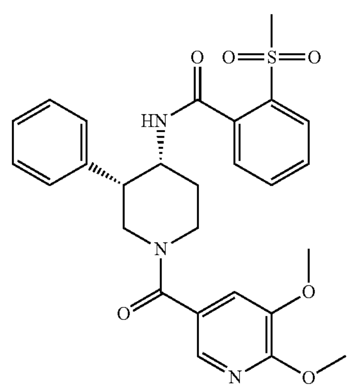 [SMILES: COc1cc(C(=O)N2CC[C@@H](NC(=O)c3ccccc3S(C)(=O)=O)[C@@H](c3ccccc3)C2)cnc1OC] | | 524.2 |
| 142B | 2-cyano-N-((3S,4R)-1-((5,6-dimethoxypyridin-3-yl)carbonyl)-3-phenylpiperidin-4-yl)benzamide | 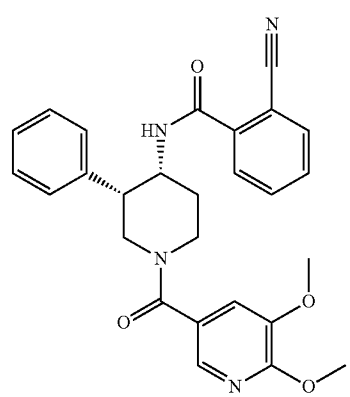 [SMILES: COc1cc(C(=O)N2CC[C@@H](NC(=O)c3ccccc3C#N)[C@@H](c3ccccc3)C2)cnc1OC] | | 471.1 |

TABLE 2-1-continued

| Ex. No. | IUPAC Name | Structure | Salt | MS |
|---|---|---|---|---|
| 143B | N-((3S,4R)-1-((5,6-dimethoxypyridin-3-yl)carbonyl)-3-phenylpiperidin-4-yl)-1-isopropyl-1H-pyrazole-5-carboxamide | 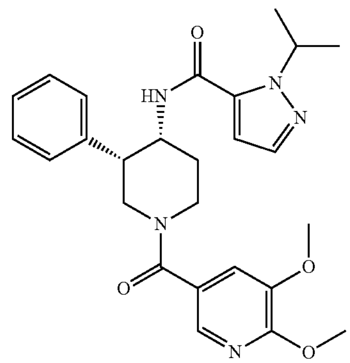 [SMILES: COc1cc(C(=O)N2CC[C@@H](NC(=O)c3ccnn3C(C)C)[C@@H](c3ccccc3)C2)cnc1OC] | | 478.1 |
| 144B | N-((3S,4R)-1-((5,6-dimethoxypyridin-3-yl)carbonyl)-3-phenylpiperidin-4-yl)-1-methyl-1H-pyrazole-5-carboxamide | 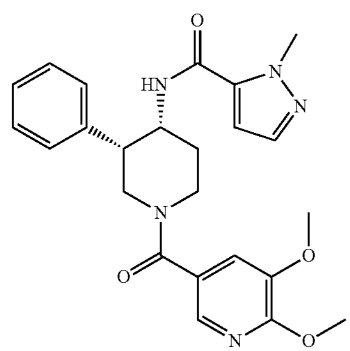 | | 449.9 |
| 145B | N-((3S,4R)-1-((5,6-dimethoxypyridin-3-yl)carbonyl)-3-phenylpiperidin-4-yl)-1-methyl-1H-imidazole-5-carboxamide | 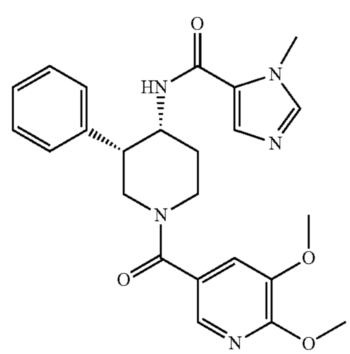 [SMILES: COc1cc(C(=O)N2CC[C@@H](NC(=O)c3cncn3C)[C@@H](c3ccccc3)C2)cnc1OC] | | 450.0 |
| 146B | N-((3S,4R)-1-((5,6-dimethoxypyridin-3-yl)carbonyl)-3-phenylpiperidin-4-yl)-1-methyl-1H-imidazole-2-carboxamide | 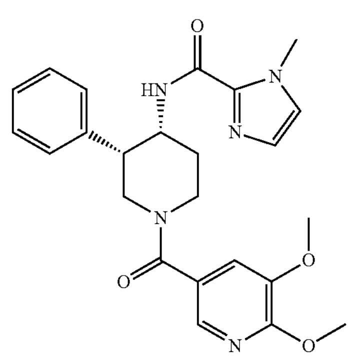 [SMILES: COc1cc(C(=O)N2CC[C@@H](NC(=O)c3nccn3C)[C@@H](c3ccccc3)C2)cnc1OC] | | 450.0 |

TABLE 2-1-continued

| Ex. No. | IUPAC Name | Structure | Salt | MS |
|---|---|---|---|---|
| 147B | N-((3S,4R)-1-((5,6-dimethoxypyridin-3-yl)carbonyl)-3-phenylpiperidin-4-yl)-5-methyl-1,3-thiazole-4-carboxamide | 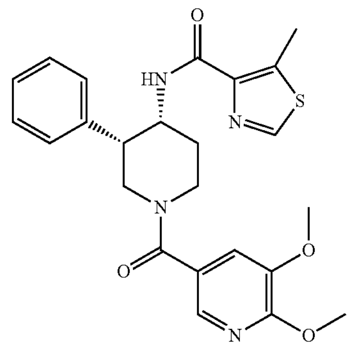 [SMILES: COc1cc(C(=O)N2CC[C@@H](NC(=O)c3ncsc3C)[C@@H](c3ccccc3)C2)cnc1OC] | | 467.0 |
| 148B | N-((3S,4R)-1-((5,6-dimethoxypyridin-3-yl)carbonyl)-3-phenylpiperidin-4-yl)-5-methyl-1,3-oxazole-4-carboxamide | 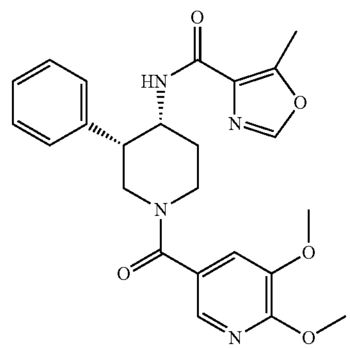 [SMILES: COc1cc(C(=O)N2CC[C@@H](NC(=O)c3ncoc3C)[C@@H](c3ccccc3)C2)cnc1OC] | | 451.0 |
| 149B | N-((3S,4R)-1-((5,6-dimethoxypyridin-3-yl)carbonyl)-3-phenylpiperidin-4-yl)-5-methyl-2-oxo-2,3-dihydro-1,3-oxazole-4-carboxamide | 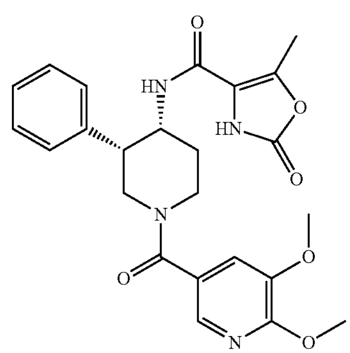 [SMILES: COc1cc(C(=O)N2CC[C@@H](NC(=O)c3[nH]c(=O)oc3C)[C@@H](c3ccccc3)C2)cnc1OC] | | 467.1 |
| 150B | 5-chloro-N-((3S,4R)-1-((5,6-dimethoxypyridin-3-yl)carbonyl)-3-phenylpiperidin-4-yl)-1-methyl-1H-pyrazole-4-carboxamide | 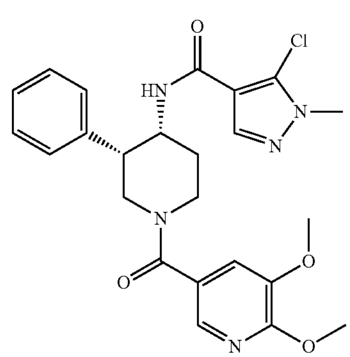 [SMILES: COc1cc(C(=O)N2CC[C@@H](NC(=O)c3cnn(C)c3Cl)[C@@H](c3ccccc3)C2)cnc1OC] | | 484.1 |

US 10,519,110 B2

TABLE 2-1-continued

| Ex. No. | IUPAC Name | Structure | Salt | MS |
|---|---|---|---|---|
| 151B | N-((3S,4R)-1-((5,6-dimethoxypyridin-3-yl)carbonyl)-3-phenylpiperidin-4-yl)-1,3-dimethyl-1H-pyrazole-5-carboxamide | 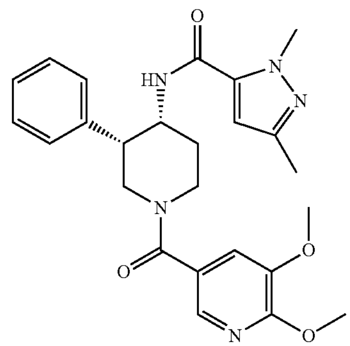 [SMILES: COc1cc(C(=O)N2CC[C@@H](NC(=O)c3cc(C)nn3C)[C@@H](c3ccccc3)C2)cnc1OC] | | 464.1 |
| 152B | N-((3S,4R)-1-((5,6-dimethoxypyridin-3-yl)carbonyl)-3-phenylpiperidin-4-yl)-1,3-dimethyl-1H-pyrazole-4-carboxamide | 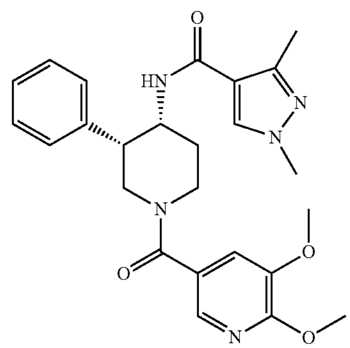 [SMILES: COc1cc(C(=O)N2CC[C@@H](NC(=O)c3cn(C)nc3C)[C@@H](c3ccccc3)C2)cnc1OC] | | 464.1 |
| 153B | N-((3S,4R)-1-((5,6-dimethoxypyridin-3-yl)carbonyl)-3-phenylpiperidin-4-yl)-5-methyl-1,2-oxazole-4-carboxamide | 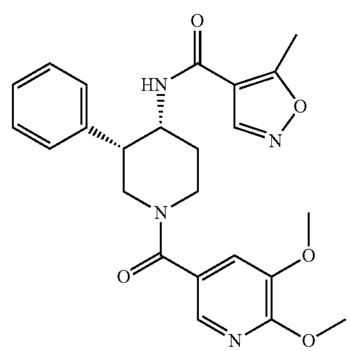 [SMILES: COc1cc(C(=O)N2CC[C@@H](NC(=O)c3cnoc3C)[C@@H](c3ccccc3)C2)cnc1OC] | | 451.0 |
| 154B | N-((3R,4R)-1-((8-chloroquinoxalin-6-yl)carbonyl)-3-phenylpiperidin-4-yl)-3-(trifluoromethyl)pyridine-2-carboxamide | 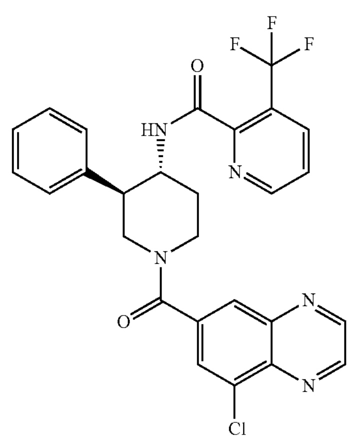 [SMILES: O=C(N[C@@H]1CCN(C(=O)c2cc(Cl)c3nccnc3c2)C[C@H]1c1ccccc1)c1ncccc1C(F)(F)F] | | 540.2 |

TABLE 2-1-continued

| Ex. No. | IUPAC Name | Structure | Salt | MS |
|---|---|---|---|---|
| 155B | N-((3R,4R)-1-((8-chloroquinoxalin-6-yl)carbonyl)-3-(4-(trifluoromethyl)phenyl)piperidin-4-yl)-2-(difluoromethoxy)benzamide | 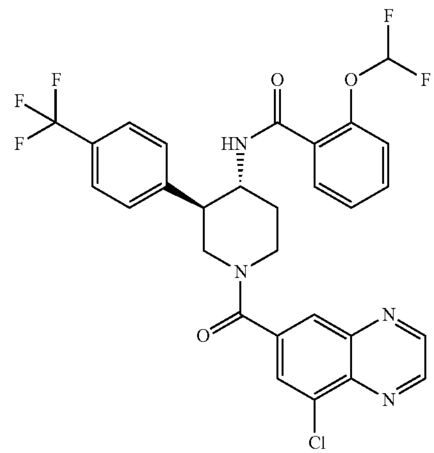 [SMILES: O=C(N[C@@H]1CCN(C(=O)c2cc(Cl)c3nccnc3c2)C[C@H]1c1ccc(C(F)(F)F)cc1)c1ccccc1OC(F)F] | | 605.2 |
| 156B | N-((3S,4S)-1-((8-chloroquinoxalin-6-yl)carbonyl)-3-phenylpiperidin-4-yl)-3-(trifluoromethyl)pyridine-2-carboxamide | 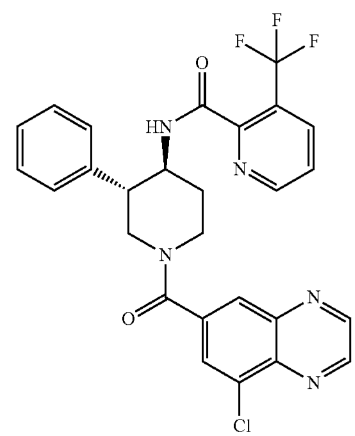 [SMILES: O=C(N[C@H]1CCN(C(=O)c2cc(Cl)c3nccnc3c2)C[C@@H]1c1ccccc1)c1ncccc1C(F)(F)F] | | 540.2 |
| 157B | N-((3S,4S)-1-((8-chloroquinoxalin-6-yl)carbonyl)-3-(4-(trifluoromethyl)phenyl)piperidin-4-yl)-2-(difluoromethoxy)benzamide | 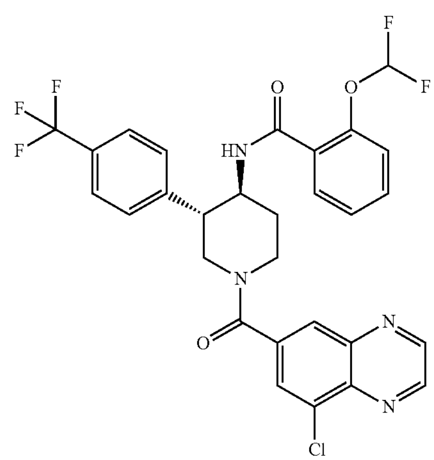 [SMILES: O=C(N[C@H]1CCN(C(=O)c2cc(Cl)c3nccnc3c2)C[C@@H]1c1ccc(C(F)(F)F)cc1)c1ccccc1OC(F)F] | | 603.2 |

TABLE 2-1-continued

| Ex. No. | IUPAC Name | Structure | Salt | MS |
|---|---|---|---|---|
| 158B | 6-chloro-N-((3S,4R)-1-((8-chloroquinoxalin-6-yl)carbonyl)-3-phenylpiperidin-4-yl)nicotinamide | 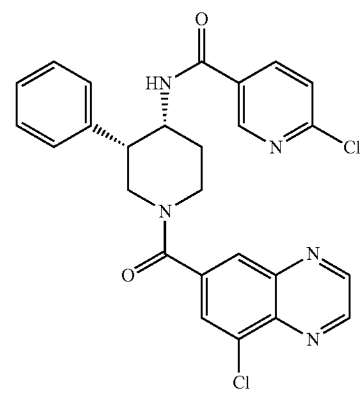 [SMILES: O=C(N[C@@H]1CCN(C(=O)c2cc(Cl)c3nccnc3c2)C[C@@H]1c1ccccc1)c1ccc(Cl)nc1] | | 506.0 |
| 159B | 5-bromo-N-((3S,4R)-1-((8-chloroquinoxalin-6-yl)carbonyl)-3-phenylpiperidin-4-yl)pyridine-2-carboxamide | 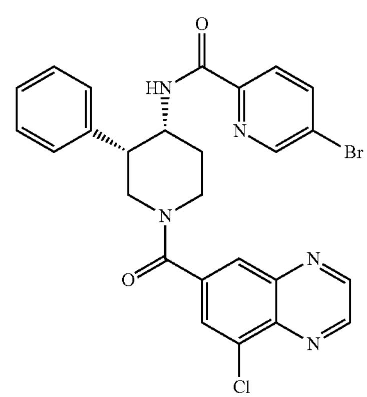 [SMILES: O=C(N[C@@H]1CCN(C(=O)c2cc(Cl)c3nccnc3c2)C[C@@H]1c1ccccc1)c1ccc(Br)cn1] | | 550.0 |
| 160B | N-((3S,4R)-1-((8-chloroquinoxalin-6-yl)carbonyl)-3-phenylpiperidin-4-yl)-1,4-dimethyl-1H-pyrazole-5-carboxamide | 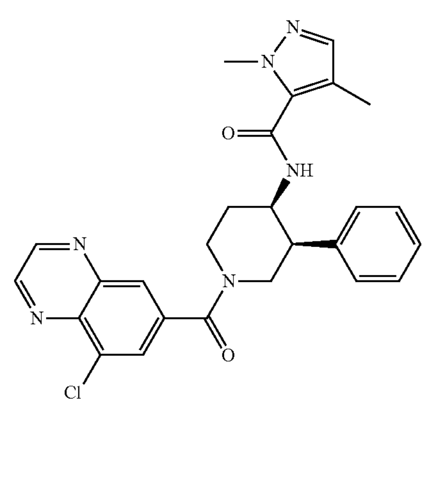 [SMILES: Cc1cnn(C)c1C(=O)N[C@@H]1CCN(C(=O)c2cc(Cl)c3nccnc3c2)C[C@@H]1c1ccccc1] | | 489.0 |

TABLE 2-1-continued

| Ex. No. | IUPAC Name | Structure | Salt | MS |
|---|---|---|---|---|
| 161B | 4-chloro-N-((3S,4R)-1-((8-chloroquinoxalin-6-yl)carbonyl)-3-phenylpiperidin-4-yl)-1-methyl-3-(trifluoromethyl)-1H-pyrazole-5-carboxamide | 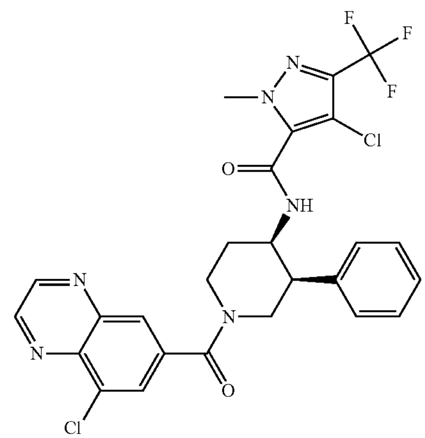 [SMILES: Cn1nc(C(F)(F)F)c(Cl)c1C(=O)N[C@@H]1CCN(C(=O)c2cc(Cl)c3nccnc3c2)C[C@@H]1c1ccccc1] | | 575.1 |
| 162B | N-((3S,4R)-1-((8-chloroquinoxalin-6-yl)carbonyl)-3-phenylpiperidin-4-yl)-1,5-dimethyl-1H-pyrazole-4-carboxamide | 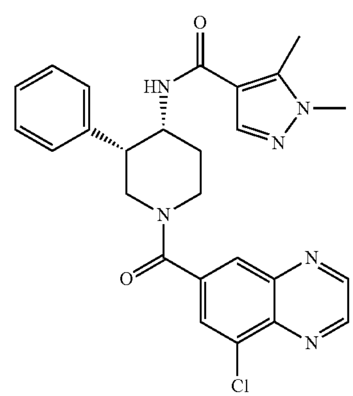 [SMILES: Cc1c(C(=O)N[C@@H]2CCN(C(=O)c3cc(Cl)c4nccnc4c3)C[C@@H]2c2ccccc2)cnn1C] | | 489.0 |
| 163B | N-((3S,4R)-1-((8-chloroquinoxalin-6-yl)carbonyl)-3-phenylpiperidin-4-yl)-5-methoxy-1-methyl-1H-pyrazole-4-carboxamide | 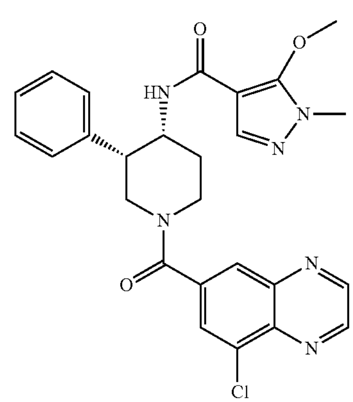 [SMILES: COc1c(C(=O)N[C@@H]2CCN(C(=O)c3cc(Cl)c4nccnc4c3)C[C@@H]2c2ccccc2)cnn1C] | | 505.1 |

TABLE 2-1-continued

| Ex. No. | IUPAC Name | Structure | Salt | MS |
|---|---|---|---|---|
| 164B | N-((3S,4R)-1-((8-chloroquinoxalin-6-yl)carbonyl)-3-phenylpiperidin-4-yl)-3-cyclopropyl-1-methyl-1H-pyrazole-4-carboxamide | 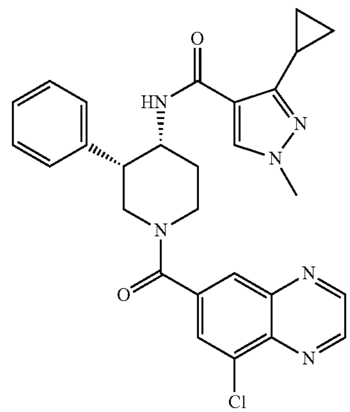 [SMILES: Cn1cc(C(=O)N[C@@H]2CCN(C(=O)c3cc(Cl)c4nccnc4c3)C[C@@H]2c2ccccc2)c(C2CC2)n1] | | 515.1 |
| 165B | N-((3S,4R)-1-((8-chloroquinoxalin-6-yl)carbonyl)-3-phenylpiperidin-4-yl)-5-ethoxy-1-methyl-1H-pyrazole-4-carboxamide | 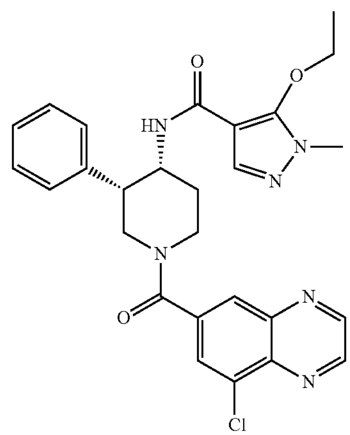 [SMILES: CCOc1c(C(=O)N[C@@H]2CCN(C(=O)c3cc(Cl)c4nccnc4c3)C[C@@H]2c2ccccc2)cnn1C] | | 519.1 |
| 166B | 5-chloro-N-((3S,4R)-1-((8-chloroquinoxalin-6-yl)carbonyl)-3-phenylpiperidin-4-yl)-1,3-dimethyl-1H-pyrazole-4-carboxamide | 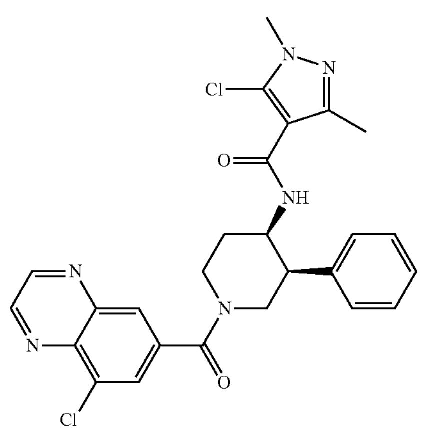 [SMILES: Cc1nn(C)c(Cl)c1C(=O)N[C@@H]1CCN(C(=O)c2cc(Cl)c3nccnc3c2)C[C@@H]1c1ccccc1] | | 523.0 |

TABLE 2-1-continued

| Ex. No. | IUPAC Name | Structure | Salt | MS |
|---|---|---|---|---|
| 167B | 5-chloro-N-((3S,4R)-1-((8-chloroquinoxalin-6-yl)carbonyl)-3-phenylpiperidin-4-yl)-1-methyl-3-(trifluoromethyl)-1H-pyrazole-4-carboxamide | 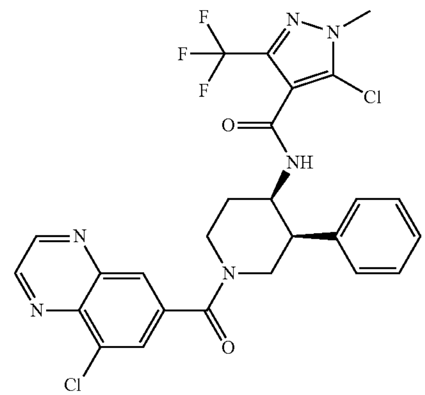 [SMILES: Cn1nc(C(F)(F)F)c(C(=O)N[C@@H]2CCN(C(=O)c3cc(Cl)c4nccnc4c3)C[C@@H]2c2ccccc2)c1Cl] | | 577.0 |
| 168B | 1-tert-butyl-N-((3S,4R)-1-((8-chloroquinoxalin-6-yl)carbonyl)-3-phenylpiperidin-4-yl)-5-(trifluoromethyl)-1H-pyrazole-4-carboxamide | 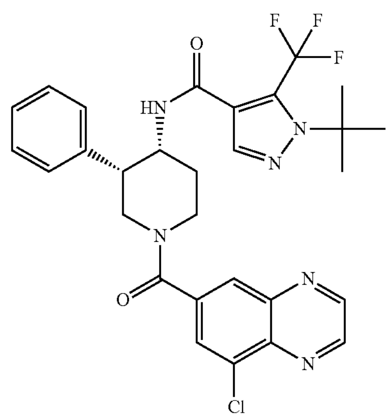 [SMILES: CC(C)(C)n1ncc(C(=O)N[C@@H]2CCN(C(=O)c3cc(Cl)c4nccnc4c3)C[C@@H]2c2ccccc2)c1C(F)(F)F] | | 585.1 |
| 169B | 1-tert-butyl-N-((3S,4R)-1-((8-chloroquinoxalin-6-yl)carbonyl)-3-phenylpiperidin-4-yl)-5-cyclopropyl-1H-pyrazole-4-carboxamide | 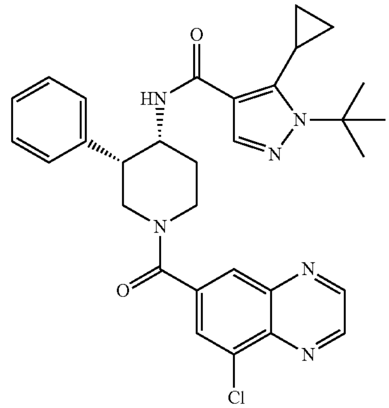 [SMILES: CC(C)(C)n1ncc(C(=O)N[C@@H]2CCN(C(=O)c3cc(Cl)c4nccnc4c3)C[C@@H]2c2ccccc2)c1C1CC1] | | 557.2 |

TABLE 2-1-continued

| Ex. No. | IUPAC Name | Structure | Salt | MS |
|---|---|---|---|---|
| 170B | N-((3S,4R)-1-((8-chloroquinoxalin-6-yl)carbonyl)-3-phenylpiperidin-4-yl)-3-ethoxy-1-methyl-1H-pyrazole-5-carboxamide | 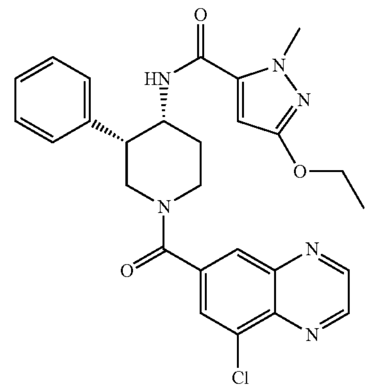 [SMILES: CCOc1cc(C(=O)N[C@@H]2CCN(C(=O)c3cc(Cl)c4nccnc4c3)C[C@@H]2c2ccccc2)n(C)n1] | | 519.1 |
| 171B | N-((3S,4R)-1-((8-chloroquinoxalin-6-yl)carbonyl)-3-phenylpiperidin-4-yl)-3-(2-methoxyethoxy)-1-methyl-1H-pyrazole-5-carboxamide | 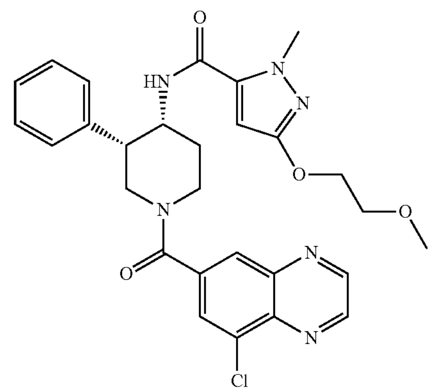 [SMILES: COCCOc1cc(C(=O)N[C@@H]2CCN(C(=O)c3cc(Cl)c4nccnc4c3)C[C@@H]2c2ccccc2)n(C)n1] | | 549.1 |
| 172B | N-((3S,4R)-1-((8-chloroquinoxalin-6-yl)carbonyl)-3-phenylpiperidin-4-yl)-3-cyclopropyl-methyl-1H-pyrazole-5-carboxamide | 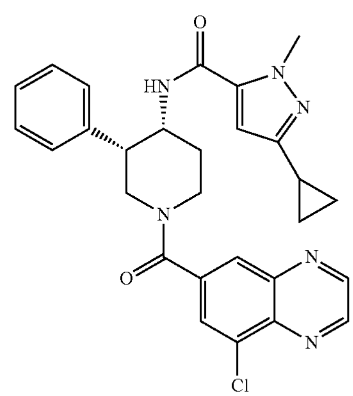 [SMILES: Cn1nc(C2CC2)cc1C(=O)N[C@@H]1CCN(C(=O)c2cc(Cl)c3nccnc3c2)C[C@@H]1c1ccccc1] | | 515.1 |
| 173B | N-((3S,4R)-1-((8-chloroquinoxalin-6-yl)carbonyl)-3-phenylpiperidin-4-yl)-3-isopropyl-1-methyl-1H-pyrazole-5-carboxamide | 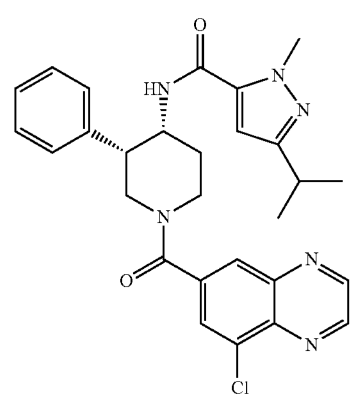 [SMILES: CC(C)c1cc(C(=O)N[C@@H]2CCN(C(=O)c3cc(Cl)c4nccnc4c3)C[C@@H]2c2ccccc2)n(C)n1] | | 517.1 |

TABLE 2-1-continued

| Ex. No. | IUPAC Name | Structure | Salt | MS |
|---|---|---|---|---|
| 174B | 3-tert-butyl-N-((3S,4R)-1-((8-chloroquinoxalin-6-yl)carbonyl)-3-phenylpiperidin-4-yl)-1-methyl-1H-pyrazole-5-carboxamide | 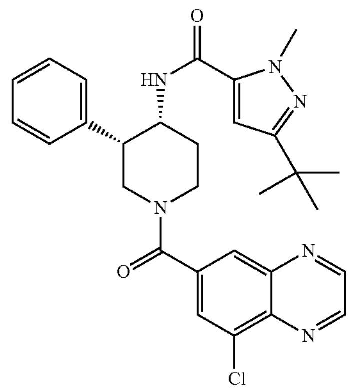 [SMILES: Cn1nc(C(C)(C)C)cc1C(=O)N[C@@H]1CCN(C(=O)c2cc(Cl)c3nccnc3c2)C[C@@H]1c1ccccc1] | | 531.1 |
| 175B | N-((3S,4R)-1-((8-chloroquinoxalin-6-yl)carbonyl)-3-phenylpiperidin-4-yl)-3-methoxy-1-methyl-1H-pyrazole-4-carboxamide | 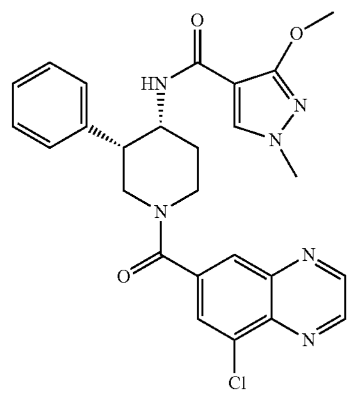 [SMILES: COc1nn(C)cc1C(=O)N[C@@H]1CCN(C(=O)c2cc(Cl)c3nccnc3c2)C[C@@H]1c1ccccc1] | | 505.1 |
| 176B | 3-chloro-N-((3S,4R)-1-((8-chloroquinoxalin-6-yl)carbonyl)-3-phenylpiperidin-4-yl)-1-methyl-5-(methylsulfonyl)-1H-pyrazole-4-carboxamide | 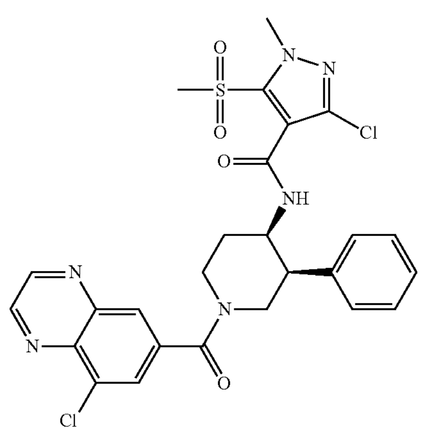 [SMILES: Cn1nc(Cl)c(C(=O)N[C@@H]2CCN(C(=O)c3cc(Cl)c4nccnc4c3)C[C@@H]2c2ccccc2)c1S(C)(=O)=O] | | 587.0 |

TABLE 2-1-continued

| Ex. No. | IUPAC Name | Structure | Salt | MS |
|---|---|---|---|---|
| 177B | N-((3S,4R)-1-((8-chloroquinoxalin-6-yl)carbonyl)-3-phenylpiperidin-4-yl)-1-methyl-3-(trifluoromethyl)-1H-pyrazole-4-carboxamide | 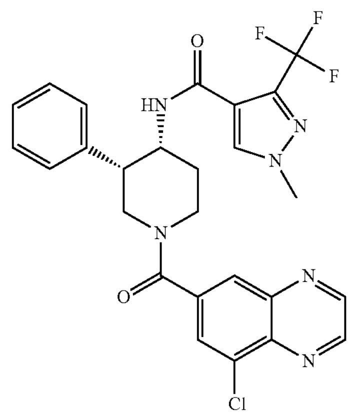 [SMILES: Cn1cc(C(=O)N[C@@H]2CCN(C(=O)c3cc(Cl)c4nccnc4c3)C[C@@H]2c2ccccc2)c(C(F)(F)F)n1] | | 543.1 |
| 178B | 3-chloro-N-((3S,4R)-1-((8-chloroquinoxalin-6-yl)carbonyl)-3-phenylpiperidin-4-yl)-1-methyl-5-(methylsulfanyl)-1H-pyrazole-4-carboxamide | 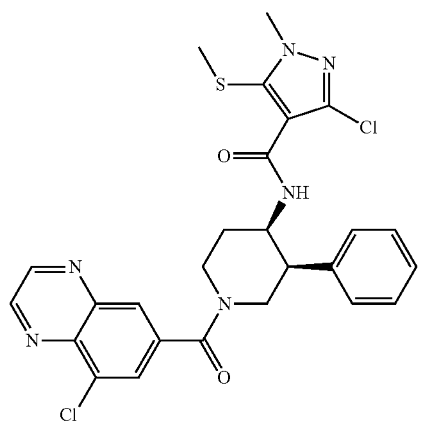 [SMILES: CSc1c(C(=O)N[C@@H]2CCN(C(=O)c3cc(Cl)c4nccnc4c3)C[C@@H]2c2ccccc2)c(Cl)nn1C] | | 555.0 |
| 179B | N-((3S,4R)-1-((8-chloroquinoxalin-6-yl)carbonyl)-3-phenylpiperidin-4-yl)-3-(difluoromethoxy)-1-methyl-1H-pyrazole-4-carboxamide | 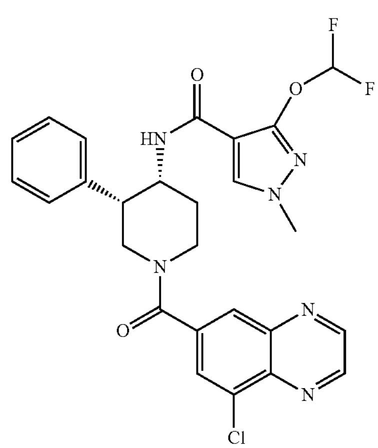 [SMILES: Cn1cc(C(=O)N[C@@H]2CCN(C(=O)c3cc(Cl)c4nccnc4c3)C[C@@H]2c2ccccc2)c(OC(F)F)n1] | | 541.1 |

TABLE 2-1-continued

| Ex. No. | IUPAC Name | Structure | Salt | MS |
|---|---|---|---|---|
| 180B | N-((3S,4R)-1-((8-chloroquinoxalin-6-yl)carbonyl)-3-phenylpiperidin-4-yl)-5-(difluoromethoxy)-1-methyl-1H-pyrazole-4-carboxamide | 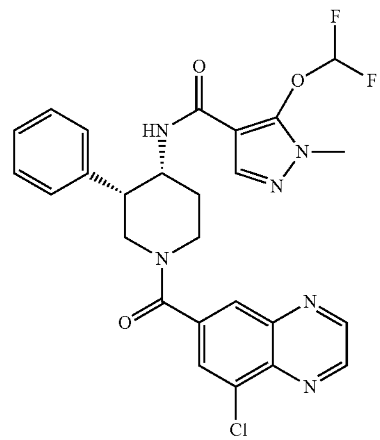 [SMILES: Cn1ncc(C(=O)N[C@@H]2CCN(C(=O)c3cc(Cl)c4nccnc4c3)C[C@@H]2c2ccccc2)c1OC(F)F] | | 541.1 |
| 181B | N-((3S,4R)-1-((8-chloroquinoxalin-6-yl)carbonyl)-3-phenylpiperidin-4-yl)-1-(difluoromethyl)-1H-pyrazole-4-carboxamide | 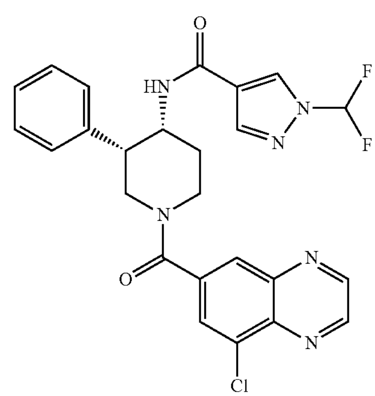 [SMILES: O=C(N[C@@H]1CCN(C(=O)c2cc(Cl)c3nccnc3c2)C[C@@H]1c1ccccc1)c1cnn(C(F)F)c1] | | 511.0 |
| 182B | N-((3S,4R)-1-((8-chloroquinoxalin-6-yl)carbonyl)-3-phenylpiperidin-4-yl)-1-cyclopropyl-1H-pyrazole-4-carboxamide | 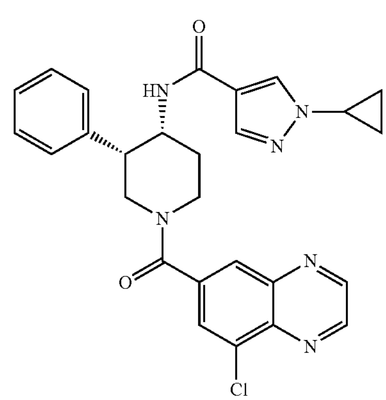 [SMILES: O=C(N[C@@H]1CCN(C(=O)c2cc(Cl)c3nccnc3c2)C[C@@H]1c1ccccc1)c1cnn(C2CC2)c1] | | 501.1 |

TABLE 2-1-continued

| Ex. No. | IUPAC Name | Structure | Salt | MS |
|---|---|---|---|---|
| 183B | N-((3S,4R)-1-((8-chloroquinoxalin-6-yl)carbonyl)-3-phenylpiperidin-4-yl)-5-cyclopropyl-1-methyl-1H-pyrazole-4-carboxamide | 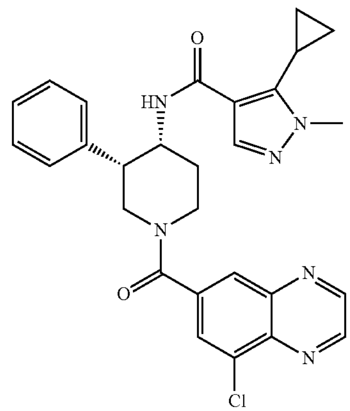 [SMILES: Cn1ncc(C(=O)N[C@@H]2CCN(C(=O)c3cc(Cl)c4nccnc4c3)C[C@@H]2c2ccccc2)c1C1CC1] | | 515.1 |
| 184B | N-((3S,4R)-1-((8-chloroquinoxalin-6-yl)carbonyl)-3-phenylpiperidin-4-yl)-1-(2,2-difluoroethyl)-3-methyl-1H-pyrazole-5-carboxamide | 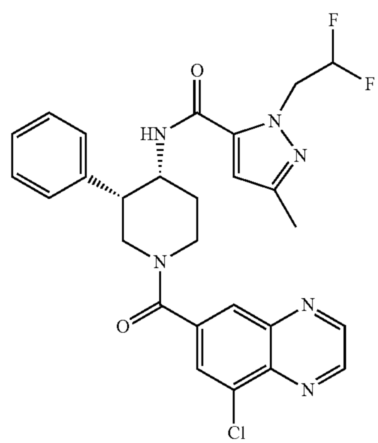 [SMILES: Cc1cc(C(=O)N[C@@H]2CCN(C(=O)c3cc(Cl)c4nccnc4c3)C[C@@H]2c2ccccc2)n(CC(F)F)n1] | | 539.0 |
| 185B | N-((3S,4R)-1-((8-chloroquinoxalin-6-yl)carbonyl)-3-phenylpiperidin-4-yl)-1-(difluoromethyl)-5-methyl-1H-pyrazole-3-carboxamide | 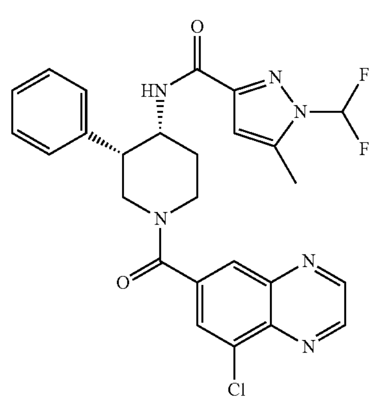 [SMILES: Cc1cc(C(=O)N[C@@H]2CCN(C(=O)c3cc(Cl)c4nccnc4c3)C[C@@H]2c2ccccc2)nn1C(F)F] | | 525.1 |

TABLE 2-1-continued

| Ex. No. | IUPAC Name | Structure | Salt | MS |
|---|---|---|---|---|
| 186B | N-((3S,4R)-1-((8-chloroquinoxalin-6-yl)carbonyl)-3-phenylpiperidin-4-yl)-1-methyl-5-(trifluoromethyl)-1H-pyrazole-4-carboxamide | 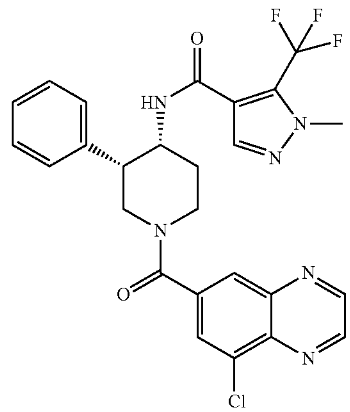 [SMILES: Cn1ncc(C(=O)N[C@@H]2CCN(C(=O)c3cc(Cl)c4nccnc4c3)C[C@@H]2c2ccccc2)c1C(F)(F)F] | | 543.1 |
| 187B | N-((3S,4R)-1-((8-chloroquinoxalin-6-yl)carbonyl)-3-phenylpiperidin-4-yl)-1-isopropyl-1H-pyrazole-4-carboxamide | 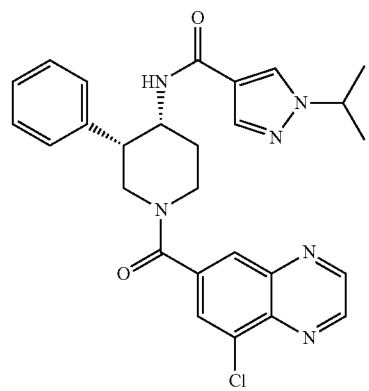 [SMILES: CC(C)n1cc(C(=O)N[C@@H]2CCN(C(=O)c3cc(Cl)c4nccnc4c3)C[C@@H]2c2ccccc2)cn1] | | 503.1 |
| 188B | N-((3S,4R)-1-((8-chloroquinoxalin-6-yl)carbonyl)-3-phenylpiperidin-4-yl)-1-methyl-1H-pyrazole-4-carboxamide | 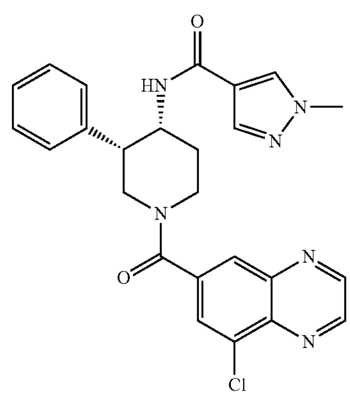 [SMILES: Cn1cc(C(=O)N[C@@H]2CCN(C(=O)c3cc(Cl)c4nccnc4c3)C[C@@H]2c2ccccc2)cn1] | | 475.1 |
| 189B | N-((3S,4R)-1-((8-chloroquinoxalin-6-yl)carbonyl)-3-phenylpiperidin-4-yl)-1,3-dimethyl-1H-pyrazole-4-carboxamide | 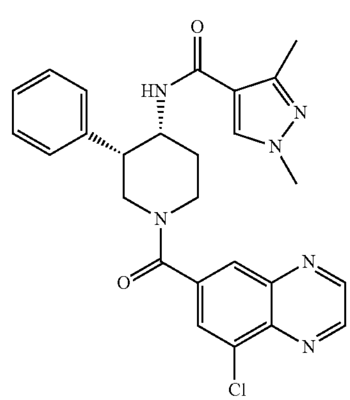 [SMILES: Cc1nn(C)cc1C(=O)N[C@@H]1CCN(C(=O)c2cc(Cl)c3nccnc3c2)C[C@@H]1c1ccccc1] | | 489.0 |

TABLE 2-1-continued

| Ex. No. | IUPAC Name | Structure | Salt | MS |
|---|---|---|---|---|
| 190B | N-((3S,4R)-1-((8-chloroquinoxalin-6-yl)carbonyl)-3-phenylpiperidin-4-yl)-1,3,5-trimethyl-1H-pyrazole-4-carboxamide | 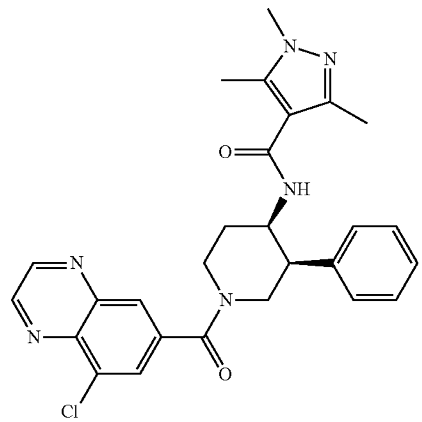 [SMILES: Cc1nn(C)c(C)c1C(=O)N[C@@H]1CCN(C(=O)c2cc(Cl)c3nccnc3c2)C[C@@H]1c1ccccc1] | | 503.1 |
| 191B | N-((3S,4R)-1-((5,6-dimethoxypyridin-3-yl)carbonyl)-3-(4-fluorophenyl)piperidin-4-yl)-3-(trifluoromethyl)pyridine-2-carboxamide | 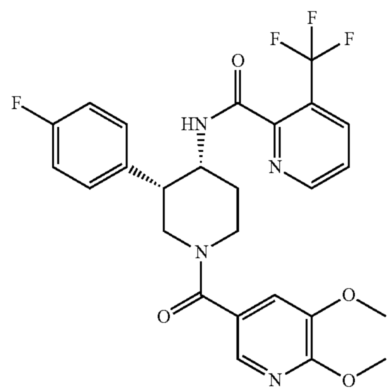 [SMILES: COc1cc(C(=O)N2CC[C@@H](NC(=O)c3ncccc3C(F)(F)F)[C@@H](c3ccc(F)cc3)C2)cnc1OC] | | 533.1 |
| 192B | N-((3S,4R)-3-phenyl-1-(1H-pyrazolo[3,4-b]pyridin-5-ylcarbonyl)piperidin-4-yl)-3-(trifluoromethyl)pyridine-2-carboxamide | 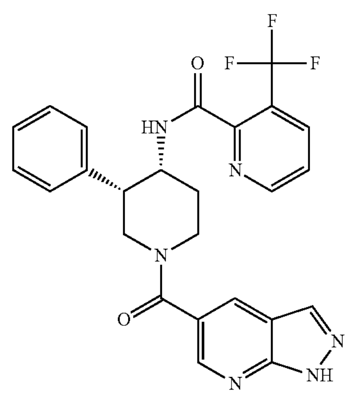 [SMILES: O=C(N[C@@H]1CCN(C(=O)c2cnc3[nH]ncc3c2)C[C@@H]1c1ccccc1)c1ncccc1C(F)(F)F] | | 495.0 |
| 193B | N-((3S,4R)-1-((1-methyl-1H-benzimidazol-6-yl)carbonyl)-3-phenylpiperidin-4-yl)-3-(trifluoromethyl)pyridine-2-carboxamide | 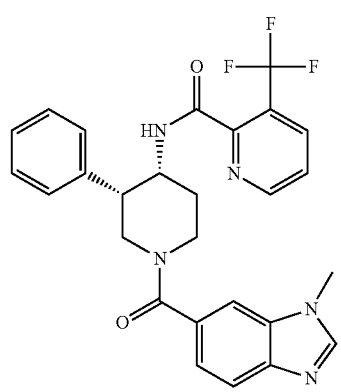 [SMILES: Cn1cnc2ccc(C(=O)N3CC[C@@H](NC(=O)c4ncccc4C(F)(F)F)[C@@H](c4ccccc4)C3)cc21] | | 508.1 |

TABLE 2-1-continued

| Ex. No. | IUPAC Name | Structure | Salt | MS |
|---|---|---|---|---|
| 194B | N-((3S,4R)-1-((3-methyl-1H-pyrazolo[3,4-b]pyridin-5-yl)carbonyl)-3-phenylpiperidin-4-yl)-3-(trifluoromethyl)pyridine-2-carboxamide | 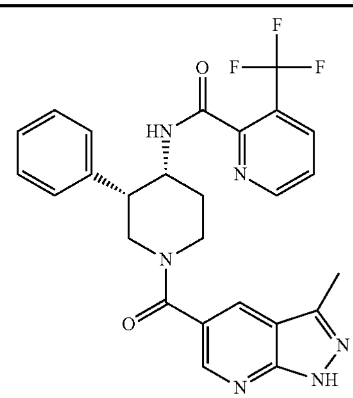 | | 509.3 |
| 195B | N-((3S,4R)-1-((5-chloro-6-(2,2,2-trifluoroethoxy)pyridin-3-yl)carbonyl)-3-phenylpiperidin-4-yl)-2-(trifluoromethoxy)benzamide | 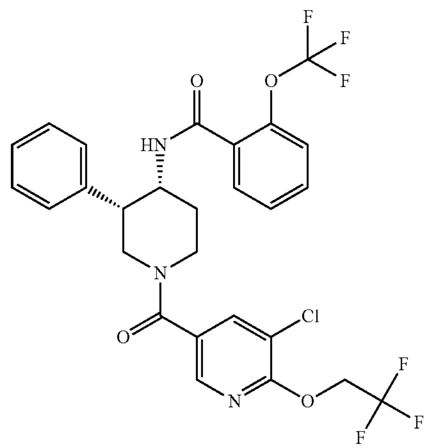 [SMILES: O=C(N[C@@H]1CCN(C(=O)c2cnc(OCC(F)(F)F)c(Cl)c2)C[C@@H]1c1ccccc1)c1ccccc1OC(F)(F)F] | | 602.0 |
| 196B | N-((3S,4R)-1-((5-chloro-6-(2,2-difluoroethoxy)pyridin-3-yl)carbonyl)-3-phenylpiperidin-4-yl)-2-(trifluoromethoxy)benzamide | 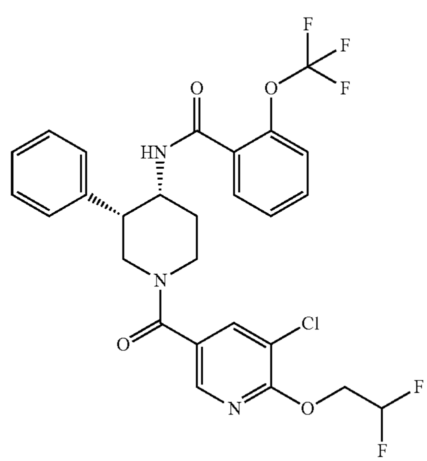 [SMILES: O=C(N[C@@H]1CCN(C(=O)c2cnc(OCC(F)F)c(Cl)c2)C[C@@H]1c1ccccc1)c1ccccc1OC(F)(F)F] | | 584.0 |

TABLE 2-1-continued

| Ex. No. | IUPAC Name | Structure | Salt | MS |
|---|---|---|---|---|
| 197B | N-((3S,4R)-1-((5-chloro-6-(($^2$H$_3$)methyloxy)pyridin-3-yl)carbonyl)-3-phenylpiperidin-4-yl)-2-(trifluoromethoxy)benzamide | 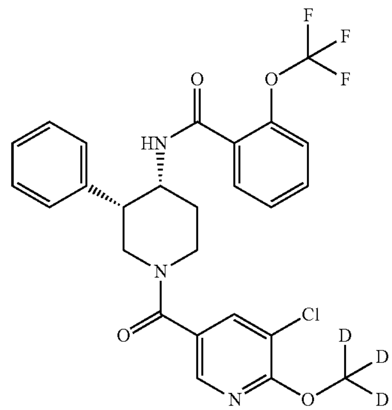 | | 537.1 |
| 198B | N-((3S,4R)-1-((5-bromo-6-chloropyridin-3-yl)carbonyl)-3-phenylpiperidin-4-yl)-2-(trifluoromethoxy)benzamide | 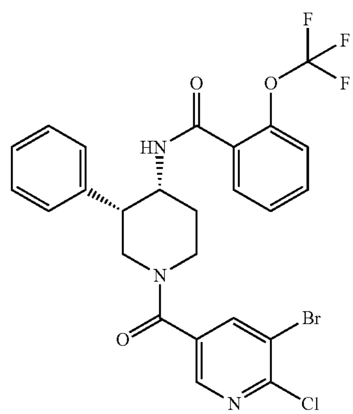 [SMILES: O=C(N[C@@H]1CCN(C(=O)c2cnc(Cl)c(Br)c2)C[C@@H]1c1ccccc1)c1ccccc1OC(F)(F)F] | | 582.0 |
| 199B | N-((3S,4R)-1-((5-bromo-6-methoxypyridin-3-yl)carbonyl)-3-phenylpiperidin-4-yl)-2-(trifluoromethoxy)benzamide | 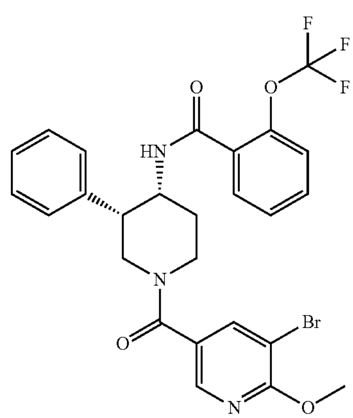 [SMILES: COc1ncc(C(=O)N2CC[C@@H](NC(=O)c3ccccc3OC(F)(F)F)[C@@H](c3ccccc3)C2)cc1Br] | | 578.0 |

TABLE 2-1-continued

| Ex. No. | IUPAC Name | Structure | Salt | MS |
|---|---|---|---|---|
| 200B | N-((3S,4R)-1-((5-bromo-6-((²H₃)methyloxy)pyridin-3-yl)carbonyl)-3-phenylpiperidin-4-yl)-2-(trifluoromethoxy)benzamide | 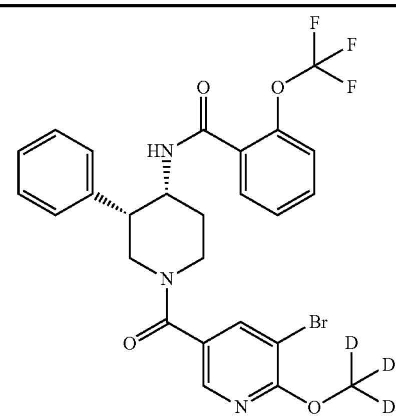 | | 581.0 |
| 201B | N-((3R,4R)-1-((8-chloroquinoxalin-6-yl)carbonyl)-3-phenylpiperidin-4-yl)-2-(difluoromethoxy)benzamide | 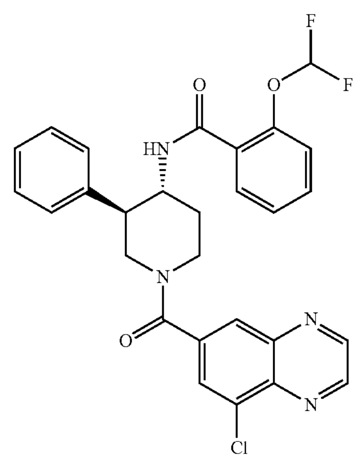 [SMILES: O=C(N[C@@H]1CCN(C(=O)c2cc(Cl)c3nccnc3c2)C[C@H]1c1ccccc1)c1ccccc1OC(F)F] | | 537.2 |
| 202B | N-((3R,4R)-1-((8-chloroquinoxalin-6-yl)carbonyl)-3-(4-fluorophenyl)piperidin-4-yl)-2-(difluoromethoxy)benzamide | 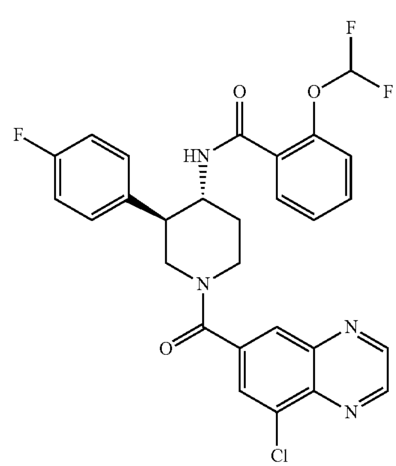 [SMILES: O=C(N[C@@H]1CCN(C(=O)c2cc(Cl)c3nccnc3c2)C[C@H]1c1ccc(F)cc1)c1ccccc1OC(F)F] | | 555.2 |

TABLE 2-1-continued

| Ex. No. | IUPAC Name | Structure | Salt | MS |
|---|---|---|---|---|
| 203B | N-((3S,4S)-1-((8-chloroquinoxalin-6-yl)carbonyl)-3-phenylpiperidin-4-yl)-2-(difluoromethoxy)benzamide | 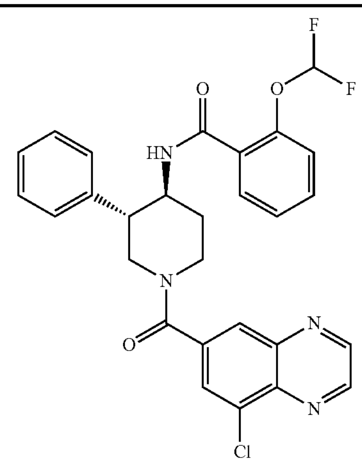 | | 537.2 |
| 204B | N-((3S,4S)-1-((8-chloroquinoxalin-6-yl)carbonyl)-3-(4-fluorophenyl)piperidin-4-yl)-2-(difluoromethoxy)benzamide | 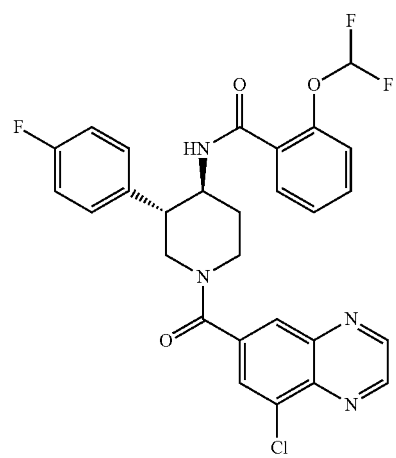 [SMILES: O=C(N[C@H]1CCN(C(=O)c2cc(Cl)c3nccnc3c2)C[C@@H]1c1ccc(F)cc1)c1ccccc1OC(F)F] | | 555.1 |
| 205B | 2-chloro-N-((3S,4R)-1-((5-chloro-6-methoxypyridin-3-yl)carbonyl)-3-phenylpiperidin-4-yl)benzamide | 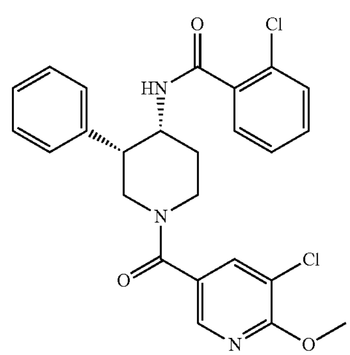 [SMILES: COc1ncc(C(=O)N2CC[C@@H](NC(=O)c3ccccc3Cl)[C@@H](c3ccccc3)C2)cc1Cl] | | 484.1 |
| 206B | 2-chloro-N-((3S,4R)-1-((5,6-dimethoxypyridin-3-yl)carbonyl)-3-phenylpiperidin-4-yl)benzamide | 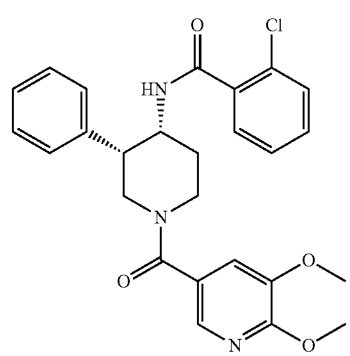 [SMILES: COc1cc(C(=O)N2CC[C@@H](NC(=O)c3ccccc3Cl)[C@@H](c3ccccc3)C2)cnc1OC] | | 480.1 |

TABLE 2-1-continued

| Ex. No. | IUPAC Name | Structure | Salt | MS |
|---|---|---|---|---|
| 207B | N-((3S,4R)-1-(3,4-dimethoxybenzoyl)-3-phenylpiperidin-4-yl)-2-(trifluoromethoxy)benzamide | 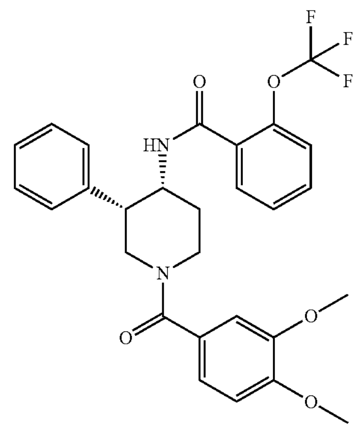 [SMILES: COc1ccc(C(=O)N2CC[C@@H](NC(=O)c3ccccc3OC(F)(F)F)[C@@H](c3ccccc3)C2)cc1OC] | | 529.1 |
| 208B | N-((3S,4R)-1-((2-methyl-2H-indazol-6-yl)carbonyl)-3-phenylpiperidin-4-yl)-2-(trifluoromethoxy)benzamide | 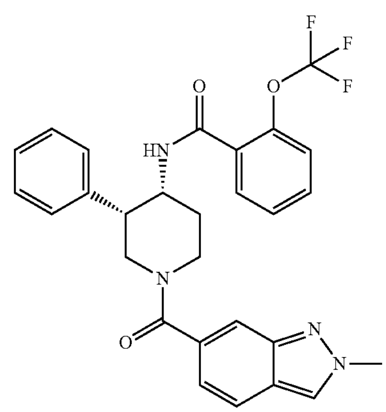 [SMILES: Cn1cc2ccc(C(=O)N3CC[C@@H](NC(=O)c4ccccc4OC(F)(F)F)[C@@H](c4ccccc4)C3)cc2n1] | | 523.1 |
| 209B | N-((3S,4R)-1-(1H-indazol-5-ylcarbonyl)-3-phenylpiperidin-4-yl)-2-(trifluoromethoxy)benzamide | 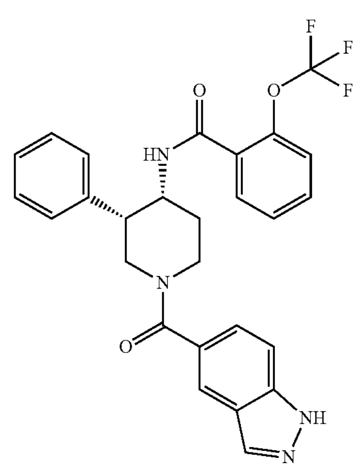 [SMILES: O=C(N[C@@H]1CCN(C(=O)c2ccc3[nH]ncc3c2)C[C@@H]1c1ccccc1)c1ccccc1OC(F)(F)F] | | 509.1 |

TABLE 2-1-continued

| Ex. No. | IUPAC Name | Structure | Salt | MS |
|---|---|---|---|---|
| 210B | N-((3S,4R)-3-phenyl-1-(1H-pyrrolo[2,3-b]pyridin-5-ylcarbonyl)piperidin-4-yl)-2-(trifluoromethoxy)benzamide | 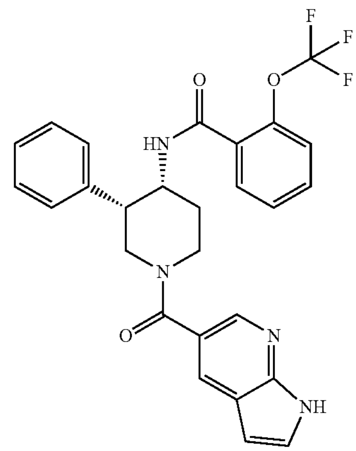 [SMILES: O=C(N[C@@H]1CCN(C(=O)c2cnc3[nH]ccc3c2)C[C@@H]1c1ccccc1)c1ccccc1OC(F)(F)F] | | 509.1 |
| 213B | N-((3S,4R)-1-((2-methyl-7-oxo-4,7-dihydro[1,2,4]triazolo[1,5-a]pyrimidin-6-yl)carbonyl)-3-phenylpiperidin-4-yl)-2-(trifluoromethoxy)benzamide | 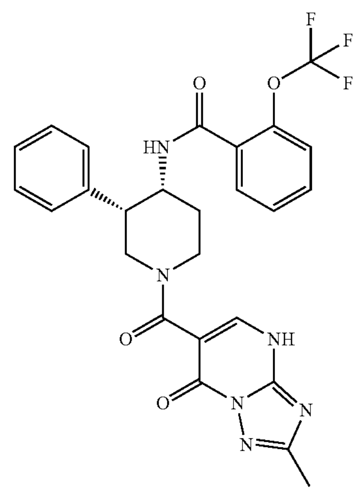 [SMILES: Cc1nc2[nH]cc(C(=O)N3CC[C@@H](NC(=O)c4ccccc4OC(F)(F)F)[C@@H](c4ccccc4)C3)c(=O)n2n1] | | 541.2 |
| 214B | N-((3S,4R)-1-((2-oxo-2,3-dihydro-1H-benzimidazol-5-yl)carbonyl)-3-phenylpiperidin-4-yl)-2-(trifluoromethoxy)benzamide | 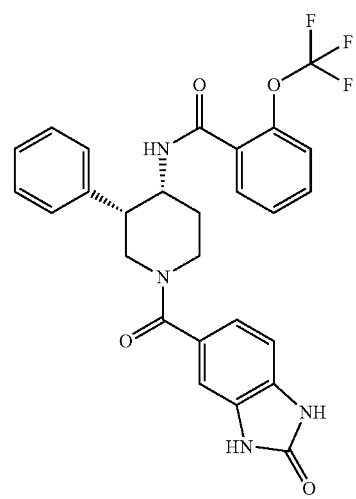 [SMILES: O=C(N[C@@H]1CCN(C(=O)c2ccc3[nH]c(=O)[nH]c3c2)C[C@@H]1c1ccccc1)c1ccccc1OC(F)(F)F] | | 525.1 |

TABLE 2-1-continued

| Ex. No. | IUPAC Name | Structure | Salt | MS |
|---|---|---|---|---|
| 216B | N-((3S,4R)-3-phenyl-1-(1H-pyrazolo[3,4-b]pyridin-5-ylcarbonyl)piperidin-4-yl)-2-(trifluoromethoxy)benzamide | 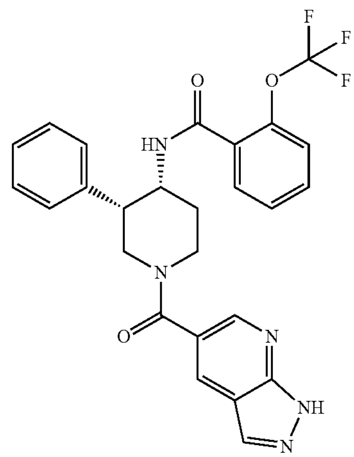 [SMILES: O=C(N[C@@H]1CCN(C(=O)c2cnc3[nH]ncc3c2)C[C@@H]1c1ccccc1)c1ccccc1OC(F)(F)F] | | 510.1 |
| 217B | N-((3S,4R)-1-(1H-benzotriazol-5-ylcarbonyl)-3-phenylpiperidin-4-yl)-2-(trifluoromethoxy)benzamide | 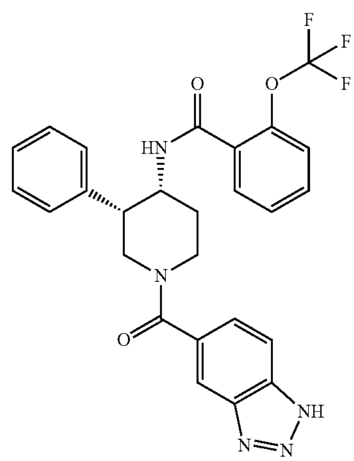 [SMILES: O=C(N[C@@H]1CCN(C(=O)c2ccc3[nH]nnc3c2)C[C@@H]1c1ccccc1)c1ccccc1OC(F)(F)F] | | 510.0 |
| 218B | N-((3S,4R)-1-((2-methyl-2H-indazol-5-yl)carbonyl)-3-phenylpiperidin-4-yl)-2-(trifluoromethoxy)benzamide | 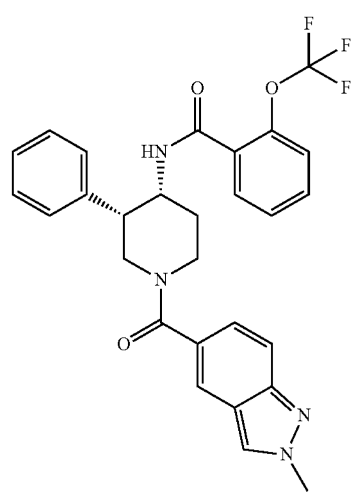 [SMILES: Cn1cc2cc(C(=O)N3CC[C@@H](NC(=O)c4ccccc4OC(F)(F)F)[C@@H](c4ccccc4)C3)ccc2n1] | | 523.1 |

TABLE 2-1-continued

| Ex. No. | IUPAC Name | Structure | Salt | MS |
|---|---|---|---|---|
| 219B | N-((3S,4R)-1-(4-methoxy-2,5-dimethylbenzoyl)-3-phenylpiperidin-4-yl)-2-(trifluoromethoxy)benzamide | 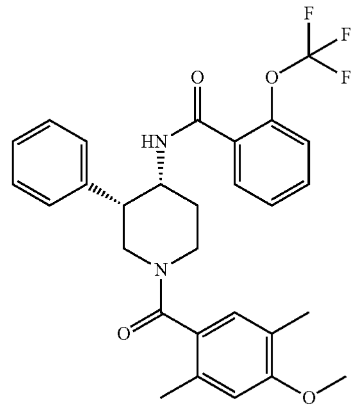 [SMILES: COc1cc(C)c(C(=O)N2CC[C@@H](NC(=O)c3ccccc3OC(F)(F)F)[C@@H](c3ccccc3)C2)cc1C] | | 527.1 |
| 221B | N-((3S,4R)-1-((8-methoxyquinolin-5-yl)carbonyl)-3-phenylpiperidin-4-yl)-2-(trifluoromethoxy)benzamide | 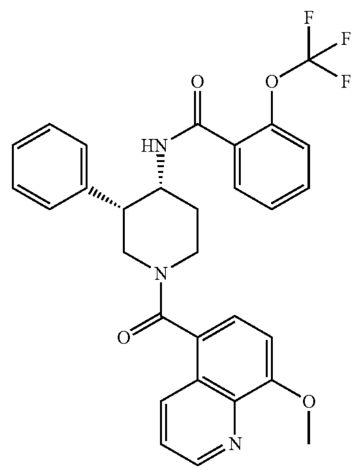 [SMILES: COc1ccc(C(=O)N2CC[C@@H](NC(=O)c3ccccc3OC(F)(F)F)[C@@H](c3ccccc3)C2)c2cccnc12] | | 550.1 |
| 222B | N-((3S,4R)-1-(3-chloro-4-ethoxy-5-fluorobenzoyl)-3-phenylpiperidin-4-yl)-2-(trifluoromethoxy)benzamide | 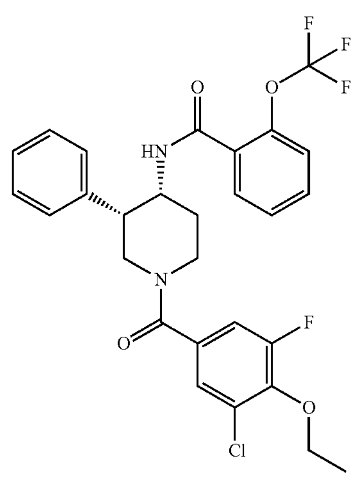 [SMILES: CCOc1c(F)cc(C(=O)N2CC[C@@H](NC(=O)c3ccccc3OC(F)(F)F)[C@@H](c3ccccc3)C2)cc1Cl] | | 565.1 |

TABLE 2-1-continued

| Ex. No. | IUPAC Name | Structure | Salt | MS |
|---|---|---|---|---|
| 223B | N-((3S,4R)-1-((3-bromo-8-methylquinolin-6-yl)carbonyl)-3-phenylpiperidin-4-yl)-2-(trifluoromethoxy)benzamide | 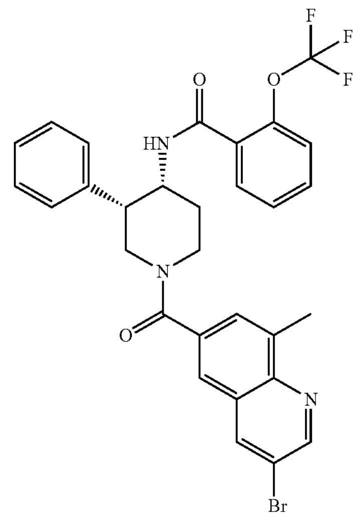 [SMILES: Cc1cc(C(=O)N2CC[C@@H](NC(=O)c3ccccc3OC(F)(F)F)[C@@H](c3ccccc3)C2)cc2cc(Br)cnc12] | | 612.0 |
| 224B | N-((3S,4R)-1-(3-cyano-4-fluorobenzoyl)-3-phenylpiperidin-4-yl)-2-(trifluoromethoxy)benzamide | 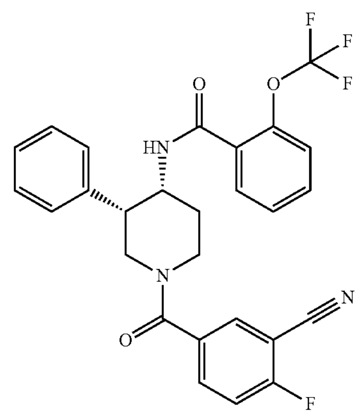 [SMILES: N#Cc1cc(C(=O)N2CC[C@@H](NC(=O)c3ccccc3OC(F)(F)F)[C@@H](c3ccccc3)C2)ccc1F] | | 512.0 |
| 225B | N-((3S,4R)-1-((6-chloroimidazo[1,2-b]pyridazin-2-yl)carbonyl)-3-phenylpiperidin-4-yl)-2-(trifluoromethoxy)benzamide | 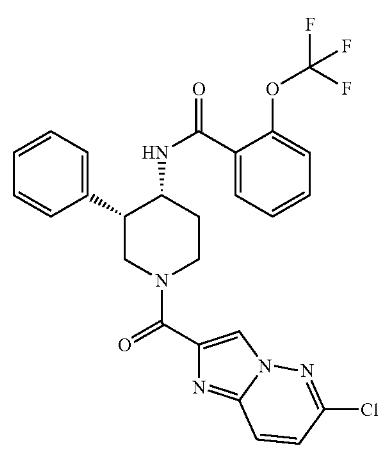 [SMILES: O=C(N[C@@H]1CCN(C(=O)c2cn3nc(Cl)ccc3n2)C[C@@H]1c1ccccc1)c1ccccc1OC(F)(F)F] | | 544.0 |

TABLE 2-1-continued

| Ex. No. | IUPAC Name | Structure | Salt | MS |
|---|---|---|---|---|
| 226B | N-((3S,4R)-3-phenyl-1-(thieno[2,3-c]pyridin-2-ylcarbonyl)piperidin-4-yl)-2-(trifluoromethoxy)benzamide | 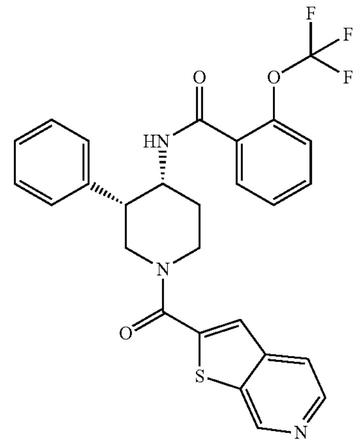 [SMILES: O=C(N[C@@H]1CCN(C(=O)c2cc3ccncc3s2)C[C@@H]1c1ccccc1)c1ccccc1OC(F)(F)F] | | 526.1 |
| 227B | N-((3S,4R)-1-((6-chloroimidazo[1,2-a]pyrimidin-2-yl)carbonyl)-3-phenylpiperidin-4-yl)-2-(trifluoromethoxy)benzamide | 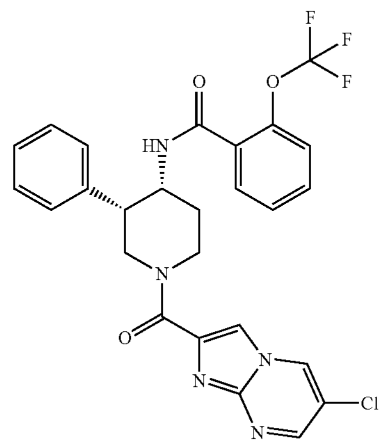 [SMILES: O=C(N[C@@H]1CCN(C(=O)c2cn3cc(Cl)cnc3n2)C[C@@H]1c1ccccc1)c1ccccc1OC(F)(F)F] | | 542.1 |
| 228B | N-((3S,4R)-1-((5-methoxy-1-benzothiophen-2-yl)carbonyl)-3-phenylpiperidin-4-yl)-2-(trifluoromethoxy)benzamide | 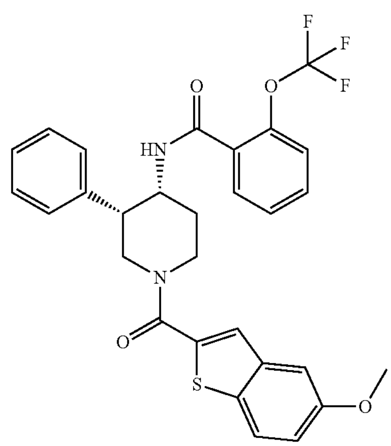 [SMILES: COc1ccc2sc(C(=O)N3CC[C@@H](NC(=O)c4ccccc4OC(F)(F)F)[C@@H](c4ccccc4)C3)cc2c1] | | 555.0 |

TABLE 2-1-continued

| Ex. No. | IUPAC Name | Structure | Salt | MS |
|---|---|---|---|---|
| 229B | N-((3S,4R)-3-phenyl-1-(1H-pyrrolo[3,2-b]pyridin-2-ylcarbonyl)piperidin-4-yl)-2-(trifluoromethoxy)benzamide | 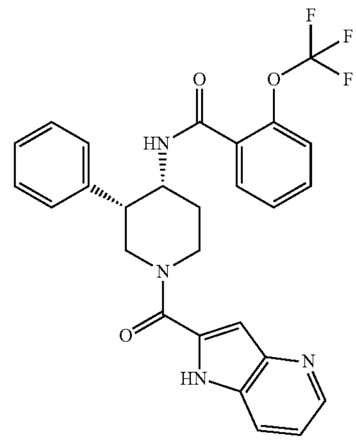 [SMILES: O=C(N[C@@H]1CCN(C(=O)c2cc3ncccc3[nH]2)C[C@@H]1c1ccccc1)c1ccccc1OC(F)(F)F] | | 509.1 |
| 230B | N-((3S,4R)-1-((5-methoxy-1H-pyrrolo[2,3-c]pyridin-2-yl)carbonyl)-3-phenylpiperidin-4-yl)-2-(trifluoromethoxy)benzamide | 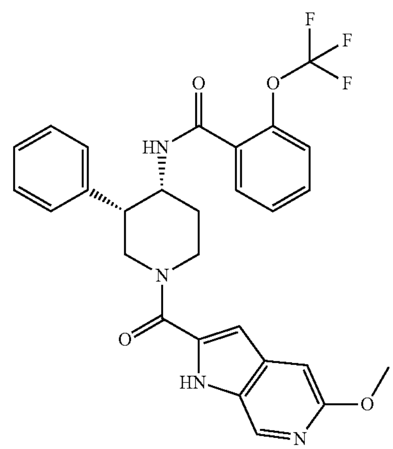 [SMILES: COc1cc2cc(C(=O)N3CC[C@@H](NC(=O)c4ccccc4OC(F)(F)F)[C@@H](c4ccccc4)C3)[nH]c2cn1] | | 539.1 |
| 231B | N-((3S,4R)-1-((1-methyl-1H-benzimidazol-5-yl)carbonyl)-3-phenylpiperidin-4-yl)-2-(trifluoromethoxy)benzamide | 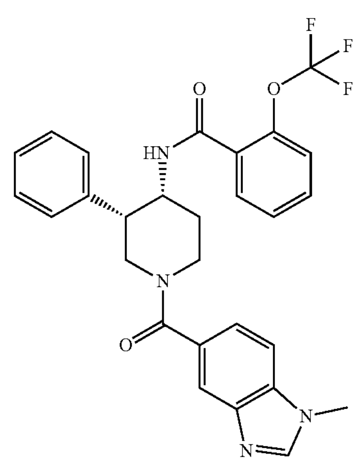 [SMILES: Cn1cnc2cc(C(=O)N3CC[C@@H](NC(=O)c4ccccc4OC(F)(F)F)[C@@H](c4ccccc4)C3)ccc21] | | 523.1 |

TABLE 2-1-continued

| Ex. No. | IUPAC Name | Structure | Salt | MS |
|---|---|---|---|---|
| 232B | N-((3S,4R)-1-(1,3-benzothiazol-5-ylcarbonyl)-3-phenylpiperidin-4-yl)-2-(trifluoromethoxy)benzamide | 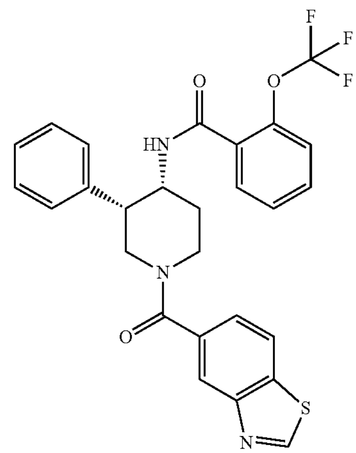 [SMILES: O=C(N[C@@H]1CCN(C(=O)c2ccc3scnc3c2)C[C@@H]1c1ccccc1)c1ccccc1OC(F)(F)F] | | 526.1 |
| 233B | N-((3S,4R)-1-((4-chloro-1H-pyrrolo[2,3-b]pyridin-5-yl)carbonyl)-3-phenylpiperidin-4-yl)-2-(trifluoromethoxy)benzamide | 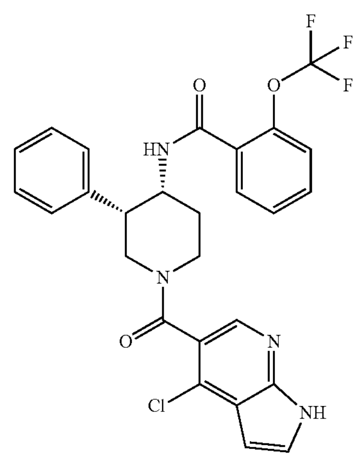 [SMILES: O=C(N[C@@H]1CCN(C(=O)c2cnc3[nH]ccc3c2Cl)C[C@@H]1c1ccccc1)c1ccccc1OC(F)(F)F] | | 543.0 |
| 234B | N-((3S,4R)-1-((5-fluoro-1-benzofuran-2-yl)carbonyl)-3-phenylpiperidin-4-yl)-2-(trifluoromethoxy)benzamide | 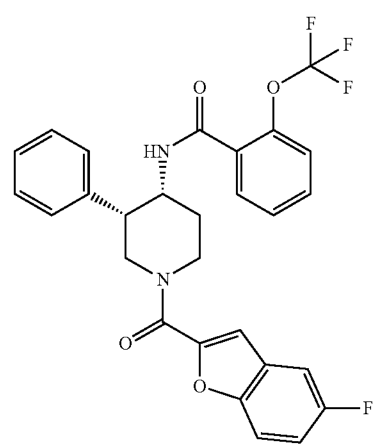 [SMILES: O=C(N[C@@H]1CCN(C(=O)c2cc3cc(F)ccc3o2)C[C@@H]1c1ccccc1)c1ccccc1OC(F)(F)F] | | 527.0 |

TABLE 2-1-continued

| Ex. No. | IUPAC Name | Structure | Salt | MS |
|---|---|---|---|---|
| 235B | N-((3S,4R)-1-((5-acetyl-2-thienyl)carbonyl)-3-phenylpiperidin-4-yl)-2-(trifluoromethoxy)benzamide | 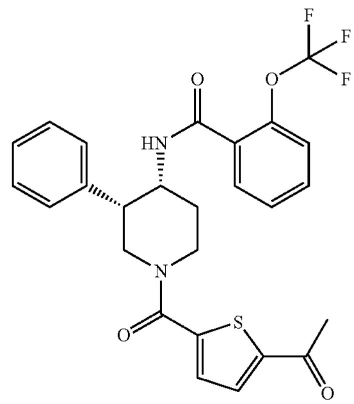 [SMILES: CC(=O)c1ccc(C(=O)N2CC[C@@H](NC(=O)c3ccccc3OC(F)(F)F)[C@@H](c3ccccc3)C2)s1] | | 517.0 |
| 236B | N-((3S,4R)-1-(3-fluoro-4-methoxybenzoyl)-3-phenylpiperidin-4-yl)-2-(trifluoromethoxy)benzamide | 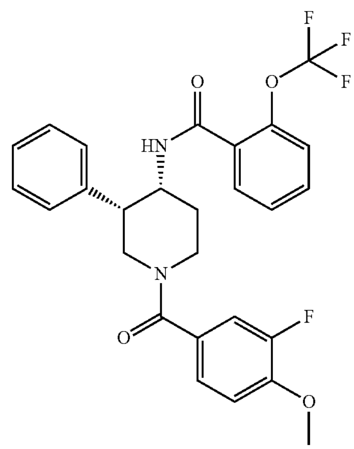 [SMILES: COc1ccc(C(=O)N2CC[C@@H](NC(=O)c3ccccc3OC(F)(F)F)[C@@H](c3ccccc3)C2)cc1F] | | 517.1 |
| 237B | N-((3S,4R)-1-((3-methoxy-1,2-oxazol-5-yl)carbonyl)-3-phenylpiperidin-4-yl)-2-(trifluoromethoxy)benzamide | 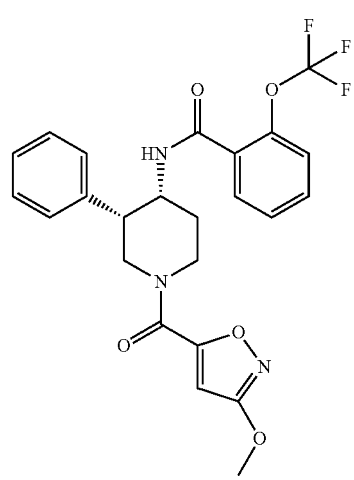 [SMILES: COc1cc(C(=O)N2CC[C@@H](NC(=O)c3ccccc3OC(F)(F)F)[C@@H](c3ccccc3)C2)on1] | | 489.9 |

TABLE 2-1-continued

| Ex. No. | IUPAC Name | Structure | Salt | MS |
|---|---|---|---|---|
| 238B | N-((3S,4R)-1-((3-oxo-2,3-dihydro-1,2-oxazol-5-yl)carbonyl)-3-phenylpiperidin-4-yl)-2-(trifluoromethoxy)benzamide | 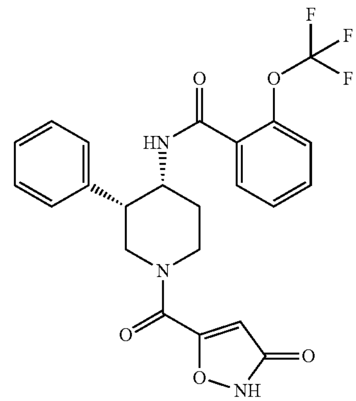 [SMILES: O=C(N[C@@H]1CCN(C(=O)c2cc(=O)[nH]o2)C[C@@H]1c1ccccc1)c1ccccc1OC(F)(F)F] | | 476.0 |
| 239B | methyl 5-(((3S,4R)-3-phenyl-4-((2-(trifluoromethoxy)benzoyl)amino)piperidin-1-yl)carbonyl)pyridine-2-carboxylate | 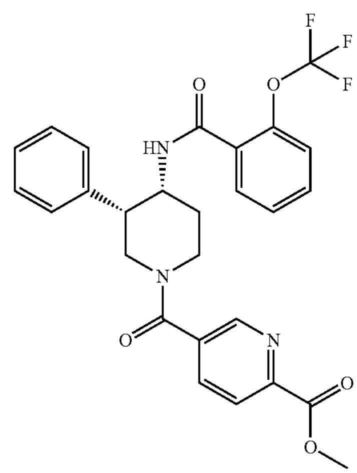 [SMILES: COC(=O)c1ccc(C(=O)N2CC[C@@H](NC(=O)c3ccccc3OC(F)(F)F)[C@@H](c3ccccc3)C2)cn1] | | 528.0 |
| 240B | N-((3S,4R)-1-((2-amino-1,3-benzoxazol-6-yl)carbonyl)-3-phenylpiperidin-4-yl)-2-(trifluoromethoxy)benzamide | 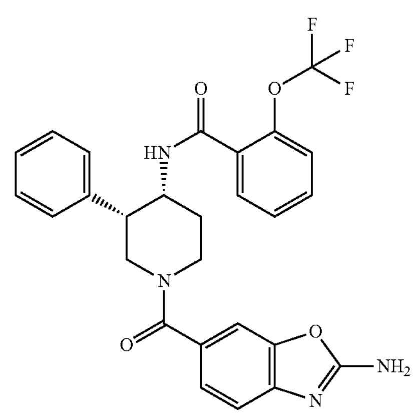 [SMILES: Nc1nc2ccc(C(=O)N3CC[C@@H](NC(=O)c4ccccc4OC(F)(F)F)[C@@H](c4ccccc4)C3)cc2o1] | | 525.1 |

TABLE 2-1-continued

| Ex. No. | IUPAC Name | Structure | Salt | MS |
|---|---|---|---|---|
| 241B | N-((3S,4R)-1-((8-chloroquinoxalin-6-yl)carbonyl)-3-phenylpiperidin-4-yl)-3-(trifluoromethyl)pyridine-2-carboxamide | 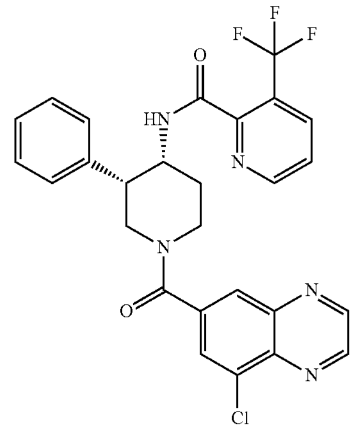 [SMILES: O=C(N[C@@H]1CCN(C(=O)c2cc(Cl)c3nccnc3c2)C[C@@H]1c1ccccc1)c1ncccc1C(F)(F)F] | | 540.1 |
| 242B | 6-chloro-N-((3S,4R)-1-((8-chloroquinoxalin-6-yl)carbonyl)-3-phenylpiperidin-4-yl)-4-(trifluoromethyl)nicotinamide | 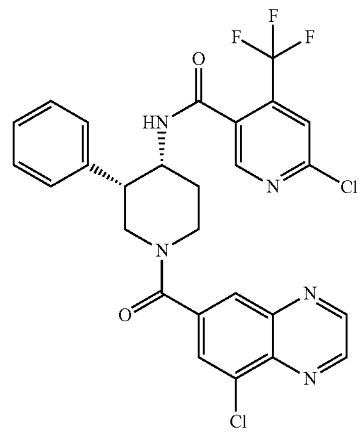 [SMILES: O=C(N[C@@H]1CCN(C(=O)c2cc(Cl)c3nccnc3c2)C[C@@H]1c1ccccc1)c1cnc(Cl)cc1C(F)(F)F] | | 574.0 |
| 243B | 5-chloro-N-((3S,4R)-1-((8-chloroquinoxalin-6-yl)carbonyl)-3-phenylpiperidin-4-yl)-1-methyl-1H-pyrazole-4-carboxamide | 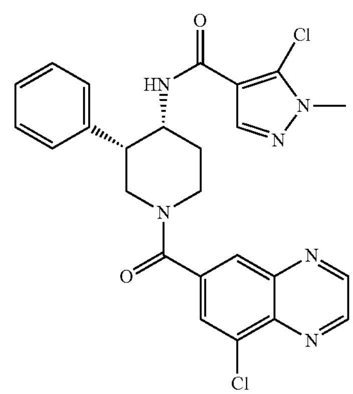 [SMILES: Cn1ncc(C(=O)N[C@@H]2CCN(C(=O)c3cc(Cl)c4nccnc4c3)C[C@@H]2c2ccccc2)c1Cl] | | 509.1 |
| 244B | 2-chloro-N-(trans-1-(3,4-dimethoxybenzoyl)-3-(pyridin-4-yl)piperidin-4-yl)benzamide | 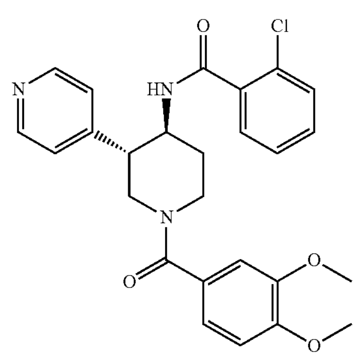 [SMILES: COc1ccc(C(=O)N2CC[C@H](NC(=O)c3ccccc3Cl)[C@@H](c3ccncc3)C2)cc1OC] | | 480.0 |

TABLE 2-1-continued

| Ex. No. | IUPAC Name | Structure | Salt | MS |
|---|---|---|---|---|
| 245B | N-((3S,4R)-1-((8-chloroquinoxalin-6-yl)carbonyl)-3-(4-fluorophenyl)piperidin-4-yl)-3-(trifluoromethyl)pyridine-2-carboxamide | 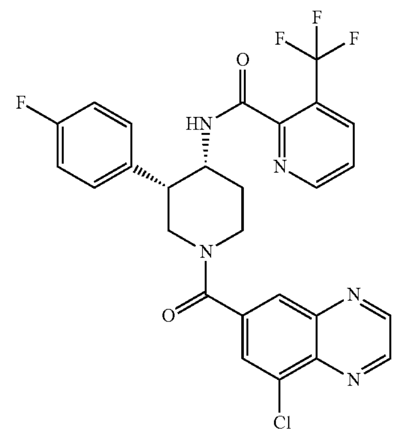 [SMILES: O=C(N[C@@H]1CCN(C(=O)c2cc(Cl)c3nccnc3c2)C[C@@H]1c1ccc(F)cc1)c1ncccc1C(F)(F)F] | | 558.2 |
| 246B | 3-chloro-N-((3S,4R)-1-((8-chloroquinoxalin-6-yl)carbonyl)-3-phenylpiperidin-4-yl)pyridine-2-carboxamide | 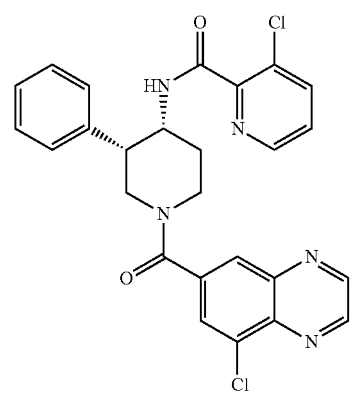 | | 506.0 |
| 247B | N-((3S,4R)-1-((8-chloroquinoxalin-6-yl)carbonyl)-3-phenylpiperidin-4-yl)-6-(1H-pyrazol-yl)-4-(trifluoromethyl)nicotinamide | 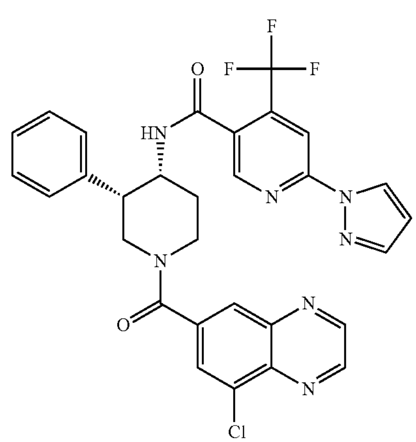 [SMILES: O=C(N[C@@H]1CCN(C(=O)c2cc(Cl)c3nccnc3c2)C[C@@H]1c1ccccc1)c1cnc(-n2cccn2)cc1C(F)(F)F] | | 606.1 |

TABLE 2-1-continued

| Ex. No. | IUPAC Name | Structure | Salt | MS |
|---|---|---|---|---|
| 248B | N-((3S,4R)-1-((8-chloroquinoxalin-6-yl)carbonyl)-3-phenylpiperidin-4-yl)-6-(2,2,2-trifluoroethoxy)-4-(trifluoromethyl)nicotinamide | 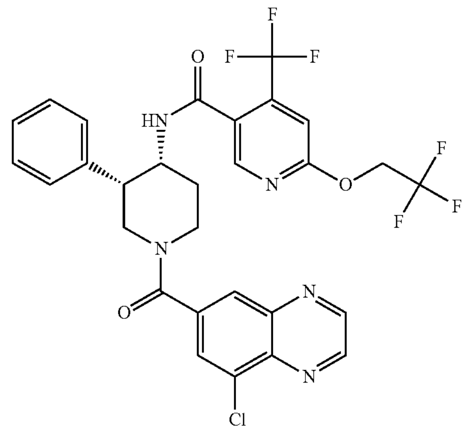 [SMILES: O=C(N[C@@H]1CCN(C(=O)c2cc(Cl)c3nccnc3c2)C[C@@H]1c1ccccc1)c1cnc(OCC(F)(F)F)cc1C(F)(F)F] | | 638.1 |
| 249B | N-((3S,4R)-1-((8-chloroquinoxalin-6-yl)carbonyl)-3-phenylpiperidin-4-yl)-6-(2,2-difluoroethoxy)-4-(trifluoromethyl)nicotinamide | 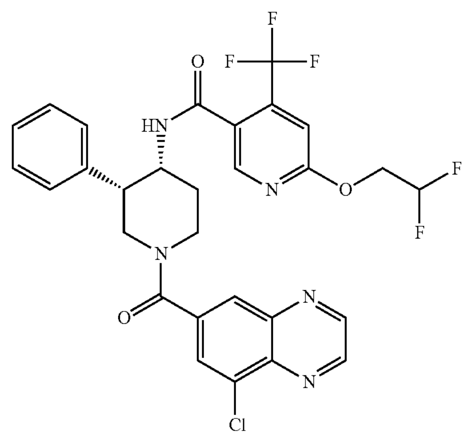 [SMILES: O=C(N[C@@H]1CCN(C(=O)c2cc(Cl)c3nccnc3c2)C[C@@H]1c1ccccc1)c1cnc(OCC(F)F)cc1C(F)(F)F] | | 619.9 |
| 250B | N-((3S,4R)-1-((8-chloroquinoxalin-6-yl)carbonyl)-3-phenylpiperidin-4-yl)-6-methoxy-4-(trifluoromethyl)nicotinamide | 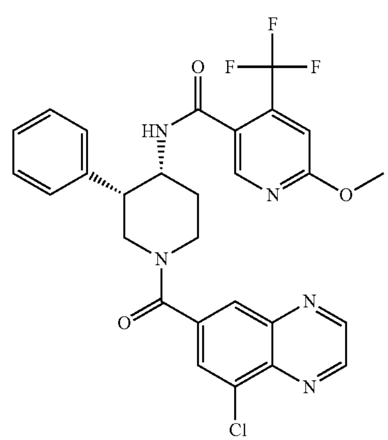 [SMILES: COc1cc(C(F)(F)F)c(C(=O)N[C@@H]2CCN(C(=O)c3cc(Cl)c4nccnc4c3)C[C@@H]2c2ccccc2)cn1] | | 570.1 |

TABLE 2-1-continued
| Ex. No. | IUPAC Name | Structure | Salt | MS |
|---|---|---|---|---|
| 251B | N-((3S,4R)-1-((5,6-dichloropyridin-3-yl)carbonyl)-3-phenylpiperidin-4-yl)-2-(trifluoromethoxy)benzamide | 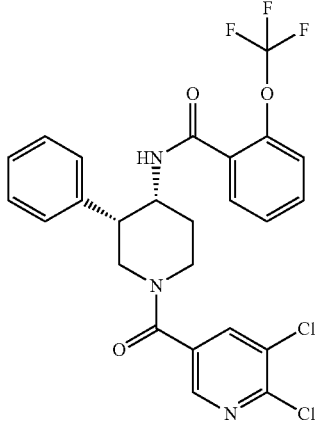 [SMILES: O=C(N[C@@H]1CCN(C(=O)c2cnc(Cl)c(Cl)c2)C[C@@H]1c1ccccc1)c1ccccc1OC(F)(F)F] | | 538.1 |
| 252B | N-((3S,4R)-1-((5-bromopyridin-2-yl)carbonyl)-3-phenylpiperidin-4-yl)-2-(trifluoromethoxy)benzamide | 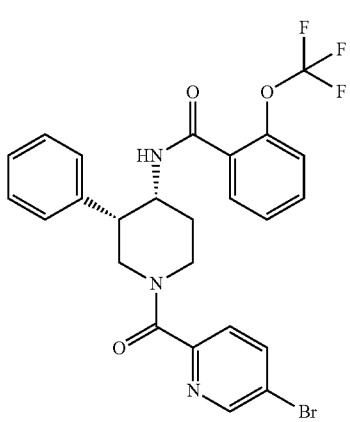 [SMILES: O=C(N[C@@H]1CCN(C(=O)c2ccc(Br)cn2)C[C@@H]1c1ccccc1)c1ccccc1OC(F)(F)F] | | 548.0 |
| 253B | N-(trans-1'-((5,6-dimethoxypyridin-3-yl)carbonyl)-1,3'-bipiperidin-4'-yl)-2-(trifluoromethoxy)benzamide | 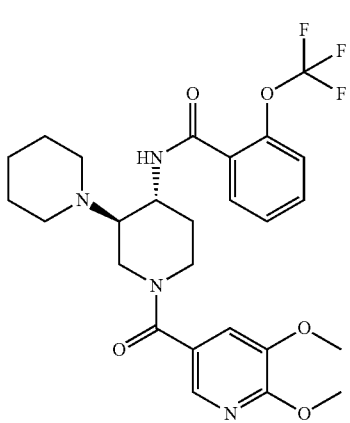 [SMILES: COc1cc(C(=O)N2CC[C@@H](NC(=O)c3ccccc3OC(F)(F)F)[C@H](N3CCCCC3)C2)cnc1OC] | | 537.1 |

TABLE 2-1-continued

| Ex. No. | IUPAC Name | Structure | Salt | MS |
|---|---|---|---|---|
| 254B | N-((3S,4R)-1-((8-chloroquinoxalin-6-yl)carbonyl)-3-phenylpiperidin-4-yl)-2-(trifluoromethoxy)benzamide | 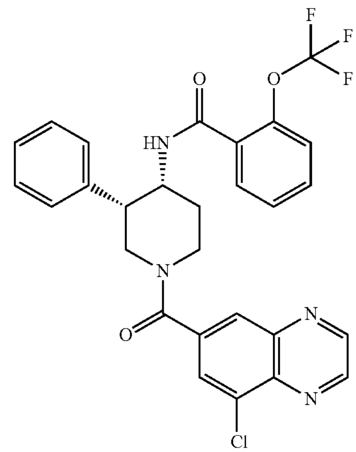 [SMILES: O=C(N[C@@H]1CCN(C(=O)c2cc(Cl)c3nccnc3c2)C[C@@H]1c1ccccc1)c1ccccc1OC(F)(F)F] | | 555.0 |
| 255B | N-((3S,4R)-1-((5-cyano-6-methoxypyridin-3-yl)carbonyl)-3-phenylpiperidin-4-yl)-2-(trifluoromethoxy)benzamide | 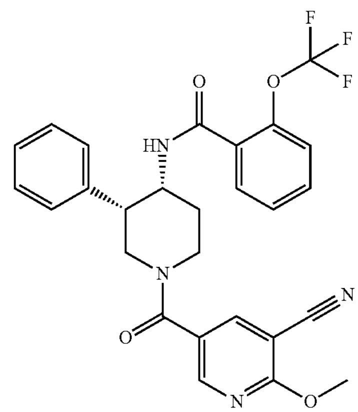 [SMILES: COc1ncc(C(=O)N2CC[C@@H](NC(=O)c3ccccc3OC(F)(F)F)[C@@H](c3ccccc3)C2)cc1C#N] | | 525.1 |
| 256B | N-((3S,4R)-1-((5-cyano-6-(($^2$H$_3$)methyloxy)pyridin-3-yl)carbonyl)-3-phenylpiperidin-4-yl)-2-(trifluoromethoxy)benzamide | 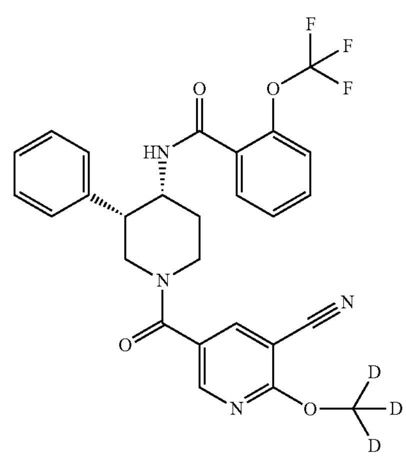 [SMILES: [2H]C([2H])([2H])Oc1ncc(C(=O)N2CC[C@@H](NC(=O)c3ccccc3OC(F)(F)F)[C@@H](c3ccccc3)C2)cc1C#N] | | 528.1 |

TABLE 2-1-continued

| Ex. No. | IUPAC Name | Structure | Salt | MS |
|---|---|---|---|---|
| 257B | N-((3S,4R)-1-((5,6-bis(($^2$H$_3$) methyloxy)pyridin-3-yl)carbonyl)-3-phenylpiperidin-4-yl)-2-(trifluoromethoxy)benzamide | 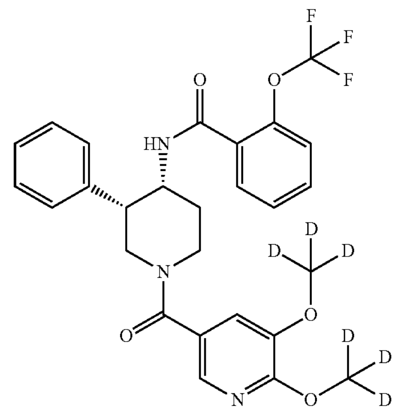 [SMILES: [2H]C([2H])([2H])Oc1cc(C(=O)N2CC[C@@H](NC(=O)c3ccccc3OC(F)(F)F)[C@@H](c3ccccc3)C2)cnc1OC([2H])([2H])[2H]] | | 536.2 |
| 258B | N-((3S,4R)-1-((6-(($^2$H$_3$) methyloxy)(5-$^2$H)pyridin-3-yl) carbonyl)-3-phenylpiperidin-4-yl)-2-(trifluoromethoxy)benzamide | 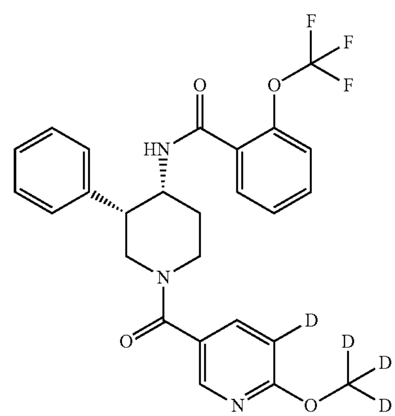 | | 504.1 |
| 259B | N-((3S,4R)-1-((5-chloro-6-(1H-pyrazol-1-yl)pyridin-3-yl) carbonyl)-3-phenylpiperidin-4-yl)-2-(trifluoromethoxy) benzamide | 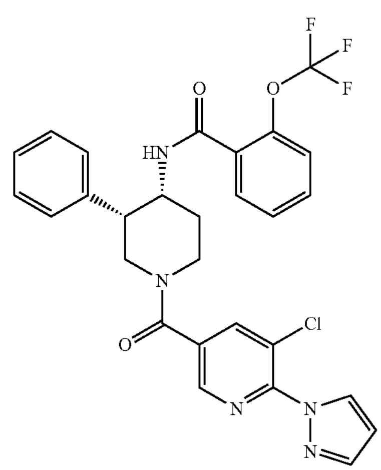 [SMILES: O=C(N[C@@H]1CCN(C(=O)c2cnc(-n3cccn3)c(Cl)c2)C[C@@H]1c1ccccc1)c1ccccc1OC(F)(F)F] | | 570.0 |

TABLE 2-1-continued

| Ex. No. | IUPAC Name | Structure | Salt | MS |
|---|---|---|---|---|
| 260B | N-((3S,4R)-1-((5-chloro-6-oxo-1,6-dihydropyridin-3-yl)carbonyl)-3-phenylpiperidin-4-yl)-2-(trifluoromethoxy)benzamide | 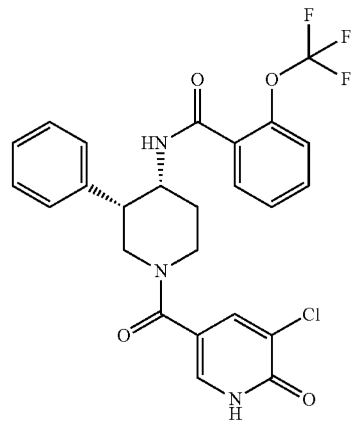 [SMILES: O=C(N[C@@H]1CCN(C(=O)c2c[nH]c(=O)c(Cl)c2)C[C@@H]1c1ccccc1)c1ccccc1OC(F)(F)F] | | 520.0 |
| 261B | N-((3S,4R)-1-((6-amino-5-chloropyridin-3-yl)carbonyl)-3-phenylpiperidin-4-yl)-2-(trifluoromethoxy)benzamide | 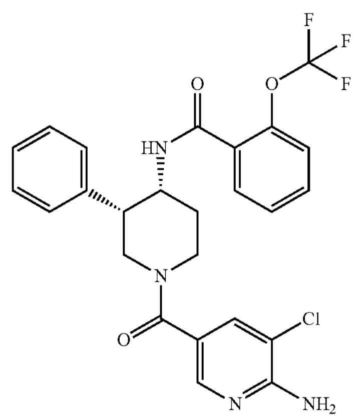 [SMILES: Nc1ncc(C(=O)N2CC[C@@H](NC(=O)c3ccccc3OC(F)(F)F)[C@@H](c3ccccc3)C2)cc1Cl] | | 519.1 |
| 262B | N-((3S,4R)-1-((5-bromo-6-(dimethylamino)pyridin-3-yl)carbonyl)-3-phenylpiperidin-4-yl)-2-(trifluoromethoxy)benzamide | 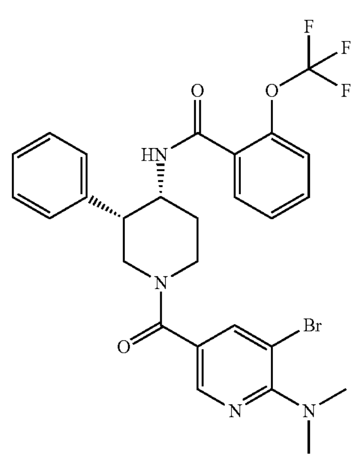 [SMILES: CN(C)c1ncc(C(=O)N2CC[C@@H](NC(=O)c3ccccc3OC(F)(F)F)[C@@H](c3ccccc3)C2)cc1Br] | | 591.0 |

TABLE 2-1-continued

| Ex. No. | IUPAC Name | Structure | Salt | MS |
|---|---|---|---|---|
| 263B | 2-(difluoromethoxy)-N-((3S,4R)-3-phenyl-1-(quinoxalin-6-ylcarbonyl)piperidin-4-yl)benzamide | 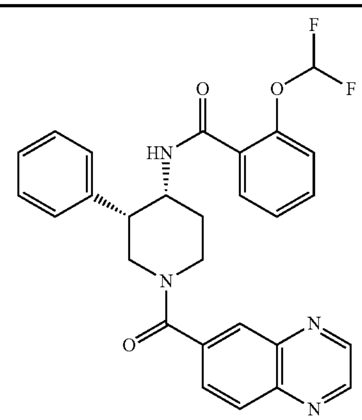 | | 503.1 |
| 264B | 2-(difluoromethoxy)-N-((3S,4R)-1-((5,6-dimethoxypyridin-3-yl)carbonyl)-3-phenylpiperidin-4-yl)benzamide | 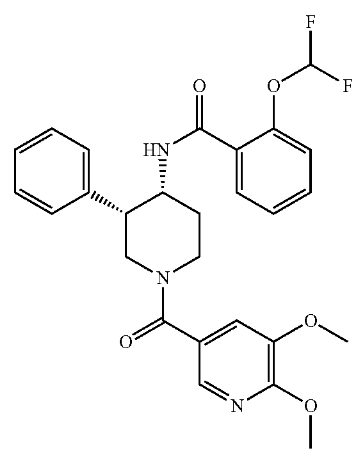 [SMILES: COc1cc(C(=O)N2CC[C@@H](NC(=O)c3ccccc3OC(F)F)[C@@H](c3ccccc3)C2)cnc1OC] | | 512.1 |
| 265B | N-((3S,4R)-1-((6-(bis(cyclopropylcarbonyl)amino)-5-chloropyridin-3-yl)carbonyl)-3-phenylpiperidin-4-yl)-2-(trifluoromethoxy)benzamide | 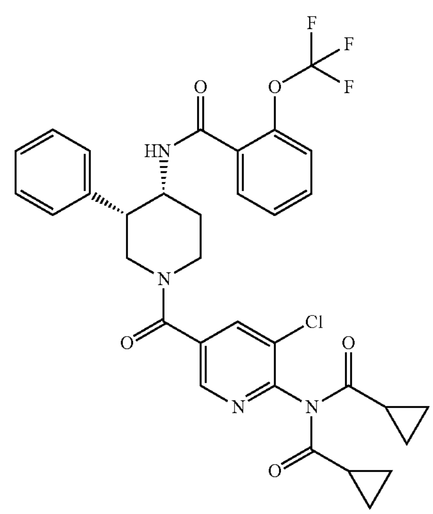 [SMILES: O=C(N[C@@H]1CCN(C(=O)c2cnc(N(C(=O)C3CC3)C(=O)C3CC3)c(Cl)c2)C[C@@H]1c1ccccc1)c1ccccc1OC(F)(F)F] | | 653.3 |

TABLE 2-1-continued

| Ex. No. | IUPAC Name | Structure | Salt | MS |
|---|---|---|---|---|
| 266B | N-((3S,4R)-1-((5-chloro-6-((cyclopropylcarbonyl)amino)pyridin-3-yl)carbonyl)-3-phenylpiperidin-4-yl)-2-(trifluoromethoxy)benzamide | 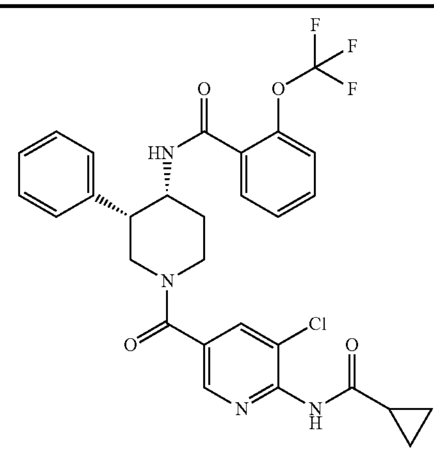 | | 587.0 |
| 267B | N-((3S,4R)-1-((8-chloro[1,2,4]triazolo[4,3-a]pyridin-6-yl)carbonyl)-3-phenylpiperidin-4-yl)-2-(trifluoromethoxy)benzamide | 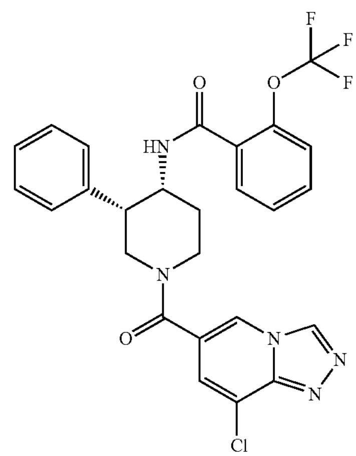 [SMILES: O=C(N[C@@H]1CCN(C(=O)c2cc(Cl)c3nncn3c2)C[C@@H]1c1ccccc1)c1ccccc1OC(F)(F)F] | | 544.0 |
| 268B | 2-chloro-N-(cis-1-(3,4-dimethoxybenzoyl)-3-(pyridin-4-yl)piperidin-4-yl)benzamide | 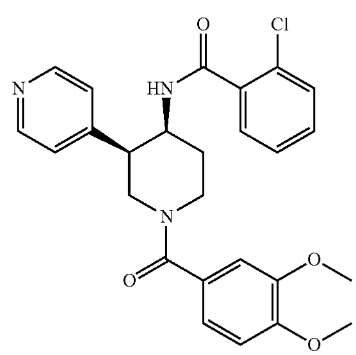 [SMILES: COc1ccc(C(=O)N2CC[C@H](NC(=O)c3ccccc3Cl)[C@H](c3ccncc3)C2)cc1OC] | | 480.0 |
| 269B | 2-chloro-N-(cis-3-(3-chloro-4-fluorophenyl)-1-(3,4-dimethoxybenzoyl)piperidin-4-yl)benzamide | 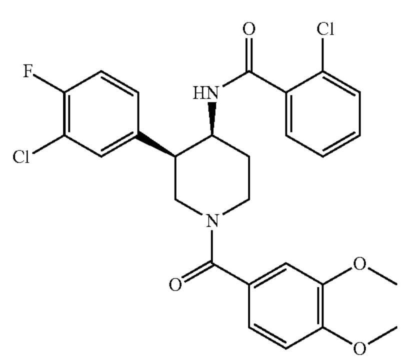 [SMILES: COc1ccc(C(=O)N2CC[C@H](NC(=O)c3ccccc3Cl)[C@H](c3ccc(F)c(Cl)c3)C2)cc1OC] | | 531.0 |

TABLE 2-1-continued

| Ex. No. | IUPAC Name | Structure | Salt | MS |
|---|---|---|---|---|
| 270B | 2-chloro-N-(trans-1-(3,4-dimethoxybenzoyl)-3-(3-methyl-2-thienyl)piperidin-4-yl)benzamide | 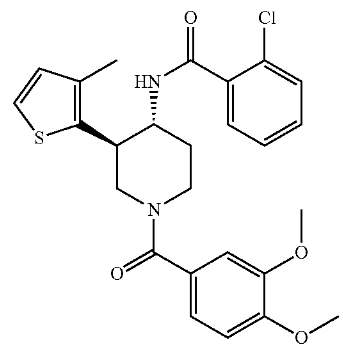 [SMILES: COc1ccc(C(=O)N2CC[C@@H](NC(=O)c3ccccc3Cl)[C@H](c3sccc3C)C2)cc1OC] | | 499.0 |
| 271B | 2-chloro-N-(trans-1-(3,4-dimethoxybenzoyl)-3-(1-methyl-1H-pyrazol-3-yl)piperidin-4-yl)benzamide | 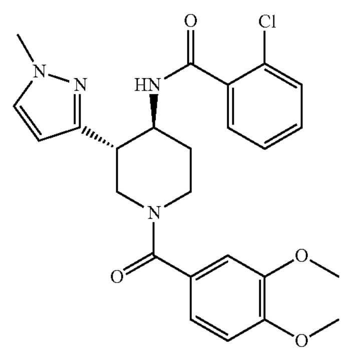 [SMILES: COc1ccc(C(=O)N2CC[C@H](NC(=O)c3ccccc3Cl)[C@@H](c3ccn(C)n3)C2)cc1OC] | | 483.1 |
| 272B | 2-chloro-N-(cis-1-(3,4-dimethoxybenzoyl)-3-(1-methyl-1H-pyrazol-4-yl)piperidin-4-yl)benzamide | 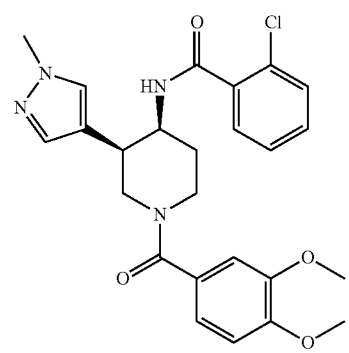 [SMILES: COc1ccc(C(=O)N2CC[C@H](NC(=O)c3ccccc3Cl)[C@H](c3cnn(C)c3)C2)cc1OC] | | 483.2 |
| 273B | 2-chloro-N-(cis-1-(3,4-dimethoxybenzoyl)-3-(1-methyl-1H-pyrazol-5-yl)piperidin-4-yl)benzamide | 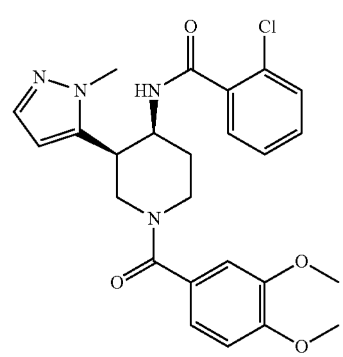 [SMILES: COc1ccc(C(=O)N2CC[C@H](NC(=O)c3ccccc3Cl)[C@H](c3ccnn3C)C2)cc1OC] | | 483.2 |

TABLE 2-1-continued

| Ex. No. | IUPAC Name | Structure | Salt | MS |
|---|---|---|---|---|
| 274B | 2-chloro-N-(trans-1-(3,4-dimethoxybenzoyl)-3-(1-methyl-1H-pyrazol-4-yl)piperidin-4-yl)benzamide | 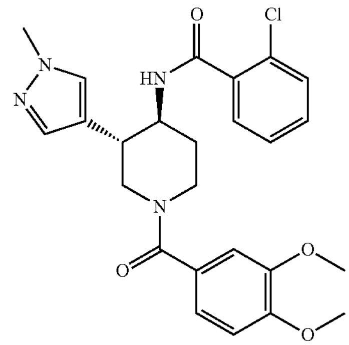 [SMILES: COc1ccc(C(=O)N2CC[C@H](NC(=O)c3ccccc3Cl)[C@@H](c3cnn(C)c3)C2)cc1OC] | | 483.2 |
| 275B | 2-chloro-N-(trans-1-(3,4-dimethoxybenzoyl)-3-(1-methyl-1H-pyrazol-5-yl)piperidin-4-yl)benzamide | 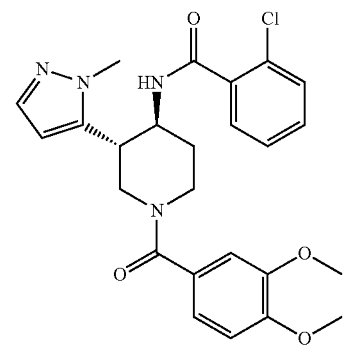 [SMILES: COc1ccc(C(=O)N2CC[C@H](NC(=O)c3ccccc3Cl)[C@@H](c3ccnn3C)C2)cc1OC] | | 483.2 |
| 276B | N-(trans-1-((5,6-dimethoxypyridin-3-yl)carbonyl)-3-(1H-pyrazol-1-yl)piperidin-4-yl)-2-(trifluoromethoxy)benzamide | 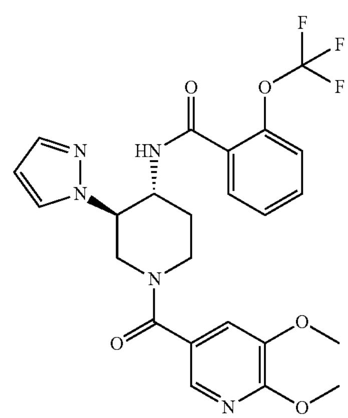 [SMILES: COc1cc(C(=O)N2CC[C@@H](NC(=O)c3ccccc3OC(F)(F)F)[C@H](n3cccn3)C2)cnc1OC] | | 520.1 |
| 277B | 2-chloro-N-(cis-1-(3,4-dimethoxybenzoyl)-3-(1-methyl-1H-pyrazol-3-yl)piperidin-4-yl)benzamide | 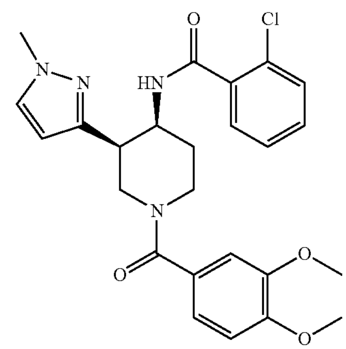 [SMILES: COc1ccc(C(=O)N2CC[C@H](NC(=O)c3ccccc3Cl)[C@H](c3ccn(C)n3)C2)cc1OC] | | 483.0 |

TABLE 2-1-continued

| Ex. No. | IUPAC Name | Structure | Salt | MS |
|---|---|---|---|---|
| 278B | N-(trans-1-((5,6-dimethoxypyridin-3-yl)carbonyl)-3-(1H-1,2,3-triazol-1-yl)piperidin-4-yl)-2-(trifluoromethoxy)benzamide | 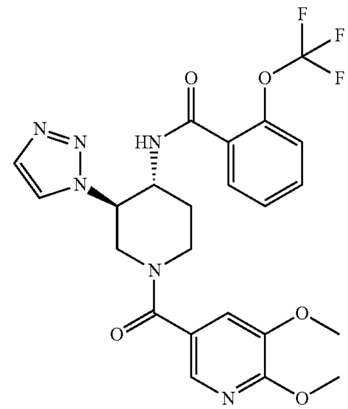 [SMILES: COc1cc(C(=O)N2CC[C@@H](NC(=O)c3ccccc3OC(F)(F)F)[C@H](n3ccnn3)C2)cnc1OC] | | 521.0 |
| 279B | N-((3S,4R)-1-((3,8-dimethylimidazo[1,2-a]pyridin-6-yl)carbonyl)-3-phenylpiperidin-4-yl)-3-(trifluoromethyl)pyridine-2-carboxamide | 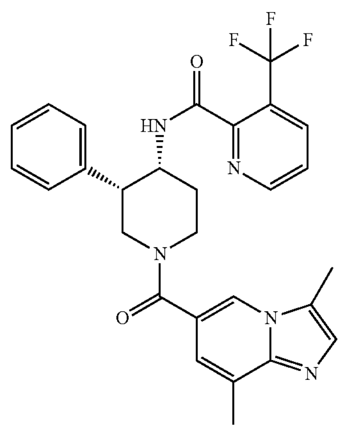 [SMILES: Cc1cc(C(=O)N2CC[C@@H](NC(=O)c3ncccc3C(F)(F)F)[C@@H](c3ccccc3)C2)cn2c(C)cnc12] | | 522.2 |
| 280B | N-((3S,4R)-1-((2-methoxy-1,4-dimethyl-1H-benzimidazol-6-yl)carbonyl)-3-phenylpiperidin-4-yl)-3-(trifluoromethyl)pyridine-2-carboxamide | 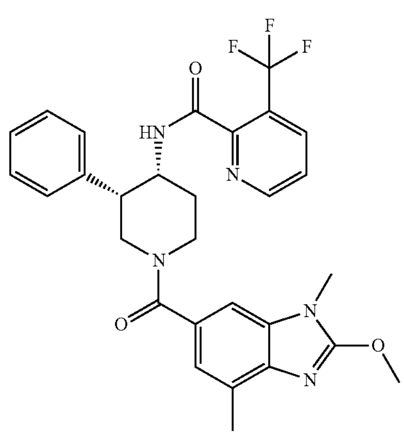 [SMILES: COc1nc2c(C)cc(C(=O)N3CC[C@@H](NC(=O)c4ncccc4C(F)(F)F)[C@@H](c4ccccc4)C3)cc2n1C] | | 552.2 |

TABLE 2-1-continued

| Ex. No. | IUPAC Name | Structure | Salt | MS |
|---|---|---|---|---|
| 281B | 3-cyclopropyl-N-((3S,4R)-1-((8-methylquinoxalin-6-yl)carbonyl)-3-phenylpiperidin-4-yl)pyridine-2-carboxamide | 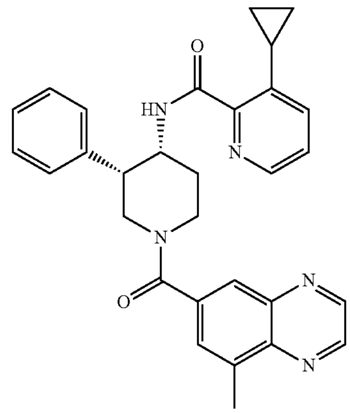 [SMILES: Cc1cc(C(=O)N2CC[C@@H](NC(=O)c3ncccc3C3CC3)[C@@H](c3ccccc3)C2)cc2nccnc12] | | 492.3 |
| 282B | 3-cyclopropyl-N-((3S,4R)-1-((8-methoxyquinoxalin-6-yl)carbonyl)-3-phenylpiperidin-4-yl)pyridine-2-carboxamide | 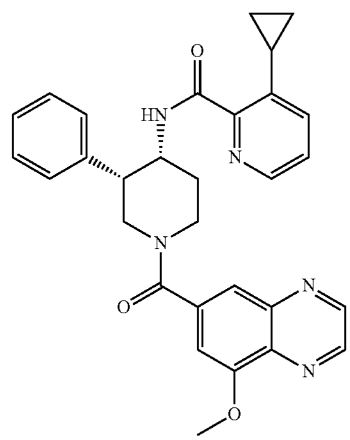 [SMILES: COc1cc(C(=O)N2CC[C@@H](NC(=O)c3ncccc3C3CC3)[C@@H](c3ccccc3)C2)cc2nccnc12] | | 508.2 |
| 283B | 3-cyclopropyl-N-((3S,4R)-1-((1,4-dimethyl-1H-benzimidazol-6-yl)carbonyl)-3-phenylpiperidin-4-yl)pyridine-2-carboxamide | 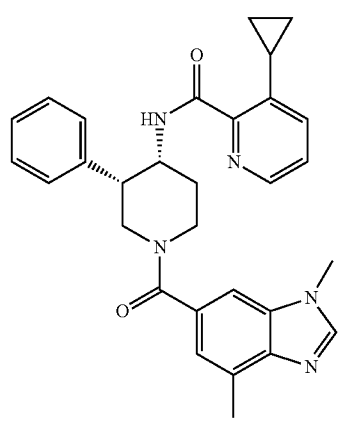 [SMILES: Cc1cc(C(=O)N2CC[C@@H](NC(=O)c3ncccc3C3CC3)[C@@H](c3ccccc3)C2)cc2c1ncn2C] | | 494.2 |

TABLE 2-1-continued

| Ex. No. | IUPAC Name | Structure | Salt | MS |
|---|---|---|---|---|
| 284B | 3-cyclopropyl-N-((3S,4R)-1-((2-methoxy-1,4-dimethyl-1H-benzimidazol-6-yl)carbonyl)-3-phenylpiperidin-4-yl)pyridine-2-carboxamide | 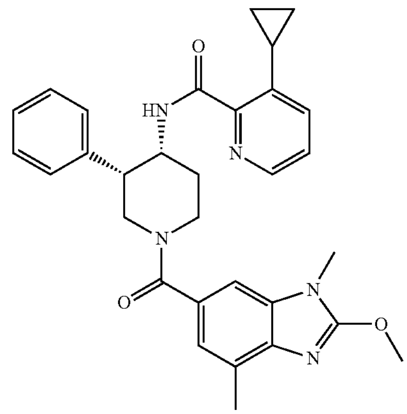 [SMILES: COc1nc2c(C)cc(C(=O)N3CC[C@@H](NC(=O)c4ncccc4C4CC4)[C@@H](c4ccccc4)C3)cc2n1C] | | 524.3 |
| 285B | 3-(difluoromethoxy)-N-((3S,4R)-1-((8-methoxyquinoxalin-6-yl)carbonyl)-3-phenylpiperidin-4-yl)pyridine-2-carboxamide | 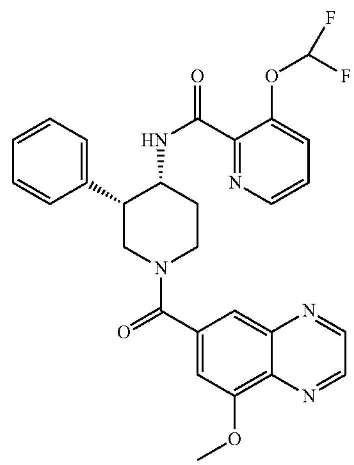 [SMILES: COc1cc(C(=O)N2CC[C@@H](NC(=O)c3ncccc3OC(F)F)[C@@H](c3ccccc3)C2)cc2nccnc12] | | 534.2 |
| 286B | 3-(difluoromethoxy)-N-((3S,4R)-1-((3,8-dimethylimidazo[1,2-a]pyridin-6-yl)carbonyl)-3-phenylpiperidin-4-yl)pyridine-2-carboxamide | 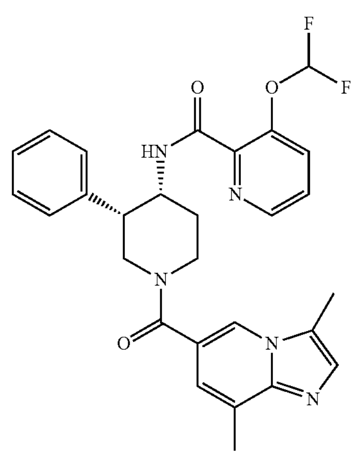 [SMILES: Cc1cc(C(=O)N2CC[C@@H](NC(=O)c3ncccc3OC(F)F)[C@@H](c3ccccc3)C2)cn2c(C)cnc12] | | 520.2 |

TABLE 2-1-continued

| Ex. No. | IUPAC Name | Structure | Salt | MS |
|---|---|---|---|---|
| 287B | 3-(difluoromethoxy)-N-((3S,4R)-1-((1,4-dimethyl-1H-benzimidazol-6-yl)carbonyl)-3-phenylpiperidin-4-yl)pyridine-2-carboxamide | 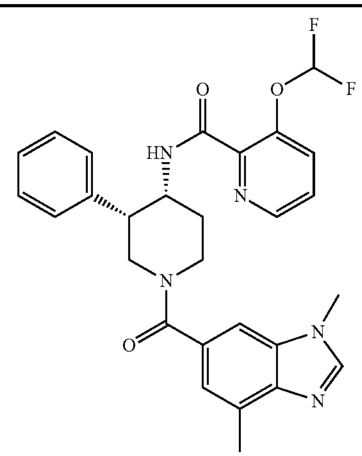 | | 520.2 |
| 288B | N-((3S,4R)-1-((8-chloro-3-methylimidazo[1,2-a]pyridin-6-yl)carbonyl)-3-phenylpiperidin-4-yl)-3-(difluoromethoxy)pyridine-2-carboxamide | 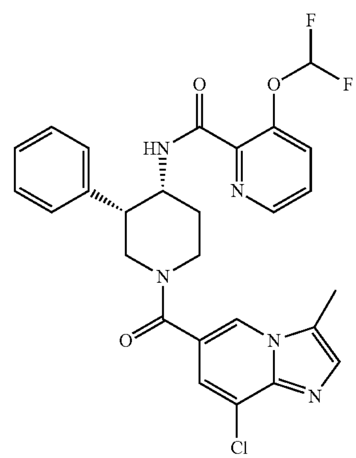 [SMILES: Cc1cnc2c(Cl)cc(C(=O)N3CC[C@@H](NC(=O)c4ncccc4OC(F)F)[C@@H](c4ccccc4)C3)cn12] | | 540.2 |
| 289B | 3-(difluoromethoxy)-N-((3S,4R)-1-((2-methoxy-1,4-dimethyl-1H-benzimidazol-6-yl)carbonyl)-3-phenylpiperidin-4-yl)pyridine-2-carboxamide | 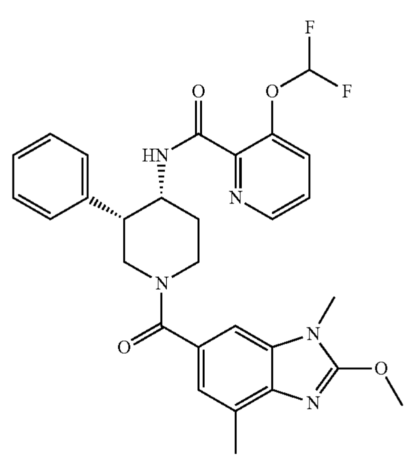 [SMILES: COc1nc2c(C)cc(C(=O)N3CC[C@@H](NC(=O)c4ncccc4OC(F)F)[C@@H](c4ccccc4)C3)cc2n1C] | | 550.2 |

TABLE 2-1-continued

| Ex. No. | IUPAC Name | Structure | Salt | MS |
|---|---|---|---|---|
| 290B | 3-(difluoromethoxy)-N-((3S,4R)-1-((8-methylquinoxalin-6-yl)carbonyl)-3-phenylpiperidin-4-yl)pyridine-2-carboxamide | 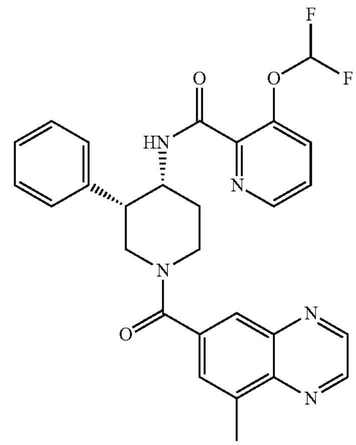 [SMILES: Cc1cc(C(=O)N2CC[C@@H](NC(=O)c3ncccc3OC(F)F)[C@@H](c3ccccc3)C2)cc2nccnc12] | | 518.2 |
| 291B | N-((3S,4R)-1-((8-methoxyquinoxalin-6-yl)carbonyl)-3-phenylpiperidin-4-yl)-1,3-dimethyl-1H-pyrazole-5-carboxamide | 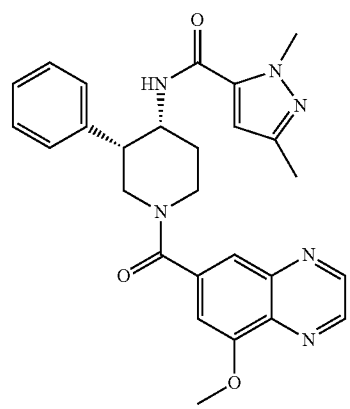 [SMILES: COc1cc(C(=O)N2CC[C@@H](NC(=O)c3cc(C)nn3C)[C@@H](c3ccccc3)C2)cc2nccnc12] | | 485.2 |
| 292B | N-((3S,4R)-1-((3,8-dimethylimidazo[1,2-a]pyridin-6-yl)carbonyl)-3-phenylpiperidin-4-yl)-1,3-dimethyl-1H-pyrazole-5-carboxamide | 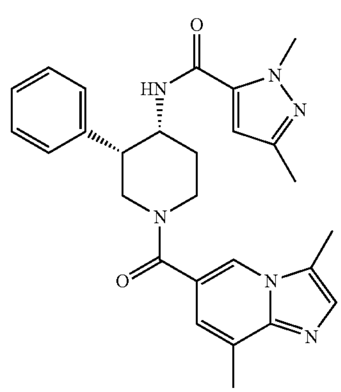 [SMILES: Cc1cc(C(=O)N[C@@H]2CCN(C(=O)c3cc(C)c4ncc(C)n4c3)C[C@@H]2c2ccccc2)n(C)n1] | | 471.3 |

TABLE 2-1-continued

| Ex. No. | IUPAC Name | Structure | Salt | MS |
|---|---|---|---|---|
| 293B | N-((3S,4R)-1-((8-chloro-3-methylimidazo[1,2-a]pyridin-6-yl)carbonyl)-3-phenylpiperidin-4-yl)-1,3-dimethyl-1H-pyrazole-5-carboxamide | 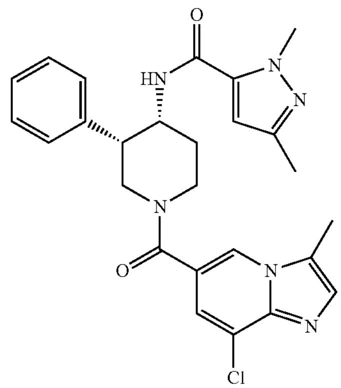 [SMILES: Cc1cc(C(=O)N[C@@H]2CCN(C(=O)c3cc(Cl)c4ncc(C)n4c3)C[C@@H]2c2ccccc2)n(C)n1] | | 491.2 |
| 294B | 1,3-dimethyl-N-((3S,4R)-1-((8-methylquinoxalin-6-yl)carbonyl)-3-phenylpiperidin-4-yl)-1H-pyrazole-5-carboxamide | 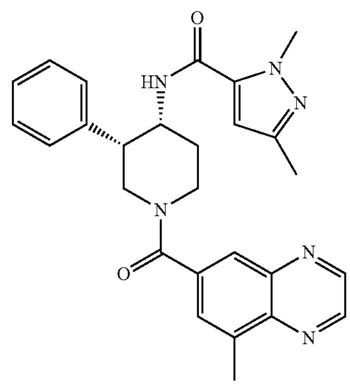 [SMILES: Cc1cc(C(=O)N[C@@H]2CCN(C(=O)c3cc(C)c4nccnc4c3)C[C@@H]2c2ccccc2)n(C)n1] | | 469.2 |
| 295B | 1-(2,2-difluoroethyl)-N-((3S,4R)-1-((2-methoxy-1,4-dimethyl-1H-benzimidazol-6-yl)carbonyl)-3-phenylpiperidin-4-yl)-3-methyl-1H-pyrazole-5-carboxamide | 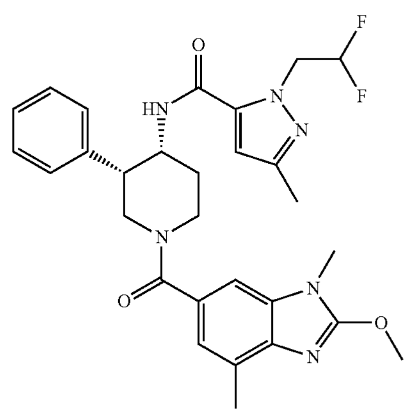 [SMILES: COc1nc2c(C)cc(C(=O)N3CC[C@@H](NC(=O)c4cc(C)nn4CC(F)F)[C@@H](c4ccccc4)C3)cc2n1C] | | 551.2 |
| 296B | 1-(2,2-difluoroethyl)-3-methyl-N-((3S,4R)-1-((8-methylquinoxalin-6-yl)carbonyl)-3-phenylpiperidin-4-yl)-1H-pyrazole-5-carboxamide | 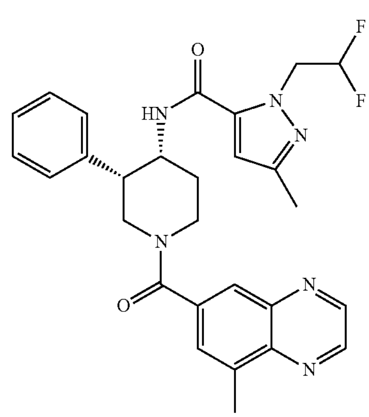 [SMILES: Cc1cc(C(=O)N[C@@H]2CCN(C(=O)c3cc(C)c4nccnc4c3)C[C@@H]2c2ccccc2)n(CC(F)F)n1] | | 519.1 |

TABLE 2-1-continued

| Ex. No. | IUPAC Name | Structure | Salt | MS |
|---|---|---|---|---|
| 297B | 1-(2,2-difluoroethyl)-N-((3S,4R)-1-((8-methoxyquinoxalin-6-yl)carbonyl)-3-phenylpiperidin-4-yl)-3-methyl-1H-pyrazole-5-carboxamide | 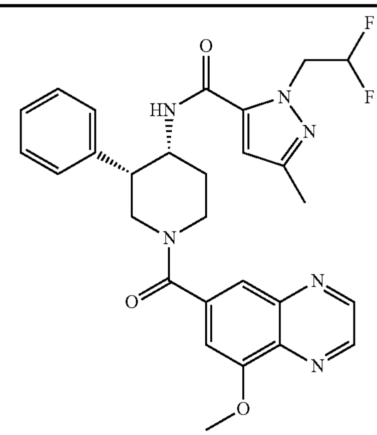 | | 535.2 |
| 298B | N-((3S,4R)-1-((2-methoxy-1,4-dimethyl-1H-benzimidazol-6-yl)carbonyl)-3-phenylpiperidin-4-yl)-1-methyl-3-(trifluoromethyl)-1H-pyrazole-5-carboxamide | 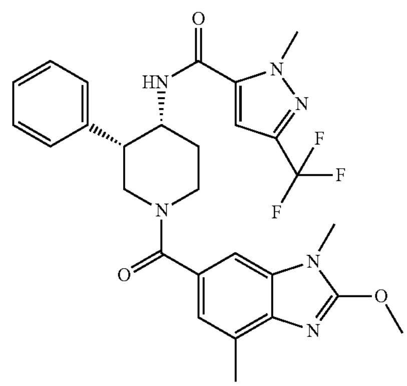 [SMILES: COc1nc2c(C)cc(C(=O)N3CC[C@@H](NC(=O)c4cc(C(F)(F)F)nn4C)[C@@H](c4ccccc4)C3)cc2n1C] | | 555.2 |
| 299B | 1-methyl-N-((3S,4R)-1-((8-methylquinoxalin-6-yl)carbonyl)-3-phenylpiperidin-4-yl)-3-(trifluoromethyl)-1H-pyrazole-5-carboxamide | 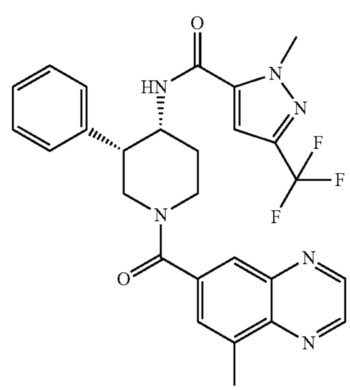 [SMILES: Cc1cc(C(=O)N2CC[C@@H](NC(=O)c3cc(C(F)(F)F)nn3C)[C@@H](c3ccccc3)C2)cc2nccnc12] | | 523.2 |
| 300B | N-((3S,4R)-1-((8-chloro-3-methylimidazo[1,2-a]pyridin-6-yl)carbonyl)-3-phenylpiperidin-4-yl)-1-methyl-3-(trifluoromethyl)-1H-pyrazole-5-carboxamide | 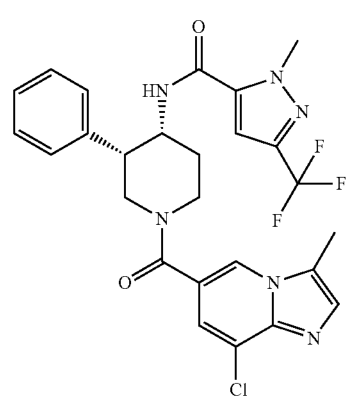 [SMILES: Cc1cnc2c(Cl)cc(C(=O)N3CC[C@@H](NC(=O)c4cc(C(F)(F)F)nn4C)[C@@H](c4ccccc4)C3)cn12] | | 545.1 |

TABLE 2-1-continued

| Ex. No. | IUPAC Name | Structure | Salt | MS |
|---|---|---|---|---|
| 301B | N-((3S,4R)-1-((3,8-dimethylimidazo[1,2-a]pyridin-6-yl)carbonyl)-3-phenylpiperidin-4-yl)-1-methyl-3-(trifluoromethyl)-1H-pyrazole-5-carboxamide | 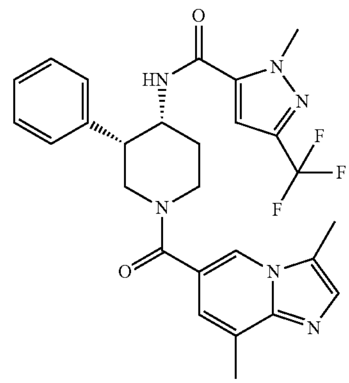 [SMILES: Cc1cc(C(=O)N2CC[C@@H](NC(=O)c3cc(C(F)(F)F)nn3C)[C@@H](c3ccccc3)C2)cn2c(C)cnc12] | | 525.2 |
| 302B | N-((3S,4R)-1-((1,4-dimethyl-1H-benzimidazol-6-yl)carbonyl)-3-phenylpiperidin-4-yl)-1-methyl-3-(trifluoromethyl)-1H-pyrazole-5-carboxamide | 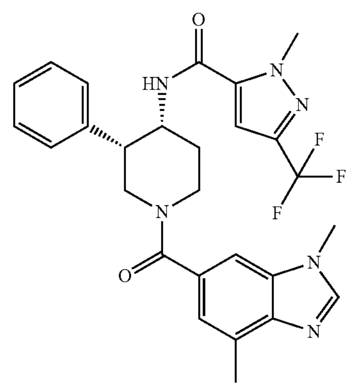 [SMILES: Cc1cc(C(=O)N2CC[C@@H](NC(=O)c3cc(C(F)(F)F)nn3C)[C@@H](c3ccccc3)C2)cc2c1ncn2C] | | 525.2 |
| 303B | 3-ethoxy-1-methyl-N-((3S,4R)-1-((8-methylquinoxalin-6-yl)carbonyl)-3-phenylpiperidin-4-yl)-1H-pyrazole-5-carboxamide | 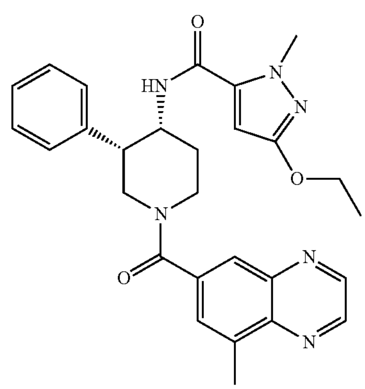 [SMILES: CCOc1cc(C(=O)N[C@@H]2CCN(C(=O)c3cc(C)c4nccnc4c3)C[C@@H]2c2ccccc2)n(C)n1] | | 499.2 |
| 304B | N-((3S,4R)-1-((8-chloro-3-methylimidazo[1,2-a]pyridin-6-yl)carbonyl)-3-phenylpiperidin-4-yl)-3-ethoxy-1-methyl-1H-pyrazole-5-carboxamide | 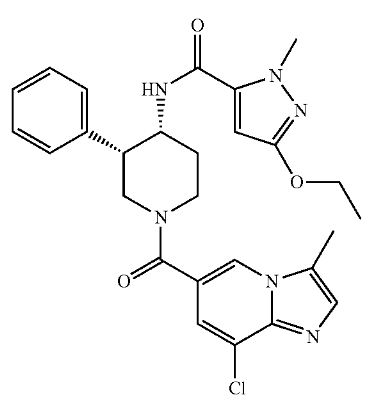 [SMILES: CCOc1cc(C(=O)N[C@@H]2CCN(C(=O)c3cc(Cl)c4ncc(C)n4c3)C[C@@H]2c2ccccc2)n(C)n1] | | 521.2 |

TABLE 2-1-continued

| Ex. No. | IUPAC Name | Structure | Salt | MS |
|---|---|---|---|---|
| 305B | 3-ethoxy-N-((3S,4R)-1-((2-methoxy-1,4-dimethyl-1H-benzimidazol-6-yl)carbonyl)-3-phenylpiperidin-4-yl)-1-methyl-1H-pyrazole-5-carboxamide | 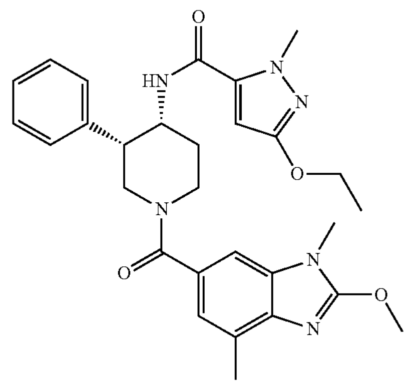 [SMILES: CCOc1cc(C(=O)N[C@@H]2CCN(C(=O)c3cc(C)c4nc(OC)n(C)c4c3)C[C@@H]2c2ccccc2)n(C)n1] | | 531.2 |
| 306B | 3-ethoxy-N-((3S,4R)-1-((8-methoxyquinoxalin-6-yl)carbonyl)-3-phenylpiperidin-4-yl)-1-methyl-1H-pyrazole-5-carboxamide | 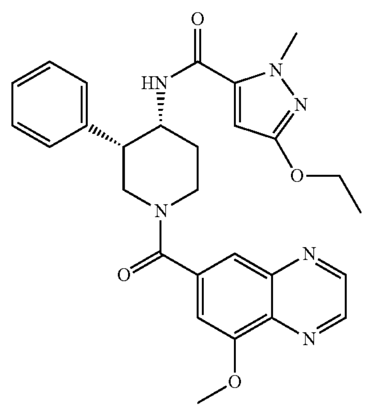 [SMILES: CCOc1cc(C(=O)N[C@@H]2CCN(C(=O)c3cc(OC)c4nccnc4c3)C[C@@H]2c2ccccc2)n(C)n1] | | 515.2 |
| 307B | N-((3S,4R)-1-((1,4-dimethyl-1H-benzimidazol-6-yl)carbonyl)-3-phenylpiperidin-4-yl)-3-ethoxy-1-methyl-1H-pyrazole-5-carboxamide | 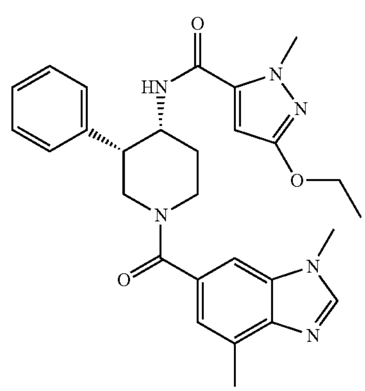 [SMILES: CCOc1cc(C(=O)N[C@@H]2CCN(C(=O)c3cc(C)c4ncn(C)c4c3)C[C@@H]2c2ccccc2)n(C)n1] | | 501.3 |
| 308B | N-((3S,4R)-1-((1,4-dimethyl-1H-benzimidazol-6-yl)carbonyl)-3-phenylpiperidin-4-yl)-3-methoxy-1-methyl-1H-pyrazole-5-carboxamide | 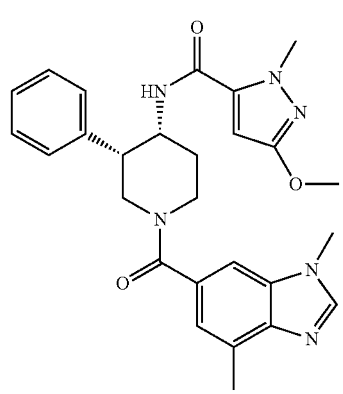 [SMILES: COc1cc(C(=O)N[C@@H]2CCN(C(=O)c3cc(C)c4ncn(C)c4c3)C[C@@H]2c2ccccc2)n(C)n1] | | 487.1 |

TABLE 2-1-continued

| Ex. No. | IUPAC Name | Structure | Salt | MS |
|---|---|---|---|---|
| 309B | 3-methoxy-1-methyl-N-((3S,4R)-1-((8-methylquinoxalin-6-yl)carbonyl)-3-phenylpiperidin-4-yl)-1H-pyrazole-5-carboxamide | 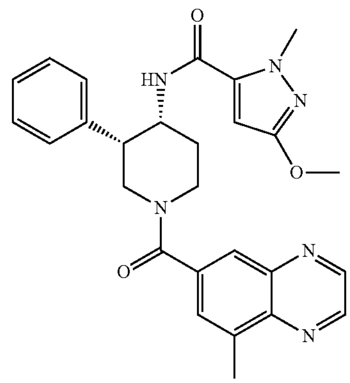 [SMILES: COc1cc(C(=O)N[C@@H]2CCN(C(=O)c3cc(C)c4nccnc4c3)C[C@@H]2c2ccccc2)n(C)n1] | | 485.2 |
| 310B | N-((3S,4R)-1-((8-chloro-3-methylimidazo[1,2-a]pyridin-6-yl)carbonyl)-3-phenylpiperidin-4-yl)-3-methoxy-1-methyl-1H-pyrazole-5-carboxamide | 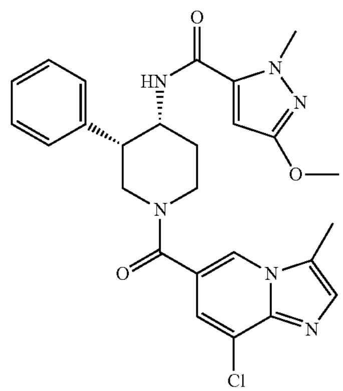 [SMILES: COc1cc(C(=O)N[C@@H]2CCN(C(=O)c3cc(Cl)c4ncc(C)n4c3)C[C@@H]2c2ccccc2)n(C)n1] | | 507.2 |
| 311B | 3-methoxy-N-((3S,4R)-1-((8-methoxyquinoxalin-6-yl)carbonyl)-3-phenylpiperidin-4-yl)-1-methyl-1H-pyrazole-5-carboxamide | 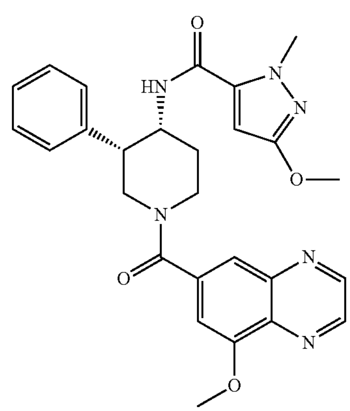 [SMILES: COc1cc(C(=O)N[C@@H]2CCN(C(=O)c3cc(OC)c4nccnc4c3)C[C@@H]2c2ccccc2)n(C)n1] | | 501.2 |
| 312B | 3-(difluoromethoxy)-1-methyl-N-((3S,4R)-1-((8-methylquinoxalin-6-yl)carbonyl)-3-phenylpiperidin-4-yl)-1H-pyrazole-5-carboxamide | 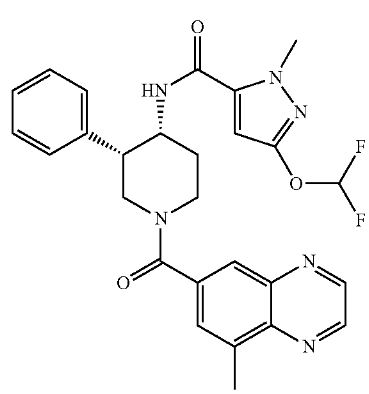 [SMILES: Cc1cc(C(=O)N2CC[C@@H](NC(=O)c3cc(OC(F)F)nn3C)[C@@H](c3ccccc3)C2)cc2nccnc12] | | 521.2 |

TABLE 2-1-continued

| Ex. No. | IUPAC Name | Structure | Salt | MS |
|---|---|---|---|---|
| 313B | 3-(difluoromethoxy)-N-((3S,4R)-1-((8-methoxyquinoxalin-6-yl)carbonyl)-3-phenylpiperidin-4-yl)-1-methyl-1H-pyrazole-5-carboxamide | 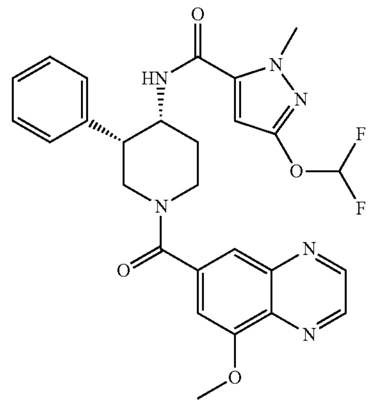 [SMILES: COc1cc(C(=O)N2CC[C@@H](NC(=O)c3cc(OC(F)F)nn3C)[C@@H](c3ccccc3)C2)cc2nccnc12] | | 537.2 |
| 314B | N-((3S,4R)-1-((8-chloro-3-methylimidazo[1,2-a]pyridin-6-yl)carbonyl)-3-phenylpiperidin-4-yl)-3-(difluoromethoxy)-1-methyl-1H-pyrazole-5-carboxamide | 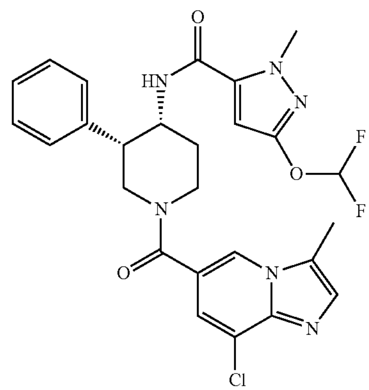 [SMILES: Cc1cnc2c(Cl)cc(C(=O)N3CC[C@@H](NC(=O)c4cc(OC(F)F)nn4C)[C@@H](c4ccccc4)C3)cn12] | | 543.2 |
| 315B | 3-(difluoromethoxy)-N-((3S,4R)-1-((1,4-dimethyl-1H-benzimidazol-6-yl)carbonyl)-3-phenylpiperidin-4-yl)-1-methyl-1H-pyrazole-5-carboxamide | 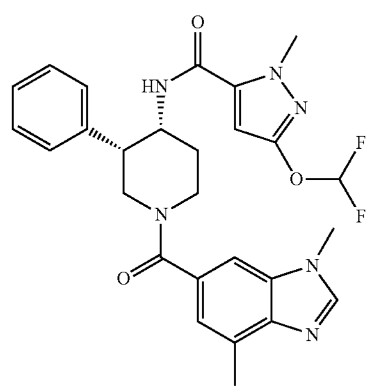 [SMILES: Cc1cc(C(=O)N2CC[C@@H](NC(=O)c3cc(OC(F)F)nn3C)[C@@H](c3ccccc3)C2)cc2c1ncn2C] | | 523.2 |
| 316B | 3-(difluoromethoxy)-N-((3S,4R)-1-((2-methoxy-1,4-dimethyl-1H-benzimidazol-6-yl)carbonyl)-3-phenylpiperidin-4-yl)-1-methyl-1H-pyrazole-5-carboxamide | 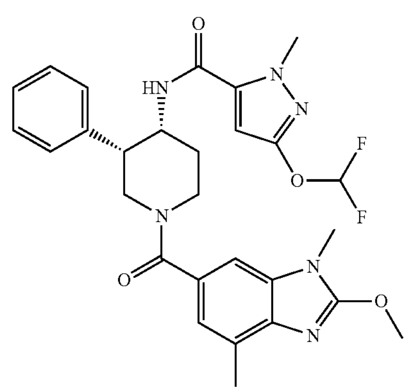 [SMILES: COc1nc2c(C)cc(C(=O)N3CC[C@@H](NC(=O)c4cc(OC(F)F)nn4C)[C@@H](c4ccccc4)C3)cc2n1C] | | 553.2 |

TABLE 2-1-continued

| Ex. No. | IUPAC Name | Structure | Salt | MS |
|---|---|---|---|---|
| 317B | 3-(difluoromethoxy)-1,4-dimethyl-N-((3S,4R)-1-((8-methylquinoxalin-6-yl)carbonyl)-3-phenylpiperidin-4-yl)-1H-pyrazole-5-carboxamide | 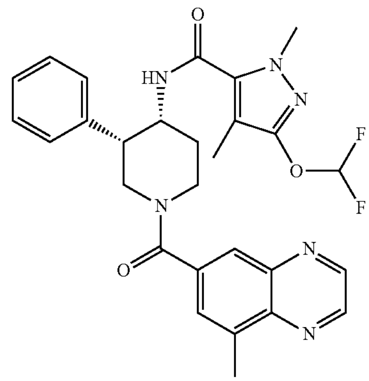 [SMILES: Cc1c(OC(F)F)nn(C)c1C(=O)N[C@@H]1CCN(C(=O)c2cc(C)c3nccnc3c2)C[C@@H]1c1ccccc1] | | 535.2 |
| 318B | N-((3S,4R)-1-((8-chloro-3-methylimidazo[1,2-a]pyridin-6-yl)carbonyl)-3-phenylpiperidin-4-yl)-3-(difluoromethoxy)-1,4-dimethyl-1H-pyrazole-5-carboxamide | 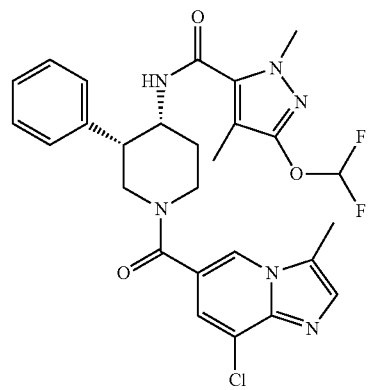 [SMILES: Cc1c(OC(F)F)nn(C)c1C(=O)N[C@@H]1CCN(C(=O)c2cc(Cl)c3ncc(C)n3c2)C[C@@H]1c1ccccc1] | | 557.2 |
| 319B | 3-(difluoromethoxy)-N-((3S,4R)-1-((3,8-dimethylimidazo[1,2-a]pyridin-6-yl)carbonyl)-3-phenylpiperidin-4-yl)-1,4-dimethyl-1H-pyrazole-5-carboxamide | 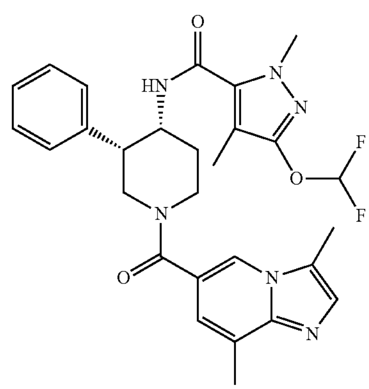 [SMILES: Cc1c(OC(F)F)nn(C)c1C(=O)N[C@@H]1CCN(C(=O)c2cc(C)c3ncc(C)n3c2)C[C@@H]1c1ccccc1] | | 537.2 |
| 320B | 3-(difluoromethoxy)-N-((3S,4R)-1-((1,4-dimethyl-1H-benzimidazol-6-yl)carbonyl)-3-phenylpiperidin-4-yl)-1,4-dimethyl-1H-pyrazole-5-carboxamide | 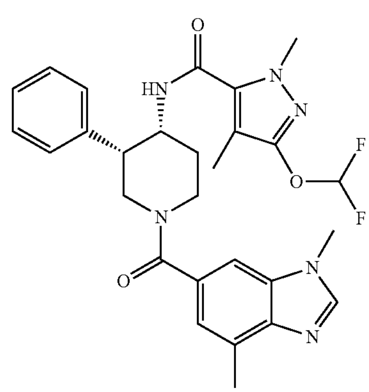 [SMILES: Cc1c(OC(F)F)nn(C)c1C(=O)N[C@@H]1CCN(C(=O)c2cc(C)c3ncn(C)c3c2)C[C@@H]1c1ccccc1] | | 537.2 |

TABLE 2-1-continued

| Ex. No. | IUPAC Name | Structure | Salt | MS |
|---|---|---|---|---|
| 321B | 3-(difluoromethoxy)-N-((3S,4R)-1-((8-methoxyquinoxalin-6-yl)carbonyl)-3-phenylpiperidin-4-yl)-1,4-dimethyl-1H-pyrazole-5-carboxamide | 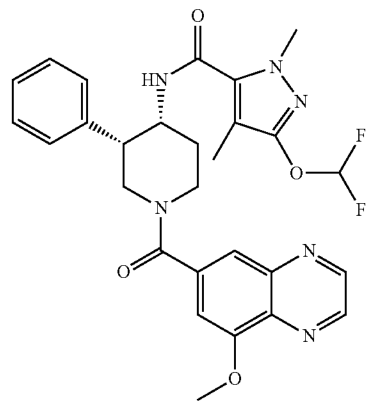 [SMILES: COc1cc(C(=O)N2CC[C@@H](NC(=O)c3c(C)c(OC(F)F)nn3C)[C@@H](c3ccccc3)C2)cc2nccnc12] | | 551.2 |
| 322B | N-((3S,4R)-1-((3,8-dimethylimidazo[1,2-a]pyridin-6-yl)carbonyl)-3-phenylpiperidin-4-yl)-1,3,4-trimethyl-1H-pyrazole-5-carboxamide | 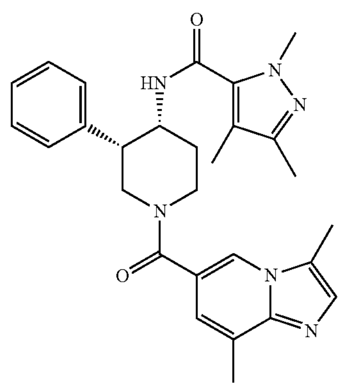 [SMILES: Cc1nn(C)c(C(=O)N[C@@H]2CCN(C(=O)c3cc(C)c4ncc(C)n4c3)C[C@@H]2c2ccccc2)c1C] | | 485.3 |
| 323B | N-((3S,4R)-1-((1,4-dimethyl-1H-benzimidazol-6-yl)carbonyl)-3-phenylpiperidin-4-yl)-1,3,4-trimethyl-1H-pyrazole-5-carboxamide | 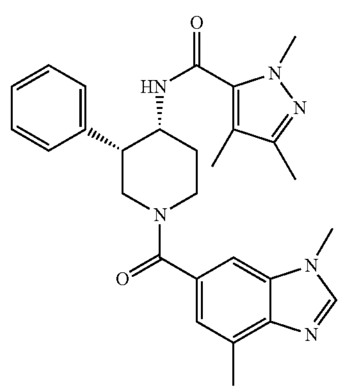 [SMILES: Cc1nn(C)c(C(=O)N[C@@H]2CCN(C(=O)c3cc(C)c4ncn(C)c4c3)C[C@@H]2c2ccccc2)c1C] | | 485.3 |
| 324B | N-((3S,4R)-1-((8-methoxyquinoxalin-6-yl)carbonyl)-3-phenylpiperidin-4-yl)-1,3,4-trimethyl-1H-pyrazole-5-carboxamide | 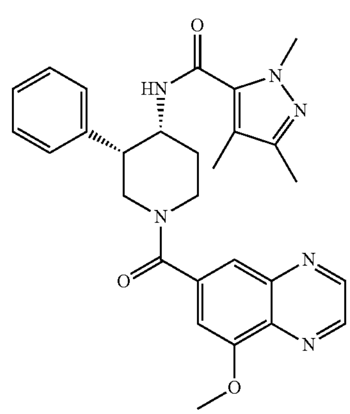 [SMILES: COc1cc(C(=O)N2CC[C@@H](NC(=O)c3c(C)c(C)nn3C)[C@@H](c3ccccc3)C2)cc2nccnc12] | | 499.2 |

TABLE 2-1-continued

| Ex. No. | IUPAC Name | Structure | Salt | MS |
|---|---|---|---|---|
| 325B | 1,3,4-trimethyl-N-((3S,4R)-1-((8-methylquinoxalin-6-yl)carbonyl)-3-phenylpiperidin-4-yl)-1H-pyrazole-5-carboxamide | 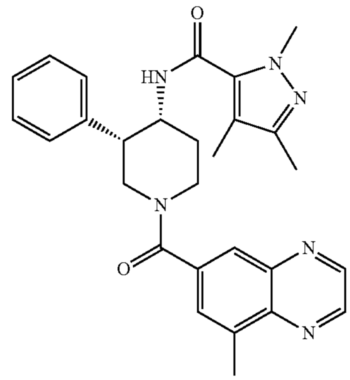 [SMILES: Cc1nn(C)c(C(=O)N[C@@H]2CCN(C(=O)c3cc(C)c4nccnc4c3)C[C@@H]2c2ccccc2)c1C] | | 483.2 |
| 326B | 3-cyclopropyl-N-((3S,4R)-1-((2-methoxy-1,4-dimethyl-1H-benzimidazol-6-yl)carbonyl)-3-phenylpiperidin-4-yl)-1-methyl-1H-pyrazole-5-carboxamide | 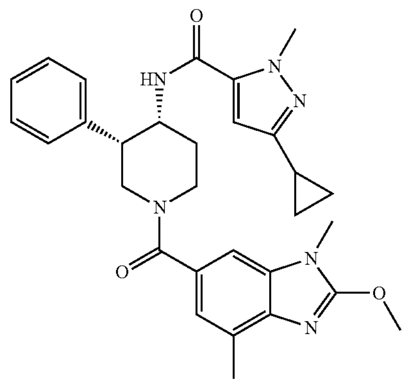 [SMILES: COc1nc2c(C)cc(C(=O)N3CC[C@@H](NC(=O)c4cc(C5CC5)nn4C)[C@@H](c4ccccc4)C3)cc2n1C] | | 527.2 |
| 327B | 3-cyclopropyl-methyl-N-((3S,4R)-1-((8-methylquinoxalin-6-yl)carbonyl)-3-phenylpiperidin-4-yl)-1H-pyrazole-5-carboxamide | 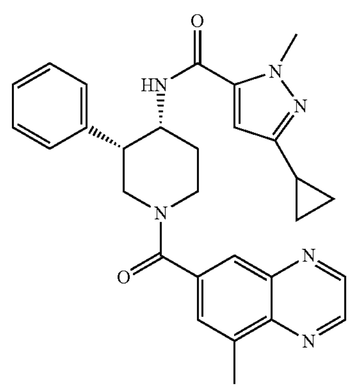 [SMILES: Cc1cc(C(=O)N2CC[C@@H](NC(=O)c3cc(C4CC4)nn3C)[C@@H](c3ccccc3)C2)cc2nccnc12] | | 495.2 |
| 328B | 3-cyclopropyl-N-((3S,4R)-1-((1,4-dimethyl-1H-benzimidazol-6-yl)carbonyl)-3-phenylpiperidin-4-yl)-1-methyl-1H-pyrazole-5-carboxamide | 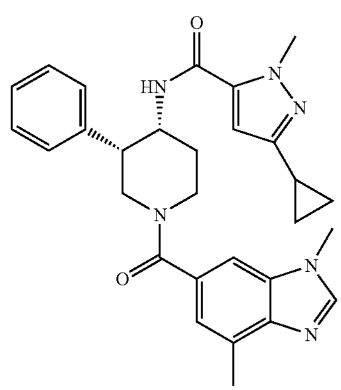 [SMILES: Cc1cc(C(=O)N2CC[C@@H](NC(=O)c3cc(C4CC4)nn3C)[C@@H](c3ccccc3)C2)cc2c1ncn2C] | | 497.2 |

TABLE 2-1-continued

| Ex. No. | IUPAC Name | Structure | Salt | MS |
|---|---|---|---|---|
| 329B | N-((3S,4R)-1-((8-chloro-3-methylimidazo[1,2-a]pyridin-6-yl)carbonyl)-3-phenylpiperidin-4-yl)-3-cyclopropyl-1-methyl-1H-pyrazole-5-carboxamide | 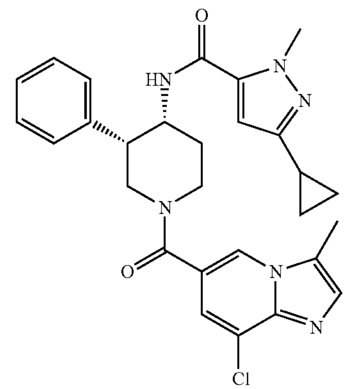 [SMILES: Cc1cnc2c(Cl)cc(C(=O)N3CC[C@@H](NC(=O)c4cc(C5CC5)nn4C)[C@@H](c4ccccc4)C3)cn12] | | 517.2 |
| 330B | 3-cyclopropyl-N-((3S,4R)-1-((8-methoxyquinoxalin-6-yl)carbonyl)-3-phenylpiperidin-4-yl)-1-methyl-1H-pyrazole-5-carboxamide | 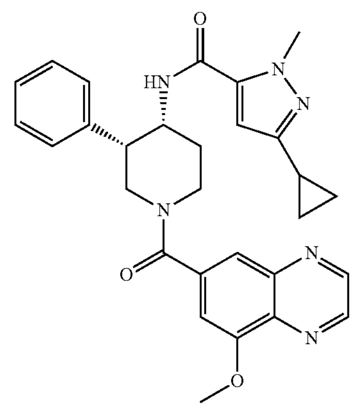 [SMILES: COc1cc(C(=O)N2CC[C@@H](NC(=O)c3cc(C4CC4)nn3C)[C@@H](c3ccccc3)C2)cc2nccnc12] | | 511.2 |
| 331B | 3-cyclopropyl-N-((3S,4R)-1-((3,8-dimethylimidazo[1,2-a]pyridin-6-yl)carbonyl)-3-phenylpiperidin-4-yl)-1-methyl-1H-pyrazole-5-carboxamide | 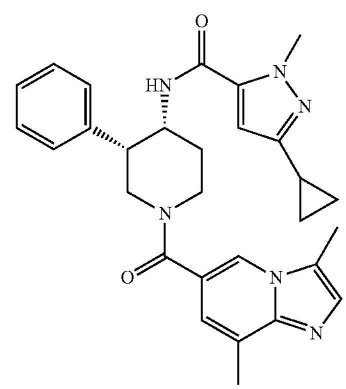 [SMILES: Cc1cc(C(=O)N2CC[C@@H](NC(=O)c3cc(C4CC4)nn3C)[C@@H](c3ccccc3)C2)cn2c(C)cnc12] | | 497.2 |
| 332B | N-((3S,4R)-1-((8-chloro-3-methylimidazo[1,2-a]pyridin-6-yl)carbonyl)-3-phenylpiperidin-4-yl)-1,3-dimethyl-4-(trifluoromethyl)-1H-pyrazole-5-carboxamide | 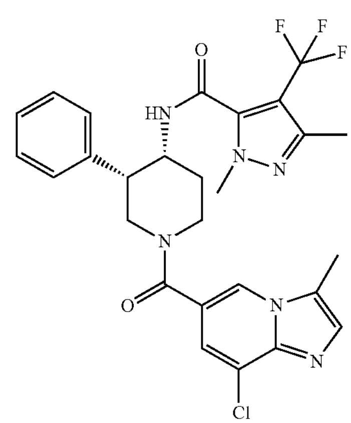 [SMILES: Cc1nn(C)c(C(=O)N[C@@H]2CCN(C(=O)c3cc(Cl)c4ncc(C)n4c3)C[C@@H]2c2ccccc2)c1C(F)(F)F] | | 559.2 |

TABLE 2-1-continued

| Ex. No. | IUPAC Name | Structure | Salt | MS |
|---|---|---|---|---|
| 333B | N-((3S,4R)-((3,8-dimethylimidazo[1,2-a]pyridin-6-yl)carbonyl)-3-phenylpiperidin-4-yl)-1,3-dimethyl-4-(trifluoromethyl)-1H-pyrazole-5-carboxamide | 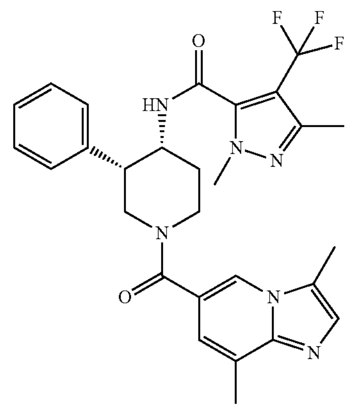 [SMILES: Cc1nn(C)c(C(=O)N[C@@H]2CCN(C(=O)c3cc(C)c4ncc(C)n4c3)C[C@@H]2c2ccccc2)c1C(F)(F)F] | | 539.2 |
| 334B | N-((3S,4R)-1-((8-methoxyquinoxalin-6-yl)carbonyl)-3-phenylpiperidin-4-yl)-1,3-dimethyl-4-(trifluoromethyl)-1H-pyrazole-5-carboxamide | 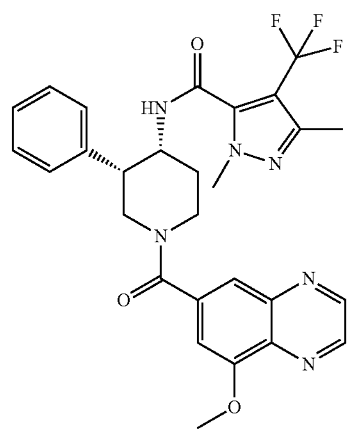 [SMILES: COc1cc(C(=O)N2CC[C@@H](NC(=O)c3c(C(F)(F)F)c(C)nn3C)[C@@H](c3ccccc3)C2)cc2nccnc12] | | 553.2 |
| 335B | N-((3S,4R)-1-((2-methoxy-1,4-dimethyl-1H-benzimidazol-6-yl)carbonyl)-3-phenylpiperidin-4-yl)-1,3-dimethyl-4-(trifluoromethyl)-1H-pyrazole-5-carboxamide | 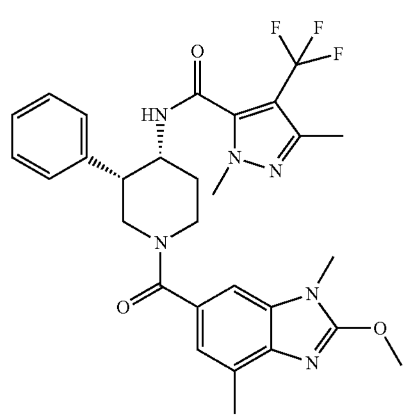 [SMILES: COc1nc2c(C)cc(C(=O)N3CC[C@@H](NC(=O)c4c(C(F)(F)F)c(C)nn4C)[C@@H](c4ccccc4)C3)cc2n1C] | | 569.2 |

TABLE 2-1-continued

| Ex. No. | IUPAC Name | Structure | Salt | MS |
|---|---|---|---|---|
| 336B | 5-chloro-N-((3S,4R)-1-((8-methoxyquinoxalin-6-yl)carbonyl)-3-phenylpiperidin-4-yl)-1-methyl-3-(trifluoromethyl)-1H-pyrazole-4-carboxamide | 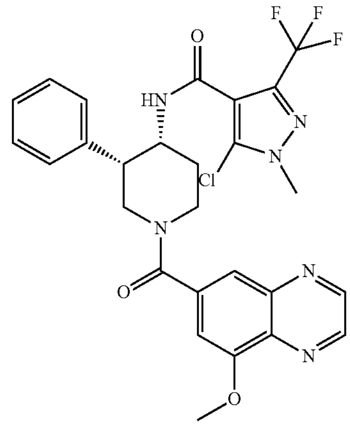 [SMILES: COc1cc(C(=O)N2CC[C@@H](NC(=O)c3c(C(F)(F)F)nn(C)c3Cl)[C@@H](c3ccccc3)C2)cc2nccnc12] | | 573.2 |
| 337B | 5-chloro-N-((3S,4R)-1-((2-methoxy-1,4-dimethyl-1H-benzimidazol-6-yl)carbonyl)-3-phenylpiperidin-4-yl)-1-methyl-3-(trifluoromethyl)-1H-pyrazole-4-carboxamide | 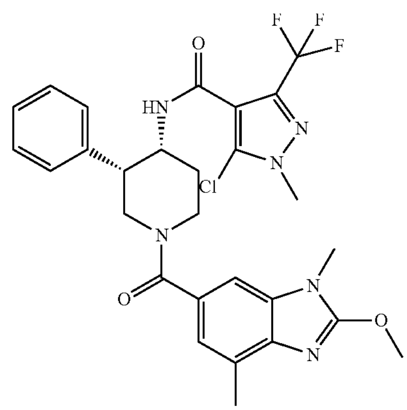 [SMILES: COc1nc2c(C)cc(C(=O)N3CC[C@@H](NC(=O)c4c(C(F)(F)F)nn(C)c4Cl)[C@@H](c4ccccc4)C3)cc2n1C] | | 589.3 |
| 338B | 5-chloro-N-((3S,4R)-1-((8-chloro-3-methylimidazo[1,2-a]pyridin-6-yl)carbonyl)-3-phenylpiperidin-4-yl)-1-methyl-3-(trifluoromethyl)-1H-pyrazole-4-carboxamide | 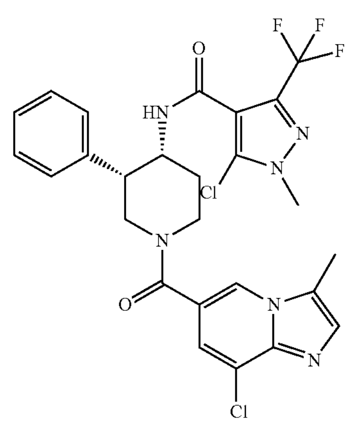 [SMILES: Cc1cnc2c(Cl)cc(C(=O)N3CC[C@@H](NC(=O)c4c(C(F)(F)F)nn(C)c4Cl)[C@@H](c4ccccc4)C3)cn12] | | 579.1 |

TABLE 2-1-continued

| Ex. No. | IUPAC Name | Structure | Salt | MS |
|---|---|---|---|---|
| 339B | 5-chloro-N-((3S,4R)-1-((3,8-dimethylimidazo[1,2-a]pyridin-6-yl)carbonyl)-3-phenylpiperidin-4-yl)-1-methyl-3-(trifluoromethyl)-1H-pyrazole-4-carboxamide | 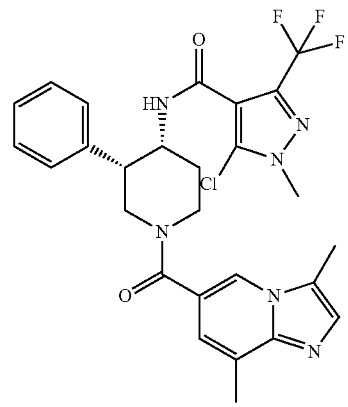 [SMILES: Cc1cc(C(=O)N2CC[C@@H](NC(=O)c3c(C(F)(F)F)nn(C)c3Cl)[C@@H](c3ccccc3)C2)cn2c(C)cnc12] | | 559.2 |
| 340B | 5-chloro-1-methyl-N-((3S,4R)-1-((8-methoxyquinoxalin-6-yl)carbonyl)-3-phenylpiperidin-4-yl)-3-(trifluoromethyl)-1H-pyrazole-4-carboxamide | 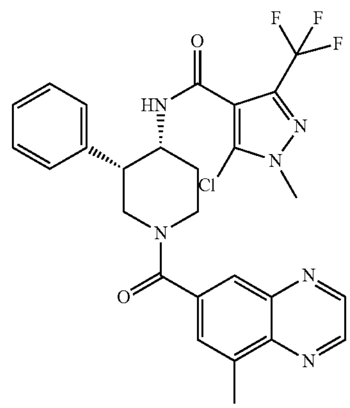 [SMILES: Cc1cc(C(=O)N2CC[C@@H](NC(=O)c3c(C(F)(F)F)nn(C)c3Cl)[C@@H](c3ccccc3)C2)cc2nccnc12] | | 557.2 |
| 341B | 5-chloro-1,3-dimethyl-N-((3S,4R)-1-((8-methylquinoxalin-6-yl)carbonyl)-3-phenylpiperidin-4-yl)-1H-pyrazole-4-carboxamide | 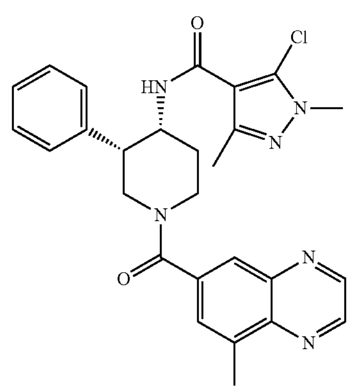 [SMILES: Cc1nn(C)c(Cl)c1C(=O)N[C@@H]1CCN(C(=O)c2cc(C)c3nccnc3c2)C[C@@H]1c1ccccc1] | | 503.2 |
| 342B | 5-chloro-N-((3S,4R)-1-((8-chloro-3-methylimidazo[1,2-a]pyridin-6-yl)carbonyl)-3-phenylpiperidin-4-yl)-1,3-dimethyl-1H-pyrazole-4-carboxamide | 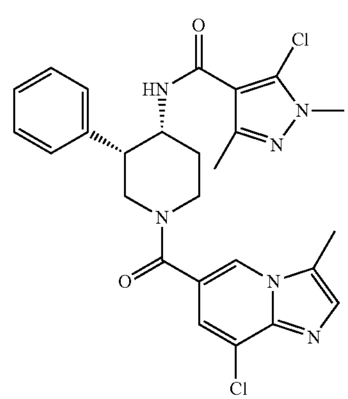 [SMILES: Cc1nn(C)c(Cl)c1C(=O)N[C@@H]1CCN(C(=O)c2cc(Cl)c3ncc(C)n3c2)C[C@@H]1c1ccccc1] | | 525.2 |

TABLE 2-1-continued

| Ex. No. | IUPAC Name | Structure | Salt | MS |
|---|---|---|---|---|
| 343B | 5-chloro-N-((3S,4R)-1-((2-methoxy-1,4-dimethyl-1H-benzimidazol-6-yl)carbonyl)-3-phenylpiperidin-4-yl)-1,3-dimethyl-1H-pyrazole-4-carboxamide | 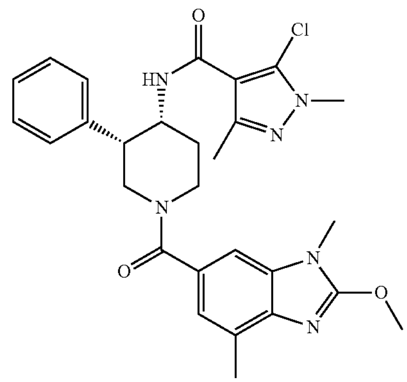 [SMILES: COc1nc2c(C)cc(C(=O)N3CC[C@@H](NC(=O)c4c(C)nn(C)c4Cl)[C@@H](c4ccccc4)C3)cc2n1C] | | 535.2 |
| 344B | 5-chloro-N-((3S,4R)-1-((3,8-dimethylimidazo[1,2-a]pyridin-6-yl)carbonyl)-3-phenylpiperidin-4-yl)-1,3-dimethyl-1H-pyrazole-4-carboxamide | 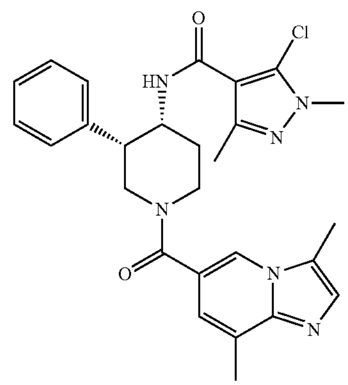 [SMILES: Cc1nn(C)c(Cl)c1C(=O)N[C@@H]1CCN(C(=O)c2cc(C)c3ncc(C)n3c2)C[C@@H]1c1ccccc1] | | 505.2 |
| 345B | 5-chloro-N-((3S,4R)-1-((8-methoxyquinoxalin-6-yl)carbonyl)-3-phenylpiperidin-4-yl)-1,3-dimethyl-1H-pyrazole-4-carboxamide | 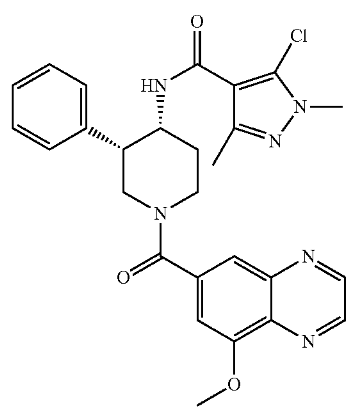 [SMILES: COc1cc(C(=O)N2CC[C@@H](NC(=O)c3c(C)nn(C)c3Cl)[C@@H](c3ccccc3)C2)cc2nccnc12] | | 519.1 |
| 346B | N-((3S,4R)-1-((8-methoxyquinoxalin-6-yl)carbonyl)-3-phenylpiperidin-4-yl)-1-methyl-5-(trifluoromethyl)-1H-pyrazole-4-carboxamide | 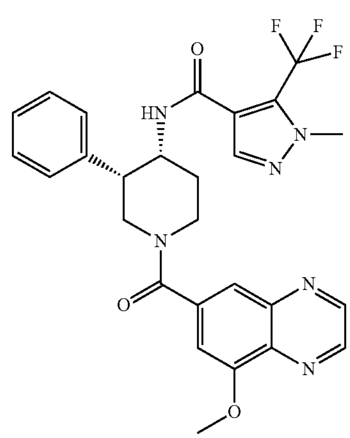 [SMILES: COc1cc(C(=O)N2CC[C@@H](NC(=O)c3cnn(C)c3C(F)(F)F)[C@@H](c3ccccc3)C2)cc2nccnc12] | | 539.2 |

TABLE 2-1-continued

| Ex. No. | IUPAC Name | Structure | Salt | MS |
|---|---|---|---|---|
| 347B | N-((3S,4R)-1-((8-chloro-3-methylimidazo[1,2-a]pyridin-6-yl)carbonyl)-3-phenylpiperidin-4-yl)-1-methyl-5-(trifluoromethyl)-1H-pyrazole-4-carboxamide | 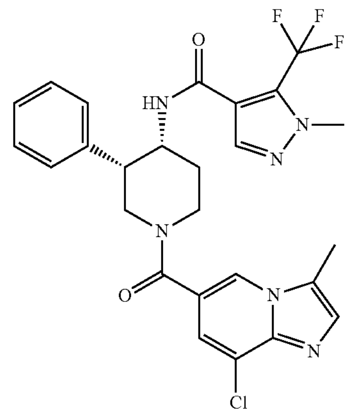 [SMILES: Cc1cnc2c(Cl)cc(C(=O)N3CC[C@@H](NC(=O)c4cnn(C)c4C(F)(F)F)[C@@H](c4ccccc4)C3)cn12] | | 545.1 |
| 348B | N-((3S,4R)-1-((2-methoxy-1,4-dimethyl-1H-benzimidazol-6-yl)carbonyl)-3-phenylpiperidin-4-yl)-1-methyl-5-(trifluoromethyl)-1H-pyrazole-4-carboxamide | 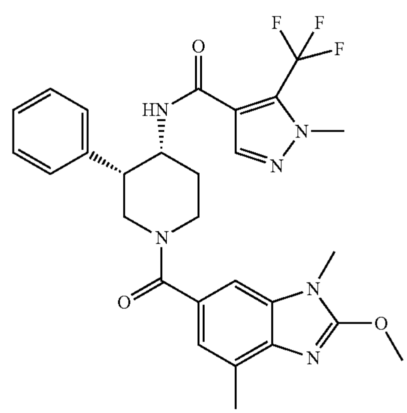 [SMILES: COc1nc2c(C)cc(C(=O)N3CC[C@@H](NC(=O)c4cnn(C)c4C(F)(F)F)[C@@H](c4ccccc4)C3)cc2n1C] | | 555.2 |
| 349B | 1-methyl-N-((3S,4R)-1-((8-methylquinoxalin-6-yl)carbonyl)-3-phenylpiperidin-4-yl)-5-(trifluoromethyl)-1H-pyrazole-4-carboxamide | 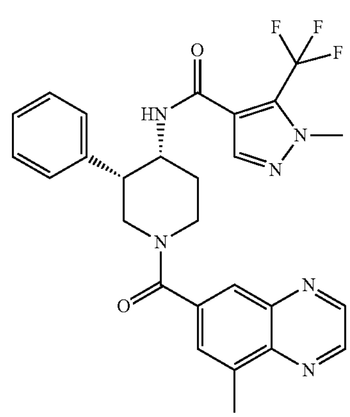 [SMILES: Cc1cc(C(=O)N2CC[C@@H](NC(=O)c3cnn(C)c3C(F)(F)F)[C@@H](c3ccccc3)C2)cc2nccnc12] | | 523.2 |

TABLE 2-1-continued

| Ex. No. | IUPAC Name | Structure | Salt | MS |
|---|---|---|---|---|
| 350B | N-((3S,4R)-1-((1,4-dimethyl-1H-benzimidazol-6-yl)carbonyl)-3-phenylpiperidin-4-yl)-1-methyl-5-(trifluoromethyl)-1H-pyrazole-4-carboxamide | 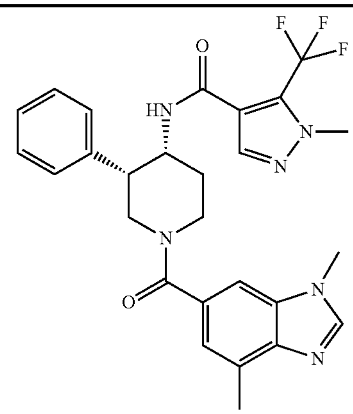 | | 525.2 |
| 351B | N-((3S,4R)-3-(4-fluorophenyl)-1-((2-methoxy-1,4-dimethyl-1H-benzimidazol-6-yl)carbonyl)piperidin-4-yl)-1-methyl-3-(trifluoromethyl)-1H-pyrazole-5-carboxamide | 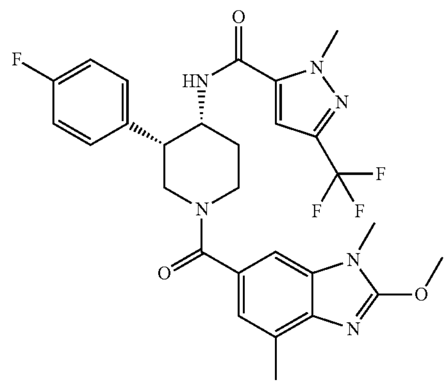 [SMILES: COc1nc2c(C)cc(C(=O)N3CC[C@@H](NC(=O)c4cc(C(F)(F)F)nn4C)[C@@H](c4ccc(F)cc4)C3)cc2n1C] | | 573.2 |
| 352B | N-((3S,4R)-3-(4-fluorophenyl)-1-((8-methoxyquinoxalin-6-yl)carbonyl)piperidin-4-yl)-1-methyl-3-(trifluoromethyl)-1H-pyrazole-5-carboxamide | 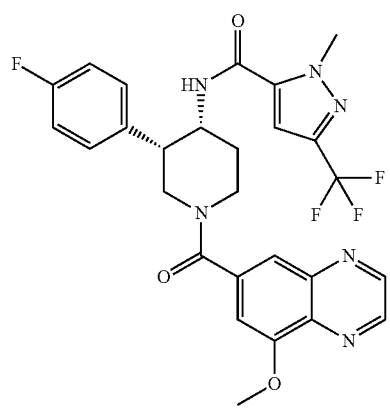 [SMILES: COc1cc(C(=O)N2CC[C@@H](NC(=O)c3cc(C(F)(F)F)nn3C)[C@@H](c3ccc(F)cc3)C2)cc2nccnc12] | | 557.2 |
| 353B | N-((3S,4R)-3-(4-fluorophenyl)-1-((4-methoxy-1-methyl-1H-benzimidazol-6-yl)carbonyl)piperidin-4-yl)-1-methyl-3-(trifluoromethyl)-1H-pyrazole-5-carboxamide | 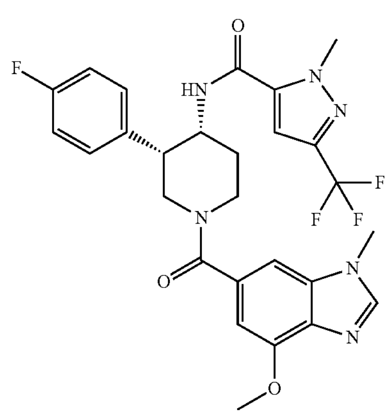 [SMILES: COc1cc(C(=O)N2CC[C@@H](NC(=O)c3cc(C(F)(F)F)nn3C)[C@@H](c3ccc(F)cc3)C2)cc2c1ncn2C] | | 559.2 |

TABLE 2-1-continued

| Ex. No. | IUPAC Name | Structure | Salt | MS |
|---|---|---|---|---|
| 354B | N-((3S,4R)-1-((8-chloroquinoxalin-6-yl)carbonyl)-3-(4-fluorophenyl)piperidin-4-yl)-3-(difluoromethoxy)pyridine-2-carboxamide | 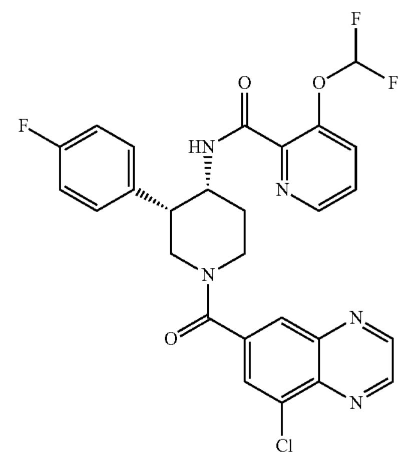 [SMILES: O=C(N[C@@H]1CCN(C(=O)c2cc(Cl)c3nccnc3c2)C[C@@H]1c1ccc(F)cc1)c1ncccc1OC(F)F] | | 556.2 |
| 355B | N-((3S,4R)-1-((8-chloroquinoxalin-6-yl)carbonyl)-3-(4-fluorophenyl)piperidin-4-yl)-3-ethoxy-1-methyl-1H-pyrazole-5-carboxamide | 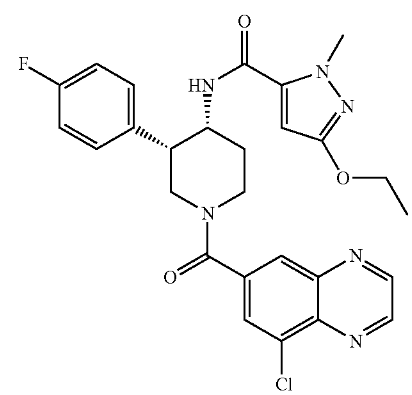 [SMILES: CCOc1cc(C(=O)N[C@@H]2CCN(C(=O)c3cc(Cl)c4nccnc4c3)C[C@@H]2c2ccc(F)cc2)n(C)n1] | | 537.1 |
| 356B | 2-(difluoromethoxy)-N-((3S,4S)-1-((5,6-dimethoxypyridin-3-yl)carbonyl)-3-(4-(trifluoromethyl)phenyl)piperidin-4-yl)benzamide | 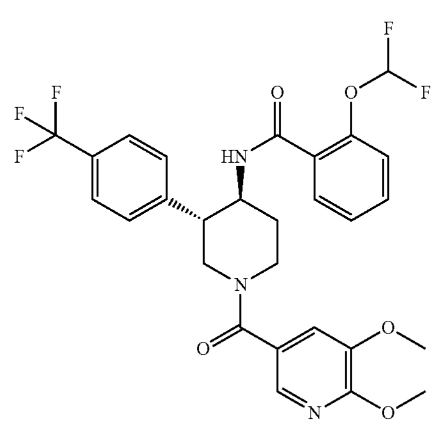 [SMILES: COc1cc(C(=O)N2CC[C@H](NC(=O)c3ccccc3OC(F)F)[C@@H](c3ccc(C(F)(F)F)cc3)C2)cnc1OC] | | 580.1 |

TABLE 2-1-continued

| Ex. No. | IUPAC Name | Structure | Salt | MS |
|---|---|---|---|---|
| 357B | 2-(difluoromethoxy)-N-((3R,4R)-1-((5,6-dimethoxypyridin-3-yl)carbonyl)-3-phenylpiperidin-4-yl)benzamide | 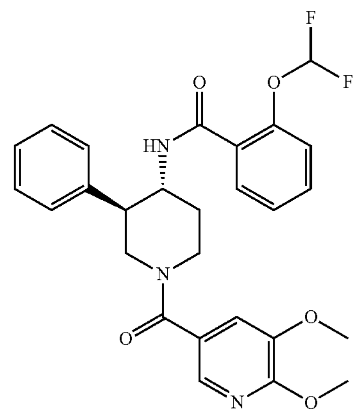 [SMILES: COc1cc(C(=O)N2CC[C@@H](NC(=O)c3ccccc3OC(F)F)[C@H](c3ccccc3)C2)cnc1OC] | | 512.2 |
| 358B | 2-(difluoromethoxy)-N-((3S,4S)-1-((5,6-dimethoxypyridin-3-yl)carbonyl)-3-(4-fluorophenyl)piperidin-4-yl)benzamide | 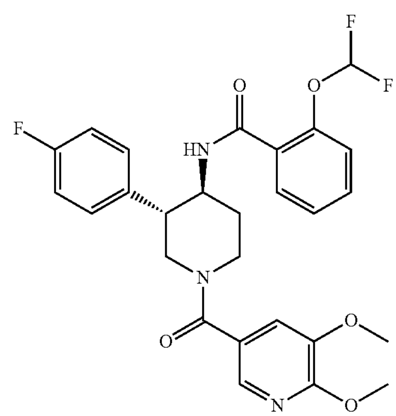 [SMILES: COc1cc(C(=O)N2CC[C@H](NC(=O)c3ccccc3OC(F)F)[C@@H](c3ccc(F)cc3)C2)cnc1OC] | | 530.2 |
| 359B | N-((3S,4S)-1-((5,6-dimethoxypyridin-3-yl)carbonyl)-3-(4-(trifluoromethyl)phenyl)piperidin-4-yl)-3-(trifluoromethyl)pyridine-2-carboxamide | 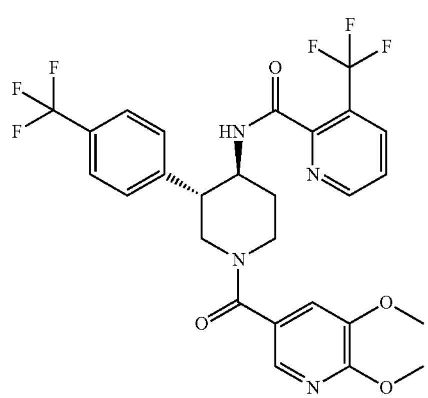 [SMILES: COc1cc(C(=O)N2CC[C@H](NC(=O)c3ncccc3C(F)(F)F)[C@@H](c3ccc(C(F)(F)F)cc3)C2)cnc1OC] | | 583.2 |

TABLE 2-1-continued

| Ex. No. | IUPAC Name | Structure | Salt | MS |
|---|---|---|---|---|
| 360B | 2-(difluoromethoxy)-N-((3R,4R)-1-((5,6-dimethoxypyridin-3-yl)carbonyl)-3-(4-(trifluoromethyl)phenyl)piperidin-4-yl)benzamide | 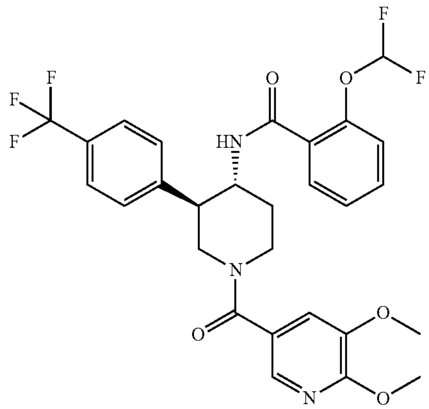 [SMILES: COc1cc(C(=O)N2CC[C@@H](NC(=O)c3ccccc3OC(F)F)[C@H](c3ccc(C(F)(F)F)cc3)C2)cnc1OC] | | 580.1 |
| 361B | 2-(difluoromethoxy)-N-((3R,4R)-1-((5,6-dimethoxypyridin-3-yl)carbonyl)-3-(4-fluorophenyl)piperidin-4-yl)benzamide | 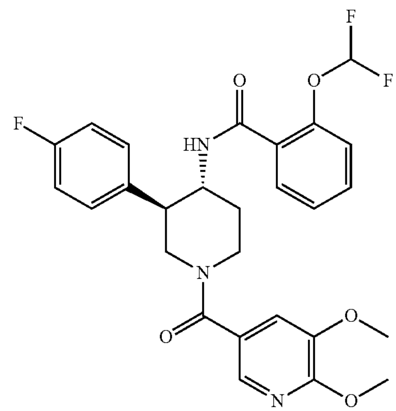 [SMILES: COc1cc(C(=O)N2CC[C@@H](NC(=O)c3ccccc3OC(F)F)[C@H](c3ccc(F)cc3)C2)cnc1OC] | | 530.2 |
| 362B | N-((3R,4R)-1-((5,6-dimethoxypyridin-3-yl)carbonyl)-3-(4-(trifluoromethyl)phenyl)piperidin-4-yl)-3-(trifluoromethyl)pyridine-2-carboxamide | 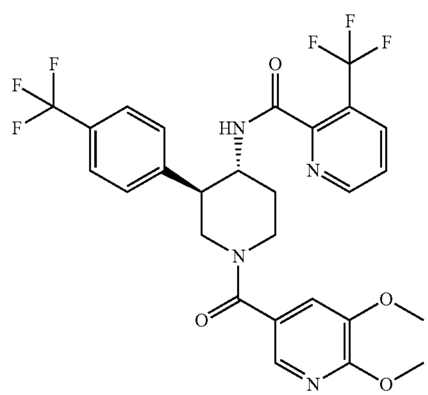 [SMILES: COc1cc(C(=O)N2CC[C@@H](NC(=O)c3ncccc3C(F)(F)F)[C@H](c3ccc(C(F)(F)F)cc3)C2)cnc1OC] | | 583.2 |
| 363B | N-((3S,4R)-1-((8-chloroquinoxalin-6-yl)carbonyl)-3-(4-fluorophenyl)piperidin-4-yl)-3-(difluoromethoxy)-1,4-dimethyl-1H-pyrazole-5-carboxamide | 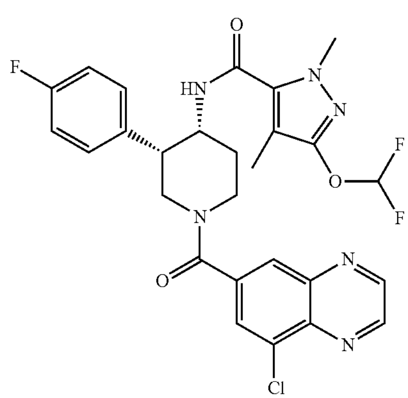 [SMILES: Cc1c(OC(F)F)nn(C)c1C(=O)N[C@@H]1CCN(C(=O)c2cc(Cl)c3nccnc3c2)C[C@@H]1c1ccc(F)cc1] | | 573.2 |

TABLE 2-1-continued

| Ex. No. | IUPAC Name | Structure | Salt | MS |
|---|---|---|---|---|
| 364B | N-((3S,4R)-1-((8-chloroquinoxalin-6-yl)carbonyl)-3-(4-fluorophenyl)piperidin-4-yl)-3-cyclopropylpyridine-2-carboxamide | 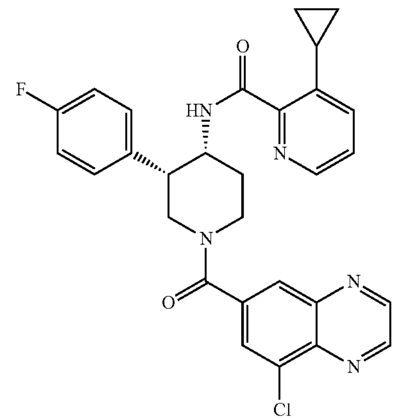 [SMILES: O=C(N[C@@H]1CCN(C(=O)c2cc(Cl)c3nccnc3c2)C[C@@H]1c1ccc(F)cc1)c1ncccc1C1CC1] | | 530.1 |
| 365B | 2-(difluoromethoxy)-N-((3S,4S)-1-((5,6-dimethoxypyridn-3-yl)carbonyl)-3-phenylpiperidin-4-yl)benzamide | 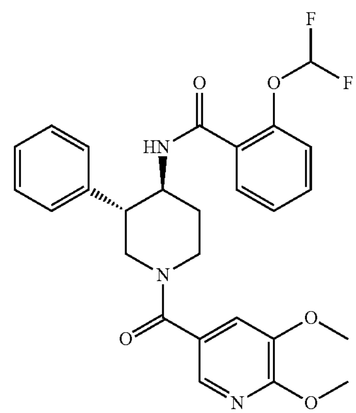 [SMILES: COc1cc(C(=O)N2CC[C@H](NC(=O)c3ccccc3OC(F)F)[C@@H](c3ccccc3)C2)cnc1OC] | | 512.2 |
| 366B | N-((3S,4R)-1-((4-methoxy-1-methyl-1H-benzimidazol-6-yl)carbonyl)-3-phenylpiperidin-4-yl)-3-(trifluoromethyl)pyridine-2-carboxamide | 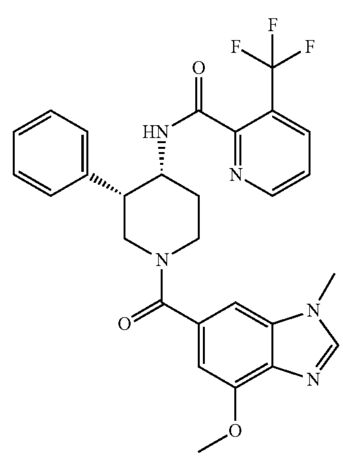 [SMILES: COc1cc(C(=O)N2CC[C@@H](NC(=O)c3ncccc3C(F)(F)F)[C@@H](c3ccccc3)C2)cc2c1ncn2C] | | 538.2 |

TABLE 2-1-continued

| Ex. No. | IUPAC Name | Structure | Salt | MS |
|---|---|---|---|---|
| 367B | 3-cyclopropyl-N-((3S,4R)-1-((4-methoxy-1-methyl-1H-benzimidazol-6-yl)carbonyl)-3-phenylpiperidin-4-yl)pyridine-2-carboxamide | 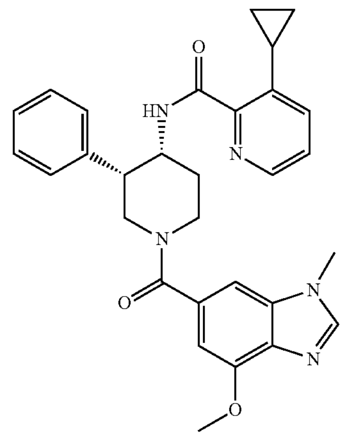 [SMILES: COc1cc(C(=O)N2CC[C@@H](NC(=O)c3ncccc3C3CC3)[C@@H](c3ccccc3)C2)cc2c1ncn2C] | | 510.2 |
| 368B | N-((3S,4R)-1-((8-chloro-3-methylimidazo[1,2-a]pyridin-6-yl)carbonyl)-3-phenylpiperidin-4-yl)-3-cyclopropylpyridine-2-carboxamide | 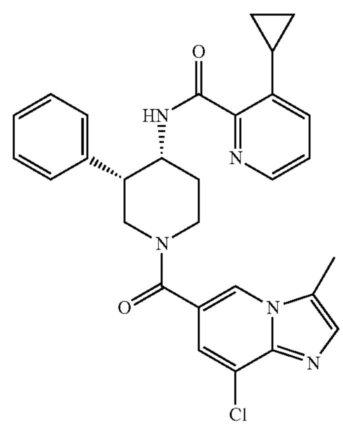 [SMILES: Cc1cnc2c(Cl)cc(C(=O)N3CC[C@@H](NC(=O)c4ncccc4C4CC4)[C@@H](c4ccccc4)C3)cn12] | | 514.1 |
| 369B | N-((3S,4R)-1-((2-methoxy-1,4-dimethyl-1H-benzimidazol-6-yl)carbonyl)-3-phenylpiperidin-4-yl)-1,3-dimethyl-1H-pyrazole-5-carboxamide | 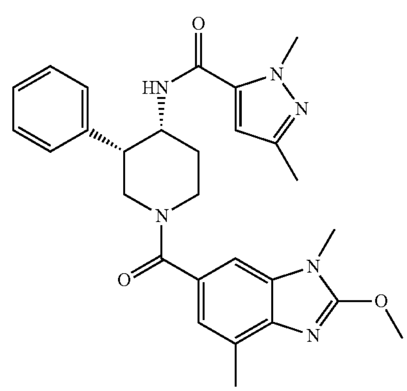 [SMILES: COc1nc2c(C)cc(C(=O)N3CC[C@@H](NC(=O)c4cc(C)nn4C)[C@@H](c4ccccc4)C3)cc2n1C] | | 501.3 |

TABLE 2-1-continued

| Ex. No. | IUPAC Name | Structure | Salt | MS |
|---|---|---|---|---|
| 370B | N-((3S,4R)-1-((1,4-dimethyl-1H-benzimidazol-6-yl)carbonyl)-3-phenylpiperidin-4-yl)-1,3-dimethyl-1H-pyrazole-5-carboxamide | 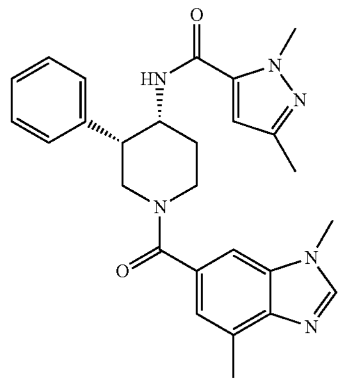 [SMILES: Cc1cc(C(=O)N[C@@H]2CCN(C(=O)c3cc(C)c4ncn(C)c4c3)C[C@@H]2c2ccccc2)n(C)n1] | | 471.3 |
| 371B | N-((3S,4R)-1-((4-methoxy-1-methyl-1H-benzimidazol-6-yl)carbonyl)-3-phenylpiperidin-4-yl)-1,3-dimethyl-1H-pyrazole-5-carboxamide | 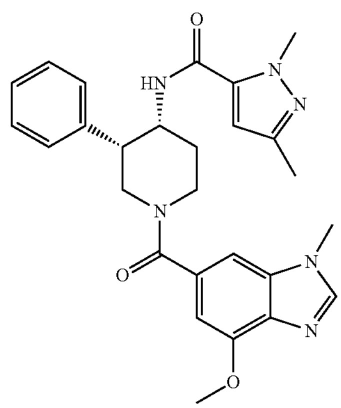 [SMILES: COc1cc(C(=O)N2CC[C@@H](NC(=O)c3cc(C)nn3C)[C@@H](c3ccccc3)C2)cc2c1ncn2C] | | 487.2 |
| 372B | N-((3S,4R)-1-((4-chloro-1-methyl-1H-benzimidazol-6-yl)carbonyl)-3-phenylpiperidin-4-yl)-1,3-dimethyl-1H-pyrazole-5-carboxamide | 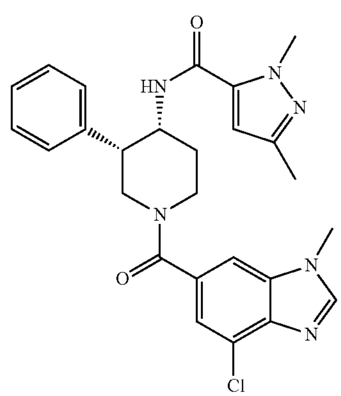 [SMILES: Cc1cc(C(=O)N[C@@H]2CCN(C(=O)c3cc(Cl)c4ncn(C)c4c3)C[C@@H]2c2ccccc2)n(C)n1] | | 491.2 |
| 373B | 1-(2,2-difluoroethyl)-N-((3S,4R)-1-((3,8-dimethylimidazo[1,2-a]pyridin-6-yl)carbonyl)-3-phenylpiperidin-4-yl)-3-methyl-1H-pyrazole-5-carboxamide | 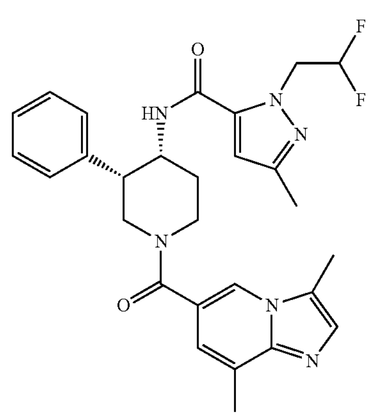 [SMILES: Cc1cc(C(=O)N[C@@H]2CCN(C(=O)c3cc(C)c4ncc(C)n4c3)C[C@@H]2c2ccccc2)n(CC(F)F)n1] | | 521.2 |

TABLE 2-1-continued

| Ex. No. | IUPAC Name | Structure | Salt | MS |
|---|---|---|---|---|
| 374B | 1-(2,2-difluoroethyl)-N-((3S,4R)-1-((4-methoxy-1-methyl-1H-benzimidazol-6-yl)carbonyl)-3-phenylpiperidin-4-yl)-3-methyl-1H-pyrazole-5-carboxamide | 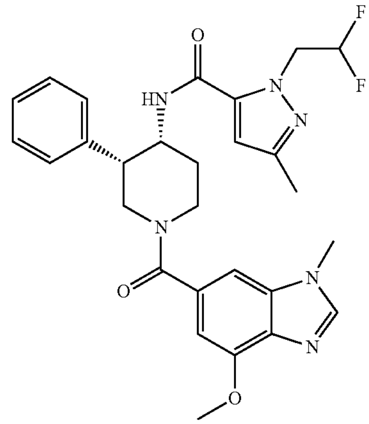 [SMILES: COc1cc(C(=O)N2CC[C@@H](NC(=O)c3cc(C)nn3CC(F)F)[C@@H](c3ccccc3)C2)cc2c1ncn2C] | | 537.2 |
| 375B | N-((3S,4R)-1-((8-chloro-3-methylimidazo[1,2-a]pyridin-6-yl)carbonyl)-3-phenylpiperidin-4-yl)-1-(2,2-difluoroethyl)-3-methyl-1H-pyrazole-5-carboxamide | 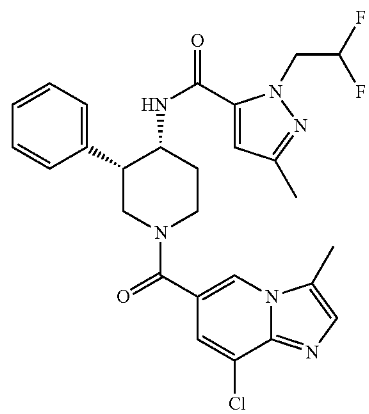 [SMILES: Cc1cc(C(=O)N[C@@H]2CCN(C(=O)c3cc(Cl)c4ncc(C)n4c3)C[C@@H]2c2ccccc2)n(CC(F)F)n1] | | 541.3 |
| 376B | N-((3S,4R)-1-((4-methoxy-1-methyl-1H-benzimidazol-6-yl)carbonyl)-3-phenylpiperidin-4-yl)-1-methyl-3-(trifluoromethyl)-1H-pyrazole-5-carboxamide | 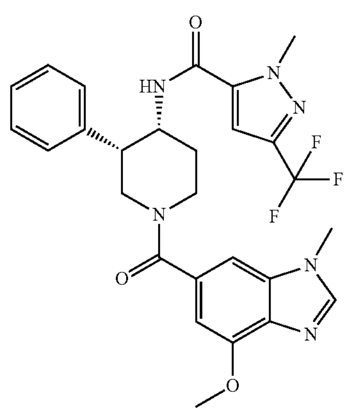 [SMILES: COc1cc(C(=O)N2CC[C@@H](NC(=O)c3cc(C(F)(F)F)nn3C)[C@@H](c3ccccc3)C2)cc2c1ncn2C] | | 541.3 |

TABLE 2-1-continued

| Ex. No. | IUPAC Name | Structure | Salt | MS |
|---|---|---|---|---|
| 377B | 3-ethoxy-N-((3S,4R)-1-((4-methoxy-1-methyl-1H-benzimidazol-6-yl)carbonyl)-3-phenylpiperidin-4-yl)-1-methyl-1H-pyrazole-5-carboxamide | 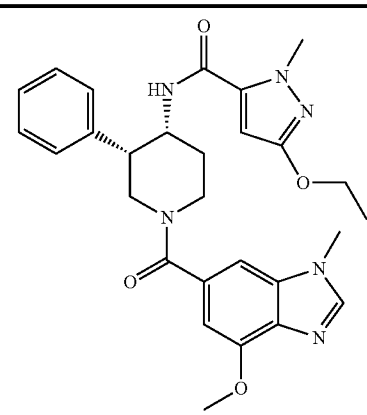 | | 517.2 |
| 378B | N-((3S,4R)-1-((4-chloro-1-methyl-1H-benzimidazol-6-yl)carbonyl)-3-phenylpiperidin-4-yl)-3-ethoxy-1-methyl-1H-pyrazole-5-carboxamide | 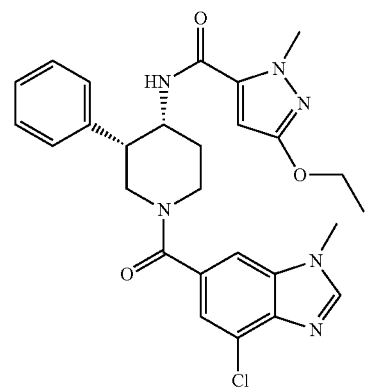 [SMILES: CCOc1cc(C(=O)N[C@@H]2CCN(C(=O)c3cc(Cl)c4ncn(C)c4c3)C[C@@H]2c2ccccc2)n(C)n1] | | 521.2 |
| 379B | N-((3S,4R)-1-((3,8-dimethylimidazo[1,2-a]pyridin-6-yl)carbonyl)-3-phenylpiperidin-4-yl)-3-ethoxy-1-methyl-1H-pyrazole-5-carboxamide | 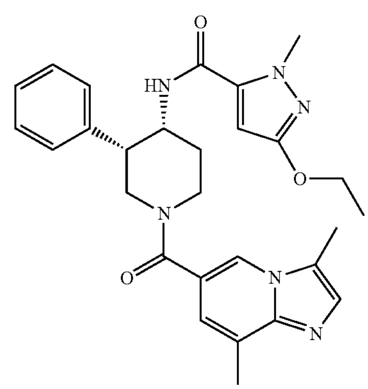 [SMILES: CCOc1cc(C(=O)N[C@@H]2CCN(C(=O)c3cc(C)c4ncc(C)n4c3)C[C@@H]2c2ccccc2)n(C)n1] | | 501.3 |
| 380B | N-((3S,4R)-1-((4-chloro-1-methyl-1H-benzimidazol-6-yl)carbonyl)-3-phenylpiperidin-4-yl)-3-methoxy-1-methyl-1H-pyrazole-5-carboxamide | 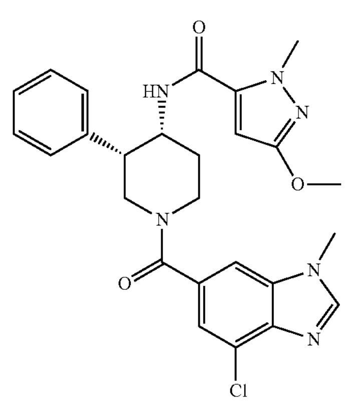 [SMILES: COc1cc(C(=O)N[C@@H]2CCN(C(=O)c3cc(Cl)c4ncn(C)c4c3)C[C@@H]2c2ccccc2)n(C)n1] | | 507.2 |

| Ex. No. | IUPAC Name | Structure | Salt | MS |
|---|---|---|---|---|
| 381B | 3-methoxy-N-((3S,4R)-1-((2-methoxy-1,4-dimethyl-1H-benzimidazol-6-yl)carbonyl)-3-phenylpiperidin-4-yl)-1-methyl-1H-pyrazole-5-carboxamide | 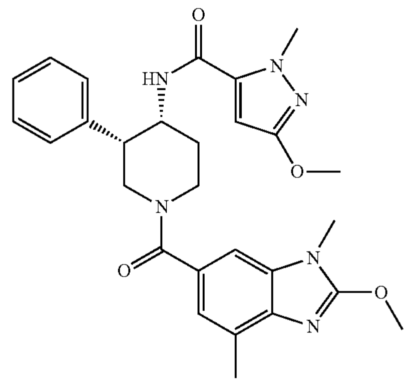 [SMILES: COc1cc(C(=O)N[C@@H]2CCN(C(=O)c3cc(C)c4nc(OC)n(C)c4c3)C[C@@H]2c2ccccc2)n(C)n1] | | 517.2 |
| 382B | N-((3S,4R)-1-((3,8-dimethylimidazo[1,2-a]pyridin-6-yl)carbonyl)-3-phenylpiperidin-4-yl)-3-methoxy-1-methyl-1H-pyrazole-5-carboxamide | 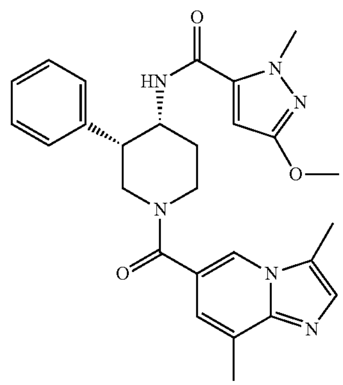 [SMILES: COc1cc(C(=O)N[C@@H]2CCN(C(=O)c3cc(C)c4ncc(C)n4c3)C[C@@H]2c2ccccc2)n(C)n1] | | 487.2 |
| 383B | 3-methoxy-N-((3S,4R)-1-((4-methoxy-1-methyl-1H-benzimidazol-6-yl)carbonyl)-3-phenylpiperidin-4-yl)-1-methyl-1H-pyrazole-5-carboxamide | 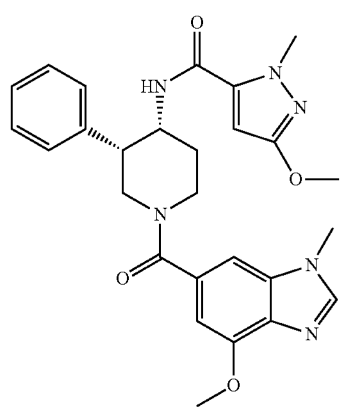 [SMILES: COc1cc(C(=O)N[C@@H]2CCN(C(=O)c3cc(OC)c4ncn(C)c4c3)C[C@@H]2c2ccccc2)n(C)n1] | | 503.2 |
| 384B | 3-(difluoromethoxy)-N-((3S,4R)-1-((4-methoxy-1-methyl-1H-benzimidazol-6-yl)carbonyl)-3-phenylpiperidin-4-yl)-1-methyl-1H-pyrazole-5-carboxamide | 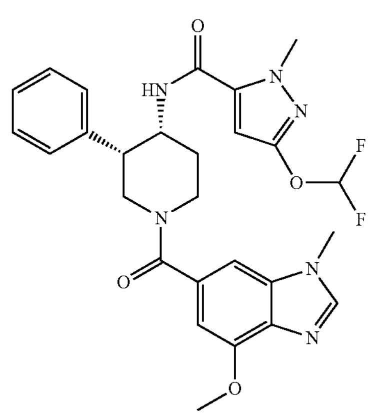 [SMILES: COc1cc(C(=O)N2CC[C@@H](NC(=O)c3cc(OC(F)F)nn3C)[C@@H](c3ccccc3)C2)cc2c1ncn2C] | | 539.2 |

TABLE 2-1-continued

| Ex. No. | IUPAC Name | Structure | Salt | MS |
|---|---|---|---|---|
| 385B | 3-(difluoromethoxy)-N-((3S,4R)-1-((3,8-dimethylimidazo[1,2-a]pyridin-6-yl)carbonyl)-3-phenylpiperidin-4-yl)-1-methyl-1H-pyrazole-5-carboxamide | 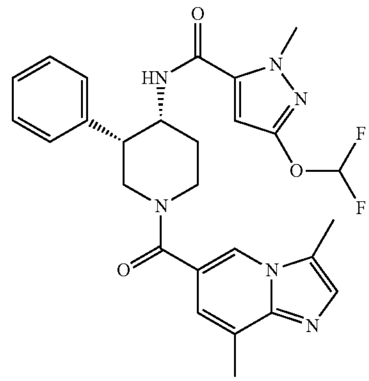 [SMILES: Cc1cc(C(=O)N2CC[C@@H](NC(=O)c3cc(OC(F)F)nn3C)[C@@H](c3ccccc3)C2)cn2c(C)cnc12] | | 523.2 |
| 386B | 3-(difluoromethoxy)-N-((3S,4R)-1-((2-methoxy-1,4-dimethyl-1H-benzimidazol-6-yl)carbonyl)-3-phenylpiperidin-4-yl)-1,4-dimethyl-1H-pyrazole-5-carboxamide | 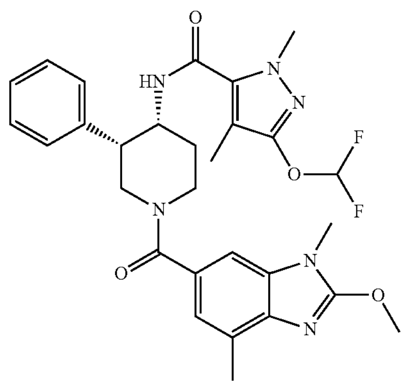 [SMILES: COc1nc2c(C)cc(C(=O)N3CC[C@@H](NC(=O)c4c(C)c(OC(F)F)nn4C)[C@@H](c4ccccc4)C3)cc2n1C] | | 567.3 |
| 387B | N-((3S,4R)-1-((4-chloro-1-methyl-1H-benzimidazol-6-yl)carbonyl)-3-phenylpiperidin-4-yl)-3-(difluoromethoxy)-1,4-dimethyl-1H-pyrazole-5-carboxamide | 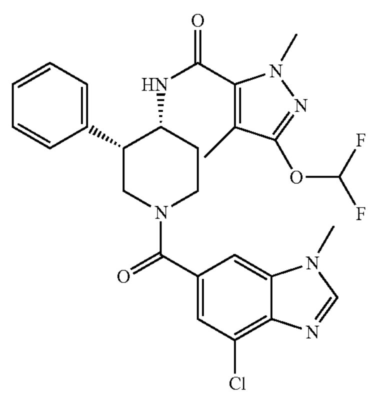 [SMILES: Cc1c(OC(F)F)nn(C)c1C(=O)N[C@@H]1CCN(C(=O)c2cc(Cl)c3ncn(C)c3c2)C[C@@H]1c1ccccc1] | | 557.2 |
| 388B | N-((3S,4R)-1-((8-chloro-3-methylimidazo[1,2-a]pyridin-6-yl)carbonyl)-3-phenylpiperidin-4-yl)-1,3,4-trimethyl-1H-pyrazole-5-carboxamide | 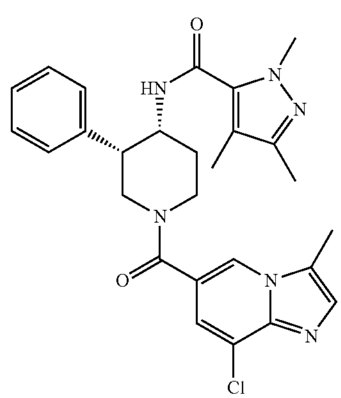 [SMILES: Cc1nn(C)c(C(=O)N[C@@H]2CCN(C(=O)c3cc(Cl)c4ncc(C)n4c3)C[C@@H]2c2ccccc2)c1C] | | 505.2 |

TABLE 2-1-continued

| Ex. No. | IUPAC Name | Structure | Salt | MS |
|---|---|---|---|---|
| 389B | N-((3S,4R)-1-((4-methoxy-1-methyl-1H-benzimidazol-6-yl)carbonyl)-3-phenylpiperidin-4-yl)-1,3,4-trimethyl-1H-pyrazole-5-carboxamide | 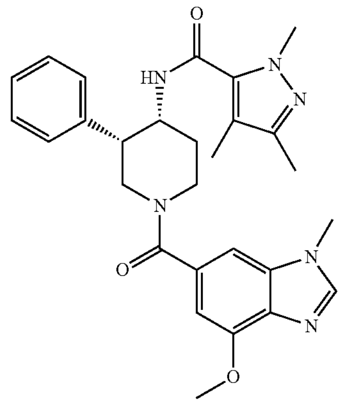 [SMILES: COc1cc(C(=O)N2CC[C@@H](NC(=O)c3c(C)c(C)nn3C)[C@@H](c3ccccc3)C2)cc2c1ncn2C] | | 501.3 |
| 390B | N-((3S,4R)-1-((2-methoxy-1,4-dimethyl-1H-benzimidazol-6-yl)carbonyl)-3-phenylpiperidin-4-yl)-1,3,4-trimethyl-1H-pyrazole-5-carboxamide | 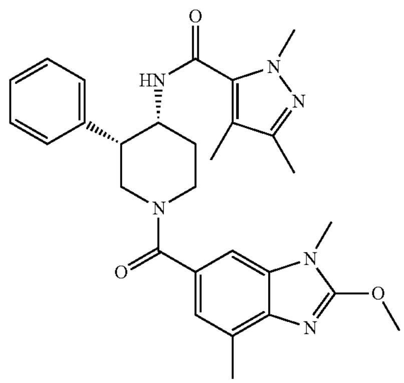 [SMILES: COc1nc2c(C)cc(C(=O)N3CC[C@@H](NC(=O)c4c(C)c(C)nn4C)[C@@H](c4ccccc4)C3)cc2n1C] | | 515.2 |
| 391B | 1,3-dimethyl-N-((3S,4R)-1-((8-methylquinoxalin-6-yl)carbonyl)-3-phenylpiperidin-4-yl)-4-(trifluoromethyl)-1H-pyrazole-5-carboxamide | 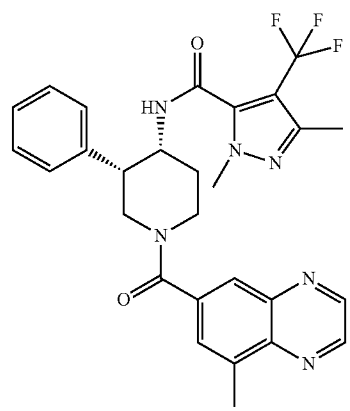 [SMILES: Cc1nn(C)c(C(=O)N[C@@H]2CCN(C(=O)c3cc(C)c4nccnc4c3)C[C@@H]2c2ccccc2)c1C(F)(F)F] | | 537.2 |
| 392B | N-((3S,4R)-1-((4-chloro-1-methyl-1H-benzimidazol-6-yl)carbonyl)-3-phenylpiperidin-4-yl)-1,3-dimethyl-4-(trifluoromethyl)-1H-pyrazole-5-carboxamide | 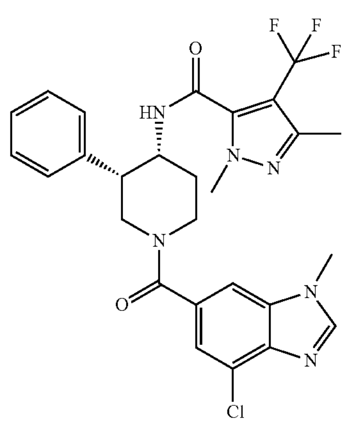 [SMILES: Cc1nn(C)c(C(=O)N[C@@H]2CCN(C(=O)c3cc(Cl)c4ncn(C)c4c3)C[C@@H]2c2ccccc2)c1C(F)(F)F] | | 559.2 |

TABLE 2-1-continued

| Ex. No. | IUPAC Name | Structure | Salt | MS |
|---|---|---|---|---|
| 393B | N-((3S,4R)-1-((4-methoxy-1-methyl-1H-benzimidazol-6-yl)carbonyl)-3-phenylpiperidin-4-yl)-1,3-dimethyl-4-(trifluoromethyl)-1H-pyrazole-5-carboxamide | 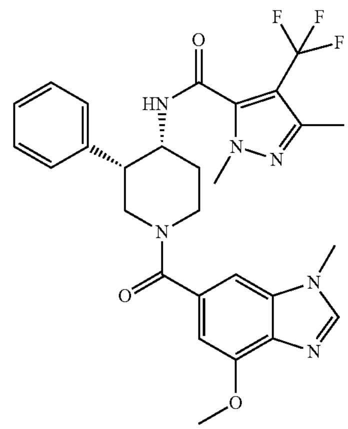 [SMILES: COc1cc(C(=O)N2CC[C@@H](NC(=O)c3c(C(F)(F)F)c(C)nn3C)[C@@H](c3ccccc3)C2)cc2c1ncn2C] | | 555.2 |
| 394B | 5-chloro-N-((3S,4R)-1-((4-methoxy-1-methyl-1H-benzimidazol-6-yl)carbonyl)-3-phenylpiperidin-4-yl)-1-methyl-3-(trifluoromethyl)-1H-pyrazole-4-carboxamide | 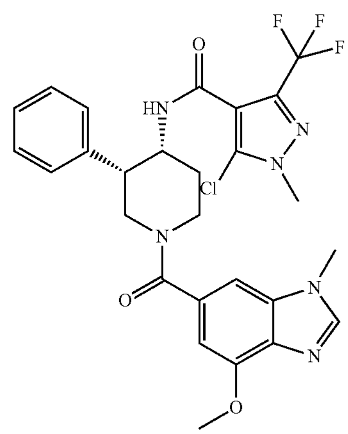 [SMILES: COc1cc(C(=O)N2CC[C@@H](NC(=O)c3c(C(F)(F)F)nn(C)c3Cl)[C@@H](c3ccccc3)C2)cc2c1ncn2C] | | 575.2 |
| 395B | 5-chloro-N-((3S,4R)-1-((4-chloro-1-methyl-1H-benzimidazol-6-yl)carbonyl)-3-phenylpiperidin-4-yl)-1,3-dimethyl-1H-pyrazole-4-carboxamide | 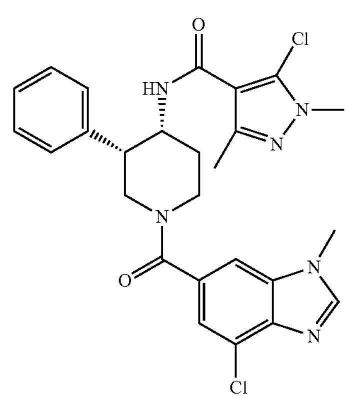 [SMILES: Cc1nn(C)c(Cl)c1C(=O)N[C@@H]1CCN(C(=O)c2cc(Cl)c3ncn(C)c3c2)C[C@@H]1c1ccccc1] | | 525.2 |

TABLE 2-1-continued

| Ex. No. | IUPAC Name | Structure | Salt | MS |
|---|---|---|---|---|
| 396B | 5-chloro-N-((3S,4R)-1-((4-methoxy-1-methyl-1H-benzimidazol-6-yl)carbonyl)-3-phenylpiperidin-4-yl)-1,3-dimethyl-1H-pyrazole-4-carboxamide | 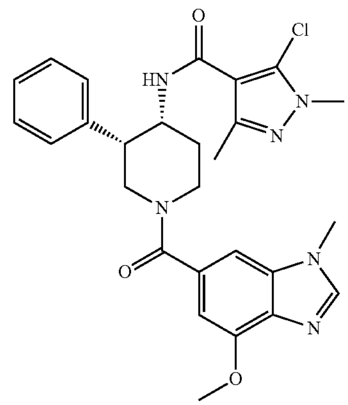 [SMILES: COc1cc(C(=O)N2CC[C@@H](NC(=O)c3c(C)nn(C)c3Cl)[C@@H](c3ccccc3)C2)cc2c1ncn2C] | | 521.2 |
| 397B | N-((3S,4R)-1-((4-methoxy-1-methyl-1H-benzimidazol-6-yl)carbonyl)-3-phenylpiperidin-4-yl)-1-methyl-5-(trifluoromethyl)-1H-pyrazole-4-carboxamide | 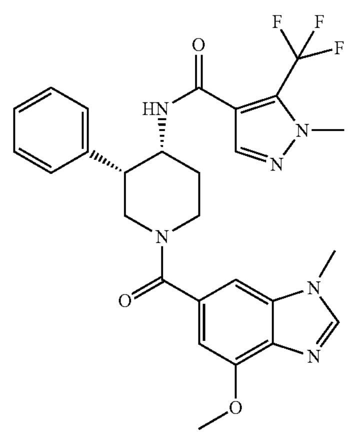 [SMILES: COc1cc(C(=O)N2CC[C@@H](NC(=O)c3cnn(C)c3C(F)(F)F)[C@@H](c3ccccc3)C2)cc2c1ncn2C] | | 541.3 |
| 398B | N-((3S,4R)-1-((4-chloro-1-methyl-1H-benzimidazol-6-yl)carbonyl)-3-phenylpiperidin-4-yl)-1-methyl-5-(trifluoromethyl)-1H-pyrazole-4-carboxamide | 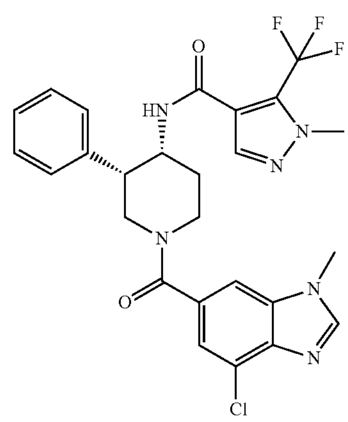 [SMILES: Cn1ncc(C(=O)N[C@@H]2CCN(C(=O)c3cc(Cl)c4ncn(C)c4c3)C[C@@H]2c2ccccc2)c1C(F)(F)F] | | 545.1 |

TABLE 2-1-continued

| Ex. No. | IUPAC Name | Structure | Salt | MS |
|---|---|---|---|---|
| 399B | N-((3R,4R)-1-((5,6-dimethoxypyridin-3-yl)carbonyl)-3-(4-trifluorophenyl)piperidin-4-yl)-3-(trifluoromethyl)pyridine-2-carboxamide | 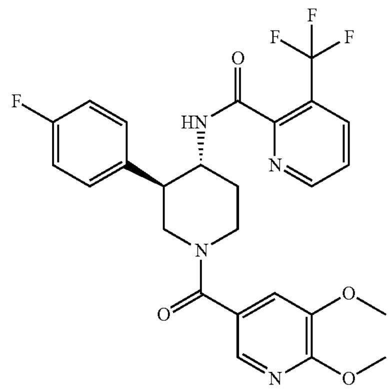 [SMILES: COc1cc(C(=O)N2CC[C@@H](NC(=O)c3ncccc3C(F)(F)F)[C@H](c3ccc(F)cc3)C2)cnc1OC] | | 533.2 |
| 400B | N-((3R,4R)-1-((5,6-dimethoxypyridin-3-yl)carbonyl)-3-(4-fluorophenyl)piperidin-4-yl)-1-methyl-3-(trifluoromethyl)-1H-pyrazole-5-carboxamide | 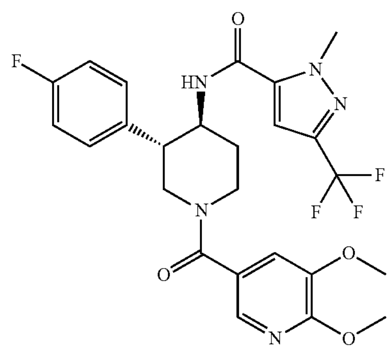 [SMILES: COc1cc(C(=O)N2CC[C@H](NC(=O)c3cc(C(F)(F)F)nn3C)[C@@H](c3ccc(F)cc3)C2)cnc1OC] | | 536.2 |
| 401B | N-((3S,4S)-1-((5,6-dimethoxypyridin-3-yl)carbonyl)-3-phenylpiperidin-4-yl)-3-(trifluoromethyl)pyridine-2-carboxamide | 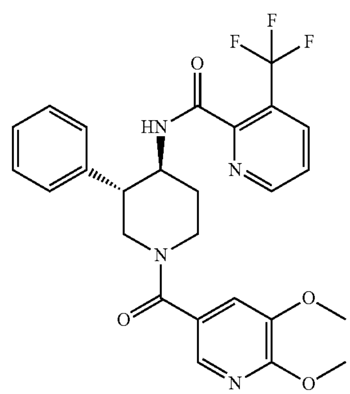 [SMILES: COc1cc(C(=O)N2CC[C@H](NC(=O)c3ncccc3C(F)(F)F)[C@@H](c3ccccc3)C2)cnc1OC] | | 515.2 |
| 402B | N-((3R,4R)-1-((5,6-dimethoxypyridin-3-yl)carbonyl)-3-(4-fluorophenyl)piperidin-4-yl)-methyl-3-(trifluoromethyl)-1H-pyrazole-5-carboxamide | 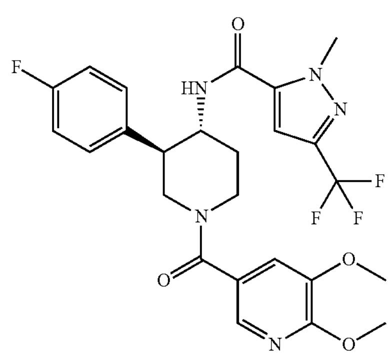 [SMILES: COc1cc(C(=O)N2CC[C@@H](NC(=O)c3cc(C(F)(F)F)nn3C)[C@H](c3ccc(F)cc3)C2)cnc1OC] | | 536.2 |

TABLE 2-1-continued

| Ex. No. | IUPAC Name | Structure | Salt | MS |
|---|---|---|---|---|
| 403B | N-((3R,4R)-1-((5,6-dimethoxypyridin-3-yl)carbonyl)-3-(4-(trifluoromethyl)phenyl)piperidin-4-yl)-1-methyl-3-(trifluoromethyl)-1H-pyrazole-5-carboxamide | 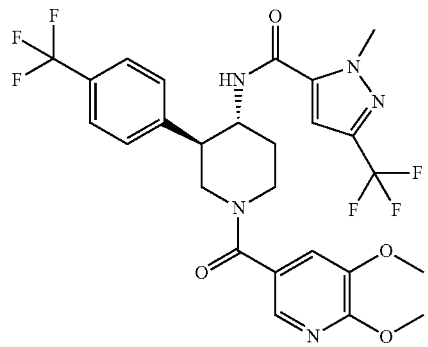 [SMILES: COc1cc(C(=O)N2CC[C@@H](NC(=O)c3cc(C(F)(F)F)nn3C)[C@H](c3ccc(C(F)(F)F)cc3)C2)cnc1OC] | | 586.1 |
| 404B | N-((3R,4R)-1-((5,6-dimethoxypyridin-3-yl)carbonyl)-3-phenylpiperidin-4-yl)-3-(trifluoromethyl)pyridine-2-carboxamide | 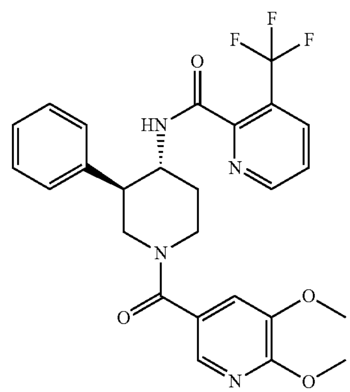 [SMILES: COc1cc(C(=O)N2CC[C@@H](NC(=O)c3ncccc3C(F)(F)F)[C@H](c3ccccc3)C2)cnc1OC] | | 515.2 |
| 405B | N-((3S,4R)-1-((8-chloroquinoxalin-6-yl)carbonyl)-3-(4-fluorophenyl)piperidin-4-yl)-5-(difluoromethoxy)-1,4-dimethyl-1H-pyrazole-3-carboxamide | 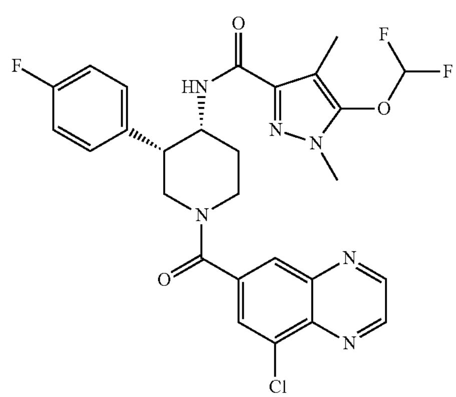 [SMILES: Cc1c(C(=O)N[C@@H]2CCN(C(=O)c3cc(Cl)c4nccnc4c3)C[C@@H]2c2ccc(F)cc2)nn(C)c1OC(F)F] | | 573.2 |
| 406B | N-((3S,4S)-1-((5,6-dimethoxypyridin-3-yl)carbonyl)-3-(4-fluorophenyl)piperidin-4-yl)-3-(trifluoromethyl)pyridine-2-carboxamide | 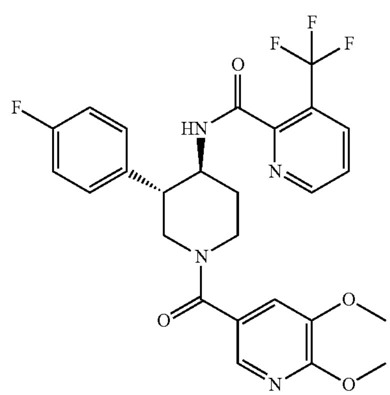 [SMILES: COc1cc(C(=O)N2CC[C@H](NC(=O)c3ncccc3C(F)(F)F)[C@@H](c3ccc(F)cc3)C2)cnc1OC] | | 533.2 |

TABLE 2-1-continued

| Ex. No. | IUPAC Name | Structure | Salt | MS |
|---|---|---|---|---|
| 407B | N-((3S,4S)-1-((5,6-dimethoxypyridin-3-yl)carbonyl)-3-phenylpiperidin-4-yl)-1-methyl-3-(trifluoromethyl)-1H-pyrazole-5-carboxamide | 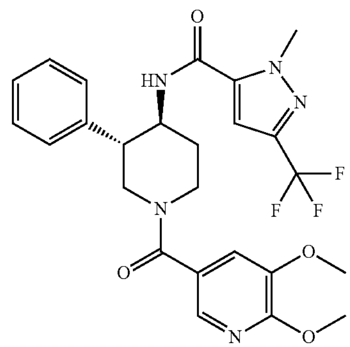 [SMILES: COc1cc(C(=O)N2CC[C@H](NC(=O)c3cc(C(F)(F)F)nn3C)[C@@H](c3ccccc3)C2)cnc1OC] | | 518.2 |
| 408B | N-((3S,4S)-1-((5,6-dimethoxypyridin-3-yl)carbonyl)-3-(4-(trifluoromethyl)phenyl)piperidin-4-yl)-1-methyl-3-(trifluoromethyl)-1H-pyrazole-5-carboxamide | 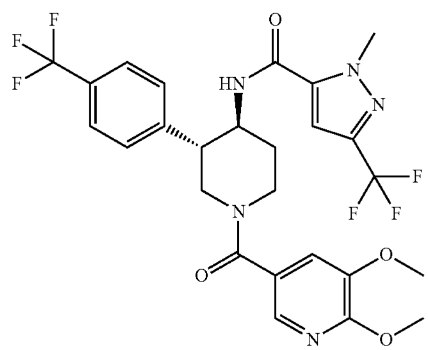 [SMILES: COc1cc(C(=O)N2CC[C@H](NC(=O)c3cc(C(F)(F)F)nn3C)[C@@H](c3ccc(C(F)(F)F)cc3)C2)cnc1OC] | | 586.1 |
| 409B | N-((3R,4R)-1-((5,6-dimethoxypyridin-3-yl)carbonyl)-3-phenylpiperidin-4-yl)-1-methyl-3-(trifluoromethyl)-1H-pyrazole-5-carboxamide | 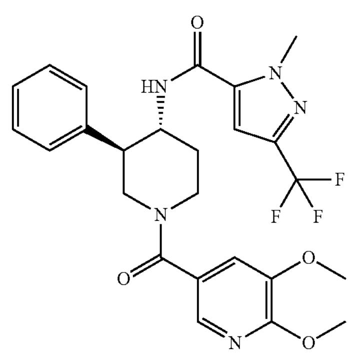 [SMILES: COc1cc(C(=O)N2CC[C@@H](NC(=O)c3cc(C(F)(F)F)nn3C)[C@H](c3ccccc3)C2)cnc1OC] | | 518.2 |
| 410B | N-((3S,4R)-1-((8-chloroquinoxalin-6-yl)carbonyl)-3-(4-fluorophenyl)piperidin-4-yl)-1,3,4-trimethyl-1H-pyrazole-5-carboxamide | 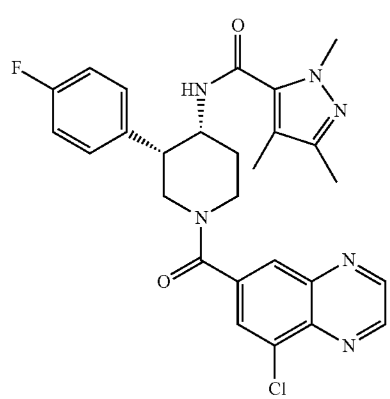 [SMILES: Cc1nn(C)c(C(=O)N[C@@H]2CCN(C(=O)c3cc(Cl)c4nccnc4c3)C[C@@H]2c2ccc(F)cc2)c1C] | | 521.2 |

TABLE 2-1-continued

| Ex. No. | IUPAC Name | Structure | Salt | MS |
|---|---|---|---|---|
| 411B | N-((3S,4R)-1-((8-chloroquinoxalin-6-yl)carbonyl)-3-(4-fluorophenyl)piperidin-4-yl)-1,3-dimethyl-5-(methylsulfonyl)-1H-pyrazole-4-carboxamide | 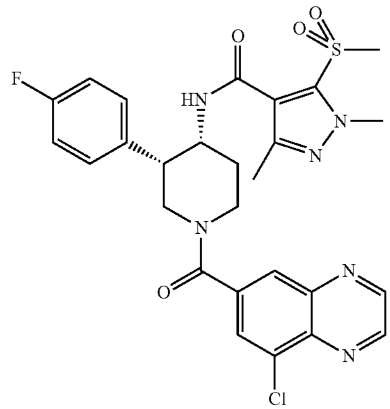 [SMILES: Cc1nn(C)c(S(C)(=O)=O)c1C(=O)N[C@@H]1CCN(C(=O)c2cc(Cl)c3nccnc3c2)C[C@@H]1c1ccc(F)cc1] | | 585.1 |
| 412B | N-((3S,4R)-1-((8-methoxyquinoxalin-6-yl)carbonyl)-3-phenylpiperidin-4-yl)-1-methyl-3-(trifluoromethyl)-1H-pyrazole-5-carboxamide | 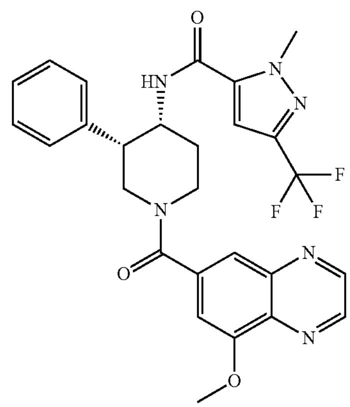 [SMILES: COc1cc(C(=O)N2CC[C@@H](NC(=O)c3cc(C(F)(F)F)nn3C)[C@@H](c3ccccc3)C2)cc2nccnc12] | | 539.2 |
| 413B | 3-cyclopropyl-N-((3S,4R)-1-((3,8-dimethylimidazo[1,2-a]pyridin-6-yl)carbonyl)-3-phenylpiperidin-4-yl)pyridine-2-carboxamide | 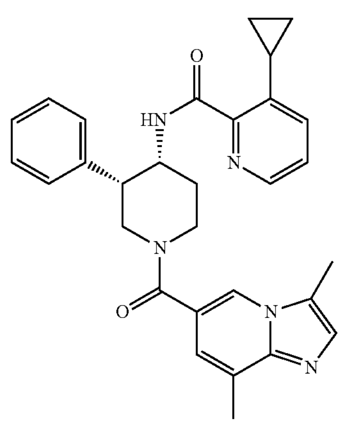 [SMILES: Cc1cc(C(=O)N2CC[C@@H](NC(=O)c3ncccc3C3CC3)[C@@H](c3ccccc3)C2)cn2c(C)cnc12] | | 494.2 |

TABLE 2-1-continued

| Ex. No. | IUPAC Name | Structure | Salt | MS |
|---|---|---|---|---|
| 414B | N-((3S,4R)-1-((4-chloro-1-methyl-1H-benzimidazol-6-yl)carbonyl)-3-phenylpiperidin-4-yl)-3-cyclopropylpyridine-2-carboxamide | 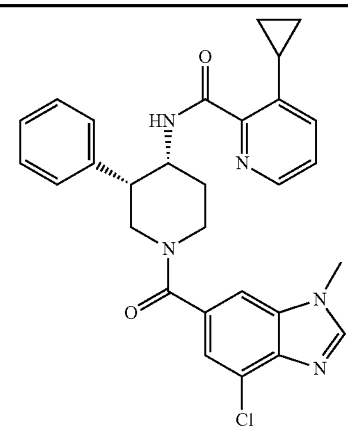 | | 514.1 |
| 415B | 3-(difluoromethoxy)-N-((3S,4R)-1-((4-methoxy-1-methyl-1H-benzimidazol-6-yl)carbonyl)-3-phenylpiperidin-4-yl)pyridine-2-carboxamide | 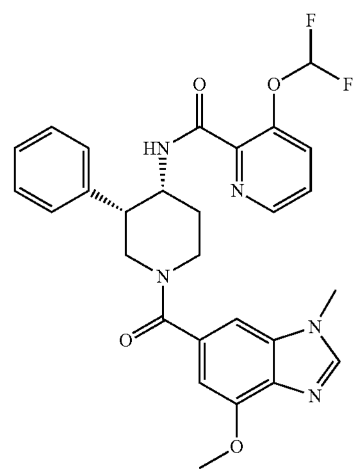 [SMILES: COc1cc(C(=O)N2CC[C@@H](NC(=O)c3ncccc3OC(F)F)[C@@H](c3ccccc3)C2)cc2c1ncn2C] | | 536.2 |
| 416B | N-((3S,4R)-1-((4-chloro-1-methyl-1H-benzimidazol-6-yl)carbonyl)-3-phenylpiperidin-4-yl)-3-(difluoromethoxy)pyridine-2-carboxamide | 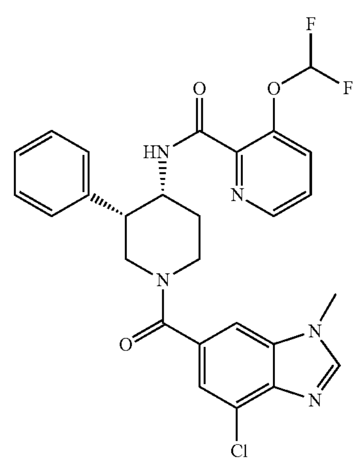 [SMILES: Cn1cnc2c(Cl)cc(C(=O)N3CC[C@@H](NC(=O)c4ncccc4OC(F)F)[C@@H](c4ccccc4)C3)cc21] | | 540.2 |

TABLE 2-1-continued

| Ex. No. | IUPAC Name | Structure | Salt | MS |
|---|---|---|---|---|
| 417B | N-((3S,4R)-1-((4-chloro-1-methyl-1H-benzimidazol-6-yl)carbonyl)-3-phenylpiperidin-4-yl)-1-(2,2-difluoroethyl)-3-methyl-1H-pyrazole-5-carboxamide | 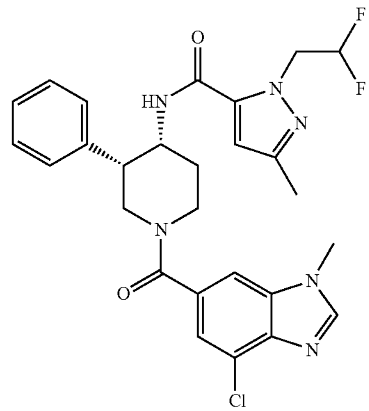 [SMILES: Cc1cc(C(=O)N[C@@H]2CCN(C(=O)c3cc(Cl)c4ncn(C)c4c3)C[C@@H]2c2ccccc2)n(CC(F)F)n1] | | 541.3 |
| 418B | 1-(2,2-difluoroethyl)-N-((3S,4R)-1-((1,4-dimethyl-1H-benzimidazol-6-yl)carbonyl)-3-phenylpiperidin-4-yl)-3-methyl-1H-pyrazole-5-carboxamide | 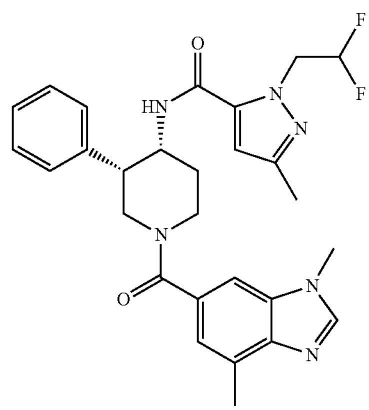 [SMILES: Cc1cc(C(=O)N[C@@H]2CCN(C(=O)c3cc(C)c4ncn(C)c4c3)C[C@@H]2c2ccccc2)n(CC(F)F)n1] | | 521.2 |
| 419B | 3-(difluoromethoxy)-N-((3S,4R)-1-((4-methoxy-1-methyl-1H-benzimidazol-6-yl)carbonyl)-3-phenylpiperidin-4-yl)-1,4-dimethyl-1H-pyrazole-5-carboxamide | 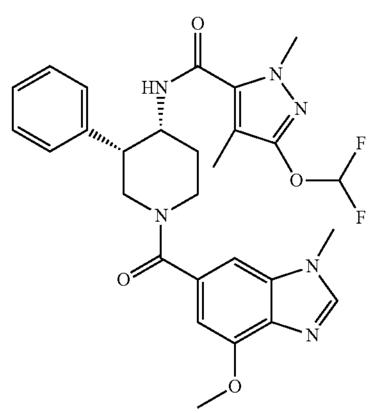 [SMILES: COc1cc(C(=O)N2CC[C@@H](NC(=O)c3c(C)c(OC(F)F)nn3C)[C@@H](c3ccccc3)C2)cc2c1ncn2C] | | 553.2 |

TABLE 2-1-continued

| Ex. No. | IUPAC Name | Structure | Salt | MS |
|---|---|---|---|---|
| 420B | 3-cyclopropyl-N-((3S,4R)-1-((4-methoxy-1-methyl-1H-benzimidazol-6-yl)carbonyl)-3-phenylpiperidin-4-yl)-1-methyl-1H-pyrazole-5-carboxamide | 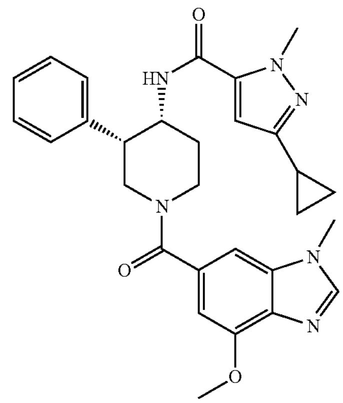 [SMILES: COc1cc(C(=O)N2CC[C@@H](NC(=O)c3cc(C4CC4)nn3C)[C@@H](c3ccccc3)C2)cc2c1ncn2C] | | 513.2 |
| 421B | N-((3S,4R)-1-((1,4-dimethyl-1H-benzimidazol-6-yl)carbonyl)-3-phenylpiperidin-4-yl)-1,3-dimethyl-4-(trifluoromethyl)-1H-pyrazole-5-carboxamide | 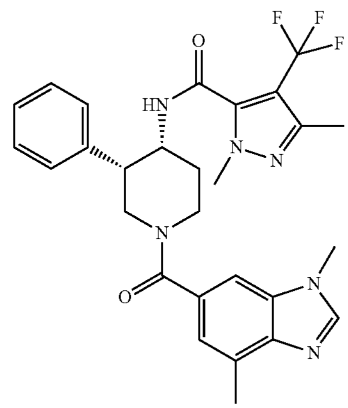 [SMILES: Cc1nn(C)c(C(=O)N[C@@H]2CCN(C(=O)c3cc(C)c4ncn(C)c4c3)C[C@@H]2c2ccccc2)c1C(F)(F)F] | | 539.2 |
| 422B | 5-chloro-N-((3S,4R)-1-((1,4-dimethyl-1H-benzimidazol-6-yl)carbonyl)-3-phenylpiperidin-4-yl)-1,3-dimethyl-1H-pyrazole-4-carboxamide | 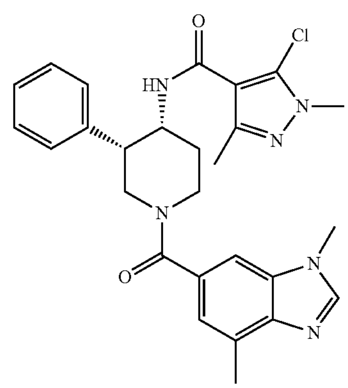 [SMILES: Cc1nn(C)c(Cl)c1C(=O)N[C@@H]1CCN(C(=O)c2cc(C)c3ncn(C)c3c2)C[C@@H]1c1ccccc1] | | 505.2 |
| 423B | 1,3-dimethyl-N-((3S,4R)-1-((8-methylquinoxalin-6-yl)carbonyl)-3-phenylpiperidin-4-yl)-5-(methylsulfonyl)-1H-pyrazole-4-carboxamide | 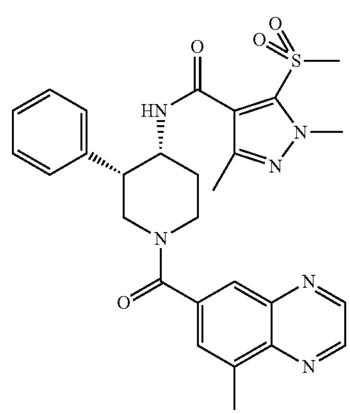 [SMILES: Cc1nn(C)c(S(C)(=O)=O)c1C(=O)N[C@@H]1CCN(C(=O)c2cc(C)c3nccnc3c2)C[C@@H]1c1ccccc1] | | 547.2 |

TABLE 2-1-continued

| Ex. No. | IUPAC Name | Structure | Salt | MS |
|---|---|---|---|---|
| 424B | N-((3S,4R)-1-((2-methoxy-1,4-dimethyl-1H-benzimidazol-6-yl)carbonyl)-3-phenylpiperidin-4-yl)-1,3-dimethyl-5-(methylsulfonyl)-1H-pyrazole-4-carboxamide | 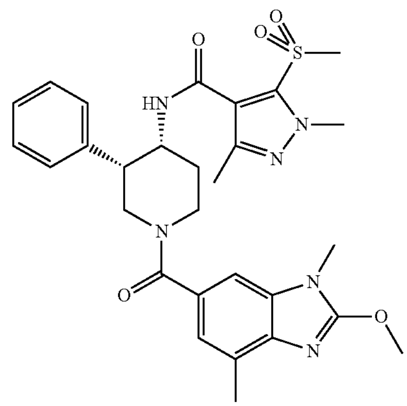 [SMILES: COc1nc2c(C)cc(C(=O)N3CC[C@@H](NC(=O)c4c(C)nn(C)c4S(C)(=O)=O)[C@@H](c4ccccc4)C3)cc2n1C] | | 579.2 |
| 425B | N-((3S,4R)-1-((3,8-dimethylimidazo[1,2-a]pyridin-6-yl)carbonyl)-3-phenylpiperidin-4-yl)-1,3-dimethyl-5-(methylsulfonyl)-1H-pyrazole-4-carboxamide | 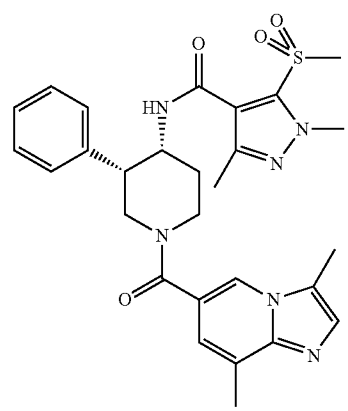 [SMILES: Cc1nn(C)c(S(C)(=O)=O)c1C(=O)N[C@@H]1CCN(C(=O)c2cc(C)c3ncc(C)n3c2)C[C@@H]1c1ccccc1] | | 549.2 |
| 426B | N-((3S,4R)-1-((4-chloro-1-methyl-1H-benzimidazol-6-yl)carbonyl)-3-phenylpiperidin-4-yl)-1,3-dimethyl-5-(methylsulfonyl)-1H-pyrazole-4-carboxamide | 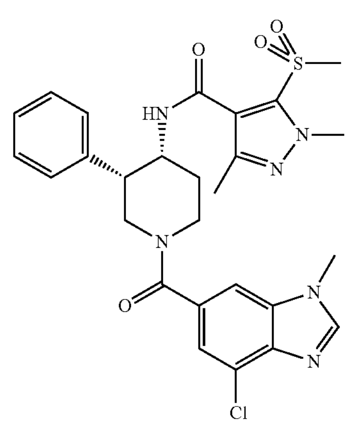 [SMILES: Cc1nn(C)c(S(C)(=O)=O)c1C(=O)N[C@@H]1CCN(C(=O)c2cc(Cl)c3ncn(C)c3c2)C[C@@H]1c1ccccc1] | | 569.1 |

TABLE 2-1-continued

| Ex. No. | IUPAC Name | Structure | Salt | MS |
|---|---|---|---|---|
| 427B | N-((3S,4R)-1-((8-methoxyquinoxalin-6-yl)carbonyl)-3-phenylpiperidin-4-yl)-1,3-dimethyl-5-(methylsulfonyl)-1H-pyrazole-4-carboxamide | 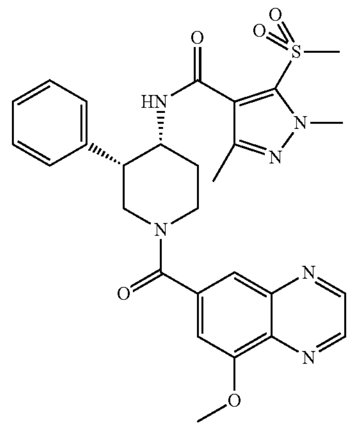 [SMILES: COc1cc(C(=O)N2CC[C@@H](NC(=O)c3c(C)nn(C)c3S(C)(=O)=O)[C@@H](c3ccccc3)C2)cc2nccnc12] | | 563.2 |
| 428B | N-((3S,4R)-1-((3,8-dimethylimidazo[1,2-a]pyridin-6-yl)carbonyl)-3-phenylpiperidin-4-yl)-1-methyl-5-(trifluoromethyl)-1H-pyrazole-4-carboxamide | 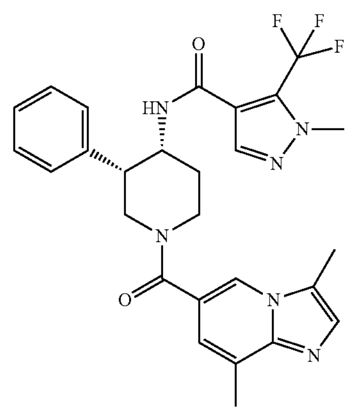 [SMILES: Cc1cc(C(=O)N2CC[C@@H](NC(=O)c3cnn(C)c3C(F)(F)F)[C@@H](c3ccccc3)C2)cn2c(C)cnc12] | | 525.2 |
| 429B | N-((3S,4R)-1-((8-chloro-3-methylimidazo[1,2-a]pyridin-6-yl)carbonyl)-3-phenylpiperidin-4-yl)-3-(trifluoromethyl)pyridine-2-carboxamide | 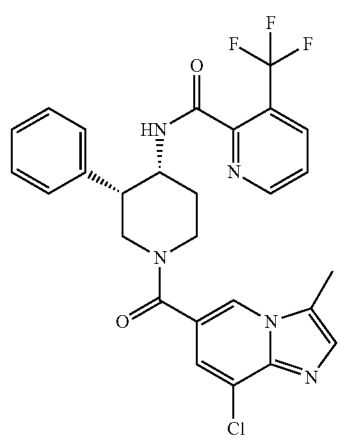 [SMILES: Cc1cnc2c(Cl)cc(C(=O)N3CC[C@@H](NC(=O)c4ncccc4C(F)(F)F)[C@@H](c4ccccc4)C3)cn12] | | 542.2 |

TABLE 2-1-continued

| Ex. No. | IUPAC Name | Structure | Salt | MS |
|---|---|---|---|---|
| 430B | N-((3S,4R)-1-((4-chloro-1-methyl-1H-benzimidazol-6-yl)carbonyl)-3-phenylpiperidin-4-yl)-3-(difluoromethoxy)-1-methyl-1H-pyrazole-5-carboxamide | 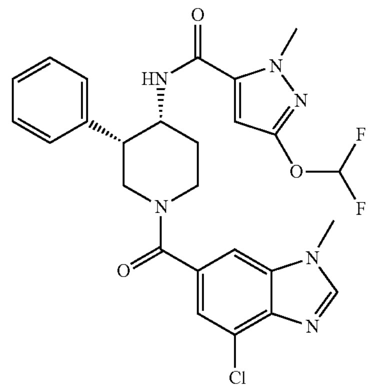 [SMILES: Cn1nc(OC(F)F)cc1C(=O)N[C@@H]1CCN(C(=O)c2cc(Cl)c3ncn(C)c3c2)C[C@@H]1c1ccccc1] | | 543.2 |
| 431B | N-((3S,4R)-1-((4-chloro-1-methyl-1H-benzimidazol-6-yl)carbonyl)-3-phenylpiperidin-4-yl)-1,3,4-trimethyl-1H-pyrazole-5-carboxamide | 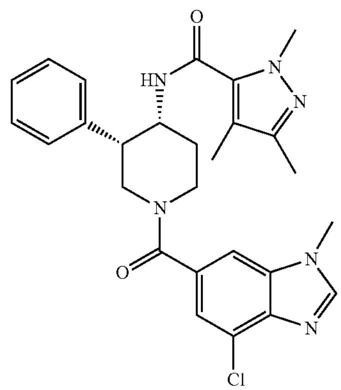 [SMILES: Cc1nn(C)c(C(=O)N[C@@H]2CCN(C(=O)c3cc(Cl)c4ncn(C)c4c3)C[C@@H]2c2ccccc2)c1C] | | 505.2 |
| 432B | 5-chloro-N-((3S,4R)-1-((4-chloro-1-methyl-1H-benzimidazol-6-yl)carbonyl)-3-phenylpiperidin-4-yl)-1-methyl-3-(trifluoromethyl)-1H-pyrazole-4-carboxamide | 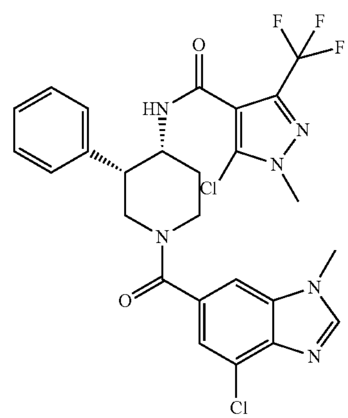 [SMILES: Cn1nc(C(F)(F)F)c(C(=O)N[C@@H]2CCN(C(=O)c3cc(Cl)c4ncn(C)c4c3)C[C@@H]2c2ccccc2)c1Cl] | | 579.0 |
| 433B | 5-chloro-N-((3S,4R)-1-((1,4-dimethyl-1H-benzimidazol-6-yl)carbonyl)-3-phenylpiperidin-4-yl)-1-methyl-3-(trifluoromethyl)-1H-pyrazole-4-carboxamide | 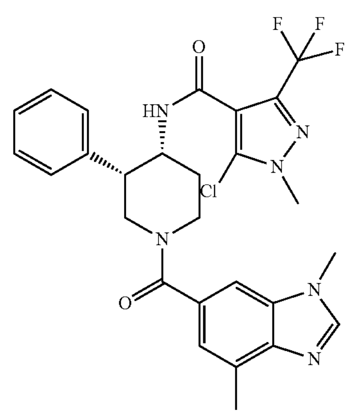 [SMILES: Cc1cc(C(=O)N2CC[C@@H](NC(=O)c3c(C(F)(F)F)nn(C)c3Cl)[C@@H](c3ccccc3)C2)cc2c1ncn2C] | | 559.2 |

TABLE 2-1-continued

| Ex. No. | IUPAC Name | Structure | Salt | MS |
|---|---|---|---|---|
| 434B | N-((3S,4R)-1-((8-chloro-3-methylimidazo[1,2-a]pyridin-6-yl)carbonyl)-3-phenylpiperidin-4-yl)-1,3-dimethyl-5-(methylsulfonyl)-1H-pyrazole-4-carboxamide | 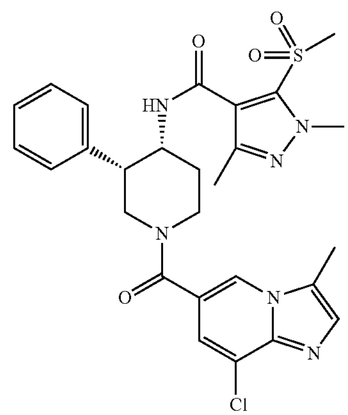 [SMILES: Cc1nn(C)c(S(C)(=O)=O)c1C(=O)N[C@@H]1CCN(C(=O)c2cc(Cl)c3ncc(C)n3c2)C[C@@H]1c1ccccc1] | | 569.1 |
| 435B | N-((3S,4R)-1-((1,4-dimethyl-1H-benzimidazol-6-yl)carbonyl)-3-phenylpiperidin-4-yl)-1,3-dimethyl-5-(methylsulfonyl)-1H-pyrazole-4-carboxamide | 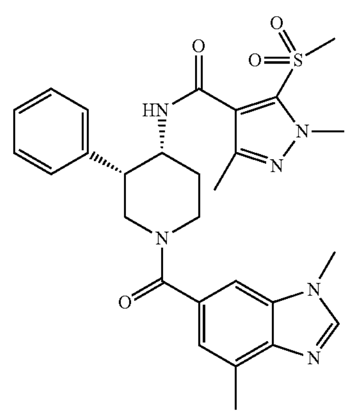 [SMILES: Cc1nn(C)c(S(C)(=O)=O)c1C(=O)N[C@@H]1CCN(C(=O)c2cc(C)c3ncn(C)c3c2)C[C@@H]1c1ccccc1] | | 549.2 |
| 436B | N-((3S,4R)-1-((8-methoxy-3-methylimidazo[1,2-a]pyridin-6-yl)carbonyl)-3-phenylpiperidin-4-yl)-1,4-dimethyl-3-(trifluoromethyl)-1H-pyrazole-5-carboxamide | 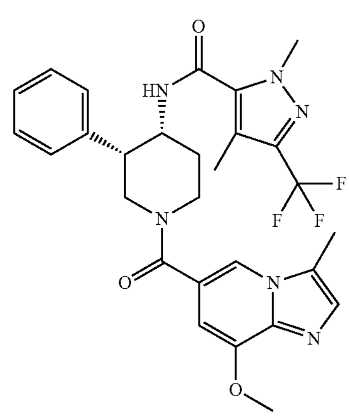 [SMILES: COc1cc(C(=O)N2CC[C@@H](NC(=O)c3c(C)c(C(F)(F)F)nn3C)[C@@H](c3ccccc3)C2)cn2c(C)cnc12] | | 555.2 |

TABLE 2-1-continued

| Ex. No. | IUPAC Name | Structure | Salt | MS |
|---|---|---|---|---|
| 437B | N-((3S,4R)-1-((3,8-dimethylimidazo[1,2-a]pyridin-6-yl)carbonyl)-3-phenylpiperidin-4-yl)-1,4-dimethyl-3-(trifluoromethyl)-1H-pyrazole-5-carboxamide | 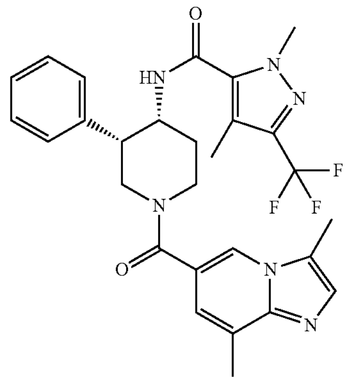 [SMILES: Cc1c(C(F)(F)F)nn(C)c1C(=O)N[C@@H]1CCN(C(=O)c2cc(C)c3ncc(C)n3c2)C[C@@H]1c1ccccc1] | | 539.3 |
| 438B | N-((3S,4R)-1-((4-methoxy-1-methyl-1H-benzimidazol-6-yl)carbonyl)-3-phenylpiperidin-4-yl)-1,4-dimethyl-3-(trifluoromethyl)-1H-pyrazole-5-carboxamide | 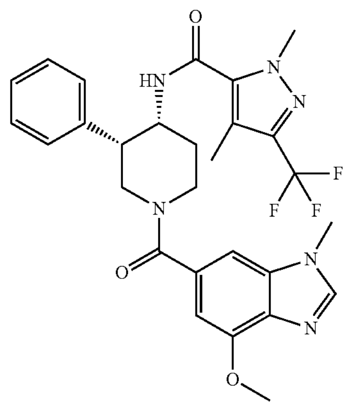 [SMILES: COc1cc(C(=O)N2CC[C@@H](NC(=O)c3c(C)c(C(F)(F)F)nn3C)[C@@H](c3ccccc3)C2)cc2c1ncn2C] | | 555.2 |
| 439B | N-((3S,4R)-1-((8-methoxyquinoxalin-6-yl)carbonyl)-3-phenylpiperidin-4-yl)-1,4-dimethyl-3-(trifluoromethyl)-1H-pyrazole-5-carboxamide | 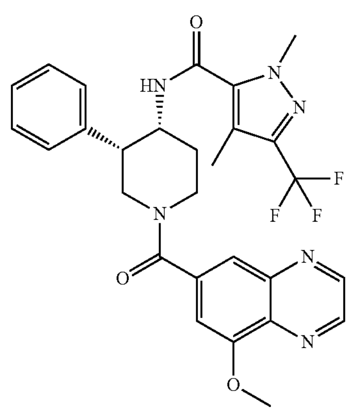 [SMILES: COc1cc(C(=O)N2CC[C@@H](NC(=O)c3c(C)c(C(F)(F)F)nn3C)[C@@H](c3ccccc3)C2)cc2nccnc12] | | 553.2 |
| 440B | N-(cis-3-cyclopropyl-1-(3,4-dimethoxybenzoyl)piperidin-4-yl)-2-(trifluoromethoxy)benzamide | 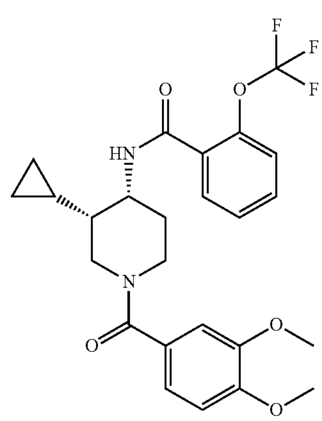 [SMILES: COc1ccc(C(=O)N2CC[C@@H](NC(=O)c3ccccc3OC(F)(F)F)[C@@H](C3CC3)C2)cc1OC] | | 493.2 |

TABLE 2-1-continued
| Ex. No. | IUPAC Name | Structure | Salt | MS |
|---|---|---|---|---|
| 441B | N-(cis-3-cyclohexyl-1-(3,4-dimethoxybenzoyl)piperidin-4-yl)-2-(trifluoromethoxy)benzamide | 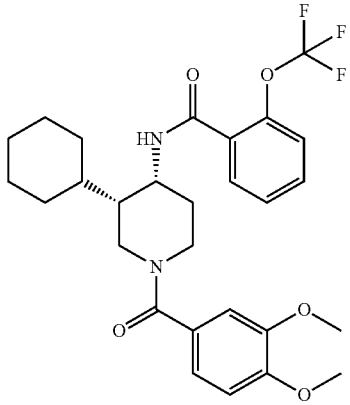 [SMILES: COc1ccc(C(=O)N2CC[C@@H](NC(=O)c3ccccc3OC(F)(F)F)[C@@H](C3CCCCC3)C2)cc1OC] | | 535.2 |
| 442B | N-(trans-3-cyclohexyl-1-(3,4-dimethoxybenzoyl)piperidin-4-yl)-2-(trifluoromethoxy)benzamide | 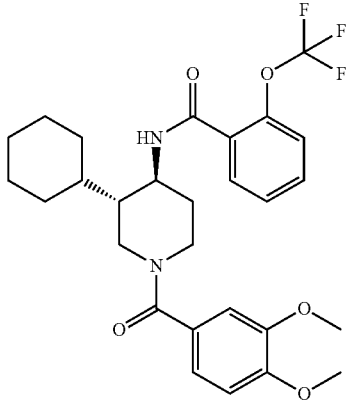 [SMILES: COc1ccc(C(=O)N2CC[C@H](NC(=O)c3ccccc3OC(F)(F)F)[C@@H](C3CCCCC3)C2)cc1OC] | | 535.2 |
| 443B | N-(tras-3-cyclopentyl-1-(3,4-dimethoxybenzoyl)piperidin-4-yl)-2-(trifluoromethoxy)benzamide | 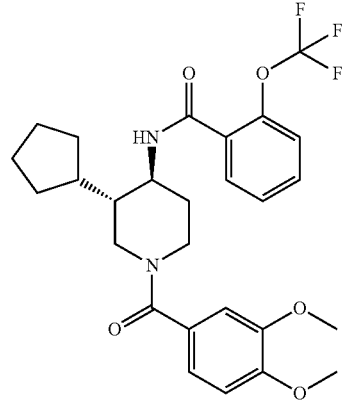 [SMILES: COc1ccc(C(=O)N2CC[C@H](NC(=O)c3ccccc3OC(F)(F)F)[C@@H](C3CCCC3)C2)cc1OC] | | 521.2 |

TABLE 2-1-continued

| Ex. No. | IUPAC Name | Structure | Salt | MS |
|---|---|---|---|---|
| 444B | N-(cis-3-cyclopentyl-1-(3,4-dimethoxybenzoyl)piperidin-4-yl)-2-(trifluoromethoxy)benzamide | 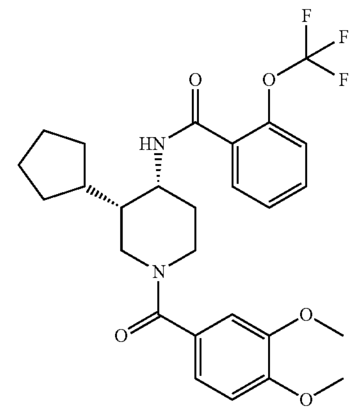 [SMILES: COc1ccc(C(=O)N2CC[C@@H](NC(=O)c3ccccc3OC(F)(F)F)[C@@H](C3CCCC3)C2)cc1OC] | | 521.2 |
| 445B | 3-cyclopropyl-N-((3S,4R)-1-((8-methoxy-3-methylimidazo[1,2-a]pyridin-6-yl)carbonyl)-3-phenylpiperidin-4-yl)-1-methyl-1H-pyrazole-5-carboxamide | 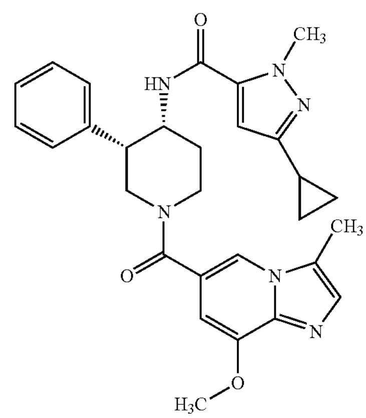 [SMILES: COc1cc(C(=O)N2CC[C@@H](NC(=O)c3cc(C4CC4)nn3C)[C@@H](c3ccccc3)C2)cn2c(C)cnc12] | | 513.2 |
| 446B | N-((3S,4R)-1-((8-methoxy-3-methylimidazo[1,2-a]pyridin-6-yl)carbonyl)-3-phenylpiperidin-4-yl)-3-(trifluoromethyl)pyridine-2-carboxamide | 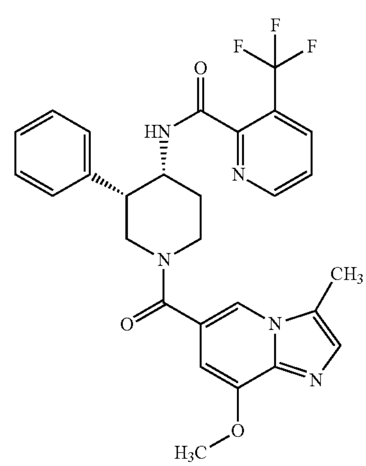 [SMILES: COc1cc(C(=O)N2CC[C@@H](NC(=O)c3ncccc3C(F)(F)F)[C@@H](c3ccccc3)C2)cn2c(C)cnc12] | | 538.2 |

TABLE 2-1-continued

| Ex. No. | IUPAC Name | Structure | Salt | MS |
|---|---|---|---|---|
| 447B | 3-ethoxy-N-((3S,4R)-1-((8-methoxy-3-methylimidazo[1,2-a]pyridin-6-yl)carbonyl)-3-phenylpiperidin-4-yl)-1-methyl-1H-pyrazole-5-carboxamide | 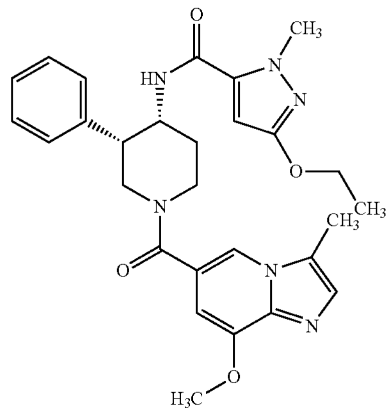 [SMILES: CCOc1cc(C(=O)N[C@@H]2CCN(C(=O)c3cc(OC)c4ncc(C)n4c3)C[C@@H]2c2ccccc2)n(C)n1] | | 517.2 |
| 448B | 3-cyclopropyl-N-((3S,4R)-1-((8-methoxy-3-methylimidazo[1,2-a]pyridin-6-yl)carbonyl)-3-phenylpiperidin-4-yl)pyridine-2-carboxamide | 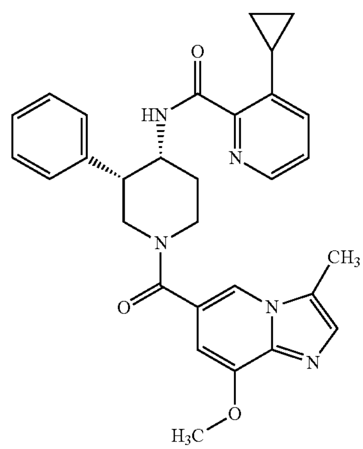 [SMILES: COc1cc(C(=O)N2CC[C@@H](NC(=O)c3ncccc3C3CC3)[C@@H](c3ccccc3)C2)cn2c(C)cnc12] | | 510.3 |
| 449B | N-((3S,4R)-1-((8-methoxy-3-methylimidazo[1,2-a]pyridin-6-yl)carbonyl)-3-phenylpiperidin-4-yl)-1,3,4-trimethyl-1H-pyrazole-5-carboxamide | 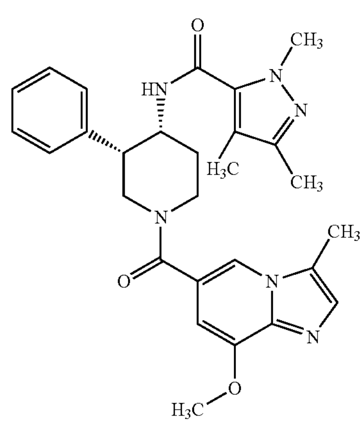 [SMILES: COc1cc(C(=O)N2CC[C@@H](NC(=O)c3c(C)c(C)nn3C)[C@@H](c3ccccc3)C2)cn2c(C)cnc12] | | 501.3 |

TABLE 2-1-continued

| Ex. No. | IUPAC Name | Structure | Salt | MS |
|---|---|---|---|---|
| 450B | N-((3S,4R)-1-((8-methoxy-3-methylimidazo[1,2-a]pyridin-6-yl)carbonyl)-3-phenylpiperidin-4-yl)-1,3-dimethyl-4-(trifluoromethyl)-1H-pyrazole-5-carboxamide | 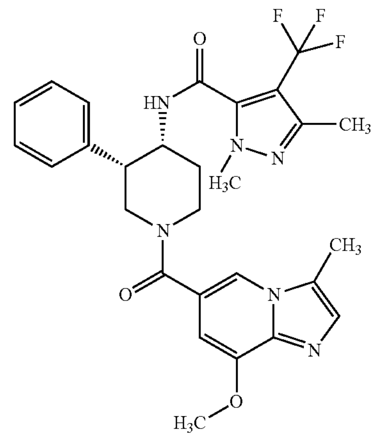 [SMILES: COc1cc(C(=O)N2CC[C@@H](NC(=O)c3c(C(F)(F)F)c(C)nn3C)[C@@H](c3ccccc3)C2)cn2c(C)cnc12] | | 555.2 |
| 451B | N-((3S,4R)-1-((8-methoxy-3-methylimidazo[1,2-a]pyridin-6-yl)carbonyl)-3-phenylpiperidin-4-yl)-1-methyl-3-(trifluoromethyl)-1H-pyrazole-5-carboxamide | 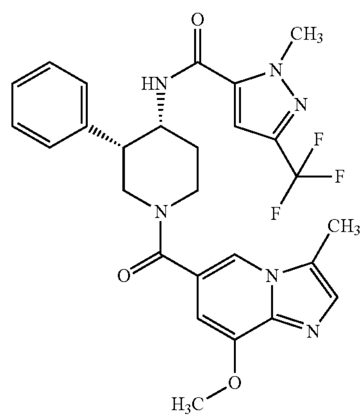 [SMILES: COc1cc(C(=O)N2CC[C@@H](NC(=O)c3cc(C(F)(F)F)nn3C)[C@@H](c3ccccc3)C2)cn2c(C)cnc12] | | 541.3 |
| 452B | N-((3S,4R)-1-((8-methoxy-3-methylimidazo[1,2-a]pyridin-6-yl)carbonyl)-3-phenylpiperidin-4-yl)-1-methyl-5-(trifluoromethyl)-1H-pyrazole-4-carboxamide | 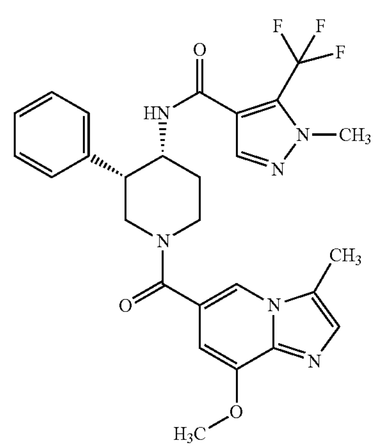 [SMILES: COc1cc(C(=O)N2CC[C@@H](NC(=O)c3cnn(C)c3C(F)(F)F)[C@@H](c3ccccc3)C2)cn2c(C)cnc12] | | 541.3 |

TABLE 2-1-continued

| Ex. No. | IUPAC Name | Structure | Salt | MS |
|---|---|---|---|---|
| 453B | 1-(2,2-difluoroethyl)-N-((3S,4R)-1-((8-methoxy-3-methylimidazo[1,2-a]pyridin-6-yl)carbonyl)-3-phenylpiperidin-4-yl)-3-methyl-1H-pyrazole-5-carboxamide | 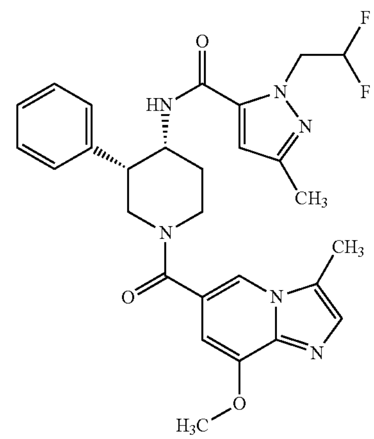 [SMILES: COc1cc(C(=O)N2CC[C@@H](NC(=O)c3cc(C)nn3CC(F)F)[C@@H](c3ccccc3)C2)cn2c(C)cnc12] | | 537.2 |
| 454B | 3-(difluoromethoxy)-N-((3S,4R)-1-((8-methoxy-3-methylimidazo[1,2-a]pyridin-6-yl)carbonyl)-3-phenylpiperidin-4-yl)-1,4-dimethyl-1H-pyrazole-5-carboxamide | 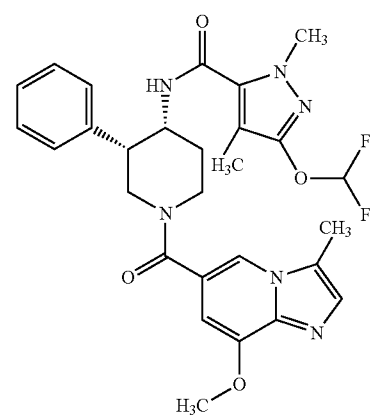 [SMILES: COc1cc(C(=O)N2CC[C@@H](NC(=O)c3c(C)c(OC(F)F)nn3C)[C@@H](c3ccccc3)C2)cn2c(C)cnc12] | | 553.2 |
| 455B | N-((3S,4R)-1-((8-methoxy-3-methylimidazo[1,2-a]pyridin-6-yl)carbonyl)-3-phenylpiperidin-4-yl)-1,3-dimethyl-1H-pyrazole-5-carboxamide | 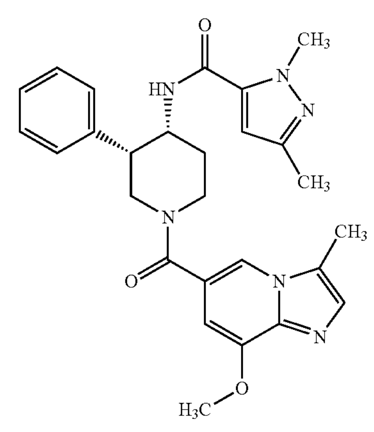 [SMILES: COc1cc(C(=O)N2CC[C@@H](NC(=O)c3cc(C)nn3C)[C@@H](c3ccccc3)C2)cn2c(C)cnc12] | | 487.2 |

TABLE 2-1-continued

| Ex. No. | IUPAC Name | Structure | Salt | MS |
|---|---|---|---|---|
| 456B | 3-methoxy-N-((3S,4R)-1-((8-methoxy-3-methylimidazo[1,2-a]pyridin-6-yl)carbonyl)-3-phenylpiperidin-4-yl)-1-methyl-1H-pyrazole-5-carboxamide | 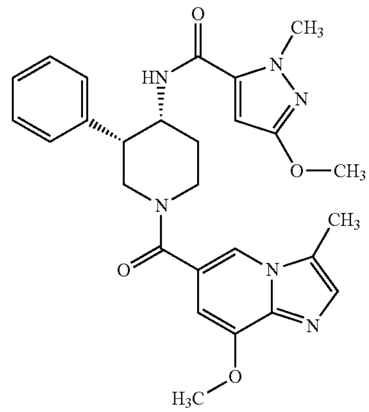 [SMILES: COc1cc(C(=O)N[C@@H]2CCN(C(=O)c3cc(OC)c4ncc(C)n4c3)C[C@@H]2c2ccccc2)n(C)n1] | | 503.2 |
| 457B | 5-chloro-N-((3S,4R)-1-((8-methoxy-3-methylimidazo[1,2-a]pyridin-6-yl)carbonyl)-3-phenylpiperidin-4-yl)-1-methyl-3-(trifluoromethyl)-1H-pyrazole-4-carboxamide | 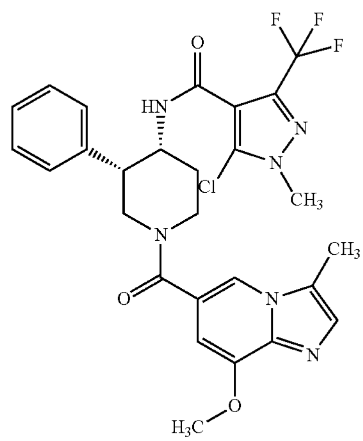 [SMILES: COc1cc(C(=O)N2CC[C@@H](NC(=O)c3c(C(F)(F)F)nn(C)c3Cl)[C@@H](c3ccccc3)C2)cn2c(C)cnc12] | | 575.2 |
| 458B | 5-chloro-N-((3S,4R)-1-((8-methoxy-3-methylimidazo[1,2-a]pyridin-6-yl)carbonyl)-3-phenylpiperidin-4-yl)-1,3-dimethyl-1H-pyrazole-4-carboxamide | 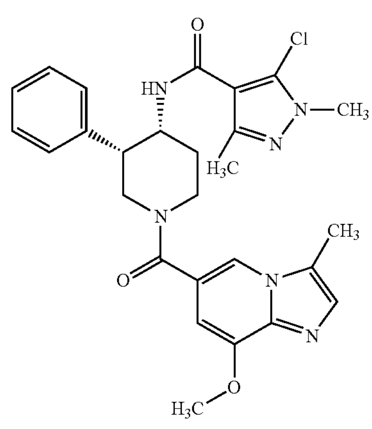 [SMILES: COc1cc(C(=O)N2CC[C@@H](NC(=O)c3c(C)nn(C)c3Cl)[C@@H](c3ccccc3)C2)cn2c(C)cnc12] | | 521.2 |

TABLE 2-1-continued

| Ex. No. | IUPAC Name | Structure | Salt | MS |
|---|---|---|---|---|
| 459B | N-((3S,4R)-1-((8-methoxy-3-methylimidazo[1,2-a]pyridin-6-yl)carbonyl)-3-phenylpiperidin-4-yl)-1,3-dimethyl-5-(methylsulfonyl)-1H-pyrazole-4-carboxamide | 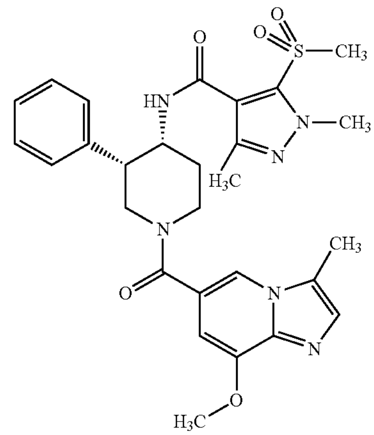 [SMILES: COc1cc(C(=O)N2CC[C@@H](NC(=O)c3c(C)nn(C)c3S(C)(=O)=O)[C@@H](c3ccccc3)C2)cn2c(C)cnc12] | | 565.3 |
| 460B | 3-(difluoromethoxy)-N-((3S,4R)-1-((8-methoxy-3-methylimidazo[1,2-a]pyridin-6-yl)carbonyl)-3-phenylpiperidin-4-yl)pyridine-2-carboxamide | 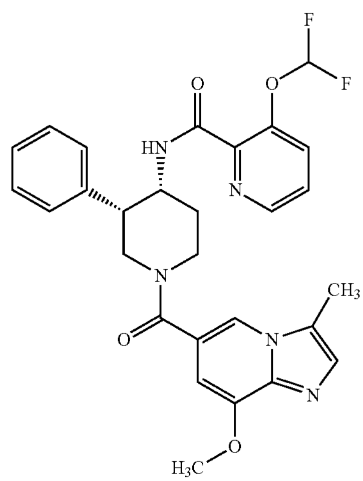 [SMILES: COc1cc(C(=O)N2CC[C@@H](NC(=O)c3ncccc3OC(F)F)[C@@H](c3ccccc3)C2)cn2c(C)cnc12] | | 536.3 |
| 461B | 2-chloro-N-((3S,4S)-1-(3,4-dimethoxybenzoyl)-3-phenylpiperidin-4-yl)benzamide | 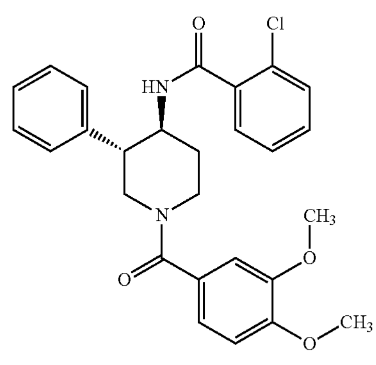 [SMILES: COc1ccc(C(=O)N2CC[C@H](NC(=O)c3ccccc3Cl)[C@@H](c3ccccc3)C2)cc1OC] | | 479.1 |

TABLE 2-1-continued

| Ex. No. | IUPAC Name | Structure | Salt | MS |
|---|---|---|---|---|
| 462B | N-((3S,4R)-1-((8-chloroquinoxalin-6-yl)carbonyl)-3-(4-fluorophenyl)piperidin-4-yl)-1,4-dimethyl-3-(trifluoromethyl)-1H-pyrazole-5-carboxamide | 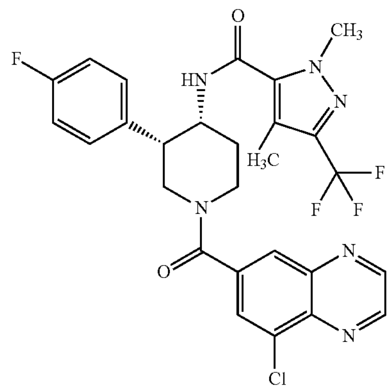 [SMILES: Cc1c(C(F)(F)F)nn(C)c1C(=O)N[C@@H]1CCN(C(=O)c2cc(Cl)c3nccnc3c2)C[C@@H]1c1ccc(F)cc1] | | 575.1 |

Formulation Example 1

Each medicament containing the compound of the present invention as an active ingredient can be produced, for example, according to the following recipe:

[Expression 1]

| Capsule | |
|---|---|
| (1) Compound obtained in Example 1 | 40 mg |
| (2) Lactose | 70 mg |
| (3) Microcrystalline cellulose | 9 mg |
| (4) Magnesium stearate | 1 mg |
| One capsule | 120 mg |

The components (1), (2) and (3) and a ½ amount of the component (4) are mixed and then granulated. The remaining amount of the component (4) is added thereto, and the whole is encapsulated in a gelatin capsule shell.

[Expression 2]

| 2. Tablet | |
|---|---|
| (1) Compound obtained in Example 1 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| One tablet | 120 mg |

The components (1), (2) and (3), a ⅔ amount of the component (4) and a ½ amount of the component (5) are mixed and then granulated. The remaining amounts of the components (4) and (5) are added to this granule, which is then molded into a tablet by compression.

Formulation Example 2

50 mg of the compound obtained in Example 1 is dissolved in 50 mL of Japanese Pharmacopoeia distilled water for injection, and then, the amount of the solution is adjusted to 100 mL by the addition of Japanese Pharmacopoeia distilled water for injection. This solution is filtered under sterile conditions. Next, vials for injection are filled with this solution at 1 mL/vial under sterile conditions, freeze-dried, and hermetically sealed.

Test Example 1 SPT Enzyme Inhibition Test

Full-length human SPT1, human SPT2 and human ssSPTa used had amino acid sequences identical to NCBI Accession Nos. NM_006415, NM_004863 and NM_138288, respectively. pcDNA3.1 vectors having an insert of a sequence of interest were prepared, and FreeStyle 293 cells (Life Technologies, Inc., Carlsbad, Calif., US) were cotransfected with the human SPT1, human SPT2, and human ssSPTa expression vectors according to the protocol of FreeStyle 293 Expression system. After culture for 3 days, the cells were recovered and frozen at −80° C. to obtain expressing cells. The frozen cells were suspended in a 50 mM Hepes buffer (pH 7.5) containing 250 mM sucrose, 5 mM ethylenediaminetetraacetic acid (EDTA), 5 mM dithiothreitol (DTT) and Complete, EDTA-free (Roche Applied Science, Penzberg, Upper Bavaria, Germany). The cells were disrupted (on ice, 20,000 rpm, 20 sec×2) using POLYTORON (Central Scientific Commerce, Inc.). After centrifugation at 2000 rpm (850×g) for 10 minutes, the supernatant was recovered. Subsequently, the supernatant was centrifuged at 40,000 rpm (186,010×g) for 60 minutes, and the supernatant was discarded. The pellets were suspended in a 50 mM Hepes buffer (pH 7.5) containing 5 mM EDTA, 5 mM DTT and Complete, EDTA-free, passed through a 40-µm cell strainer and stored at −80° C. The resultant was used as a SPT2-expressing membrane fraction. The protein concentration was determined using CBB Protein Assay with bovine serum albumin used as standards.

5 µL of each test compound was mixed with 10 µL of the 100 µg/mL SPT2-expressing membrane fraction using an assay buffer (100 mM Hepes (pH 8.0) containing 2.5 mM EDTA, 5 mM DTT and 0.01% fatty acid-free bovine serum albumin), and the mixture was left standing at room temperature for 60 minutes. Subsequently, 5 µL of a substrate solution containing 2 mM L-serine and 20 µM palmitoyl CoA was added thereto, and an enzyme reaction was carried out in a 384-well plate using 20 µL in total of the reaction system. After reaction at room temperature for 15 minutes, the reaction was terminated by the addition of 20 µL of a 2% aqueous formic acid solution. Subsequently, 40 µL of acetonitrile containing 600 nM C17-sphinganine (Avanti Polar Lipids, Inc., Alabaster, Ala., US) was added thereto as an internal standard. The reaction sample was subjected to on-line solid-layer extraction using RapidFire 300 (Agilent Technologies Inc., Santa Clara, Calif., US). The SRM transition of 3-ketodihydrosphingosine (reaction product) and C17-sphinganine (internal standard) was set to 300.5/270.3 and 288.4/60.2, respectively, on a positive SRM mode using API-4000 (AB SCIEX, Framingham, Mass., US) equipped with ESI probes. Mass chromatograms were obtained using Analyst software (version 1.5.0, AB SCIEX). Their mass chromatogram areas were respectively calculated, and the rate of inhibition (%) by the test compound was calculated using an area ratio (the value of the reaction product was divided by the value of the internal standard).

The test results are shown in Table 3.

TABLE 3

| Example No. | Rate of inhibition (%) at 1 μM |
|---|---|
| 1A | 91 |
| 2A | 98 |
| 3A | 98 |
| 17A | 84 |
| 30A | 93 |
| 36A | 101 |
| 64A | 82 |
| 74A | 99 |
| 80A | 99 |
| 84A | 98 |
| 85A | 99 |
| 91A | 94 |
| 100A | 97 |
| 103A | 95 |
| 117A | 84 |
| 126A | 101 |
| 132A | 102 |
| 133A | 101 |
| 153A | 101 |
| 155A | 103 |
| 162A | 100 |
| 165A | 101 |
| 170A | 99 |
| 171A | 101 |
| 172A | 93 |
| 178A | 101 |
| 186A | 101 |
| 201A | 100 |
| 217A | 102 |
| 2B | 99 |
| 3B | 98 |
| 23B | 101 |
| 25B | 100 |
| 31B | 102 |
| 35B | 101 |
| 38B | 101 |
| 44B | 98 |
| 55B | 95 |
| 57B | 96 |
| 58B | 101 |
| 59B | 101 |
| 64B | 100 |
| 70B | 100 |
| 72B | 94 |
| 74B | 100 |
| 81B | 100 |
| 96B | 102 |
| 102B | 100 |
| 104B | 101 |
| 114B | 99 |
| 132B | 98 |
| 139B | 100 |
| 140B | 101 |
| 141B | 101 |
| 144B | 98 |
| 150B | 101 |
| 151B | 99 |
| 152B | 96 |
| 166B | 101 |
| 170B | 100 |
| 191B | 100 |
| 241B | 101 |
| 245B | 100 |
| 246B | 101 |
| 253B | 97 |
| 254B | 99 |
| 270B | 89 |
| 276B | 82 |
| 279B | 103 |
| 324B | 99 |
| 330B | 102 |
| 342B | 101 |
| 344B | 103 |
| 345B | 102 |
| 352B | 102 |
| 361B | 102 |
| 412B | 102 |

These results demonstrated that the compound of the present invention has an inhibitory effect on SPT.

Test Example 2 HCC4006 Cell Growth Inhibition Test

A lung adenocarcinoma cell line HCC4006 (ATCC) was cultured using an RPMI-1640 medium (Wako Pure Chemical Industries, Ltd.) containing 10% fetal bovine serum and penicillin/streptomycin. 250 cells per well were inoculated into 40 μL of a medium in a 384-well culture plate. On the next day, 10 μL of each test compound was added to the cells. After culture for 5 days, the medium was discarded, and 30 μL of CellTiter-Glo Luminescent Cell Viability Assay solution (Promega Corp., Fitchburg, Wis., US) was added to each well. Light emission signals were measured using EnVision (PerkinElmer, Inc., Waltham, Mass., US). The rate of inhibition (%) by the test compound was calculated according to the following expression:

Rate of inhibition (%)=(1−(Count of the test compound−Blank)/(Control−Blank))×100

In the above expression, a count under compound non-addition conditions was indicated as a control, and a count under cell-free conditions was indicated as a blank.

The test results are shown in Table 4.

TABLE 4

| Example No. | Rate of inhibition (%) at 1 μM |
|---|---|
| 2A | 36 |
| 3A | 41 |
| 36A | 47 |
| 74A | 51 |
| 80A | 44 |
| 84A | 32 |
| 85A | 39 |
| 100A | 39 |
| 126A | 45 |
| 132A | 52 |
| 133A | 50 |
| 153A | 53 |
| 155A | 53 |
| 162A | 56 |
| 165A | 52 |
| 170A | 50 |
| 171A | 50 |
| 178A | 53 |
| 186A | 47 |
| 201A | 40 |

TABLE 4-continued

| Example No. | Rate of inhibition (%) at 1 μM |
|---|---|
| 2B | 55 |
| 3B | 44 |
| 23B | 53 |
| 25B | 53 |
| 31B | 57 |
| 35B | 40 |
| 38B | 46 |
| 44B | 47 |
| 57B | 54 |
| 58B | 49 |
| 59B | 53 (Rate of inhibition at 0.3 μM) |
| 64B | 49 |
| 70B | 56 |
| 74B | 45 |
| 81B | 54 |
| 96B | 49 |
| 102B | 46 |
| 104B | 53 |
| 114B | 56 |
| 132B | 45 |
| 139B | 52 |
| 140B | 49 |
| 141B | 52 |
| 150B | 47 |
| 151B | 51 |
| 152B | 33 |
| 166B | 53 |
| 170B | 50 |
| 191B | 47 |
| 241B | 54 |
| 245B | 53 |
| 246B | 55 |
| 254B | 55 |
| 279B | 44 |
| 324B | 49 |
| 330B | 49 |
| 342B | 51 |
| 344B | 51 |
| 345B | 48 |
| 352B | 50 |
| 361B | 45 |
| 412B | 47 |

These results demonstrated that the compound of the present invention inhibits the growth of lung adenocarcinoma cells.

Test Example 3 Antitumor Test Using PL-21 Cell

The compound of the present invention was evaluated for its antitumor effect on human leukemia cell line PL-21 cancer-bearing mice by the following method.

The human leukemia cell line PL-21 (JCRB) was transplanted to each 6-week-old Icr-scid female mouse (CLEA Japan Inc.) by the subcutaneous injection of $3.0 \times 10^6$ cells. The tumor size of successfully engrafted tumor was measured 13 days after the transplantation. The tumor volume was calculated according to the following expression:

Tumor volume=Major axis×Minor axis×Minor axis× (½)

Individuals in which the volume of the engrafted tumor reached 100 to 150 mm³ were selected and used in the experiment as groups each involving 5 or 6 individuals. A 0.5% methylcellulose suspension of each test compound was orally administered to each mouse using the dose (indicated by single dose), the number of doses and the dosing period shown in Table 5. The tumor sizes at the day before the start of the administration and one day after the completion of the administration were measured and the tumor volume was calculated.

The rate of tumor growth (T/C (%)) in the test compound administration group compared with a control administration group was calculated according to the following expression:

T/C (%)=(Tumor volume after the completion of the administration of the test compound administration group−Tumor volume before the start of the administration of the test compound administration group)/(Tumor volume after the completion of the administration of the control administration group−Tumor volume before the start of the administration of the control administration group)×100

The test results are shown in Table 5.

TABLE 5

| Example No. | T/C (%) | Dose (mg/kg) | The number of doses, dosing period |
|---|---|---|---|
| 162A | 52 | 10 | Administered once every two days, 14 days |
| 162A | 38 | 30 | Administered once every two days, 14 days |
| 81B | 63 | 10 | Administered once every two days, 14 days |
| 81B | 32 | 30 | Administered once every two days, 14 days |
| 81B | 16 | 10 | Administered every day for 3 days, 4-day drug holiday, 2 cycles |

These results demonstrated that the compound of the present invention has an antitumor effect.

Test Example 4 Efficacy Evaluation Test Using Niemann-Pick Disease Model Cell

A normal line and an acidic sphingomyelinase-deficient cell line (Niemann-Pick disease model cells), which is responsible for Niemann-Pick disease, are each cultured using Iscove's Modified Dulbecco's Medium containing 10% fetal bovine serum and penicillin/streptomycin. At the day following the inoculation to the culture plate, the medium is replaced, and the cells are cultured in a medium containing each SPT inhibitor for 4 days. After the culture, the medium is discarded, and sphingolipids such as sphingomyelin in the cells are extracted with hexane and quantified by use of TLC, gas chromatography or the like.

Test Example 5 Efficacy Evaluation Test Using Niemann-Pick Disease Model Mouse

The Niemann-Pick disease-ameliorating effect of each SPT inhibitor is confirmed using Niemann-Pick disease model mice (e.g., acidic sphingomyelinase-deficient mice (FASEB J. 2000; 14: 1988) or NPC mice confirmed to have sphingomyelin accumulation (Nat Med. 2008; 14: 1247)). These model mice manifest symptoms similar to those of human Niemann-Pick disease associated with sphingomyelin accumulation, etc., in the liver, the lung or the like. Furthermore, these mice manifest liver damage and nerve dysfunction and die at the age of approximately 12 weeks without treatment.

Four-week-old Niemann-Pick disease model mice are used. The test is started at the age of 4 weeks, and a 0.5% methyl cellulose suspension of each test compound is orally administered to the mice for 2 or 4 weeks. After the continuous administration, organ samples are collected. The effect of lowering liver damage markers serum AST (aspartate aminotransferase) and ALT (alanine aminotransferase) is tested as an evaluation parameter for the ameliorating effect of the SPT inhibitor. In addition, its ameliorating effect in each tissue image of the liver, central nerve and the like is also tested. In order to confirm SPT inhibitory activity, the effect of lowering sphingolipids such as sphingomyelin in tissues is further tested.

INDUSTRIAL APPLICABILITY

The compound of the present invention can be used as a SPT inhibitor and can be useful as a prophylactic or therapeutic agent for SPT-related diseases including cancer and the like.

The present application is based on Japanese Patent Application No. 2015-086195 filed in Japan, the contents of which are incorporated herein by their entirety.

The invention claimed is:

1. A method for treating Niemann-Pick disease in a mammal, comprising administering an effective amount of a compound or a salt thereof to the mammal, wherein the compound is represented by a formula:

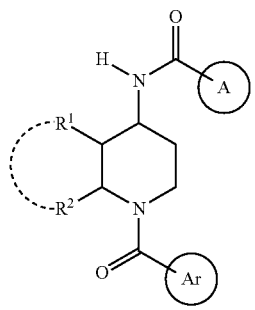

[Formula 1]

wherein
ring Ar represents an optionally further substituted aromatic heterocycle or an optionally further substituted $C_{6-14}$ aromatic hydrocarbon ring;
ring A represents an optionally further substituted $C_{6-14}$ aromatic hydrocarbon ring or an optionally further substituted heterocycle;
$R^1$ represents an optionally substituted $C_{6-14}$ aryl group, an optionally substituted $C_{3-10}$ cycloalkyl group or an optionally substituted heterocyclic group
except that when $R^1$ is an optionally substituted heterocyclic group, $R^1$ is represented by a formula:

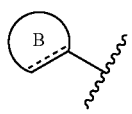

[Formula 2]

wherein ring B represents an optionally further substituted heterocycle, and

[Formula 3]

represents a single bond or a double bond, or a formula:

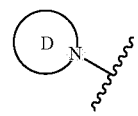

[Formula 4]

wherein ring D represents an optionally further substituted nitrogen-containing heterocycle,
$R^2$ represents a hydrogen atom, or
$R^1$ and $R^2$ are bonded to each other to form an optionally substituted 5- or 6-membered aromatic heterocycle or an optionally substituted benzene ring.

2. The method according to claim 1, wherein
ring Ar is
(I) an aromatic heterocycle optionally substituted by 1 to 3 substituents selected from
(1) a halogen atom,
(2) a cyano group,
(3) a hydroxy group,
(4) an optionally halogenated $C_{1-6}$ alkyl group,
(5) a $C_{3-10}$ cycloalkyl group,
(6) an optionally halogenated $C_{1-6}$ alkoxy group,
(7) a hydroxy-$C_{1-6}$ alkoxy group,
(8) a $C_{3-10}$ cycloalkyloxy group,
(9) a $C_{1-6}$ alkyl-carbonyl group,
(10) a $C_{1-6}$ alkoxy-carbonyl group,
(11) an amino group,
(12) a mono- or di-$C_{1-6}$ alkylamino group,
(13) a mono- or di-$C_{1-6}$ alkyl-carbonylamino group,
(14) a mono- or di-$C_{3-10}$ cycloalkyl-carbonylamino group,
(15) a 5- to 14-membered aromatic heterocyclic group, and
(16) a $C_{1-6}$ alkylsulfonyl group,
or
(II) a $C_{6-14}$ aromatic hydrocarbon ring optionally substituted by 1 to 3 substituents selected from
(1) a halogen atom,
(2) a cyano group,
(3) an optionally halogenated $C_{1-6}$ alkyl group,
(4) a $C_{3-10}$ cycloalkyl group,
(5) an optionally halogenated $C_{1-6}$ alkoxy group,
(6) a mono- or di-$C_{1-6}$ alkylamino group,
(7) a $C_{1-6}$ alkyl-5- to 14-membered aromatic heterocyclic group, and
(8) a $C_{1-6}$ alkylsulfonyl group;
ring A is
(I) a $C_{6-14}$ aromatic hydrocarbon ring optionally substituted by 1 to 3 substituents selected from
(1) a halogen atom,
(2) a cyano group,
(3) an optionally halogenated $C_{1-6}$ alkyl group,
(4) an optionally halogenated $C_{1-6}$ alkoxy group, and
(5) a $C_{1-6}$ alkylsulfonyl group,
or
(II) a heterocycle optionally substituted by 1 to 3 substituents selected from
(1) a halogen atom,
(2) an optionally halogenated $C_{1-6}$ alkyl group,
(3) a $C_{3-10}$ cycloalkyl group,
(4) an optionally halogenated $C_{1-6}$ alkoxy group,
(5) a hydroxy-$C_{1-6}$ alkoxy group,
(6) a $C_{1-6}$ alkoxy-$C_{1-6}$ alkoxy group, (7) a 3- to 14-membered non-aromatic heterocycle-$C_{1-6}$ alkoxy group,
(8) a 3- to 14-membered non-aromatic heterocyclyloxy-$C_{1-6}$ alkoxy group,
(9) a mono- or di-$C_{1-6}$ alkylamino-$C_{1-6}$ alkoxy group,
(10) a mono- or di-$C_{7-16}$ aralkyl phosphate-$C_{1-6}$ alkoxy group,
(11) a 5- to 14-membered aromatic heterocyclic group,
(12) a 5- to 14-membered aromatic heterocyclyloxy group,
(13) a $C_{1-6}$ alkylsulfonyl group, and
(14) a $C_{1-6}$ alkylsulfanyl group;
$R^1$ is
(I) a $C_{6-14}$ aryl group optionally substituted by 1 to 3 substituents selected from
(1) a halogen atom,
(2) an optionally halogenated $C_{1-6}$ alkyl group, and
(3) a $C_{1-6}$ alkoxy group,
(II) a $C_{3-10}$ cycloalkyl group, or
(III) an optionally substituted heterocyclic group represented by any of
(1) a heterocyclic group represented by a formula:

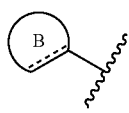

[Formula 5]

which is selected from pyrazolyl, thienyl and pyridyl and optionally substituted by 1 to 3 $C_{1-6}$ alkyl groups, and
(2) a nitrogen-containing heterocyclic group represented by a formula:

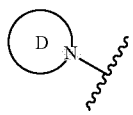

[Formula 6]

which is selected from pyrazol-1-yl, 1,2,3-triazol-1-yl and piperidinyl;
$R^2$ is a hydrogen atom; or
$R^1$ and $R^2$ are bonded to each other to form
(I) a 5- or 6-membered aromatic heterocycle optionally substituted by 1 to 3 substituents selected from
(1) a halogen atom,
(2) an optionally halogenated $C_{1-6}$ alkyl group,
(3) a $C_{7-20}$ alkyl group,
(4) a hydroxy-$C_{1-6}$ alkyl group,
(5) a $C_{1-6}$ alkoxy-$C_{1-6}$ alkyl group,
(6) an optionally halogenated $C_{3-10}$ cycloalkyl-$C_{1-6}$ alkyl group,
(7) a $C_{3-10}$ cycloalkyl group,
(8) a $C_{1-6}$ alkoxy-$C_{7-16}$ aralkyl group,
(9) a 3- to 14-membered non-aromatic heterocyclic group,
(10) an optionally halogenated $C_{1-6}$ alkyl-3- to 14-membered non-aromatic heterocyclic group,
(11) a $C_{1-6}$ alkyl-3- to 14-membered non-aromatic heterocycle-$C_{1-6}$ alkyl group,
(12) a carbamoyl-$C_{1-6}$ alkyl group,
(13) an amino-$C_{1-6}$ alkyl group,
(14) a $C_{1-6}$ alkoxy-carbonylamino-$C_{1-6}$ alkyl group,
(15) a fluorenyl-$C_{1-6}$ alkoxy-carbonylamino-$C_{1-6}$ alkyl group, and
(16) a mono- or di-$C_{1-6}$ alkyl nitrogen-containing heterocycle-$C_{1-6}$ alkyl-nitrogen-containing heterocycle-$\kappa^2 N$ (boron halide)-$C_{1-6}$ alkyl-carbonylamino-$C_{1-6}$ alkyl group,
or
(II) a benzene ring optionally substituted by one halogen atom.

3. The method according to claim 2, wherein
$R^1$ represents a $C_{6-14}$ aryl group optionally substituted by 1 to 3 substituents selected from (1) a halogen atom, (2) an optionally halogenated $C_{1-6}$ alkyl group and (3) a $C_{1-6}$ alkoxy group,
$R^2$ is a hydrogen atom, or
$R^1$ and $R^2$ are bonded to each other to form a 5- or 6-membered aromatic heterocycle optionally substituted by 1 to 3 substituents selected from (1) a halogen atom, (2) an optionally halogenated $C_{1-6}$ alkyl group, (3) a $C_{7-20}$ alkyl group, (4) a hydroxy-$C_{1-6}$ alkyl group, (5) a $C_{1-6}$ alkoxy-$C_{1-6}$ alkyl group, (6) an optionally halogenated $C_{3-10}$ cycloalkyl-$C_{1-6}$ alkyl group, (7) a $C_{3-10}$ cycloalkyl group, (8) a $C_{1-6}$ alkoxy-$C_{7-16}$ aralkyl group, (9) a 3- to 14-membered non-aromatic heterocyclic group, (10) an optionally halogenated $C_{1-6}$ alkyl-3- to 14-membered non-aromatic heterocyclic group, (11) a $C_{1-6}$ alkyl-3- to 14-membered non-aromatic heterocycle-$C_{1-6}$ alkyl group, (12) a carbamoyl-$C_{1-6}$ alkyl group, (13) an amino-$C_{1-6}$ alkyl group, (14) a $C_{1-6}$ alkoxy-carbonylamino-$C_{1-6}$ alkyl group, (15) a fluorenyl-$C_{1-6}$ alkoxy-carbonylamino-$C_{1-6}$ alkyl group, and (16) a mono- or di-$C_{1-6}$ alkyl nitrogen-containing heterocycle-$C_{1-6}$ alkyl-nitrogen-containing heterocycle-$\kappa^2 N$ (boron halide)-$C_{1-6}$ alkyl-carbonylamino-$C_{1-6}$ alkyl group.

4. The method according to claim 2, wherein
ring Ar represents an aromatic heterocycle optionally substituted by 1 to 3 substituents selected from (1) a halogen atom, (2) a cyano group, (3) a hydroxy group, (4) an optionally halogenated $C_{1-6}$ alkyl group, (5) a $C_{3-10}$ cycloalkyl group, (6) an optionally halogenated $C_{1-6}$ alkoxy group, (7) a hydroxy-$C_{1-6}$ alkoxy group, (8) a $C_{3-10}$ cycloalkyloxy group, (9) a $C_{1-6}$ alkyl-carbonyl group, (10) a $C_{1-6}$ alkoxy-carbonyl group, (11) an amino group, (12) a mono- or di-$C_{1-6}$ alkylamino group, (13) a mono- or di-$C_{1-6}$ alkyl-carbonylamino group, (14) a mono- or di-$C_{3-10}$ cycloalkyl-carbonylamino group, (15) a 5- to 14-membered aromatic heterocyclic group, and (16) a $C_{1-6}$ alkylsulfonyl group.

5. The method according to claim 4, wherein
(I) ring A represents a heterocycle optionally substituted by 1 to 3 substituents selected from (1) a halogen atom, (2) an optionally halogenated $C_{1-6}$ alkyl group, (3) a $C_{3-10}$ cycloalkyl group, (4) an optionally halogenated $C_{1-6}$ alkoxy group, (5) a hydroxy-$C_{1-6}$ alkoxy group, (6) a $C_{1-6}$ alkoxy-$C_{1-6}$ alkoxy group, (7) a 3- to 14-membered non-aromatic heterocycle-$C_{1-6}$ alkoxy group, (8) a 3- to 14-membered non-aromatic heterocyclyloxy-$C_{1-6}$ alkoxy group, (9) a mono- or di-$C_{1-6}$ alkylamino-$C_{1-6}$ alkoxy group, (10) a mono- or di-$C_{7-16}$ aralkyl phosphate-$C_{1-6}$ alkoxy group, (11) a 5- to 14-membered aromatic heterocyclic group, (12) a 5- to 14-membered aromatic heterocyclyloxy group, (13) a $C_{1-6}$ alkylsulfonyl group, and (14) a $C_{1-6}$ alkylsulfanyl group, $R^1$ represents a $C_{6-14}$ aryl group optionally substituted by 1 to 3 substituents selected from (1) a halogen atom, (2) an optionally halogenated $C_{1-6}$ alkyl group and (3) a $C_{1-6}$ alkoxy group, and $R^2$ represents a hydrogen atom, or (II) ring A represents a $C_{6-14}$ aromatic hydrocarbon ring optionally substituted by 1 to 3 substituents selected from (1) a halogen atom, (2) a cyano group, (3) an optionally halogenated $C_{1-6}$ alkyl group, (4) an optionally halogenated $C_{1-6}$ alkoxy group, and (5) a $C_{1-6}$ alkylsulfonyl group, and $R^1$ and $R^2$ are bonded to each other to form a 5- or 6-membered aromatic heterocycle optionally substituted by 1 to 3 substituents selected from (1) a halogen atom, (2) an optionally halogenated $C_{1-6}$ alkyl group, (3) a $C_{7-20}$ alkyl group, (4) a hydroxy-$C_{1-6}$ alkyl group, (5) a $C_{1-6}$ alkoxy-$C_{1-6}$ alkyl group, (6) an optionally halogenated $C_{3-10}$ cycloalkyl-$C_{1-6}$ alkyl group, (7) a $C_{3-10}$ cycloalkyl group, (8) a $C_{1-6}$ alkoxy-$C_{7-16}$ aralkyl group, (9) a 3- to 14-membered non-aromatic heterocyclic group, (10) an optionally halogenated $C_{1-6}$ alkyl-3- to 14-membered non-aromatic heterocyclic group, (11) a $C_{1-6}$ alkyl-3- to 14-membered non-aromatic heterocycle-$C_{1-6}$ alkyl group, (12) a carbamoyl-$C_{1-6}$ alkyl group, (13) an amino-$C_{1-6}$ alkyl group, (14) a $C_{1-6}$ alkoxy-carbonylamino-$C_{1-6}$ alkyl group, (15) a fluorenyl-$C_{1-6}$ alkoxy-carbonylamino-$C_{1-6}$ alkyl group, and (16) a mono- or di-$C_{1-6}$ alkyl nitrogen-containing heterocycle-$C_{1-6}$ alkyl-nitrogen-containing heterocycle-κ2N (boron halide)-$C_{1-6}$ alkyl-carbonylamino-$C_{1-6}$ alkyl group.

* * * * *